(12) United States Patent
Zieler

(10) Patent No.: US 10,077,441 B2
(45) Date of Patent: Sep. 18, 2018

(54) METHODS AND COMPOSITIONS FOR CREATING ALTERED AND IMPROVED CELLS AND ORGANISMS

(71) Applicant: Helge Zieler, Del Mar, CA (US)

(72) Inventor: Helge Zieler, Del Mar, CA (US)

(73) Assignee: PRIMORDIAL GENETICS INC., Del Mar, CA (US)

( * ) Notice: Subject to any disclaimer, the term of this patent is extended or adjusted under 35 U.S.C. 154(b) by 0 days.

(21) Appl. No.: 15/110,712

(22) PCT Filed: Jan. 9, 2015

(86) PCT No.: PCT/US2015/010812
§ 371 (c)(1),
(2) Date: Jul. 8, 2016

(87) PCT Pub. No.: WO2015/106097
PCT Pub. Date: Jul. 16, 2015

(65) Prior Publication Data
US 2016/0326521 A1    Nov. 10, 2016

Related U.S. Application Data

(60) Provisional application No. 61/925,230, filed on Jan. 9, 2014.

(51) Int. Cl.
| | | |
|---|---|---|
| C12N 15/74 | (2006.01) |
| C12P 21/04 | (2006.01) |
| C12P 21/06 | (2006.01) |
| C07H 21/04 | (2006.01) |
| C12N 15/10 | (2006.01) |

(52) U.S. Cl.
CPC ......... *C12N 15/1079* (2013.01); *C12N 15/10* (2013.01); *C07H 21/04* (2013.01); *C07K 2319/00* (2013.01); *C12N 15/74* (2013.01)

(58) Field of Classification Search
CPC .... C12N 15/10; C12N 15/1079; C12N 15/74; C07K 2319/00; C07H 21/04
USPC ...................... 435/471, 69.1, 69.7; 536/23.1
See application file for complete search history.

(56) References Cited

U.S. PATENT DOCUMENTS

| | | |
|---|---|---|
| 6,156,511 A | 12/2000 | Schatz et al. |
| 2001/0003650 A1 | 6/2001 | Anderson et al. |
| 2010/0055125 A1 | 3/2010 | Jungbauer et al. |

OTHER PUBLICATIONS

Biles BD et al, Low-Fidelity Pyrococcus furiosus DNA polymerase mutants useful in error-prone PCR, Nucleic Acids Research, 2004, 32(22):e176.

Brachmann et al, Designer deletion strains derived from Saccharomyces cerevisiae S288C: a useful set of strains and plasmids for PCR-mediated gene disruption and other applications. Yeast 1998; 14(2):115-132.

Chenna R et al, Multiple sequence alignment with the Clustal series of programs, Nucleic Acids Research, 2003, 31 (13):3497-3500.

Cline J et al, PCR fidelity of pfu DNA polymerase and other thermostable DNA polymerases, Nucleic Acids Research, 1996, 24(18):3546-3551.

Da Costa LJ et al, Use of T7 gene 6 exonuclease and phosphorothioated primers for the manipulation of HIV-1 Infectious clones, J. Viral Methods,1998, 72(1):117-121.

Ding et al, Tolerance and stress response to ethanol in the yeast Saccharomyces cerevisiae, Appl Microbiology and Biotechnology, 2009, 85(2):253-263.

Dismukes et al, Aquatic phototrophs: efficient alternatives to land-based crops for biofuels, Current Opinion in Biotechnology, 2008, 19(3):235-240.

Dolganov and Grossman, Insertional inactivation of genes to isolate mutants of *Synechococcus* sp. strain PCC 7942: isolation of filamentous strains, J Bacteriology, 1993, 175(23):7644-7651.

Dunlop MJ, Engineering microbes for tolerance to next-generation biofuels, Biotechnol Biofuels, 2011, 4:32.

Funk M et al, Vector systems for heterologous expression of proteins in Saccharomyces cerevisiae, Methods Enzymology, 2002, 350:248-57.

Gibson DG et al, Chemical synthesis of the mouse mitochondrial genome, Nature Methods, 2010, 7(11):901-903.

Gibson DG et al, Enzymatic assembly of DNA molecules up to several hundred kilobases, Nature Methods, 2009, 6 (5):343-345.

Gietz RD and Woods, Transformation of yeast by lithium acetate/single-stranded carrier DNA/polyethylene glycol method, Methods Enzymology, 2002, 350:87-96.

Gietz RD and Schiestl, High-efficiency yeast transformation using the LiAc/SS carrier DNA/PEG method, Nature Protocols, 2007, 2(1):31-34.

Gietz RD and Woods, Yeast transformation by the LiAc/SS Carrier DNA/PEG method, Methods in Molecular Biology, 2006, 313:107-120.

(Continued)

*Primary Examiner* — Shin Lin Chen
(74) *Attorney, Agent, or Firm* — Gorman IP Law, APC

(57) ABSTRACT

The present invention relates to compositions involving randomized in-frame fusion polynucleotides and their introduction into a host organism to identify desirable phenotypic changes. The present invention further relates to methods of generating these randomized in-frame fusion polynucleotides by introducing randomized in-frame fusion polynucleotides into an organism, selecting for organisms with new or altered phenotypes, re-isolating the randomized in-frame fusion polynucleotides from the selected organisms, re-assembling the constituent polynucleotides of the re-isolated randomized in-frame fusion polynucleotides into new collections of randomized in-frame fusion polynucleotides, and repeating the selection for organisms with new or altered phenotypes.

16 Claims, 10 Drawing Sheets
Specification includes a Sequence Listing.

(56) References Cited

OTHER PUBLICATIONS

International Search Report dated May 6, 2015.
Irwin CR et al, In-fusion® cloning with vaccinia virus DNA polymerase, Methods in Molecular Biology, 2012, 890:23-35.
Jang YS et al, Bio-based production of C2-C6 platform chemicals, Biotechnology and Bioengineering, . 2012, 109 (10):2437-2459, Wiley Periodicals Inc.
Jia et al, Systematic engineering of microorganisms to improve alcohol tolerance, Engineering in Life Sciences, 2009, 10(5): 422-429.
Kamiya H et al, Induction of transition and transversion mutations during random mutagenesis PCR by the addition of 2-hydroxy-dATP, Biological and Pharmaceutical Bulletin, 2004, 27(5):621-623.
Kamiya H et al, Induction of various mutations during PCRs with manganese and 8-hydroxy-dGTP, Biological and Pharmaceutical Bulletin, 2007, 30(4):842-844.
Keefe et al, Functional proteins from a random-sequence library, Nature, Apr. 5, 2001, vol. 410, pp. 715-718.
Kuipers OP, Random mutagenesis by using mixtures of dNTP and dITP in PCR, Methods in Molecular Biology, 1996, 57:351-356.
Lathe et al, Linker tailing: unphosphorylated linker oligonucleotides for joining DNA termini, DNA, 1984, 3(2):173-182.
Lee et al, Systems metabolic engineering of microorganisms for natural and non-natural chemicals, Nature Chemical Biology, 2012, 8(6):536-546.
Li and Elledge, Harnessing homologous recombination in vitro to generate recombinant DNA via SLIC, Nature Methods, 2007, 4(3): 251-256.
Li C et al, FastCloning: a highly simplified, purification-free, sequence- and ligation-independent PCR cloning method, BMC Biotechnology, 2011, 11:92.
Li MZ and Elledge SJ, SLIC: a method for sequence- and ligation-independent cloning. Methods in Molecular Biology, 2012, 852:51-59.
Liu XP and Liu JH, The terminal 5' phosphate and proximate phosphorothioate promote ligation-independent cloning, Protein Science, 2010, 19(5):967-973.
Lobban PE and Kaiser AD, Enzymatic end-to end joining of DNA molecules, Journal of Molecular Biology, 1973, 78 (3): 453-471.
Ma X et al, the mutagenic properties of BrdUTP in a random mutagenesis process, Molecular Biology Reports, 2008, 35(4):663-667.
Mascal M, Chemicals from biobutanol: technologies and markets. Biofuels, Bioproducts Biorefining, 2012, 6(4):483-493.
Petrie KL and Joyce GF, Deep sequencing analysis of mutations resulting from the incorporation of dNTP analogs, Nucleic Acids Research, 2010, 38(22):8095-8104.
Quan J and Tian J, Circular polymerase extension cloning for high-throughput cloning of complex and combinatorial DNA libraries Nature Protocols, 2011, 6(2):242-251.
Quan J and Tian J, Circular polymerase extension cloning of complex gene libraries and pathways. PLoS One, 2009, 4(7): e6441.
Sambrook J et al, Molecular Cloning: A Laboratory Manual, Second Ed., 1989, Cold Spring Harbor Laboratory Press, Plainview, New York.
Sikorski RS et al, A system of shuttle vectors and yeast host strains designed for efficient manipulation of DNA in Saccharomyces cerevisiae, Gentics, 1989, 122(1):19-27.
Spee H et al, Efficient random mutagenesis method with adjustable mutation frequency by use of PCR and dITP, Nucleic Acid Research, 1993, 21(3):777-778.
Thieme F et al, Quick and clean cloning: a ligation-independent cloning strategy for selective cloning of specific PCR products from non-specific mixes. PLoS One 2011, 6(6): e20556.
Vroom Z and Wang CL, Modular construction of plasmids through ligation-free assembly of vector components with oligonucleotide linkers Biotechniques, 2008, 44(7): 924-926.
Wang Z et al, A simple and reproducible method for directed evolution: combination of random mutation with dITP and DNA fragmentation with endonuclease, V. Moleuclar Biotechnology, 2012a, 53(1):49-54.
Ward AC, Single-step purification of shuttle vectors from yeast for high frequency back-transformation into *E. coli*, Nucleic Acids Research, 1990, 8(17):5319.
Zaccolo M et al, An approach to random mutagenesis of DNA using mixtures of triphosphate derivatives of nucleoside analogues, Journal of Molecular Biology, 1996, 255(4):589-603.
Zaccolo M et al, The effect of high-frequency random mutagenesis on in vitro protein evolution: a study on TEM-1 beta-lactamase, Journal of Molecular Biology, 1999, 285(2):775-783.
Zhu et al, In-fusion assembly: seamless engineering of multidomain fusion proteins, modular vectors, and mutations, BioTechniques, 2007, 43:354-359.

Figure 5
A
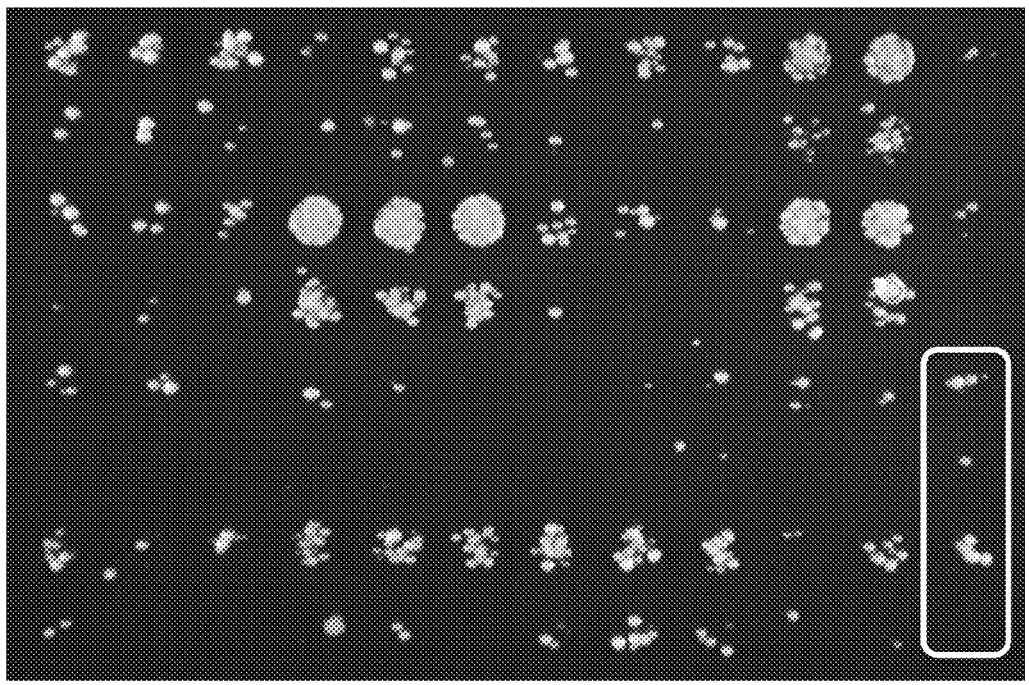
B
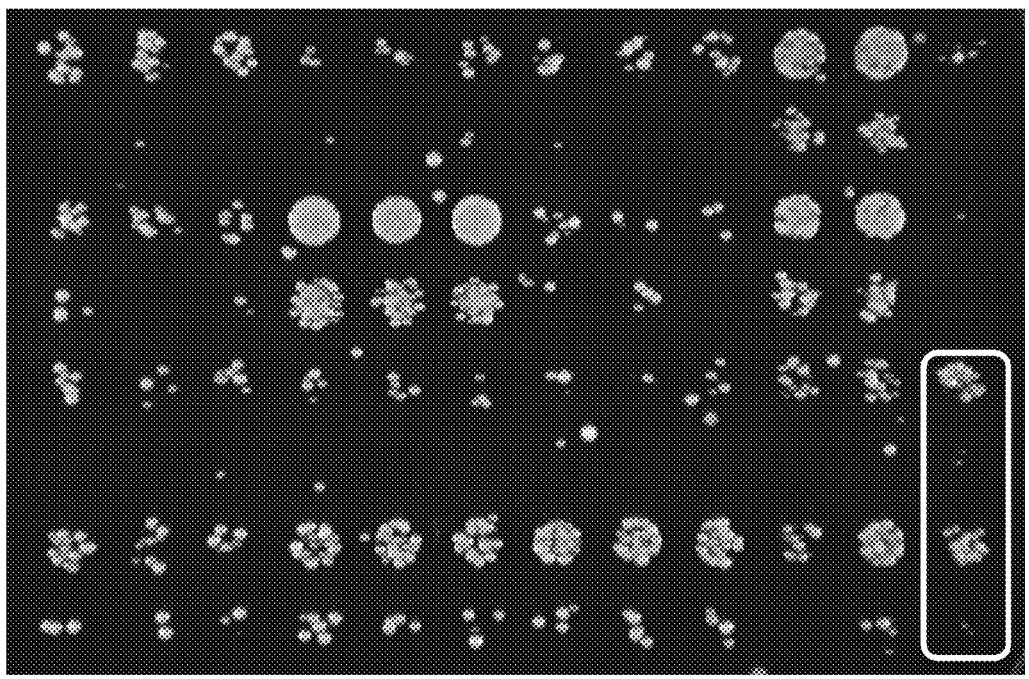

Figure 5
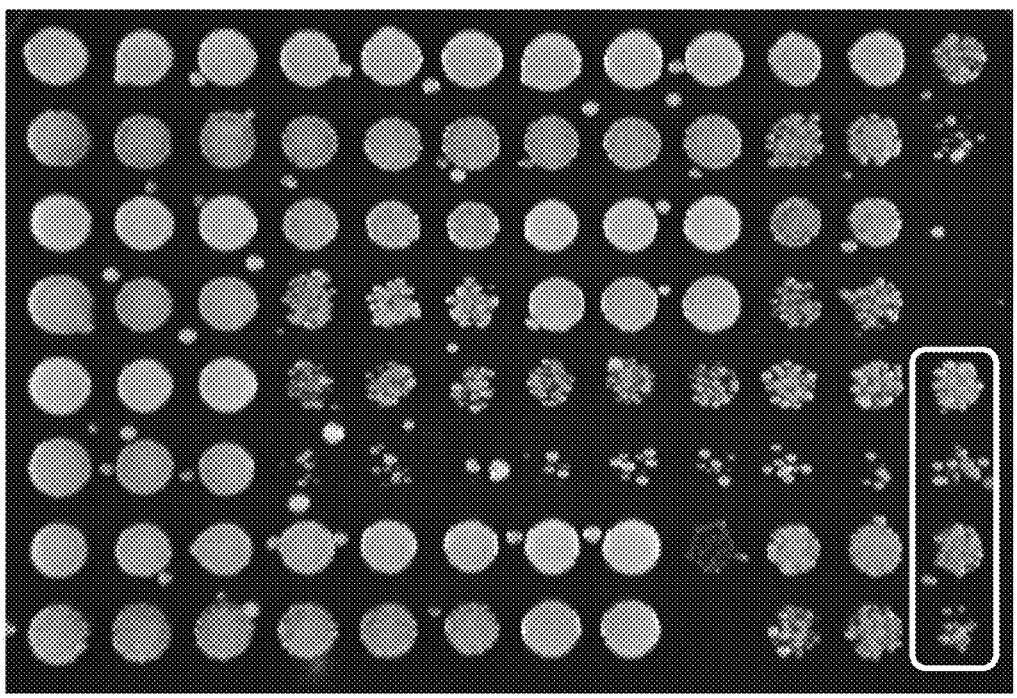
C
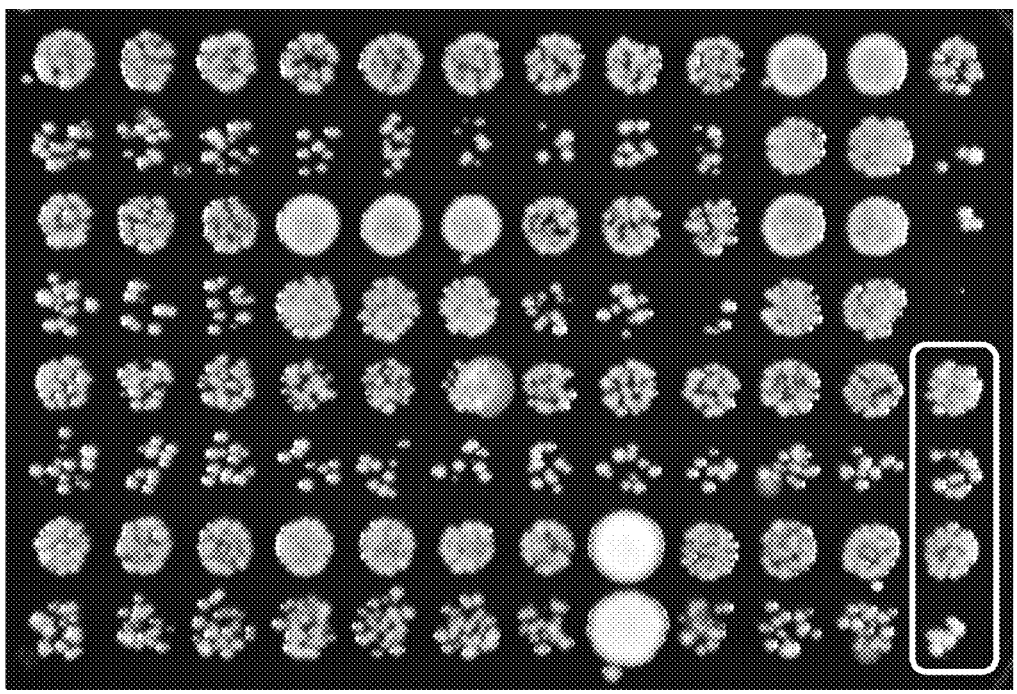
D

Figure 5

| | 1 | 2 | 3 | 4 | 5 | 6 | 7 | 8 | 9 | 10 | 11 | 12 |
|---|---|---|---|---|---|---|---|---|---|---|---|---|
| A | M25-E1 | M25-E1 | M25-E1 | M25-F4 | M25-F4 | M25-F4 | M25-G8 | M25-G8 | M25-G8 | M25-G10 | M25-G10 | - |
| B | M25-E1 | M25-E1 | M25-E1 | M25-F4 | M25-F4 | M25-F4 | M25-G8 | M25-G8 | M25-G8 | M25-G10 | M25-G10 | - |
| C | M25-H11 | M25-H11 | M25-H11 | M26-A12 | M26-A12 | M26-A12 | M26-D6 | M26-D6 | M26-D6 | M27-A1 | M27-A1 | - |
| D | M25-H11 | M25-H11 | M25-H11 | M26-A12 | M26-A12 | M26-A12 | M26-D6 | M26-D6 | M26-D6 | M27-A1 | M27-A1 | - |
| E | M27-B7 | M27-B7 | M27-B7 | M27-F8 | M27-F8 | M27-F8 | M28-A4 | M28-A4 | M28-A4 | M28-C9 | M28-C9 | p416-GAL1 |
| F | M27-B7 | M27-B7 | M27-B7 | M27-F8 | M27-F8 | M27-F8 | M28-A4 | M28-A4 | M28-A4 | M28-C9 | M28-C9 | p416-GAL1 |
| G | M28-D6 | M28-D6 | M28-D6 | M28-E4 | M28-E4 | M28-E4 | M29-E7 | M29-E7 | M29-E7 | M30-E11 | M30-E11 | p416-GAL1 |
| H | M28-D6 | M28-D6 | M28-D6 | M28-E4 | M28-E4 | M28-E4 | M29-E7 | M29-E7 | M29-E7 | M30-E11 | M30-E11 | p416-GAL1 |

Top row of each pair of rows: selective culture spotted without dilution
Bottom row of each pair of rows: selective culture diluted 1:10 before spotting Figure 6
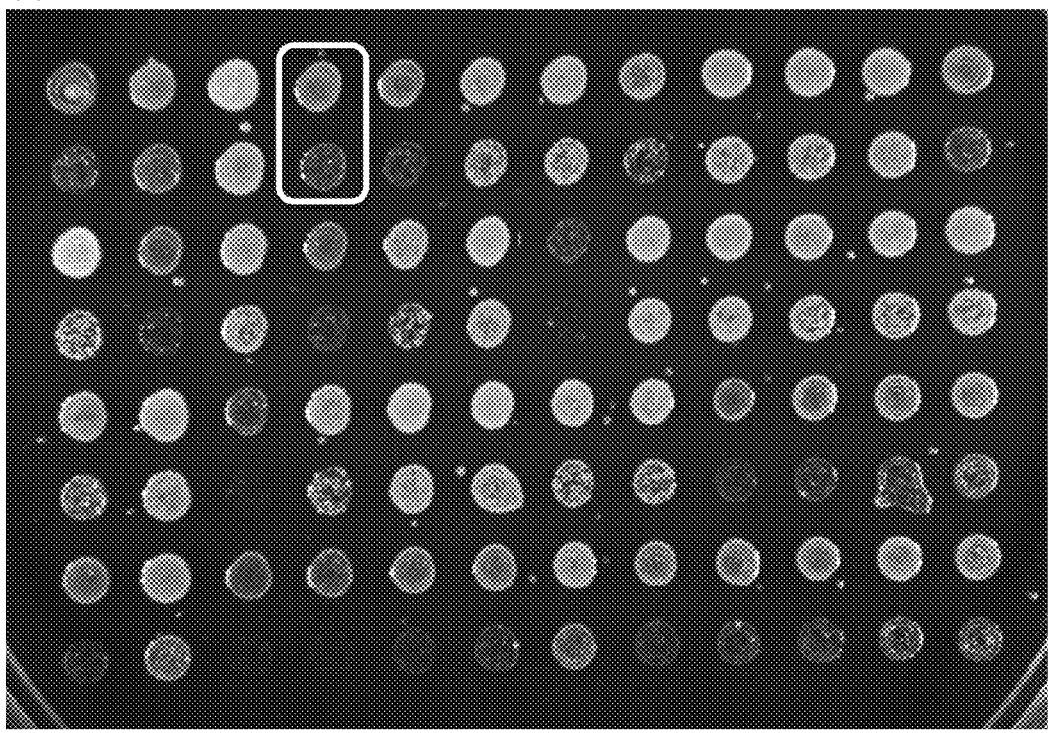
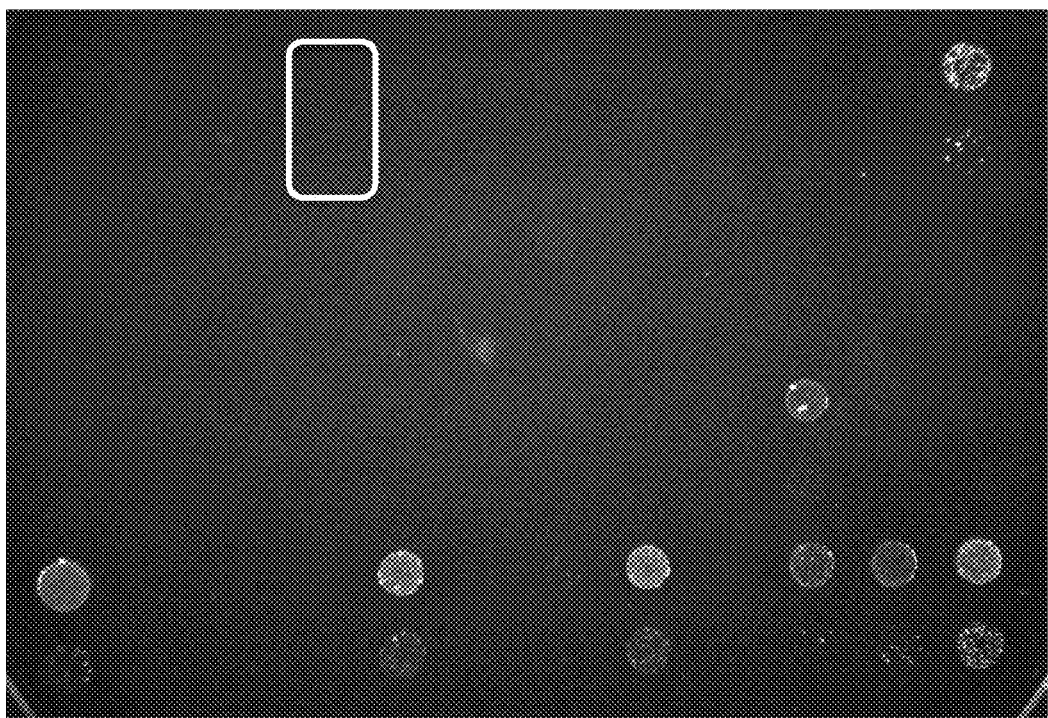

| | 1 | 2 | 3 | 4 | 5 | 6 | 7 | 8 | 9 | 10 | 11 | 12 |
|---|---|---|---|---|---|---|---|---|---|---|---|---|
| A | M44-G2 | M48-A2 | M48-A3 | Vector | M48-A5 | M48-A6 | M48-A7 | M48-A8 | M48-A9 | M48-A10 | M48-A11 | M44-G4 |
| B | M44-G2 | M48-A2 | M48-A3 | Vector | M48-A5 | M48-A6 | M48-A7 | M48-A8 | M48-A9 | M48-A10 | M48-A11 | M44-G4 |
| C | M48-B1 | M44-G5 | M48-B3 | M48-B4 | M48-B5 | M48-B6 | M48-B7 | M48-B8 | M48-B9 | M48-B10 | M48-B11 | M48-B12 |
| D | M48-B1 | M44-G5 | M48-B3 | M48-B4 | M48-B5 | M48-B6 | M48-B7 | M48-B8 | M48-B9 | M48-B10 | M48-B11 | M48-B12 |
| E | M48-C1 | M48-C2 | M44-G6 | M48-C4 | M48-C5 | M48-C6 | M48-C7 | M48-C8 | M48-C9 | M48-C10 | M44-G7 | M48-C12 |
| F | M48-C1 | M48-C2 | M44-G6 | M48-C4 | M48-C5 | M48-C6 | M48-C7 | M48-C8 | M48-C9 | M48-C10 | M44-G7 | M48-C12 |
| G | M48-D1 | M48-D2 | M48-D3 | M44-G8 | M48-D5 | M48-D6 | M48-D7 | M48-D8 | M44-G9 | M48-D10 | M48-D11 | M48-D12 |
| H | M48-D1 | M48-D2 | M48-D3 | M44-G8 | M48-D5 | M48-D6 | M48-D7 | M48-D8 | M44-G9 | M48-D10 | M48-D11 | M48-D12 |

Top row of each pair of rows: selective culture spotted without dilution
Bottom row of each pair of rows: selective culture diluted 1:10 before spotting

SEQUENCE LISTING

<160> NUMBER OF SEQ ID NOS: 148

<210> SEQ ID NO 1
<211> LENGTH: 1719
<212> TYPE: DNA
<213> ORGANISM: Saccharomyces cerevisiae

<400> SEQUENCE: 1

| | | | | | |
|---|---|---|---|---|---|
| atgcgccgcc | tatatcgtca | tcttgcttcc | ttttcttac | tcccttcctg | ccctggaaac | 60 |
| accatacaat | ccatcacatc | atatcctgcc | aatgcactat | tacgcagctt | tcggcacgtg | 120 |
| agtacggaaa | caccagttcg | gaaccgggta | cacaataggg | atagtcaaag | ctgtccattt | 180 |
| tttccgctga | tggatgacgg | aagtgcagct | cctggtgcat | cagctgctcc | aggtgctggt | 240 |
| tctggaagtg | gttcaggaat | ggacgatata | atcacgcaag | tttctccaga | taatgcagag | 300 |
| tccgctccga | ttctacaaga | acagcaacag | caacagaact | cacagtacga | aggtaacgag | 360 |
| gaggattatg | tgattcatt | gattcatttg | aatattcaag | aaaaccatta | tttcattacg | 420 |
| agggaccagt | tgatgtctct | acctgaatcc | ctattactgt | gtttatttcc | ctcaggtgtt | 480 |
| tttttggacc | gttgtggtca | ggtcattact | aatttgacca | gagacgatga | ggtctacatt | 540 |
| gttaatttcc | ctcctgattg | ttttgagtac | atcatggaga | tatatacaaa | agcgcatgat | 600 |
| gatttgtata | atcatcctgt | ggagaaattt | tttgacagac | catcaagtag | ctttgtttcg | 660 |
| aatgcaaagg | gatttttgg | actgagtagc | aataattcaa | tttcgagcaa | caatgagcag | 720 |
| gatattttac | atcaaaagcc | cgctattatt | gttttgagag | aagacttgga | ttattattgt | 780 |
| gtacctcagg | aggaatttca | gtttgattcc | actaatgaag | aaaataatga | ggatttattg | 840 |
| cgacatttta | tggctcaagt | gaaaatggct | gctggcagtt | atttaacttc | aaaaacatcg | 900 |
| attttccaag | gtttgtattc | ttcgaataga | ctaaagcaac | aacagcaaca | acagaaaatt | 960 |
| gaaaagggt | ccaattcttc | ttcaaatact | aaatctactt | cgaaaaaatt | gggacctgct | 1020 |
| gaacaacatt | taatggatat | gttgtgctcc | tccggattca | ccaaggaaac | ttgttggggt | 1080 |
| aacagaactc | aagaaactgg | caaaacggtt | ataagttcac | tgtctctttg | ccgattggct | 1140 |
| aacgagacaa | ctgaaggatt | taggcaaaaa | tttaacgagg | ctaaggctaa | gtgggaggca | 1200 |
| gagcacaaac | cttctcaaga | caacttcatc | accccaatgc | aatctaacat | atcgattaac | 1260 |
| tctttatctg | caagtaaatc | taacagtacc | atttctacag | caaggaattt | aacaagcgga | 1320 |
| agtacagcac | ctgctacagc | acgtgataag | agaaaatcaa | ggctgtcgaa | actagcagat | 1380 |
| aacgttcgtt | cgcactcttc | ctcgagacat | agttcgcaga | ccagaagtaa | acctccggag | 1440 |
| ttgcccaaat | tgtatgatct | agtgccaaaa | cctaatatca | acgctaagct | actattattt | 1500 |
| tggagaaaac | ctgctcgtaa | atgttggtgg | ggtgaagaag | acatagagct | agaagtggaa | 1560 |
| gtcttcggct | cttggaaaga | tgaatcaaag | aaaatcattg | aattgatctt | gccaacaaac | 1620 |
| gttgatcctg | aagcagaact | acataaaatc | attgtacccg | tccgattaca | tattcgtaga | 1680 |
| gtttggactt | tagagttgag | cgttattggg | gtgcagtga | | | 1719 |

<210> SEQ ID NO 2
<211> LENGTH: 1998
<212> TYPE: DNA
<213> ORGANISM: Saccharomyces cerevisiae

<400> SEQUENCE: 2

| | | | | | |
|---|---|---|---|---|---|
| atgaagtgca | ctttagtttc | cacattgttt | gccatcacca | atattctagt | tgcacatgca | 60 |
| caagtaagca | actcctcaga | cacgttggac | gtacaatttg | cgaatagtac | gaactcgtac | 120 |

```
atagaaggaa aatttaattc gactgatgaa gccttcaaca gcagcgcatc ttggtcctta      180
gcagctcagc agaaaaagat atctaatgca gctgtatatg atgtgggtgg ttggaatggc      240
tcattgtatc gttccaatag aagcgctgtt gcagatcatc aacccggcaa aaagcaagat      300
gccgctattt cacagatcag tgatggtcaa atccaagcca ctgcgtctgg acctgagact      360
accgctgcta ctaccccaag tagtaccgca aatgtctctg tctatgaagg tgctggtatg      420
aaggttgaat ccaagaacat gggttatata gttggagtag cagcgctatt attttttagga     480 agtgcagctc ctggtgcatc agctgctcca ggtgctggtt ctggaagtgg ttcaggaatg      540
gacgatataa tcacgcaagt ttctccagat aatgcagagt ccgctccgat tctacaagaa      600
cagcaacagc aacagaactc acagtacgaa ggtaacgagg aggattatgg tgattcattg      660
attcatttga atattcaaga aaaccattat ttcattacga gggaccagtt gatgtctcta      720
cctgaatccc tattactgtg tttatttccc tcaggtgttt ttttggaccg ttgtggtcag      780
gtcattacta atttgaccag agacgatgag gtctacattg ttaatttccc tcctgattgt      840
tttgagtaca tcatggagat atatacaaaa gcgcatgatg atttgtataa tcatcctgtg      900
gagaaatttt ttgacagacc atcaagtagc tttgtttcga atgcaaaggg attttttgga      960
ctgagtagca ataattcaat ttcgagcaac aatgagcagg atattttaca tcaaaagccc     1020
gctattattg ttttgagaga agacttggat tattattgtg tacctcagga ggaatttcag     1080
tttgattcca ctaatgaaga aaataatgag gatttattgc gacattttat ggctcaagtg     1140
aaaatggctg ctggcagtta tttaacttca aaaacatcga ttttccaagg tttgtattct     1200
tcgaatagac taaagcaaca acagcaacaa cagaaaattg aaaagggggtc caattcttct     1260 tcaaatacta aatctacttc gaaaaaattg ggacctgctg aacaacattt aatggatatg     1320
ttgtgctcct ccggattcac caaggaaact tgttggggta acagaactca agaaactggc     1380
aaaacggtta taagttcact gtctctttgc cgattggcta acgagacaac tgaaggattt     1440
aggcaaaaat ttaacgaggc taaggctaag tgggaggcag agcacaaacc ttctcaagac     1500
aacttcatca ccccaatgca atctaacata tcgattaact cttatctgc aagtaaatct     1560 aacagtacca tttctacagc aaggaattta acaagcggaa gtacagcacc tgctacagca     1620
cgtgataaga gaaatcaag gctgtcgaaa ctagcagata acgttcgttc gcactcttcc     1680
tcgagacata gttcgcagac cagaagtaaa cctccggagt tgcccaaatt gtatgatcta     1740
gtgccaaaac ctaatatcaa cgctaagcta ctattatttt ggagaaaacc tgctcgtaaa     1800
tgttggtggg gtgaagaaga catagagcta gaagtggaag tcttcggctc ttggaaagat     1860
gaatcaaaga aaatcattga attgatcttg ccaacaaacg ttgatcctga agcagaacta     1920
cataaaatca ttgtacccgt ccgattacat attcgtagag tttggacttt agagttgagc     1980
gttattgggg tgcagtga                                                   1998
```

<210> SEQ ID NO 3
<211> LENGTH: 1908
<212> TYPE: DNA
<213> ORGANISM: Saccharomyces cerevisiae

<400> SEQUENCE: 3

```
atgacagagg ttgtgggatt ctgggagagc gtgtcagatg acgaatcaga agacaaagac       60
tgtatggagg tgcagaacac agtgagtgcc gacgagagcc cacttgtgca gagccttgta      120
tcctttgtag gctcgtgctc catcaaccta cttttgccct tcctcaacgg catgatgctc      180
```

```
ggcttcggcg agctatttgc tcacgagctc tgctggagat tcaattggtt taaccataga      240
aacaaggggt ataaggtgta cccagagtcg cgcaaaatag cagcattgaa agagatttca      300
agccctggca cccgtgggag ggttgcgtcc aagttccttg gaagtgcagc tcctggtgca      360
tcagctgctc caggtgctgg ttctggaagt ggttcaggaa tgctgctgga cgtgaacaca      420
aatcacacac taatgcacga tgctcatgtg catgaacatt gcctcatcaa aagcatacgt      480
gatgatggcg cattgcactc atggagcgac tcatcaaagg tattttatcc caagtcattt      540
tacgctaccg ctactaataa gaagaataac aagttagcca gcgccagcat gaacaagacc      600
gccacaagta ataggacggt gagcgatgag atttatttcc actccactaa gccgcagttc      660
gatggtcaag gaagcgctga acgtactaga acactaacca agaggaatag cttcaagagg      720
actagaatac tgaaggctcg agacgattcc gaactgctga acgaaaatcg ctcatctttg      780
atgaccccgt ccttaagctc ggtcatgtcg caagttagga aaacaaattc cgccaagacg      840
ttatcgggcg aatgccccat acatgagggc cacttaacac agagcataaa gaggaagttc      900
tccgaggaag ctcaaagcga ctgttcttca ttgagctcct ctaaacttca tcccttgaca      960
gatgatattg ctgacgctgt cgatttgcag acccccgcga ttggcgatga ggtactggct     1020
gagccggtcg tgcccaaaat gaaaataata acataaatg atctcgattt gttcgacgac       1080
tgggaggtta aggatttagt cgatatcttt cctcccgtat acgaacggcg tccgcgatcg     1140
tcctctgccc tttcactggt ttctgcgtcg tccgatgcca aacttcgtcc gacctctgtg     1200
gacttccaaa tcatcgacaa gaaaggcggc aagacttcaa gaaggaagag taggagcaaa     1260
tcgactacag aaaacatgat ttacgaaaat gacctggtag aattgaaaca atggccatct     1320
gcatcaccat cgcccgagac cgacggttcg attgcatcta gcgagctctt gcccaataaa     1380
agaataagac aaaaaagttt gaataccaat ttcctaaagt tatactctat tgaaacatca     1440
tgtaaaagga agagtatttt acccgaagtc gaagtagatg accatctgtt gaagcagcta     1500
acgtattccg aaattcggtc tttggaaatc aaaaaggagc caaatgtctc tacgaacgat     1560
attaagcttg ccctaattac taggaaaaaa ttatggtctg acatggtcca tgaaacaaga     1620
aatgatcttt ttggcgattc taccccctgg aatttgcact tgttgcaac gacaagcaat       1680 acggaacctt cgcaaggccg tgaatccgca agcgaacatg caacggcgga tttgaaaagt     1740
tctttggtcc gcgtacactc agacgtcaag ccatggttca acaatggcgg cacaatgctc     1800
aaaccatgcg gaaaactaaa tttaggcaaa gtcaccaata agacttccgc acctacgaga     1860
gagattcaat atgtcgtaaa gggctggtgt gacagcaggt ttctctga                  1908
```

<210> SEQ ID NO 4
<211> LENGTH: 3120
<212> TYPE: DNA
<213> ORGANISM: Saccharomyces cerevisiae

<400> SEQUENCE: 4

```
atggagcgat tgaagcaact ggaggaaaaa aggagacaat tgaaagagct gcgtgagagg       60
cgaaaacaag ccagcttgtt ccctgggagc gagacgatgg ccaccatcc cacagaggtg       120 cacgctaagg caaccatggt cagcgtttca gtgcagaccg acatggagga aggctcaaag     180
attcaagagc cccaatctgc atatcttcga cgtaaggagg ttataacata cgacaaaggc     240
attcaaacag atcaaattga ggaagaacaa ctgcaagaaa atgaaaatca caccactact     300
gatgctgtcg ccattgaaac tactgctgcc gacgaaaata taaagacaa agctgaaaac       360 gaccagccaa ggttagaact agccaaacct tttcttgttg aagaggcggc ggcaacgctg     420
```

```
agcaacgcta gttttgcgcg gctggagaca gaggtttctg cgtcaggcca gcaggcgcca    480
tcgaacatgc aacaggataa agacaacctc atgcaatgga acatggtcag tgagaattta    540
caatcagaga cagactgcga ttgtatcgct caggagtatg acccaggaaa aggcgtcttg    600
gttgtggttt atctacgatt gccgccggca gacctacagt atgctagcag cgaagcggcg    660
tggtctgtgg tgaatgtagt caagtgcgat aatgccagcg gacgcaacgg cctcttgata    720
gatatggtag agttccgtgg tacgcggatc atgacagcca cgatcctccg tcggtatcat    780
ccggaaagca atgtaatatc aatcttgttg gcgaccttga cgggcaagat catattgtac    840
gagcttagat tgaaacagaa aaagccagaa acaccggtag tgtatgtcgt gcagcgaaat    900
atggtggcaa gacactactt tcagcaccca gtggtggctg taattgaaac aagcagcgtg    960
caagatcaag agagagtact tgtggcagct gataatggca atattatgga gttgagctgc   1020
ctggacttga ctgttttgcg gaagccacag cagctccgtc ctgtaccgct atcacagctt   1080
ttatctttgg agaatgatac ttgcacatat acggagcgat tgcagcggtt ggcaaagttt   1140
gatgaggtag gtatagcttg catggcgtac acgagtgagg acccgcagta cgtctggatc   1200
ggtggcgaag acggtggtat atacaaggtt ttctgggacc aacctgggcc gctgtacctc   1260
tctttggaca acaatgggtt ccaacctgca gaaaaccact ctacgagggt aaccgggtta   1320
gagtttcatt gggacgatgc tcggcggcta atgcttctat tatcatgttc cacggactgg   1380
acggtgcggc tgtgggacgc gcgagcaggg aaagctatca taggggcgcc attgttgtta   1440
gggggggccg tactacgtgc acgctggctc gaaaaaaaca atggagggga aaatagtcgc   1500
actctacggt gtcaagtgtg gtgtgcagat ggtcgcctcg ttgttgtaaa ttgggctttc   1560
gatgctaaga cgtccctcta cacggccact gttatctccg gaagtgcagc tcctggtgca   1620
tcagctgctc caggtgctgg ttctggaagt ggttcaggaa tggacgatat aatcacgcaa   1680
gtttctccag ataatgcaga gtccgctccg attctacaag aacagcaaca gcaacagaac   1740
tcacagtacg aaggtaacga ggaggattat ggtgattcat tgattcatt gaatattcaa     1800 gaaaaccatt atttcattac gagggaccag ttgatgtctc tacctgaatc cctattactg   1860
tgtttatttc cctcaggtgt ttttttggac cgttgtggtc aggtcattac taatttgacc   1920
agagacgatg aggtctacat tgttaatttc cctcctgatt gttttgagta catcatggag   1980
atatatacaa aagcgcatga tgatttgtat aatcatcctg tggagaaatt ttttgacaga   2040
ccatcaagta gctttgtttc gaatgcaaag ggattttttg gactgagtag caataattca   2100
atttcgagca acaatgagca ggatatttta catcaaaagc ccgctattat tgttttgaga   2160
gaagacttgg attattattg tgtacctcag gaggaatttc agtttgattc cactaatgaa   2220
gaaaataatg aggatttatt gcgacatttt atggctcaag tgaaaatggc tgctggcagt   2280
tatttaactt caaaaacatc gatttttccaa ggtttgtatt cttcgaatag actaaagcaa   2340
caacagcaac aacagaaaat tgaaaagggg tccaattctt cttcaaatac taaatctact   2400
tcgaaaaaat tgggacctgc tgaacaacat ttaatggata tgttgtgctc ctccggattc   2460
accaaggaaa cttgttgggg taacagaact caagaaactg gcaaaacggt tataagttca   2520
ctgtctcttt gccgattggc taacgagaca actgaaggat ttaggcaaaa atttaacgag   2580
gctaaggcta gtgggaggc agagcacaaa ccttctcaag acaacttcat caccccaatg   2640
caatctaaca tatcgattaa ctctttatct gcaagtaaat ctaacagtac catttctaca   2700
gcaaggaatt taacaagcgg aagtacagca cctgctacag cacgtgataa gagaaaatca   2760
```

| aggctgtcga aactagcaga taacgttcgt tcgcactctt cctcgagaca tagttcgcag | 2820 |
| accagaagta aacctccgga gttgcccaaa ttgtatgatc tagtgccaaa acctaatatc | 2880 |
| aacgctaagc tactattatt ttggagaaaa cctgctcgta aatgttggtg gggtgaagaa | 2940 |
| gacatagagc tagaagtgga agtcttcggc tcttggaaag atgaatcaaa gaaaatcatt | 3000 |
| gaattgatct tgccaacaaa cgttgatcct gaagcagaac tacataaaat cattgtaccc | 3060 |
| gtccgattac atattcgtag agtttggact ttagagttga gcgttattgg ggtgcagtga | 3120 |

<210> SEQ ID NO 5
<211> LENGTH: 2400
<212> TYPE: DNA
<213> ORGANISM: Saccharomyces cerevisiae

<400> SEQUENCE: 5

| atggacgata taatcacgca agtttctcca gataatgcag agtccgctcc gattctacaa | 60 |
| gaacagcaac agcaacagaa ctcacagtac gaaggtaacg aggaggatta tggtgattca | 120 |
| ttgattcatt tgaatattca agaaaaccat tatttcatta cgagggacca gttgatgtct | 180 |
| ctacctgaat ccctattact gtgtttattt ccctcaggtg ttttttttgga ccgttgtggt | 240 |
| caggtcatta ctaatttgac cagagacgat gaggtctaca ttgttaattt ccctcctgat | 300 |
| tgttttgagt acatcatgga gatatataca aaagcgcatg atgatttgta taatcatcct | 360 |
| gtggagaaat ttttgacag accatcaagt agctttgttt cgaatgcaaa gggatttttt | 420 |
| ggactgagta gcaataattc aatttcgagc aacaatgagc aggatatttt acatcaaaag | 480 |
| cccgctatta ttgttttgag agaagacttg gattattatt gtgtacctca ggaggaattt | 540 |
| cagtttgatt ccactaatga agaaaataat gaggatttat tgcgacattt tatggctcaa | 600 |
| gtgaaaatgg ctgctggcag ttatttaact tcaaaaacat cgattttcca aggtttgtat | 660 |
| tcttcgaata gactaaagca acaacagcaa caacagaaaa ttgaaaaggg gtccaattct | 720 |
| tcttcaaata ctaaatctac ttcgaaaaaa ttgggacctg ctgaacaaca tttaatggat | 780 |
| atgttgtgct cctccggatt caccaaggaa acttgttggg gtaacagaac tcaagaaact | 840 |
| ggcaaaacgg ttataagttc actgtctctt tgccgattgg ctaacgagac aactgaagga | 900 |
| tttaggcaaa aatttaacga ggctaaggct aagtgggagg cagagcacaa accttctcaa | 960 |
| gacaacttca tcaccccaat gcaatctaac atatcgatta actctttatc tgcaagtaaa | 1020 |
| tctaacagta ccatttctac agcaaggaat ttaacaagcg gaagtacagc acctgctaca | 1080 |
| gcacgtgata agagaaaatc aaggctgtcg aaactagcag ataacgttcg ttcgcactct | 1140 |
| tcctcgagac atagttcgca gaccagaagt aaacctccgg agttgcccaa attgtatgat | 1200 |
| ctagtgccaa aacctaatat caacgctaag ctactattat tttggagaaa acctgctcgt | 1260 |
| aaatgttggt ggggtgaaga agacatagag ctagaagtgg aagtcttcgg ctcttggaaa | 1320 |
| gatgaatcaa agaaaatcat tgaattgatc ttgccaacaa acgttgatcc tgaagcagaa | 1380 |
| ctacataaaa tcattgtacc cgtccgatta catattcgta gagtttggac tttagagttg | 1440 |
| agcgttattg gggtgcaggg aagtgcagct cctggtgcat cagctgctcc aggtgctggt | 1500 |
| tctggaagtg gttcaggaat ggcatctgtg aacaattacc aggttgattg cgggtcaagg | 1560 |
| tctgctcgca ttcaacccag aattaataac ggcattcacg atgaagaatc gctatttgaa | 1620 |
| gtcctggaac tctcagaaga ggaatttgag ctagacttcc atagattaaa gtcattcaat | 1680 |
| gatgtaaggg ttatcaataa cccagattta tctccagaat gtacaaatac tgccattagt | 1740 |
| cgcgatgaga cactggaatc tgcaagtagt gccttcgaag ttccttctga cgaaattgct | 1800 |

| | |
|---|---|
| atactgtcga tatccagtga cagcaataaa aattctccgc cctcagagca gccggcgccc | 1860 |
| gctcttcgta acattcgatc gtctagtaac tctgaccgga tcgatgagtg gtgtttgggc | 1920 |
| agccatttat ttaatgagct gcatcaaaat gtccctcaat caagcgacgg tgtcaatcat | 1980 |
| ggatttcccg tttattcctt taaggaaaga aactttata cctctgcgaa attaaagaaa | 2040 |
| cttacaaatg cccaaagaat tgctgtgcag aaactatcaa gagacttgta tccaattcta | 2100 |
| agaacatgct accgcgagaa aactcgccgg caattattga cataccatca tgaaagaata | 2160 |
| tttgacgata taccatcttt ttttcccccag cgtgacttta ttttcaatta ctactcgatg | 2220 |
| cctcttgaat tcgacaggtt gtcagacgta gatatagatt cgtcatcgcg gtcacgattt | 2280 |
| acagatgaga gcactggaga aacattaaac cgttcaccaa gcgcagcgtc ttcgtcgttg | 2340 |
| gaaaacacat cttggtttgg ctggacttta ctttctaggt ttttggacag agaatggtag | 2400 |

<210> SEQ ID NO 6
<211> LENGTH: 2142
<212> TYPE: DNA
<213> ORGANISM: Saccharomyces cerevisiae

<400> SEQUENCE: 6

| | |
|---|---|
| atgagtaatg caaacaatag tgctatgaac cacatcacgt tgcctcccat ctcgtcattt | 60 |
| gacaacctta tcaaggcagc cgagagacaa tataatggcg aggcttcgtc cgcctcgaca | 120 |
| catccgacac tgcctaatat gaacattagt aacggcagtg gcagtgcggg cgcatcatcg | 180 |
| tcgatgctga gctatcagtt gcttccgcac tccaatgatg tgtcccggtc gaactccagc | 240 |
| tcgagcttcc ttccctccgt gcagcagcct acggaaggtt ccgcttctgc atcggaaact | 300 |
| tcttcatctg catcacccttc acgttccatt tcaccaattt taaaagtggc tggtccttca | 360 |
| tctgttggcg gtgccggggt gagtaccccc catagcacca aaatcaataa gccaaggaaa | 420 |
| aagaagcaat gtccaatttg tcgtaatttt tatgccaatc tgaccacgca caaggcaacg | 480 |
| cacttgacgc cagaggatcg gcctcacaag tgtcccatct gccaccgcgg gttcgccagg | 540 |
| aacaatgact tattgaggca taagaaaaga cattggaagg atgagatact gtcccaatcg | 600 |
| ggagtacttt cgaaccataa tgatggtaag ggaggatccg tttctcccaa tgatgatgat | 660 |
| acccatgaaa aaatgacacc gatgaattct gtcacagatt atgcacaatt gaaatcgttg | 720 |
| catcaaatca agggcacatt caagtgccca ttcaactcca ccttaataca attggacatg | 780 |
| gatatgtacc cgtataaact gaaacccttta aattttgaga cttccaattg tcaccagacg | 840 |
| ggggtgttct cacgttgcga caccttcaaa aaccatttaa aggctttgca ttttgaatac | 900 |
| ccgccaggca cgaagaaaaa ggatagaaat gttgttcctg gtagatgtaa gcattgcggc | 960 |
| ctgaagttcg agaacgttga cgtttggctc aacgaacacg taggtaaaca atgcggctat | 1020 |
| aaataccatg gaagtgcagc tcctggtgca tcagctgctc caggtgctgg ttctggaagt | 1080 |
| ggttcaggaa tgaattggct gttttttggtc tcgctggttt tcttctgcgg cgtgtcaacc | 1140 |
| catcctgccc tggcaatgtc cagcaacaga ctactaaagc tggctaataa atctcccaag | 1200 |
| aaaattatac ctctgaagga ctcaagtttt gaaaacatct tggcaccacc tcacgaaaat | 1260 |
| gcctatatag ttgctctgtt tactgccaca gcgcccgaaa ttggctgttc tctgtgtctc | 1320 |
| gagctagaat ccgaatacga caccatagtg gcctcctggt ttgatgatca tccggatgca | 1380 |
| aaatcgtcca attccgatac atctattttc ttcacaaagg tcaatttgga ggacccttct | 1440 |
| aagaccattc ctaaagcgtt ccagttttttc caactaaaca atgttcctag attgttcatc | 1500 |

| | | | | |
|---|---|---|---|---|
| ttcaaaccaa | actctccctc | tattctggac | cacagcgtga | tcagtatttc | cactgatact | 1560 |
| ggctcagaaa | gaatgaagca | aatcatacaa | gccattaagc | agttctcgca | agtaaacgac | 1620 |
| ttctctttac | acttacctat | ggactggact | ccaattatta | cctcgacaat | aattaccttc | 1680 |
| atcaccgtct | tactcttcaa | aaagcagtcc | aaactcatgt | tctccatcat | atcttccagg | 1740 |
| atcatctggg | caaccttgtc | aacttttttc | atcatttgca | tgatcagtgc | ctatatgttc | 1800 |
| aaccaaatca | ggaatacccca | attggcaggc | gttggtccta | agggcgaggt | tatgtatttc | 1860 |
| ttgcccaatg | aattccaaca | ccaattcgcc | attgaaactc | aagtcatggt | tcttatttac | 1920 |
| ggaacattgg | ccgcgttggt | tgtcgtattg | gtcaagggta | tacaattctt | gcggtctcat | 1980 |
| ttgtatccag | agaccaagaa | agcgtacttc | attgatgcta | ttttggcctc | cttttgtgcc | 2040 |
| ttattcattt | atgtcttctt | tgctgctttg | acaaccgtgt | tcacgataaa | gagtcctgct | 2100 |
| tacccttttc | ctttactaag | gttatcggca | ccattcaaat | aa | | 2142 |

<210> SEQ ID NO 7
<211> LENGTH: 2697
<212> TYPE: DNA
<213> ORGANISM: Saccharomyces cerevisiae

<400> SEQUENCE: 7

| | | | | | | |
|---|---|---|---|---|---|---|
| atggacgata | taatcacgca | agtttctcca | gataatgcag | agtccgctcc | gattctacaa | 60 |
| gaacagcaac | agcaacagaa | ctcacagtac | gaaggtaacg | aggaggatta | tggtgattca | 120 |
| ttgattcatt | tgaatattca | agaaaaccat | tatttcatta | cgagggacca | gttgatgtct | 180 |
| ctacctgaat | ccctattact | gtgtttattt | ccctcaggtg | ttttttttgga | ccgttgtggt | 240 |
| caggtcatta | ctaatttgac | cagagacgat | gaggtctaca | tgttaatttt | ccctcctgat | 300 |
| tgttttgagt | acatcatgga | gatatataca | aaagcgcatg | atgatttgta | taatcatcct | 360 |
| gtggagaaat | tttttgacag | accatcaagt | agctttgttt | cgaatgcaaa | gggatttttt | 420 |
| ggactgagta | gcaataattc | aatttcgagc | aacaatgagc | aggatatttt | acatcaaaag | 480 |
| cccgctatta | ttgttttgag | agaagacttg | gattattatt | gtgtacctca | ggaggaattt | 540 |
| cagtttgatt | ccactaatga | agaaaataat | gaggatttat | tgcgacattt | tatggctcaa | 600 |
| gtgaaaatgg | ctgctggcag | ttatttaact | tcaaaaacat | cgattttcca | aggtttgtat | 660 |
| tcttcgaata | gactaaagca | acaacagcaa | caacagaaaa | ttgaaaaggg | gtccaattct | 720 |
| tcttcaaata | ctaaatctac | ttcgaaaaaa | ttgggacctg | ctgaacaaca | tttaatggat | 780 |
| atgttgtgct | cctccggatt | caccaaggaa | acttgttggg | gtaacagaac | tcaagaaact | 840 |
| ggcaaaacgg | ttataagttc | actgtctctt | tgccgattgg | ctaacgagac | aactgaagga | 900 |
| tttaggcaaa | aatttaacga | ggctaaggct | aagtgggagg | cagagcacaa | accttctcaa | 960 |
| gacaacttca | tcaccccaat | gcaatctaac | atatcgatta | actctttatc | tgcaagtaaa | 1020 |
| tctaacagta | ccatttctac | agcaaggaat | ttaacaagcg | gaagtacagc | acctgctaca | 1080 |
| gcacgtgata | agagaaaatc | aaggctgtcg | aaactagcag | ataacgttcg | ttcgcactct | 1140 |
| tcctcgagac | atagttcgca | gaccagaagt | aaacctccgg | agttgcccaa | attgtatgat | 1200 |
| ctagtgccaa | aacctaatat | caacgctaag | ctactattat | tttggagaaa | acctgctcgt | 1260 |
| aaatgttggt | ggggtgaaga | agacatagag | ctagaagtgg | aagtcttcgg | ctcttggaaa | 1320 |
| gatgaatcaa | agaaaatcat | tgaattgatc | ttgccaacaa | acgttgatcc | tgaagcagaa | 1380 |
| ctacataaaa | tcattgtacc | cgtccgatta | catattcgta | gagtttggac | tttagagttg | 1440 |
| agcgttattg | gggtgcaggg | aagtgcagct | cctggtgcat | cagctgctcc | aggtgctggt | 1500 |

-continued

```
tctggaagtg gttcaggaat ggcagacaca ccctctgtgg cagtacaggc cccaccgggc    1560
tatggtaaga cggagttatt tcatctcccc ttgatagcac tggcgtctaa gggcgacgtg    1620
aaatatgtgt cgtttctgtt tgtaccgtac acagtgttgc ttgctaattg catgatcagg    1680
ttgggccgac gcggttgctt gaatgtgcc cctgtaagaa actttattga agaaggttac     1740
gatggcgtta ctgatttata cgtggggatc tacgatgatc ttgctagcac taatttcaca    1800
gacaggatag ctgcgtggga gaatattgtt gagtgcacct ttaggaccaa caacgtaaaa    1860
ttgggttacc tcattgtaga tgagtttcac aactttgaaa cggaggtcta ccggcagtcg    1920
caatttgggg gcataactaa ccttgatttt gacgcttttg agaaagcaat cttttttgagc   1980 ggcacagccc ctgaggctgt agctgatgct gcgttgcagc gtattgggct tacgggactg    2040
gccaagaagt cgatggacat caacgagctc aaacggtcgg aagatctcag cagaggtcta    2100
tccagctatc caacacggat gtttaatcta atcaaggaga aatccgaggt gcctttaggg    2160
catgttcata aaatttggaa gaaagtggaa tcacagcccg aagaagcact gaagcttctt    2220
ttagccctct ttgaaattga accagagtcg aaggccattg tagttgcaag cacaaccaac    2280
gaagtggaag aattggcctg ctcttggaga aagtatttta gggtggtatg gatacacggg    2340
aagctgggtg ctgcagaaaa ggtgtctcgc acaaaggagt ttgtcactga cggtagcatg    2400
caagttctca tcggaacgaa attagtgact gaaggaattg acattaagca attgatgatg    2460
gtgatcatgc ttgataatag acttaatatt attgagctca ttcaaggtgt agggagacta    2520
agagatgggg gcctctgtta tctattatct agaaaaaaca gttgggcggc aaggaatcgt    2580
aagggtgaat taccaccaat taaggaaggc tgtataaccg aacaggtacg cgagttctat    2640
ggacttgaat caaagaaagg aaaaaagggc cagcatgttg gatgctgtgt ctgctga       2697
```

<210> SEQ ID NO 8
<211> LENGTH: 3336
<212> TYPE: DNA
<213> ORGANISM: Saccharomyces cerevisiae

<400> SEQUENCE: 8

```
atgcagacgt caatggtgag cgcaaaagtt agtatatggc tagtatgtag cgttatatgc     60
agtagcctgg tacgggctac gcaatctgtg tgttcgtcgc aaaacacagc gaccactgac    120
ggtgtacgaa atcaatttca gagtaatggt tggtgttcaa ataactgtgc tggtcatcag    180
tttgccatcg tacaggggtt catgtgctgg tgcagtgatt cggaaccgag cactcagaca    240
tcggtgggag actgcagtgg cacttgtccc ggttatggct acgaagattg tggtaatgcg    300
gataaggatc tttttggtta tatatatctg gggcaaaccc cgctaagttc tgtacagagt    360
gtggaaacgt caacgagtc cagtgtgtac gtttcaagta gctctatcac gagtagtagt    420
agtacgagta ttgtggacac aaccacaatc tcgccgactc tgacgtcaac gagtacgacc    480
ccattgacaa ccgcctcaac cagtacaaca ccatcaactg atataacatc ggcactgccc    540
acgactacaa gcacaaagtt gtcaacatcc attccacaa gcacgacatc gtcaacctct    600
accaccacaa gtacctcatc gtcgacttct acgaccgtaa gtgtcacatc atcaacatct    660
accaccacaa gtactacgtc gtcaaccctc atttccacga gcacatcatc atcatcatca    720
tcaactccaa cccacaacatc gtcagcccc atttctacaa gcacgacgtc gtcaacttcc    780
acttcaacaa gtacaacatc gccaacttct tcttcagcac ctacaagctc gtctaataca    840
acaccaacga gcacaacgtt cactacgaca tcacccagta cagccccttc aagcactacg    900
```

```
gttacttaca ccagtaccac agcatctcca ataacgtcca ctataacttc tgtaaacctg    960
cagacctcct taaagtattc tgtgataaca gtgacttcag tgcacaccat ggacactaac   1020
atttcggaaa tcacctcgag atatctcacc atgaaaaaag taataacgca gatttactct   1080
tccaccctcg gggctactcc tacttctgca gtggctacta cgtctgccag cgtaggtggt   1140
agaataacaa acaataacaa tagtaacacc accaacagca atacaccaac taacaagtct   1200
acagaaaaga aagggtactg ggattcgccc gggaaaatag ccgctacttt cgtcgtggtt   1260
ggagtggtat gtttggtaat tatatgcata ctaatatact taatacatca ttatagaaca   1320
agacccgctc ggaaggctca agattttgag aatgaatatc agagtaagtt ttaccagtcc   1380
aagtacccaa atgaagttac cactaccacg ttacacacgc cttcaccatc ttcaaattca   1440
actttctcga ccccaagatt aatatacact gatgaaaagg gacaaattat gtctgaatca   1500 ccatcccac gtcaatctac gtattccttg actgcaggca gtccaccaaa tgacccaagc   1560
acgttggcaa gccatttca cgatcccatt cttcccagaa gaacttctac ttttcttcat   1620
tcgcccattc aaaagcaaca cgaaaaaatg gaatcaaacg ttactctagg tgaagacacg   1680
gtactggtgg atcagaggct agacccaagt aagatgctta acactttagc aaatgacgat   1740
gccacaaacc actctaccat ttcgttatca gacaacgtag actactccag gagggttctg   1800
cggctaatga acgaaggaag tgcagctcct ggtgcatcag ctgctccagg tgctggttct   1860
ggaagtggtt caggaatgga cgatataatc acgcaagttt ctccagataa tgcagagtcc   1920
gctccgattc tacaagaaca gcaacagcaa cagaactcac agtacgaagg taacgaggag   1980
gattatggtg attcattgat tcatttgaat attcaagaaa accattattt cattacgagg   2040
gaccagttga tgtctctacc tgaatcccta ttactgtgtt tatttccctc aggtgttttt   2100
ttggaccgtt gtggtcaggt cattactaat ttgaccagag acgatgaggt ctacattgtt   2160
aatttccctc ctgattgttt tgagtacatc atggagatat atacaaaagc gcatgatgat   2220
ttgtataatc atcctgtgga gaattttttt gacagaccat caagtagctt tgtttcgaat   2280
gcaaagggat tttttggact gagtagcaat aattcaattt cgagcaacaa tgagcaggat   2340
attttacata aaaagcccgc tattattgtt ttgagagaag acttggatta ttattgtgta   2400
cctcaggagg aatttcagtt tgattccact aatgaagaaa ataatgagga tttattgcga   2460
cattttatgg ctcaagtgaa aatggctgct ggcagttatt taacttcaaa acatcgatt   2520 ttccaaggtt tgtattcttc gaatagacta aagcaacaac agcaacaaca gaaaattgaa   2580
aaggggtcca attcttcttc aaatactaaa tctacttcga aaaaattggg acctgctgaa   2640
caacatttaa tggatatgtt gtgctcctcc ggattcacca aggaaacttg ttggggtaac   2700
agaactcaag aaactggcaa aacggttata agttcactgt ctctttgccg attggctaac   2760
gagacaactg aaggatttag gcaaaaattt aacgaggcta aggctaagtg ggaggcagag   2820
cacaaacctt ctcaagacaa cttcatcacc ccaatgcaat ctaacatatc gattaactct   2880
ttatctgcaa gtaaatctaa cagtaccatt tctacagcaa ggaatttaac aagcggaagt   2940
acagcacctg ctacagcacg tgataagaga aaatcaaggc tgtcgaaact agcagataac   3000
gttcgttcgc actcttcctc gagacatagt tcgcagacca gaagtaaacc tccggagttg   3060
cccaaattgt atgatctagt gccaaaacct aatatcaacg ctaagctact attattttgg   3120
agaaaacctg ctcgtaaatg ttggtggggt gaagaagaca tagagctaga agtggaagtc   3180
ttcggctctt ggaagatga atcaaagaaa atcattgaat tgatcttgcc aacaaacgtt   3240
gatcctgaag cagaactaca taaaatcatt gtacccgtcc gattacatat tcgtagagtt   3300
```
tggactttag agttgagcgt tattggggtg cagtga 3336

<210> SEQ ID NO 9
<211> LENGTH: 2358
<212> TYPE: DNA
<213> ORGANISM: Saccharomyces cerevisiae

<400> SEQUENCE: 9

| | | |
|---|---|---|
| atgggcgacg aattacacaa ccgtttactt caccaaaacg atggcaccaa ggacgccata | 60 |
| ctttataaga taatagaatc gttagtttgc tccatctgcc acgattatat gtttgtaccg | 120 |
| atgatgcacac cttgtggtca taattattgc tatggttgtc tgaacacctg gtttgccagc | 180 |
| aatactcaaa aagaattggc ttgtccgcag tgcagatctg atattaccac cattcccgca | 240 |
| ttgaatacaa cgttgcaaca gtatctatca ttcattttag agaaattaag ggaccagaat | 300 |
| gatgaatctt ttaaaaaact tttaacaact aaaaccaagg aggaaaatga ttacaagaat | 360 |
| gacaaggaaa aggacacatt gtttgacaaa gtatttaaga atagcgcatt ggcagtggcc | 420 |
| gacgactcgg atgatggtat cacacgttgt agtaattgtc attgggaatt agacccagac | 480 |
| gaagtagagg acgaaatgt ttgtccccac tgcaatgcca gaatacggaa ttacgcaggt | 540 |
| ggtcgcgacg aatttgatga agaagaatac agtgaaggag agttggatga atccgggaa | 600 |
| agcatgcgta ggcgtagaga gaatcgattt gcgtctacca atccgtttgc taatagagat | 660 |
| gatgtaagtt ctgaagacga tgatagcagt gaagaggagc ccatgcgaga acatatccca | 720 |
| ctaggccgtt gggccaggtc acataatcgt agtattgctg tggatgctgt ggatgatgaa | 780 |
| gacgacgaag gaagtgcagc tcctggtgca tcagctgctc caggtgctgg ttctggaagt | 840 |
| ggttcaggaa tgctgctgga cgtgaacaca aatcacacac taatgcacga tgctcatgtg | 900 |
| catgaacatt gcctcatcaa aagcatacgt gatgatggcg cattgcactc atggagcgac | 960 |
| tcatcaaagg tattttatcc caagtcattt tacgctaccg ctactaataa gaagaataac | 1020 |
| aagttagcca gcgccagcat gaacaagacc gccacaagta ataggacggt gagcgatgag | 1080 |
| atttatttcc actccactaa gccgcagttc gatggtcaag gaagcgctga acgtactaga | 1140 |
| acactaacca agaggaatag cttcaagagg actagaaatac tgaaggctcg agacgattcc | 1200 |
| gaactgctga cgaaaatcg ctcatctttg atgaccccgt ccttaagctc ggtcatgtcg | 1260 |
| caagttagga aaacaaattc cgccaagacg ttatcgggcg aatgccccat acatgagggc | 1320 |
| cacttaacac agagcataaa gaggaagttc tccgaggaag ctcaaagcga ctgttcttca | 1380 |
| ttgagctcct ctaaacttca tcccttgaca gatgatattg ctgacgctgt cgatttgcag | 1440 |
| accccccgcga ttggcgatga ggtactggct gagccggtcg tgcccaaaat gaaaataata | 1500 |
| aacataaatg atctcgattt gttcgacgac tgggaggtta aggatttagt cgatatcttt | 1560 |
| cctcccgtat acgaacggcg tccgcgatcg tcctctgccc tttcactggt ttctgcgtcg | 1620 |
| tccgatgcca aacttcgtcc gacctctgtg gacttccaaa tcatcgacaa gaaaggcggc | 1680 |
| aagacttcaa gaaggaagag taggagcaaa tcgactacag aaaacatgat ttacgaaaat | 1740 |
| gacctggtag aattagaaca atggccatct gcatcaccat cgcccgagac cgacggttcg | 1800 |
| attgcatcta gcgagctctt gcccaataaa agaataagac aaaaaagttt gaataccaat | 1860 |
| ttcctaaagt tatactctat tgaaacatca tgtaaaagga agagtatttt acccgaagtc | 1920 |
| gaagtagatg accatctgtt gaagcagcta acgtattccg aaattcggtc tttgaaatc | 1980 |
| aaaaaggagc caaatgtctc tacgaacgat attaagcttg ccctaattac taggaaaaaa | 2040 |

| | |
|---|---|
| ttatggtctg acatggtcca tgaaacaaga aatgatcttt ttggcgattc taccccctgg | 2100 |
| aatttgcact tgttgcaac gacaagcaat acggaacctt cgcaaggccg tgaatccgca | 2160 |
| agcgaacatg caacggcgga tttgaaaagt tctttggtcc gcgtacactc agacgtcaag | 2220 |
| ccatggttca acaatggcgg cacaatgctc aaaccatgcg gaaaactaaa tttaggcaaa | 2280 |
| gtcaccaata agacttccgc acctacgaga gagattcaat atgtcgtaaa gggctggtgt | 2340 |
| gacagcaggt ttctctga | 2358 |

<210> SEQ ID NO 10
<211> LENGTH: 2697
<212> TYPE: DNA
<213> ORGANISM: Saccharomyces cerevisiae

<400> SEQUENCE: 10

| | |
|---|---|
| atggcagaca caccctctgt ggcagtacag gccccaccgg gctatggtaa gacggagtta | 60 |
| tttcatctcc ccttgatagc actggcgtct aagggcgacg tgaaatatgt gtcgtttctg | 120 |
| tttgtaccgt acacagtgtt gcttgctaat tgcatgatca ggttgggccg acgcggttgc | 180 |
| ttgaatgtgg cccctgtaag aaactttatt gaagaaggtt acgatggcgt tactgattta | 240 |
| tacgtgggga tctacgatga tcttgctagc actaatttca cagacaggat agctgcgtgg | 300 |
| gagaatattg ttgagtgcac ctttaggacc aacaacgtaa aattgggtta cctcattgta | 360 |
| gatgagtttc acaactttga aacggaggtc taccggcagt cgcaatttgg gggcataact | 420 |
| aaccttgatt tgacgctttt tgagaaagca atctttttga gcggcacagc ccctgaggct | 480 |
| gtagctgatg ctgcgttgca gcgtattggg cttacgggac tggccaagaa gtcgatggac | 540 |
| atcaacgagc tcaaacggtc ggaagatctc agcagaggtc tatccagcta ccaacacgg | 600 |
| atgtttaatc taatcaagga gaaatccgag gtgccttag ggcatgttca taaaatttgg | 660 |
| aagaaagtgg aatcacagcc cgaagaagca ctgaagcttc ttttagccct ctttgaaatt | 720 |
| gaaccagagt cgaaggccat tgtagttgca agcacaacca acgaagtgga agaattggcc | 780 |
| tgctcttgga gaaagtattt tagggtggta tggatacacg ggaagctggg tgctgcagaa | 840 |
| aaggtgtctc gcacaaagga gtttgtcact gacggtagca tgcaagttct catcggaacg | 900 |
| aaattagtga ctgaaggaat tgacattaag caattgatga tggtgatcat gcttgataat | 960 |
| agacttaata ttattgagct cattcaaggt gtagggagac taagagatgg gggcctctgt | 1020 |
| tatctattat ctagaaaaaa cagttgggcg gcaaggaatc gtaagggtga attaccacca | 1080 |
| attaaggaag gctgtataac cgaacaggta cgcgagttct atggacttga atcaaagaaa | 1140 |
| ggaaaaaagg gccagcatgt tggatgctgt gtctgcggaa gtgcagctcc tggtgcatca | 1200 |
| gctgctccag gtgctggttc tggaagtggt tcaggaatgg acgatataat cacgcaagtt | 1260 |
| tctccagata atgcagagtc cgctccgatt ctacaagaac agcaacagca acagaactca | 1320 |
| cagtacgaag gtaacgagga ggattatggt gattcattga ttcatttgaa tattcaagaa | 1380 |
| aaccattatt tcattacgag ggaccagttg atgtctctac ctgaatccct attactgtgt | 1440 |
| ttatttccct caggtgtttt tttggaccgt tgtggtcagg tcattactaa tttgaccaga | 1500 |
| gacgatgagg tctacattgt taatttccct cctgattgtt ttgagtacat catggagata | 1560 |
| tatacaaaag cgcatgatga tttgtataat catcctgtgg agaaattttt tgacagacca | 1620 |
| tcaagtagct ttgttttcgaa tgcaaaggga ttttttggac tgagtagcaa taattcaatt | 1680 |
| tcgagcaaca atgagcagga tattttacat caaaagcccg ctattattgt tttgagagaa | 1740 |
| gacttggatt attattgtgt acctcaggag gaatttcagt ttgattccac taatgaagaa | 1800 |

```
aataatgagg atttattgcg acattttatg gctcaagtga aaatggctgc tggcagttat    1860
ttaacttcaa aaacatcgat tttccaaggt ttgtattctt cgaatagact aaagcaacaa    1920
cagcaacaac agaaaattga aaagggggtcc aattcttctt caaatactaa atctacttcg   1980
aaaaaattgg gacctgctga acaacattta atggatatgt tgtgctcctc cggattcacc    2040
aaggaaactt gttggggtaa cagaactcaa gaaactggca aaacggttat aagttcactg    2100
tctctttgcc gattggctaa cgagacaact gaaggattta ggcaaaaatt taacgaggct    2160
aaggctaagt gggaggcaga gcacaaacct tctcaagaca acttcatcac cccaatgcaa    2220
tctaacatat cgattaactc tttatctgca agtaaatcta acagtaccat ttctacagca    2280
aggaatttaa caagcggaag tacagcacct gctacagcac gtgataagag aaaatcaagg    2340
ctgtcgaaac tagcagataa cgttcgttcg cactcttcct cgagacatag ttcgcagacc    2400
agaagtaaac ctccggagtt gcccaaattg tatgatctag tgccaaaacc taatatcaac    2460
gctaagctac tattattttg gagaaaacct gctcgtaaat gttggtgggg tgaagaagac    2520
atagagctag aagtggaagt cttcggctct tggaaagatg aatcaaagaa aatcattgaa    2580
ttgatcttgc caacaaacgt tgatcctgaa gcagaactac ataaaatcat tgtacccgtc    2640
cgattacata ttcgtagagt ttggacttta gagttgagcg ttattggggt gcagtga      2697

<210> SEQ ID NO 11
<211> LENGTH: 2448
<212> TYPE: DNA
<213> ORGANISM: Saccharomyces cerevisiae

<400> SEQUENCE: 11
atgtctgccg ttttcaacaa cgctacccct tcaggtctag tccaagcaag cacctactca      60
caaactttgc aaaatgtcgc ccattaccaa cctcaattga atttcatgga gaaatactgg     120
gccgcatggt acagttacat gaacaatgat gttttggcca ccgtctaat gttctttta      180 ttgcatgaat ttatgtattt ctttagatgt ttgccatggt tcatcatcga ccaaattcca     240
tactttagaa gatggaagtt acaaccaact aagattccaa gtgctaagga caactatac      300 tgtttgaaat ccgttcttct atctcatttc ttggtcgagg ccatcccttat ctggaccttc     360 cacccaatgt gtgaaaaatt aggtattact gtcgaagttc cattcccatc tttgaaaaca     420
atggctctag aaattggtct attcttcgtc ttggaagata catggcatta ctgggctcac     480
cgtctattcc actacggtgt cttctacaag tacattcaca agcaacatca cagatacgct     540
gctccattcg gtctttctgc tgaatatgct catcctgctg aaactttgtc tttgggtttt     600
ggtaccgttg gtatgccaat tctttacgtc atgtacactg gtaaattaca cttgttcact     660
ctatgtgtat ggatcacct aagattattc caagctgttg actctcattc tggttatgac     720
ttcccatggt cttgaacaa gatcatgcca ttctgggctg cgctgaaca ccacgatttg     780 catcatcact actttattgg taactacgct tcctcttcca gatggtggga ttactgtcta     840
gacactgaat ctggtccaga agctaaggcc tccagagaag aaagaatgaa gaagagagct     900
gaaaacaatg ctcaaaagaa gactaacgga agtgcagctc ctggtgcatc agctgctcca     960
ggtgctggtt ctggaagtgg ttcaggaatg acgatataa tcacgcaagt ttctccagat    1020
aatgcagagt ccgctccgat tctacaagaa cagcaacagc aacagaactc acagtacgaa    1080
ggtaacgagg aggattatgg tgattcattg attcattga atattcaaga aaaccattat    1140
ttcattacga gggaccagtt gatgtctcta cctgaatccc tattactgtg ttatttccc     1200
```

-continued

```
tcaggtgttt ttttggaccg ttgtggtcag gtcattacta atttgaccag agacgatgag    1260
gtctacattg ttaatttccc tcctgattgt tttgagtaca tcatggagat atatacaaaa    1320
gcgcatgatg atttgtataa tcatcctgtg agaaatttt ttgacagacc atcaagtagc     1380
tttgtttcga atgcaaaggg atttttttgga ctgagtagca ataattcaat ttcgagcaac   1440
aatgagcagg atattttaca tcaaaagccc gctattattg ttttgagaga agacttggat   1500
tattattgtg tacctcagga ggaatttcag tttgattcca ctaatgaaga aaataatgag   1560
gatttattgc gacattttat ggctcaagtg aaaatggctg ctggcagtta tttaacttca   1620
aaaacatcga ttttccaagg tttgtattct tcgaatagac taaagcaaca acagcaacaa   1680
cagaaaattg aaaagggggtc caattcttct tcaaatacta aatctacttc gaaaaaattg   1740
ggacctgctg aacaacattt aatggatatg ttgtgctcct ccggattcac caaggaaact    1800
tgttggggta acagaactca agaaactggc aaaacggtta taagttcact gtctctttgc   1860
cgattggcta acgagacaac tgaaggattt aggcaaaaat ttaacgaggc taaggctaag   1920
tgggaggcag agcacaaacc ttctcaagac aacttcatca ccccaatgca atctaacata   1980
tcgattaact ctttatctgc aagtaaatct aacagtacca tttctacagc aaggaattta   2040
acaagcggaa gtacagcacc tgctacagca cgtgataaga gaaaatcaag gctgtcgaaa   2100
ctagcagata acgttcgttc gcactcttcc tcgagacata gttcgcagac cagaagtaaa   2160
cctccggagt tgcccaaatt gtatgatcta gtgccaaaac ctaatatcaa cgctaagcta   2220
ctattatttt ggagaaaacc tgctcgtaaa tgttggtggg gtgaagaaga catagagcta   2280
gaagtggaag tcttcggctc ttggaaagat gaatcaaaga aaatcattga attgatcttg   2340
ccaacaaacg ttgatcctga agcagaacta cataaaatca ttgtacccgt ccgattacat   2400
attcgtagag tttggacttt agagttgagc gttattgggg tgcagtga                 2448
```

<210> SEQ ID NO 12
<211> LENGTH: 2022
<212> TYPE: DNA
<213> ORGANISM: Saccharomyces cerevisiae

<400> SEQUENCE: 12

```
atgaacaacg agactagtgg taaagaaacg gcgtctgcac ctctgtgttc gcccaagtta      60
cctgtagaaa aagtgcagag aatagccaag aatgatccag aatatatgga cacttcggat    120
gacgcattcg tagccacagc gtttgctaca gaattcttcg tccaggtgct gacacatgag    180
tccctacata ggcaacagca gcagcaacaa caacaggtac cgccgctccc agatgaactc    240
acgctgtcgt acgatgacat ctctgccgca attgtgcact cttctgacgg ccatctgcag    300 ttttttgaatg atgtgatacc aacaacaaag aatttgaggc ttctagtgga agaaaaccga    360
gttagatata ctacaagtgt catgcccct aatgaagttt actccgccta tgtggtgaac    420
gatacggctc cgaagcccaa cattgtcgag attgatcttg ataatgacga agacgacgac    480
gaagacgtta ctgatcaaga aggaagtgca gctcctggtg catcagctgc tccaggtgct    540
ggttctggaa gtggttcagg aatggacgat ataatcacgc aagtttctcc agataatgca   600
gagtccgctc cgattctaca agaacagcaa cagcaacaga actcacagta cgaaggtaac   660
gaggaggatt atggtgattc attgattcat ttgaatattc aagaaaacca ttatttcatt    720
acgagggacc agttgatgtc tctacctgaa tccctattac tgtgtttatt tccctcaggt   780 gttttttttgg accgttgtgg tcaggtcatt actaatttga ccagagacga tgaggtctac    840
attgttaatt tccctcctga ttgttttgag tacatcatgg agatatata ccaaaagcgcat     900
```

```
gatgatttgt ataatcatcc tgtggagaaa tttttttgaca gaccatcaag tagctttgtt    960
tcgaatgcaa agggattttt tggactgagt agcaataatt caatttcgag caacaatgag   1020
caggatattt tacatcaaaa gcccgctatt attgttttga gagaagactt ggattattat   1080
tgtgtacctc aggaggaatt tcagtttgat tccactaatg aagaaaataa tgaggattta   1140
ttgcgacatt ttatggctca agtgaaaatg gctgctggca gttatttaac ttcaaaaaca   1200 tcgatttttcc aaggtttgta ttcttcgaat agactaaagc aacaacagca acaacagaaa   1260
attgaaaagg ggtccaattc ttcttcaaat actaaatcta cttcgaaaaa attgggacct   1320
gctgaacaac atttaatgga tatgttgtgc tcctccggat tcaccaagga aacttgttgg   1380
ggtaacagaa ctcaagaaac tggcaaaacg gttataagtt cactgtctct tgccgattg    1440 gctaacgaga caactgaagg atttaggcaa aaatttaacg aggctaaggc taagtgggag   1500
gcagagcaca aaccttctca agacaacttc atcacccccaa tgcaatctaa catatcgatt   1560
aactctttat ctgcaagtaa atctaacagt accatttcta cagcaaggaa tttaacaagc   1620
ggaagtacag cacctgctac agcacgtgat aagagaaaat caaggctgtc gaaactagca   1680
gataacgttc gttcgcactc ttcctcgaga catagttcgc agaccagaag taaacctccg   1740
gagttgccca aattgtatga tctagtgcca aaacctaata tcaacgctaa gctactatta   1800
ttttggagaa aacctgctcg taaatgttgg tggggtgaag aagacataga gctagaagtg   1860
gaagtcttcg gctcttggaa agatgaatca agaaaatca ttgaattgat cttgccaaca   1920
aacgttgatc ctgaagcaga actacataaa atcattgtac ccgtccgatt acatattcgt   1980
agagtttgga ctttagagtt gagcgttatt ggggtgcagt ga                      2022

<210> SEQ ID NO 13
<211> LENGTH: 2217
<212> TYPE: DNA
<213> ORGANISM: Saccharomyces cerevisiae

<400> SEQUENCE: 13
atgctgctgg acgtgaacac aaatcacaca ctaatgcacg atgctcatgt gcatgaacat     60
tgcctcatca aaagcatacg tgatgatggc gcattgcact catggagcga ctcatcaaag    120
gtattttatc ccaagtcatt ttacgctacc gctactaata agaagaataa caagttagcc    180
agcgccagca tgaacaagac cgccacaagt aataggacgg tgagcgatga gatttatttc    240
cactccacta agccgcagtt cgatggtcaa ggaagcgctg aacgtactag aacactaacc    300
aagaggaata gcttcaagag gactagaata ctgaaggctc gagacgattc cgaactgctg    360
aacgaaaatc gctcatcttt gatgaccccg tccttaagct cggtcatgtc gcaagttagg    420
aaaacaaatt ccgccaagac gttatcgggc gaatgcccca tacatgaggg ccacttaaca    480
cagagcataa agaggaagtt ctccgaggaa gctcaaagcg actgttcttc attgagctcc    540
tctaaacttc atcccttgac agatgatatt gctgacgctg tcgatttgca gaccccgcgc    600
attggcgatg aggtactggc tgagccggtc gtgcccaaaa tgaaataat aaacataaat    660 gatctcgatt tgttcgacga ctgggaggtt aaggatttag tcgatatctt tcctcccgta    720
tacgaacggc gtccgcgatc gtcctctgcc ctttcactgg tttctgcgtc gtccgatgcc    780
aaacttcgtc cgacctctgt ggacttccaa atcatcgaca agaaaggcgg caagacttca    840
agaaggaaga gtaggagcaa atcgactaca gaaaacatga tttacgaaaa tgacctggta    900
gaattagaac aatggccatc tgcatcacca tcgcccgaga ccgacggttc gattgcatct    960
```

```
agcgagctct tgcccaataa agaataaga caaaaaagtt tgaataccaa tttcctaaag    1020
ttatactcta ttgaaacatc atgtaaaagg aagagtattt tacccgaagt cgaagtagat    1080
gaccatctgt tgaagcagct aacgtattcc gaaattcggt ctttggaaat caaaaggag     1140 ccaaatgtct ctacgaacga tattaagctt gccctaatta ctaggaaaaa attatggtct    1200
gacatggtcc atgaaacaag aaatgatctt tttggcgatt ctacccctg gaatttgcac    1260 tttgttgcaa cgacaagcaa tacgaacct tcgcaaggcc gtgaatccgc aagcgaacat    1320
gcaacggcgg atttgaaaag ttctttggtc cgcgtacact cagacgtcaa gccatggttc    1380
aacaatggcg gcacaatgct caaaccatgc ggaaaactaa atttaggcaa agtcaccaat    1440
aagacttccg cacctacgag agagattcaa tatgtcgtaa agggctggtg tgacagcagg    1500
tttctcggaa gtgcagctcc tggtgcatca gctgctccag gtgctggttc tggaagtggt    1560
tcaggaatgt ccgataaagt tattaaccct caagttgcat gggctcaaag gtctagtact    1620
actgatccag aaagaaatta tgtcttaata actgtgtcaa ttgcagactg tgatgcccct    1680
gagttaacca ttaagccatc atacatcgaa ttaaaggctc aatcaaagcc tcatgttggc    1740
gatgaaaatg tccatcatta tcaattacac attgatctat acaaggaaat tatacctgaa    1800
aaaacaatgc ataaggttgc taatggccag cactactttt tgaaattgta taaaaaggat    1860
ttagaatctg aatactggcc acgtttgaca aaggaaaagg tgaagtaccc ttacatcaaa    1920
actgatttcg ataaatgggt tgatgaagat gaacaagacg aagttgaagc tgaaggtaat    1980
gatgccgctc aaggaatgga tttcagccaa atgatgggag gtgctggagg tgctggaggt    2040
gctggaggca tggacttcag ccaaatgatg ggaggtgctg gtggcgctgg ttctccagat    2100
atggctcaat gcagcaatt attggctcaa agcggtggta atttggacat gggagatttc    2160
aaagaaaacg atgaagaaga tgaagaagag gaaatagagc cggaagtgaa agcttaa     2217
```

<210> SEQ ID NO 14
<211> LENGTH: 2247
<212> TYPE: DNA
<213> ORGANISM: Saccharomyces cerevisiae

<400> SEQUENCE: 14

```
atggctacac caagcacggg agcaaacaat tctatacctg cggtacgaaa tcaggttgaa     60
gttcaggttg gattagtagg ggatgcacaa gtagggaaaa catcgctgat ggtgaagtac    120
gtacagaaca tatacgataa ggaatacaca cagacgctgg gagtgaactt tttgaaaaga    180
aaagtaagca tacgctccac ggatattata ttttctataa tggatttagg cggacaaaga    240
gaattcatca acatgctccc aattgcgacg gtagggtctt cagtgatcat atttctgttt    300
gacctgacac gtccagagac gttgagttca ataaaggagt ggtataggca ggcgtacggg    360
ctaaatgatt cggcaattcc tattttggtg ggcacaaagt acgatttact aatagactta    420
gacccggaat atcaggaaca aatctcgaga acgagtatga agtatgcaca ggtcatgaat    480
gctcctctta tattctgctc tactgccaaa tctataaaca ttcaaaaaat tttcaaaatt    540
gcactggcaa agatctttaa tttgacatta accatcccag aaatcaatga atcggcgat    600 cctcttttga tatataagca cctaggtggc cagcaacatc gacatcataa caaaagtcag    660
gatagaaaga gccataatat caggaagccc tcctcgtcgc cctcatctaa ggcaccatcg    720
ccgggcggaa gtgcagctcc tggtgcatca gctgctccag gtgctggttc tggaagtggt    780
tcaggaatgg acgatataat cacgcaagtt tctccagata atgcagagtc cgctccgatt    840
ctacaagaac agcaacagca acagaactca cagtacgaag gtaacgagga ggattatggt    900
```

```
gattcattga ttcatttgaa tattcaagaa aaccattatt tcattacgag ggaccagttg      960
atgtctctac ctgaatccct attactgtgt ttatttccct caggtgtttt tttggaccgt     1020
tgtggtcagg tcattactaa tttgaccaga gacgatgagg tctacattgt taatttccct     1080
cctgattgtt ttgagtacat catggagata tatacaaaag cgcatgatga tttgtataat     1140
catcctgtgg agaaattttt tgacagacca tcaagtagct ttgtttcgaa tgcaaaggga     1200
ttttttggac tgagtagcaa taattcaatt tcgagcaaca atgagcagga tattttacat     1260
caaaagcccg ctattattgt tttgagagaa gacttggatt attattgtgt acctcaggag     1320
gaatttcagt ttgattccac taatgaagaa ataatgagg atttattgcg acattttatg      1380
gctcaagtga aaatggctgc tggcagttat ttaacttcaa aaacatcgat tttccaaggt     1440
ttgtattctt cgaatagact aaagcaacaa cagcaacaac agaaaattga aaaggggtcc     1500
aattcttctt caaatactaa atctacttcg aaaaaattgg gacctgctga caacacattta    1560 atggatatgt tgtgctcctc cggattcacc aaggaaactt gttggggtaa cagaactcaa     1620
gaaactggca aaacggttat aagttcactg tctctttgcc gattggctaa cgagacaact     1680
gaaggattta ggcaaaaatt taacgaggct aaggctaagt gggaggcaga gcacaaacct     1740
tctcaagaca acttcatcac cccaatgcaa tctaacatat cgattaactc tttatctgca     1800
agtaaatcta acagtaccat ttctacagca aggaatttaa caagcggaag tacagcacct     1860
gctacagcac gtgataagag aaaatcaagg ctgtcgaaac tagcagataa cgttcgttcg     1920
cactcttcct cgagacatag ttcgcagacc agaagtaaac ctccggagtt gcccaaattg     1980
tatgatctag tgccaaaacc taatatcaac gctaagctac tattattttg gagaaaacct     2040
gctcgtaaat gttggtgggg tgaagaagac atagagctag aagtggaagt cttcggctct     2100
tggaaagatg aatcaaagaa aatcattgaa ttgatcttgc caacaaacgt tgatcctgaa     2160
gcagaactac ataaaatcat tgtacccgtc cgattacata ttcgtagagt ttggacttta     2220
gagttgagcg ttattggggt gcagtga                                         2247
```

<210> SEQ ID NO 15
<211> LENGTH: 2170
<212> TYPE: DNA
<213> ORGANISM: Saccharomyces cerevisiae

<400> SEQUENCE: 15

```
atggtagtat ccatcatacc gcaatttcct gatatcaagg tttcactagc attgtttgaa       60
caggttaaaa atgctaaaga aatacgctct aaaatgagtg aattgtcgac atcctttgcc      120
tttattgacc cccggttagt ctgttcgggg gagcagatgt attctgcaat ttacaagacc      180
ttaatagaag tgaaatataa caagatgaga acaagaaatt tgaattccga gtgcgtacta      240
tgtctttcac ccacttccaa tattagtgat gctttcctca aattcggaat caaagacgat      300
tcgtcacagt taatatgcct taagttccat actaatactg acgatgtaga caagagcaa       360 ttgaggacga ttatgacttc tatagtaaaa ggacaagaga tcgagtttaa tgatgacaat      420
ttatcgagat tttatgacga agcgctcata agaaaagtat gttttaataa taaattcgag      480
gtaaaaactt caacagcctc accagaaaca cattgtacta acttcacctt tgttttcctt     540
ttattttgtt tttacctatt agatctataa attaagtgat gatttcaagc cccaagacgt      600
aaatggtctc tcaagagctt tggtagacgc tattcaattg aggggtgtgg gaagtgcagc      660
tcctggtgca tcagctgctc caggtgctgg ttctggaagt ggttcaggaa tggacgatat      720
```

```
aatcacgcaa gtttctccag ataatgcaga gtccgctccg attctacaag aacagcaaca    780
gcaacagaac tcacagtacg aaggtaacga ggaggattat ggtgattcat tgattcattt    840
gaatattcaa gaaaccatt atttcattac gagggaccag ttgatgtctc tacctgaatc     900
cctattactg tgtttatttc cctcaggtgt ttttttggac cgttgtggtc aggtcattac    960
taatttgacc agagacgatg aggtctacat tgttaatttc cctcctgatt gttttgagta   1020
catcatggag atatatacaa aagcgcatga tgatttgtat aatcatcctg tggagaaatt   1080
ttttgacaga ccatcaagta gctttgtttc gaatgcaaag ggattttttg gactgagtag   1140
caataattca atttcgagca acaatgagca ggatatttta catcaaaagc ccgctattat   1200
tgttttgaga gaagacttgg attattattg tgtacctcag gaggaatttc agtttgattc   1260
cactaatgaa gaaaataatg aggatttatt gcgacatttt atggctcaag tgaaaatggc   1320
tgctggcagt tatttaactt caaaaacatc gattttccaa ggtttgtatt cttcgaatag   1380
actaaagcaa caacagcaac aacagaaaat tgaaaagggg tccaattctt cttcaaatac   1440
taaatctact tcgaaaaaat tgggacctgc tgaacaacat ttaatggata tgttgtgctc   1500
ctccggattc accaaggaaa cttgttgggg taacagaact caagaaactg caaaacggt    1560 tataagttca ctgtctcttt gccgattggc taacgagaca actgaaggat ttaggcaaaa   1620
atttaacgag gctaaggcta agtgggaggc agagcacaaa ccttctcaag caacttcat    1680 caccccaatg caatctaaca tatcgattaa ctctttatct gcaagtaaat ctaacagtac   1740
catttctaca gcaaggaatt taacaagcgg aagtacagca cctgctacag cacgtgataa   1800
gagaaaatca aggctgtcga aactagcaga taacgttcgt tcgcactctt cctcgagaca   1860
tagttcgcag accagaagta aacctccgga gttgcccaaa ttgtatgatc tagtgccaaa   1920
acctaatatc aacgctaagc tactattatt ttggagaaaa cctgctcgta aatgttggtg   1980
gggtgaagaa gacatagagc tagaagtgga agtcttcggc tcttggaaag atgaatcaaa   2040
gaaaatcatt gaattgatct tgccaacaaa cgttgatcct gaagcagaac tacataaaat   2100
cattgtaccc gtccgattac atattcgtag agtttggact ttagagttga gcgttattgg   2160
ggtgcagtga                                                          2170
```

<210> SEQ ID NO 16
<211> LENGTH: 1635
<212> TYPE: DNA
<213> ORGANISM: Saccharomyces cerevisiae

<400> SEQUENCE: 16

```
atgtccctac ggccttgtct aacaccatcc agcatgcaat acagtgacat atatataccc     60
acacactctc tcacatctac ctctactctc gctgtcatac cttacccggc tttcggaagt    120
gcagctcctg gtgcatcagc tgctccaggt gctggttctg gaagtggttc aggaatggac    180
gatataatca cgcaagtttc tccagataat gcagagtccg ctccgattct acaagaacag    240
caacagcaac agaactcaca gtacgaaggt aacgaggagg attatggtga ttcattgatt    300
catttgaata ttcaagaaaa ccattatttc attacgaggg accagttgat gtctctacct    360
gaatccctat tactgtgttt atttccctca ggtgtttttt tggaccgttg tggtcaggtc    420
attactaatt tgaccagaga cgatgaggtc tacattgtta atttccctcc tgattgtttt    480
gagtacatca tggagatata tacaaaagcg catgatgatt tgtataatca tcctgtggag    540
aaattttttg acagaccatc aagtagcttt gtttcgaatg caaagggatt ttttggactg    600
agtagcaata attcaatttc gagcaacaat gagcaggata ttttacatca aaagcccgct    660
```

```
attattgttt tgagagaaga cttggattat tattgtgtac ctcaggagga atttcagttt      720
gattccacta atgaagaaaa taatgaggat ttattgcgac atttatggc tcaagtgaaa       780
atggctgctg gcagttattt aacttcaaaa acatcgattt tccaaggttt gtattcttcg      840
aatagactaa agcaacaaca gcaacaacag aaaattgaaa aggggtccaa ttcttcttca      900
aatactaaat ctacttcgaa aaaattggga cctgctgaac aacatttaat ggatatgttg      960
tgctcctccg gattcaccaa ggaaacttgt tggggtaaca gaactcaaga aactggcaaa     1020
acggttataa gttcactgtc tctttgccga ttggctaacg agacaactga aggatttagg     1080
caaaaattta acgaggctaa ggctaagtgg gaggcagagc acaaaccttc tcaagacaac     1140
ttcatcaccc caatgcaatc taacatatcg attaactctt tatctgcaag taaatctaac     1200
agtaccattt ctacagcaag gaatttaaca agcggaagta cagcacctgc tacagcacgt     1260
gataagagaa aatcaaggct gtcgaaacta gcagataacg ttcgttcgca ctcttcctcg     1320
agacatagtt cgcagaccag aagtaaacct ccggagttgc ccaaattgta tgatctagtg     1380
ccaaaaccta atatcaacgc taagctacta ttattttgga gaaaacctgc tcgtaaatgt     1440
tggtggggtg aagaagacat agagctagaa gtggaagtct tcggctcttg gaaagatgaa     1500
tcaaagaaaa tcattgaatt gatcttgcca acaaacgttg atcctgaagc agaactacat     1560
aaaatcattg tacccgtccg attacatatt cgtagagttt ggactttaga gttgagcgtt     1620
attggggtgc agtga                                                      1635

<210> SEQ ID NO 17
<211> LENGTH: 3462
<212> TYPE: DNA
<213> ORGANISM: Saccharomyces cerevisiae

<400> SEQUENCE: 17
atggaagctg gcaggagtgc tgatgaagtg ctataccaca atcagtcgtc agtaaagtta       60
ggtgagttag aaagatacgt tattacatat gagctatacc agggtgatag tattcccgct      120
gatatcacac tggattccct atgggtaaag atcaaaaata ccacaaagct atcctataaa      180
ccagcctatc tattgggccc atttatctta tattgtgacg tgcgagcaaa agattacgaa      240
agctcgtata agatcatatg ttcggcggat aaaccagtat ttcaatcaaa cctacaggca      300
caacaaaagt ttattgcaga gttgtccttg caccacatta agccacgcta tgtatggata      360
gtggatattg tcagtcaaat actatttaat aaagaaacta aggtaacttt tgagatagta      420
gtcggcaatt caaaggcctc tttgaaaaga aaaatacgat gtaatgattc attgcctgat      480
aaagcctgca atattttaca cacaggatta tcggtgcata gacttaccac cgcagatata      540
tggaaagtac cacgacccat agacatgtcg caaaaatccc atttagtcat tctcacgcat      600
ggttttcaat caaacgtttc ggcagatatg gaatacttaa tggaagaaat atacaaggct      660
caaatgaaca atccaaatga gcgactagtt attaagggat atatgaagaa tgcttgtgag      720
actgagaagg gtattaagtt tttgggtgtt ggattggcaa actacatcat cgacgagtta      780
tatgatgact ctgttgggaa aatttcattt attggtcatt ccctgggtgg attaacacaa      840
actttttgcta tttgttacat aaagaccaaa tatccatatt tctttaagaa agtggagcca      900
atcaattta tctcactggc gtcaccattg ctaggcattg ctaccagcac gcccaattac      960
gtaaaaatgt cattgtcgat gggtatcatt ggtactacgg ggcaagaact gggtcttaag     1020
gatggaaatt atggtgataa gcccctactt tacctgctat ccgaggaatc cttaatcagt     1080
```

```
gtgcttgctc gattcaaaag aagaacactt tatgctaatg ccgtcaacga cggaatagtt    1140
cccttgtact cctcttcttt acttttttg gactactctc aattacttca gaaactggga     1200
ggtcaaacta cggcaccttg tgatcctctc ttccagcctg aagtaagtcc tattggggaa    1260
cttccaaatc atagcgatgt tgctaatgat gatgatggaa tcaatgcatc gtcatggaac    1320
acgttttgga agagcaagga aaataactgc gacaagaaat ctaaacgctt gatgaatgct    1380
tccgtcatca aatctatgaa gtctgtgctt ctatcaccat gccccgacgc aaagttcttc    1440
tcagatcccg atgcaagggt cgcaacaatc atacatgata agatctacac agaaaagaat    1500
ttaccgcctc catcaccaac actttatgaa ggaacagcag ccaaggaagg cgaaacgagg    1560
aagacgagaa aagagatgga ggaaatcata gcacgccgct ggcacaaggg gatgcattgg    1620
aggaaagtcg tggtattgct gaaaccagat gcccacaata acatcatcgt aagaagaagg    1680
ttttccaacg cttacggctg gccggtggtt gaccaccttg ttaccgccca tttccaaaga    1740
gatgacccaa tcgcctcacc aatgcaagat aaacagtttg ctgaggaaga tataaacatg    1800
gcaaccggag gggtggaacc aaacaagttc tactcatggc tcaccaagat cgaggatcct    1860
agtgtgtacc atggtggaat agtctccaca gctagccagc tcgccagctc ctggattagc    1920
aagcattcct ctgtgacaga tggaagtgca gctcctggtg catcagctgc tccaggtgct    1980
ggttctggaa gtggttcagg aatggacgat ataatcacgc aagtttctcc agataatgca    2040
gagtccgctc cgattctaca agaacagcaa cagcaacaga actcacagta cgaaggtaac    2100
gaggaggatt atggtgattc attgattcat ttgaatattc aagaaaacca ttatttcatt    2160
acgagggacc agttgatgtc tctacctgaa tccctattac tgtgtttatt tccctcaggt    2220 gttttttttgg accgttgtgg tcaggtcatt actaatttga ccagagacga tgaggtctac    2280
attgttaatt tccctcctga ttgttttgag tacatcatgg agatatatac aaaagcgcat    2340
gatgatttgt ataatcatcc tgtggagaaa ttttttgaca gaccatcaag tagctttgtt    2400
tcgaatgcaa agggattttt tggactgagt agcaataatt caatttcgag caacaatgag    2460
caggatattt tacatcaaaa gcccgctatt attgttttga gagaagactt ggattattat    2520
tgtgtacctc aggaggaatt tcagtttgat tccactaatg aagaaaataa tgaggattta    2580
ttgcgacatt ttatggctca agtgaaaatg gctgctggca gttatttaac ttcaaaaaca    2640
tcgattttcc aaggtttgta ttcttcgaat agactaaagc aacaacagca acaacagaaa    2700
attgaaaagg ggtccaattc ttcttcaaat actaaatcta cttcgaaaaa attgggacct    2760
gctgaacaac atttaatgga tatgttgtgc tcctccggat tcaccaagga aacttgttgg    2820
ggtaacagaa ctcaagaaac tggcaaaacg gttataagtt cactgtctct ttgccgattg    2880
gctaacgaga caactgaagg atttaggcaa aaatttaacg aggctaaggc taagtgggag    2940
gcagagcaca aaccttctca agacaacttc atcaccccaa tgcaatctaa catatcgatt    3000
aactctttat ctgcaagtaa atctaacagt accatttcta cagcaaggaa tttaacaagc    3060
ggaagtacag cacctgctac agcacgtgat aagagaaaat caaggctgtc gaaactagca    3120
gataacgttc gttcgcactc ttcctcgaga catagttcgc agaccagaag taaacctccg    3180
gagttgccca aattgtatga tctagtgcca aaacctaata tcaacgctaa gctactatta    3240
ttttggagaa aacctgctcg taaatgttgg tggggtgaag aagacataga gctagaagtg    3300
gaagtcttcg gctcttggaa agatgaatca aagaaaatca ttgaattgat cttgccaaca    3360
aacgttgatc tgaagcagaa actacataaa atcattgtac ccgtccgatt acatattcgt    3420
agagtttgga ctttagagtt gagcgttatt ggggtgcagt ga                      3462
```

<210> SEQ ID NO 18
<211> LENGTH: 1668
<212> TYPE: DNA
<213> ORGANISM: Saccharomyces cerevisiae

<400> SEQUENCE: 18

```
atgtggagac gtcggcgcga gccctgggag gagttatctt ttcttcttaa cagcttatca      60
ccccggaatt ggtttatccg gagatggggt cttatggctg aagaggcca gcacctttgc     120
tggctccggt gcgcttgtga cggcccggga agtgcagctc ctggtgcatc agctgctcca     180
ggtgctggtt ctggaagtgg ttcaggaatg acgatataa tcacgcaagt ttctccagat     240
aatgcagagt ccgctccgat tctacaagaa cagcaacagc aacagaactc acagtacgaa     300
ggtaacgagg aggattatgg tgattcattg attcatttga atattcaaga aaaccattat     360
ttcattacga gggaccagtt gatgtctcta cctgaatccc tattactgtg tttatttccc     420
tcaggtgttt ttttggaccg ttgtggtcag gtcattacta atttgaccag agacgatgag     480
gtctacattg ttaatttccc tcctgattgt tttgagtaca tcatggagat atatacaaaa     540
gcgcatgatg atttgtataa tcatcctgtg gagaaatttt ttgacagacc atcaagtagc     600
tttgtttcga atgcaaaggg atttttttgga ctgagtagca ataattcaat ttcgagcaac     660
aatgagcagg atattttaca tcaaaagccc gctattattg ttttgagaga agacttggat     720
tattattgtg tacctcagga ggaatttcag tttgattcca ctaatgaaga aaataatgag     780
gatttattgc gacattttat ggctcaagtg aaaatggctg ctggcagtta tttaacttca     840
aaaacatcga ttttccaagg tttgtattct tcgaatagac taaagcaaca acagcaacaa     900
cagaaaattg aaaaggggtc caattcttct tcaaatacta atctacttc gaaaaaattg     960
ggacctgctg aacaacattt aatggatatg ttgtgctcct ccggattcac caaggaaact    1020
tgttggggta acagaactca agaaactggc aaaacggtta taagttcact gtctctttgc    1080
cgattggcta acgagacaac tgaaggattt aggcaaaaat ttaacgaggc taaggctaag    1140
tgggaggcag agcacaaacc ttctcaagac aacttcatca ccccaatgca atctaacata    1200
tcgattaact ctttatctgc aagtaaatct aacagtacca tttctacagc aaggaattta    1260
acaagcggaa gtacagcacc tgctacagca cgtgataaga aaaatcaag gctgtcgaaa    1320
ctagcagata acgttcgttc gcactcttcc tcgagacata gttcgcagac agaagtaaa    1380
cctccggagt tgcccaaatt gtatgatcta gtgccaaaac ctaatatcaa cgctaagcta    1440
ctattatttt ggagaaaacc tgctcgtaaa tgttggtggg gtgaagaaga catagagcta    1500
gaagtggaag tcttcggctc ttggaaagat gaatcaaaga aaatcattga attgatcttg    1560
ccaacaaacg ttgatcctga agcagaacta cataaaatca ttgtacccgt ccgattacat    1620
attcgtagag tttggacttt agagttgagc gttattgggg tgcagtga             1668
```

<210> SEQ ID NO 19
<211> LENGTH: 2316
<212> TYPE: DNA
<213> ORGANISM: Saccharomyces cerevisiae

<400> SEQUENCE: 19

```
atgagtggca cgaggtgttt gctaggcgtc ggactaccag ttgatgtgac tgctacggaa      60
actttgactc atgatgaaca aggaccaggt gtagagccag accgtgttc gcgaggaagt     120
tctatagatg gtctgctgcc ctcgttgctc ggtccacatg atgatgtgga tgacgattcg     180
```

```
gcggcttttc acaagtacat gacactatcg cgagatggcg caggcgccat ccatgctccg      240
tcattagtcg aagacgcctc aaggaacgac gacgacgacg atgatgaaga cgacgacgac      300
agttccatgt cgcgagacct atccaaggct ctagatatgt catcgtcatc atcgtccagc      360
ccgcgcgttc aaagtcggcg gcaccgtagt tctgtgagcg caatatctgc aatcttacac      420
caaggaaaat ctggccgcga agacataact ggaagcctta gcgttccggc agaacaagaa      480
aaactcagtt ttcttgccaa agcctcgagt attttctttc gaaggaacag tatgcccaga      540
gacaaacata cgcattcagt atgtcccgct agccgcccag attccgagag atttatcgtc      600
acatctgcag ccgcgcagtc tttacgccgc caacaacaac tggaagacgc tcagtacgct      660
cgagttatta caaactttcg tactatagga tggtgctctc ccagcgagat agagtctgtg      720
gaatataaac ggtccttgat caatgcggag tgggacgaaa agatctcgct tttgtctcac      780
gcgcaatgct ataaggaag tgcagctcct ggtgcatcag ctgctccagg tgctggttct      840
ggaagtggtt caggaatgga cgatataatc acgcaagttt ctccagataa tgcagagtcc      900
gctccgattc tacaagaaca gcaacagcaa cagaactcac agtacgaagg taacgaggag      960
gattatggtg attcattgat tcatttgaat attcaagaaa accattattt cattacgagg     1020
gaccagttga tgtctctacc tgaatcccta ttactgtgtt tatttccctc aggtgttttt     1080
ttggaccgtt gtggtcaggt cattactaat ttgaccagag acgatgaggt ctacattgtt     1140
aatttccctc ctgattgttt tgagtacatc atggagatat atacaaaagc gcatgatgat     1200
ttgtataatc atcctgtgga gaattttttt gacagaccat caagtagctt tgtttcgaat     1260
gcaaagggat tttttggact gagtagcaat aattcaattt cgagcaacaa tgagcaggat     1320
attttacatc aaaagcccgc tattattgtt ttgagagaag acttggatta ttattgtgta     1380
cctcaggagg aatttcagtt tgattccact aatgaagaaa ataatgagga tttattgcga     1440
cattttatgg ctcaagtgaa aatggctgct ggcagttatt aacttcaaa acatcgatt      1500 ttccaaggtt tgtattcttc gaatagacta aagcaacaac agcaacaaca gaaaattgaa     1560
aaggggtcca attcttcttc aaatactaaa tctacttcga aaaaattggg acctgctgaa     1620
caacatttaa tggatatgtt gtgctcctcc ggattcacca aggaaacttg ttggggtaac     1680
agaactcaag aaactggcaa aacggttata agttcactgt ctctttgccg attggctaac     1740
gagacaactg aaggatttag gcaaaaattt aacgaggcta aggctaagtg ggaggcagag     1800
cacaaacctt ctcaagacaa cttcatcacc ccaatgcaat ctaacatatc gattaactct     1860
ttatctgcaa gtaaatctaa cagtaccatt tctacagcaa ggaatttaac aagcggaagt     1920
acagcacctg ctacagcacg tgataagaga aaatcaaggc tgtcgaaact agcagataac     1980
gttcgttcgc actcttcctc gagacatagt tcgcagacca gaagtaaacc tccggagttg     2040
cccaaattgt atgatctagt gccaaaacct aatatcaacg ctaagctact attattttgg     2100
agaaaacctg ctcgtaaatg ttggtggggt gaagaagaca tagagctaga agtggaagtc     2160
ttcggctctt ggaagatgaa atcaaagaaa atcattgaat tgatcttgcc aacaaacgtt     2220
gatcctgaag cagaactaca taaaatcatt gtacccgtcc gattacatat tcgtagagtt     2280
tggactttag agttgagcgt tattggggtg cagtga                              2316
```

<210> SEQ ID NO 20
<211> LENGTH: 2184
<212> TYPE: DNA
<213> ORGANISM: Saccharomyces cerevisiae

<400> SEQUENCE: 20

```
atggccagca tagacgcatt ttcggacctt gagcgccgga tggacgggtt ccaaaaggac    60
gtggcccagg tactggcacg tcagcaaaac cacgcgcgcc aacagctgca acagttccaa   120
gcggaaatgc gtcaattaca taaccaacac caacatctca tagatgaact gcaacggctt   180
gccacccagc gcaccgctct gcagcaacaa atacatgcgg cccaacaagc tacaaatacc   240
accagagagc agtggagaag ctatcacgag cgtgaatctg agttatctag acggcagtcg   300
accttagcag cccaatcgcg cgagctggac tcgctgctgc aacagcgtgg taaagagtgt   360
gtccaattac gcgcacgttg ggctgcgcag tcgggtaacg atgccgcaga ggtcgcactg   420
tacgaacggc tgttgcagct tcgtgtacta cccggagcca gcgatgtgca tgacgtacgt   480
ttcgtattcg gcgatgattc acgctgctgg atcgaagtcg cgatgcacgg agaccacgtg   540
atcggaaact ctcacccggc gctggacccc aagagtcggg caacacttga gcacgtgctt   600
accgtccagg gcgacctcgc ggcattttta gtcgtggccc gcgatatgct tctggcatct   660
ttaggaagtg cagctcctgg tgcatcagct gctccaggtg ctggttctgg aagtggttca   720
ggaatggacg atataatcac gcaagtttct ccagataatg cagagtccgc tccgattcta   780
caagaacagc aacagcaaca gaactcacag tacgaaggta acgaggagga ttatggtgat   840
tcattgattc atttgaatat tcaagaaaac cattatttca ttacgaggga ccagttgatg   900
tctctacctg aatccctatt actgtgttta tttccctcag gtgttttttt ggaccgttgt   960
ggtcaggtca ttactaattt gaccagagac gatgaggtct acattgttaa tttccctcct  1020
gattgttttg agtacatcat ggagatatat acaaaagcgc atgatgattt gtataatcat  1080
cctgtggaga aatttttga cagaccatca agtagctttg tttcgaatgc aaagggattt  1140
tttggactga gtagcaataa ttcaatttcg agcaacaatg agcaggatat tttacatcaa  1200
aagcccgcta ttattgtttt gagagaagac ttggattatt attgtgtacc tcaggaggaa  1260
tttcagtttg attccactaa tgaagaaaat aatgaggatt tattgcgaca ttttatggct  1320
caagtgaaaa tggctgctgg cagttattta acttcaaaaa catcgatttt ccaaggtttg  1380
tattcttcga atagactaaa gcaacaacag caacaacaga aaattgaaaa ggggtccaat  1440
tcttcttcaa atactaaatc tacttcgaaa aaattgggac ctgctgaaca acatttaatg  1500
gatatgttgt gctcctccgg attcaccaag gaaacttgtt ggggtaacag aactcaagaa  1560
actggcaaaa cggttataag ttcactgtct ctttgccgat tggctaacga gacaactgaa  1620
ggatttaggc aaaaatttaa cgaggctaag gctaagtggg aggcagagca caaaccttct  1680
caagacaact tcatcacccc aatgcaatct aacatatcga ttaactcttt atctgcaagt  1740
aaatctaaca gtaccatttc tacagcaagg aatttaacaa gcggaagtac agcacctgct  1800
acagcacgtg ataagagaaa atcaaggctg tcgaaactag cagataacgt tcgttcgcac  1860
tcttcctcga gacatagttc gcagaccaga agtaaacctc cggagttgcc caattgtat  1920 gatctagtgc caaaacctaa tatcaacgct aagctactat tattttggag aaaacctgct  1980
cgtaaatgtt ggtggggtga agaagacata gagctagaag tggaagtctt cggctcttgg  2040
aaagatgaat caaagaaaat cattgaattg atcttgccaa caaacgttga tcctgaagca  2100
gaactacata aaatcattgt acccgtccga ttacatattc gtagagtttg gactttagag  2160
ttgagcgtta ttggggtgca gtga                                         2184
```

<210> SEQ ID NO 21
<211> LENGTH: 3147
<212> TYPE: DNA

<213> ORGANISM: Saccharomyces cerevisiae

<400> SEQUENCE: 21

```
atgggcaatc agtcattagt tgtgcttacg gaaagtaagg gtgagtatga gaatgagaca      60
gaactacctg ttaaaaaatc gtcacgagat aataatatcg gagaatcttt aacagcaaca     120
gcttttacgc agtctgaaga tgaaatggta gatagcaatc agaaatggca gaacccaaac     180
tattttaaat atgcatggca agaatatctt tttatattca catgcatgat aagtcagctt     240
ctaaatcaag caggcactac acagactctt tcgatcatga atattctttc ggacagtttt     300
ggctcagaag gaaactcaaa gtcatggctg atggcatctt ttccgctagt ttcaggctca     360
tttattttga ttagtggcag actaggtgac atatacggat aaaaaaaat gttgttagta     420
ggatatgttc tggttattat atggtctttg atttgtggga ttaccaagta ttctggtagc     480
gatactttt ttattattag tagagcccttc caagggctag ggattgcatt tgttttacct     540
aatgtgctgg gaataattgg taatatatat gtaggtggta cttttcgtaa aaacatcgtg     600
attagttttg ttggtgcgat ggcccctatt ggagcaactt taggttgtct ttttgcagga     660
ctgatcggta ccgaggaccc aaaacaatgg ccatgggcat tctacgcgta tagcatagcc     720
gctttcatta attttgtgct ctccatatat gccattccga gtactatacc aacaaatatt     780
catcattttt ctatggattg gattggttct gttttgggcg tgataggtct cattttatta     840
aattttgtgt ggaaccaagc tcctatatcg ggttggaacc aggcttacat catcgtaatt     900
ttaatcattt ctgtgatttt tcttgtcgtt ttcatcattt atgagattcg atttgccaag     960
actccactat tgccgcgcgc agttataaag gatcgtcata tgattcaaat tatgctggct    1020
ttattctttg atggggctc ttttggcatc tttacgttt attatttcca atttcaatta    1080
aatataaggc agtacacggc attatgggct ggtggaactt actttatgtt tttaatttgg    1140
ggtattattg ccgccttact ggtaggattt actatcaaga atgtgtctcc atcagtgttt    1200
ttgttctttt ctatggtagc attcaatgtg gctcaataa tggcaagtgt tacaccggtt    1260
cacgagacat actttcgtac tcagttagga acgatgataa ttttaagttt tgggatggat    1320
ctttcatttc ctgcttcttc cattatcttt agtgataatt taccgatgga gtaccaaggc    1380
atggctgggt cattggtgaa tactgttgtc aattactcca tgtccttgtg tctcggtatg    1440
ggtgccacag tagagacaca ggtcaattca gacggaaagc atctttttgaa aggctataga    1500
ggtgctcagt accttgggat aggattggca agtttagcat gcatgattag cgggctttac    1560
atggtcgaaa gcttcataaa aggccgcagg gcaagagctg ctgcagaata cgattgcact    1620
gtggctggaa gtgcagctcc tggtgcatca gctgctccag gtgctggttc tggaagtggt    1680
tcaggaatgg acgatataat cacgcaagtt tctccagata tgcagagtc cgctccgatt    1740
ctacaagaac agcaacagca acagaactca cagtacgaag gtaacgagga ggattatggt    1800
gattcattga ttcatttgaa tattcaagaa aaccattatt tcattacgag ggaccagttg    1860
atgtctctac ctgaatccct attactgtgt ttatttccct caggtgtttt tttggaccgt    1920
tgtggtcagg tcattactaa tttgaccaga gacgatgagg tctacattgt taatttccct    1980
cctgattgtt ttgagtacat catggagata tatacaaaag cgcatgatga tttgtataat    2040
catcctgtgg agaaattttt tgacagacca tcaagtagct ttgtttcgaa tgcaaaggga    2100
tttttttggac tgagtagcaa taattcaatt tcgagcaaca atgagcagga tattttacat    2160
caaaagcccg ctattattgt tttgagagaa gacttggatt attattgtgt acctcaggag    2220
gaatttcagt ttgattccac taatgaagaa aataatgagg atttattgcg acattttatg    2280
```

```
gctcaagtga aaatggctgc tggcagttat ttaacttcaa aaacatcgat tttccaaggt    2340
ttgtattctt cgaatagact aaagcaacaa cagcaacaac agaaaattga aaaggggtcc    2400
aattcttctt caaatactaa atctacttcg aaaaaattgg gacctgctga acaacattta    2460
atggatatgt tgtgctcctc cggattcacc aaggaaactt gttggggtaa cagaactcaa    2520
gaaactggca aaacggttat aagttcactg tctctttgcc gattggctaa cgagacaact    2580
gaaggattta ggcaaaaatt taacgaggct aaggctaagt gggaggcaga gcacaaacct    2640
tctcaagaca acttcatcac cccaatgcaa tctaacatat cgattaactc tttatctgca    2700
agtaaatcta acagtaccat ttctacagca aggaatttaa caagcggaag tacagcacct    2760
gctacagcac gtgataagag aaaatcaagg ctgtcgaaac tagcagataa cgttcgttcg    2820
cactcttcct cgagacatag ttcgcagacc agaagtaaac ctccggagtt gcccaaattg    2880
tatgatctag tgccaaaacc taatatcaac gctaagctac tattattttg gagaaaacct    2940
gctcgtaaat gttggtgggg tgaagaagac atagagctag aagtggaagt cttcggctct    3000
tggaaagatg aatcaaagaa aatcattgaa ttgatcttgc aacaaacgt tgatcctgaa     3060 gcagaactac ataaaatcat tgtacccgtc cgattacata ttcgtagagt ttggacttta    3120
gagttgagcg ttattggggt gcagtga                                        3147

<210> SEQ ID NO 22
<211> LENGTH: 3512
<212> TYPE: DNA
<213> ORGANISM: Saccharomyces cerevisiae

<400> SEQUENCE: 22
atgctgctgg acgtgaacac aaatcacaca ctaatgcacg atgctcatgt gcatgaacat      60
tgcctcatca aaagcatacg tgatgatggc gcattgcact catggagcga ctcatcaaag    120 gtatttatc ccaagtcatt ttacgctacc gctactaata agaagaataa caagttagcc     180
agcgccagca tgaacaagac cgccacaagt aataggacgg tgagcgatga gatttatttc    240
cactccacta agccgcagtt cgatggtcaa ggaagcgctg aacgtactag aacactaacc    300
aagaggaata gcttcaagag gactagaata ctgaaggctc gagacgattc cgaactgctg    360
aacgaaaatc gctcatcttt gatgaccccg tccttaagct cggtcatgtc gcaagttagg    420
aaaacaaatt ccgccaagac gttatcgggc gaatgcccca tacatgaggg ccacttaaca    480
cagagcataa agaggaagtt ctccgaggaa gctcaaagcg actgttcttc attgagctcc    540
tctaaacttc atcccttgac agatgatatt gctgacgctg tcgatttgca gaccccgcg    600 attggcgatg aggtactggc tgagccggtc gtgcccaaaa tgaaaataat aaacataaat    660
gatctcgatt tgttcgacga ctgggaggtt aaggatttag tcgatatctt tcctcccgta    720
tacgaacggc gtccgcgatc gtcctctgcc cttcactgg tttctgcgtc gtccgatgcc    780
aaacttcgtc cgacctctgt ggacttccaa atcatcgaca agaaaggcgg caagacttca    840
agaaggaaga gtaggagcaa atcgactaca gaaaacatga tttacgaaaa tgacctggta    900
gaattagaac aatggccatc tgcatcacca tcgcccgaga ccgacggttc gattgcatct    960
agcgagctct tgcccaataa aagaataaga caaaaaagtt tgaataccaa tttcctaaag   1020
ttatactcta ttgaaacatc atgtaaaagg aagagtattt tacccgaagt cgaagtagat    1080
gaccatctgt tgaagcagct aacgtattcc gaaattcggt cttttggaaat caaaaaggag   1140 ccaaatgtct ctacgaacga tattaagctt gccctaatta ctaggaaaaa attatggtct   1200
```

```
gacatggtcc atgaaacaag aaatgatctt tttggcgatt ctacccccctg gaatttgcac    1260 tttgttgcaa cgacaagcaa tacggaacct tcgcaaggcc gtgaatccgc aagcgaacat    1320
gcaacggcgg atttgaaaag ttctttggtc cgcgtacact cagacgtcaa gccatggttc    1380
aacaatggcg gcacaatgct caaaccatgc ggaaaactaa atttaggcaa agtcaccaat    1440
aagacttccg cacctacgag agagattcaa tatgtcgtaa agggctggtg tgacagcagg    1500
tttctcggaa gtgcagctcc tggtgcatca gctgctccag gtgctggttc tggaagtggt    1560
tcaggaatgg acttgaatca agaaaggaa aaagggcca gcatgttgga tgctgtggct    1620
ccaggacaga cctgtctgct gacacagtgg aactgataga agaatggac agattggctg    1680 aaaaacaggc gacagcttcc atgtcgatcg ttgcgttacc gtctagcttc caggagagca    1740
atagcagtga caggtgcaga aagtattgca gcagtgatga ggacagcaac acgtgcattc    1800
atggtagtgc taatgccagt accaatgcga ctaccaactc cagcactaat gctactacca    1860
ctgccagcac caacgtcagg actagtgcta ctaccactgc cagcatcaac gtcaggacta    1920
gtgcgactac cactgaaagt accaactcca gcactaatgc tactaccact gccagcacca    1980
acgtcaggac tagtgctact accactgcca gcatcaacgt caggactagt gcgactacca    2040
ctgaaagtac caactccaac actagtgcta ctaccaccga agtaccgac tccaacacta    2100 atgctactac cactgctagc atcaacgtca ggactagtgc gactaccact gaaagtacca    2160
actccaacac tagtgctact accaccgaaa gtaccgactc caacactagt gctactacca    2220
ctgctagcac caactccagc actaatgcca ctaccactgc tagcaccaac tccagcacta    2280
atgccactac cactgaaagt accaacgcta gtgccaagga ggacgccaat aaagatggca    2340
atgctgagga taatagattc catccagtca ccgacattaa caaagagtcg tataagcgga    2400
aagggagtca aatggttttc ctagagagaa agaaactgaa agcacaattt cccaatactt    2460
ccgagaatat gaatgtctta cagtttcttg gatttcggtc tgacgaaatt aaacatcttt    2520
tcctctatgg tattgacata tacttctgcc cagagggagt attcacacaa tacgattat    2580 gcaagggctg tcaaaagatg ttcgggctct gtgtctgttg ggctggccag aaagtatcgt    2640
atcggaggat agcttgggaa gcactagctg tggagagaat gctgcgaaat gatgaggaat    2700
acaaagaata cttggaagac atcgagccat atcatgggga ccctgtagga tatttgaaat    2760
attttagcgt aaaaaggaga gagatctact ctcagataca gagaaattat gcttggtacc    2820
tggccattac tagaagaaga gaaacaatta gtgtattgga ttcgacaaga ggcaagcaag    2880
ggagccaagt tttccgcatg tctggaaggc agatcaaaga gttgtattat aaagtatgga    2940
gcaacttgcg tgaatcgaag acagaggtgc tgcagtactt ttttgaactgg gacgaaaaaa    3000 agtgccggga agaatgggag gcaaaagacg atacggtctt tgtggaagcg ctcgagaaag    3060
ttggagtttt tcagcgttg cgttccatga cgagcgctgg actgcagggt ccgcagtacg    3120
tcaagctgca gttagcagg catcatcgac agttgaggag cagatatgaa ttaagtctag    3180
gaatgcactt gcgagatcag cttgcgctgg gagttacccc atctaaagtg ccgcattgga    3240
cggcattcct gtcgatgctg atagggctgt tctacaataa acatttcgg cagaaactgg    3300 aatatctttt ggagcagatt tcggagatgt ggttgttacc acattggctt gatttggcaa    3360
acgttgaagt tctcgctgca gataacacga gggtaccact gtacatgctg atggtagcgg    3420
ttcacaaaga gctggatagc gatgatgttc cagacggtag atttgatata atattactat    3480
gtagagattc gagcagagaa gttggagagt ga                                  3512
```

<210> SEQ ID NO 23
<211> LENGTH: 2268
<212> TYPE: DNA
<213> ORGANISM: Saccharomyces cerevisiae

<400> SEQUENCE: 23

| | | | | | |
|---|---|---|---|---|---|
| atgtccggaa | aagcttctac | agagggtagc | gttactacgg | agtttctctc | tgatatcatt | 60 |
| ggtaagacag | tgaacgtcaa | acttgcctcg | ggtttactct | acagcggaag | attggaatcc | 120 |
| attgatggtt | ttatgaatgt | tgcactatcg | agtgccactg | aacactacga | gagtaataac | 180 |
| aataagcttc | taaataagtt | caatagtgat | gtcttttga | ggggcacgca | ggtcatgtat | 240 |
| atcagtgaac | aaaaaatagg | aagtgcagct | cctggtgcat | cagctgctcc | aggtgctggt | 300 |
| tctggaagtg | gttcaggaat | gtctagagca | gttggtattg | atttgggaac | aacttactcg | 360 |
| tgtgttgctc | attttccaa | tgatagggta | gagataattg | caaatgatca | aggtaatagg | 420 |
| accactccat | cgtatgtggc | tttcacagac | accgaaagat | taattggtga | cgccgccaaa | 480 |
| aatcaagctg | caatcaatcc | tcataataca | gttttgatg | caaagcggtt | aattggtcgt | 540 |
| aaatttgatg | atcctgaagt | gacgacagat | gccaagcact | ccctttcaa | agttatatcc | 600 |
| agagatggta | aacctgtagt | gcaagtagaa | tataagggtg | aaacgaaaac | atttacgcct | 660 |
| gaggaaattt | cttccatggt | tttaagcaaa | atgaaggaaa | ctgctgagaa | ctatttggga | 720 |
| actacggtca | atgatgctgt | tgtaactgtt | cctgcatatt | tcaatgattc | tcaaagacaa | 780 |
| gccactaagg | atgcaggaac | tattgcaggg | atgaacgttt | tacgtattat | caatgaaccc | 840 |
| actgcagcag | caattgctta | tggcttggat | aagaaaggca | gggctgagca | caatgtcctg | 900 |
| attttgatt | tgggtggtgg | tactttgac | gtctctttac | tttcaattga | tgagggtgtt | 960 |
| tttgaggtta | aggctaccgc | aggagacact | catttaggtg | gtgaagattt | tgataatagg | 1020 |
| ttggtgaacc | atttagccac | tgaattcaaa | aggaaaacga | aaaaggacat | ctctaataat | 1080 |
| caaagatcgt | taagaagatt | gagaactgcg | gcagaaagag | ctaagagagc | gctttcttcc | 1140 |
| tcatctcaaa | cctcgatcga | gatcgattct | ttatttgaag | gtatggatt | ctacacttcg | 1200 |
| ttaacaaggg | caaggtttga | agagctatgt | gctgatttat | tcagatccac | attggaacca | 1260 |
| gtagaaaagg | ttcttaaaga | ttcgaagctg | gacaagtccc | aaattgatga | gattgtgtta | 1320 |
| gtcggtggat | ctaccagaat | cccaaagatt | cagaaattag | tttctgactt | cttcaatggc | 1380 |
| aaagagccta | atcgttctat | caacccggat | gaggctgttg | cttatggtgc | agccgttcaa | 1440 |
| gctgccattt | taaccggcga | tcaatcaaca | aagacacaag | atttactatt | attggatgtt | 1500 |
| gcgccattgt | ccctaggaat | tgaaactgca | ggcggcataa | tgactaagct | aattcctaga | 1560 |
| aactcaacga | ttccaacaaa | gaaatcggaa | accttctcta | cctatgcaga | taatcaacct | 1620 |
| ggtgttttaa | ttcaagtctt | tgaaggtgaa | agaacaagaa | caaggataa | taacttactt | 1680 |
| ggtaaattcg | aattaagtgg | cattccgcct | gctcccagag | gtgtgcctca | aattgatgtt | 1740 |
| accttgata | tcgacgctaa | tggtattctt | aatgtgtctg | ctttggaaaa | gggtactggt | 1800 |
| aagagtaaca | aaatcacgat | cactaacgat | aaaggtaggc | tctcgaagga | tgatattgat | 1860 |
| aggatggttt | ctgaagctga | aaatataggg | gctgacgatg | aaagggaggc | agaacgagtt | 1920 |
| caggctaaga | atcagcttga | atcgtatgca | tttactttga | agaataccat | aaacgaagca | 1980 |
| agtttcaaag | agaaagtagg | tgaagatgat | gcaaagagat | tagaaacagc | gtctcaggaa | 2040 |
| accattgact | ggttagatgc | atcgcaggca | gcctctacgg | acgaatataa | ggatagacaa | 2100 |
| aaggagttgg | aaggcattgc | caatccaata | atgacgaaat | tttacggtgc | tggtgccggc | 2160 |

```
gcaggtcctg gagcggggga atccggtgga ttccccggat ccatgcccaa ctcgggtgct    2220
acgggaggtg gagaagatac aggtccaaca gtggaagagg ttgattga                 2268

<210> SEQ ID NO 24
<211> LENGTH: 2511
<212> TYPE: DNA
<213> ORGANISM: Saccharomyces cerevisiae

<400> SEQUENCE: 24
atgctggcac aaacattcaa aaaccacac agagccgttc tagaacaggt atctgggacc      60
acggtcttca tcagaaataa gagaacaaag agcaagagct cactgtcacc tttggcacaa    120
agggtcgtca cgcagttgag tgtgatgtct gcaagcagaa agcagcccaa gttgctgaag    180
ctggcgcgtg aagacctgat taaacatcag accattgaga agtgttggtc aatttatcag    240
cagcaacaac gggagcgcag aaatttacag ttggaattac aatataagag cattgagaga    300
tctatgaacc ttctacaaga actcagccct cgtctgtttg aggctgccaa tgcttccgag    360
aagggcaagc gattcccgat ggaaatgaag gtgcccactg acttcccccc aaatacgtta    420
tggcattata acttccgaaa aggaagtgca gctcctggtg catcagctgc tccaggtgct    480
ggttctggaa gtggttcagg aatgctgcgt gtaacaacct tggcgtcttc gtgtacttca    540
tttcccttac aggtcctcag gaggcggttg accatatctt ctttgacaag cttccaaccc    600
acaaccaaga cacaggtcgt ggtcatcggt gctggacatg caggctgcga agctgcagct    660
gcgtcatcta ggactggtgc gcatactact ctcattacac catcgttaac agatattggt    720
aagtgttcgt gcaaccctc tattggtgga gtgggtaagg gcatccttgt aaaggaaatc    780
gacgctctcg atgggctgat gggcaaagta actgatctcg ctggagtgca attcaaaatg    840
ctgaacagaa gcaagggtcc tgctgtgtgg gggcccagag cccagataga cagagagtta    900
tataagaaat acatgcaaag ggaactttcc gacaagaaag cacacccaa cttgtctctg     960 ctgcagaaca agttgctga cttgatcttg tatgaccccg gatgtggcca aaggtcatc    1020 aaaggtgtgg ttctggatga cggtacccag gttggggcag atcaggtcat aatcactaca    1080
ggtacgtttc tcagtgcaga aattcacatc ggcgacaagc gtattgcagc aggaagaatt    1140
ggcgagcagc caacatatgg gatcagcaat actctacaaa atgaggtggg ctttcagtta    1200
gggcgtttga aaacaggcac tccggctagg ctggccaagg aatccattga tttcagcgct    1260
ctggaggtcc agaagggaga tgcgttgcct gtccctatga gttttctgaa tgaaaccgtg    1320
tcagtcgaac ccacgaagca actggattgc tttggcacac ataccacacc tcaaatgcac    1380
gactttttgc gcaataactt gcatcaatcc attcatattc aggacacgac catcaaaggc    1440
ccccgctatt gtccctccat cgaagctaag attctaaggt ttcctgatag atcttcccat    1500
aagatatggt tggaaccaga aggtttcaac tccgacgtca tttatccgaa cgggatatcc    1560
aattctatgc ctgaggatgt ccagttacaa atgatgaggc tcatcccggg catggcaaac    1620
gttgagatct tgcagccggc atacggcgtg gaatacgact acgtagaccc acggcaatta    1680
aagcctagct tggaaacaaa attggtggat ggactattct tggccggaca aataaatggt    1740
actacaggct acgaggaagc cgctgcacag gggatcattg caggtatcaa tgcaggatta    1800
ctatcgcgcc aagaacggga gcaattggtc ttgaaaaggt ccgaagcgta cattggtgtg    1860
ctcattgacg atctaatcaa taatgggcgtc atagaaccat atagaatgtt tacttccaga    1920
tcagaattca gaatcagcgt aagagccgat aacgcagact tcagactgac gcccattggt    1980
gctcaactag ggattatatc tcctgtccgt ttaagtcaat attcaagaga caagcaccta    2040
```

```
tatgatgaaa caatacgggc gcttcaaaat ttcaagctaa gctctcaaaa atggtctagc    2100
ttactacagg ctaatatcgc gccacaggct gaaaacagat ctgcttggga aatattcaga    2160
ttcaaagata tggatctaca taaactctac gagtgcattc ccgatttacc cattaatttg    2220
ctggacatcc caatgcatgt tgtcaccaaa attaacattc aaggtaaata cgaaccttac    2280
attgtcaaac agaaccagtt tgtgaaggca tttcaggcag acgaaaatat gctgttgccg    2340
caagattacg attaccgtca gttacccacg ctttccactg aatgcaaact actcttgaac    2400
cgcgtacagc cattgaccat aggccaagca agacggattc aaggtatcac tgcggcagcc    2460
ctatttgaac tctaccgtgt ggcacggaag ccaagccaac cagtcatgta a            2511

<210> SEQ ID NO 25
<211> LENGTH: 2568
<212> TYPE: DNA
<213> ORGANISM: Saccharomyces cerevisiae

<400> SEQUENCE: 25
atgaccttgt ggccacatcc ggggtcatac aagatcaagt cagcaacttt gttctgcagc      60
agagacaagt tggggtgtgc tttcttgtcg gaaagttccc tttgcatgta tttcttatat     120
aactctctgt ctatctgggc tctgggcccc cacacagcag gacccttgct tctgttcagc     180
attttgaatt gcactccagc gagatcagtt actttgccca tcagcccatc gagagcgtcg     240
atttccttta caaggatgcc cttacccact ccaccaatag aggggttgca cgaacactta     300
ccaatatctg ttaacgatgg tgtaatgaga gtagtatgcg caccagtcct agatgacgca     360
gctgcagctt cgcagcctgc atgtccagca ccgatgacca cgacctgtgt cttggttgtg     420
ggttggaagc ttgtcaaaga agatatggtc aaccgcctcc tgaggacctg taagggaaat     480
gaagtacacg aagacgccaa ggttgttaca cgcagcatcg ttctttgggg cgttggaagt     540
gcagctcctg gtgcatcagc tgctccaggt gctggttctg gaagtggttc aggaatgctt     600
aaatctggta gactcaactt tctcaagttg aatatcaatt cacgattact atactcaacg     660
aaccctcaac tgactaagaa ggtcattggt atcgacctgg gtaccacgaa tagtgctgtt     720
gcatatatcc gtgattctaa cgacaaaaaa tcagctacaa tcatagaaaa tgatgaagga     780
caacgaacca caccatctat agttgccttt gatgtcaaaa gctcgccaca gaataaagat     840
caaatgaaaa ctcttgtagg gatggcagct aaaaggcaaa atgctattaa ttctgaaaac     900
actttctttg ctacaaagag acttattggc cgtgcattca acgacaagga agttcagcga     960
gatatggctg ttatgccata taagattgtc aaatgtgagt caaatgggca agcctatctc    1020
agcacgtcta atggtctcat tcaatcacca agccagatag catctatatt actgaaatac    1080
ctgaaacaaa cttcagaaga atacttaggc gaaaaggtta attggcagt tattacagtt    1140 ccagcatatt ttaatgattc tcaaaggcaa gccacaaaag atgccggcaa gttagctggc    1200
ctaaatgttt tgagagttat taacgaacca actgcggccg ccttaagctt tggaattgat    1260
gataagagga ataatggatt aattgcagtt tacgatttgg gtggtggtac atttgacata    1320
tccatcttgg acattgaaga tggcgtgttt gaggttcgtg ctactaatgg tgacacgcat    1380
ttaggtggag aagattttga caacgtcatt gtaaactata ttatagatac cttcattcat    1440
gaaaaccctg aaattacacg ggaagaaatt acgaagaaca gggagacaat gcaaaggtta    1500
aaagatgttt ctgaaagagc taagatagat ttatcccatg tgaagaaaac ttttatcgaa    1560
cttccatttg tatacaaaag caaacatcta cgagtgccaa tgacagagga agagctggat    1620
```

```
aatatgactt tgtcattaat caacaggact atcccacctg tgaagcaagc attgaaagat    1680
gccgatatcg aaccggagga tatagatgaa gtaatccttg ttggtggtat gacccgtatg    1740
ccaaagatta gatctgttgt aaaagatctt tttggtaagt ctccaaattc tagtgttaac    1800
ccagatgaaa cagttgcttt aggagcagct attcaaggtg gtattctatc cggtgaaata    1860
aagaatgtct acttttgga tgtgacacca ttgacattag ggattgaaac atttggagga     1920
gcgttctcac ccttgatacc tagaaatacg acagttccag taaaaaaaac agagatattt    1980
agtactggtg ttgatgggca agcgggtgtt gatatcaaag ttttcaggg tgaaagaggg      2040 ttagtgcgta acaacaagtt gattggtgat ttgaaactta caggaatcac ccctttgcct    2100
aaaggcattc cccaaatata tgttactttt gatatcgatg cggatggtat catcaacgta    2160
tctgccgctg agaaaagtag tgggaaacaa caatccatta ctgtaatacc aaattctggg    2220
ttaagcgaag aggaaattgc aaaacttatt gaagaagcaa atgcaaatag gcacaagat     2280 aacttgatca ggcaaaggtt agagcttatc tctaaggctg acattatgat aagtgatact    2340
gagaatttat ttaaaagata tgaaaaactg atttctagcg aaaaagagta ttctaatatc    2400
gtagaggaca tcaaagctct gagacaagct ataaagaatt ttaaggctaa cgaaaatgac    2460
atgtcaattg atgtaaacgg aataaaaaaa gctacggatg cgctacaggg tagggcatta    2520
aaattattcc aaagcgcaac aaaaaaccag cagaatcaag gtaaataa                  2568

<210> SEQ ID NO 26
<211> LENGTH: 1398
<212> TYPE: DNA
<213> ORGANISM: Saccharomyces cerevisiae

<400> SEQUENCE: 26
atgcagattt tcgtcaagac tttgaccggt aaaaccataa cattggaagt tgaatcttcc      60
gataccatcg acaacgttaa gtcgaaaatt caagacaagg aaggtattcc tccagaccag     120
caaagattga ttttgccgg taagcaacta gaagatggta gaacgctgtc ggactacaat     180
attcaaaagg agtccactct tcaccttgtc ttgaggttga ggggtggtaa cggaagtgca     240
gctcctggtg catcagctgc tccaggtgct ggttctggaa gtggttcagg aatgccaggc    300
cagataatca gcattccgtt tttgtcgcag aacgaggaca tggataaata cttgttggag    360
taccgcagtt tgaagctcct tcatcagtcc agtaattcct tccagtctca caatgcgccc    420
tcccaccagt cgaactacca ccccattac aatcacatga atacaacaa cactggtagc      480 tattactatt acaacaacaa caataacagc agtgtaaacc cacataacca agctggtcta    540
caatccatta acagatctat tccatcggcc ccgtacgggg cttacaacca gaacagagct    600
aatgacgtac catatatgaa tacccaaaag aaacaccaca gatttagcgc taacaataat    660
ttgaaccagc aaaaatacaa gcaatatccc cagtatacgt ccaatccaat ggttactgca    720
catctgaagc aaacgtaccc tcaactgtac tacaatagca cgtcaatgc tcacaacaac     780 aacaacaaca gcaacaacaa caacaacaac aacaacaaca gcaacaacaa caacaatctt    840
tacaaccaga cgcagttctc cacgaggtac ttcaactcga actcctctcc ctcgttgact    900
tcttccactt ctaactcatc ctctccatac aaccaaagca cctcgaata catttttgccg    960 tcaacttcgg cagcttccac aaatttatcg tcgtcatcat caaacaactc tatgcacacc    1020
aacccaacca ctgcaacatc gacatccgcc gatttaatca atgatttacc cgtgggcccc    1080
acgtccagtt cgcttatctc ggatctacat tctccaccaa ctgtatcttt cctaccagca    1140
agccaaaccc tgctcatgtc ctccaccaca tctagctcta ttggcaccaa cataaaccca    1200
```

```
ccgcaacatt caccatcccc atcgcaaagg gaggattttt cgacggcacc agtgaacatg    1260
tcttcgtccg catcactctt gatgaatgat tcttctttag gatggggtc taaccacatg     1320 aacgtatctt catcctctca accagcatca tcaagaccct ttggcatttg gaatactgac    1380
atgagcgttt ggagttga                                                  1398

<210> SEQ ID NO 27
<211> LENGTH: 2328
<212> TYPE: DNA
<213> ORGANISM: Saccharomyces cerevisiae

<400> SEQUENCE: 27
atgtggagac gtcggcgcga gccctgggag gagttatctt tcttcttaa cagcttatca      60 ccccggaatt ggtttatccg gagatggggt cttatggctg aagaggcca gcacctttgc    120 tggctccggt gcgcttgtga cggcccggga agtgcagctc ctggtgcatc agctgctcca    180
ggtgctggtt ctggaagtgg ttcaggaatg tcgtttttgc cactaaggtc taggtcacga    240
tcaggcgctc ctcattgggt atacatcatc ttatatcaca tctttacgat accgaagata    300
tattcactgc cgttgttatc cggatcacac gtactcaatt ctaggatgt tgccgattcc     360 ggccatagcg taggtgatga ggcaagcgtt accacgtact atattatctc tatcatccta    420
gtgctgctgg gtggtgtatt tgcaggattg acgctgggt tgatgggtca agatgaagtc     480
tacctgaagg taatcagcac ttcaggctcg aattctgaaa agaaactggc caagcgggtg    540
cttgacctaa tatctagggg gaagcattgg gttctagtca cactgctgct ttctaatgtt    600
ataaccaacg aaacattgcc tattgttttg gacaggtgtc ttgggggtgg ttggcaggct    660
gtagtgtcgt caactattct aattgtgatc ttcggtgaaa ttattccgca gagtgtctgt    720
gttaaatacg ggctgcaagt tggggcattc ttctgcccct ttgttcttgt actgatgtat    780
ctgatgtacc cagtcgcata tccgatcgcg actctcctgg actatatgct gggtgaagat    840
catggtacga tgtacaaaaa atccggctta aagactttgg tcaccttgca taggaccatg    900
ggggtggaac ggttgactaa agacgaagtt acaatcatct ctgctgtttt ggatctaaag    960
gcaaagaggg ttgaggaaat catgactccg attgaaaacg tgttcacaat gagtgccgat    1020
accatcctag acgataaaac tgtcgaaaaa atcttcaact cagggttttc tagaatcccg    1080
atttttttgc ccaatgaacc aaacaacttc atcggcatgt tacttgtcag ggtgcttatc    1140
tcctacgatc ctgatgactg cctcccaatc tcccacttcc ccctagccac gttgccagaa    1200
acttccccga acacatcttg tttgaatatt ctgaattact tccaggaggg gaaagctcac    1260
atgtgcgtcg ttagtaaaga gccgggctcc tcgcatggcg ctattggtgt tttaactttg    1320
gaggatgtca ttgaagaatt gatcggtgaa gaaatcgtgg acgagtctga tgtctttgtg    1380
gacatgcatc agcatattat gagacaacaa ccgggccct tgagcaaaag gcacattact    1440
tcctatttgc atcatttgta cactagctct cacaaggagc acaaagctgc tgaccaagct    1500
gatgaatcgt ctccactctt gtctccatcc aattctaatc acccatccga gcacccacag    1560
caagatttga ataataagtc ttggaagcag aagtcaaatg atggttacga caggtccaac    1620
gctgtattgt ctccaactcc acaagtgacg gaacatggca ccatcatacc ttcaaatcta    1680
gcgtccaacc cgttgaacgt aaataaatct tttgttacca ttaaaaagcc tgccaatgtt    1740
ccgaaaatca ttactacaca cactcctcat tctagcaaag agccttctcc agcaccacac    1800
tcaaatgata aatcactctc cgccgaagaa caacaactat taagtgatca tgcagagcta    1860
```

| | |
|---|---|
| tctcgccaag ctgttctcca tactcaacgg tcgggtcaac caactcaagt tactacctcg | 1920 |
| actaaaaccaa cgagaaatag ccctgatagt atatcaattc caaattctgg cgcgaatcac | 1980 |
| ggcaacgaaa atcaaaacgt tacaatctca acctcttacc aaaatacgaa gaatggtatt | 2040 |
| gtggaatctg tcatcacagt caaaggtgtt ccaaaaacca tcattggccc cgcaaaagat | 2100 |
| tgggacgaat ccaaaagtga aatggaaac gagaatatca atcaagagaa ttctaatcga | 2160 |
| agtgacgata gagaaagttc aagttcaaat gcaagtttat tttccagtat taagaataaa | 2220 |
| tttaagaacg aaaacgctaa caacaatgat cgttctaatt tcaccgactc tttgtcaaga | 2280 |
| acttccaatt atgatgccaa cggctcctcg tcgaccataa aaagatga | 2328 |

<210> SEQ ID NO 28
<211> LENGTH: 2573
<212> TYPE: DNA
<213> ORGANISM: Saccharomyces cerevisiae

<400> SEQUENCE: 28

| | |
|---|---|
| atggacgata taatcacgca agtttctcca gataatgcag agtccgctcc gattctacaa | 60 |
| gaacagcaac agcaacagaa ctcacagtac gaaggtaacg aggaggatta tggtgattca | 120 |
| ttgattcatt tgaatattca agaaaaccat tatttcatta cgagggacca gttgatgtct | 180 |
| ctacctgaat ccctattact gtgtttattt ccctcaggtg ttttttttgga ccgttgtggt | 240 |
| caggtcatta ctaatttgac cagagacgat gaggtctaca ttgttaattt ccctcctgat | 300 |
| tgttttgagt acatcatgga gatatataca aaagcgcatg atgatttgta taatcatcct | 360 |
| gtggagaaat tttttgacag accatcaagt agctttgttt cgaatgcaaa gggattttt | 420 |
| ggactgagta gcaataattc aatttcgagc aacaatgagc aggatatttt acatcaaaag | 480 |
| cccgctatta ttgttttgag agaagacttg gattattat gtgtacctca ggaggaattt | 540 |
| cagtttgatt ccactaatga agaaaataat gaggatttat tgcgacattt tatggctcaa | 600 |
| gtgaaaatgg ctgctggcag ttatttaact tcaaaaacat cgattttcca aggtttgtat | 660 |
| tcttcgaata gactaaagca acaacagcaa caacagaaaa ttgaaaaggg gtccaattct | 720 |
| tcttcaaata ctaaatctac ttcgaaaaaa ttgggacctg ctgaacaaca tttaatggat | 780 |
| atgttgtgct cctccggatt caccaaggaa acttgttggg gtaacagaac tcaagaaact | 840 |
| ggcaaaacgg ttataagttc actgtctctt tgccgattgg ctaacgagac aactgaagga | 900 |
| tttaggcaaa aatttaacga ggctaaggct aagtgggagg cagagcacaa accttctcaa | 960 |
| gacaacttca tcaccccaat gcaatctaac atatcgatta actctttatc tgcaagtaaa | 1020 |
| tctaacagta ccatttctac agcaaggaat ttaacaagcg gaagtacagc acctgctaca | 1080 |
| gcacgtgata gagaaaaatc aaggctgtcg aaactagcag ataacgttcg ttcgcactct | 1140 |
| tcctcgagac atagttcgca gaccagaagt aaacctccgg agttgcccaa attgtatgat | 1200 |
| ctagtgccaa aacctaatat caacgctaag ctactattat tttggagaaa acctgctcgt | 1260 |
| aaatgttggt ggggtgaaga agacatagag ctagaagtgg aagtcttcgg ctcttggaaa | 1320 |
| gatgaatcaa agaaaatcat tgaattgatc ttgccaacaa acgttgatcc tgaagcagaa | 1380 |
| ctacataaaa tcattgtacc cgtccgatta catattcgta gagtttggac tttagagttg | 1440 |
| agcgttattg gggtgcaggg aagtgcagct cctggtgcat cagctgctcc aggtgctggt | 1500 |
| tctggaagtg gttcaggaat ggctagagga ccgtatgttg atttccacct aaaaaaatga | 1560 |
| agagttggca aaacaagata atagtttct ttgaagatgg gtaccctctc atgattggta | 1620 |
| caagtgattt gcaccaaagt gacgatgcgg actaaagaaa gaatataaga gttgtgttta | 1680 |

```
tctatctgga agatagaatt ctgatgagaa actttatcct tgttaagtaa cagataagca      1740
ttgcgggata tttttactaa caagagtacg tttaataatg ttaatacgat ttttcatata      1800
gaaagaagca tctaaagaga ttagcagctc cacaccattg gttattggac aagttgtccg      1860
gttgttacgc cccaagacca tctgctggtc cacacaaatt gcgtgaatcc ttgccattga      1920
ttgtctttct aagaaacaga ttaaagtatg ctttgaacgg ccgtgaagtc aaggctatct      1980
tgatgcaacg tcacgtcaaa gttgacggta aggttagaac tgacaccacc tacccagctg      2040
gtttcatgga cgtcatcact ctagatgcca ccaatgaaaa cttcagattg gtctacgatg      2100
tcaagggtag attcgctgtc caccgtatca ccgatgaaga agcctcttac aaattgggta      2160
aggtcaagaa ggtccaatta ggtaagaagg gtgttccata cgttgttacc cacgatggta      2220
gaactatcag atacccagac ccaaacatca aggtcaatga cactgttaag attgatttgg      2280
cctctggtaa gattactgat ttcatcaagt tcgatgccgg taagttggtt tacgttactg      2340
gtggtcgtaa cttgggtcgt atcggtacta tcgttcacaa ggaaagacac gatggtggtt      2400
tcgatttggt tcacatcaag gactccttgg acaacacttt cgtcactaga ttgaacaatg      2460
tcttcgtcat tggtgaacaa ggtaagcctt acatttcttt gccaaagggt aagggtatca      2520
agttgtctat tgctgaagaa cgtgacagaa gaagagctca acaaggtttg taa             2573
```

<210> SEQ ID NO 29
<211> LENGTH: 3027
<212> TYPE: DNA
<213> ORGANISM: Saccharomyces cerevisiae

<400> SEQUENCE: 29

```
atggacgata taatcacgca agtttctcca gataatgcag agtccgctcc gattctacaa       60
gaacagcaac agcaacagaa ctcacagtac gaaggtaacg aggaggatta tggtgattca      120
ttgattcatt tgaatattca agaaaaccat tatttcatta cgagggacca gttgatgtct      180
ctacctgaat ccctattact gtgtttattt ccctcaggtg tttttttgga ccgttgtggt      240
caggtcatta ctaatttgac cagagacgat gaggtctaca ttgttaattt ccctcctgat      300
tgttttgagt acatcatgga gatatataca aaagcgcatg atgatttgta taatcatcct      360
gtggagaaat tttttgacag accatcaagt agctttgttt cgaatgcaaa gggattttttt      420 ggactgagta gcaataattc aatttcgagc aacaatgagc aggatatttt acatcaaaag      480
cccgctatta ttgttttgag agaagacttg gattattatt gtgtacctca ggaggaattt      540
cagtttgatt ccactaatga agaaaataat gaggatttat tgcgacattt tatggctcaa      600
gtgaaaatgg ctgctggcag ttatttaact tcaaaaacat cgattttcca aggtttgtat      660
tcttcgaata gactaaagca acaacagcaa caacagaaaa ttgaaaaggg gtccaattct      720
tcttcaaata ctaaatctac ttcgaaaaaa ttgggacctg ctgaacaaca tttaatggat      780
atgttgtgct cctccggatt caccaaggaa acttgtgggg gtaacagaac tcaagaaact      840
ggcaaaacgg ttataagttc actgtctctt tgccgattgg ctaacgagac aactgaagga      900
tttaggcaaa aatttaacga ggctaaggct aagtgggagg cagagcacaa accttctcaa      960
gacaacttca tcacccccaat gcaatctaac atatcgatta actctttatc tgcaagtaaa     1020
tctaacagta ccatttctac agcaaggaat ttaacaagcg gaagtacagc acctgctaca     1080
gcacgtgata gagaaaaatc aaggctgtcg aaactagcag ataacgttcg ttcgcactct     1140
tcctcgagac atagttcgca gaccagaagt aaacctccgg agttgcccaa attgtatgat     1200
```

| | |
|---|---:|
| ctagtgccaa aacctaatat caacgctaag ctactattat tttggagaaa acctgctcgt | 1260 |
| aaatgttggt ggggtgaaga agacatagag ctagaagtgg aagtcttcgg ctcttggaaa | 1320 |
| gatgaatcaa agaaaatcat tgaattgatc ttgccaacaa acgttgatcc tgaagcagaa | 1380 |
| ctacataaaa tcattgtacc cgtccgatta catattcgta gagtttggac tttagagttg | 1440 |
| agcgttattg gggtgcaggg aagtgcagct cctggtgcat cagctgctcc aggtgctggt | 1500 |
| tctggaagtg gttcaggaat gctgctggac gtgaacacaa atcacacact aatgcacgat | 1560 |
| gctcatgtgc atgaacattg cctcatcaaa agcatacgtg atgatggcgc attgcactca | 1620 |
| tggagcgact catcaaaggt attttatccc aagtcatttt acgctaccgc tactaataag | 1680 |
| aagaataaca agttagccag cgccagcatg aacaagaccg ccacaagtaa taggacggtg | 1740 |
| agcgatgaga tttatttcca ctccactaag ccgcagttcg atggtcaagg aagcgctgaa | 1800 |
| cgtactagaa cactaaccaa gaggaatagc ttcaagagga ctagaatact gaaggctcga | 1860 |
| gacgattccg aactgctgaa cgaaaatcgc tcatctttga tgaccccgtc cttaagctcg | 1920 |
| gtcatgtcgc aagttaggaa aacaaattcc gccaagacgt tatcgggcga atgccccata | 1980 |
| catgagggcc acttaacaca gagcataaag aggaagttct ccgaggaagc tcaaagcgac | 2040 |
| tgttcttcat tgagctcctc taaacttcat cccttgacag atgatattgc tgacgctgtc | 2100 |
| gatttgcaga ccccccgcgat tggcgatgag gtactggctg agccggtcgt gcccaaaatg | 2160 |
| aaaataataa acataaatga tctcgatttg ttcgacgact gggaggttaa ggatttagtc | 2220 |
| gatatctttc ctcccgtata cgaacggcgt ccgcgatcgt cctctgccct ttcactggtt | 2280 |
| tctgcgtcgt ccgatgccaa acttcgtccg acctctgtgg acttccaaat catcgacaag | 2340 |
| aaaggcggca agacttcaag aaggaagagt aggagcaaat cgactacaga aaacatgatt | 2400 |
| tacgaaaatg acctggtaga attagaacaa tggccatctg catcaccatc gcccgagacc | 2460 |
| gacggttcga ttgcatctag cgagctcttg cccaataaaa gaataagaca aaaaagtttg | 2520 |
| aataccaatt tcctaaagtt atactctatt gaaacatcat gtaaaaggaa gagtattta | 2580 |
| cccgaagtcg aagtagatga ccatctgttg aagcagctaa cgtattccga aattcggtct | 2640 |
| ttggaaatca aaaaggagcc aaatgtctct acgaacgata ttaagcttgc cctaattact | 2700 |
| aggaaaaaat tatggtctga catggtccat gaaacaagaa atgatctttt tggcgattct | 2760 |
| acccctgga atttgcactt tgttgcaacg acaagcaata cggaaccttc gcaaggccgt | 2820 |
| gaatccgcaa gcgaacatgc aacggcggat ttgaaaagtt cttggtccg cgtacactca | 2880 |
| gacgtcaagc catggttcaa caatggcggc acaatgctca aaccatgcgg aaaactaaat | 2940 |
| ttaggcaaag tcaccaataa gacttccgca cctacgagag agattcaata tgtcgtaaag | 3000 |
| ggctggtgtg acagcaggtt tctctga | 3027 |

<210> SEQ ID NO 30
<211> LENGTH: 1833
<212> TYPE: DNA
<213> ORGANISM: Saccharomyces cerevisiae

<400> SEQUENCE: 30

| | |
|---|---:|
| atggtcactc aattaaaatc cgcttctgaa tacgacagtg ctttagcatc tggcgacaag | 60 |
| ttagtcgttg ttgacttttt tgccacatgg tgtgggccat gtaaaatgat tgcaccaatg | 120 |
| attgaaaagt ttgcagaaca atattctgac gctgcttttt acaagttgga tgttgatgaa | 180 |
| gtctcagatg ttgctcaaaa agctgaagtt cttccatgc ctaccctaat cttctacaag | 240 |
| ggcggtaagg aggttaccag agtcgtcggt gccaacccag ctgctatcaa gcaagctatt | 300 |

-continued

```
gcttccaacg taggaagtgc agctcctggt gcatcagctg ctccaggtgc tggttctgga    360
agtggttcag gaatggacga tataatcacg caagtttctc cagataatgc agagtccgct    420
ccgattctac aagaacagca acagcaacag aactcacagt acgaaggtaa cgaggaggat    480
tatggtgatt cattgattca tttgaatatt caagaaaacc attatttcat tacgagggac    540
cagttgatgt ctctacctga atccctatta ctgtgtttat ttccctcagg tgttttttg     600 gaccgttgtg gtcaggtcat tactaatttg accagagacg atgaggtcta cattgttaat    660
ttccctcctg attgttttga gtacatcatg gagatatata caaaagcgca tgatgatttg    720
tataatcatc ctgtggagaa atttttgac agaccatcaa gtagctttgt ttcgaatgca     780
aagggatttt ttggactgag tagcaataat tcaatttcga gcaacaatga gcaggatatt    840
ttacatcaaa agcccgctat tattgttttg agagaagact tggattatta ttgtgtacct    900
caggaggaat ttcagtttga ttccactaat gaagaaaata atgaggattt attgcgacat    960
tttatggctc aagtgaaaat ggctgctggc agttatttaa cttcaaaaac atcgattttc   1020
caaggtttgt attcttcgaa tagactaaag caacaacagc aacaacagaa aattgaaaag   1080
gggtccaatt cttcttcaaa tactaaatct acttcgaaaa aattgggacc tgctgaacaa   1140
catttaatgg atatgttgtg ctcctccgga ttcaccaagg aaacttgttg gggtaacaga   1200
actcaagaaa ctggcaaaac ggttataagt tcactgtctc tttgccgatt ggctaacgag   1260
acaactgaag gatttaggca aaaatttaac gaggctaagg ctaagtggga ggcagagcac   1320
aaaccttctc aagacaactt catcaccca atgcaatcta acatatcgat taactcttta    1380
tctgcaagta atctaacag taccattct acagcaagga atttaacaag cggaagtaca      1440
gcacctgcta cagcacgtga taagagaaaa tcaaggctgt cgaaactagc agataacgtt   1500
cgttcgcact cttcctcgag acatagttcg cagaccagaa gtaaacctcc ggagttgccc   1560
aaattgtatg atctagtgcc aaaacctaat atcaacgcta agctactatt attttggaga   1620
aaacctgctc gtaaatgttg gtggggtgaa gaagacatag agctagaagt ggaagtcttc   1680
ggctcttgga agatgaatc aaagaaaat attgaattga tcttgccaac aaacgttgat    1740
cctgaagcag aactacataa aatcattgta cccgtccgat tacatattcg tagagtttgg   1800
actttagagt tgagcgttat tggggtgcag tga                               1833
```

<210> SEQ ID NO 31
<211> LENGTH: 1965
<212> TYPE: DNA
<213> ORGANISM: Saccharomyces cerevisiae

<400> SEQUENCE: 31

```
atggactcgt actcaataac aaacgtaaaa tacctggatc cgactgaatt gcatcgttgg     60
atgcaagaag gacacactac tacgctgagg gagcctttcc aggtagtgga tgtgcgaggc    120
tcagattata tggggggcca tatcaaggac ggatggcact acgcctattc gcgccttaag    180
caggatccgg agtacttacg tgagctaaag cacagattgt tggaaaagca agcggacggc    240
cgcggagcgc tgaacgtgat tttccattgt atgttatcgc agcagcgcgg accgtctgca    300
gcgatgctgc tgcttcggtc gcttgacacg gcggaacttt ctcgctgtcg tctatgggtg    360
ttgcgtgggg ggttctcgcg ctggcaatcc gtatacggtg acgacgagag cgttacggcg    420
ggttacctac ccgatctgtg gcgtggaagt gcagctcctg gtgcatcagc tgctccaggt    480
gctggttctg gaagtggttc aggaatggac gatataatca cgcaagtttc tccagataat    540
```

```
gcagagtccg ctccgattct acaagaacag caacagcaac agaactcaca gtacgaaggt      600
aacgaggagg attatggtga ttcattgatt catttgaata ttcaagaaaa ccattatttc      660
attacgaggg accagttgat gtctctacct gaatccctat tactgtgttt atttccctca      720
ggtgtttttt tggaccgttg tggtcaggtc attactaatt tgaccagaga cgatgaggtc      780
tacattgtta atttccctcc tgattgtttt gagtacatca tggagatata tacaaaagcg      840
catgatgatt tgtataatca tcctgtggag aaattttttg acagaccatc aagtagcttt      900
gtttcgaatg caaagggatt ttttggactg agtagcaata attcaatttc gagcaacaat      960
gagcaggata ttttacatca aaagcccgct attattgttt tgagagaaga cttggattat     1020
tattgtgtac ctcaggagga atttcagttt gattccacta atgaagaaaa taatgaggat     1080
ttattgcgac attttatggc tcaagtgaaa atggctgctg gcagttattt aacttcaaaa     1140
acatcgattt tccaaggttt gtattcttcg aatagactaa agcaacaaca gcaacaacag     1200
aaaattgaaa aggggtccaa ttcttcttca aatactaaat ctacttcgaa aaaattggga     1260
cctgctgaac aacatttaat ggatatgttg tgctcctccg gattcaccaa ggaaacttgt     1320
tggggtaaca gaactcaaga aactggcaaa acggttataa gttcactgtc tctttgccga     1380
ttggctaacg agacaactga aggatttagg caaaaattta cgaggctaa ggctaagtgg      1440 gaggcagagc acaaaccttc tcaagacaac ttcatcaccc caatgcaatc taacatatcg     1500
attaactctt tatctgcaag taaatctaac agtaccattt ctacagcaag gaatttaaca     1560
agcggaagta cagcacctgc tacagcacgt gataagagaa atcaaggct gtcgaaacta      1620 gcagataacg ttcgttcgca ctcttcctcg agacatagtt cgcagaccag aagtaaacct     1680
ccggagttgc ccaaattgta tgatctagtg ccaaaaccta atatcaacgc taagctacta     1740
ttattttgga gaaaacctgc tcgtaaatgt tggtggggtg aagaagacat agagctagaa     1800
gtggaagtct tcggctcttg gaaagatgaa tcaaagaaaa tcattgaatt gatcttgcca     1860
acaaacgttg atcctgaagc agaactacat aaaatcattg tacccgtccg attacatatt     1920
cgtagagttt ggactttaga gttgagcgtt attggggtgc agtga                     1965
```

<210> SEQ ID NO 32
<211> LENGTH: 2007
<212> TYPE: DNA
<213> ORGANISM: Saccharomyces cerevisiae

<400> SEQUENCE: 32

```
atggtgatgc tccattctaa aaacgttaaa gggtttctgg aaaacacttt gaaaccgtat       60
gatttgcatt cggtagactt caagacatcg tctttgcaat cgtctatgat tataaccgcc      120
actaatgggg gtatactgtc ctatgcgacg tcaaacaacg atgtaccgaa aaattccata      180
aacgaaataa actcggtcaa taacttgaaa atgatgagct tattgattaa ggataagtgg      240
tcagaggatg aaaacgatac tgaggaacag cactccaata gctgttaccc tgtggaaatc      300
gactcctttt agacaaaaat atatacttac gaaatggaag atttacatac ctgtgtcgca      360
cagatacccg atagcgacct tttgctattg ttcattgcgg aaggtagctt cccttacgga      420
ctactggtaa ttaaaattga agagctatg agagagttga ctgatttgtt tggctacaag       480
ctaggtggaa gtgcagctcc tggtgcatca gctgctccag gtgctggttc tggaagtggt      540
tcaggaatgg acgatataat cacgcaagtt tctccagata atgcagagtc cgctccgatt      600
ctacaagaac agcaacagca acagaactca cagtacgaag gtaacgagga ggattatggt      660
gattcattga ttcatttgaa tattcaagaa aaccattatt tcattacgag ggaccagttg      720
```

| | |
|---|---|
| atgtctctac ctgaatccct attactgtgt ttatttccct caggtgtttt tttggaccgt | 780 |
| tgtggtcagg tcattactaa tttgaccaga gacgatgagg tctacattgt taatttccct | 840 |
| cctgattgtt ttgagtacat catggagata tatacaaaag cgcatgatga tttgtataat | 900 |
| catcctgtgg agaaattttt tgacagacca tcaagtagct ttgtttcgaa tgcaaaggga | 960 |
| ttttttggac tgagtagcaa taattcaatt tcgagcaaca atgagcagga tattttacat | 1020 |
| caaaagcccg ctattattgt tttgagagaa gacttggatt attattgtgt acctcaggag | 1080 |
| gaatttcagt tgattccac taatgaagaa ataatgagg atttattgcg acattttatg | 1140 |
| gctcaagtga aaatggctgc tggcagttat ttaacttcaa aaacatcgat tttccaaggt | 1200 |
| ttgtattctt cgaatagact aaagcaacaa cagcaacaac agaaaattga aaggggtcc | 1260 |
| aattcttctt caaatactaa atctacttcg aaaaaattgg gacctgctga caacacattta | 1320 |
| atggatatgt tgtgctcctc cggattcacc aaggaaactt gttggggtaa cagaactcaa | 1380 |
| gaaactggca aaacggttat aagttcactg tctctttgcc gattggctaa cgagacaact | 1440 |
| gaaggattta ggcaaaaatt taacgaggct aaggctaagt gggaggcaga gcacaaacct | 1500 |
| tctcaagaca acttcatcac cccaatgcaa tctaacatat cgattaactc tttatctgca | 1560 |
| agtaaatcta acagtaccat ttctacagca aggaatttaa caagcggaag tacagcacct | 1620 |
| gctacagcac gtgataagag aaaatcaagg ctgtcgaaac tagcagataa cgttcgttcg | 1680 |
| cactcttcct cgagacatag ttcgcagacc agaagtaaac ctccggagtt gcccaaattg | 1740 |
| tatgatctag tgccaaaacc taatatcaac gctaagctac tattattttg gagaaaacct | 1800 |
| gctcgtaaat gttggtgggg tgaagaagac atagagctag aagtggaagt cttcggctct | 1860 |
| tggaaagatg aatcaagaa aatcattgaa ttgatcttgc caacaaacgt tgatcctgaa | 1920 |
| gcagaactac ataaaatcat tgtacccgtc cgattacata ttcgtagagt ttggactta | 1980 |
| gagttgagcg ttattggggt gcagtga | 2007 |

<210> SEQ ID NO 33
<211> LENGTH: 1827
<212> TYPE: DNA
<213> ORGANISM: Saccharomyces cerevisiae

<400> SEQUENCE: 33

| | |
|---|---|
| atggcagggg atagtataag cgctgacggc actggcgtcc atccagttga actgtcggtg | 60 |
| tattcagtat tgtccaccga tttagacgga ctgtatcaat cgatcaatga attacgcgag | 120 |
| tcgcaagcac tactcatcct tatgcttcgg aaggttcgcg ataaacttcg aagagaaggt | 180 |
| caagtccttt atgacccaga accattcaaa ccaaccatgg ataaactggc tgacttatct | 240 |
| gcccgtgtgc gcattctctc acaaagatac gaggagcttc aggggaatgc tagagccctc | 300 |
| aacaacggaa gtgcagctcc tggtgcatca gctgctccag gtgctggttc tggaagtggt | 360 |
| tcaggaatgg acgatataat cacgcaagtt tctccagata tgcagagtc cgctccgatt | 420 |
| ctacaagaac agcaacagca acagaactca cagtacgaag gtaacgagga ggattatggt | 480 |
| gattcattga ttcatttgaa tattcaagaa aaccattatt tcattacgag ggaccagttg | 540 |
| atgtctctac ctgaatccct attactgtgt ttatttccct caggtgtttt tttggaccgt | 600 |
| tgtggtcagg tcattactaa tttgaccaga gacgatgagg tctacattgt taatttccct | 660 |
| cctgattgtt ttgagtacat catggagata tatacaaaag cgcatgatga tttgtataat | 720 |
| catcctgtgg agaaattttt tgacagacca tcaagtagct ttgtttcgaa tgcaaaggga | 780 |

| | |
|---|---|
| ttttttggac tgagtagcaa taattcaatt tcgagcaaca atgagcagga tattttacat | 840 |
| caaaagcccg ctattattgt tttgagagaa gacttggatt attattgtgt acctcaggag | 900 |
| gaatttcagt ttgattccac taatgaagaa aataatgagg atttattgcg acattttatg | 960 |
| gctcaagtga aaatggctgc tggcagttat ttaacttcaa aaacatcgat tttccaaggt | 1020 |
| ttgtattctt cgaatagact aaagcaacaa cagcaacaac agaaaattga aaaggggtcc | 1080 |
| aattcttctt caaatactaa atctacttcg aaaaaattgg gacctgctga acaacattta | 1140 |
| atggatatgt tgtgctcctc cggattcacc aaggaaactt gttggggtaa cagaactcaa | 1200 |
| gaaactggca aaacggttat aagttcactg tctctttgcc gattggctaa cgagacaact | 1260 |
| gaaggattta ggcaaaaatt taacgaggct aaggctaagt gggaggcaga gcacaaacct | 1320 |
| tctcaagaca acttcatcac cccaatgcaa tctaacatat cgattaactc tttatctgca | 1380 |
| agtaaatcta acagtaccat ttctacagca aggaatttaa caagcggaag tacagcacct | 1440 |
| gctacagcac gtgataagag aaaatcaagg ctgtcgaaac tagcagataa cgttcgttcg | 1500 |
| cactcttcct cgagacatag ttcgcagacc agaagtaaac ctccggagtt gcccaaattg | 1560 |
| tatgatctag tgccaaaacc taatatcaac gctaagctac tattattttg gagaaaacct | 1620 |
| gctcgtaaat gttggtgggg tgaagaagac atagagctag aagtggaagt cttcggctct | 1680 |
| tggaaagatg aatcaaagaa aatcattgaa ttgatcttgc caacaaacgt tgatcctgaa | 1740 |
| gcagaactac ataaaatcat tgtacccgtc cgattacata ttcgtagagt tttggacttta | 1800 |
| gagttgagcg ttattggggt gcagtga | 1827 |

<210> SEQ ID NO 34
<211> LENGTH: 2895
<212> TYPE: DNA
<213> ORGANISM: Saccharomyces cerevisiae

<400> SEQUENCE: 34

| | |
|---|---|
| atgggtaaag agaagtctca cattaacgtt gtcgttatcg gtcatgtcga ttctggtaag | 60 |
| tctaccacta ccggtcattt gatttacaag tgtggtggta ttgacaagag aaccatcgaa | 120 |
| aagttcgaaa aggaagccgc tgaattaggt aagggttctt tcaagtacgc ttgggttttg | 180 |
| gacaagttaa aggctgaaag agaaagaggt atcactatcg atattgcttt gtggaagttc | 240 |
| gaaactccaa agtaccaagt taccgttatt gatgctccag gtcacagaga tttcatcaag | 300 |
| aacatgatta ctggtacttc tcaagctgac tgtgctatct tgattattgc tggtggtgtc | 360 |
| ggtgaattcg aagccggtat ctctaaggat ggtcaaacca gagaacacgc tttgttggct | 420 |
| ttcaccttgg gtgttagaca attgattgtt gctgtcaaca gatggactc cgtcaaatgg | 480 |
| gacgaatcca gattccaaga aattgtcaag gaaacctcca actttatcaa gaaggttggt | 540 |
| tacaacccaa agactgttcc attcgtccca atctctggtt ggaacggtga aaacatgatt | 600 |
| gaagctacca ccaacgctcc atggtacaag ggttgggaaa aggaaaccaa ggccggtgtc | 660 |
| gtcaagggta gactttgtt ggaagccatt gacgccattg aacaaccatc tagaccaact | 720 |
| gacaagccat tgagattgcc attgcaagat gtttacaaga ttggtggtat tggtactgtg | 780 |
| ccagtcggta gagttgaaac cggtgtcatc aagccaggta tggttgttac ttttgcccca | 840 |
| gctggtgtta ccactgaagt caagtccgtt gaaatgcatc acgaacaatt ggaacaaggt | 900 |
| gttccaggtg acaacgttgg tttcaacgtc aagaacgttt ccgttaagga aatcagaaga | 960 |
| ggtaacgtct gtggtgacgc taagaacgat ccaccaaagg gttgcgcttc tttcaacgct | 1020 |
| accgtcattg ttttgaacca tccaggtcaa atctctgctg ttactctcc agtttttgat | 1080 |

```
tgtcacactg ctcacattgc ttgtagattc gacgaattgt tggaaaagaa cgacagaaga    1140
tctggtaaga agttggaaga ccatccaaag ttcttgaagt ccggtgacgc tgctttggtc    1200
aagttcgttc catctaagcc aatgtgtgtt gaagctttca gtgaataccc accattaggt    1260
agattcgctg tcagagacat gagacaaact gtcgctgtcg tgttatcaa gtctgttgac     1320 aagactgaaa aggccgctaa ggttaccaag gctgctcaaa aggctgctaa gaaaggaagt    1380
gcagctcctg gtgcatcagc tgctccaggt gctggttctg gaagtggttc aggaatggac    1440
gatataatca cgcaagtttc tccagataat gcagagtccg ctccgattct acaagaacag    1500
caacagcaac agaactcaca gtacgaaggt aacgaggagg attatggtga ttcattgatt    1560
catttgaata ttcaagaaaa ccattatttc attacgaggg accagttgat gtctctacct    1620
gaatccctat tactgtgttt atttccctca ggtgttttt tggaccgttg tggtcaggtc     1680
attactaatt tgaccagaga cgatgaggtc tacattgtta atttccctcc tgattgtttt    1740
gagtacatca tggagatata tacaaaagcg catgatgatt tgtataatca tcctgtggag    1800
aaattttttg acagaccatc aagtagcttt gtttcgaatg caaagggatt ttttggactg    1860
agtagcaata attcaatttc gagcaacaat gagcaggata ttttacatca aaagcccgct    1920
attattgttt tgagagaaga cttggattat tattgtgtac ctcaggagga atttcagttt    1980
gattccacta atgaagaaaa taatgaggat ttattgcgac attttatggc tcaagtgaaa    2040
atggctgctg gcagttattt aacttcaaaa acatcgattt tccaaggttt gtattcttcg    2100
aatagactaa agcaacaaca gcaacaacag aaaattgaaa aggggtccaa ttcttcttca    2160
aatactaaat ctacttcgaa aaaattggga cctgctgaac aacatttaat ggatatgttg    2220
tgctcctccg gattcaccaa ggaaacttgt tggggtaaca gaactcaaga aactggcaaa    2280
acggttataa gttcactgtc tctttgccga ttggctaacg agacaactga aggatttagg    2340
caaaaattta cgaggctaa ggctaagtgg gaggcagagc acaaaccttc tcaagacaac     2400
ttcatcaccc caatgcaatc taacatatcg attaactctt tatctgcaag taaatctaac    2460
agtaccattt ctacagcaag gaatttaaca agcggaagta cagcacctgc tacagcacgt    2520
gataagagaa atcaaggct gtcgaaacta gcagataacg ttcgttcgca ctcttcctcg     2580
agacatagtt cgcagaccag aagtaaacct ccggagttgc ccaaattgta tgatctagtg    2640
ccaaaaccta atatcaacgc taagctacta ttatttggga aaaacctgc tcgtaaatgt     2700 tggtggggtg aagaagacat agagctagaa gtggaagtct tcggctcttg gaaagatgaa    2760
tcaaagaaaa tcattgaatt gatcttgcca acaaacgttg atcctgaagc agaactacat    2820
aaaatcattg tacccgtccg attacatatt cgtagagttt ggactttaga gttgagcgtt    2880
attggggtgc agtga                                                      2895
```

<210> SEQ ID NO 35
<211> LENGTH: 1860
<212> TYPE: DNA
<213> ORGANISM: Saccharomyces cerevisiae

<400> SEQUENCE: 35

```
atgacaagca aacgggaaaa gtcactggat cacacattgt aagtagaagc agttttttcaa    60 tgggaagacc gcactgcata gtttactaac tatttaaact ttccaaacat tagagaacta    120
aagataccgt tgaaacgga gcgacaagcg accatagcaa ccaaagtcct atctccggac    180 ccgatttga agccacaaga ttttcaagta gactacagtt ccgagaaaaa tgtcatgcta    240
```

-continued

| | |
|---|---|
| gtccagttca gaagcattga tgatagggtg cttcgagtgg gagttagcag tatcatagac | 300 |
| agtatcaaaa ccattgtgga agccatggac gttctatcag gaagtgcagc tcctggtgca | 360 |
| tcagctgctc caggtgctgg ttctggaagt ggttcaggaa tggacgatat aatcacgcaa | 420 |
| gtttctccag ataatgcaga gtccgctccg attctacaag aacagcaaca gcaacagaac | 480 |
| tcacagtacg aaggtaacga ggaggattat ggtgattcat tgattcattt gaatattcaa | 540 |
| gaaaaccatt atttcattac gagggaccag ttgatgtctc tacctgaatc cctattactg | 600 |
| tgtttatttc cctcaggtgt tttttggac cgttgtggtc aggtcattac taatttgacc | 660 |
| agagacgatg aggtctacat tgttaatttc cctcctgatt gttttgagta catcatggag | 720 |
| atatatacaa aagcgcatga tgatttgtat aatcatcctg tggagaaatt ttttgacaga | 780 |
| ccatcaagta gctttgtttc gaatgcaaag ggatttttg gactgagtag caataattca | 840 |
| atttcgagca acaatgagca ggatatttta catcaaaagc ccgctattat tgttttgaga | 900 |
| gaagacttgg attattattg tgtacctcag gaggaaattc agtttgattc cactaatgaa | 960 |
| gaaaataatg aggatttatt gcgacatttt atggctcaag tgaaaatggc tgctggcagt | 1020 |
| tatttaactt caaaaacatc gattttccaa ggtttgtatt cttcgaatag actaaagcaa | 1080 |
| caacagcaac aacagaaaat tgaaaagggg tccaattctt cttcaaatac taaatctact | 1140 |
| tcgaaaaat tgggacctgc tgaacaacat ttaatggata tgttgtgctc ctccggattc | 1200 |
| accaaggaaa cttgttgggg taacagaact caagaaactg gcaaaacggt tataagttca | 1260 |
| ctgtctcttt gccgattggc taacgagaca actgaaggat ttaggcaaaa atttaacgag | 1320 |
| gctaaggcta gtgggaggc agagcacaaa ccttctcaag acaacttcat caccccaatg | 1380 |
| caatctaaca tatcgattaa ctctttatct gcaagtaaat ctaacagtac catttctaca | 1440 |
| gcaaggaatt taacaagcgg aagtacagca cctgctacag cacgtgataa gagaaaatca | 1500 |
| aggctgtcga aactagcaga taacgttcgt tcgcactctt cctcgagaca tagttcgcag | 1560 |
| accagaagta aacctccgga gttgcccaaa ttgtatgatc tagtgccaaa acctaatatc | 1620 |
| aacgctaagc tactattatt ttggagaaaa cctgctcgta aatgttggtg gggtgaagaa | 1680 |
| gacatagagc tagaagtgga agtcttcggc tcttggaaag atgaatcaaa gaaaatcatt | 1740 |
| gaattgatct tgccaacaaa cgttgatcct gaagcagaac tacataaaat cattgtaccc | 1800 |
| gtccgattac atattcgtag agtttggact ttagagttga gcgttattgg ggtgcagtga | 1860 |

<210> SEQ ID NO 36
<211> LENGTH: 1953
<212> TYPE: DNA
<213> ORGANISM: Saccharomyces cerevisiae

<400> SEQUENCE: 36

| | |
|---|---|
| atgggcaaga aagcacacgg aggaaagatg aaacctgaga tcgacgaaaa tggtactctg | 60 |
| ctagtaccgc caccaaggac gattgcgaac caggaccatt tccatagatt aaactacctc | 120 |
| taccaaatat ccgcttacca acaagagca agacagaaag caagaacaga cgcacatacg | 180 |
| cctttggcac gcaattatat caaatcaatg gacctaatta gtaagaaaac caagacatca | 240 |
| ctgcttccta cgataaagag aacaatttgt aaaaaatgcc atcggttgtt atggaccca | 300 |
| aaaaaactgg aaatcacatc cgacggagcg ctttcggtaa tgtgtgggtg cggtaccgtt | 360 |
| aaacgtttta atattggcgc cgatcctaat tacaggacct actcggagcg ggagggtaat | 420 |
| ctactaaatt ctggaagtgc agctcctggt gcatcagctg ctccaggtgc tggttctgga | 480 |
| agtggttcag gaatggacga tataatcacg caagtttctc cagataatgc agagtccgct | 540 |

```
ccgattctac aagaacagca acagcaacag aactcacagt acgaaggtaa cgaggaggat    600
tatggtgatt cattgattca tttgaatatt caagaaaacc attatttcat tacgagggac    660
cagttgatgt ctctacctga atccctatta ctgtgtttat ttccctcagg tgttttttg    720 gaccgttgtg gtcaggtcat tactaatttg accagagacg atgaggtcta cattgttaat    780
ttccctcctg attgttttga gtacatcatg gagatatata caaaagcgca tgatgatttg    840
tataatcatc ctgtggagaa attttttgac agaccatcaa gtagctttgt ttcgaatgca    900
aagggatttt ttggactgag tagcaataat tcaatttcga gcaacaatga gcaggatatt    960
ttacatcaaa agcccgctat tattgttttg agagaagact tggattatta ttgtgtacct   1020
caggaggaat ttcagtttga ttccactaat gaagaaaata atgaggattt attgcgacat   1080
tttatggctc aagtgaaaat ggctgctggc agttatttaa cttcaaaaac atcgattttc   1140
caaggtttgt attcttcgaa tagactaaag caacaacagc aacaacagaa aattgaaaag   1200
gggtccaatt cttcttcaaa tactaaatct acttcgaaaa aattgggacc tgctgaacaa   1260
catttaatgg atatgttgtg ctcctccgga ttcaccaagg aaacttgttg gggtaacaga   1320
actcaagaaa ctggcaaaac ggttataagt tcactgtctc tttgccgatt ggctaacgag   1380
acaactgaag gatttaggca aaaatttaac gaggctaagg ctaagtggga ggcagagcac   1440
aaaccttctc aagacaactt catcacccca atgcaatcta acatatcgat taactcttta   1500
tctgcaagta aatctaacag taccatttct acagcaagga atttaacaag cggaagtaca   1560
gcacctgcta cagcacgtga taagagaaaa tcaaggctgt cgaaactagc agataacgtt   1620
cgttcgcact cttcctcgag acatagttcg cagaccagaa gtaaacctcc ggagttgccc   1680
aaattgtatg atctagtgcc aaaacctaat atcaacgcta agctactatt attttggaga   1740
aaacctgctc gtaaatgttg gtggggtgaa gaagacatag agctagaagt ggaagtcttc   1800
ggctcttgga agatgaatc aaagaaaat attgaattga tcttgccaac aaacgttgat   1860
cctgaagcag aactacataa aatcattgta cccgtccgat tacatattcg tagagtttgg   1920
actttagagt tgagcgttat tggggtgcag tga                                 1953
```

<210> SEQ ID NO 37
<211> LENGTH: 1890
<212> TYPE: DNA
<213> ORGANISM: Saccharomyces cerevisiae

<400> SEQUENCE: 37

```
atgaaactac cggtagcaca gtacagtgca ccagatggtg tggaaaaaag ttttgcacca     60
atacgcgatg accctcgata catgaccaca gagggaagga caactgggcc cagtgaccat    120
gtgctaaacg ctggccaaat cgatagagac aaaccttcag aaccggaacg cacgaaagat    180
ggctcacaac tgacatactt aggccagctg cgcacgcagc tgacggggct acaggacgat    240
attaacgagt ttttgacagg aagaatggaa ttggcaaaaa ataagaagaa agccggcgca    300
gacgagaagc ggatccagga agagattaac cagctattag atggtggtga cggtgacgaa    360
gatgctgttg gaagtgcagc tcctggtgca tcagctgctc caggtgctgg ttctggaagt    420
ggttcaggaa tggacgatat aatcacgcaa gtttctccag ataatgcaga gtccgctccg    480
attctacaag aacagcaaca gcaacagaac tcacagtacg aaggtaacga ggaggattat    540
ggtgattcat tgattcattt gaatattcaa gaaaaccatt atttcattac gagggaccag    600
ttgatgtctc tacctgaatc cctattactg tgtttatttc cctcaggtgt tttttggac    660
```

```
cgttgtggtc aggtcattac taatttgacc agagacgatg aggtctacat tgttaatttc    720
cctcctgatt gttttgagta catcatggag atatatacaa aagcgcatga tgatttgtat    780
aatcatcctg tggagaaatt ttttgacaga ccatcaagta gctttgtttc gaatgcaaag    840
ggattttttg gactgagtag caataattca atttcgagca acaatgagca ggatatttta    900
catcaaaagc ccgctattat tgttttgaga gaagacttgg attattattg tgtacctcag    960
gaggaatttc agtttgattc cactaatgaa gaaaataatg aggatttatt gcgacatttt   1020
atggctcaag tgaaaatggc tgctggcagt tatttaactt caaaaacatc gattttccaa   1080
ggtttgtatt cttcgaatag actaaagcaa caacagcaac aacagaaaat gaaaagggg    1140
tccaattctt cttcaaatac taaatctact tcgaaaaaat gggacctgc tgaacaacat    1200
ttaatggata tgttgtgctc ctccggattc accaaggaaa cttgttgggg taacagaact   1260
caagaaactg gcaaaacggt tataagttca ctgtctcttt gccgattggc taacgagaca   1320
actgaaggat ttaggcaaaa atttaacgag gctaaggcta gtgggaggc agagcacaaa    1380
ccttctcaag acaacttcat caccccaatg caatctaaca tatcgattaa ctctttatct   1440
gcaagtaaat ctaacagtac catttctaca gcaaggaatt taacaagcgg aagtacagca   1500
cctgctacag cacgtgataa gagaaaatca aggctgtcga actagcaga taacgttcgt    1560
tcgcactctt cctcgagaca tagttcgcag accagaagta aacctccgga gttgcccaaa   1620
ttgtatgatc tagtgccaaa acctaatatc aacgctaagc tactattatt ttggagaaaa   1680
cctgctcgta atgttggtg gggtgaagaa gacatagagc tagaagtgga agtcttcggc    1740
tcttggaaag atgaatcaaa gaaaatcatt gaattgatct tgccaacaaa cgttgatcct   1800
gaagcagaac tacataaaat cattgtaccc gtccgattac atattcgtag agtttggact   1860
ttagagttga gcgttattgg ggtgcagtga                                    1890

<210> SEQ ID NO 38
<211> LENGTH: 773
<212> TYPE: DNA
<213> ORGANISM: Saccharomyces cerevisiae

<400> SEQUENCE: 38
atgtcctctg tggaatcttc ccccatctcg cgctatgaag acgaggtctt ccctctttcg     60
ttttcaaacg ttgcttttcga gccccctatg ctctcgcata gcccgacag atcgacttat    120
gccgatgact tttctcaatc ttaccagcaa gaattgctaa cttttccgct atcgtacccg    180
attgtcgatg agtcagaatg cacgcacact aaagataaga cggacagcaa cataataacg    240
agtactgaag acgattgcat gttcgatatg gaatttaacg gcaacgccgc cagtgcagtt    300
gctgctgcta gtaaggaatc taactctgcc tctgggtttg cctttgcaag taacgatgcc    360
tttgccaatg tcgcacaaca gaactacaga ctgtggttgt catcggtagg aagtgcagct    420
cctggtgcat cagctgctcc aggtgctggt tctggaagtg gttcaggaat ggttcagtac    480
gctcccttc tattaggaaa gtatgttcat tcttcatacg ctattctatt ttttttttt     540
tcacacttat tcttttacta acgcatagtt aaccatttgc tgtttcgaag aggcaacatc    600
aaacaagtcg atgtgctctt tcccaagctg gtctctattg cagattttct gatccgttat    660
tggcaattat ggtaggctgt ctcagctact atgtgtacga aggaaaatg gggcgtccac     720
aaggtcatca tttacacgag ctcataaaga agcgatggga cgatcgcaaa taa           773

<210> SEQ ID NO 39
<211> LENGTH: 2130
```

<212> TYPE: DNA
<213> ORGANISM: Saccharomyces cerevisiae

<400> SEQUENCE: 39

```
atgtcccaag gtagaaaagc tgcagaaaga ttggctaaga agactgtcct cattacaggt      60
gcatctgctg gtattggtaa ggcgaccgca ttagagtact tggaggcatc caatggtgat     120
atgaaactga tcttggctgc tagaagatta gaaaagctcg aggaattgaa gaagaccatt     180
gatcaagagt ttccaaacgc aaaagttcat gtgcccagc tggatatcac tcaagcagaa      240
aaaatcaagc ccttcattga aaacttgcca agagttca aggatattga cattctggtg        300
aacaatgccg aaaggctct tggcagtgac cgtgtgggcc agatcgcaac ggaggatatc      360
caggacgtgt ttgacaccaa cgtcacggct ttaatcaata tcacacaagc tgtactgccc     420
atattccaag ccaagaattc aggagatatt gtaaatttgg gttcaatcgc tggcagagac     480
gcatacccaa caggttctat ctattgtgcc tctaagtttg ccgtggggc gttcactgat      540
agtttgagaa aggagctcat caacactaaa attagagtca ttctaattgc accagggcta     600
gtcgagactg aattttcact agttagatac agaggtaacg aggaacaagc caagaatgtt     660
tacaaggata ctaccccatt gatggctgat gacgtggctg atctgatcgt ctatgcaact     720
tccagaaaac aaaatactgt aattgcagac actttaatct ttccaacaaa ccaagcgtca     780
cctcatcata tcttccgtgg aggaagtgca gctcctggtg catcagctgc tccaggtgct     840
ggttctggaa gtggttcagg aatgaatcag tgcgcgaagg acataactca tgaagcctcc     900
agtatacccca tcgatttgca agaaagatac tcgcactgga agaaaaacac taaactactt    960
tatgattacc taaacacgaa ttcaacaaag tggccgtcct aacgtgcca gttctttcct     1020
gatttagata ccacttcgga tgagcatcgc atcttgttat cctcatttac atcttcccaa    1080
aaacctgaag atgagaccat atatattagc aaaatatcca cgttgggtca tataaaatgg    1140
tcatctttaa ataatttcga catggacgaa atggaattca aaccggagaa ctcgacaagg    1200
tttccctcca aacacttagt aaatgacatc agtattttct tcccaaacgg ggaatgcaat    1260
agggcaagat atttgcctca aaatccagat attatagccg gcgcctcttc agatggtgca    1320
atctacatat tcgatagaac aaaacacggc tctactagaa taagacagtc caaaatttca    1380
catcccttg agacaaagct gttgggttca catggtgtta ttcaagacgt ggaggcaatg    1440
gatacttctt cggcagatat aaatgaggcg acttctttag cctggaactt gcagcaggag    1500
gccctttac tttcttctca ctccaacggc caagttcaag tttgggacat taaacaatat    1560
tcgcatgaga acctataat agatttaccc ttagtgtcaa taaacagcga cggaacagcg     1620
gtgaatgatg taacttggat gccaacacac gattccctct ttgctgcttg tactgaagga    1680
aatgcggtct ccctattaga tctgaggact aagaaagaga agctccagag taaccgtgaa    1740
aaacacgatg gtggagtaaa ctcctgtaga tttaactata agaactcttt aattctagca    1800
tctgcagatt caaatgggag gctaaattta tgggatatta gaaacatgaa caaaagccca    1860
atcgctacca tggagcacgg tacttccgtt tcaactttag aatggagtcc aaatttcgat    1920
actgtattgg caacggctgg ccaagaagat gggttagtca agctatggga tacctcctgc    1980
gaagaaacta tatttaccca tggtggtcat atgctcggtg tgaacgacat ttcgtgggac    2040
gctcatgacc cttggttaat gtgcagtgtg gcaaatgata attcagttca catatggaaa    2100
cctgcaggaa accttgttgg acattcgtga                                     2130
```

<210> SEQ ID NO 40

<211> LENGTH: 1992
<212> TYPE: DNA
<213> ORGANISM: Saccharomyces cerevisiae

<400> SEQUENCE: 40

| | | | | | |
|---|---|---|---|---|---|
| atgtctgacg | aagaacatac | ctttgaaact | gctgacgctg | gttcctccgc | cacctaccca | 60 |
| atgcaatgtt | ctgccttgag | aaagaacggt | ttcgttgtca | tcaagagtag | accatgtaag | 120 |
| attgtcgaca | tgtccacttc | taagactggt | aagcacggtc | acgctaaagt | ccatttggtt | 180 |
| gccattgata | tcttcactgg | taagaagttg | aagatttgt | ctccatctac | tcacaacatg | 240 |
| gaagttccag | ttgtcaagag | aaacgaatac | caattgttgg | acattgatga | cggtttcttg | 300 |
| tctttgatga | acatggacgg | tgacactaag | gatgatgtca | aggctccaga | aggtgaattg | 360 |
| ggtgacagtt | tgcaaactgc | ttttgatgaa | ggtaaggact | tgatggttac | catcatctcc | 420 |
| gctatgggtg | aagaagccgc | catctccttc | aaggaagctg | ctagaaccga | tggaagtgca | 480 |
| gctcctggtg | catcagctgc | tccaggtgct | ggttctggaa | gtggttcagg | aatggacgat | 540 |
| ataatcacgc | aagtttctcc | agataatgca | gagtccgctc | cgattctaca | agaacagcaa | 600 |
| cagcaacaga | actcacagta | cgaaggtaac | gaggaggatt | atggtgattc | attgattcat | 660 |
| ttgaatattc | aagaaaacca | ttatttcatt | acgagggacc | agttgatgtc | tctacctgaa | 720 |
| tccctattac | tgtgtttatt | tccctcaggt | gttttttgg | accgttgtgg | tcaggtcatt | 780 |
| actaatttga | ccagagacga | tgaggtctac | attgttaatt | tccctcctga | ttgttttgag | 840 |
| tacatcatgg | agatatatac | aaaagcgcat | gatgatttgt | ataatcatcc | tgtggagaaa | 900 |
| tttttgaca | gaccatcaag | tagctttgtt | tcgaatgcaa | agggattttt | tggactgagt | 960 |
| agcaataatt | caatttcgag | caacaatgag | caggatattt | tacatcaaaa | gcccgctatt | 1020 |
| attgttttga | gagaagactt | ggattattat | tgtgtacctc | aggaggaatt | tcagtttgat | 1080 |
| tccactaatg | aagaaaataa | tgaggattta | ttgcgacatt | ttatggctca | agtgaaaatg | 1140 |
| gctgctggca | gttattaac | ttcaaaaaca | tcgattttcc | aaggtttgta | ttcttcgaat | 1200 |
| agactaaagc | aacaacagca | acaacagaaa | attgaaaagg | ggtccaattc | ttcttcaaat | 1260 |
| actaaatcta | cttcgaaaaa | attgggacct | gctgaacaac | atttaatgga | tatgttgtgc | 1320 |
| tcctccggat | tcaccaagga | aacttgttgg | ggtaacagaa | ctcaagaaac | tggcaaaacg | 1380 |
| gttataagtt | cactgtctct | ttgccgattg | gctaacgaga | caactgaagg | atttaggcaa | 1440 |
| aaatttaacg | aggctaaggc | taagtgggag | gcagagcaca | aaccttctca | agacaacttc | 1500 |
| atcaccccaa | tgcaatctaa | catatcgatt | aactctttat | ctgcaagtaa | atctaacagt | 1560 |
| accatttcta | cagcaaggaa | tttaacaagc | ggaagtacag | cacctgctac | agcacgtgat | 1620 |
| aagagaaaat | caaggctgtc | gaaactagca | gataacgttc | gttcgcactc | ttcctcgaga | 1680 |
| catagttcgc | agaccagaag | taaacctccg | gagttgccca | aattgtatga | tctagtgcca | 1740 |
| aaacctaata | tcaacgctaa | gctactatta | ttttggagaa | aacctgctcg | taaatgttgg | 1800 |
| tggggtgaag | aagacataga | gctagaagtg | gaagtcttcg | gctcttggaa | agatgaatca | 1860 |
| aagaaaatca | ttgaattgat | cttgccaaca | aacgttgatc | ctgaagcaga | actacataaa | 1920 |
| atcattgtac | ccgtccgatt | acatattcgt | agagtttgga | ctttagagtt | gagcgttatt | 1980 |
| ggggtgcagt | ga | | | | | 1992 |

<210> SEQ ID NO 41
<211> LENGTH: 1929
<212> TYPE: DNA
<213> ORGANISM: Saccharomyces cerevisiae

<400> SEQUENCE: 41

```
atgtcctctg tggaatcttc ccccatctcg cgctatgaag acgaggtctt ccctctttcg       60
ttttcaaacg ttgctttcga gcccctatg ctctcgcata gcccggacag atcgacttat      120
gccgatgact tttctcaatc ttaccagcaa gaattgctaa cttttccgct atcgtacccg      180
attgtcgatg agtcagaatg cacgcacact aaagataaga cggacagcaa cataataacg      240
agtactgaag acgattgcat gttcgatatg gaatttaacg gcaacgccgc cagtgcagtt      300
gctgctgcta gtaaggaatc taactctgcc tctgggtttg cctttgcaag taacgatgcc      360
tttgccaatg tcgcacaaca gaactacaga ctgtggttgt catcggtagg aagtgcagct      420
cctggtgcat cagctgctcc aggtgctggt tctggaagtg gttcaggaat ggacgatata      480
atcacgcaag tttctccaga taatgcagag tccgctccga ttctacaaga acagcaacag      540
caacagaact cacagtacga aggtaacgag gaggattatg gtgattcatt gattcatttg      600
aatattcaag aaaaccatta tttcattacg agggaccagt tgatgtctct acctgaatcc      660
ctattactgt gtttatttcc ctcaggtgtt tttttggacc gttgtggtca ggtcattact      720
aatttgacca gagacgatga ggtctacatt gttaatttcc ctcctgattg ttttgagtac      780
atcatggaga tatatacaaa agcgcatgat gatttgtata atcatcctgt ggagaaattt      840
tttgacagac catcaagtag ctttgtttcg aatgcaaagg gatttttttgg actgagtagc      900
aataattcaa tttcgagcaa caatgagcag gatattttac atcaaaagcc cgctattatt      960
gttttgagag aagacttgga ttattattgt gtacctcagg aggaatttca gtttgattcc     1020
actaatgaag aaaataatga ggatttattg cgacatttta tggctcaagt gaaaatggct     1080
gctggcagtt atttaacttc aaaaacatcg attttccaag gtttgtattc ttcgaataga     1140
ctaaagcaac aacagcaaca acagaaaatt gaaaaggggt ccaattcttc ttcaaatact     1200
aaatctactt cgaaaaaatt gggacctgct gaacaacatt taatggatat gttgtgctcc     1260
tccggattca ccaaggaaac ttgttggggt aacagaactc aagaaactgg caaaacggtt     1320
ataagttcac tgtctctttg ccgattggct aacgagacaa ctgaaggatt taggcaaaaa     1380
tttaacgagg ctaaggctaa gtgggaggca gagcacaaac cttctcaaga caacttcatc     1440
accccaatgc aatctaacat atcgattaac tctttatctg caagtaaatc taacagtacc     1500
atttctacag caaggaattt aacaagcgga agtacagcac ctgctacagc acgtgataag     1560
agaaaatcaa ggctgtcgaa actagcagat aacgttcgtt cgcactcttc ctcgagacat     1620
agttcgcaga ccagaagtaa acctccggag ttgcccaaat tgtatgatct agtgccaaaa     1680
cctaatatca acgctaagct actattattt tggagaaaac ctgctcgtaa atgttggtgg     1740
ggtgaagaag acatagagct agaagtggaa gtcttcggct cttggaaaga tgaatcaaag     1800
aaaatcattg aattgatctt gccaacaaac gttgatcctg aagcagaact acataaaatc     1860
attgtacccg tccgattaca tattcgtaga gtttggactt tagagttgag cgttattggg     1920
gtgcagtga                                                             1929
```

<210> SEQ ID NO 42
<211> LENGTH: 516
<212> TYPE: DNA
<213> ORGANISM: Saccharomyces cerevisiae

<400> SEQUENCE: 42

```
atgtggagac gtcggcgcga gccctgggag gagttatctt ttcttcttaa cagcttatca       60
```

```
cccggaatt ggtttatccg agatggggt cttatggctg aagaggcca gcacctttgc    120 tggctccggt gcgcttgtga cggcccggga agtgcagctc ctggtgcatc agctgctcca    180
ggtgctggtt ctggaagtgg ttcaggaatg tctagtgaaa gagcctgtat gctgtgtggc    240
atagtgcaga ccacaaatga gtttaataga gatggttgtc ccaactgtca gggtattttt    300
gaagaggcag gtgtttctac aatggaatgt acgtcgcctt ctttcgaggg cctcgtagga    360
atgtgtaagc ctactaagtc gtgggtagca aagtggctga gcgtagatca tagtatagct    420
ggtatgtacg ccatcaaggt cgatggtaga ctaccagctg aggttgtgga gctgttgcct    480
cactacaaac cgagggatgg cagtcaagtt gagtaa    516
```

<210> SEQ ID NO 43
<211> LENGTH: 2151
<212> TYPE: DNA
<213> ORGANISM: Saccharomyces cerevisiae
<400> SEQUENCE: 43

```
atgatgagtc aagtatcgca ttcccaagaa ggatccgggc gattttggaa caagtttaag    60
tcgtcaacca aatcgttatc tacatcgttg gcacatttat ccattaaagc agaaaaagat    120
ggtgatactg taaatactac attggtccat aaagggcttg tgaaattcta tgaaaatcag    180
catcctttcc aggggttccc aggatggttg ggggagaagg aagatttacc gaacgaacgt    240
aaaatattag atactcaagt gaagcatgat atgaagaagc aaaactcgcg tcatttctcg    300
ccatcctttt ctaacagaag gaaggcttct tcagaagatc ctatgggtac accttcttca    360
aacgggaaca caccggagta cacgcctgcg agtaaatcgt ttcaagatat atacaataat    420
catacaagct cctctagcgc gacaccgaga agagcttcat cacggccgac tagaccttca    480
gcaggccaag aattcagggc aagtctcggt cgaagtaaaa cgtcgaacag tttcaacacc    540
tccagcacgc caacgccgcc accagacgca agtagtggag taatggcaat gaaggacaga    600
ctaaagagac gcaataacga ttatggattt ggaagtgcag ctcctggtgc atcagctgct    660
ccaggtgctg gttctggaag tggttcagga atggacgata taatcacgca gtttctcca    720 gataatgcag agtccgctcc gattctacaa gaacagcaac agcaacgaa ctcacagtac    780 gaaggtaacg aggaggatta tggtgattca ttgattcatt tgaatattca agaaaaccat    840
tatttcatta cgagggacca gttgatgtct ctacctgaat ccctattact gtgtttattt    900
ccctcaggtg ttttttttgga ccgttgtggt caggtcatta ctaatttgac cagagacgat    960
gaggtctaca ttgttaattt ccctcctgat tgttttgagt acatcatgga gatatataca    1020
aaagcgcatg atgatttgta taatcatcct gtggagaaat tttttgacag accatcaagt    1080
agctttgttt cgaatgcaaa gggattttttt ggactgagta gcaataattc aatttcgagc    1140
aacaatgagc aggatatttt acatcaaaag cccgctatta ttgttttgag agaagacttg    1200
gattattatt gtgtacctca ggaggaattt cagtttgatt ccactaatga gaaaataat    1260 gaggatttat tgcgacattt tatggctcaa gtgaaaatgg ctgctggcag ttatttaact    1320
tcaaaaacat cgatttttcca aggtttgtat tcttcgaata gactaaagca acaacagcaa    1380
caacagaaaa ttgaaaaggg gtccaattct tcttcaaata ctaaatctac ttcgaaaaaa    1440 ttgggaccctg ctgaacaaca tttaatggat atgttgtgct cctccggatt caccaaggaa    1500
acttgttggg gtaacagaac tcaagaaact ggcaaaacgg ttataagttc actgtctctt    1560
tgccgattgg ctaacgagac aactgaagga tttaggcaaa aatttaacga ggctaaggct    1620
aagtgggagg cagagcacaa accttctcaa gacaacttca tcaccccaat gcaatctaac    1680
```

```
atatcgatta actctttatc tgcaagtaaa tctaacagta ccatttctac agcaaggaat    1740
ttaacaagcg gaagtacagc acctgctaca gcacgtgata agagaaaatc aaggctgtcg    1800
aaactagcag ataacgttcg ttcgcactct tcctcgagac atagttcgca gaccagaagt    1860
aaacctccgg agttgcccaa attgtatgat ctagtgccaa aacctaatat caacgctaag    1920
ctactattat tttggagaaa acctgctcgt aaatgttggt ggggtgaaga agacatagag    1980
ctagaagtgg aagtcttcgg ctcttggaaa gatgaatcaa agaaaatcat tgaattgatc    2040
ttgccaacaa acgttgatcc tgaagcagaa ctacataaaa tcattgtacc cgtccgatta    2100
catattcgta gagtttggac tttagagttg agcgttattg gggtgcagtg a             2151

<210> SEQ ID NO 44
<211> LENGTH: 2235
<212> TYPE: DNA
<213> ORGANISM: Saccharomyces cerevisiae

<400> SEQUENCE: 44
atgtcccaca aattaacaat cctgccattt ctgattaagt tcacgcccaa gtttccacaa      60
tccattgatc acgacgagca tggtctaaac gtttatgcct ttgatctgga ccatacaatt    120
atcaaaccaa agtcccccaa tataagtttt agtagaagcg caagtgattg gcagtttatt    180
aattttaact ccaagaaatc caccctggat tacctgtgta atatcattga taatgatccc    240
acggccgtca tagtcatatt ttctaaccaa ggtggtgtca tcaccgtccc aagaacttct    300
aaaagttgca ccaagtacac taataaaatt ttgctatttt taaaggcaat caaaaacgat    360
gagagaggag aaacgttatc acacaggtta tggctatatg cagcacctaa aaggccgaaa    420
acttttgcag caaatcatag taagatcaca ttcgcaagct taggtgaaag ttataacaat    480
gatcctaaca tattcgaaaa agttcgaaaa ccaatgacag gaatggtaga gttttttaaa    540
agggacctgg aaagtgcata cagggtttca gaacaaattt ctcccatcaa gttgaattgg    600
atatattatt gcggtgacgc tgctgggagg aaaaaggact tcagtgattc tgacataaag    660
tttgctgaaa acttgcacgt tgaattcaag taccctgagg aaatatttca cgggggaagt    720
gcagctcctg gtgcatcagc tgctccaggt gctggttctg gaagtggttc aggaatggac    780
gatataatca cgcaagtttc tccagataat gcagagtccg ctccgattct acaagaacag    840
caacagcaac agaactcaca gtacgaaggt aacgaggagg attatggtga ttcattgatt    900
catttgaata ttcaagaaaa ccattatttc attacgaggg accagttgat gtctctacct    960
gaatccctat tactgtgttt atttccctca ggtgtttttt tggaccgttg tggtcaggtc   1020
attactaatt tgaccagaga cgatgaggtc tacattgtta atttccctcc tgattgtttt   1080
gagtacatca tggagatata tacaaaagcg catgatgatt tgtataatca tcctgtggag   1140
aaattttttg acagaccatc aagtagcttt gtttcgaatg caagggatt ttttggactg   1200 agtagcaata attcaatttc gagcaacaat gagcaggata ttttacatca aaagcccgct   1260
attattgttt tgagagaaga cttggattat tattgtgtac ctcaggagga atttcagttt   1320
gattccacta atgaagaaaa taatgaggat ttattgcgac attttatggc tcaagtgaaa   1380
atggctgctg gcagttattt aacttcaaaa acatcgattt tccaaggttt gtattcttcg   1440
aatagactaa agcaacaaca gcaacaacag aaaattgaaa aggggtccaa ttcttcttca   1500
aatactaaat ctacttcgaa aaaattggga cctgctgaac acatttaat ggatatgttg   1560 tgctcctccg gattcaccaa ggaaacttgt tggggtaaca gaactcaaga aactggcaaa   1620
```

-continued

| | |
|---|---|
| acggttataa gttcactgtc tctttgccga ttggctaacg agacaactga aggatttagg | 1680 |
| caaaaattta acgaggctaa ggctaagtgg gaggcagagc acaaaccttc tcaagacaac | 1740 |
| ttcatcaccc caatgcaatc taacatatcg attaactctt tatctgcaag taaatctaac | 1800 |
| agtaccattt ctacagcaag gaatttaaca agcggaagta cagcacctgc tacagcacgt | 1860 |
| gataagagaa aatcaaggct gtcgaaacta gcagataacg ttcgttcgca ctcttcctcg | 1920 |
| agacatagtt cgcagaccag aagtaaacct ccggagttgc ccaaattgta tgatctagtg | 1980 |
| ccaaaaccta atatcaacgc taagctacta ttattttgga gaaaacctgc tcgtaaatgt | 2040 |
| tggtggggtg aagaagacat agagctagaa gtggaagtct tcggctcttg gaaagatgaa | 2100 |
| tcaaagaaaa tcattgaatt gatcttgcca acaaacgttg atcctgaagc agaactacat | 2160 |
| aaaatcattg tacccgtccg attacatatt cgtagagttt ggactttaga gttgagcgtt | 2220 |
| attggggtgc agtga | 2235 |

<210> SEQ ID NO 45
<211> LENGTH: 2256
<212> TYPE: DNA
<213> ORGANISM: Saccharomyces cerevisiae

<400> SEQUENCE: 45

| | |
|---|---|
| atgaatcagt gcgcgaagga cataactcat gaagcctcca gtatacccat cgatttgcaa | 60 |
| gaaagatact cgcactggaa gaaaaacact aaactacttt atgattacct aaacacgaat | 120 |
| tcaacaaagt ggccgtcctt aacgtgccag ttctttcctg atttagatac cacttcggat | 180 |
| gagcatcgca tcttgttatc ctcatttaca tcttcccaaa aacctgaaga tgagaccata | 240 |
| tatattagca aaatatccac gttgggtcat ataaaatggt catctttaaa taatttcgac | 300 |
| atggacgaaa tggaattcaa accggagaac tcgacaaggt ttccctccaa acacttagta | 360 |
| aatgacatca gtattttctt cccaaacggg gaatgcaata gggcaagata tttgcctcaa | 420 |
| aatccagata ttatagccgg cgcctcttca gatggtgcaa tctacatatt cgatagaaca | 480 |
| aaacacggct actagaat aagacagtcc aaaatttcac atcccttga gacaaagctg | 540 |
| tttggttcac atggtgttat tcaagacgtg gaggcaatgg atacttcttc ggcagatata | 600 |
| aatgaggcga cttctttagc ctggaacttg cagcaggagg cccttttact ttcttctcac | 660 |
| tccaacggcc aagttcaagt ttgggacatt aaacaatatt cgcatgagaa ccctataata | 720 |
| gatttaccct tagtgtcaat aaacagcgac ggaacagcgg tgaatgatgt aacttggatg | 780 |
| ccaacacacg attccctctt tgctgcttgt actgaaggaa atgcggtctc cctattagat | 840 |
| ctgaggacta agaaagagaa gctccagagt aaccgtgaaa aacacgatgg tggagtaaac | 900 |
| tcctgtagat ttaactataa gaactcttta attctagcat ctgcagattc aaatgggagg | 960 |
| ctaaatttat gggatattag aaacatgaac aaaagcccaa tcgctaccat ggagcacggt | 1020 |
| acttccgttt caactttaga atggagtcca aatttcgata ctgtattggc aacggctggc | 1080 |
| caagaagatg ggttagtcaa gctatgggat acctcctgcg aagaaactat atttacccat | 1140 |
| ggtggtcata tgctcggtgt gaacgacatt tcgtgggacg ctcatgaccc ttggttaatg | 1200 |
| tgcagtgtgg caaatgataa ttcagttcac atatggaaac ctgcaggaaa ccttgttgga | 1260 |
| cattcgggaa gtgcagctcc tggtgcatca gctgctccag gtgctggttc tggaagtggt | 1320 |
| tcaggaatgc agggaaataa atcaactata agagagtata agatagtagt tgtcggtgga | 1380 |
| ggtggcgttg gtaaatctgc tttaacaatt caattcattc aatcatactt tgtggacgaa | 1440 |
| tatgacccta ctatcgaaga ttcttacaga aaacaagttg tcatcgatga caaagtatcc | 1500 |

```
attttggaca ttctagatac tgctggacaa gaagagtatt ctgcgatgag agaacagtac    1560
atgaggactg gggaaggttt cctactggtc tattccgtca cctctagaaa ttcctttgat    1620
gagttactgt cttattatca gcaaattcaa agagtaaaag attctgacta cattcctgta    1680
gtcgtggtag gtaacaaatt ggaccttgaa aatgaaagca aagtctctta tgaagacggg    1740
ttacgcctgg ccaagcagtt gaatgcaccc tttctagaaa cgtctgcgaa acaagccatc    1800
aacgtagacg aggcctttta tagccttatt cgtttggtaa gggacgacgg tgggaaatac    1860
aatagcatga atcgtcaact ggataatacg aatgaaataa gagattcgga gctaacctca    1920
tctgcaacag cggatagaga aaaaagaac aacgggtctt atgtactcga taattctttg    1980
accaatgctg gcactggctc cagttcaaag tcagccgtta accataacgg tgaaactact    2040
aaacgaactg atgaaaagaa ttacgttaat caaaacaata caatgaagg aaataccaag    2100 tactccagta acggcaacgg aaatcgaagt gatattagtc gtggtaatca aaataatgcc    2160
ttaaattcga gaagtaaaca gtctgctgag ccacaaaaaa attcaagcgc caacgctaga    2220
aaagaatcta gtggtggttg ttgtataatt tgttga                              2256

<210> SEQ ID NO 46
<211> LENGTH: 2013
<212> TYPE: DNA
<213> ORGANISM: Saccharomyces cerevisiae

<400> SEQUENCE: 46
atggactcgt actcaataac aaacgtaaaa tacctggatc cgactgaatt gcatcgttgg      60
atgcaagaag gacacactac tacgctgagg gagcctttcc aggtagtgga tgtgcgaggc     120
tcagattata tggggggcca tatcaaggac ggatggcact acgcctattc gcgccttaag     180
caggatccgg agtacttacg tgagctaaag cacagattgt tggaaaagca gcggacggc     240 cgcggagcgc tgaacgtgat tttccattgt atgttatcgc agcagcgcgg accgtctgca     300
gcgatgctgc tgcttcggtc gcttgacacg gcggaacttt ctcgctgtcg tctatgggtg     360
ttgcgtgggg ggttctcgcg ctggcaatcc gtatacggtg acgacgagag cgttacggcg     420
ggttacctac ccgatctgtg gcgtggaagt gcagctcctg gtgcatcagc tgctccaggt     480
gctggttctg gaagtggttc aggaatgctg ctggacgtga acacaaatca cacactaatg     540
cacgatgctc atgtgcatga acattgcctc atcaaaagca tacgtgatga tggcgcattg     600
cactcatgga gcgactcatc aaaggtattt tatcccaagt cattttacgc taccgctact     660
aataagaaga ataacaagtt agccagcgcc agcatgaaca agaccgccac aagtaatagg     720
acggtgagcg atgagattta tttccactcc actaagccgc agttcgatgg tcaaggaagc     780
gctgaacgta ctagaacact aaccaagagg aatagcttca agaggactag aatactgaag     840
gctcgagacg attccgaact gctgaacgaa atcgctcat ctttgatgac cccgtcctta     900
agctcggtca tgtcgcaagt taggaaaaca aattccgcca agacgttatc gggcgaatgc     960
cccatacatg agggccactt aacacagagc ataagagga agttctccga ggaagctcaa    1020
agcgactgtt cttcattgag ctcctctaaa cttcatccct tgacagatga tattgctgac    1080
gctgtcgatt tgcagacccc cgcgattggc gatgaggtac tggctgagcc ggtcgtgccc    1140
aaaatgaaaa taataaacat aaatgatctc gatttgttcg acgactggga ggttaaggat    1200
ttagtcgata tctttcctcc cgtatacgaa cggcgtccgc gatcgtcctc tgccctttca    1260
ctggtttctg cgtcgtccga tgccaaactt cgtccgacct ctgtggactt ccaaatcatc    1320
```

```
gacaagaaag gcggcaagac ttcaagaagg aagagtagga gcaaatcgac tacagaaaac      1380
atgatttacg aaaatgacct ggtagaatta gaacaatggc catctgcatc accatcgccc      1440
gagaccgacg gttcgattgc atctagcgag ctcttgccca ataaaagaat aagacaaaaa      1500
agtttgaata ccaatttcct aaagttatac tctattgaaa catcatgtaa aaggaagagt      1560
attttacccg aagtcgaagt agatgaccat ctgttgaagc agctaacgta ttccgaaatt      1620
cggtctttgg aaatcaaaaa ggagccaaat gtctctacga acgatattaa gcttgcccta      1680
attactagga aaaaattatg gtctgacatg gtccatgaaa caagaaatga tcttttttggc     1740 gattctaccc cctggaattt gcactttgtt gcaacgacaa gcaatacgga accttcgcaa      1800
ggccgtgaat ccgcaagcga acatgcaacg gcggatttga aaagttcttt ggtccgcgta      1860
cactcagacg tcaagccatg gttcaacaat ggcggcacaa tgctcaaacc atgcggaaaa      1920
ctaaatttag gcaaagtcac caataagact tccgcaccta cgagagagat tcaatatgtc      1980
gtaaagggct ggtgtgacag caggtttctc tga                                   2013

<210> SEQ ID NO 47
<211> LENGTH: 1704
<212> TYPE: DNA
<213> ORGANISM: Saccharomyces cerevisiae

<400> SEQUENCE: 47
atgttcagcg aattaattaa cttccaaaat gaaggtcatg agtgccaatg ccaatgtggt        60
agctgcaaaa ataatgaaca atgccaaaaa tcatgtagct gcccaacggg gtgtaacagc       120
gacgacaaat gccctgcgg taacaagtct gaagaaacca agaagtcatg ctgctctggg        180
aaaggaagtg cagctcctgg tgcatcagct gctccaggtg ctggttctgg aagtggttca       240
ggaatggacg atataatcac gcaagtttct ccagataatg cagagtccgc tccgattcta       300
caagaacagc aacagcaaca gaactcacag tacgaaggta acgaggagga ttatggtgat       360
tcattgattc atttgaatat tcaagaaaac cattatttca ttacgaggga ccagttgatg       420
tctctacctg aatccctatt actgtgttta tttccctcag gtgtttttt ggaccgttgt        480 ggtcaggtca ttactaattt gaccagagac gatgaggtct acattgttaa tttccctcct      540
gattgttttg agtacatcat ggagatatat acaaaagcgc atgatgattt gtataatcat      600
cctgtggaga aatttttga cagaccatca agtagctttg tttcgaatgc aaagggattt      660
tttggactga gtagcaataa ttcaatttcg agcaacaatg agcaggatat tttacatcaa      720
aagcccgcta ttattgtttt gagagaagac ttggattatt attgtgtacc tcaggaggaa      780
tttcagtttg attccactaa tgaagaaaat aatgaggatt tattgcgaca tttatggct      840 caagtgaaaa tggctgctgg cagttatttta acttcaaaaa catcgatttt ccaaggtttg     900
tattcttcga atagactaaa gcaacaacag caacaacaga aaattgaaaa ggggtccaat      960
tcttcttcaa atactaaatc tacttcgaaa aaattgggac ctgctgaaca acatttaatg     1020
gatatgttgt gctcctccgg attcaccaag gaaacttgtt ggggtaacag aactcaagaa     1080
actggcaaaa cggttataag ttcactgtct ctttgccgat tggctaacga gacaactgaa     1140
ggatttaggc aaaaatttaa cgaggctaag gctaagtggg aggcagagca caaaccttct     1200
caagacaact tcatcacccc aatgcaatct aacatatcga ttaactcttt atctgcaagt     1260
aaatctaaca gtaccatttc tacagcaagg aatttaacaa gcggaagtac agcacctgct     1320
acagcacgtg ataagagaaa atcaaggctg tcgaaactag cagataacgt tcgttcgcac     1380
tcttcctcga gacatagttc gcagaccaga agtaaacctc cggagttgcc caaattgtat     1440
```

```
gatctagtgc caaaacctaa tatcaacgct aagctactat tatttttggag aaaacctgct    1500 cgtaaatgtt ggtggggtga agaagacata gagctagaag tggaagtctt cggctcttgg    1560
aaagatgaat caaagaaaat cattgaattg atcttgccaa caaacgttga tcctgaagca    1620
gaactacata aaatcattgt acccgtccga ttacatattc gtagagtttg gactttagag    1680
ttgagcgtta ttggggtgca gtga                                           1704
```

<210> SEQ ID NO 48
<211> LENGTH: 1854
<212> TYPE: DNA
<213> ORGANISM: Saccharomyces cerevisiae

<400> SEQUENCE: 48

```
atgcgctggg atgttatcat cttatacgca attagccgcc catatgccac ccggcgcacc      60
gggtcgcaca cacaccccg tgattcgcga tatatagcgg ccaatcaacg gcgacctcca     120
agcgcgtgcc gggtgggccc ctcgccggcc aagcagcgca aggatattcc catcttcgag     180
ctcttagata caacgcttat aaagaacgca cttttttgcat taacctcttt tttgtattac     240
agaacaaaca ttttaacttg ccctttttta aactttcttt atctctccag acaggccaa      300 ttggataaat tttgcaaaga tcaaacagta acacaaattt tagcaaccgg aagtgcagct     360
cctggtgcat caggttctgg aagtggttca ggaatggacg atataatcac gcaagtttct     420
ccagataatg cagagtccgc tccgattcta caagaacagc aacagcaaca gaactcacag     480
tacgaaggta acgaggagga ttatggtgat tcattgattc atttgaatat tcaagaaaac     540
cattatttca ttacgaggga ccagttgatg tctctacctg aatccctatt actgtgttta     600
tttccctcag gtgtttttttt ggaccgttgt ggtcaggtca ttactaattt gaccagagac     660
gatgaggtct acattgttaa tttccctcct gattgttttg agtacatcat ggagatatat     720
acaaaagcgc atgatgattt gtataatcat cctgtggaga aatttttga cagaccatca     780 agtagctttg tttcgaatgc aaagggattt tttggactga gtagcaataa ttcaatttcg     840
agcaacaatg agcaggatat tttacatcaa aagcccgcta ttattgtttt gagagaagac     900
ttggattatt attgtgtacc tcaggaggaa tttcagtttg attccactaa tgaagaaaat     960
aatgaggatt tattgcgaca ttttatggct caagtgaaaa tggctgctgg cagttattta    1020
acttcaaaaa catcgatttt ccaaggtttg tattcttcga atagactaaa gcaacaacag    1080
caacaacaga aaattgaaaa ggggtccaat tcttcttcaa atactaaatc tacttcgaaa    1140
aaattgggac ctgctgaaca acatttaatg gatatgttgt gctcctccgg attcaccaag    1200
gaaacttgtt ggggtaacag aactcaagaa actggcaaaa cggttataag ttcactgtct    1260
ctttgccgat tggctaacga gacaactgaa ggatttaggc aaaaatttaa cgaggctaag    1320
gctaagtggg aggcagagca caaaccttct caagacaact tcatcacccc aatgcaatct    1380
aacatatcga ttaactcttt atctgcaagt aaatctaaca gtaccatttc tacagcaagg    1440
aatttaacaa gcggaagtac agcacctgct acagcacgtg ataagagaaa atcaaggctg    1500
tcgaaactag cagataacgt tcgttcgcac tcttcctcga gacatagttc gcagaccaga    1560
agtaaacctc cggagttgcc caaattgtat gatctagtgc caaaacctaa tatcaacgct    1620
aagctactat tatttttggag aaaacctgct cgtaaatgtt ggtggggtga agaagacata    1680
gagctagaag tggaagtctt cggctcttgg aaagatgaat caaagaaaat cattgaattg    1740
atcttgccaa caaacgttga tcctgaagca gaactacata aaatcattgt acccgtccga    1800
```

<210> SEQ ID NO 49
<211> LENGTH: 1689
<212> TYPE: DNA
<213> ORGANISM: Saccharomyces cerevisiae

<400> SEQUENCE: 49

```
atgttcagcg aattaattaa cttccaaaat gaaggtcatg agtgccaatg ccaatgtggt      60
agctgcaaaa ataatgaaca atgccaaaaa tcatgtagct gcccaacggg gtgtaacagc     120
gacgacaaat gccctgcgg taacaagtct gaagaaacca agaagtcatg ctgctctggg      180
aaaggaagtg cagctcctgg tgcatcaggt tctggaagtg gttcaggaat ggacgatata     240
atcacgcaag tttctccaga taatgcagag tccgctccga ttctacaaga acagcaacag     300
caacagaact cacagtacga aggtaacgag gaggattatg tgattcatt gattcatttg      360
aatattcaag aaaaccatta tttcattacg agggaccagt tgatgtctct acctgaatcc     420
ctattactgt gtttatttcc ctcaggtgtt tttttggacc gttgtggtca ggtcattact     480
aatttgacca gagacgatga ggtctacatt gttaatttcc ctcctgattg ttttgagtac     540
atcatggaga tatatacaaa agcgcatgat gatttgtata atcatcctgt ggagaaattt     600
tttgacagac catcaagtag ctttgtttcg aatgcaaagg attttttgg actgagtagc      660
aataattcaa tttcgagcaa caatgagcag atatttac atcaaaagcc cgctattatt       720
gttttgagag aagacttgga ttattattgt gtacctcagg aggaatttca gtttgattcc     780
actaatgaag aaaataatga ggattattg cgacatttta tggctcaagt gaaaatggct      840
gctggcagtt atttaacttc aaaaacatcg atttttccaag gtttgtattc ttcgaataga     900
ctaaagcaac aacagcaaca acagaaaatt gaaaagggt ccaattcttc ttcaaatact       960
aaatctactt cgaaaaaatt gggacctgct gaacaacatt taatggatat gttgtgctcc    1020
tccggattca ccaaggaaac ttgttgggggt aacagaactc aagaaactgg caaaacggtt    1080
ataagttcac tgtctctttg ccgattggct aacgagacaa ctgaaggatt taggcaaaaa    1140
tttaacgagg ctaaggctaa gtgggaggca gagcacaaac cttctcaaga caacttcatc    1200
accccaatgc aatctaacat atcgattaac tctttatctg caagtaaatc taacagtacc    1260
atttctacag caaggaattt aacaagcgga agtacagcac tgctacagc acgtgataag     1320
agaaaatcaa ggctgtcgaa actagcagat aacgttcgtt cgcactcttc ctcgagacat    1380
agttcgcaga ccagaagtaa acctccggag ttgcccaaat tgtatgatct agtgccaaaa    1440
cctaatatca acgctaagct actattattt tggagaaaac ctgctcgtaa atgttggtgg    1500
ggtgaagaag acatagagct agaagtgaa gtcttcggct cttggaaaga tgaatcaaag     1560
aaaatcattg aattgatctt gccaacaaac gttgatcctg aagcagaact acataaaatc    1620
attgtacccg tccgattaca tattcgtaga gtttggactt tagagttgag cgttattggg    1680
gtgcagtga                                                            1689
```

<210> SEQ ID NO 50
<211> LENGTH: 1980
<212> TYPE: DNA
<213> ORGANISM: Saccharomyces cerevisiae

<400> SEQUENCE: 50

```
atggtgacag ggggaatggc aagcaagtgg gatcagaagg gtatggacat tgcctatgag      60
gaggcggcct taggttacaa agagggtggt gttcctattg gcggatgtct tatcaataac     120
```

```
aaagacggaa gtgttctcgg tcgtggtcac aacatgagat ttcaaaaggg atccgccaca    180
ctacatggtg agatctccac tttggaaaac tgtgggagat tagagggcaa agtgtacaaa    240
gataccactt tgtatacgac gctgtctcca tgcgacatgt gtacaggtgc catcatcatg    300
tatggtattc cacgctgtgt tgtcggtgag aacgttaatt tcaaaagtaa gggcgagaaa    360
tatttacaaa ctagaggtca cgaggttgtt gttgttgacg atgagaggtg taaaaagatc    420
atgaaacaat ttatcgatga aagacctcag gattggtttg aagatattgg tgagggaagt    480
gcagctcctg gtgcatcagg ttctggaagt ggttcaggaa tggacgatat aatcacgcaa    540
gtttctccag ataatgcaga gtccgctccg attctacaag aacagcaaca gcaacagaac    600
tcacagtacg aaggtaacga ggaggattat ggtgattcat tgattcattt gaatattcaa    660
gaaaaccatt atttcattac gagggaccag ttgatgtctc tacctgaatc cctattactg    720
tgtttatttc cctcaggtgt ttttttggac cgttgtggtc aggtcattac taatttgacc    780
agagacgatg aggtctacat tgttaatttc cctcctgatt gttttgagta catcatggag    840
atatatacaa agcgcatga tgatttgtat aatcatcctg tggagaaatt ttttgacaga    900
ccatcaagta gctttgtttc gaatgcaaag ggatttttg gactgagtag caataattca    960
atttcgagca acaatgagca ggatatttta catcaaaagc ccgctattat tgttttgaga   1020
gaagacttgg attattattg tgtacctcag gaggaatttc agtttgattc cactaatgaa   1080
gaaaataatg aggatttatt gcgacatttt atggctcaag tgaaaatggc tgctggcagt   1140
tatttaactt caaaaacatc gatttttcaa ggtttgtatt cttcgaatag actaaagcaa   1200
caacagcaac aacagaaaat tgaaaagggg tccaattctt cttcaaatac taaatctact   1260
tcgaaaaaat tgggacctgc tgaacaacat ttaatggata tgttgtgctc ctccggattc   1320
accaaggaaa cttgttgggg taacagaact caagaaactg gcaaaacggt tataagttca   1380
ctgtctcttt gccgattggc taacgagaca actgaaggat ttaggcaaaa atttaacgag   1440
gctaaggcta gtgggaggc agagcacaaa ccttctcaag acaacttcat caccccaatg   1500
caatctaaca tatcgattaa ctctttatct gcaagtaaat ctaacagtac catttctaca   1560
gcaaggaatt taacaagcgg aagtacagca cctgctacag cacgtgataa agaaaaatca   1620
aggctgtcga aactagcaga taacgttcgt tcgcactctt cctcgagaca tagttcgcag   1680
accagaagta aacctccgga gttgcccaaa ttgtatgatc tagtgccaaa acctaatatc   1740
aacgctaagc tactattatt ttggagaaaa cctgctcgta aatgttggtg gggtgaagaa   1800
gacatagagc tagaagtgga agtcttcggc tcttggaaag atgaatcaaa gaaaatcatt   1860
gaattgatct tgccaacaaa cgttgatcct gaagcagaac tacataaaat cattgtaccc   1920
gtccgattac atattcgtag agtttggact ttagagttga gcgttattgg ggtgcagtga   1980
```

<210> SEQ ID NO 51
<211> LENGTH: 1695
<212> TYPE: DNA
<213> ORGANISM: Saccharomyces cerevisiae

<400> SEQUENCE: 51

```
atgtcttcaa actatgccac tcctttagac gatgaggtgt ttcccttatc ttttgccaat     60
tatcaattta ccgagcatgt gtcacttggt gagcattatt cactcaatac ttcggaagat    120
gccaaatata ataatttgaa tggtcctttc gtggtaccga gagacaccgg gaagttcgat    180
ttgaacacaa gttctgcctc ggacgagact gtgttctcgt tagataaccc tcaagaaaac    240
```

```
aactacaaac accaagccat gaataacgtc caggattgtc gcatggccgt cgcggccaaa    300
actacccagt cgtgtgataa attgaccgat ctttatgcca atgccgccca acaaaactac    360
agattgtggc tgtcttcatt tggaagtgca gctcctggtg catcaggttc tggaagtggt    420
tcaggaatga atcagtgcgc gaaggacata actcatgaag cctccagtat acccatcgat    480
ttgcaagaaa gatactcgca ctggaagaaa aacactaaac tactttatga ttacctaaac    540
acgaattcaa caaagtggcc gtccttaacg tgccagttct ttcctgattt agataccact    600
tcggatgagc atcgcatctt gttatcctca tttacatctt cccaaaaacc tgaagatgag    660
accatatata ttagcaaaat atccacgttg ggtcatataa aatggtcatc tttaaataat    720
ttcgacatgg acgaaatgga attcaaaccg gagaactcga caaggtttcc ctccaaacac    780
ttagtaaatg acatcagtat tttcttccca acgggggaat gcaatagggc aagatatttg    840
cctcaaaatc cagatattat agccggcgcc tcttcagatg gtgcaatcta catattcgat    900
agaacaaaac acggctctac tagaataaga cagtccaaaa tttcacatcc ctttgagaca    960
aagctgtttg gttcacatgg tgttattcaa gacgtggagg caatggatac ttcttcggca   1020
gatataaatg aggcgacttc tttagcctgg aacttgcagc aggaggccct tttactttct   1080
tctcactcca acggccaagt tcaagtttgg gacattaaac aatattcgca tgagaaccct   1140
ataatagatt taccttagt gtcaataaac agcgacggaa cagcggtgaa tgatgtaact   1200
tggatgccaa cacacgattc cctctttgct gcttgtactg aaggaaatgc ggtctcccta   1260
ttagatctga ggactaagaa agagaagctc cagagtaacc gtgaaaaaca cgatggtgga   1320
gtaaactcct gtagatttaa ctataagaac tctttaattc tagcatctgc agattcaaat   1380
gggaggctaa atttatggga tattagaaac atgaacaaaa gcccaatcgc taccatggag   1440
cacggtactt ccgtttcaac tttagaatgg agtccaaatt tcgatactgt attggcaacg   1500
gctggccaag aagatgggtt agtcaagcta tgggatacct cctgcgaaga aactatattt   1560
acccatggtg gtcatatgct cggtgtgaac gacatttcgt gggacgctca tgacccttgg   1620
ttaatgtgca gtgtggcaaa tgataattca gttcacatat ggaaacctgc aggaaaacctt   1680
gttggacatt cgtga                                                    1695

<210> SEQ ID NO 52
<211> LENGTH: 1860
<212> TYPE: DNA
<213> ORGANISM: Saccharomyces cerevisiae

<400> SEQUENCE: 52
atgcagcaca cgcttacccg gaccgcctct ctgccagaac gctcgagcag cgcccacagc    60
gccgctactg cgttacccgc acttcgccgc ccgccagaca gctgcgagac tctcgtcccg    120
ctactgtgta tcttttggtt cgtcttcgtt agtatgagcc cgctcccgcc ggctcgtgcc    180
aacaaatcag acaacaaagg cttaatctca gcagatcgta caacaaggc tactctactg    240
cttacaatac cccgttgtac atccaagtcg tatacaaatg atttatcccc actcaaaatg    300
acattgctat ccgccggcaa gcacccaagg cctttccgcc aagagcaccg ttgcggaagt    360
gcagctcctg gtgcatcagg ttctggaagt ggttcaggaa tggacgatat aatcacgcaa    420
gtttctccag ataatgcaga gtccgctccg attctacaag aacagcaaca gcaacagaac    480
tcacagtacg aaggtaacga ggaggattat ggtgattcat tgattcattt gaatattcaa    540
gaaaaccatt atttcattac gagggaccag ttgatgtctc tacctgaatc cctattactg    600
tgtttatttc cctcaggtgt tttttttggac cgttgtggtc aggtcattac taatttgacc    660
```

-continued

| | |
|---|---|
| agagacgatg aggtctacat tgttaatttc cctcctgatt gttttgagta catcatggag | 720 |
| atatatacaa aagcgcatga tgatttgtat aatcatcctg tggagaaatt ttttgacaga | 780 |
| ccatcaagta gctttgtttc gaatgcaaag ggattttttg gactgagtag caataattca | 840 |
| atttcgagca acaatgagca ggatatttta catcaaaagc ccgctattat tgttttgaga | 900 |
| gaagacttgg attattattg tgtacctcag gaggaatttc agtttgattc cactaatgaa | 960 |
| gaaaataatg aggatttatt gcgacatttt atggctcaag tgaaaatggc tgctggcagt | 1020 |
| tatttaactt caaaaacatc gattttccaa ggtttgtatt cttcgaatag actaaagcaa | 1080 |
| caacagcaac aacagaaaat tgaaaagggg tccaattctt cttcaaatac taaatctact | 1140 |
| tcgaaaaaat tgggacctgc tgaacaacat ttaatggata tgttgtgctc ctccggattc | 1200 |
| accaaggaaa cttgttgggg taacagaact caagaaactg gcaaaacggt tataagttca | 1260 |
| ctgtctcttt gccgattggc taacgagaca actgaaggat ttaggcaaaa atttaacgag | 1320 |
| gctaaggcta gtgggaggc agagcacaaa ccttctcaag acaacttcat caccccaatg | 1380 |
| caatctaaca tatcgattaa ctctttatct gcaagtaaat ctaacagtac catttctaca | 1440 |
| gcaaggaatt taacaagcgg aagtacagca cctgctacag cacgtgataa gagaaaatca | 1500 |
| aggctgtcga aactagcaga taacgttcgt tcgcactctt cctcgagaca tagttcgcag | 1560 |
| accagaagta aacctccgga gttgcccaaa ttgtatgatc tagtgccaaa acctaatatc | 1620 |
| aacgctaagc tactattatt ttggagaaaa cctgctcgta aatgttggtg gggtgaagaa | 1680 |
| gacatagagc tagaagtgga agtcttcggc tcttggaaag atgaatcaaa gaaaatcatt | 1740 |
| gaattgatct tgccaacaaa cgttgatcct gaagcagaac tacataaaat cattgtaccc | 1800 |
| gtccgattac atattcgtag agtttggact ttagagttga gcgttattgg ggtgcagtga | 1860 |

<210> SEQ ID NO 53
<211> LENGTH: 1887
<212> TYPE: DNA
<213> ORGANISM: Saccharomyces cerevisiae

<400> SEQUENCE: 53

| | |
|---|---|
| atgtcttcaa actatgccac tcctttagac gatgaggtgt ttcccttatc ttttgccaat | 60 |
| tatcaattta ccgagcatgt gtcacttggt gagcattatt cactcaatac ttcggaagat | 120 |
| gccaaatata taaatttgaa tggtcctttc gtggtaccga gagacaccgg gaagttcgat | 180 |
| ttgaacacaa gttctgcctc ggacgagact gtgttctcgt tagataaccc tcaagaaaac | 240 |
| aactacaaac accaagccat gaataacgtc caggattgtc gcatggccgt cgcggccaaa | 300 |
| actacccagt cgtgtgataa attgaccgat ctttatgcca atgccgccca acaaaactac | 360 |
| agattgtggc tgtcttcatt tggaagtgca gctcctggtg catcaggttc tggaagtggt | 420 |
| tcaggaatgg acgatataat cacgcaagtt tctccagata atgcagagtc cgctccgatt | 480 |
| ctacaagaac agcaacagca acagaactca cagtacgaag gtaacgagga ggattatggt | 540 |
| gattcattga ttcatttgaa tattcaagaa aaccattatt tcattacgag ggaccagttg | 600 |
| atgtctctac ctgaatccct attactgtgt ttatttccct caggtgtttt tttggaccgt | 660 |
| tgtggtcagg tcattactaa tttgaccaga gacgatgagg tctacattgt taatttccct | 720 |
| cctgattgtt ttgagtacat catggagata tatacaaaag cgcatgatga tttgtataat | 780 |
| catcctgtgg agaaattttt tgacagacca tcaagtagct ttgtttcgaa tgcaaaggga | 840 |
| ttttttggac tgagtagcaa taattcaatt tcgagcaaca atgagcagga tattttacat | 900 |

| | |
|---|---|
| caaaagcccg ctattattgt tttgagagaa gacttggatt attattgtgt acctcaggag | 960 |
| gaatttcagt ttgattccac taatgaagaa ataatgaggg atttattgcg acattttatg | 1020 |
| gctcaagtga aaatggctgc tggcagttat ttaacttcaa aaacatcgat tttccaaggt | 1080 |
| ttgtattctt cgaatagact aaagcaacaa cagcaacaac agaaaattga aaagggtcc | 1140 |
| aattcttctt caaatactaa atctacttcg aaaaaattgg gacctgctga caacatttta | 1200 |
| atggatatgt tgtgctcctc cggattcacc aaggaaactt gttggggtaa cagaactcaa | 1260 |
| gaaactggca aaacggttat aagttcactg tctcttttgcc gattggctaa cgagacaact | 1320 |
| gaaggattta ggcaaaaatt taacgaggct aaggctaagt gggaggcaga gcacaaacct | 1380 |
| tctcaagaca acttcatcac cccaatgcaa tctaacatat cgattaactc tttatctgca | 1440 |
| agtaaatcta acagtaccat ttctacagca aggaatttaa caagcggaag tacagcacct | 1500 |
| gctacagcac gtgataagag aaaatcaagg ctgtcgaaac tagcagataa cgttcgttcg | 1560 |
| cactcttcct cgagacatag ttcgcagacc agaagtaaac ctccggagtt gcccaaattg | 1620 |
| tatgatctag tgccaaaacc taatatcaac gctaagctac tattattttg gagaaaacct | 1680 |
| gctcgtaaat gttggtgggg tgaagaagac atagagctag aagtggaagt cttcggctct | 1740 |
| tggaaagatg aatcaaagaa aatcattgaa ttgatcttgc caacaaacgt tgatcctgaa | 1800 |
| gcagaactac ataaaatcat tgtacccgtc cgattacata ttcgtagagt ttggactta | 1860 |
| gagttgagcg ttattggggt gcagtga | 1887 |

<210> SEQ ID NO 54
<211> LENGTH: 1725
<212> TYPE: DNA
<213> ORGANISM: Saccharomyces cerevisiae

<400> SEQUENCE: 54

| | |
|---|---|
| atggcagaga taaacatta tcaattcaat gtcgtcatga cctgctcggg atgttctggt | 60 |
| gcagtcaata aagttttgac gaaattagaa ccagacgttt ccaaaataga tatatccctt | 120 |
| gaaaagcaat tagtagatgt atatactaca cttccttacg attttatttt agaaaagatt | 180 |
| aagaaaaccg gaaggaagt tagatctggc aaacaattgg gaagtgcagc tcctggtgca | 240 |
| tcaggttctg gaagtggttc aggaatggac gatataatca cgcaagtttc tccagataat | 300 |
| gcagagtccg ctccgattct acaagaacag caacagcaac agaactcaca gtacgaaggt | 360 |
| aacgaggagg attatggtga ttcattgatt catttgaata ttcaagaaaa ccattatttc | 420 |
| attacgaggg accagttgat gtctctacct gaatccctat tactgtgttt atttccctca | 480 |
| ggtgtttttt tggaccgttg tggtcaggtc attactaatt tgaccagaga cgatgaggtc | 540 |
| tacattgtta atttccctcc tgattgtttt gagtacatca tggagatata tacaaaagcg | 600 |
| catgatgatt tgtataatca tcctgtggag aaattttttg acagaccatc aagtagcttt | 660 |
| gtttcgaatg caagggatt ttttggactg agtagcaata attcaatttc gagcaacaat | 720 |
| gagcaggata ttttacatca aaagcccgct attattgttt tgagagaaga cttggattat | 780 |
| tattgtgtac ctcaggagga atttcagttt gattccacta atgaagaaaa taatgaggat | 840 |
| ttattgcgac attttatggc tcaagtgaaa atggctgctg cagttatttt aacttcaaaa | 900 |
| acatcgattt tccaaggttt gtattcttcg aatagactaa agcaacaaca gcaacaacag | 960 |
| aaaattgaaa aggggtccaa ttcttcttca aatactaaat ctacttcgaa aaaattggga | 1020 |
| cctgctgaac acatttaat ggatatgttg tgctcctccg gattcaccaa ggaaacttgt | 1080 |
| tggggtaaca gaactcaaga aactggcaaa acggttataa gttcactgtc tcttttgccga | 1140 |

```
ttggctaacg agacaactga aggatttagg caaaaattta acgaggctaa ggctaagtgg    1200
gaggcagagc acaaaccttc tcaagacaac ttcatcaccc caatgcaatc taacatatcg    1260
attaactctt tatctgcaag taaatctaac agtaccattt ctacagcaag gaatttaaca    1320
agcggaagta cagcacctgc tacagcacgt gataagagaa aatcaaggct gtcgaaacta    1380
gcagataacg ttcgttcgca ctcttcctcg agacatagtt cgcagaccag aagtaaacct    1440
ccggagttgc ccaaattgta tgatctagtg ccaaaaccta atatcaacgc taagctacta    1500
ttattttgga gaaaacctgc tcgtaaatgt tggtggggtg aagaagacat agagctagaa    1560
gtggaagtct tcggctcttg gaaagatgaa tcaagaaaaa tcattgaatt gatcttgcca    1620
acaaacgttg atcctgaagc agaactacat aaaatcattg tacccgtccg attacatatt    1680
cgtagagttt ggactttaga gttgagcgtt attggggtgc agtga                    1725
```

<210> SEQ ID NO 55
<211> LENGTH: 2763
<212> TYPE: DNA
<213> ORGANISM: Saccharomyces cerevisiae

<400> SEQUENCE: 55

```
atgtctgaag ctcaagaaac tcacgtagag caactaccag aatctgttgt cgatgcccca      60
gtcgaagaac agcaccaaga accaccacag gctccagatg ctccacaaga accacaagtt     120
ccacaggaat ctgctccaca ggaatctgct ccacaagaac caccagctcc acaagaacaa     180
aatgacgttc ctccaccatc taatgctcca atttatgaag gcgaagaatc ccacagtgtc     240
caagactacc aagaggccca ccagcaccac caaccacctg aaccccaacc atattatcct     300
cctcctcctc caggtgaaca catgcacggt cgcccaccaa tgcaccaccg tcaagaagga     360
gaactctcga caccagatt gtttgttaga cctttcccat ggacgttca agaatccgag       420 ttgaatgaaa tctttggtcc atttggacca atgaaggaag tcaagatctt gaacggcttc     480
gcgtttgttg aatttgaaga agcagaatcc gctgccaaag ccattgaaga agttcacggt     540
aagagttttg ctaaccaacc tttggaagtt gtttactcta aattgcctgc caagagatac     600
cgtatcacca tgaaaaactt accagaaggt tgttcatggc aagatcttaa agatttagcc     660
agggaaaata gtttagaaac tacttttct agcgtcaata ccagagattt tgatggtacc      720
ggtgctctag aattccctag tgaagaaatc ttggtcgaag ctttggagag attaaacaat     780
attgaattca gaggttctgt cattactgtt gaaagagatg acaatcctcc accaatcaga     840
agatcaaata gaggtggctt cagaggtcgc ggcggcttca gaggcggctt cagaggtggc     900
ttcagaggcg gtttctccag aggcggcttc ggtggcccca gaggtggatt tggtggtcca     960
agaggtggtt acggtggcta ttccagaggt ggctacggtg gctactccag aggcggatat    1020
ggtggctcca gaggtggtta cgatagtcct agaggtggtt acgatagtcc aagaggtggt    1080
tattccagag gtggctatgg tggtccaaga aatgattacg gtcctccaag aggtagctac    1140
ggtggttcaa gaggtggtta tgatggtcca agaggcgatt atggtcctcc aagagatgca    1200
tacagaacca gagatgctcc acgtgaaaga tcaccaacca ggggaagtgc agctcctggt    1260
gcatcagctg ctccaggtgc tggttctgga agtggttcag gaatgacga tataatcacg    1320 caagtttctc cagataatgc agagtccgct ccgattctac aagaacagca acagcaacag    1380
aactcacagt acgaaggtaa cgaggaggat tatggtgatt cattgattca tttgaatatt    1440
caagaaaacc attatttcat tacgagggac cagttgatgt ctctacctga atccctatta    1500
```

```
ctgtgtttat tccctcagg tgttttttg gaccgttgtg gtcaggtcat tactaatttg     1560
accagagacg atgaggtcta cattgttaat ttccctcctg attgttttga gtacatcatg    1620
gagatatata caaaagcgca tgatgatttg tataatcatc ctgtggagaa attttttgac    1680
agaccatcaa gtagctttgt ttcgaatgca aagggatttt ttggactgag tagcaataat    1740
tcaatttcga gcaacaatga gcaggatatt ttacatcaaa agcccgctat tattgttttg    1800
agagaagact tggattatta ttgtgtacct caggaggaat ttcagtttga ttccactaat    1860
gaagaaaata tgaggatttt attgcgacat tttatggctc aagtgaaaat ggctgctggc    1920
agttatttaa cttcaaaaac atcgattttc caaggtttgt attcttcgaa tagactaaag    1980
caacaacagc aacaacagaa aattgaaaag gggtccaatt cttcttcaaa tactaaatct    2040
acttcgaaaa aattgggacc tgctgaacaa catttaatgg atatgttgtg ctcctccgga    2100
ttcaccaagg aaacttgttg gggtaacaga actcaagaaa ctggcaaaac ggttataagt    2160
tcactgtctc tttgccgatt ggctaacgag acaactgaag gatttaggca aaaatttaac    2220
gaggctaagg ctaagtggga ggcagagcac aaaccttctc aagacaactt catcacccca    2280
atgcaatcta acatatcgat taactcttta tctgcaagta aatctaacag taccatttct    2340
acagcaagga atttaacaag cggaagtaca gcacctgcta cagcacgtga taagagaaaa    2400
tcaaggctgt cgaaactagc agataacgtt cgttcgcact cttcctcgag acatagttcg    2460
cagaccagaa gtaaacctcc ggagttgccc aaattgtatg atctagtgcc aaaacctaat    2520
atcaacgcta agctactatt attttggaga aaacctgctc gtaaatgttg gtggggtgaa    2580
gaagacatag agctagaagt ggaagtcttc ggctcttgga agatgaatc aaagaaaatc    2640
attgaattga tcttgccaac aaacgttgat cctgaagcag aactacataa aatcattgta    2700
cccgtccgat tacatattcg tagagtttgg actttagagt tgagcgttat tggggtgcag    2760
tga                                                                  2763

<210> SEQ ID NO 56
<211> LENGTH: 2170
<212> TYPE: DNA
<213> ORGANISM: Saccharomyces cerevisiae

<400> SEQUENCE: 56
atggacgata taatcacgca gtttctcca gataatgcag agtccgctcc gattctacaa      60
gaacagcaac agcaacagaa ctcacagtac gaaggtaacg aggaggatta tggtgattca    120
ttgattcatt tgaatattca agaaaaccat tatttcatta cgagggacca gttgatgtct    180
ctacctgaat ccctattact gtgtttattt ccctcaggtg ttttttggga ccgttgtggt    240
caggtcatta ctaatttgac cagagacgat gaggtctaca ttgttaattt cctcctgat    300
tgttttgagt acatcatgga gatatataca aaagcgcatg atgatttgta taatcatcct    360
gtggagaaat ttttgacag accatcaagt agctttgttt cgaatgcaaa gggatttttt    420
ggactgagta gcaataattc aatttcgagc aacaatgagc aggatatttt acatcaaaag    480
cccgctatta ttgttttgag agaagacttg gattattatt gtgtacctca ggaggaattt    540
cagtttgatt ccactaatga agaaaataat gaggattat tgcgacattt tatggctcaa    600
gtgaaaatgg ctgctggcag ttatttaact tcaaaaacat cgattttcca aggtttgtat    660
tcttcgaata gactaaagca acaacagcaa caacagaaa ttgaaaaggg gtccaattct    720
tcttcaaata ctaaatctac ttcgaaaaaa ttgggacctg ctgaacaaca tttaatggat    780
atgttgtgct cctccggatt caccaaggaa acttgttggg gtaacagaac tcaagaaact    840
```

```
ggcaaaacgg ttataagttc actgtctctt tgccgattgg ctaacgagac aactgaagga    900
tttaggcaaa aatttaacga ggctaaggct aagtgggagg cagagcacaa accttctcaa    960
gacaacttca tcaccccaat gcaatctaac atatcgatta actctttatc tgcaagtaaa   1020
tctaacagta ccatttctac agcaaggaat ttaacaagcg gaagtacagc acctgctaca   1080
gcacgtgata agagaaaatc aaggctgtcg aaactagcag ataacgttcg ttcgcactct   1140
tcctcgagac atagttcgca gaccagaagt aaacctccgg agttgcccaa attgtatgat   1200
ctagtgccaa aacctaatat caacgctaag ctactattat tttggagaaa acctgctcgt   1260
aaatgttggt ggggtgaaga agacatagag ctagaagtgg aagtcttcgg ctcttggaaa   1320
gatgaatcaa agaaaatcat tgaattgatc ttgccaacaa acgttgatcc tgaagcagaa   1380
ctacataaaa tcattgtacc cgtccgatta catattcgta gagtttggac tttagagttg   1440
agcgttattg gggtgcaggg aagtgcagct cctggtgcat cagctgctcc aggtgctggt   1500
tctggaagtg gttcaggaat ggtagtatcc atcataccgc aatttcctga tatcaaggtt   1560
tcactagcat tgtttgaaca ggttaaaaat gctaaagaaa tacgctctaa aatgagtgaa   1620
ttgtcgacat cctttgcctt tattgacccc cggttagtct gttcggggga gcagatgtat   1680
tctgcaattt acaagacctt aatagaagtg aaatataaca agatgagaac aagaaatttg   1740
aattccgagt gcgtactatg tctttcaccc acttccaata ttagtgatgc tttcctcaaa   1800 tcggaatca aagacgattc gtcacagtta atatgcctta agttccatac taatactgac   1860
gatgtagaca aagagcaatt gaggacgatt atgacttcta tagtaaaagg acaagagatc   1920
gagtttaatg atgacaattt atcgagattt tatgacgaag cgctcataag aaaagtatgt   1980
tttaataata aattcgaggt aaaaacttca acagcctcac cagaaacaca ttgtactaac   2040
ttcacctttg tttccttttt attttgtttt tacctattag atctataaat taagtgatga   2100
tttcaagccc caagacgtaa atggtctctc aagagctttg gtagacgcta ttcaattgag   2160
gggtgtgtag                                                          2170

<210> SEQ ID NO 57
<211> LENGTH: 960
<212> TYPE: DNA
<213> ORGANISM: Saccharomyces cerevisiae

<400> SEQUENCE: 57
atgcgccgcc tatatcgtca tcttgcttcc tttttcttac tcccttcctg ccctggaaac     60
accatacaat ccatcacatc atatcctgcc aatgcactat tacgcagctt tcggcacgtg    120
agtacggaaa caccagttcg gaaccgggta cacaataggg atagtcaaag ctgtccattt    180
tttccgctga tggatgacgg aagtgcagct cctggtgcat cagctgctcc aggtgctggt    240
tctggaagtg gttcaggaat gttcgcgaaa acagcagctg ctaatttaac caagaagggt    300
ggtttgtcat tgctctccac cacagcaagg agaaccaaag tcaccttgcc agacttgaag    360
tgggacttcg gtgcattgga accttatatc tccggtcaaa tcaacgaatt gcattacacc    420
aagcaccatc aaacttatgt gaacggattc aacactgctg ttgaccaatt ccaagaactc    480
tcagatcttc tggccaagga gccctctccc gcaaacgcaa gaaaaatgat tgctatccaa    540
caaaacatca gttccatggc cgtggtttc acaaaccact gtctattctg ggaaaacctg    600
gctccagagt cgcagggcgg tggtgaacca cccaccggcg cttttggcaaa ggcaatcgac    660 gagcagtttg gcagtctgga cgagctgatt aagttgacca acacaaagct agcaggcgtg    720
```

| | |
|---|---|
| cagggctccg gatgggcctt cattgtgaaa aacctctcta atggaggcaa gctggacgtt | 780 |
| gttcaaacct acaaccagga taccgtcaca ggcccactag ttcctctagt tgccattgac | 840 |
| gcctgggaac acgcctacta cttgcagtac caaaacaaga aagccgacta cttcaaagcc | 900 |
| atttggaatg tggtcaactg gaaagaagca tccagaagat tcgatgctgg caagatctga | 960 |

<210> SEQ ID NO 58
<211> LENGTH: 981
<212> TYPE: DNA
<213> ORGANISM: Saccharomyces cerevisiae

<400> SEQUENCE: 58

| | |
|---|---|
| atggccagca tagacgcatt ttcggacctt gagcgccgga tggacgggtt ccaaaaggac | 60 |
| gtggcccagg tactggcacg tcagcaaaac cacgcgcgcc aacagctgca acagttccaa | 120 |
| gcggaaatgc gtcaattaca taaccaacac caacatctca tagatgaact gcaacggctt | 180 |
| gccacccagc gcaccgctct gcagcaacaa atacatgcgg cccaacaagc tacaaatacc | 240 |
| accagagagc agtggagaag ctatcacgag cgtgaatctg agttatctag acggcagtcg | 300 |
| accttagcag cccaatcgcg cgagctggac tcgctgctgc aacagcgtgg taaagagtgt | 360 |
| gtccaattac gcgcacgttg ggctgcgcag tcgggtaacg atgccgcaga ggtcgcactg | 420 |
| tacgaacggc tgttgcagct tcgtgtacta cccggagcca gcgatgtgca tgacgtacgt | 480 |
| ttcgtattcg gcgatgattc acgctgctgg atcgaagtcg cgatgcacgg agaccacgtg | 540 |
| atcggaaact ctcacccggc gctggacccc aagagtcggg caacacttga gcacgtgctt | 600 |
| accgtccagg gcgacctcgc ggcattttta gtcgtggccc gcgatatgct tctggcatct | 660 |
| ttaggaagtg cagctcctgg tgcatcagct gctccaggtg ctggttctgg aagtggttca | 720 |
| ggaatgattc tcgctttggg cgacttcctg cctaaacagg aagacaaagc atgcgagagg | 780 |
| ccctgggttc aattcccagc tcgccccgtt atcttttttc accatcaggg cggaattttt | 840 |
| ttgtttagca tcaatcaacc taacctctca tgcttctcca agctgaaaga agtaaaactca | 900 |
| ctctatgtac gtgttgcaac atatatctgc caaaagaatg aaagtaggtt cagaacaaac | 960 |
| agattgaaag gagaccagta a | 981 |

<210> SEQ ID NO 59
<211> LENGTH: 1206
<212> TYPE: DNA
<213> ORGANISM: Saccharomyces cerevisiae

<400> SEQUENCE: 59

| | |
|---|---|
| atgcgccgcc tatatcgtca tcttgcttcc tttttcttac tcccttcctg ccctggaaac | 60 |
| accatacaat ccatcacatc atatcctgcc aatgcactat tacgcagctt tcggcacgtg | 120 |
| agtacggaaa caccagttcg gaaccgggta cacaataggg atagtcaaag ctgtccattt | 180 |
| tttccgctga tggatgacgg aagtgcagct cctggtgcat cagctgctcc aggtgctggt | 240 |
| tctggaagtg gttcaggaat gggaaggaca tttattcatg cttcgaaaat aaaacatgcg | 300 |
| gcacgcaaaa gaaaacatca ttccaacttt agaactctga tcaaattatt gaacaatgat | 360 |
| gcctataaga tagaatcatc aaaaccgttg aaaaatggta aactttttcaa atactggaaa | 420 |
| aataggcgta gattgttttc aaagatagat tcggcgtcga tatatatgac tgatgagctg | 480 |
| tggttcagtg tgacgcccga aagaattgcc tgcttcctgg caaattttgt taaggcatgc | 540 |
| atgccaaatg ccgaaagaat actggatgtt ttctgtggtg ggggcgggaa caccatacaa | 600 |
| tttgccatgc aatttcctta cgtctatgga gtggactaca gtattgaaca catatattgt | 660 |

| | |
|---|---|
| actgcgaaaa acgcccaaag ctacggtgtg gacgacagaa tatggctgaa gcggggatcc | 720 |
| tggaaaaagc tagtctctaa gcagaaactt tccaaaataa agtacgactg tgtatttgga | 780 |
| tcaccccgt ggggtggtcc agaatactta agaaacgatg tgtatgactt agagcaacat | 840 |
| ctaaagccta tgggattac caagatgttg aaaagttttc ttaaactaag ccctaatgtg | 900 |
| attatgtttt tgccaaggaa ctctgatttg aaccagcttt ctcgagctac gaggaaagta | 960 |
| ctaggtccat ttgccaaatg taaagtatta tatgtaaagg agaatggata tatgaaagga | 1020 |
| atattttgca tgtgggggga atgcttttt aactacgaac cagcaagtac ggagaatagt | 1080 |
| cgaagggagt cgtccgaaaa ggaagagctg agttctgaaa acgaagagct ctcgaaaaga | 1140 |
| aaaaagcatg aatccacaac aacgaccaaa gataatactg tagacattta cgacgtaaat | 1200 |
| ggttaa | 1206 |

<210> SEQ ID NO 60
<211> LENGTH: 2220
<212> TYPE: DNA
<213> ORGANISM: Saccharomyces cerevisiae

<400> SEQUENCE: 60

| | |
|---|---|
| atgggagtga agcaaacccc accagtccag gtgaaagtaa gcgacgcgga ttccaccaac | 60 |
| agaaggaaat ctagtagcca ggaaggaaac cctcagctgg ttcaattaaa ggcaaagagc | 120 |
| gacaaagata aagaaaggg atcttcagat tccactgcct ctataatggg cagttccaac | 180 |
| gcacttccga ccaaaaacct aaccacgcct ccagcactaa accccttaac gaccagcatt | 240 |
| agtaggggta atactgcata cgaaagaagc gtaaatggta gccgtataac aatgcactca | 300 |
| aacctggcac ctacggagac gcaagacgta tcatggtctg aaatcgatac actggatgat | 360 |
| gtgaagaaga tggcgaaaga acctatcgtc aacgacgggt tcccacgaga ttttgagagc | 420 |
| aatctcacgc aaatgcgcaa gtcgcacgct caactactgc gattaatgag ggaaagaaat | 480 |
| cagcgactaa agtatgccaa gctgaggagc cctcctcata aggatcagca taattctgcc | 540 |
| acgaataaag atcaagaacc agacgaggta ttgcatgacc cggaaatcgc acttgacggt | 600 |
| gagaagtacg tgagccaagt tgtcgatact attaaagatg ttcaccgatg cggaagtgca | 660 |
| gctcctggtg catcagctgc tccaggtgct ggttctggaa gtggttcagg aatgctgctg | 720 |
| gacgtgaaca caaatcacac actaatgcac gatgctcatg tgcatgaaca ttgcctcatc | 780 |
| aaaagcatac gtgatgatgg cgcattgcac tcatggagcg actcatcaaa ggtattttat | 840 |
| cccaagtcat tttacgctac cgctactaat aagaagaata acaagttagc cagcgccagc | 900 |
| atgaacaaga ccgccacaag taataggacg gtgagcgatg agatttattt ccactccact | 960 |
| aagccgcagt cgatggtca aggaagcgct gaacgtacta gaacactaac caagaggaat | 1020 |
| agcttcaaga ggactagaat actgaaggct cgagacgatt ccgaactgct gaacgaaaat | 1080 |
| cgctcatctt tgatgacccc gtccttaagc tcggtcatgt cgcaagttag gaaaacaaat | 1140 |
| tccgccaaga cgttatcggg cgaatgcccc atacatgagg gccacttaac acagagcata | 1200 |
| aagaggaagt tctccgagga agctcaaagc gactgttctt cattgagctc ctctaaactt | 1260 |
| catcccttga cagatgatat tgctgacgct gtcgatttgc agaccccgc gattggcgat | 1320 |
| gaggtactgg ctgagccggt cgtgcccaaa atgaaaataa taaacataaa tgatctcgat | 1380 |
| ttgttcgacg actgggaggt taaggattta gtcgatatct ttcctcccgt atacgaacgg | 1440 |
| cgtccgcgat cgtcctctgc cctttcactg gtttctgcgt cgtccgatgc caaacttcgt | 1500 |

```
ccgacctctg tggacttcca aatcatcgac aagaaaggcg gcaagacttc aagaaggaag   1560
agtaggagca aatcgactac agaaaacatg atttacgaaa atgacctggt agaattagaa   1620
caatggccat ctgcatcacc atcgcccgag accgacggtt cgattgcatc tagcgagctc   1680
ttgcccaata aaagaataag acaaaaaagt ttgaatacca atttcctaaa gttatactct   1740
attgaaacat catgtaaaag gaagagtatt ttacccgaag tcgaagtaga tgaccatctg   1800
ttgaagcagc taacgtattc cgaaattcgg tctttggaaa tcaaaaagga gccaaatgtc   1860
tctacgaacg atattaagct tgccctaatt actaggaaaa aattatggtc tgacatggtc   1920
catgaaacaa gaaatgatct tttttggcgat tctaccccct ggaatttgca ctttgttgca   1980
acgacaagca atacggaacc ttcgcaaggc cgtgaatccg caagcgaaca tgcaacggcg   2040
gatttgaaaa gttctttggt ccgcgtacac tcagacgtca agccatggtt caacaatggc   2100
ggcacaatgc tcaaaccatg cggaaaacta aatttaggca aagtcaccaa taagacttcc   2160
gcacctacga gagagattca atatgtcgta aagggctggt gtgacagcag gtttctctga   2220
```

<210> SEQ ID NO 61
<211> LENGTH: 1827
<212> TYPE: DNA
<213> ORGANISM: Saccharomyces cerevisiae

<400> SEQUENCE: 61

```
atgtccggaa aagcttctac agagggtagc gttactacgg agtttctctc tgatatcatt     60
ggtaagacag tgaacgtcaa acttgcctcg ggtttactct acagcggaag attggaatcc    120
attgatggtt ttatgaatgt tgcactatcg agtgccactg aacactacga gagtaataac    180
aataagcttc taaataagtt caatagtgat gtcttttttga ggggcacgca ggtcatgtat    240
atcagtgaac aaaaaatagg aagtgcagct cctggtgcat cagctgctcc aggtgctggt    300
tctggaagtg gttcaggaat gctgctggac gtgaacacaa atcacacact aatgcacgat    360
gctcatgtgc atgaacattg cctcatcaaa agcatacgtg atgatggcgc attgcactca    420
tggagcgact catcaaaggt atttttatccc aagtcatttt acgctaccgc tactaataag    480
aagaataaca agttagccag cgccagcatg aacaagaccg ccacaagtaa taggacggtg    540
agcgatgaga tttatttcca ctccactaag ccgcagttcg atggtcaagg aagcgctgaa    600
cgtactagaa cactaaccaa gaggaatagc ttcaagagga ctagaatact gaaggctcga    660
gacgattccg aactgctgaa cgaaaatcgc tcatctttga tgaccccgtc cttaagctcg    720
gtcatgtcgc aagttaggaa aacaaattcc gccaagacgt tatcgggcga atgccccata    780
catgagggcc acttaacaca gagcataaag aggaagttct ccgaggaagc tcaaagcgac    840
tgttcttcat tgagctcctc taaacttcat cccttgacag atgatattgc tgacgctgtc    900
gatttgcaga ccccccgcgat tggcgatgag gtactggctg agccggtcgt gcccaaaatg    960
aaaataataa acataaatga tctcgatttg ttcgacgact gggaggttaa ggatttagtc   1020
gatatctttc ctcccgtata cgaacggcgt ccgcgatcgt cctctgccct ttcactggtt   1080
tctgcgtcgt ccgatgccaa acttcgtccg acctctgtgg acttccaaat catcgacaag   1140
aaaggcggca agacttcaag aaggaagagt aggagcaaat cgactacaga aacatgatt    1200 tacgaaaatg acctggtaga attagaacaa tggccatctg catcaccatc gcccgagacc   1260
gacggttcga ttgcatctag cgagctcttg cccaataaaa gaataagaca aaaaagtttg   1320
aataccaatt tcctaaagtt atactctatt gaaacatcat gtaaaggaa gagtatttta   1380 cccgaagtcg aagtagatga ccatctgttg aagcagctaa cgtattccga aattcggtct   1440
```

```
ttggaaatca aaaaggagcc aaatgtctct acgaacgata ttaagcttgc cctaattact   1500
aggaaaaaat tatggtctga catggtccat gaaacaagaa atgatctttt tggcgattct   1560
accccctgga atttgcactt tgttgcaacg acaagcaata cggaaccttc gcaaggccgt   1620
gaatccgcaa gcgaacatgc aacggcggat ttgaaaagtt ctttggtccg cgtacactca   1680
gacgtcaagc catggttcaa caatggcggc acaatgctca aaccatgcgg aaaactaaat   1740
ttaggcaaag tcaccaataa gacttccgca cctacgagag agattcaata tgtcgtaaag   1800
ggctggtgtg acagcaggtt tctctga                                      1827
```

<210> SEQ ID NO 62
<211> LENGTH: 1827
<212> TYPE: DNA
<213> ORGANISM: Saccharomyces cerevisiae

<400> SEQUENCE: 62

```
atgtctagtg aaagagcctg tatgctgtgt ggcatagtgc agaccacaaa tgagtttaat     60
agagatggtt gtcccaactg tcagggtatt tttgaagagg caggtgtttc tacaatggaa    120
tgtacgtcgc cttcttcga  gggcctcgta ggaatgtgta agcctactaa gtcgtgggta    180
gcaaagtggc tgagcgtaga tcatagtata gctggtatgt acgccatcaa ggtcgatggt    240
agactaccag ctgaggttgt ggagctgttg cctcactaca aaccgaggga tggcagtcaa    300
gttgagggaa gtgcagctcc tggtgcatca gctgctccag gtgctggttc tggaagtggt    360
tcaggaatgg acgatataat cacgcaagtt tctccagata atgcagagtc cgctccgatt    420
ctacaagaac agcaacagca acagaactca cagtacgaag gtaacgagga ggattatggt    480
gattcattga ttcatttgaa tattcaagaa aaccattatt tcattacgag ggaccagttg    540
atgtctctac ctgaatccct attactgtgt ttatttccct caggtgtttt tttggaccgt    600
tgtggtcagg tcattactaa tttgaccaga gacgatgagg tctacattgt taatttccct    660
cctgattgtt ttgagtacat catggagata tatacaaaag cgcatgatga tttgtataat    720
catcctgtgg agaaatttt  tgacagacca tcaagtagct ttgtttcgaa tgcaaaggga    780
ttttttggac tgagtagcaa taattcaatt tcgagcaaca atgagcagga tattttacat    840
caaaagcccg ctattattgt tttgagagaa gacttggatt attattgtgt acctcaggag    900
gaatttcagt tgattccac  taatgaagaa ataatgagg attattgcg  acatttttatg    960 gctcaagtga aatggctgc  tggcagttat ttaacttcaa aacatcgat  tttccaaggt   1020 ttgtattctt cgaatagact aaagcaacaa cagcaacaac agaaaattga aaagggtcc   1080 aattcttctt caaatactaa atctacttcg aaaaaattgg gacctgctga caacatttta   1140
atggatatgt tgtgctcctc cggattcacc aaggaaactt gttggggtaa cagaactcaa   1200
gaaactggca aaacggttat aagttcactg tctctttgcc gattggctaa cgagacaact   1260
gaaggattta ggcaaaaatt taacgaggct aaggctaagt gggaggcaga gcacaaacct   1320
tctcaagaca acttcatcac cccaatgcaa tctaacatat cgattaactc tttatctgca   1380
agtaaatcta acagtaccat ttctacagca aggaatttaa caagcggaag tacagcacct   1440
gctacagcac gtgataagag aaaatcaagg ctgtcgaaac tagcagataa cgttcgttcg   1500
cactcttcct cgagacatag ttcgcagacc agaagtaaac ctccggagtt gcccaaattg   1560
tatgatctag tgccaaaacc taatatcaac gctaagctac tattattttg gagaaaacct   1620
gctcgtaaat gttggtgggg tgaagaagac atagagctag aagtggaagt cttcggctct   1680
```

| | |
|---|---:|
| tggaaagatg aatcaaagaa aatcattgaa ttgatcttgc caacaaacgt tgatcctgaa | 1740 |
| gcagaactac ataaaatcat tgtacccgtc cgattacata ttcgtagagt ttggacttta | 1800 |
| gagttgagcg ttattggggt gcagtga | 1827 |

<210> SEQ ID NO 63
<211> LENGTH: 3000
<212> TYPE: DNA
<213> ORGANISM: Saccharomyces cerevisiae

<400> SEQUENCE: 63

| | |
|---|---:|
| atgtctgaaa ttactttggg taaatatttg ttcgaaagat taaagcaagt caacgttaac | 60 |
| accgttttcg gtttgccagg tgacttcaac ttgtccttgt tggacaagat ctacgaagtt | 120 |
| gaaggtatga gatgggctgg taacgccaac gaattgaacg ctgcttacgc cgctgatggt | 180 |
| tacgctcgta tcaagggtat gtcttgtatc atcaccacct tcggtgtcgg tgaattgtct | 240 |
| gctttgaacg gtattgccgg ttcttacgct gaacacgtcg gtgttttgca cgttgttggt | 300 |
| gtcccatcca tctctgctca agctaagcaa ttgttgttgc accacacctt gggtaacggt | 360 |
| gacttcactg tttccacag aatgtctgcc aacatttctg aaaccactgc tatgatcact | 420 |
| gacattgcta ccgccccagc tgaaattgac agatgtatca gaaccactta cgtcacccaa | 480 |
| agaccagtct acttaggttt gccagctaac ttggtcgact tgaacgtccc agctaagttg | 540 |
| ttgcaaactc caattgacat gtctttgaag ccaaacgatg ctgaatccga aaaggaagtc | 600 |
| attgacacca tcttggcttt ggtcaaggat gctaagaacc cagttatctt ggctgatgct | 660 |
| tgttgttcca gacacgacgt caaggctgaa actaagaagt tgattgactt gactcaattc | 720 |
| ccagcttcg tcaccccaat gggtaagggt tccattgacg aacaacaccc aagatacggt | 780 |
| ggtgtttacg tcggtaccct tgtccaagcca gaagttaagg aagccgttga atctgctgac | 840 |
| ttgattttgt ctgtcggtgc tttgttgtct gatttcaaca ccggttcttt ctcttactct | 900 |
| tacaagacca gaacattgt cgaattccac tccgaccaca tgaagatcag aaacgccact | 960 |
| ttcccaggtg tccaaatgaa attcgttttg caaaagttgt tgaccactat tgctgacgcc | 1020 |
| gctaagggtt acaagccagt tgctgtccca gctagaactc cagctaacgc tgctgtccca | 1080 |
| gcttctaccc cattgaagca agaatggatg tggaaccaat tgggtaactt cttgcaagaa | 1140 |
| ggtgatgttg tcattgctga aaccggtacc tccgcttcg gtatcaacca aaccactttc | 1200 |
| ccaaacaaca cctacggtat ctctcaagtc ttatggggtt ccattggttt caccactggt | 1260 |
| gctaccttgg gtgctgcttt cgctgctgaa gaaattgatc aaagaagag agttatctta | 1320 |
| ttcattggtg acggttcttt gcaattgact gttcaagaaa tctccaccat gatcagatgg | 1380 |
| ggcttgaagc catacttgtt cgtcttgaac aacgatggtt acaccattga aaagttgatt | 1440 |
| cacggtccaa aggctcaata caacgaaatt caaggttggg accacctatc cttgttgcca | 1500 |
| actttcggtg ctaaggacta tgaaaccac agagtcgcta ccaccggtga atgggacaag | 1560 |
| ttgacccaag acaagtcttt caacgacaac tctaagatca gaatgattga atcatgttg | 1620 |
| ccagtcttcg atgctccaca aaacttggtt gaacaagcta agttgactgc tgctaccaac | 1680 |
| gctaagcaag aagtgcagc tcctggtgca tcagctgctc caggtgctgg ttctggaagt | 1740 |
| ggttcaggaa tggtatcttc tttgcccaag gaatcgcaag ccgaattgca actgttccag | 1800 |
| aacgaaatca acgccgctaa tccgtccgac tttcttcagt tctccgccaa ctatttcaat | 1860 |
| aaaaggctgg aacaacagag agcgttcctc aaggccaggg agcctgaatt taaggcaaag | 1920 |
| aacattgttc tatttccgga accagaggag tcatttttcca gacctcaatc agctcaatct | 1980 |

```
caatcaagat ccagatcgag tgttatgttc aaatcccct ttgtgaacga ggacccacac    2040
tccaacgtgt ttaaaagtgg gtttaattta gacccgcacg aacaggacac tcaccagcaa    2100
gcacaggaag aacaacagca tactagagaa aagacatcaa ctcctccact cccaatgcac    2160
ttcaacgccc aaaggcgtac ttctgttagt ggtgagacct acaaccaaa caattttgac    2220 gattggactc cagatcacta taaggaaaag tccgagcagc aattgcaaag actggaaaaa    2280
tcgatccgta ataactttct gttcaacaag ctggattccg actcaaaaag ctggtcata    2340 aattgtctgg aggagaagtc cgtccccaaa ggtgctacga taatcaagca aggtgaccaa    2400
ggggactact tctatgtcgt cgaaaagggt actgttgact tctacgtcaa cgacaacaag    2460
gtcaactctt ccgggccagg ctccagtttc ggggaacttg ctcttatgta acagccct     2520 cgtgctgcca ccgttgtagc aacctccgac tgtttgttgt gggctctaga caggctcacc    2580
ttcagaaaaa tactttggg cagctctttc aagaagagac tcatgtatga cgatcttttg    2640
aagagcatgc cagttttgaa gagtttgact acgtacgacc gtgccaaact tgccgatgca    2700
ctggatacca agatctacca gccgggtgaa acaatcattc gcgagggtga tcaaggggag    2760
aacttttatt taattgagta cggagctgtg gacgtctcta agaagggcca aggtgtcata    2820
aataaactga aagaccatga ttatttcggt gaagtggcct tgctaaacga tttgcccaga    2880
caggccactg tgactgctac aaagagaacc aaagttgcca cattgggaa aagtggtttt    2940 caacgtttac tgggtcctgc agtagacgta ttaaagctca atgatcctac aagacattaa    3000
```

<210> SEQ ID NO 64
<211> LENGTH: 572
<212> TYPE: PRT
<213> ORGANISM: Saccharomyces cerevisiae

<400> SEQUENCE: 64

```
Met Arg Arg Leu Tyr Arg His Leu Ala Ser Phe Phe Leu Leu Pro Ser
1               5                   10                  15

Cys Pro Gly Asn Thr Ile Gln Ser Ile Thr Ser Tyr Pro Ala Asn Ala
            20                  25                  30

Leu Leu Arg Ser Phe Arg His Val Ser Thr Glu Thr Pro Val Arg Asn
        35                  40                  45

Arg Val His Asn Arg Asp Ser Gln Ser Cys Pro Phe Phe Pro Leu Met
    50                  55                  60

Asp Asp Gly Ser Ala Ala Pro Gly Ala Ser Ala Ala Pro Gly Ala Gly
65                  70                  75                  80

Ser Gly Ser Gly Ser Gly Met Asp Asp Ile Ile Thr Gln Val Ser Pro
                85                  90                  95

Asp Asn Ala Glu Ser Ala Pro Ile Leu Gln Glu Gln Gln Gln Gln Gln
            100                 105                 110

Asn Ser Gln Tyr Glu Gly Asn Glu Glu Asp Tyr Gly Asp Ser Leu Ile
        115                 120                 125

His Leu Asn Ile Gln Glu Asn His Tyr Phe Ile Thr Arg Asp Gln Leu
    130                 135                 140

Met Ser Leu Pro Glu Ser Leu Leu Cys Leu Phe Pro Ser Gly Val
145                 150                 155                 160

Phe Leu Asp Arg Cys Gly Gln Val Ile Thr Asn Leu Thr Arg Asp Asp
                165                 170                 175

Glu Val Tyr Ile Val Asn Phe Pro Pro Asp Cys Phe Gly Tyr Ile Met
            180                 185                 190
```

Glu Ile Tyr Thr Lys Ala His Asp Asp Leu Tyr Asn His Pro Val Glu
            195                 200                 205

Lys Phe Phe Asp Arg Pro Ser Ser Ser Phe Val Ser Asn Ala Lys Gly
    210                 215                 220

Phe Phe Gly Leu Ser Ser Asn Asn Ser Ile Ser Ser Asn Asn Glu Gln
225                 230                 235                 240

Asp Ile Leu His Gln Lys Pro Ala Ile Ile Val Leu Arg Glu Asp Leu
                245                 250                 255

Asp Tyr Tyr Cys Val Pro Gln Glu Glu Phe Gln Phe Asp Ser Thr Asn
            260                 265                 270

Glu Glu Asn Asn Glu Asp Leu Leu Arg His Phe Met Ala Gln Val Lys
    275                 280                 285

Met Ala Ala Gly Ser Tyr Leu Thr Ser Lys Thr Ser Ile Phe Gln Gly
290                 295                 300

Leu Tyr Ser Ser Asn Arg Leu Lys Gln Gln Gln Gln Gln Lys Ile
305                 310                 315                 320

Glu Lys Gly Ser Asn Ser Ser Ser Asn Thr Lys Ser Thr Ser Lys Lys
            325                 330                 335

Leu Gly Pro Ala Glu Gln His Leu Met Asp Met Leu Cys Ser Ser Gly
    340                 345                 350

Phe Thr Lys Glu Thr Cys Trp Gly Asn Arg Thr Gln Glu Thr Gly Lys
355                 360                 365

Thr Val Ile Ser Ser Leu Ser Leu Cys Arg Leu Ala Asn Glu Thr Thr
            370                 375                 380

Glu Gly Phe Arg Gln Lys Phe Asn Glu Ala Lys Ala Lys Trp Glu Ala
385                 390                 395                 400

Glu His Lys Pro Ser Gln Asp Asn Phe Ile Thr Pro Met Gln Ser Asn
            405                 410                 415

Ile Ser Ile Asn Ser Leu Ser Ala Ser Lys Ser Asn Ser Thr Ile Ser
    420                 425                 430

Thr Ala Arg Asn Leu Thr Ser Gly Ser Thr Ala Pro Thr Ala Arg
            435                 440                 445

Asp Lys Arg Lys Ser Arg Leu Ser Lys Leu Ala Asp Asn Val Arg Ser
450                 455                 460

His Ser Ser Ser Arg His Ser Ser Gln Thr Arg Ser Lys Pro Pro Glu
465                 470                 475                 480

Leu Pro Lys Leu Tyr Asp Leu Val Pro Lys Pro Asn Ile Asn Ala Lys
                485                 490                 495

Leu Leu Leu Phe Trp Arg Lys Pro Ala Arg Lys Cys Trp Trp Gly Glu
            500                 505                 510

Glu Asp Ile Glu Leu Glu Val Glu Val Phe Gly Ser Trp Lys Asp Glu
    515                 520                 525

Ser Lys Lys Ile Ile Glu Leu Ile Leu Pro Thr Asn Val Asp Pro Glu
530                 535                 540

Ala Glu Leu His Lys Ile Ile Val Pro Val Arg Leu His Ile Arg Arg
545                 550                 555                 560

Val Trp Thr Leu Glu Leu Ser Val Ile Gly Val Gln
                565                 570

<210> SEQ ID NO 65
<211> LENGTH: 665
<212> TYPE: PRT
<213> ORGANISM: Saccharomyces cerevisiae

<400> SEQUENCE: 65

```
Met Lys Cys Thr Leu Val Ser Thr Leu Phe Ala Ile Thr Asn Ile Leu
1               5                   10                  15

Val Ala His Ala Gln Val Ser Asn Ser Ser Asp Thr Leu Asp Val Gln
            20                  25                  30

Phe Ala Asn Ser Thr Asn Ser Tyr Ile Glu Gly Lys Phe Asn Ser Thr
            35                  40                  45

Asp Glu Ala Phe Asn Ser Ser Ala Ser Trp Ser Leu Ala Ala Gln Gln
50                      55                  60

Lys Lys Ile Ser Asn Ala Ala Val Tyr Asp Val Gly Gly Trp Asn Gly
65              70                  75                      80

Ser Leu Tyr Arg Ser Asn Arg Ser Ala Val Ala Asp His Gln Pro Gly
                85                  90                  95

Lys Lys Gln Asp Ala Ala Ile Ser Gln Ile Ser Asp Gly Gln Ile Gln
            100                 105                 110

Ala Thr Ala Ser Gly Pro Glu Thr Thr Ala Ala Thr Thr Pro Ser Ser
            115                 120                 125

Thr Ala Asn Val Ser Val Tyr Glu Gly Ala Gly Met Lys Val Glu Ser
            130                 135                 140

Lys Asn Met Gly Tyr Ile Val Gly Val Ala Ala Leu Leu Phe Leu Gly
145                 150                 155                 160

Ser Ala Ala Pro Gly Ala Ser Ala Ala Pro Gly Ala Gly Ser Gly Ser
                165                 170                 175

Gly Ser Gly Met Asp Asp Ile Ile Thr Gln Val Ser Pro Asp Asn Ala
                180                 185                 190

Glu Ser Ala Pro Ile Leu Gln Glu Gln Gln Gln Gln Asn Ser Gln
                195                 200                 205

Tyr Glu Gly Asn Glu Glu Asp Tyr Gly Asp Ser Leu Ile His Leu Asn
210                 215                 220

Ile Gln Glu Asn His Tyr Phe Ile Thr Arg Asp Gln Leu Met Ser Leu
225                 230                 235                 240

Pro Glu Ser Leu Leu Leu Cys Leu Phe Pro Ser Gly Val Phe Leu Asp
                245                 250                 255

Arg Cys Gly Gln Val Ile Thr Asn Leu Thr Arg Asp Asp Glu Val Tyr
                260                 265                 270

Ile Val Asn Phe Pro Pro Asp Cys Phe Glu Tyr Ile Met Glu Ile Tyr
                275                 280                 285

Thr Lys Ala His Asp Asp Leu Tyr Asn His Pro Val Glu Lys Phe Phe
            290                 295                 300

Asp Arg Pro Ser Ser Ser Phe Val Ser Asn Ala Lys Gly Phe Phe Gly
305                 310                 315                 320

Leu Ser Ser Asn Asn Ser Ile Ser Ser Asn Asn Glu Gln Asp Ile Leu
                325                 330                 335

His Gln Lys Pro Ala Ile Ile Val Leu Arg Glu Asp Leu Asp Tyr Tyr
            340                 345                 350

Cys Val Pro Gln Glu Glu Phe Gln Phe Asp Ser Thr Asn Glu Glu Asn
            355                 360                 365

Asn Glu Asp Leu Leu Arg His Phe Met Ala Gln Val Lys Met Ala Ala
370                 375                 380

Gly Ser Tyr Leu Thr Ser Lys Thr Ser Ile Phe Gln Gly Leu Tyr Ser
385                 390                 395                 400

Ser Asn Arg Leu Lys Gln Gln Gln Gln Gln Lys Ile Glu Lys Gly
                405                 410                 415
```

```
Ser Asn Ser Ser Ser Asn Thr Lys Ser Thr Ser Lys Lys Leu Gly Pro
            420                 425                 430

Ala Glu Gln His Leu Met Asp Met Leu Cys Ser Ser Gly Phe Thr Lys
            435                 440                 445

Glu Thr Cys Trp Gly Asn Arg Thr Gln Glu Thr Gly Lys Thr Val Ile
        450                 455                 460

Ser Ser Leu Ser Leu Cys Arg Leu Ala Asn Glu Thr Thr Glu Gly Phe
465                 470                 475                 480

Arg Gln Lys Phe Asn Glu Ala Lys Ala Lys Trp Glu Ala Glu His Lys
                485                 490                 495

Pro Ser Gln Asp Asn Phe Ile Thr Pro Met Gln Ser Asn Ile Ser Ile
            500                 505                 510

Asn Ser Leu Ser Ala Ser Lys Ser Asn Ser Thr Ile Ser Thr Ala Arg
        515                 520                 525

Asn Leu Thr Ser Gly Ser Thr Ala Pro Ala Thr Ala Arg Asp Lys Arg
        530                 535                 540

Lys Ser Arg Leu Ser Lys Leu Ala Asp Asn Val Arg Ser His Ser Ser
545                 550                 555                 560

Ser Arg His Ser Ser Gln Thr Arg Ser Lys Pro Pro Glu Leu Pro Lys
                565                 570                 575

Leu Tyr Asp Leu Val Pro Lys Pro Asn Ile Asn Ala Lys Leu Leu Leu
            580                 585                 590

Phe Trp Arg Lys Pro Ala Arg Lys Cys Trp Trp Gly Glu Glu Asp Ile
            595                 600                 605

Glu Leu Glu Val Glu Val Phe Gly Ser Trp Lys Asp Glu Ser Lys Lys
        610                 615                 620

Ile Ile Glu Leu Ile Leu Pro Thr Asn Val Asp Pro Glu Ala Glu Leu
625                 630                 635                 640

His Lys Ile Ile Val Pro Val Arg Leu His Ile Arg Arg Val Trp Thr
                645                 650                 655

Leu Glu Leu Ser Val Ile Gly Val Gln
            660                 665

<210> SEQ ID NO 66
<211> LENGTH: 635
<212> TYPE: PRT
<213> ORGANISM: Saccharomyces cerevisiae

<400> SEQUENCE: 66

Met Thr Glu Val Val Gly Phe Trp Glu Ser Val Ser Asp Asp Glu Ser
1               5                   10                  15

Glu Asp Lys Asp Cys Met Glu Val Gln Asn Thr Val Ser Ala Asp Glu
            20                  25                  30

Ser Pro Leu Val Gln Ser Leu Val Ser Phe Val Gly Ser Cys Ser Ile
        35                  40                  45

Asn Leu Leu Leu Pro Phe Leu Asn Gly Met Met Leu Gly Phe Gly Glu
    50                  55                  60

Leu Phe Ala His Glu Leu Cys Trp Arg Phe Asn Trp Phe Asn His Arg
65                  70                  75                  80

Asn Lys Gly Tyr Lys Val Tyr Pro Glu Ser Arg Lys Ile Ala Ala Leu
                85                  90                  95

Lys Glu Ile Ser Ser Pro Gly Thr Arg Gly Arg Val Ala Ser Lys Phe
            100                 105                 110

Leu Gly Ser Ala Ala Pro Gly Ala Ser Ala Ala Pro Gly Ala Gly Ser
        115                 120                 125
```

Gly Ser Gly Ser Gly Met Leu Leu Asp Val Asn Thr Asn His Thr Leu
130                 135                 140

Met His Asp Ala His Val His Glu His Cys Leu Ile Lys Ser Ile Arg
145                 150                 155                 160

Asp Asp Gly Ala Leu His Ser Trp Ser Asp Ser Ser Lys Val Phe Tyr
                165                 170                 175

Pro Lys Ser Phe Tyr Ala Thr Ala Thr Asn Lys Lys Asn Asn Lys Leu
            180                 185                 190

Ala Ser Ala Ser Met Asn Lys Thr Ala Thr Ser Asn Arg Thr Val Ser
        195                 200                 205

Asp Glu Ile Tyr Phe His Ser Thr Lys Pro Gln Phe Asp Gly Gln Gly
    210                 215                 220

Ser Ala Glu Arg Thr Arg Thr Leu Thr Lys Arg Asn Ser Phe Lys Arg
225                 230                 235                 240

Thr Arg Ile Leu Lys Ala Arg Asp Asp Ser Glu Leu Leu Asn Glu Asn
                245                 250                 255

Arg Ser Ser Leu Met Thr Pro Ser Leu Ser Ser Val Met Ser Gln Val
                260                 265                 270

Arg Lys Thr Asn Ser Ala Lys Thr Leu Ser Gly Glu Cys Pro Ile His
            275                 280                 285

Glu Gly His Leu Thr Gln Ser Ile Lys Arg Lys Phe Ser Glu Glu Ala
    290                 295                 300

Gln Ser Asp Cys Ser Ser Leu Ser Ser Ser Lys Leu His Pro Leu Thr
305                 310                 315                 320

Asp Asp Ile Ala Asp Ala Val Asp Leu Gln Thr Pro Ala Ile Gly Asp
                325                 330                 335

Glu Val Leu Ala Glu Pro Val Val Pro Lys Met Lys Ile Ile Asn Ile
                340                 345                 350

Asn Asp Leu Asp Leu Phe Asp Asp Trp Glu Val Lys Asp Leu Val Asp
            355                 360                 365

Ile Phe Pro Pro Val Tyr Glu Arg Arg Pro Arg Ser Ser Ser Ala Leu
    370                 375                 380

Ser Leu Val Ser Ala Ser Ser Asp Ala Lys Leu Arg Pro Thr Ser Val
385                 390                 395                 400

Asp Phe Gln Ile Ile Asp Lys Lys Gly Gly Lys Thr Ser Arg Arg Lys
                405                 410                 415

Ser Arg Ser Lys Ser Thr Thr Glu Asn Met Ile Tyr Glu Asn Asp Leu
            420                 425                 430

Val Glu Leu Glu Gln Trp Pro Ser Ala Ser Pro Ser Pro Glu Thr Asp
    435                 440                 445

Gly Ser Ile Ala Ser Ser Glu Leu Leu Pro Asn Lys Arg Ile Arg Gln
450                 455                 460

Lys Ser Leu Asn Thr Asn Phe Leu Lys Leu Tyr Ser Ile Glu Thr Ser
465                 470                 475                 480

Cys Lys Arg Lys Ser Ile Leu Pro Glu Val Glu Val Asp Asp His Leu
                485                 490                 495

Leu Lys Gln Leu Thr Tyr Ser Glu Ile Arg Ser Leu Glu Ile Lys Lys
            500                 505                 510

Glu Pro Asn Val Ser Thr Asn Asp Ile Lys Leu Ala Leu Ile Thr Arg
    515                 520                 525

Lys Lys Leu Trp Ser Asp Met Val His Glu Thr Arg Asn Asp Leu Phe
530                 535                 540

```
Gly Asp Ser Thr Pro Trp Asn Leu His Phe Val Ala Thr Thr Ser Asn
545                 550                 555                 560

Thr Glu Pro Ser Gln Gly Arg Glu Ser Ala Ser Glu His Ala Thr Ala
                565                 570                 575

Asp Leu Lys Ser Ser Leu Val Arg Val His Ser Asp Val Lys Pro Trp
            580                 585                 590

Phe Asn Asn Gly Gly Thr Met Leu Lys Pro Cys Gly Lys Leu Asn Leu
        595                 600                 605

Gly Lys Val Thr Asn Lys Thr Ser Ala Pro Thr Arg Glu Ile Gln Tyr
    610                 615                 620

Val Val Lys Gly Trp Cys Asp Ser Arg Phe Leu
625                 630                 635

<210> SEQ ID NO 67
<211> LENGTH: 1039
<212> TYPE: PRT
<213> ORGANISM: Saccharomyces cerevisiae

<400> SEQUENCE: 67

Met Glu Arg Leu Lys Gln Leu Glu Glu Lys Arg Gln Leu Lys Glu
1               5                   10                  15

Leu Arg Glu Arg Arg Lys Gln Ala Ser Leu Phe Pro Gly Ser Glu Thr
            20                  25                  30

Met Gly His His Pro Thr Glu Val His Ala Lys Ala Thr Met Val Ser
        35                  40                  45

Val Ser Val Gln Thr Asp Met Glu Glu Gly Ser Lys Ile Gln Glu Pro
    50                  55                  60

Gln Ser Ala Tyr Leu Arg Arg Lys Glu Val Ile Thr Tyr Asp Lys Gly
65                  70                  75                  80

Ile Gln Thr Asp Gln Ile Glu Glu Gln Leu Gln Glu Asn Glu Asn
                85                  90                  95

His Thr Thr Thr Asp Ala Val Ala Ile Glu Thr Thr Ala Ala Asp Glu
            100                 105                 110

Asn Asn Lys Asp Lys Ala Glu Asn Asp Gln Pro Arg Leu Glu Leu Ala
        115                 120                 125

Lys Pro Phe Leu Val Glu Glu Ala Ala Ala Thr Leu Ser Asn Ala Ser
130                 135                 140

Phe Ala Arg Leu Glu Thr Glu Val Ser Ala Ser Gly Gln Gln Ala Pro
145                 150                 155                 160

Ser Asn Met Gln Gln Asp Lys Asp Asn Leu Met Gln Trp Asn Met Val
                165                 170                 175

Ser Glu Asn Leu Gln Ser Glu Thr Asp Cys Asp Cys Ile Ala Gln Glu
            180                 185                 190

Tyr Asp Pro Gly Lys Gly Val Leu Val Val Tyr Leu Arg Leu Pro
        195                 200                 205

Pro Ala Asp Leu Gln Tyr Ala Ser Ser Glu Ala Ala Trp Ser Val Val
210                 215                 220

Asn Val Val Lys Cys Asp Asn Ala Ser Gly Arg Asn Gly Leu Leu Ile
225                 230                 235                 240

Asp Met Val Glu Phe Arg Gly Thr Arg Ile Met Thr Ala Thr Ile Leu
                245                 250                 255

Arg Arg Tyr His Pro Glu Ser Asn Val Ile Ser Ile Leu Leu Ala Thr
            260                 265                 270

Leu Thr Gly Lys Ile Ile Leu Tyr Glu Leu Arg Leu Lys Gln Lys Lys
        275                 280                 285
```

```
Pro Glu Thr Pro Val Val Tyr Val Val Gln Arg Asn Met Val Ala Arg
    290                 295                 300

His Tyr Phe Gln His Pro Val Val Ala Val Ile Glu Thr Ser Ser Val
305                 310                 315                 320

Gln Asp Gln Glu Arg Val Leu Val Ala Ala Asp Asn Gly Asn Ile Met
                325                 330                 335

Glu Leu Ser Cys Leu Asp Leu Thr Val Leu Arg Lys Pro Gln Gln Leu
            340                 345                 350

Arg Pro Val Pro Leu Ser Gln Leu Leu Ser Leu Glu Asn Asp Thr Cys
        355                 360                 365

Thr Tyr Thr Glu Arg Leu Gln Arg Leu Ala Lys Phe Asp Glu Val Gly
    370                 375                 380

Ile Ala Cys Met Ala Tyr Thr Ser Glu Asp Pro Gln Tyr Val Trp Ile
385                 390                 395                 400

Gly Gly Glu Asp Gly Gly Ile Tyr Lys Val Phe Trp Asp Gln Pro Gly
                405                 410                 415

Pro Leu Tyr Leu Ser Leu Asp Asn Asn Gly Phe Gln Pro Ala Glu Asn
            420                 425                 430

His Ser Thr Arg Val Thr Gly Leu Glu Phe His Trp Asp Asp Ala Arg
        435                 440                 445

Arg Leu Met Leu Leu Ser Cys Ser Thr Asp Trp Thr Val Arg Leu
    450                 455                 460

Trp Asp Ala Arg Ala Gly Lys Ala Ile Ile Gly Ala Pro Leu Leu Leu
465                 470                 475                 480

Gly Gly Pro Val Leu Arg Ala Arg Trp Leu Glu Lys Asn Asn Gly Gly
                485                 490                 495

Glu Asn Ser Arg Thr Leu Arg Cys Gln Val Trp Cys Ala Asp Gly Arg
            500                 505                 510

Leu Val Val Val Asn Trp Ala Phe Asp Ala Lys Thr Ser Leu Tyr Thr
        515                 520                 525

Ala Thr Val Ile Ser Gly Ser Ala Ala Pro Gly Ala Ser Ala Ala Pro
    530                 535                 540

Gly Ala Gly Ser Gly Ser Gly Ser Gly Met Asp Asp Ile Ile Thr Gln
545                 550                 555                 560

Val Ser Pro Asp Asn Ala Glu Ser Ala Pro Ile Leu Gln Glu Gln Gln
                565                 570                 575

Gln Gln Gln Asn Ser Gln Tyr Glu Gly Asn Glu Glu Asp Tyr Gly Asp
            580                 585                 590

Ser Leu Ile His Leu Asn Ile Gln Glu Asn His Tyr Phe Ile Thr Arg
        595                 600                 605

Asp Gln Leu Met Ser Leu Pro Glu Ser Leu Leu Leu Cys Leu Phe Pro
    610                 615                 620

Ser Gly Val Phe Leu Asp Arg Cys Gly Gln Val Ile Thr Asn Leu Thr
625                 630                 635                 640

Arg Asp Asp Glu Val Tyr Ile Val Asn Phe Pro Asp Cys Phe Glu
                645                 650                 655

Tyr Ile Met Glu Ile Tyr Thr Lys Ala His Asp Asp Leu Tyr Asn His
            660                 665                 670

Pro Val Glu Lys Phe Phe Asp Arg Pro Ser Ser Phe Val Ser Asn
        675                 680                 685

Ala Lys Gly Phe Phe Gly Leu Ser Ser Asn Asn Ser Ile Ser Ser Asn
    690                 695                 700
```

```
Asn Glu Gln Asp Ile Leu His Gln Lys Pro Ala Ile Ile Val Leu Arg
705                 710                 715                 720

Glu Asp Leu Asp Tyr Tyr Cys Val Pro Gln Glu Glu Phe Gln Phe Asp
            725                 730                 735

Ser Thr Asn Glu Glu Asn Asn Glu Asp Leu Leu Arg His Phe Met Ala
        740                 745                 750

Gln Val Lys Met Ala Ala Gly Ser Tyr Leu Thr Ser Lys Thr Ser Ile
    755                 760                 765

Phe Gln Gly Leu Tyr Ser Ser Asn Arg Leu Lys Gln Gln Gln Gln Gln
770                 775                 780

Gln Lys Ile Glu Lys Gly Ser Asn Ser Ser Asn Thr Lys Ser Thr
785                 790                 795                 800

Ser Lys Lys Leu Gly Pro Ala Glu Gln His Leu Met Asp Met Leu Cys
                805                 810                 815

Ser Ser Gly Phe Thr Lys Glu Thr Cys Trp Gly Asn Arg Thr Gln Glu
            820                 825                 830

Thr Gly Lys Thr Val Ile Ser Ser Leu Ser Leu Cys Arg Leu Ala Asn
        835                 840                 845

Glu Thr Thr Glu Gly Phe Arg Gln Lys Phe Asn Glu Ala Lys Ala Lys
    850                 855                 860

Trp Glu Ala Glu His Lys Pro Ser Gln Asp Asn Phe Ile Thr Pro Met
865                 870                 875                 880

Gln Ser Asn Ile Ser Ile Asn Ser Leu Ser Ala Ser Lys Ser Asn Ser
                885                 890                 895

Thr Ile Ser Thr Ala Arg Asn Leu Thr Ser Gly Ser Thr Ala Pro Ala
            900                 905                 910

Thr Ala Arg Asp Lys Arg Lys Ser Arg Leu Ser Lys Leu Ala Asp Asn
        915                 920                 925

Val Arg Ser His Ser Ser Ser Arg His Ser Ser Gln Thr Arg Ser Lys
    930                 935                 940

Pro Pro Glu Leu Pro Lys Leu Tyr Asp Leu Val Pro Lys Pro Asn Ile
945                 950                 955                 960

Asn Ala Lys Leu Leu Leu Phe Trp Arg Lys Pro Ala Arg Lys Cys Trp
                965                 970                 975

Trp Gly Glu Glu Asp Ile Glu Leu Glu Val Glu Val Phe Gly Ser Trp
            980                 985                 990

Lys Asp Glu Ser Lys Lys Ile Ile Glu Leu Ile Leu Pro Thr Asn Val
        995                 1000                1005

Asp Pro Glu Ala Glu Leu His Lys Ile Ile Val Pro Val Arg Leu
    1010                1015                1020

His Ile Arg Arg Val Trp Thr Leu Glu Leu Ser Val Ile Gly Val
    1025                1030                1035

Gln
```

<210> SEQ ID NO 68
<211> LENGTH: 799
<212> TYPE: PRT
<213> ORGANISM: Saccharomyces cerevisiae

<400> SEQUENCE: 68

```
Met Asp Asp Ile Ile Thr Gln Val Ser Pro Asp Asn Ala Glu Ser Ala
1               5                   10                  15

Pro Ile Leu Gln Glu Gln Gln Gln Gln Asn Ser Gln Tyr Glu Gly
            20                  25                  30
```

-continued

Asn Glu Glu Asp Tyr Gly Asp Ser Leu Ile His Leu Asn Ile Gln Glu
            35                  40                  45
Asn His Tyr Phe Ile Thr Arg Asp Gln Leu Met Ser Leu Pro Glu Ser
50                  55                  60
Leu Leu Leu Cys Leu Phe Pro Ser Gly Val Phe Leu Asp Arg Cys Gly
65                  70                  75                  80
Gln Val Ile Thr Asn Leu Thr Arg Asp Asp Glu Val Tyr Ile Val Asn
                85                  90                  95
Phe Pro Pro Asp Cys Phe Glu Tyr Ile Met Glu Ile Tyr Thr Lys Ala
            100                 105                 110
His Asp Asp Leu Tyr Asn His Pro Val Glu Lys Phe Phe Asp Arg Pro
            115                 120                 125
Ser Ser Ser Phe Val Ser Asn Ala Lys Gly Phe Phe Gly Leu Ser Ser
        130                 135                 140
Asn Asn Ser Ile Ser Ser Asn Asn Glu Gln Asp Ile Leu His Gln Lys
145                 150                 155                 160
Pro Ala Ile Ile Val Leu Arg Glu Asp Leu Asp Tyr Tyr Cys Val Pro
                165                 170                 175
Gln Glu Glu Phe Gln Phe Asp Ser Thr Asn Glu Glu Asn Asn Glu Asp
            180                 185                 190
Leu Leu Arg His Phe Met Ala Gln Val Lys Met Ala Ala Gly Ser Tyr
        195                 200                 205
Leu Thr Ser Lys Thr Ser Ile Phe Gln Gly Leu Tyr Ser Ser Asn Arg
        210                 215                 220
Leu Lys Gln Gln Gln Gln Gln Lys Ile Glu Lys Gly Ser Asn Ser
225                 230                 235                 240
Ser Ser Asn Thr Lys Ser Thr Ser Lys Lys Leu Gly Pro Ala Glu Gln
                245                 250                 255
His Leu Met Asp Met Leu Cys Ser Ser Gly Phe Thr Lys Glu Thr Cys
            260                 265                 270
Trp Gly Asn Arg Thr Gln Glu Thr Gly Lys Thr Val Ile Ser Ser Leu
        275                 280                 285
Ser Leu Cys Arg Leu Ala Asn Glu Thr Thr Glu Gly Phe Arg Gln Lys
        290                 295                 300
Phe Asn Glu Ala Lys Ala Lys Trp Glu Ala Glu His Lys Pro Ser Gln
305                 310                 315                 320
Asp Asn Phe Ile Thr Pro Met Gln Ser Asn Ile Ser Ile Asn Ser Leu
                325                 330                 335
Ser Ala Ser Lys Ser Asn Ser Thr Ile Ser Thr Ala Arg Asn Leu Thr
            340                 345                 350
Ser Gly Ser Thr Ala Pro Ala Thr Ala Arg Asp Lys Arg Lys Ser Arg
        355                 360                 365
Leu Ser Lys Leu Ala Asp Asn Val Arg Ser His Ser Ser Arg His
        370                 375                 380
Ser Ser Gln Thr Arg Ser Lys Pro Pro Glu Leu Pro Lys Leu Tyr Asp
385                 390                 395                 400
Leu Val Pro Lys Pro Asn Ile Asn Ala Lys Leu Leu Leu Phe Trp Arg
                405                 410                 415
Lys Pro Ala Arg Lys Cys Trp Trp Gly Glu Glu Asp Ile Glu Leu Glu
            420                 425                 430
Val Glu Val Phe Gly Ser Trp Lys Asp Glu Ser Lys Lys Ile Ile Glu
        435                 440                 445
Leu Ile Leu Pro Thr Asn Val Asp Pro Glu Ala Glu Leu His Lys Ile

```
            450                 455                 460
Ile Val Pro Val Arg Leu His Ile Arg Arg Val Trp Thr Leu Glu Leu
465                 470                 475                 480

Ser Val Ile Gly Val Gln Gly Ser Ala Ala Pro Gly Ala Ser Ala Ala
                485                 490                 495

Pro Gly Ala Gly Ser Gly Ser Gly Met Ala Ser Val Asn Asn
                500                 505                 510

Tyr Gln Val Asp Cys Gly Ser Arg Ser Ala Arg Ile Gln Pro Arg Ile
                515                 520                 525

Asn Asn Gly Ile His Asp Glu Glu Ser Leu Phe Glu Val Leu Glu Leu
            530                 535                 540

Ser Glu Glu Glu Phe Glu Leu Asp Phe His Arg Leu Lys Ser Phe Asn
545                 550                 555                 560

Asp Val Arg Val Ile Asn Asn Pro Asp Leu Ser Pro Glu Cys Thr Asn
                565                 570                 575

Thr Ala Ile Ser Arg Asp Glu Thr Leu Glu Ser Ala Ser Ser Ala Phe
                580                 585                 590

Glu Val Pro Ser Asp Glu Ile Ala Ile Leu Ser Ile Ser Ser Asp Ser
                595                 600                 605

Asn Lys Asn Ser Pro Pro Ser Glu Gln Pro Ala Pro Ala Leu Arg Asn
610                 615                 620

Ile Arg Ser Ser Ser Asn Ser Asp Arg Ile Asp Glu Trp Cys Leu Gly
625                 630                 635                 640

Ser His Leu Phe Asn Glu Leu His Gln Asn Val Pro Gln Ser Ser Asp
                645                 650                 655

Gly Val Asn His Gly Phe Pro Val Tyr Ser Phe Lys Glu Arg Glu Leu
                660                 665                 670

Tyr Thr Ser Ala Lys Leu Lys Lys Leu Thr Asn Ala Gln Arg Ile Ala
                675                 680                 685

Val Gln Lys Leu Ser Arg Asp Leu Tyr Pro Ile Leu Arg Thr Cys Tyr
            690                 695                 700

Arg Glu Lys Thr Arg Arg Gln Leu Leu Thr Tyr His His Glu Arg Ile
705                 710                 715                 720

Phe Asp Asp Ile Pro Ser Phe Phe Pro Gln Arg Asp Phe Ile Phe Asn
                725                 730                 735

Tyr Tyr Ser Met Pro Leu Glu Phe Asp Arg Leu Ser Ala Val Asp Ile
                740                 745                 750

Asp Ser Ser Ser Arg Ser Arg Phe Thr Asp Glu Ser Thr Gly Glu Thr
                755                 760                 765

Leu Asn Arg Ser Pro Ser Ala Ala Ser Ser Leu Glu Asn Thr Ser
770                 775                 780

Trp Phe Gly Trp Thr Leu Leu Ser Arg Phe Leu Asp Arg Glu Trp
785                 790                 795

<210> SEQ ID NO 69
<211> LENGTH: 713
<212> TYPE: PRT
<213> ORGANISM: Saccharomyces cerevisiae

<400> SEQUENCE: 69

Met Ser Asn Ala Asn Asn Ser Ala Met Asn His Ile Thr Leu Pro Pro
1               5                   10                  15

Ile Ser Ser Phe Asp Asn Leu Ile Lys Ala Ala Glu Arg Gln Tyr Asn
            20                  25                  30
```

```
Gly Glu Ala Ser Ser Ala Ser Thr His Pro Thr Leu Pro Asn Met Asn
         35                  40                  45

Ile Ser Asn Gly Ser Gly Ser Ala Gly Ala Ser Ser Ser Met Leu Ser
 50                  55                  60

Tyr Gln Leu Leu Pro His Ser Asn Asp Val Ser Arg Ser Asn Ser Ser
 65                  70                  75                  80

Ser Ser Phe Leu Pro Ser Val Gln Gln Pro Thr Glu Gly Ser Ala Ser
             85                  90                  95

Ala Ser Glu Thr Ser Ser Ser Ala Ser Pro Ser Arg Ser Ile Ser Pro
             100                 105                 110

Ile Leu Lys Val Ala Gly Pro Ser Ser Val Gly Gly Ala Gly Val Ser
         115                 120                 125

Thr Pro His Ser Thr Lys Ile Asn Lys Pro Arg Lys Lys Lys Gln Cys
         130                 135                 140

Pro Ile Cys Arg Asn Phe Tyr Ala Asn Leu Thr Thr His Lys Ala Thr
145                 150                 155                 160

His Leu Thr Pro Glu Asp Arg Pro His Lys Cys Pro Ile Cys His Arg
                 165                 170                 175

Gly Phe Ala Arg Asn Asn Asp Leu Leu Arg His Lys Lys Arg His Trp
             180                 185                 190

Lys Asp Glu Ile Leu Ser Gln Ser Gly Val Leu Ser Asn His Asn Asp
         195                 200                 205

Gly Lys Gly Gly Ser Val Ser Pro Asn Asp Asp Thr His Glu Lys
         210                 215                 220

Met Thr Pro Met Asn Ser Val Thr Asp Tyr Ala Gln Leu Lys Ser Leu
225                 230                 235                 240

His Gln Ile Lys Gly Thr Phe Lys Cys Pro Phe Asn Ser Thr Leu Ile
                 245                 250                 255

Gln Leu Asp Met Asp Met Tyr Pro Tyr Lys Leu Lys Pro Leu Asn Phe
             260                 265                 270

Glu Thr Ser Asn Cys His Gln Thr Gly Val Phe Ser Arg Cys Asp Thr
             275                 280                 285

Phe Lys Asn His Leu Lys Ala Leu His Phe Glu Tyr Pro Pro Gly Thr
290                 295                 300

Lys Lys Lys Asp Arg Asn Val Val Pro Gly Arg Cys Lys His Cys Gly
305                 310                 315                 320

Leu Lys Phe Glu Asn Val Asp Val Trp Leu Asn Glu His Val Gly Lys
                 325                 330                 335

Gln Cys Gly Tyr Lys Tyr His Gly Ser Ala Ala Pro Gly Ala Ser Ala
             340                 345                 350

Ala Pro Gly Ala Gly Ser Gly Ser Gly Met Asn Trp Leu Phe
             355                 360                 365

Leu Val Ser Leu Val Phe Phe Cys Gly Val Ser Thr His Pro Ala Leu
         370                 375                 380

Ala Met Ser Ser Asn Arg Leu Leu Lys Leu Ala Asn Lys Ser Pro Lys
385                 390                 395                 400

Lys Ile Ile Pro Leu Lys Asp Ser Ser Phe Glu Asn Ile Leu Ala Pro
                 405                 410                 415

Pro His Glu Asn Ala Tyr Ile Val Ala Leu Phe Thr Ala Thr Ala Pro
                 420                 425                 430

Glu Ile Gly Cys Ser Leu Cys Leu Glu Leu Glu Ser Glu Tyr Asp Thr
             435                 440                 445

Ile Val Ala Ser Trp Phe Asp Asp His Pro Asp Ala Lys Ser Ser Asn
```

```
                450                 455                 460
Ser Asp Thr Ser Ile Phe Phe Thr Lys Val Asn Leu Glu Asp Pro Ser
465                 470                 475                 480

Lys Thr Ile Pro Lys Ala Phe Gln Phe Phe Gln Leu Asn Asn Val Pro
                485                 490                 495

Arg Leu Phe Ile Phe Lys Pro Asn Ser Pro Ser Ile Leu Asp His Ser
            500                 505                 510

Val Ile Ser Ile Ser Thr Asp Thr Gly Ser Glu Arg Met Lys Gln Ile
        515                 520                 525

Ile Gln Ala Ile Lys Gln Phe Ser Gln Val Asn Asp Phe Ser Leu His
    530                 535                 540

Leu Pro Met Asp Trp Thr Pro Ile Ile Thr Ser Thr Ile Ile Thr Phe
545                 550                 555                 560

Ile Thr Val Leu Leu Phe Lys Lys Gln Ser Lys Leu Met Phe Ser Ile
                565                 570                 575

Ile Ser Ser Arg Ile Ile Trp Ala Thr Leu Ser Thr Phe Phe Ile Ile
            580                 585                 590

Cys Met Ile Ser Ala Tyr Met Phe Asn Gln Ile Arg Asn Thr Gln Leu
        595                 600                 605

Ala Gly Val Gly Pro Lys Gly Glu Val Met Tyr Phe Leu Pro Asn Glu
    610                 615                 620

Phe Gln His Gln Phe Ala Ile Glu Thr Gln Val Met Val Leu Ile Tyr
625                 630                 635                 640

Gly Thr Leu Ala Ala Leu Val Val Val Leu Val Lys Gly Ile Gln Phe
                645                 650                 655

Leu Arg Ser His Leu Tyr Pro Glu Thr Lys Lys Ala Tyr Phe Ile Asp
            660                 665                 670

Ala Ile Leu Ala Ser Phe Cys Ala Leu Phe Ile Tyr Val Phe Phe Ala
        675                 680                 685

Ala Leu Thr Thr Val Phe Thr Ile Lys Ser Pro Ala Tyr Pro Phe Pro
    690                 695                 700

Leu Leu Arg Leu Ser Ala Pro Phe Lys
705                 710

<210> SEQ ID NO 70
<211> LENGTH: 898
<212> TYPE: PRT
<213> ORGANISM: Saccharomyces cerevisiae

<400> SEQUENCE: 70

Met Asp Asp Ile Ile Thr Gln Val Ser Pro Asp Asn Ala Glu Ser Ala
1               5                   10                  15

Pro Ile Leu Gln Glu Gln Gln Gln Gln Asn Ser Gln Tyr Glu Gly
            20                  25                  30

Asn Glu Glu Asp Tyr Gly Asp Ser Leu Ile His Leu Asn Ile Gln Glu
        35                  40                  45

Asn His Tyr Phe Ile Thr Arg Asp Gln Leu Met Ser Leu Pro Glu Ser
    50                  55                  60

Leu Leu Leu Cys Leu Phe Pro Ser Gly Val Phe Leu Asp Arg Cys Gly
65                  70                  75                  80

Gln Val Ile Thr Asn Leu Thr Arg Asp Asp Glu Val Tyr Ile Val Asn
                85                  90                  95

Phe Pro Pro Asp Cys Phe Glu Tyr Ile Met Glu Ile Tyr Thr Lys Ala
            100                 105                 110
```

```
His Asp Asp Leu Tyr Asn His Pro Val Glu Lys Phe Phe Asp Arg Pro
            115                 120                 125

Ser Ser Ser Phe Val Ser Asn Ala Lys Gly Phe Phe Gly Leu Ser Ser
130                 135                 140

Asn Asn Ser Ile Ser Ser Asn Asn Glu Gln Asp Ile Leu His Gln Lys
145                 150                 155                 160

Pro Ala Ile Ile Val Leu Arg Glu Asp Leu Asp Tyr Tyr Cys Val Pro
                165                 170                 175

Gln Glu Glu Phe Gln Phe Asp Ser Thr Asn Glu Asn Asn Glu Asp
            180                 185                 190

Leu Leu Arg His Phe Met Ala Gln Val Lys Met Ala Ala Gly Ser Tyr
            195                 200                 205

Leu Thr Ser Lys Thr Ser Ile Phe Gln Gly Leu Tyr Ser Ser Asn Arg
    210                 215                 220

Leu Lys Gln Gln Gln Gln Gln Lys Ile Glu Lys Gly Ser Asn Ser
225                 230                 235                 240

Ser Ser Asn Thr Lys Ser Thr Ser Lys Lys Leu Gly Pro Ala Glu Gln
                245                 250                 255

His Leu Met Asp Met Leu Cys Ser Ser Gly Phe Thr Lys Glu Thr Cys
                260                 265                 270

Trp Gly Asn Arg Thr Gln Glu Thr Gly Lys Thr Val Ile Ser Ser Leu
                275                 280                 285

Ser Leu Cys Arg Leu Ala Asn Glu Thr Thr Glu Gly Phe Arg Gln Lys
    290                 295                 300

Phe Asn Glu Ala Lys Ala Lys Trp Glu Ala Glu His Lys Pro Ser Gln
305                 310                 315                 320

Asp Asn Phe Ile Thr Pro Met Gln Ser Asn Ile Ser Ile Asn Ser Leu
                325                 330                 335

Ser Ala Ser Lys Ser Asn Ser Thr Ile Ser Thr Ala Arg Asn Leu Thr
                340                 345                 350

Ser Gly Ser Thr Ala Pro Ala Thr Ala Arg Asp Lys Arg Lys Ser Arg
                355                 360                 365

Leu Ser Lys Leu Ala Asp Asn Val Arg Ser His Ser Ser Arg His
    370                 375                 380

Ser Ser Gln Thr Arg Ser Lys Pro Pro Glu Leu Pro Lys Leu Tyr Asp
385                 390                 395                 400

Leu Val Pro Lys Pro Asn Ile Asn Ala Lys Leu Leu Leu Phe Trp Arg
                405                 410                 415

Lys Pro Ala Arg Lys Cys Trp Trp Gly Glu Glu Asp Ile Glu Leu Glu
                420                 425                 430

Val Glu Val Phe Gly Ser Trp Lys Asp Glu Ser Lys Lys Ile Ile Glu
                435                 440                 445

Leu Ile Leu Pro Thr Asn Val Asp Pro Glu Ala Glu Leu His Lys Ile
    450                 455                 460

Ile Val Pro Val Arg Leu His Ile Arg Arg Val Trp Thr Leu Glu Leu
465                 470                 475                 480

Ser Val Ile Gly Val Gln Gly Ser Ala Ala Pro Gly Ala Ser Ala Ala
                485                 490                 495

Pro Gly Ala Gly Ser Gly Ser Gly Ser Gly Met Ala Asp Thr Pro Ser
                500                 505                 510

Val Ala Val Gln Ala Pro Pro Gly Tyr Gly Lys Thr Glu Leu Phe His
                515                 520                 525

Leu Pro Leu Ile Ala Leu Ala Ser Lys Gly Asp Val Lys Tyr Val Ser
```

```
                    530                 535                 540
Phe Leu Phe Val Pro Tyr Thr Val Leu Leu Ala Asn Cys Met Ile Arg
545                 550                 555                 560

Leu Gly Arg Arg Gly Cys Leu Asn Val Ala Pro Val Arg Asn Phe Ile
                    565                 570                 575

Glu Glu Gly Tyr Asp Gly Val Thr Asp Leu Tyr Val Gly Ile Tyr Asp
                580                 585                 590

Asp Leu Ala Ser Thr Asn Phe Thr Asp Arg Ile Ala Ala Trp Glu Asn
                595                 600                 605

Ile Val Glu Cys Thr Phe Arg Thr Asn Asn Val Lys Leu Gly Tyr Leu
610                 615                 620

Ile Val Asp Glu Phe His Asn Phe Glu Thr Glu Val Tyr Arg Gln Ser
625                 630                 635                 640

Gln Phe Gly Gly Ile Thr Asn Leu Asp Phe Asp Ala Phe Glu Lys Ala
                645                 650                 655

Ile Phe Leu Ser Gly Thr Ala Pro Glu Ala Val Ala Asp Ala Ala Leu
                660                 665                 670

Gln Arg Ile Gly Leu Thr Gly Leu Ala Lys Lys Ser Met Asp Ile Asn
                675                 680                 685

Glu Leu Lys Arg Ser Glu Asp Leu Ser Arg Gly Leu Ser Ser Tyr Pro
690                 695                 700

Thr Arg Met Phe Asn Leu Ile Lys Glu Lys Ser Glu Val Pro Leu Gly
705                 710                 715                 720

His Val His Lys Ile Trp Lys Lys Val Glu Ser Gln Pro Glu Ala
                725                 730                 735

Leu Lys Leu Leu Leu Ala Leu Phe Glu Ile Glu Pro Glu Ser Lys Ala
                740                 745                 750

Ile Val Val Ala Ser Thr Thr Asn Glu Val Glu Leu Ala Cys Ser
                755                 760                 765

Trp Arg Lys Tyr Phe Arg Val Val Trp Ile His Gly Lys Leu Gly Ala
770                 775                 780

Ala Glu Lys Val Ser Arg Thr Lys Glu Phe Val Thr Asp Gly Ser Met
785                 790                 795                 800

Gln Val Leu Ile Gly Thr Lys Leu Val Thr Glu Gly Ile Asp Ile Lys
                805                 810                 815

Gln Leu Met Met Val Ile Met Leu Asp Asn Arg Leu Asn Ile Ile Glu
                820                 825                 830

Leu Ile Gln Gly Val Gly Arg Leu Arg Asp Gly Gly Leu Cys Tyr Leu
                835                 840                 845

Leu Ser Arg Lys Asn Ser Trp Ala Ala Arg Asn Arg Lys Gly Glu Leu
850                 855                 860

Pro Pro Ile Lys Glu Gly Cys Ile Thr Glu Gln Val Arg Glu Phe Tyr
865                 870                 875                 880

Gly Leu Glu Ser Lys Lys Gly Lys Gly Gln His Val Gly Cys Cys
                885                 890                 895

Val Cys

<210> SEQ ID NO 71
<211> LENGTH: 1111
<212> TYPE: PRT
<213> ORGANISM: Saccharomyces cerevisiae

<400> SEQUENCE: 71

Met Gln Thr Ser Met Val Ser Ala Lys Val Ser Ile Trp Leu Val Cys
```

```
1               5                   10                  15
Ser Val Ile Cys Ser Ser Leu Val Arg Ala Thr Gln Ser Val Cys Ser
                20                  25                  30
Ser Gln Asn Thr Ala Thr Thr Asp Gly Val Arg Asn Gln Phe Gln Ser
                35                  40                  45
Asn Gly Trp Cys Ser Asn Asn Cys Ala Gly His Gln Phe Ala Ile Val
    50                  55                  60
Gln Gly Phe Met Cys Trp Cys Ser Asp Ser Glu Pro Ser Thr Gln Thr
65                  70                  75                  80
Ser Val Gly Asp Cys Ser Gly Thr Cys Pro Gly Tyr Gly Tyr Glu Asp
                85                  90                  95
Cys Gly Asn Ala Asp Lys Asp Leu Phe Gly Tyr Ile Tyr Leu Gly Gln
                100                 105                 110
Thr Pro Leu Ser Ser Val Gln Ser Val Glu Thr Ser Thr Glu Ser Ser
                115                 120                 125
Val Tyr Val Ser Ser Ser Ile Thr Ser Ser Ser Thr Ser Ser Thr Ile
                130                 135                 140
Val Asp Thr Thr Thr Ile Ser Pro Thr Leu Thr Ser Thr Ser Thr Thr
145                 150                 155                 160
Pro Leu Thr Thr Ala Ser Thr Ser Thr Thr Pro Ser Thr Asp Ile Thr
                165                 170                 175
Ser Ala Leu Pro Thr Thr Thr Ser Thr Lys Leu Ser Thr Ser Ile Pro
                180                 185                 190
Thr Ser Thr Thr Ser Ser Thr Ser Thr Thr Ser Thr Ser Ser Ser Ser
                195                 200                 205
Thr Ser Thr Thr Val Ser Val Thr Ser Ser Thr Ser Thr Thr Thr Ser
                210                 215                 220
Thr Thr Ser Ser Thr Leu Ile Ser Thr Ser Thr Ser Ser Ser Ser Ser
225                 230                 235                 240
Ser Thr Pro Thr Thr Thr Ser Ser Ala Pro Ile Ser Thr Ser Thr Thr
                245                 250                 255
Ser Ser Thr Ser Thr Ser Thr Ser Thr Thr Ser Pro Thr Ser Ser Ser
                260                 265                 270
Ala Pro Thr Ser Ser Ser Asn Thr Thr Pro Thr Ser Thr Thr Phe Thr
                275                 280                 285
Thr Thr Ser Pro Ser Thr Ala Pro Ser Ser Thr Val Thr Tyr Thr
                290                 295                 300
Ser Thr Thr Ala Ser Pro Ile Thr Ser Thr Ile Thr Ser Val Asn Leu
305                 310                 315                 320
Gln Thr Ser Leu Lys Tyr Ser Val Ile Thr Val Ser Val His Thr
                325                 330                 335
Met Asp Thr Asn Ile Ser Glu Ile Thr Ser Arg Tyr Leu Thr Met Lys
                340                 345                 350
Lys Val Ile Thr Gln Ile Tyr Ser Ser Thr Leu Gly Ala Thr Pro Thr
                355                 360                 365
Ser Ala Val Ala Thr Thr Ser Ala Ser Val Gly Gly Arg Ile Thr Asn
                370                 375                 380
Asn Asn Asn Ser Asn Thr Thr Asn Ser Asn Thr Pro Thr Asn Lys Ser
385                 390                 395                 400
Thr Glu Lys Lys Gly Tyr Trp Asp Ser Pro Gly Lys Ile Ala Ala Thr
                405                 410                 415
Phe Val Val Gly Val Val Cys Leu Val Ile Ile Cys Ile Leu Ile
                420                 425                 430
```

```
Tyr Leu Ile His His Tyr Arg Thr Arg Pro Ala Arg Lys Ala Gln Asp
            435                 440                 445

Phe Glu Asn Glu Tyr Gln Ser Lys Phe Tyr Gln Ser Lys Tyr Pro Asn
        450                 455                 460

Glu Val Thr Thr Thr Thr Leu His Thr Pro Ser Pro Ser Ser Asn Ser
465                 470                 475                 480

Thr Phe Ser Thr Pro Arg Leu Ile Tyr Thr Asp Glu Lys Gly Gln Ile
                485                 490                 495

Met Ser Glu Ser Pro Ser Pro Arg Gln Ser Thr Tyr Ser Leu Thr Ala
                500                 505                 510

Gly Ser Pro Pro Asn Asp Pro Ser Thr Leu Ala Ser Pro Phe His Asp
            515                 520                 525

Pro Ile Leu Pro Arg Arg Thr Ser Thr Phe Leu His Ser Pro Ile Gln
            530                 535                 540

Lys Gln His Glu Lys Met Glu Ser Asn Val Thr Leu Gly Glu Asp Thr
545                 550                 555                 560

Val Leu Val Asp Gln Arg Leu Asp Pro Ser Lys Met Leu Asn Thr Leu
                565                 570                 575

Ala Asn Asp Asp Ala Thr Asn His Ser Thr Ile Ser Leu Ser Asp Asn
            580                 585                 590

Val Asp Tyr Ser Arg Arg Val Leu Arg Leu Met Asn Glu Gly Ser Ala
            595                 600                 605

Ala Pro Gly Ala Ser Ala Ala Pro Gly Ala Gly Ser Gly Ser Gly Ser
            610                 615                 620

Gly Met Asp Asp Ile Ile Thr Gln Val Ser Pro Asp Asn Ala Glu Ser
625                 630                 635                 640

Ala Pro Ile Leu Gln Glu Gln Gln Gln Gln Asn Ser Gln Tyr Glu
            645                 650                 655

Gly Asn Glu Glu Asp Tyr Gly Asp Ser Leu Ile His Leu Asn Ile Gln
            660                 665                 670

Glu Asn His Tyr Phe Ile Thr Arg Asp Gln Leu Met Ser Leu Pro Glu
            675                 680                 685

Ser Leu Leu Leu Cys Leu Phe Pro Ser Gly Val Phe Leu Asp Arg Cys
            690                 695                 700

Gly Gln Val Ile Thr Asn Leu Thr Arg Asp Asp Glu Val Tyr Ile Val
705                 710                 715                 720

Asn Phe Pro Pro Asp Cys Phe Glu Tyr Ile Met Glu Ile Tyr Thr Lys
                725                 730                 735

Ala His Asp Asp Leu Tyr Asn His Pro Val Glu Lys Phe Phe Asp Arg
                740                 745                 750

Pro Ser Ser Ser Phe Val Ser Asn Ala Lys Gly Phe Phe Gly Leu Ser
            755                 760                 765

Ser Asn Asn Ser Ile Ser Ser Asn Asn Glu Gln Asp Ile Leu His Gln
            770                 775                 780

Lys Pro Ala Ile Ile Val Leu Arg Glu Asp Leu Asp Tyr Tyr Cys Val
785                 790                 795                 800

Pro Gln Glu Glu Phe Gln Phe Asp Ser Thr Asn Glu Glu Asn Asn Glu
                805                 810                 815

Asp Leu Leu Arg His Phe Met Ala Gln Val Lys Met Ala Ala Gly Ser
            820                 825                 830

Tyr Leu Thr Ser Lys Thr Ser Ile Phe Gln Gly Leu Tyr Ser Ser Asn
            835                 840                 845
```

Arg Leu Lys Gln Gln Gln Gln Gln Lys Ile Glu Lys Gly Ser Asn
    850                 855                 860

Ser Ser Ser Asn Thr Lys Ser Thr Ser Lys Lys Leu Gly Pro Ala Glu
865                 870                 875                 880

Gln His Leu Met Asp Met Leu Cys Ser Ser Gly Phe Thr Lys Glu Thr
                885                 890                 895

Cys Trp Gly Asn Arg Thr Gln Glu Thr Gly Lys Thr Val Ile Ser Ser
                900                 905                 910

Leu Ser Leu Cys Arg Leu Ala Asn Glu Thr Thr Glu Gly Phe Arg Gln
            915                 920                 925

Lys Phe Asn Glu Ala Lys Ala Lys Trp Glu Ala Glu His Lys Pro Ser
930                 935                 940

Gln Asp Asn Phe Ile Thr Pro Met Gln Ser Asn Ile Ser Ile Asn Ser
945                 950                 955                 960

Leu Ser Ala Ser Lys Ser Asn Ser Thr Ile Ser Thr Ala Arg Asn Leu
                965                 970                 975

Thr Ser Gly Ser Thr Ala Pro Ala Thr Ala Arg Asp Lys Ser Arg Lys Ser
                980                 985                 990

Arg Leu Ser Lys Leu Ala Asp Asn Val Arg Ser His Ser Ser Ser Arg
            995                 1000                1005

His Ser Ser Gln Thr Arg Ser Lys Pro Pro Glu Leu Pro Lys Leu
    1010                1015                1020

Tyr Asp Leu Val Pro Lys Pro Asn Ile Asn Ala Lys Leu Leu Leu
    1025                1030                1035

Phe Trp Arg Lys Pro Ala Arg Lys Cys Trp Trp Gly Glu Glu Asp
    1040                1045                1050

Ile Glu Leu Glu Val Glu Val Phe Gly Ser Trp Lys Asp Glu Ser
    1055                1060                1065

Lys Lys Ile Ile Glu Leu Ile Leu Pro Thr Asn Val Asp Pro Glu
    1070                1075                1080

Ala Glu Leu His Lys Ile Ile Val Pro Val Arg Leu His Ile Arg
    1085                1090                1095

Arg Val Trp Thr Leu Glu Leu Ser Val Ile Gly Val Gln
    1100                1105                1110

<210> SEQ ID NO 72
<211> LENGTH: 785
<212> TYPE: PRT
<213> ORGANISM: Saccharomyces cerevisiae

<400> SEQUENCE: 72

Met Gly Asp Glu Leu His Asn Arg Leu Leu His Gln Asn Asp Gly Thr
1               5                   10                  15

Lys Asp Ala Ile Leu Tyr Lys Ile Ile Glu Ser Leu Val Cys Ser Ile
                20                  25                  30

Cys His Asp Tyr Met Phe Val Pro Met Met Thr Pro Cys Gly His Asn
            35                  40                  45

Tyr Cys Tyr Gly Cys Leu Asn Thr Trp Phe Ala Ser Asn Thr Gln Lys
    50                  55                  60

Glu Leu Ala Cys Pro Gln Cys Arg Ser Asp Ile Thr Thr Ile Pro Ala
65                  70                  75                  80

Leu Asn Thr Thr Leu Gln Gln Tyr Leu Ser Phe Ile Leu Glu Lys Leu
                85                  90                  95

Arg Asp Gln Asn Asp Glu Ser Phe Lys Lys Leu Leu Thr Thr Lys Thr
                100                 105                 110

```
Lys Glu Glu Asn Asp Tyr Lys Asn Asp Lys Glu Lys Asp Thr Leu Phe
        115                 120                 125

Asp Lys Val Phe Lys Asn Ser Ala Leu Ala Val Ala Asp Ser Asp
130                 135                 140

Asp Gly Ile Thr Arg Cys Ser Asn Cys His Trp Glu Leu Asp Pro Asp
145                 150                 155                 160

Glu Val Glu Asp Gly Asn Val Cys Pro His Cys Asn Ala Arg Ile Arg
                165                 170                 175

Asn Tyr Ala Gly Gly Arg Asp Glu Phe Asp Glu Glu Tyr Ser Glu
                180                 185                 190

Gly Glu Leu Asp Glu Ile Arg Ser Met Arg Arg Arg Glu Asn
        195                 200                 205

Arg Phe Ala Ser Thr Asn Pro Phe Ala Asn Arg Asp Asp Val Ser Ser
        210                 215                 220

Glu Asp Asp Asp Ser Ser Glu Glu Pro Met Arg Glu His Ile Pro
225                 230                 235                 240

Leu Gly Arg Trp Ala Arg Ser His Asn Arg Ser Ile Ala Val Asp Ala
                245                 250                 255

Val Asp Asp Glu Asp Glu Gly Ser Ala Ala Pro Gly Ala Ser Ala
        260                 265                 270

Ala Pro Gly Ala Gly Ser Gly Ser Gly Met Leu Leu Asp Val
        275                 280                 285

Asn Thr Asn His Thr Leu Met His Asp Ala His Val His Glu His Cys
        290                 295                 300

Leu Ile Lys Ser Ile Arg Asp Asp Gly Ala Leu His Ser Trp Ser Asp
305                 310                 315                 320

Ser Ser Lys Val Phe Tyr Pro Lys Ser Phe Tyr Ala Thr Ala Thr Asn
                325                 330                 335

Lys Lys Asn Asn Lys Leu Ala Ser Ala Ser Met Asn Lys Thr Ala Thr
                340                 345                 350

Ser Asn Arg Thr Val Ser Asp Glu Ile Tyr Phe His Ser Thr Lys Pro
        355                 360                 365

Gln Phe Asp Gly Gln Gly Ser Ala Glu Arg Thr Arg Thr Leu Thr Lys
        370                 375                 380

Arg Asn Ser Phe Lys Arg Thr Arg Ile Leu Lys Ala Arg Asp Asp Ser
385                 390                 395                 400

Glu Leu Leu Asn Glu Asn Arg Ser Ser Leu Met Thr Pro Ser Leu Ser
                405                 410                 415

Ser Val Met Ser Gln Val Arg Lys Thr Asn Ser Ala Lys Thr Leu Ser
                420                 425                 430

Gly Glu Cys Pro Ile His Glu Gly His Leu Thr Gln Ser Ile Lys Arg
        435                 440                 445

Lys Phe Ser Glu Glu Ala Gln Ser Asp Cys Ser Ser Leu Ser Ser Ser
        450                 455                 460

Lys Leu His Pro Leu Thr Asp Asp Ile Ala Asp Ala Val Asp Leu Gln
465                 470                 475                 480

Thr Pro Ala Ile Gly Asp Glu Val Leu Ala Glu Pro Val Val Pro Lys
                485                 490                 495

Met Lys Ile Ile Asn Ile Asn Asp Leu Asp Leu Phe Asp Asp Trp Glu
                500                 505                 510

Val Lys Asp Leu Val Asp Ile Phe Pro Pro Val Tyr Glu Arg Arg Pro
        515                 520                 525
```

```
Arg Ser Ser Ala Leu Ser Leu Val Ser Ala Ser Ser Asp Ala Lys
    530             535                 540

Leu Arg Pro Thr Ser Val Asp Phe Gln Ile Ile Asp Lys Lys Gly Gly
545                 550                 555                 560

Lys Thr Ser Arg Arg Lys Ser Arg Ser Lys Ser Thr Thr Glu Asn Met
                565                 570                 575

Ile Tyr Glu Asn Asp Leu Val Glu Leu Glu Gln Trp Pro Ser Ala Ser
            580                 585                 590

Pro Ser Pro Glu Thr Asp Gly Ser Ile Ala Ser Ser Glu Leu Leu Pro
        595                 600                 605

Asn Lys Arg Ile Arg Gln Lys Ser Leu Asn Thr Asn Phe Leu Lys Leu
610                 615                 620

Tyr Ser Ile Glu Thr Ser Cys Lys Arg Lys Ser Ile Leu Pro Glu Val
625                 630                 635                 640

Glu Val Asp Asp His Leu Leu Lys Gln Leu Thr Tyr Ser Glu Ile Arg
                645                 650                 655

Ser Leu Glu Ile Lys Lys Glu Pro Asn Val Ser Thr Asn Asp Ile Lys
            660                 665                 670

Leu Ala Leu Ile Thr Arg Lys Lys Leu Trp Ser Asp Met Val His Glu
        675                 680                 685

Thr Arg Asn Asp Leu Phe Gly Asp Ser Thr Pro Trp Asn Leu His Phe
690                 695                 700

Val Ala Thr Thr Ser Asn Thr Glu Pro Ser Gln Gly Arg Glu Ser Ala
705                 710                 715                 720

Ser Glu His Ala Thr Ala Asp Leu Lys Ser Ser Leu Val Arg Val His
                725                 730                 735

Ser Asp Val Lys Pro Trp Phe Asn Asn Gly Gly Thr Met Leu Lys Pro
            740                 745                 750

Cys Gly Lys Leu Asn Leu Gly Lys Val Thr Asn Lys Thr Ser Ala Pro
        755                 760                 765

Thr Arg Glu Ile Gln Tyr Val Val Lys Gly Trp Cys Asp Ser Arg Phe
770                 775                 780

Leu
785

<210> SEQ ID NO 73
<211> LENGTH: 898
<212> TYPE: PRT
<213> ORGANISM: Saccharomyces cerevisiae

<400> SEQUENCE: 73

Met Ala Asp Thr Pro Ser Val Ala Val Gln Ala Pro Gly Tyr Gly
1               5                   10                  15

Lys Thr Glu Leu Phe His Leu Pro Leu Ile Ala Leu Ala Ser Lys Gly
                20                  25                  30

Asp Val Lys Tyr Val Ser Phe Leu Phe Val Pro Tyr Thr Val Leu Leu
            35                  40                  45

Ala Asn Cys Met Ile Arg Leu Gly Arg Arg Gly Cys Leu Asn Val Ala
        50                  55                  60

Pro Val Arg Asn Phe Ile Glu Glu Gly Tyr Asp Gly Thr Asp Leu
65                  70                  75                  80

Tyr Val Gly Ile Tyr Asp Asp Leu Ala Ser Thr Asn Phe Thr Asp Arg
                85                  90                  95

Ile Ala Ala Trp Glu Asn Ile Val Glu Cys Thr Phe Arg Thr Asn Asn
            100                 105                 110
```

```
Val Lys Leu Gly Tyr Leu Ile Val Asp Glu Phe His Asn Phe Glu Thr
        115                 120                 125
Glu Val Tyr Arg Gln Ser Gln Phe Gly Gly Ile Thr Asn Leu Asp Phe
    130                 135                 140
Asp Ala Phe Glu Lys Ala Ile Phe Leu Ser Gly Thr Ala Pro Glu Ala
145                 150                 155                 160
Val Ala Asp Ala Ala Leu Gln Arg Ile Gly Leu Thr Gly Leu Ala Lys
                165                 170                 175
Lys Ser Met Asp Ile Asn Glu Leu Lys Arg Ser Glu Asp Leu Ser Arg
            180                 185                 190
Gly Leu Ser Ser Tyr Pro Thr Arg Met Phe Asn Leu Ile Lys Glu Lys
        195                 200                 205
Ser Glu Val Pro Leu Gly His Val His Lys Ile Trp Lys Lys Val Glu
    210                 215                 220
Ser Gln Pro Glu Glu Ala Leu Lys Leu Leu Ala Leu Phe Glu Ile
225                 230                 235                 240
Glu Pro Glu Ser Lys Ala Ile Val Val Ala Ser Thr Thr Asn Glu Val
                245                 250                 255
Glu Glu Leu Ala Cys Ser Trp Arg Lys Tyr Phe Arg Val Val Trp Ile
            260                 265                 270
His Gly Lys Leu Gly Ala Ala Glu Lys Val Ser Arg Thr Lys Glu Phe
        275                 280                 285
Val Thr Asp Gly Ser Met Gln Val Leu Ile Gly Thr Lys Leu Val Thr
    290                 295                 300
Glu Gly Ile Asp Ile Lys Gln Leu Met Met Val Ile Met Leu Asp Asn
305                 310                 315                 320
Arg Leu Asn Ile Ile Glu Leu Ile Gln Gly Val Gly Arg Leu Arg Asp
                325                 330                 335
Gly Gly Leu Cys Tyr Leu Leu Ser Arg Lys Asn Ser Trp Ala Ala Arg
            340                 345                 350
Asn Arg Lys Gly Glu Leu Pro Pro Ile Lys Glu Gly Cys Ile Thr Glu
        355                 360                 365
Gln Val Arg Glu Phe Tyr Gly Leu Glu Ser Lys Lys Gly Lys Lys Gly
    370                 375                 380
Gln His Val Gly Cys Val Cys Gly Ser Ala Ala Pro Gly Ala Ser
385                 390                 395                 400
Ala Ala Pro Gly Ala Gly Ser Gly Ser Gly Met Asp Asp Ile
                405                 410                 415
Ile Thr Gln Val Ser Pro Asp Asn Ala Glu Ser Ala Pro Ile Leu Gln
            420                 425                 430
Glu Gln Gln Gln Gln Asn Ser Gln Tyr Glu Gly Asn Glu Glu Asp
        435                 440                 445
Tyr Gly Asp Ser Leu Ile His Leu Asn Ile Gln Glu Asn His Tyr Phe
    450                 455                 460
Ile Thr Arg Asp Gln Leu Met Ser Leu Pro Glu Ser Leu Leu Leu Cys
465                 470                 475                 480
Leu Phe Pro Ser Gly Val Phe Leu Asp Arg Cys Gly Gln Val Ile Thr
                485                 490                 495
Asn Leu Thr Arg Asp Asp Glu Val Tyr Ile Val Asn Phe Pro Pro Asp
            500                 505                 510
Cys Phe Glu Tyr Ile Met Glu Ile Tyr Thr Lys Ala His Asp Asp Leu
        515                 520                 525
```

```
Tyr Asn His Pro Val Glu Lys Phe Phe Asp Arg Pro Ser Ser Ser Phe
    530                 535                 540

Val Ser Asn Ala Lys Gly Phe Phe Gly Leu Ser Ser Asn Asn Ser Ile
545                 550                 555                 560

Ser Ser Asn Asn Glu Gln Asp Ile Leu His Gln Lys Pro Ala Ile Ile
            565                 570                 575

Val Leu Arg Glu Asp Leu Asp Tyr Tyr Cys Val Pro Gln Glu Glu Phe
            580                 585                 590

Gln Phe Asp Ser Thr Asn Glu Glu Asn Asn Glu Asp Leu Leu Arg His
        595                 600                 605

Phe Met Ala Gln Val Lys Met Ala Ala Gly Ser Tyr Leu Thr Ser Lys
    610                 615                 620

Thr Ser Ile Phe Gln Gly Leu Tyr Ser Ser Asn Arg Leu Lys Gln Gln
625                 630                 635                 640

Gln Gln Gln Gln Lys Ile Glu Lys Gly Ser Asn Ser Ser Ser Asn Thr
                645                 650                 655

Lys Ser Thr Ser Lys Lys Leu Gly Pro Ala Glu Gln His Leu Met Asp
            660                 665                 670

Met Leu Cys Ser Ser Gly Phe Thr Lys Glu Thr Cys Trp Gly Asn Arg
        675                 680                 685

Thr Gln Glu Thr Gly Lys Thr Val Ile Ser Ser Leu Ser Leu Cys Arg
    690                 695                 700

Leu Ala Asn Glu Thr Thr Glu Gly Phe Arg Gln Lys Phe Asn Glu Ala
705                 710                 715                 720

Lys Ala Lys Trp Glu Ala Glu His Lys Pro Ser Gln Asp Asn Phe Ile
                725                 730                 735

Thr Pro Met Gln Ser Asn Ile Ser Ile Asn Ser Leu Ser Ala Ser Lys
            740                 745                 750

Ser Asn Ser Thr Ile Ser Thr Ala Arg Asn Leu Thr Ser Gly Ser Thr
        755                 760                 765

Ala Pro Ala Thr Ala Arg Asp Lys Arg Lys Ser Arg Leu Ser Lys Leu
    770                 775                 780

Ala Asp Asn Val Arg Ser His Ser Ser Ser Arg His Ser Ser Gln Thr
785                 790                 795                 800

Arg Ser Lys Pro Pro Glu Leu Pro Lys Leu Tyr Asp Leu Val Pro Lys
                805                 810                 815

Pro Asn Ile Asn Ala Lys Leu Leu Phe Trp Arg Lys Pro Ala Arg
            820                 825                 830

Lys Cys Trp Trp Gly Glu Glu Asp Ile Glu Leu Glu Val Glu Val Phe
    835                 840                 845

Gly Ser Trp Lys Asp Glu Ser Lys Lys Ile Ile Glu Leu Ile Leu Pro
850                 855                 860

Thr Asn Val Asp Pro Glu Ala Glu Leu His Lys Ile Ile Val Pro Val
865                 870                 875                 880

Arg Leu His Ile Arg Arg Val Trp Thr Leu Glu Leu Ser Val Ile Gly
                885                 890                 895

Val Gln

<210> SEQ ID NO 74
<211> LENGTH: 815
<212> TYPE: PRT
<213> ORGANISM: Saccharomyces cerevisiae

<400> SEQUENCE: 74
```

```
Met Ser Ala Val Phe Asn Asn Ala Thr Leu Ser Gly Leu Val Gln Ala
1               5                   10                  15

Ser Thr Tyr Ser Gln Thr Leu Gln Asn Val Ala His Tyr Gln Pro Gln
            20                  25                  30

Leu Asn Phe Met Glu Lys Tyr Trp Ala Ala Trp Tyr Ser Tyr Met Asn
            35                  40                  45

Asn Asp Val Leu Ala Thr Gly Leu Met Phe Phe Leu Leu His Glu Phe
        50                  55                  60

Met Tyr Phe Phe Arg Cys Leu Pro Trp Phe Ile Ile Asp Gln Ile Pro
65              70                  75                  80

Tyr Phe Arg Arg Trp Lys Leu Gln Pro Thr Lys Ile Pro Ser Ala Lys
                85                  90                  95

Glu Gln Leu Tyr Cys Leu Lys Ser Val Leu Leu Ser His Phe Leu Val
            100                 105                 110

Glu Ala Ile Pro Ile Trp Thr Phe His Pro Met Cys Glu Lys Leu Gly
            115                 120                 125

Ile Thr Val Glu Val Pro Phe Pro Ser Leu Lys Thr Met Ala Leu Glu
        130                 135                 140

Ile Gly Leu Phe Phe Val Leu Glu Asp Thr Trp His Tyr Trp Ala His
145                 150                 155                 160

Arg Leu Phe His Tyr Gly Val Phe Tyr Lys Tyr Ile His Lys Gln His
                165                 170                 175

His Arg Tyr Ala Ala Pro Phe Gly Leu Ser Ala Glu Tyr Ala His Pro
            180                 185                 190

Ala Glu Thr Leu Ser Leu Gly Phe Gly Thr Val Gly Met Pro Ile Leu
            195                 200                 205

Tyr Val Met Tyr Thr Gly Lys Leu His Leu Phe Thr Leu Cys Val Trp
        210                 215                 220

Ile Thr Leu Arg Leu Phe Gln Ala Val Asp Ser His Ser Gly Tyr Asp
225                 230                 235                 240

Phe Pro Trp Ser Leu Asn Lys Ile Met Pro Phe Trp Ala Gly Ala Glu
                245                 250                 255

His His Asp Leu His His His Tyr Phe Ile Gly Asn Tyr Ala Ser Ser
            260                 265                 270

Phe Arg Trp Trp Asp Tyr Cys Leu Asp Thr Glu Ser Gly Pro Glu Ala
            275                 280                 285

Lys Ala Ser Arg Glu Glu Arg Met Lys Lys Arg Ala Glu Asn Asn Ala
        290                 295                 300

Gln Lys Lys Thr Asn Gly Ser Ala Ala Pro Gly Ala Ser Ala Ala Pro
305                 310                 315                 320

Gly Ala Gly Ser Gly Ser Gly Ser Gly Met Asp Asp Ile Ile Thr Gln
                325                 330                 335

Val Ser Pro Asp Asn Ala Glu Ser Ala Pro Ile Leu Gln Glu Gln Gln
            340                 345                 350

Gln Gln Gln Asn Ser Gln Tyr Glu Gly Asn Glu Asp Tyr Gly Asp
            355                 360                 365

Ser Leu Ile His Leu Asn Ile Gln Glu Asn His Tyr Phe Ile Thr Arg
        370                 375                 380

Asp Gln Leu Met Ser Leu Pro Glu Ser Leu Leu Leu Cys Leu Phe Pro
385                 390                 395                 400

Ser Gly Val Phe Leu Asp Arg Cys Gly Gln Val Ile Thr Asn Leu Thr
                405                 410                 415

Arg Asp Asp Glu Val Tyr Ile Val Asn Phe Pro Pro Asp Cys Phe Glu
```

```
                420                 425                 430
Tyr Ile Met Glu Ile Tyr Thr Lys Ala His Asp Asp Leu Tyr Asn His
            435                 440                 445
Pro Val Glu Lys Phe Phe Asp Arg Pro Ser Ser Ser Phe Val Ser Asn
        450                 455                 460
Ala Lys Gly Phe Phe Gly Leu Ser Ser Asn Asn Ser Ile Ser Ser Asn
465                 470                 475                 480
Asn Glu Gln Asp Ile Leu His Gln Lys Pro Ala Ile Ile Val Leu Arg
                485                 490                 495
Glu Asp Leu Asp Tyr Tyr Cys Val Pro Gln Glu Glu Phe Gln Phe Asp
            500                 505                 510
Ser Thr Asn Glu Glu Asn Asn Glu Asp Leu Leu Arg His Phe Met Ala
        515                 520                 525
Gln Val Lys Met Ala Ala Gly Ser Tyr Leu Thr Ser Lys Thr Ser Ile
        530                 535                 540
Phe Gln Gly Leu Tyr Ser Ser Asn Arg Leu Lys Gln Gln Gln Gln Gln
545                 550                 555                 560
Gln Lys Ile Glu Lys Gly Ser Asn Ser Ser Asn Thr Lys Ser Thr
                565                 570                 575
Ser Lys Lys Leu Gly Pro Ala Glu Gln His Leu Met Asp Met Leu Cys
            580                 585                 590
Ser Ser Gly Phe Thr Lys Glu Thr Cys Trp Gly Asn Arg Thr Gln Glu
        595                 600                 605
Thr Gly Lys Thr Val Ile Ser Ser Leu Ser Leu Cys Arg Leu Ala Asn
        610                 615                 620
Glu Thr Thr Glu Gly Phe Arg Gln Lys Phe Asn Glu Ala Lys Ala Lys
625                 630                 635                 640
Trp Glu Ala Glu His Lys Pro Ser Gln Asp Asn Phe Ile Thr Pro Met
                645                 650                 655
Gln Ser Asn Ile Ser Ile Asn Ser Leu Ser Ala Ser Lys Ser Asn Ser
            660                 665                 670
Thr Ile Ser Thr Ala Arg Asn Leu Thr Ser Gly Ser Thr Ala Pro Ala
        675                 680                 685
Thr Ala Arg Asp Lys Arg Lys Ser Arg Leu Ser Lys Leu Ala Asp Asn
        690                 695                 700
Val Arg Ser His Ser Ser Arg His Ser Ser Gln Thr Arg Ser Lys
705                 710                 715                 720
Pro Pro Glu Leu Pro Lys Leu Tyr Asp Leu Val Pro Lys Pro Asn Ile
                725                 730                 735
Asn Ala Lys Leu Leu Leu Phe Trp Arg Lys Pro Ala Arg Lys Cys Trp
            740                 745                 750
Trp Gly Glu Glu Asp Ile Glu Leu Glu Val Glu Val Phe Gly Ser Trp
        755                 760                 765
Lys Asp Glu Ser Lys Lys Ile Ile Glu Leu Ile Leu Pro Thr Asn Val
        770                 775                 780
Asp Pro Glu Ala Glu Leu His Lys Ile Ile Val Pro Val Arg Leu His
785                 790                 795                 800
Ile Arg Arg Val Trp Thr Leu Glu Leu Ser Val Ile Gly Val Gln
                805                 810                 815

<210> SEQ ID NO 75
<211> LENGTH: 673
<212> TYPE: PRT
<213> ORGANISM: Saccharomyces cerevisiae
```

<400> SEQUENCE: 75

```
Met Asn Asn Glu Thr Ser Gly Lys Glu Thr Ala Ser Ala Pro Leu Cys
1               5                   10                  15

Ser Pro Lys Leu Pro Val Glu Lys Val Gln Arg Ile Ala Lys Asn Asp
            20                  25                  30

Pro Glu Tyr Met Asp Thr Ser Asp Asp Ala Phe Val Ala Thr Ala Phe
        35                  40                  45

Ala Thr Glu Phe Phe Val Gln Val Leu Thr His Glu Ser Leu His Arg
    50                  55                  60

Gln Gln Gln Gln Gln Gln Gln Val Pro Pro Leu Pro Asp Glu Leu
65                  70                  75                  80

Thr Leu Ser Tyr Asp Asp Ile Ser Ala Ala Ile Val His Ser Ser Asp
                85                  90                  95

Gly His Leu Gln Phe Leu Asn Asp Val Ile Pro Thr Thr Lys Asn Leu
            100                 105                 110

Arg Leu Leu Val Glu Glu Asn Arg Val Arg Tyr Thr Thr Ser Val Met
            115                 120                 125

Pro Pro Asn Glu Val Tyr Ser Ala Tyr Val Val Asn Asp Thr Ala Pro
130                 135                 140

Lys Pro Asn Ile Val Glu Ile Asp Leu Asp Asn Asp Glu Asp Asp
145                 150                 155                 160

Glu Asp Val Thr Asp Gln Glu Gly Ser Ala Ala Pro Gly Ala Ser Ala
                165                 170                 175

Ala Pro Gly Ala Gly Ser Gly Ser Gly Met Asp Asp Ile Ile
            180                 185                 190

Thr Gln Val Ser Pro Asp Asn Ala Glu Ser Ala Pro Ile Leu Gln Glu
            195                 200                 205

Gln Gln Gln Gln Asn Ser Gln Tyr Glu Gly Asn Glu Glu Asp Tyr
210                 215                 220

Gly Asp Ser Leu Ile His Leu Asn Ile Gln Glu Asn His Tyr Phe Ile
225                 230                 235                 240

Thr Arg Asp Gln Leu Met Ser Leu Pro Glu Ser Leu Leu Cys Leu
            245                 250                 255

Phe Pro Ser Gly Val Phe Leu Asp Arg Cys Gly Gln Val Ile Thr Asn
            260                 265                 270

Leu Thr Arg Asp Asp Glu Val Tyr Ile Val Asn Phe Pro Pro Asp Cys
            275                 280                 285

Phe Glu Tyr Ile Met Glu Ile Tyr Thr Lys Ala His Asp Asp Leu Tyr
            290                 295                 300

Asn His Pro Val Glu Lys Phe Asp Arg Pro Ser Ser Ser Phe Val
305                 310                 315                 320

Ser Asn Ala Lys Gly Phe Phe Gly Leu Ser Ser Asn Asn Ser Ile Ser
            325                 330                 335

Ser Asn Asn Glu Gln Asp Ile Leu His Gln Lys Pro Ala Ile Ile Val
            340                 345                 350

Leu Arg Glu Asp Leu Asp Tyr Tyr Cys Val Pro Gln Glu Glu Phe Gln
            355                 360                 365

Phe Asp Ser Thr Asn Glu Glu Asn Asn Glu Asp Leu Leu Arg His Phe
            370                 375                 380

Met Ala Gln Val Lys Met Ala Ala Gly Ser Tyr Leu Thr Ser Lys Thr
385                 390                 395                 400

Ser Ile Phe Gln Gly Leu Tyr Ser Ser Asn Arg Leu Lys Gln Gln Gln
```

```
                    405                 410                 415
Gln Gln Gln Lys Ile Glu Lys Gly Ser Asn Ser Ser Asn Thr Lys
            420                 425                 430

Ser Thr Ser Lys Lys Leu Gly Pro Ala Glu Gln His Leu Met Asp Met
        435                 440                 445

Leu Cys Ser Ser Gly Phe Thr Lys Glu Thr Cys Trp Gly Asn Arg Thr
450                 455                 460

Gln Glu Thr Gly Lys Thr Val Ile Ser Ser Leu Ser Leu Cys Arg Leu
465                 470                 475                 480

Ala Asn Glu Thr Thr Glu Gly Phe Arg Gln Lys Phe Asn Glu Ala Lys
            485                 490                 495

Ala Lys Trp Glu Ala Glu His Lys Pro Ser Gln Asp Asn Phe Ile Thr
        500                 505                 510

Pro Met Gln Ser Asn Ile Ser Ile Asn Ser Leu Ser Ala Ser Lys Ser
        515                 520                 525

Asn Ser Thr Ile Ser Thr Ala Arg Asn Leu Thr Ser Gly Ser Thr Ala
    530                 535                 540

Pro Ala Thr Ala Arg Asp Lys Arg Lys Ser Arg Leu Ser Lys Leu Ala
545                 550                 555                 560

Asp Asn Val Arg Ser His Ser Ser Arg His Ser Ser Gln Thr Arg
                565                 570                 575

Ser Lys Pro Pro Glu Leu Pro Lys Leu Tyr Asp Leu Val Pro Lys Pro
            580                 585                 590

Asn Ile Asn Ala Lys Leu Leu Leu Phe Trp Arg Lys Pro Ala Arg Lys
            595                 600                 605

Cys Trp Trp Gly Glu Glu Asp Ile Glu Leu Glu Val Glu Val Phe Gly
        610                 615                 620

Ser Trp Lys Asp Glu Ser Lys Lys Ile Ile Glu Leu Ile Leu Pro Thr
625                 630                 635                 640

Asn Val Asp Pro Glu Ala Glu Leu His Lys Ile Ile Val Pro Val Arg
            645                 650                 655

Leu His Ile Arg Arg Val Trp Thr Leu Glu Leu Ser Val Ile Gly Val
                660                 665                 670

Gln

<210> SEQ ID NO 76
<211> LENGTH: 738
<212> TYPE: PRT
<213> ORGANISM: Saccharomyces cerevisiae

<400> SEQUENCE: 76

Met Leu Leu Asp Val Asn Thr Asn His Thr Leu Met His Asp Ala His
1               5                   10                  15

Val His Glu His Cys Leu Ile Lys Ser Ile Arg Asp Asp Gly Ala Leu
            20                  25                  30

His Ser Trp Ser Asp Ser Ser Lys Val Phe Tyr Pro Lys Ser Phe Tyr
        35                  40                  45

Ala Thr Ala Thr Asn Lys Lys Asn Asn Lys Leu Ala Ser Ala Ser Met
    50                  55                  60

Asn Lys Thr Ala Thr Ser Asn Arg Thr Val Ser Asp Glu Ile Tyr Phe
65                  70                  75                  80

His Ser Thr Lys Pro Gln Phe Asp Gly Gln Gly Ser Ala Glu Arg Thr
                85                  90                  95

Arg Thr Leu Thr Lys Arg Asn Ser Phe Lys Arg Thr Arg Ile Leu Lys
```

```
                100             105             110
Ala Arg Asp Asp Ser Glu Leu Leu Asn Glu Asn Arg Ser Ser Leu Met
            115             120             125
Thr Pro Ser Leu Ser Ser Val Met Ser Gln Val Arg Lys Thr Asn Ser
130             135             140
Ala Lys Thr Leu Ser Gly Glu Cys Pro Ile His Glu Gly His Leu Thr
145             150             155             160
Gln Ser Ile Lys Arg Lys Phe Ser Glu Ala Gln Ser Asp Cys Ser
            165             170             175
Ser Leu Ser Ser Ser Lys Leu His Pro Leu Thr Asp Asp Ile Ala Asp
            180             185             190
Ala Val Asp Leu Gln Thr Pro Ala Ile Gly Asp Glu Val Leu Ala Glu
            195             200             205
Pro Val Pro Lys Met Lys Ile Ile Asn Ile Asn Asp Leu Asp Leu
210             215             220
Phe Asp Asp Trp Glu Val Lys Asp Leu Val Asp Ile Phe Pro Pro Val
225             230             235             240
Tyr Glu Arg Arg Pro Arg Ser Ser Ala Leu Ser Leu Val Ser Ala
            245             250             255
Ser Ser Asp Ala Lys Leu Arg Pro Thr Ser Val Asp Phe Gln Ile Ile
            260             265             270
Asp Lys Lys Gly Gly Lys Thr Ser Arg Arg Lys Ser Arg Ser Lys Ser
            275             280             285
Thr Thr Glu Asn Met Ile Tyr Glu Asn Asp Leu Val Glu Leu Glu Gln
            290             295             300
Trp Pro Ser Ala Ser Pro Ser Pro Glu Thr Asp Gly Ser Ile Ala Ser
305             310             315             320
Ser Glu Leu Leu Pro Asn Lys Arg Ile Arg Gln Lys Ser Leu Asn Thr
            325             330             335
Asn Phe Leu Lys Leu Tyr Ser Ile Glu Thr Ser Cys Lys Arg Lys Ser
            340             345             350
Ile Leu Pro Glu Val Glu Val Asp Asp His Leu Leu Lys Gln Leu Thr
            355             360             365
Tyr Ser Glu Ile Arg Ser Leu Glu Ile Lys Lys Glu Pro Asn Val Ser
            370             375             380
Thr Asn Asp Ile Lys Leu Ala Leu Ile Thr Arg Lys Lys Leu Trp Ser
385             390             395             400
Asp Met Val His Glu Thr Arg Asn Asp Leu Phe Gly Asp Ser Thr Pro
            405             410             415
Trp Asn Leu His Phe Val Ala Thr Thr Ser Asn Thr Glu Pro Ser Gln
            420             425             430
Gly Arg Glu Ser Ala Ser Glu His Ala Thr Ala Asp Leu Lys Ser Ser
            435             440             445
Leu Val Arg Val His Ser Asp Val Lys Pro Trp Phe Asn Asn Gly Gly
            450             455             460
Thr Met Leu Lys Pro Cys Gly Lys Leu Asn Leu Gly Lys Val Thr Asn
465             470             475             480
Lys Thr Ser Ala Pro Thr Arg Glu Ile Gln Tyr Val Lys Gly Trp
            485             490             495
Cys Asp Ser Arg Phe Leu Gly Ser Ala Ala Pro Gly Ala Ser Ala Ala
            500             505             510
Pro Gly Ala Gly Ser Gly Ser Gly Ser Gly Met Ser Asp Lys Val Ile
            515             520             525
```

-continued

Asn Pro Gln Val Ala Trp Ala Gln Arg Ser Ser Thr Thr Asp Pro Glu
        530                 535                 540

Arg Asn Tyr Val Leu Ile Thr Val Ser Ile Ala Asp Cys Asp Ala Pro
545                 550                 555                 560

Glu Leu Thr Ile Lys Pro Ser Tyr Ile Glu Leu Lys Ala Gln Ser Lys
                565                 570                 575

Pro His Val Gly Asp Glu Asn Val His His Tyr Gln Leu His Ile Asp
            580                 585                 590

Leu Tyr Lys Glu Ile Ile Pro Glu Lys Thr Met His Lys Val Ala Asn
        595                 600                 605

Gly Gln His Tyr Phe Leu Lys Leu Tyr Lys Lys Asp Leu Glu Ser Glu
    610                 615                 620

Tyr Trp Pro Arg Leu Thr Lys Glu Lys Val Lys Tyr Pro Tyr Ile Lys
625                 630                 635                 640

Thr Asp Phe Asp Lys Trp Val Asp Glu Asp Gln Asp Glu Val Glu
                645                 650                 655

Ala Glu Gly Asn Asp Ala Ala Gln Gly Met Asp Phe Ser Gln Met Met
                660                 665                 670

Gly Gly Ala Gly Gly Ala Gly Gly Ala Gly Met Asp Phe Ser Gln
            675                 680                 685

Met Met Gly Gly Ala Gly Gly Ala Gly Ser Pro Asp Met Ala Gln Leu
    690                 695                 700

Gln Gln Leu Leu Ala Gln Ser Gly Gly Asn Leu Asp Met Gly Asp Phe
705                 710                 715                 720

Lys Glu Asn Asp Glu Glu Asp Glu Glu Glu Ile Glu Pro Glu Val
                725                 730                 735

Lys Ala

<210> SEQ ID NO 77
<211> LENGTH: 748
<212> TYPE: PRT
<213> ORGANISM: Saccharomyces cerevisiae

<400> SEQUENCE: 77

Met Ala Thr Pro Ser Thr Gly Ala Asn Asn Ser Ile Pro Ala Val Arg
1               5                   10                  15

Asn Gln Val Glu Val Gln Val Gly Leu Val Gly Asp Ala Gln Val Gly
                20                  25                  30

Lys Thr Ser Leu Met Val Lys Tyr Val Gln Asn Ile Tyr Asp Lys Glu
            35                  40                  45

Tyr Thr Gln Thr Leu Gly Val Asn Phe Leu Lys Arg Lys Val Ser Ile
        50                  55                  60

Arg Ser Thr Asp Ile Ile Phe Ser Ile Met Asp Leu Gly Gly Gln Arg
65                  70                  75                  80

Glu Phe Ile Asn Met Leu Pro Ile Ala Thr Val Gly Ser Ser Val Ile
                85                  90                  95

Ile Phe Leu Phe Asp Leu Thr Arg Pro Glu Thr Leu Ser Ser Ile Lys
            100                 105                 110

Glu Trp Tyr Arg Gln Ala Tyr Gly Leu Asn Asp Ser Ala Ile Pro Ile
        115                 120                 125

Leu Val Gly Thr Lys Tyr Asp Leu Leu Ile Asp Leu Asp Pro Glu Tyr
    130                 135                 140

Gln Glu Gln Ile Ser Arg Thr Ser Met Lys Tyr Ala Gln Val Met Asn
145                 150                 155                 160

```
Ala Pro Leu Ile Phe Cys Ser Thr Ala Lys Ser Ile Asn Ile Gln Lys
                165                 170                 175
Ile Phe Lys Ile Ala Leu Ala Lys Ile Phe Asn Leu Thr Leu Thr Ile
            180                 185                 190
Pro Glu Ile Asn Glu Ile Gly Asp Pro Leu Leu Ile Tyr Lys His Leu
        195                 200                 205
Gly Gly Gln Gln His Arg His His Asn Lys Ser Gln Asp Arg Lys Ser
210                 215                 220
His Asn Ile Arg Lys Pro Ser Ser Pro Ser Ser Lys Ala Pro Ser
225                 230                 235                 240
Pro Gly Gly Ser Ala Ala Pro Gly Ala Ser Ala Ala Pro Gly Ala Gly
                245                 250                 255
Ser Gly Ser Gly Ser Gly Met Asp Asp Ile Ile Thr Gln Val Ser Pro
                260                 265                 270
Asp Asn Ala Glu Ser Ala Pro Ile Leu Gln Glu Gln Gln Gln Gln
        275                 280                 285
Asn Ser Gln Tyr Glu Gly Asn Glu Glu Asp Tyr Gly Asp Ser Leu Ile
    290                 295                 300
His Leu Asn Ile Gln Glu Asn His Tyr Phe Ile Thr Arg Asp Gln Leu
305                 310                 315                 320
Met Ser Leu Pro Glu Ser Leu Leu Cys Leu Phe Pro Ser Gly Val
                325                 330                 335
Phe Leu Asp Arg Cys Gly Gln Val Ile Thr Asn Leu Thr Arg Asp Asp
                340                 345                 350
Glu Val Tyr Ile Val Asn Phe Pro Pro Asp Cys Phe Glu Tyr Ile Met
            355                 360                 365
Glu Ile Tyr Thr Lys Ala His Asp Asp Leu Tyr Asn His Pro Val Glu
        370                 375                 380
Lys Phe Phe Asp Arg Pro Ser Ser Phe Val Ser Asn Ala Lys Gly
385                 390                 395                 400
Phe Phe Gly Leu Ser Ser Asn Asn Ser Ile Ser Ser Asn Asn Glu Gln
                405                 410                 415
Asp Ile Leu His Gln Lys Pro Ala Ile Ile Val Leu Arg Glu Asp Leu
                420                 425                 430
Asp Tyr Tyr Cys Val Pro Gln Glu Glu Phe Gln Phe Asp Ser Thr Asn
            435                 440                 445
Glu Glu Asn Asn Glu Asp Leu Leu Arg His Phe Met Ala Gln Val Lys
        450                 455                 460
Met Ala Ala Gly Ser Tyr Leu Thr Ser Lys Thr Ser Ile Phe Gln Gly
465                 470                 475                 480
Leu Tyr Ser Ser Asn Arg Leu Lys Gln Gln Gln Gln Gln Lys Ile
                485                 490                 495
Glu Lys Gly Ser Asn Ser Ser Ser Asn Thr Lys Ser Thr Ser Lys Lys
                500                 505                 510
Leu Gly Pro Ala Glu Gln His Leu Met Asp Met Leu Cys Ser Ser Gly
            515                 520                 525
Phe Thr Lys Glu Thr Cys Trp Gly Asn Arg Thr Gln Glu Thr Gly Lys
        530                 535                 540
Thr Val Ile Ser Ser Leu Ser Leu Cys Arg Leu Ala Asn Glu Thr Thr
545                 550                 555                 560
Glu Gly Phe Arg Gln Lys Phe Asn Glu Ala Lys Ala Lys Trp Glu Ala
                565                 570                 575
```

```
Glu His Lys Pro Ser Gln Asp Asn Phe Ile Thr Pro Met Gln Ser Asn
                580                 585                 590

Ile Ser Ile Asn Ser Leu Ser Ala Ser Lys Ser Asn Ser Thr Ile Ser
            595                 600                 605

Thr Ala Arg Asn Leu Thr Ser Gly Ser Thr Ala Pro Ala Thr Ala Arg
        610                 615                 620

Asp Lys Arg Lys Ser Arg Leu Ser Lys Leu Ala Asp Asn Val Arg Ser
625                 630                 635                 640

His Ser Ser Ser Arg His Ser Ser Gln Thr Arg Ser Lys Pro Pro Glu
                645                 650                 655

Leu Pro Lys Leu Tyr Asp Leu Val Pro Lys Pro Asn Ile Asn Ala Lys
            660                 665                 670

Leu Leu Leu Phe Trp Arg Lys Pro Ala Arg Lys Cys Trp Trp Gly Glu
        675                 680                 685

Glu Asp Ile Glu Leu Glu Val Glu Val Phe Gly Ser Trp Lys Asp Glu
        690                 695                 700

Ser Lys Lys Ile Ile Glu Leu Ile Leu Pro Thr Asn Val Asp Pro Glu
705                 710                 715                 720

Ala Glu Leu His Lys Ile Ile Val Pro Val Arg Leu His Ile Arg Arg
                725                 730                 735

Val Trp Thr Leu Glu Leu Ser Val Ile Gly Val Gln
            740                 745

<210> SEQ ID NO 78
<211> LENGTH: 687
<212> TYPE: PRT
<213> ORGANISM: Saccharomyces cerevisiae

<400> SEQUENCE: 78

Met Val Val Ser Ile Ile Pro Gln Phe Pro Asp Ile Lys Val Ser Leu
1               5                   10                  15

Ala Leu Phe Glu Gln Val Lys Asn Ala Lys Glu Ile Arg Ser Lys Met
                20                  25                  30

Ser Glu Leu Ser Thr Ser Phe Ala Phe Ile Asp Pro Arg Leu Val Cys
            35                  40                  45

Ser Gly Glu Gln Met Tyr Ser Ala Ile Tyr Lys Thr Leu Ile Glu Val
        50                  55                  60

Lys Tyr Asn Lys Met Arg Thr Arg Asn Leu Asn Ser Glu Cys Val Leu
65                  70                  75                  80

Cys Leu Ser Pro Thr Ser Asn Ile Ser Asp Ala Phe Leu Lys Phe Gly
                85                  90                  95

Ile Lys Asp Asp Ser Ser Gln Leu Ile Cys Leu Lys Phe His Thr Asn
                100                 105                 110

Thr Asp Asp Val Asp Lys Glu Gln Leu Arg Thr Ile Met Thr Ser Ile
            115                 120                 125

Val Lys Gly Gln Glu Ile Glu Phe Asn Asp Asp Asn Leu Ser Arg Phe
        130                 135                 140

Tyr Asp Glu Ala Leu Ile Arg Lys Ile Tyr Lys Leu Ser Asp Asp Phe
145                 150                 155                 160

Lys Pro Gln Asp Val Asn Gly Leu Ser Arg Ala Leu Val Asp Ala Ile
                165                 170                 175

Gln Leu Arg Gly Val Gly Ser Ala Ala Pro Gly Ala Ser Ala Ala Pro
            180                 185                 190

Gly Ala Gly Ser Gly Ser Gly Ser Gly Met Asp Asp Ile Ile Thr Gln
        195                 200                 205
```

```
Val Ser Pro Asp Asn Ala Glu Ser Ala Pro Ile Leu Gln Glu Gln Gln
    210                 215                 220

Gln Gln Gln Asn Ser Gln Tyr Glu Gly Asn Glu Asp Tyr Gly Asp
225                 230                 235                 240

Ser Leu Ile His Leu Asn Ile Gln Glu Asn His Tyr Phe Ile Thr Arg
                245                 250                 255

Asp Gln Leu Met Ser Leu Pro Glu Ser Leu Leu Cys Leu Phe Pro
                260                 265                 270

Ser Gly Val Phe Leu Asp Arg Cys Gly Gln Val Ile Thr Asn Leu Thr
            275                 280                 285

Arg Asp Asp Glu Val Tyr Ile Val Asn Phe Pro Pro Asp Cys Phe Glu
    290                 295                 300

Tyr Ile Met Glu Ile Tyr Thr Lys Ala His Asp Asp Leu Tyr Asn His
305                 310                 315                 320

Pro Val Glu Lys Phe Phe Asp Arg Pro Ser Ser Phe Val Ser Asn
                325                 330                 335

Ala Lys Gly Phe Phe Gly Leu Ser Ser Asn Asn Ser Ile Ser Ser Asn
                340                 345                 350

Asn Glu Gln Asp Ile Leu His Gln Lys Pro Ala Ile Ile Val Leu Arg
            355                 360                 365

Glu Asp Leu Asp Tyr Tyr Cys Val Pro Gln Glu Glu Phe Gln Phe Asp
    370                 375                 380

Ser Thr Asn Glu Glu Asn Asn Glu Asp Leu Leu Arg His Phe Met Ala
385                 390                 395                 400

Gln Val Lys Met Ala Ala Gly Ser Tyr Leu Thr Ser Lys Thr Ser Ile
                405                 410                 415

Phe Gln Gly Leu Tyr Ser Ser Asn Arg Leu Lys Gln Gln Gln Gln Gln
            420                 425                 430

Gln Lys Ile Glu Lys Gly Ser Asn Ser Ser Asn Thr Lys Ser Thr
    435                 440                 445

Ser Lys Lys Leu Gly Pro Ala Glu Gln His Leu Met Asp Met Leu Cys
450                 455                 460

Ser Ser Gly Phe Thr Lys Glu Thr Cys Trp Gly Asn Arg Thr Gln Glu
465                 470                 475                 480

Thr Gly Lys Thr Val Ile Ser Ser Leu Ser Leu Cys Arg Leu Ala Asn
                485                 490                 495

Glu Thr Thr Glu Gly Phe Arg Gln Lys Phe Asn Glu Ala Lys Ala Lys
                500                 505                 510

Trp Glu Ala Glu His Lys Pro Ser Gln Asp Asn Phe Ile Thr Pro Met
    515                 520                 525

Gln Ser Asn Ile Ser Ile Asn Ser Leu Ser Ala Ser Lys Ser Asn Ser
    530                 535                 540

Thr Ile Ser Thr Ala Arg Asn Leu Thr Ser Gly Ser Thr Ala Pro Ala
545                 550                 555                 560

Thr Ala Arg Asp Lys Arg Lys Ser Arg Leu Ser Lys Leu Ala Asp Asn
                565                 570                 575

Val Arg Ser His Ser Ser Ser Arg His Ser Ser Gln Thr Arg Ser Lys
                580                 585                 590

Pro Pro Glu Leu Pro Lys Leu Tyr Asp Leu Val Pro Lys Pro Asn Ile
            595                 600                 605

Asn Ala Lys Leu Leu Leu Phe Trp Arg Lys Pro Ala Arg Lys Cys Trp
610                 615                 620
```

```
Trp Gly Glu Glu Asp Ile Glu Leu Glu Val Glu Val Phe Gly Ser Trp
625                 630                 635                 640

Lys Asp Glu Ser Lys Lys Ile Ile Glu Leu Ile Leu Pro Thr Asn Val
            645                 650                 655

Asp Pro Glu Ala Glu Leu His Lys Ile Ile Val Pro Val Arg Leu His
            660                 665                 670

Ile Arg Arg Val Trp Thr Leu Glu Leu Ser Val Ile Gly Val Gln
            675                 680                 685

<210> SEQ ID NO 79
<211> LENGTH: 544
<212> TYPE: PRT
<213> ORGANISM: Saccharomyces cerevisiae

<400> SEQUENCE: 79

Met Ser Leu Arg Pro Cys Leu Thr Pro Ser Ser Met Gln Tyr Ser Asp
1               5                   10                  15

Ile Tyr Ile Pro Thr His Ser Leu Thr Ser Thr Ser Thr Leu Ala Val
            20                  25                  30

Ile Pro Tyr Pro Ala Phe Gly Ser Ala Ala Pro Gly Ala Ser Ala Ala
        35                  40                  45

Pro Gly Ala Gly Ser Gly Ser Gly Ser Gly Met Asp Asp Ile Ile Thr
50                  55                  60

Gln Val Ser Pro Asp Asn Ala Glu Ser Ala Pro Ile Leu Gln Glu Gln
65                  70                  75                  80

Gln Gln Gln Gln Asn Ser Gln Tyr Glu Gly Asn Glu Glu Asp Tyr Gly
                85                  90                  95

Asp Ser Leu Ile His Leu Asn Ile Gln Glu Asn His Tyr Phe Ile Thr
            100                 105                 110

Arg Asp Gln Leu Met Ser Leu Pro Glu Ser Leu Leu Leu Cys Leu Phe
            115                 120                 125

Pro Ser Gly Val Phe Leu Asp Arg Cys Gly Gln Val Ile Thr Asn Leu
        130                 135                 140

Thr Arg Asp Asp Glu Val Tyr Ile Val Asn Phe Pro Pro Asp Cys Phe
145                 150                 155                 160

Glu Tyr Ile Met Glu Ile Tyr Thr Lys Ala His Asp Asp Leu Tyr Asn
                165                 170                 175

His Pro Val Glu Lys Phe Phe Arg Pro Ser Ser Ser Phe Val Ser
            180                 185                 190

Asn Ala Lys Gly Phe Phe Gly Leu Ser Ser Asn Asn Ser Ile Ser Ser
        195                 200                 205

Asn Asn Glu Gln Asp Ile Leu His Gln Lys Pro Ala Ile Ile Val Leu
210                 215                 220

Arg Glu Asp Leu Asp Tyr Tyr Cys Val Pro Gln Glu Glu Phe Gln Phe
225                 230                 235                 240

Asp Ser Thr Asn Glu Glu Asn Asn Glu Asp Leu Leu Arg His Phe Met
                245                 250                 255

Ala Gln Val Lys Met Ala Ala Gly Ser Tyr Leu Thr Ser Lys Thr Ser
            260                 265                 270

Ile Phe Gln Gly Leu Tyr Ser Ser Asn Arg Leu Lys Gln Gln Gln Gln
        275                 280                 285

Gln Gln Lys Ile Glu Lys Gly Ser Asn Ser Ser Asn Thr Lys Ser
290                 295                 300

Thr Ser Lys Lys Leu Gly Pro Ala Glu Gln His Leu Met Asp Met Leu
305                 310                 315                 320
```

Cys Ser Ser Gly Phe Thr Lys Glu Thr Cys Trp Gly Asn Arg Thr Gln
            325                 330                 335

Glu Thr Gly Lys Thr Val Ile Ser Ser Leu Ser Leu Cys Arg Leu Ala
            340                 345                 350

Asn Glu Thr Thr Glu Gly Phe Arg Gln Lys Phe Asn Glu Ala Lys Ala
            355                 360                 365

Lys Trp Glu Ala Glu His Lys Pro Ser Gln Asp Asn Phe Ile Thr Pro
            370                 375                 380

Met Gln Ser Asn Ile Ser Ile Asn Ser Leu Ser Ala Ser Lys Ser Asn
385                 390                 395                 400

Ser Thr Ile Ser Thr Ala Arg Asn Leu Thr Ser Gly Ser Thr Ala Pro
            405                 410                 415

Ala Thr Ala Arg Asp Lys Arg Lys Ser Arg Leu Ser Lys Leu Ala Asp
            420                 425                 430

Asn Val Arg Ser His Ser Ser Arg His Ser Ser Gln Thr Arg Ser
            435                 440                 445

Lys Pro Pro Glu Leu Pro Lys Leu Tyr Asp Leu Val Pro Lys Pro Asn
            450                 455                 460

Ile Asn Ala Lys Leu Leu Leu Phe Trp Arg Lys Pro Ala Arg Lys Cys
465                 470                 475                 480

Trp Trp Gly Glu Glu Asp Ile Glu Leu Glu Val Glu Phe Gly Ser
            485                 490                 495

Trp Lys Asp Glu Ser Lys Lys Ile Ile Glu Leu Ile Leu Pro Thr Asn
            500                 505                 510

Val Asp Pro Glu Ala Glu Leu His Lys Ile Ile Val Pro Val Arg Leu
            515                 520                 525

His Ile Arg Arg Val Trp Thr Leu Glu Leu Ser Val Ile Gly Val Gln
            530                 535                 540

<210> SEQ ID NO 80
<211> LENGTH: 1153
<212> TYPE: PRT
<213> ORGANISM: Saccharomyces cerevisiae

<400> SEQUENCE: 80

Met Glu Ala Gly Arg Ser Ala Asp Glu Val Leu Tyr His Asn Gln Ser
1                 5                   10                  15

Ser Val Lys Leu Gly Glu Leu Glu Arg Tyr Val Ile Thr Tyr Glu Leu
            20                  25                  30

Tyr Gln Gly Asp Ser Ile Pro Ala Asp Ile Thr Leu Asp Ser Leu Trp
            35                  40                  45

Val Lys Ile Lys Asn Thr Thr Lys Leu Ser Tyr Lys Pro Ala Tyr Leu
            50                  55                  60

Leu Gly Pro Phe Ile Leu Tyr Cys Asp Val Arg Ala Lys Asp Tyr Glu
65                  70                  75                  80

Ser Ser Tyr Lys Ile Ile Cys Ser Ala Asp Lys Pro Val Phe Gln Ser
            85                  90                  95

Asn Leu Gln Ala Gln Gln Lys Phe Ile Ala Glu Leu Ser Leu His His
            100                 105                 110

Ile Lys Pro Arg Tyr Val Trp Ile Val Asp Ile Val Ser Gln Ile Leu
            115                 120                 125

Phe Asn Lys Glu Thr Lys Val Thr Phe Glu Ile Val Val Gly Asn Ser
            130                 135                 140

Lys Ala Ser Leu Lys Arg Lys Ile Arg Cys Asn Asp Ser Leu Pro Asp

-continued

```
145                 150                 155                 160
Lys Ala Cys Asn Ile Leu His Thr Gly Leu Ser Val His Arg Leu Thr
                165                 170                 175
Thr Ala Asp Ile Trp Lys Val Pro Arg Pro Ile Asp Met Ser Gln Lys
                180                 185                 190
Ser His Leu Val Ile Leu Thr His Gly Phe Gln Ser Asn Val Ser Ala
                195                 200                 205
Asp Met Glu Tyr Leu Met Glu Glu Ile Tyr Lys Ala Gln Met Asn Asn
    210                 215                 220
Pro Asn Glu Arg Leu Val Ile Lys Gly Tyr Met Lys Asn Ala Cys Glu
225                 230                 235                 240
Thr Glu Lys Gly Ile Lys Phe Leu Gly Val Gly Leu Ala Asn Tyr Ile
                245                 250                 255
Ile Asp Glu Leu Tyr Asp Asp Ser Val Gly Lys Ile Ser Phe Ile Gly
                260                 265                 270
His Ser Leu Gly Gly Leu Thr Gln Thr Phe Ala Ile Cys Tyr Ile Lys
                275                 280                 285
Thr Lys Tyr Pro Tyr Phe Phe Lys Lys Val Glu Pro Ile Asn Phe Ile
    290                 295                 300
Ser Leu Ala Ser Pro Leu Leu Gly Ile Ala Thr Ser Thr Pro Asn Tyr
305                 310                 315                 320
Val Lys Met Ser Leu Ser Met Gly Ile Ile Gly Thr Thr Gly Gln Glu
                325                 330                 335
Leu Gly Leu Lys Asp Gly Asn Tyr Gly Asp Lys Pro Leu Leu Tyr Leu
                340                 345                 350
Leu Ser Glu Glu Ser Leu Ile Ser Val Leu Ala Arg Phe Lys Arg Arg
                355                 360                 365
Thr Leu Tyr Ala Asn Ala Val Asn Asp Gly Ile Val Pro Leu Tyr Ser
    370                 375                 380
Ser Ser Leu Leu Phe Leu Asp Tyr Ser Gln Leu Leu Gln Lys Leu Gly
385                 390                 395                 400
Gly Gln Thr Thr Ala Pro Cys Asp Pro Leu Phe Gln Pro Glu Val Ser
                405                 410                 415
Pro Ile Gly Glu Leu Pro Asn His Ser Asp Val Ala Asn Asp Asp
                420                 425                 430
Gly Ile Asn Ala Ser Ser Trp Asn Thr Phe Trp Lys Ser Lys Glu Asn
                435                 440                 445
Asn Cys Asp Lys Lys Ser Lys Arg Leu Met Asn Ala Ser Val Ile Lys
    450                 455                 460
Ser Met Lys Ser Val Leu Leu Ser Pro Cys Pro Asp Ala Lys Phe Phe
465                 470                 475                 480
Ser Asp Pro Asp Ala Arg Val Ala Thr Ile Ile His Asp Lys Ile Tyr
                485                 490                 495
Thr Glu Lys Asn Leu Pro Pro Ser Pro Thr Leu Tyr Glu Gly Thr
                500                 505                 510
Ala Ala Lys Glu Gly Glu Thr Arg Lys Thr Arg Lys Glu Met Glu Glu
                515                 520                 525
Ile Ile Ala Arg Arg Trp His Lys Gly Met His Trp Arg Lys Val Val
                530                 535                 540
Val Leu Leu Lys Pro Asp Ala His Asn Asn Ile Ile Val Arg Arg Arg
545                 550                 555                 560
Phe Ser Asn Ala Tyr Gly Trp Pro Val Val Asp His Leu Val Thr Ala
                565                 570                 575
```

```
His Phe Gln Arg Asp Asp Pro Ile Ala Ser Pro Met Gln Asp Lys Gln
                580                 585                 590

Phe Ala Glu Glu Asp Ile Asn Met Ala Thr Gly Gly Val Glu Pro Asn
            595                 600                 605

Lys Phe Tyr Ser Trp Leu Thr Lys Ile Glu Asp Pro Ser Val Tyr His
610                 615                 620

Gly Gly Ile Val Ser Thr Ala Ser Gln Leu Ala Ser Ser Trp Ile Ser
625                 630                 635                 640

Lys His Ser Ser Val Thr Asp Gly Ser Ala Ala Pro Gly Ala Ser Ala
                645                 650                 655

Ala Pro Gly Ala Gly Ser Gly Ser Gly Ser Gly Met Asp Asp Ile Ile
            660                 665                 670

Thr Gln Val Ser Pro Asp Asn Ala Glu Ser Ala Pro Ile Leu Gln Glu
            675                 680                 685

Gln Gln Gln Gln Gln Asn Ser Gln Tyr Glu Gly Asn Glu Glu Asp Tyr
            690                 695                 700

Gly Asp Ser Leu Ile His Leu Asn Ile Gln Glu Asn His Tyr Phe Ile
705                 710                 715                 720

Thr Arg Asp Gln Leu Met Ser Leu Pro Glu Ser Leu Leu Leu Cys Leu
                725                 730                 735

Phe Pro Ser Gly Val Phe Leu Asp Arg Cys Gly Gln Val Ile Thr Asn
            740                 745                 750

Leu Thr Arg Asp Asp Glu Val Tyr Ile Val Asn Phe Pro Pro Asp Cys
            755                 760                 765

Phe Glu Tyr Ile Met Glu Ile Tyr Thr Lys Ala His Asp Asp Leu Tyr
            770                 775                 780

Asn His Pro Val Glu Lys Phe Phe Asp Arg Pro Ser Ser Ser Phe Val
785                 790                 795                 800

Ser Asn Ala Lys Gly Phe Phe Gly Leu Ser Ser Asn Ser Ile Ser
            805                 810                 815

Ser Asn Asn Glu Gln Asp Ile Leu His Gln Lys Pro Ala Ile Ile Val
            820                 825                 830

Leu Arg Glu Asp Leu Asp Tyr Tyr Cys Val Pro Gln Glu Glu Phe Gln
            835                 840                 845

Phe Asp Ser Thr Asn Glu Glu Asn Asn Glu Asp Leu Leu Arg His Phe
            850                 855                 860

Met Ala Gln Val Lys Met Ala Ala Gly Ser Tyr Leu Thr Ser Lys Thr
865                 870                 875                 880

Ser Ile Phe Gln Gly Leu Tyr Ser Ser Asn Arg Leu Lys Gln Gln Gln
                885                 890                 895

Gln Gln Gln Lys Ile Glu Lys Gly Ser Asn Ser Ser Asn Thr Lys
            900                 905                 910

Ser Thr Ser Lys Lys Leu Gly Pro Ala Glu Gln His Leu Met Asp Met
            915                 920                 925

Leu Cys Ser Ser Gly Phe Thr Lys Glu Thr Cys Trp Gly Asn Arg Thr
            930                 935                 940

Gln Glu Thr Gly Lys Thr Val Ile Ser Ser Leu Ser Leu Cys Arg Leu
945                 950                 955                 960

Ala Asn Glu Thr Thr Glu Gly Phe Arg Gln Lys Phe Asn Glu Ala Lys
                965                 970                 975

Ala Lys Trp Glu Ala Glu His Lys Pro Ser Gln Asp Asn Phe Ile Thr
            980                 985                 990
```

```
Pro Met Gln Ser Asn Ile Ser Ile Asn Ser Leu Ser Ala Ser Lys Ser
        995                 1000                1005

Asn Ser Thr Ile Ser Thr Ala Arg Asn Leu Thr Ser Gly Ser Thr
    1010                1015                1020

Ala Pro Ala Thr Ala Arg Asp Lys Arg Lys Ser Arg Leu Ser Lys
    1025                1030                1035

Leu Ala Asp Asn Val Arg Ser His Ser Ser Arg His Ser Ser
    1040                1045                1050

Gln Thr Arg Ser Lys Pro Pro Glu Leu Pro Lys Leu Tyr Asp Leu
    1055                1060                1065

Val Pro Lys Pro Asn Ile Asn Ala Lys Leu Leu Leu Phe Trp Arg
    1070                1075                1080

Lys Pro Ala Arg Lys Cys Trp Trp Gly Glu Glu Asp Ile Glu Leu
    1085                1090                1095

Glu Val Glu Val Phe Gly Ser Trp Lys Asp Glu Ser Lys Lys Ile
    1100                1105                1110

Ile Glu Leu Ile Leu Pro Thr Asn Val Asp Pro Glu Ala Glu Leu
    1115                1120                1125

His Lys Ile Ile Val Pro Val Arg Leu His Ile Arg Arg Val Trp
    1130                1135                1140

Thr Leu Glu Leu Ser Val Ile Gly Val Gln
    1145                1150

<210> SEQ ID NO 81
<211> LENGTH: 555
<212> TYPE: PRT
<213> ORGANISM: Saccharomyces cerevisiae

<400> SEQUENCE: 81

Met Trp Arg Arg Arg Glu Pro Trp Glu Leu Ser Phe Leu Leu
1               5                   10                  15

Asn Ser Leu Ser Pro Arg Asn Trp Phe Ile Arg Arg Trp Gly Leu Met
            20                  25                  30

Ala Gly Arg Gly Gln His Leu Cys Trp Leu Arg Cys Ala Cys Asp Gly
        35                  40                  45

Pro Gly Ser Ala Ala Pro Gly Ala Ser Ala Ala Pro Gly Ala Gly Ser
    50                  55                  60

Gly Ser Gly Ser Gly Met Asp Asp Ile Ile Thr Gln Val Ser Pro Asp
65                  70                  75                  80

Asn Ala Glu Ser Ala Pro Ile Leu Gln Glu Gln Gln Gln Gln Asn
            85                  90                  95

Ser Gln Tyr Glu Gly Asn Glu Glu Asp Tyr Gly Asp Ser Leu Ile His
            100                 105                 110

Leu Asn Ile Gln Glu Asn His Tyr Phe Ile Thr Arg Asp Gln Leu Met
        115                 120                 125

Ser Leu Pro Glu Ser Leu Leu Leu Cys Leu Phe Pro Ser Gly Val Phe
    130                 135                 140

Leu Asp Arg Cys Gly Gln Val Ile Thr Asn Leu Thr Arg Asp Asp Glu
145                 150                 155                 160

Val Tyr Ile Val Asn Phe Pro Pro Asp Cys Phe Glu Tyr Ile Met Glu
                165                 170                 175

Ile Tyr Thr Lys Ala His Asp Asp Leu Tyr Asn His Pro Val Glu Lys
            180                 185                 190

Phe Phe Asp Arg Pro Ser Ser Ser Phe Val Ser Asn Ala Lys Gly Phe
        195                 200                 205
```

Phe Gly Leu Ser Ser Asn Asn Ser Ile Ser Ser Asn Glu Gln Asp
    210                 215                 220

Ile Leu His Gln Lys Pro Ala Ile Ile Val Leu Arg Glu Asp Leu Asp
225                 230                 235                 240

Tyr Tyr Cys Val Pro Gln Glu Glu Phe Gln Phe Asp Ser Thr Asn Glu
                245                 250                 255

Glu Asn Asn Glu Asp Leu Leu Arg His Phe Met Ala Gln Val Lys Met
                260                 265                 270

Ala Ala Gly Ser Tyr Leu Thr Ser Lys Thr Ser Ile Phe Gln Gly Leu
                275                 280                 285

Tyr Ser Ser Asn Arg Leu Lys Gln Gln Gln Gln Gln Lys Ile Glu
    290                 295                 300

Lys Gly Ser Asn Ser Ser Asn Thr Lys Ser Thr Ser Lys Lys Leu
305                 310                 315                 320

Gly Pro Ala Glu Gln His Leu Met Asp Met Leu Cys Ser Ser Gly Phe
                325                 330                 335

Thr Lys Glu Thr Cys Trp Gly Asn Arg Thr Gln Glu Thr Gly Lys Thr
                340                 345                 350

Val Ile Ser Ser Leu Ser Leu Cys Arg Leu Ala Asn Glu Thr Thr Glu
    355                 360                 365

Gly Phe Arg Gln Lys Phe Asn Glu Ala Lys Ala Lys Trp Glu Ala Glu
    370                 375                 380

His Lys Pro Ser Gln Asp Asn Phe Ile Thr Pro Met Gln Ser Asn Ile
385                 390                 395                 400

Ser Ile Asn Ser Leu Ser Ala Ser Lys Ser Asn Ser Thr Ile Ser Thr
                405                 410                 415

Ala Arg Asn Leu Thr Ser Gly Ser Thr Ala Pro Ala Thr Ala Arg Asp
                420                 425                 430

Lys Arg Lys Ser Arg Leu Ser Lys Leu Ala Asp Asn Val Arg Ser His
                435                 440                 445

Ser Ser Ser Arg His Ser Ser Gln Thr Arg Ser Lys Pro Pro Glu Leu
    450                 455                 460

Pro Lys Leu Tyr Asp Leu Val Pro Lys Pro Asn Ile Asn Ala Lys Leu
465                 470                 475                 480

Leu Leu Phe Trp Arg Lys Pro Ala Arg Lys Cys Trp Trp Gly Glu Glu
                485                 490                 495

Asp Ile Glu Leu Glu Val Glu Val Phe Gly Ser Trp Lys Asp Glu Ser
                500                 505                 510

Lys Lys Ile Ile Glu Leu Ile Leu Pro Thr Asn Val Asp Pro Glu Ala
                515                 520                 525

Glu Leu His Lys Ile Ile Val Pro Val Arg Leu His Ile Arg Arg Val
                530                 535                 540

Trp Thr Leu Glu Leu Ser Val Ile Gly Val Gln
545                 550                 555

<210> SEQ ID NO 82
<211> LENGTH: 771
<212> TYPE: PRT
<213> ORGANISM: Saccharomyces cerevisiae

<400> SEQUENCE: 82

Met Ser Gly Thr Arg Cys Leu Leu Gly Val Gly Leu Pro Val Asp Val
1               5                   10                  15

Thr Ala Thr Glu Thr Leu Thr His Asp Glu Gln Gly Pro Gly Val Glu

-continued

```
                20                  25                  30
Pro Gly Pro Cys Ser Arg Gly Ser Ser Ile Asp Gly Leu Leu Pro Ser
            35                  40                  45
Leu Leu Gly Pro His Asp Asp Val Asp Asp Ser Ala Ala Phe His
50                  55                  60
Lys Tyr Met Thr Leu Ser Arg Asp Gly Ala Gly Ile His Ala Pro
65                  70                  75                  80
Ser Leu Val Glu Asp Ala Ser Arg Asn Asp Asp Asp Asp Glu
                85                  90                  95
Asp Asp Asp Asp Ser Ser Met Ser Arg Asp Leu Ser Lys Ala Leu Asp
            100                 105                 110
Met Ser Ser Ser Ser Ser Ser Pro Arg Val Gln Ser Arg Arg His
            115                 120                 125
Arg Ser Ser Val Ser Ala Ile Ser Ala Ile Leu His Gln Gly Lys Ser
            130                 135                 140
Gly Arg Glu Asp Ile Thr Gly Ser Leu Ser Val Pro Ala Glu Gln Glu
145                 150                 155                 160
Lys Leu Ser Phe Leu Ala Lys Ala Ser Ser Ile Phe Phe Arg Arg Asn
                165                 170                 175
Ser Met Pro Arg Asp Lys His Thr His Ser Val Cys Pro Ala Ser Arg
            180                 185                 190
Pro Asp Ser Glu Arg Phe Ile Val Thr Ser Ala Ala Gln Ser Leu
            195                 200                 205
Arg Arg Gln Gln Gln Leu Glu Asp Ala Gln Tyr Ala Arg Val Ile Thr
            210                 215                 220
Asn Phe Arg Thr Ile Gly Trp Cys Ser Pro Ser Glu Ile Glu Ser Val
225                 230                 235                 240
Glu Tyr Lys Arg Ser Leu Ile Asn Ala Glu Trp Asp Glu Lys Ile Ser
                245                 250                 255
Leu Leu Ser His Ala Gln Cys Tyr Lys Gly Ser Ala Ala Pro Gly Ala
            260                 265                 270
Ser Ala Ala Pro Gly Ala Gly Ser Gly Ser Gly Met Asp Asp
            275                 280                 285
Ile Ile Thr Gln Val Ser Pro Asp Asn Ala Glu Ser Ala Pro Ile Leu
            290                 295                 300
Gln Glu Gln Gln Gln Gln Asn Ser Gln Tyr Glu Gly Asn Glu Glu
305                 310                 315                 320
Asp Tyr Gly Asp Ser Leu Ile His Leu Asn Ile Gln Glu Asn His Tyr
                325                 330                 335
Phe Ile Thr Arg Asp Gln Leu Met Ser Leu Pro Glu Ser Leu Leu Leu
            340                 345                 350
Cys Leu Phe Pro Ser Gly Val Phe Leu Asp Arg Cys Gly Gln Val Ile
            355                 360                 365
Thr Asn Leu Thr Arg Asp Asp Glu Val Tyr Ile Val Asn Phe Pro Pro
            370                 375                 380
Asp Cys Phe Glu Tyr Ile Met Glu Ile Tyr Thr Lys Ala His Asp Asp
385                 390                 395                 400
Leu Tyr Asn His Pro Val Glu Lys Phe Phe Asp Arg Pro Ser Ser Ser
                405                 410                 415
Phe Val Ser Asn Ala Lys Gly Phe Phe Gly Leu Ser Ser Asn Asn Ser
            420                 425                 430
Ile Ser Ser Asn Asn Glu Gln Asp Ile Leu His Gln Lys Pro Ala Ile
            435                 440                 445
```

```
Ile Val Leu Arg Glu Asp Leu Asp Tyr Tyr Cys Val Pro Gln Glu Glu
            450                 455                 460

Phe Gln Phe Asp Ser Thr Asn Glu Glu Asn Glu Asp Leu Leu Arg
465                 470                 475                 480

His Phe Met Ala Gln Val Lys Met Ala Ala Gly Ser Tyr Leu Thr Ser
                485                 490                 495

Lys Thr Ser Ile Phe Gln Gly Leu Tyr Ser Ser Asn Arg Leu Lys Gln
            500                 505                 510

Gln Gln Gln Gln Gln Lys Ile Glu Lys Gly Ser Asn Ser Ser Ser Asn
            515                 520                 525

Thr Lys Ser Thr Ser Lys Lys Leu Gly Pro Ala Glu Gln His Leu Met
530                 535                 540

Asp Met Leu Cys Ser Ser Gly Phe Thr Lys Glu Thr Cys Trp Gly Asn
545                 550                 555                 560

Arg Thr Gln Glu Thr Gly Lys Thr Val Ile Ser Ser Leu Ser Leu Cys
                565                 570                 575

Arg Leu Ala Asn Glu Thr Thr Glu Gly Phe Arg Gln Lys Phe Asn Glu
            580                 585                 590

Ala Lys Ala Lys Trp Glu Ala Glu His Lys Pro Ser Gln Asp Asn Phe
            595                 600                 605

Ile Thr Pro Met Gln Ser Asn Ile Ser Ile Asn Ser Leu Ser Ala Ser
610                 615                 620

Lys Ser Asn Ser Thr Ile Ser Thr Ala Arg Asn Leu Thr Ser Gly Ser
625                 630                 635                 640

Thr Ala Pro Ala Thr Ala Arg Asp Lys Arg Lys Ser Arg Leu Ser Lys
                645                 650                 655

Leu Ala Asp Asn Val Arg Ser His Ser Ser Ser Arg His Ser Ser Gln
            660                 665                 670

Thr Arg Ser Lys Pro Pro Glu Leu Pro Lys Leu Tyr Asp Leu Val Pro
            675                 680                 685

Lys Pro Asn Ile Asn Ala Lys Leu Leu Leu Phe Trp Arg Lys Pro Ala
690                 695                 700

Arg Lys Cys Trp Trp Gly Glu Glu Asp Ile Glu Leu Glu Val Glu Val
705                 710                 715                 720

Phe Gly Ser Trp Lys Asp Glu Ser Lys Lys Ile Ile Glu Leu Ile Leu
                725                 730                 735

Pro Thr Asn Val Asp Pro Glu Ala Glu Leu His Lys Ile Ile Val Pro
            740                 745                 750

Val Arg Leu His Ile Arg Arg Val Trp Thr Leu Glu Leu Ser Val Ile
            755                 760                 765

Gly Val Gln
    770

<210> SEQ ID NO 83
<211> LENGTH: 727
<212> TYPE: PRT
<213> ORGANISM: Saccharomyces cerevisiae

<400> SEQUENCE: 83

Met Ala Ser Ile Asp Ala Phe Ser Asp Leu Glu Arg Arg Met Asp Gly
1               5                   10                  15

Phe Gln Lys Asp Val Ala Gln Val Leu Ala Arg Gln Gln Asn His Ala
            20                  25                  30

Arg Gln Gln Leu Gln Gln Phe Gln Ala Glu Met Arg Gln Leu His Asn
```

-continued

```
                 35                  40                  45
Gln His Gln His Leu Ile Asp Glu Leu Gln Arg Leu Ala Thr Gln Arg
 50                  55                  60
Thr Ala Leu Gln Gln Gln Ile His Ala Ala Gln Gln Ala Thr Asn Thr
 65                  70                  75                  80
Thr Arg Glu Gln Trp Arg Ser Tyr His Glu Arg Ser Glu Leu Ser
                 85                  90                  95
Arg Arg Gln Ser Thr Leu Ala Ala Gln Ser Arg Glu Leu Asp Ser Leu
                100                 105                 110
Leu Gln Gln Arg Gly Lys Glu Cys Val Gln Leu Arg Ala Arg Trp Ala
                115                 120                 125
Ala Gln Ser Gly Asn Asp Ala Ala Glu Val Ala Leu Tyr Glu Arg Leu
                130                 135                 140
Leu Gln Leu Arg Val Leu Pro Gly Ala Ser Asp Val His Asp Val Arg
145                 150                 155                 160
Phe Val Phe Gly Asp Asp Ser Arg Cys Trp Ile Glu Val Ala Met His
                165                 170                 175
Gly Asp His Val Ile Gly Asn Ser His Pro Ala Leu Asp Pro Lys Ser
                180                 185                 190
Arg Ala Thr Leu Glu His Val Leu Thr Val Gln Gly Asp Leu Ala Ala
                195                 200                 205
Phe Leu Val Val Ala Arg Asp Met Leu Leu Ala Ser Leu Gly Ser Ala
210                 215                 220
Ala Pro Gly Ala Ser Ala Ala Pro Gly Ala Gly Ser Gly Ser Gly Ser
225                 230                 235                 240
Gly Met Asp Asp Ile Ile Thr Gln Val Ser Pro Asn Ala Glu Ser
                245                 250                 255
Ala Pro Ile Leu Gln Glu Gln Gln Gln Gln Asn Ser Gln Tyr Glu
                260                 265                 270
Gly Asn Glu Glu Asp Tyr Gly Asp Ser Leu Ile His Leu Asn Ile Gln
                275                 280                 285
Glu Asn His Tyr Phe Ile Thr Arg Asp Gln Leu Met Ser Leu Pro Glu
                290                 295                 300
Ser Leu Leu Leu Cys Leu Phe Pro Ser Gly Val Phe Leu Asp Arg Cys
305                 310                 315                 320
Gly Gln Val Ile Thr Asn Leu Thr Arg Asp Asp Glu Val Tyr Ile Val
                325                 330                 335
Asn Phe Pro Pro Asp Cys Phe Glu Tyr Ile Met Glu Ile Tyr Thr Lys
                340                 345                 350
Ala His Asp Asp Leu Tyr Asn His Pro Val Glu Lys Phe Phe Asp Arg
                355                 360                 365
Pro Ser Ser Phe Val Ser Asn Ala Lys Gly Phe Phe Gly Leu Ser
                370                 375                 380
Ser Asn Asn Ser Ile Ser Ser Asn Asn Glu Gln Asp Ile Leu His Gln
385                 390                 395                 400
Lys Pro Ala Ile Ile Val Leu Arg Glu Asp Leu Asp Tyr Tyr Cys Val
                405                 410                 415
Pro Gln Glu Glu Phe Gln Phe Asp Ser Thr Asn Glu Glu Asn Asn Glu
                420                 425                 430
Asp Leu Leu Arg His Phe Met Ala Gln Val Lys Met Ala Ala Gly Ser
                435                 440                 445
Tyr Leu Thr Ser Lys Thr Ser Ile Phe Gln Gly Leu Tyr Ser Ser Asn
                450                 455                 460
```

Arg Leu Lys Gln Gln Gln Gln Gln Lys Ile Glu Lys Gly Ser Asn
465                 470                 475                 480

Ser Ser Ser Asn Thr Lys Ser Thr Ser Lys Lys Leu Gly Pro Ala Glu
            485                 490                 495

Gln His Leu Met Asp Met Leu Cys Ser Ser Gly Phe Thr Lys Glu Thr
            500                 505                 510

Cys Trp Gly Asn Arg Thr Gln Glu Thr Gly Lys Thr Val Ile Ser Ser
        515                 520                 525

Leu Ser Leu Cys Arg Leu Ala Asn Glu Thr Thr Glu Gly Phe Arg Gln
530                 535                 540

Lys Phe Asn Glu Ala Lys Ala Lys Trp Glu Ala Glu His Lys Pro Ser
545                 550                 555                 560

Gln Asp Asn Phe Ile Thr Pro Met Gln Ser Asn Ile Ser Ile Asn Ser
                565                 570                 575

Leu Ser Ala Ser Lys Ser Asn Ser Thr Ile Ser Thr Ala Arg Asn Leu
            580                 585                 590

Thr Ser Gly Ser Thr Ala Pro Ala Thr Ala Arg Asp Lys Arg Lys Ser
        595                 600                 605

Arg Leu Ser Lys Leu Ala Asp Asn Val Arg Ser His Ser Ser Ser Arg
610                 615                 620

His Ser Ser Gln Thr Arg Ser Lys Pro Pro Glu Leu Pro Lys Leu Tyr
625                 630                 635                 640

Asp Leu Val Pro Lys Pro Asn Ile Asn Ala Lys Leu Leu Leu Phe Trp
                645                 650                 655

Arg Lys Pro Ala Arg Lys Cys Trp Trp Gly Glu Glu Asp Ile Glu Leu
            660                 665                 670

Glu Val Glu Val Phe Gly Ser Trp Lys Asp Glu Ser Lys Lys Ile Ile
        675                 680                 685

Glu Leu Ile Leu Pro Thr Asn Val Asp Pro Glu Ala Glu Leu His Lys
            690                 695                 700

Ile Ile Val Pro Val Arg Leu His Ile Arg Arg Val Trp Thr Leu Glu
705                 710                 715                 720

Leu Ser Val Ile Gly Val Gln
                725

<210> SEQ ID NO 84
<211> LENGTH: 1048
<212> TYPE: PRT
<213> ORGANISM: Saccharomyces cerevisiae

<400> SEQUENCE: 84

Met Gly Asn Gln Ser Leu Val Val Leu Thr Glu Ser Lys Gly Glu Tyr
1               5                   10                  15

Glu Asn Glu Thr Glu Leu Pro Val Lys Lys Ser Ser Arg Asp Asn Asn
            20                  25                  30

Ile Gly Glu Ser Leu Thr Ala Thr Ala Phe Thr Gln Ser Glu Asp Glu
        35                  40                  45

Met Val Asp Ser Asn Gln Lys Trp Gln Asn Pro Asn Tyr Phe Lys Tyr
    50                  55                  60

Ala Trp Gln Glu Tyr Leu Phe Ile Phe Thr Cys Met Ile Ser Gln Leu
65                  70                  75                  80

Leu Asn Gln Ala Gly Thr Thr Gln Thr Leu Ser Ile Met Asn Ile Leu
                85                  90                  95

Ser Asp Ser Phe Gly Ser Glu Gly Asn Ser Lys Ser Trp Leu Met Ala

```
                100                 105                 110
Ser Phe Pro Leu Val Ser Gly Ser Phe Ile Leu Ile Ser Gly Arg Leu
            115                 120                 125
Gly Asp Ile Tyr Gly Leu Lys Lys Met Leu Leu Val Gly Tyr Val Leu
            130                 135                 140
Val Ile Ile Trp Ser Leu Ile Cys Gly Ile Thr Lys Tyr Ser Gly Ser
145                 150                 155                 160
Asp Thr Phe Phe Ile Ile Ser Arg Ala Phe Gln Gly Leu Gly Ile Ala
                165                 170                 175
Phe Val Leu Pro Asn Val Leu Gly Ile Ile Gly Asn Ile Tyr Val Gly
                180                 185                 190
Gly Thr Phe Arg Lys Asn Ile Val Ile Ser Phe Val Gly Ala Met Ala
            195                 200                 205
Pro Ile Gly Ala Thr Leu Gly Cys Leu Phe Ala Gly Leu Ile Gly Thr
            210                 215                 220
Glu Asp Pro Lys Gln Trp Pro Trp Ala Phe Tyr Ala Tyr Ser Ile Ala
225                 230                 235                 240
Ala Phe Ile Asn Phe Val Leu Ser Ile Tyr Ala Ile Pro Ser Thr Ile
                245                 250                 255
Pro Thr Asn Ile His His Phe Ser Met Asp Trp Ile Gly Ser Val Leu
            260                 265                 270
Gly Val Ile Gly Leu Ile Leu Leu Asn Phe Val Trp Asn Gln Ala Pro
            275                 280                 285
Ile Ser Gly Trp Asn Gln Ala Tyr Ile Ile Val Ile Leu Ile Ile Ser
            290                 295                 300
Val Ile Phe Leu Val Val Phe Ile Ile Tyr Glu Ile Arg Phe Ala Lys
305                 310                 315                 320
Thr Pro Leu Leu Pro Arg Ala Val Ile Lys Asp Arg His Met Ile Gln
                325                 330                 335
Ile Met Leu Ala Leu Phe Phe Gly Trp Gly Ser Phe Gly Ile Phe Thr
            340                 345                 350
Phe Tyr Tyr Phe Gln Phe Gln Leu Asn Ile Arg Gln Tyr Thr Ala Leu
            355                 360                 365
Trp Ala Gly Gly Thr Tyr Phe Met Phe Leu Ile Trp Gly Ile Ile Ala
            370                 375                 380
Ala Leu Leu Val Gly Phe Thr Ile Lys Asn Val Ser Pro Ser Val Phe
385                 390                 395                 400
Leu Phe Phe Ser Met Val Ala Phe Asn Val Gly Ser Ile Met Ala Ser
                405                 410                 415
Val Thr Pro Val His Glu Thr Tyr Phe Arg Thr Gln Leu Gly Thr Met
                420                 425                 430
Ile Ile Leu Ser Phe Gly Met Asp Leu Ser Phe Pro Ala Ser Ser Ile
            435                 440                 445
Ile Phe Ser Asp Asn Leu Pro Met Glu Tyr Gln Gly Met Ala Gly Ser
            450                 455                 460
Leu Val Asn Thr Val Val Asn Tyr Ser Met Ser Leu Cys Leu Gly Met
465                 470                 475                 480
Gly Ala Thr Val Glu Thr Gln Val Asn Ser Asp Gly Lys His Leu Leu
                485                 490                 495
Lys Gly Tyr Arg Gly Ala Gln Tyr Leu Gly Ile Gly Leu Ala Ser Leu
                500                 505                 510
Ala Cys Met Ile Ser Gly Leu Tyr Met Val Glu Ser Phe Ile Lys Gly
            515                 520                 525
```

```
Arg Arg Ala Arg Ala Ala Glu Tyr Asp Cys Thr Val Ala Gly Ser
        530             535             540

Ala Ala Pro Gly Ala Ser Ala Ala Pro Gly Ala Gly Ser Gly Ser Gly
545             550             555             560

Ser Gly Met Asp Asp Ile Ile Thr Gln Val Ser Pro Asp Asn Ala Glu
                565             570             575

Ser Ala Pro Ile Leu Gln Glu Gln Gln Gln Gln Asn Ser Gln Tyr
            580             585             590

Glu Gly Asn Glu Glu Asp Tyr Gly Asp Ser Leu Ile His Leu Asn Ile
        595             600             605

Gln Glu Asn His Tyr Phe Ile Thr Arg Asp Gln Leu Met Ser Leu Pro
        610             615             620

Glu Ser Leu Leu Leu Cys Leu Phe Pro Ser Gly Val Phe Leu Asp Arg
625             630             635             640

Cys Gly Gln Val Ile Thr Asn Leu Thr Arg Asp Asp Glu Val Tyr Ile
                645             650             655

Val Asn Phe Pro Pro Asp Cys Phe Glu Tyr Ile Met Glu Ile Tyr Thr
            660             665             670

Lys Ala His Asp Asp Leu Tyr Asn His Pro Val Glu Lys Phe Phe Asp
        675             680             685

Arg Pro Ser Ser Ser Phe Val Ser Asn Ala Lys Gly Phe Phe Gly Leu
690             695             700

Ser Ser Asn Asn Ser Ile Ser Ser Asn Glu Gln Asp Ile Leu His
705             710             715             720

Gln Lys Pro Ala Ile Ile Val Leu Arg Glu Asp Leu Asp Tyr Tyr Cys
                725             730             735

Val Pro Gln Glu Glu Phe Gln Phe Asp Ser Thr Asn Glu Glu Asn Asn
            740             745             750

Glu Asp Leu Leu Arg His Phe Met Ala Gln Val Lys Met Ala Ala Gly
        755             760             765

Ser Tyr Leu Thr Ser Lys Thr Ser Ile Phe Gln Gly Leu Tyr Ser Ser
770             775             780

Asn Arg Leu Lys Gln Gln Gln Gln Gln Lys Ile Glu Lys Gly Ser
785             790             795             800

Asn Ser Ser Ser Asn Thr Lys Ser Thr Ser Lys Lys Leu Gly Pro Ala
                805             810             815

Glu Gln His Leu Met Asp Met Leu Cys Ser Ser Gly Phe Thr Lys Glu
            820             825             830

Thr Cys Trp Gly Asn Arg Thr Gln Glu Thr Gly Lys Thr Val Ile Ser
        835             840             845

Ser Leu Ser Leu Cys Arg Leu Ala Asn Glu Thr Thr Glu Gly Phe Arg
850             855             860

Gln Lys Phe Asn Glu Ala Lys Ala Lys Trp Glu Ala Glu His Lys Pro
865             870             875             880

Ser Gln Asp Asn Phe Ile Thr Pro Met Gln Ser Asn Ile Ser Ile Asn
                885             890             895

Ser Leu Ser Ala Ser Lys Ser Asn Ser Thr Ile Ser Thr Ala Arg Asn
            900             905             910

Leu Thr Ser Gly Ser Thr Ala Pro Ala Thr Ala Arg Asp Lys Arg Lys
        915             920             925

Ser Arg Leu Ser Lys Leu Ala Asp Asn Val Arg Ser His Ser Ser Ser
930             935             940
```

```
Arg His Ser Ser Gln Thr Arg Ser Lys Pro Pro Glu Leu Pro Lys Leu
945                 950                 955                 960

Tyr Asp Leu Val Pro Lys Pro Asn Ile Asn Ala Lys Leu Leu Leu Phe
                965                 970                 975

Trp Arg Lys Pro Ala Arg Lys Cys Trp Trp Gly Glu Glu Asp Ile Glu
            980                 985                 990

Leu Glu Val Glu Val Phe Gly Ser  Trp Lys Asp Glu Ser  Lys Lys Ile
        995                 1000                 1005

Ile Glu  Leu Ile Leu Pro Thr  Asn Val Asp Pro Glu  Ala Glu Leu
    1010                 1015                 1020

His Lys  Ile Ile Val Pro Val  Arg Leu His Ile Arg  Arg Val Trp
    1025                 1030                 1035

Thr Leu  Glu Leu Ser Val Ile  Gly Val Gln
    1040                 1045

<210> SEQ ID NO 85
<211> LENGTH: 551
<212> TYPE: PRT
<213> ORGANISM: Saccharomyces cerevisiae

<400> SEQUENCE: 85

Met Leu Leu Asp Val Asn Thr Asn His Thr Leu Met His Asp Ala His
1               5                   10                  15

Val His Glu His Cys Leu Ile Lys Ser Ile Arg Asp Asp Gly Ala Leu
            20                  25                  30

His Ser Trp Ser Asp Ser Ser Lys Val Phe Tyr Pro Lys Ser Phe Tyr
        35                  40                  45

Ala Thr Ala Thr Asn Lys Lys Asn Asn Lys Leu Ala Ser Ala Ser Met
    50                  55                  60

Asn Lys Thr Ala Thr Ser Asn Arg Thr Val Ser Asp Glu Ile Tyr Phe
65                  70                  75                  80

His Ser Thr Lys Pro Gln Phe Asp Gly Gln Gly Ser Ala Glu Arg Thr
                85                  90                  95

Arg Thr Leu Thr Lys Arg Asn Ser Phe Lys Arg Thr Arg Ile Leu Lys
            100                 105                 110

Ala Arg Asp Asp Ser Glu Leu Leu Asn Glu Asn Arg Ser Ser Leu Met
        115                 120                 125

Thr Pro Ser Leu Ser Ser Val Met Ser Gln Val Arg Lys Thr Asn Ser
    130                 135                 140

Ala Lys Thr Leu Ser Gly Glu Cys Pro Ile His Glu Gly His Leu Thr
145                 150                 155                 160

Gln Ser Ile Lys Arg Lys Phe Ser Glu Glu Ala Gln Ser Asp Cys Ser
                165                 170                 175

Ser Leu Ser Ser Ser Lys Leu His Pro Leu Thr Asp Asp Ile Ala Asp
            180                 185                 190

Ala Val Asp Leu Gln Thr Pro Ala Ile Gly Asp Glu Val Leu Ala Glu
        195                 200                 205

Pro Val Val Pro Lys Met Lys Ile Ile Asn Ile Asn Asp Leu Asp Leu
    210                 215                 220

Phe Asp Asp Trp Glu Val Lys Asp Leu Val Asp Ile Phe Pro Pro Val
225                 230                 235                 240

Tyr Glu Arg Arg Pro Arg Ser Ser Ala Leu Ser Leu Val Ser Ala
                245                 250                 255

Ser Ser Asp Ala Lys Leu Arg Pro Thr Ser Val Asp Phe Gln Ile Ile
            260                 265                 270
```

```
Asp Lys Lys Gly Gly Lys Thr Ser Arg Arg Lys Ser Arg Ser Lys Ser
            275                 280                 285

Thr Thr Glu Asn Met Ile Tyr Glu Asn Asp Leu Val Glu Leu Glu Gln
290                 295                 300

Trp Pro Ser Ala Ser Pro Ser Glu Thr Asp Gly Ser Ile Ala Ser
305                 310                 315                 320

Ser Glu Leu Leu Pro Asn Lys Arg Ile Arg Gln Lys Ser Leu Asn Thr
                325                 330                 335

Asn Phe Leu Lys Leu Tyr Ser Ile Glu Thr Ser Cys Lys Arg Lys Ser
                340                 345                 350

Ile Leu Pro Glu Val Glu Val Asp Asp His Leu Leu Lys Gln Leu Thr
                355                 360                 365

Tyr Ser Glu Ile Arg Ser Leu Glu Ile Lys Lys Glu Pro Asn Val Ser
                370                 375                 380

Thr Asn Asp Ile Lys Leu Ala Leu Ile Thr Arg Lys Lys Leu Trp Ser
385                 390                 395                 400

Asp Met Val His Glu Thr Arg Asn Asp Leu Phe Gly Asp Ser Thr Pro
                405                 410                 415

Trp Asn Leu His Phe Val Ala Thr Thr Ser Asn Thr Glu Pro Ser Gln
                420                 425                 430

Gly Arg Glu Ser Ala Ser Glu His Ala Thr Ala Asp Leu Lys Ser Ser
                435                 440                 445

Leu Val Arg Val His Ser Asp Val Lys Pro Trp Phe Asn Asn Gly Gly
                450                 455                 460

Thr Met Leu Lys Pro Cys Gly Lys Leu Asn Leu Gly Lys Val Thr Asn
465                 470                 475                 480

Lys Thr Ser Ala Pro Thr Arg Glu Ile Gln Tyr Val Val Lys Gly Trp
                485                 490                 495

Cys Asp Ser Arg Phe Leu Gly Ser Ala Ala Pro Gly Ala Ser Ala Ala
                500                 505                 510

Pro Gly Ala Gly Ser Gly Ser Gly Ser Gly Met Asp Leu Asn Gln Arg
                515                 520                 525

Lys Glu Lys Arg Ala Ser Met Leu Asp Ala Val Ala Pro Gly Gln Thr
                530                 535                 540

Cys Leu Leu Thr Gln Trp Asn
545                 550

<210> SEQ ID NO 86
<211> LENGTH: 755
<212> TYPE: PRT
<213> ORGANISM: Saccharomyces cerevisiae

<400> SEQUENCE: 86

Met Ser Gly Lys Ala Ser Thr Glu Gly Ser Val Thr Thr Glu Phe Leu
1               5                   10                  15

Ser Asp Ile Ile Gly Lys Thr Val Asn Val Lys Leu Ala Ser Gly Leu
                20                  25                  30

Leu Tyr Ser Gly Arg Leu Glu Ser Ile Asp Gly Phe Met Asn Val Ala
            35                  40                  45

Leu Ser Ser Ala Thr Glu His Tyr Glu Ser Asn Asn Lys Leu Leu
        50                  55                  60

Asn Lys Phe Asn Ser Asp Val Phe Leu Arg Gly Thr Gln Val Met Tyr
65              70                  75                  80

Ile Ser Glu Gln Lys Ile Gly Ser Ala Ala Pro Gly Ala Ser Ala Ala
```

```
                85                  90                  95
Pro Gly Ala Gly Ser Gly Ser Gly Met Ser Arg Ala Val Gly
            100                 105                 110
Ile Asp Leu Gly Thr Thr Tyr Ser Cys Val Ala His Phe Ser Asn Asp
            115                 120                 125
Arg Val Glu Ile Ile Ala Asn Asp Gln Gly Asn Arg Thr Thr Pro Ser
        130                 135                 140
Tyr Val Ala Phe Thr Asp Thr Glu Arg Leu Ile Gly Asp Ala Ala Lys
145                 150                 155                 160
Asn Gln Ala Ala Ile Asn Pro His Asn Thr Val Phe Asp Ala Lys Arg
                165                 170                 175
Leu Ile Gly Arg Lys Phe Asp Asp Pro Glu Val Thr Thr Asp Ala Lys
            180                 185                 190
His Phe Pro Phe Lys Val Ile Ser Arg Asp Gly Lys Pro Val Val Gln
        195                 200                 205
Val Glu Tyr Lys Gly Glu Thr Lys Thr Phe Thr Pro Glu Glu Ile Ser
        210                 215                 220
Ser Met Val Leu Ser Lys Met Lys Glu Thr Ala Glu Asn Tyr Leu Gly
225                 230                 235                 240
Thr Thr Val Asn Asp Ala Val Val Thr Val Pro Ala Tyr Phe Asn Asp
                245                 250                 255
Ser Gln Arg Gln Ala Thr Lys Asp Ala Gly Thr Ile Ala Gly Met Asn
            260                 265                 270
Val Leu Arg Ile Ile Asn Glu Pro Thr Ala Ala Ala Ile Ala Tyr Gly
        275                 280                 285
Leu Asp Lys Lys Gly Arg Ala Glu His Asn Val Leu Ile Phe Asp Leu
    290                 295                 300
Gly Gly Gly Thr Phe Asp Val Ser Leu Leu Ser Ile Asp Glu Gly Val
305                 310                 315                 320
Phe Glu Val Lys Ala Thr Ala Gly Asp Thr His Leu Gly Gly Glu Asp
                325                 330                 335
Phe Asp Asn Arg Leu Val Asn His Leu Ala Thr Glu Phe Lys Arg Lys
            340                 345                 350
Thr Lys Lys Asp Ile Ser Asn Asn Gln Arg Ser Leu Arg Arg Leu Arg
        355                 360                 365
Thr Ala Ala Glu Arg Ala Lys Arg Ala Leu Ser Ser Ser Gln Thr
    370                 375                 380
Ser Ile Glu Ile Asp Ser Leu Phe Glu Gly Met Asp Phe Tyr Thr Ser
385                 390                 395                 400
Leu Thr Arg Ala Arg Phe Glu Glu Leu Cys Ala Asp Leu Phe Arg Ser
                405                 410                 415
Thr Leu Glu Pro Val Glu Lys Val Leu Lys Asp Ser Lys Leu Asp Lys
            420                 425                 430
Ser Gln Ile Asp Glu Ile Val Leu Val Gly Gly Ser Thr Arg Ile Pro
        435                 440                 445
Lys Ile Gln Lys Leu Val Ser Asp Phe Phe Asn Gly Lys Glu Pro Asn
    450                 455                 460
Arg Ser Ile Asn Pro Asp Glu Ala Val Ala Tyr Gly Ala Ala Val Gln
465                 470                 475                 480
Ala Ala Ile Leu Thr Gly Asp Gln Ser Thr Lys Thr Gln Asp Leu Leu
                485                 490                 495
Leu Leu Asp Val Ala Pro Leu Ser Leu Gly Ile Glu Thr Ala Gly Gly
            500                 505                 510
```

```
Ile Met Thr Lys Leu Ile Pro Arg Asn Ser Thr Ile Pro Thr Lys Lys
        515                 520                 525

Ser Glu Thr Phe Ser Thr Tyr Ala Asp Asn Gln Pro Gly Val Leu Ile
        530                 535                 540

Gln Val Phe Glu Gly Glu Arg Thr Arg Thr Lys Asp Asn Asn Leu Leu
545                 550                 555                 560

Gly Lys Phe Glu Leu Ser Gly Ile Pro Pro Ala Pro Arg Gly Val Pro
                565                 570                 575

Gln Ile Asp Val Thr Phe Asp Ile Asp Ala Asn Gly Ile Leu Asn Val
                580                 585                 590

Ser Ala Leu Glu Lys Gly Thr Gly Lys Ser Asn Lys Ile Thr Ile Thr
        595                 600                 605

Asn Asp Lys Gly Arg Leu Ser Lys Asp Asp Ile Asp Arg Met Val Ser
        610                 615                 620

Glu Ala Glu Lys Tyr Arg Ala Asp Asp Glu Arg Glu Ala Glu Arg Val
625                 630                 635                 640

Gln Ala Lys Asn Gln Leu Glu Ser Tyr Ala Phe Thr Leu Lys Asn Thr
                645                 650                 655

Ile Asn Glu Ala Ser Phe Lys Glu Lys Val Gly Glu Asp Asp Ala Lys
                660                 665                 670

Arg Leu Glu Thr Ala Ser Gln Glu Thr Ile Asp Trp Leu Asp Ala Ser
        675                 680                 685

Gln Ala Ala Ser Thr Asp Glu Tyr Lys Asp Arg Gln Lys Glu Leu Glu
        690                 695                 700

Gly Ile Ala Asn Pro Ile Met Thr Lys Phe Tyr Gly Ala Gly Ala Gly
705                 710                 715                 720

Ala Gly Pro Gly Ala Gly Glu Ser Gly Gly Phe Pro Gly Ser Met Pro
                725                 730                 735

Asn Ser Gly Ala Thr Gly Gly Glu Asp Thr Gly Pro Thr Val Glu
                740                 745                 750

Glu Val Asp
        755

<210> SEQ ID NO 87
<211> LENGTH: 836
<212> TYPE: PRT
<213> ORGANISM: Saccharomyces cerevisiae

<400> SEQUENCE: 87

Met Leu Ala Gln Thr Phe Lys Lys Pro His Arg Ala Val Leu Glu Gln
1               5                   10                  15

Val Ser Gly Thr Thr Val Phe Ile Arg Asn Lys Arg Thr Lys Ser Lys
                20                  25                  30

Ser Ser Leu Ser Pro Leu Ala Gln Arg Val Val Thr Gln Leu Ser Val
        35                  40                  45

Met Ser Ala Ser Arg Lys Gln Pro Lys Leu Leu Lys Leu Ala Arg Glu
        50                  55                  60

Asp Leu Ile Lys His Gln Thr Ile Glu Lys Cys Trp Ser Ile Tyr Gln
65              70                  75                  80

Gln Gln Gln Arg Glu Arg Arg Asn Leu Gln Leu Glu Leu Gln Tyr Lys
                85                  90                  95

Ser Ile Glu Arg Ser Met Asn Leu Leu Gln Glu Leu Ser Pro Arg Leu
                100                 105                 110

Phe Glu Ala Ala Asn Ala Ser Glu Lys Gly Lys Arg Phe Pro Met Glu
```

```
            115                 120                 125
Met Lys Val Pro Thr Asp Phe Pro Pro Asn Thr Leu Trp His Tyr Asn
            130                 135                 140

Phe Arg Lys Gly Ser Ala Ala Pro Gly Ala Ser Ala Ala Pro Gly Ala
145                 150                 155                 160

Gly Ser Gly Ser Gly Ser Gly Met Leu Arg Val Thr Thr Leu Ala Ser
                165                 170                 175

Ser Cys Thr Ser Phe Pro Leu Gln Val Leu Arg Arg Arg Leu Thr Ile
            180                 185                 190

Ser Ser Leu Thr Ser Phe Gln Pro Thr Thr Lys Thr Gln Val Val Val
            195                 200                 205

Ile Gly Ala Gly His Ala Gly Cys Glu Ala Ala Ala Ser Ser Arg
            210                 215                 220

Thr Gly Ala His Thr Thr Leu Ile Thr Pro Ser Leu Thr Asp Ile Gly
225                 230                 235                 240

Lys Cys Ser Cys Asn Pro Ser Ile Gly Gly Val Gly Lys Gly Ile Leu
                245                 250                 255

Val Lys Glu Ile Asp Ala Leu Asp Gly Leu Met Gly Lys Val Thr Asp
            260                 265                 270

Leu Ala Gly Val Gln Phe Lys Met Leu Asn Arg Ser Lys Gly Pro Ala
            275                 280                 285

Val Trp Gly Pro Arg Ala Gln Ile Asp Arg Glu Leu Tyr Lys Lys Tyr
290                 295                 300

Met Gln Arg Glu Leu Ser Asp Lys Lys Ala His Pro Asn Leu Ser Leu
305                 310                 315                 320

Leu Gln Asn Lys Val Ala Asp Leu Ile Leu Tyr Asp Pro Gly Cys Gly
            325                 330                 335

His Lys Val Ile Lys Gly Val Val Leu Asp Asp Gly Thr Gln Val Gly
            340                 345                 350

Ala Asp Gln Val Ile Ile Thr Thr Gly Thr Phe Leu Ser Ala Glu Ile
            355                 360                 365

His Ile Gly Asp Lys Arg Ile Ala Ala Gly Arg Ile Gly Glu Gln Pro
            370                 375                 380

Thr Tyr Gly Ile Ser Asn Thr Leu Gln Asn Glu Val Gly Phe Gln Leu
385                 390                 395                 400

Gly Arg Leu Lys Thr Gly Thr Pro Ala Arg Leu Ala Lys Glu Ser Ile
                405                 410                 415

Asp Phe Ser Ala Leu Glu Val Gln Lys Gly Asp Ala Leu Pro Val Pro
            420                 425                 430

Met Ser Phe Leu Asn Glu Thr Val Ser Val Glu Pro Thr Lys Gln Leu
            435                 440                 445

Asp Cys Phe Gly Thr His Thr Thr Pro Gln Met His Asp Phe Leu Arg
            450                 455                 460

Asn Asn Leu His Gln Ser Ile His Ile Gln Asp Thr Thr Ile Lys Gly
465                 470                 475                 480

Pro Arg Tyr Cys Pro Ser Ile Glu Ala Lys Ile Leu Arg Phe Pro Asp
                485                 490                 495

Arg Ser Ser His Lys Ile Trp Leu Glu Pro Glu Gly Phe Asn Ser Asp
            500                 505                 510

Val Ile Tyr Pro Asn Gly Ile Ser Asn Ser Met Pro Glu Asp Val Gln
            515                 520                 525

Leu Gln Met Met Arg Leu Ile Pro Gly Met Ala Asn Val Glu Ile Leu
            530                 535                 540
```

Gln Pro Ala Tyr Gly Val Glu Tyr Asp Tyr Val Asp Pro Arg Gln Leu
545                 550                 555                 560

Lys Pro Ser Leu Glu Thr Lys Leu Val Asp Gly Leu Phe Leu Ala Gly
            565                 570                 575

Gln Ile Asn Gly Thr Thr Gly Tyr Glu Glu Ala Ala Gln Gly Ile
            580                 585                 590

Ile Ala Gly Ile Asn Ala Gly Leu Leu Ser Arg Gln Glu Arg Glu Gln
            595                 600                 605

Leu Val Leu Lys Arg Ser Glu Ala Tyr Ile Gly Val Leu Ile Asp Asp
610                 615                 620

Leu Ile Asn Asn Gly Val Ile Glu Pro Tyr Arg Met Phe Thr Ser Arg
625                 630                 635                 640

Ser Glu Phe Arg Ile Ser Val Arg Ala Asp Asn Ala Asp Phe Arg Leu
            645                 650                 655

Thr Pro Ile Gly Ala Gln Leu Gly Ile Ile Ser Pro Val Arg Leu Ser
            660                 665                 670

Gln Tyr Ser Arg Asp Lys His Leu Tyr Asp Glu Thr Ile Arg Ala Leu
            675                 680                 685

Gln Asn Phe Lys Leu Ser Ser Gln Lys Trp Ser Leu Leu Gln Ala
690                 695                 700

Asn Ile Ala Pro Gln Ala Glu Asn Arg Ser Ala Trp Glu Ile Phe Arg
705                 710                 715                 720

Phe Lys Asp Met Asp Leu His Lys Leu Tyr Glu Cys Ile Pro Asp Leu
            725                 730                 735

Pro Ile Asn Leu Leu Asp Ile Pro Met His Val Val Thr Lys Ile Asn
            740                 745                 750

Ile Gln Gly Lys Tyr Glu Pro Tyr Ile Val Lys Gln Asn Gln Phe Val
            755                 760                 765

Lys Ala Phe Gln Ala Asp Glu Asn Met Leu Leu Pro Gln Asp Tyr Asp
            770                 775                 780

Tyr Arg Gln Leu Pro Thr Leu Ser Thr Glu Cys Lys Leu Leu Leu Asn
785                 790                 795                 800

Arg Val Gln Pro Leu Thr Ile Gly Gln Ala Arg Ile Gln Gly Ile
            805                 810                 815

Thr Ala Ala Ala Leu Phe Glu Leu Tyr Arg Val Ala Arg Lys Pro Ser
            820                 825                 830

Gln Pro Val Met
        835

<210> SEQ ID NO 88
<211> LENGTH: 855
<212> TYPE: PRT
<213> ORGANISM: Saccharomyces cerevisiae

<400> SEQUENCE: 88

Met Thr Leu Trp Pro His Pro Gly Ser Tyr Lys Ile Lys Ser Ala Thr
1               5                   10                  15

Leu Phe Cys Ser Arg Asp Lys Leu Gly Cys Ala Phe Leu Ser Glu Ser
            20                  25                  30

Ser Leu Cys Met Tyr Phe Leu Tyr Asn Ser Leu Ser Ile Trp Ala Leu
        35                  40                  45

Gly Pro His Thr Ala Gly Pro Leu Leu Leu Phe Ser Ile Leu Asn Cys
    50                  55                  60

Thr Pro Ala Arg Ser Val Thr Leu Pro Ile Ser Pro Ser Arg Ala Ser

```
                65                  70                  75                  80
Ile Ser Phe Thr Arg Met Pro Leu Pro Thr Pro Pro Ile Glu Gly Leu
                    85                  90                  95
His Glu His Leu Pro Ile Ser Val Asn Asp Gly Val Met Arg Val Val
                    100                 105                 110
Cys Ala Pro Val Leu Asp Asp Ala Ala Ala Ser Gln Pro Ala Cys
                    115                 120                 125
Pro Ala Pro Met Thr Thr Thr Cys Val Leu Val Val Gly Trp Lys Leu
                    130                 135                 140
Val Lys Glu Asp Met Val Asn Arg Leu Leu Arg Thr Cys Lys Gly Asn
145                 150                 155                 160
Glu Val His Glu Asp Ala Lys Val Val Thr Arg Ser Ile Val Leu Trp
                    165                 170                 175
Gly Val Gly Ser Ala Ala Pro Gly Ala Ser Ala Ala Pro Gly Ala Gly
                    180                 185                 190
Ser Gly Ser Gly Ser Gly Met Leu Lys Ser Gly Arg Leu Asn Phe Leu
                    195                 200                 205
Lys Leu Asn Ile Asn Ser Arg Leu Leu Tyr Ser Thr Asn Pro Gln Leu
                    210                 215                 220
Thr Lys Lys Val Ile Gly Ile Asp Leu Gly Thr Thr Asn Ser Ala Val
225                 230                 235                 240
Ala Tyr Ile Arg Asp Ser Asn Asp Lys Lys Ser Ala Thr Ile Ile Glu
                    245                 250                 255
Asn Asp Glu Gly Gln Arg Thr Thr Pro Ser Ile Val Ala Phe Asp Val
                    260                 265                 270
Lys Ser Ser Pro Gln Asn Lys Asp Gln Met Lys Thr Leu Val Gly Met
                    275                 280                 285
Ala Ala Lys Arg Gln Asn Ala Ile Asn Ser Glu Asn Thr Phe Phe Ala
                    290                 295                 300
Thr Lys Arg Leu Ile Gly Arg Ala Phe Asn Asp Lys Glu Val Gln Arg
305                 310                 315                 320
Asp Met Ala Val Met Pro Tyr Lys Ile Val Lys Cys Glu Ser Asn Gly
                    325                 330                 335
Gln Ala Tyr Leu Ser Thr Ser Asn Gly Leu Ile Gln Ser Pro Ser Gln
                    340                 345                 350
Ile Ala Ser Ile Leu Leu Lys Tyr Leu Lys Gln Thr Ser Glu Glu Tyr
                    355                 360                 365
Leu Gly Glu Lys Val Asn Leu Ala Val Ile Thr Val Pro Ala Tyr Phe
    370                 375                 380
Asn Asp Ser Gln Arg Gln Ala Thr Lys Asp Ala Gly Lys Leu Ala Gly
385                 390                 395                 400
Leu Asn Val Leu Arg Val Ile Asn Glu Pro Thr Ala Ala Ala Leu Ser
                    405                 410                 415
Phe Gly Ile Asp Asp Lys Arg Asn Asn Gly Leu Ile Ala Val Tyr Asp
                    420                 425                 430
Leu Gly Gly Gly Thr Phe Asp Ile Ser Ile Leu Asp Ile Glu Asp Gly
                    435                 440                 445
Val Phe Glu Val Arg Ala Thr Asn Gly Asp Thr His Leu Gly Gly Glu
                    450                 455                 460
Asp Phe Asp Asn Val Ile Val Asn Tyr Ile Ile Asp Thr Phe Ile His
465                 470                 475                 480
Glu Asn Pro Glu Ile Thr Arg Glu Ile Thr Lys Asn Arg Glu Thr
                    485                 490                 495
```

Met Gln Arg Leu Lys Asp Val Ser Glu Arg Ala Lys Ile Asp Leu Ser
                500                 505                 510

His Val Lys Lys Thr Phe Ile Glu Leu Pro Phe Val Tyr Lys Ser Lys
            515                 520                 525

His Leu Arg Val Pro Met Thr Glu Glu Leu Asp Asn Met Thr Leu
        530                 535                 540

Ser Leu Ile Asn Arg Thr Ile Pro Pro Val Lys Gln Ala Leu Lys Asp
545                 550                 555                 560

Ala Asp Ile Glu Pro Glu Asp Ile Asp Glu Val Ile Leu Val Gly Gly
                565                 570                 575

Met Thr Arg Met Pro Lys Ile Arg Ser Val Val Lys Asp Leu Phe Gly
            580                 585                 590

Lys Ser Pro Asn Ser Ser Val Asn Pro Asp Glu Thr Val Ala Leu Gly
        595                 600                 605

Ala Ala Ile Gln Gly Gly Ile Leu Ser Gly Glu Ile Lys Asn Val Leu
610                 615                 620

Leu Leu Asp Val Thr Pro Leu Thr Leu Gly Ile Glu Thr Phe Gly Gly
625                 630                 635                 640

Ala Phe Ser Pro Leu Ile Pro Arg Asn Thr Thr Val Pro Val Lys Lys
                645                 650                 655

Thr Glu Ile Phe Ser Thr Gly Val Asp Gly Gln Ala Gly Val Asp Ile
            660                 665                 670

Lys Val Phe Gln Gly Glu Arg Gly Leu Val Arg Asn Asn Lys Leu Ile
        675                 680                 685

Gly Asp Leu Lys Leu Thr Gly Ile Thr Pro Leu Pro Lys Gly Ile Pro
690                 695                 700

Gln Ile Tyr Val Thr Phe Asp Ile Asp Ala Asp Gly Ile Ile Asn Val
705                 710                 715                 720

Ser Ala Ala Glu Lys Ser Ser Gly Lys Gln Gln Ser Ile Thr Val Ile
                725                 730                 735

Pro Asn Ser Gly Leu Ser Glu Glu Glu Ile Ala Lys Leu Ile Glu Glu
            740                 745                 750

Ala Asn Ala Asn Arg Ala Gln Asp Asn Leu Ile Arg Gln Arg Leu Glu
        755                 760                 765

Leu Ile Ser Lys Ala Asp Ile Met Ile Ser Asp Thr Glu Asn Leu Phe
770                 775                 780

Lys Arg Tyr Glu Lys Leu Ile Ser Ser Glu Lys Glu Tyr Ser Asn Ile
785                 790                 795                 800

Val Glu Asp Ile Lys Ala Leu Arg Gln Ala Ile Lys Asn Phe Lys Ala
                805                 810                 815

Asn Glu Asn Asp Met Ser Ile Asp Val Asn Gly Ile Lys Lys Ala Thr
            820                 825                 830

Asp Ala Leu Gln Gly Arg Ala Leu Lys Leu Phe Gln Ser Ala Thr Lys
        835                 840                 845

Asn Gln Gln Asn Gln Gly Lys
    850                 855

<210> SEQ ID NO 89
<211> LENGTH: 465
<212> TYPE: PRT
<213> ORGANISM: Saccharomyces cerevisiae

<400> SEQUENCE: 89

Met Gln Ile Phe Val Lys Thr Leu Thr Gly Lys Thr Ile Thr Leu Glu

```
1               5                   10                  15
Val Glu Ser Ser Asp Thr Ile Asp Asn Val Lys Ser Lys Ile Gln Asp
                20                  25                  30
Lys Glu Gly Ile Pro Pro Asp Gln Gln Arg Leu Ile Phe Ala Gly Lys
                35                  40                  45
Gln Leu Glu Asp Gly Arg Thr Leu Ser Asp Tyr Asn Ile Gln Lys Glu
                50                  55                  60
Ser Thr Leu His Leu Val Leu Arg Leu Arg Gly Gly Asn Gly Ser Ala
65                  70                  75                  80
Ala Pro Gly Ala Ser Ala Ala Pro Gly Ala Gly Ser Gly Ser Gly Ser
                85                  90                  95
Gly Met Pro Gly Gln Ile Ile Ser Ile Pro Phe Leu Ser Gln Asn Glu
                100                 105                 110
Asp Met Asp Lys Tyr Leu Leu Glu Tyr Arg Ser Leu Lys Leu Leu His
                115                 120                 125
Gln Ser Ser Asn Ser Phe Gln Ser His Asn Ala Pro Ser His Gln Ser
                130                 135                 140
Asn Tyr His Pro His Tyr Asn His Met Lys Tyr Asn Asn Thr Gly Ser
145                 150                 155                 160
Tyr Tyr Tyr Tyr Asn Asn Asn Asn Ser Asn Val Asn Pro His Asn
                165                 170                 175
Gln Ala Gly Leu Gln Ser Ile Asn Arg Ser Ile Pro Ser Ala Pro Tyr
                180                 185                 190
Gly Ala Tyr Asn Gln Asn Arg Ala Asn Asp Val Pro Tyr Met Asn Thr
                195                 200                 205
Gln Lys Lys His His Arg Phe Ser Ala Asn Asn Asn Leu Asn Gln Gln
                210                 215                 220
Lys Tyr Lys Gln Tyr Pro Gln Tyr Thr Ser Asn Pro Met Val Thr Ala
225                 230                 235                 240
His Leu Lys Gln Thr Tyr Pro Gln Leu Tyr Tyr Asn Ser Asn Val Asn
                245                 250                 255
Ala His Asn Asn Asn Asn Ser Asn Asn Asn Asn Asn Asn Asn
                260                 265                 270
Asn Ser Asn Asn Asn Asn Asn Leu Tyr Asn Gln Thr Gln Phe Ser Thr
                275                 280                 285
Arg Tyr Phe Asn Ser Asn Ser Ser Pro Ser Leu Thr Ser Ser Thr Ser
                290                 295                 300
Asn Ser Ser Ser Pro Tyr Asn Gln Ser Thr Phe Glu Tyr Ile Leu Pro
305                 310                 315                 320
Ser Thr Ser Ala Ala Ser Thr Asn Leu Ser Ser Ser Ser Asn Asn
                325                 330                 335
Ser Met His Thr Asn Pro Thr Thr Ala Thr Ser Thr Ser Ala Asp Leu
                340                 345                 350
Ile Asn Asp Leu Pro Val Gly Pro Thr Ser Ser Ser Leu Ile Ser Asp
                355                 360                 365
Leu His Ser Pro Pro Thr Val Ser Phe Leu Pro Ala Ser Gln Thr Leu
                370                 375                 380
Leu Met Ser Ser Thr Thr Ser Ser Ser Ile Gly Thr Asn Ile Asn Pro
385                 390                 395                 400
Pro Gln His Ser Pro Ser Pro Ser Gln Arg Glu Asp Phe Ser Thr Ala
                405                 410                 415
Pro Val Asn Met Ser Ser Ser Ala Ser Leu Leu Met Asn Asp Ser Ser
                420                 425                 430
```

Leu Gly Trp Gly Ser Asn His Met Asn Val Ser Ser Ser Gln Pro
        435                 440                 445

Ala Ser Ser Arg Pro Phe Gly Ile Trp Asn Thr Asp Met Ser Val Trp
450                 455                 460

Ser
465

<210> SEQ ID NO 90
<211> LENGTH: 775
<212> TYPE: PRT
<213> ORGANISM: Saccharomyces cerevisiae

<400> SEQUENCE: 90

Met Trp Arg Arg Arg Glu Pro Trp Glu Glu Leu Ser Phe Leu Leu
1               5                   10                  15

Asn Ser Leu Ser Pro Arg Asn Trp Phe Ile Arg Arg Trp Gly Leu Met
            20                  25                  30

Ala Gly Arg Gly Gln His Leu Cys Trp Leu Arg Cys Ala Cys Asp Gly
        35                  40                  45

Pro Gly Ser Ala Ala Pro Gly Ala Ser Ala Ala Pro Gly Ala Gly Ser
    50                  55                  60

Gly Ser Gly Ser Gly Met Ser Phe Leu Pro Leu Arg Ser Arg Ser Arg
65                  70                  75                  80

Ser Gly Ala Pro His Trp Val Tyr Ile Ile Leu Tyr His Ile Phe Thr
                85                  90                  95

Ile Pro Lys Ile Tyr Ser Leu Pro Leu Leu Ser Gly Ser His Val Leu
            100                 105                 110

Asn Ser Arg Asp Val Ala Asp Ser Gly His Ser Val Gly Asp Glu Ala
        115                 120                 125

Ser Val Thr Thr Tyr Tyr Ile Ile Ser Ile Ile Leu Val Leu Leu Gly
    130                 135                 140

Gly Val Phe Ala Gly Leu Thr Leu Gly Leu Met Gly Gln Asp Glu Val
145                 150                 155                 160

Tyr Leu Lys Val Ile Ser Thr Ser Gly Ser Asn Ser Glu Lys Lys Leu
                165                 170                 175

Ala Lys Arg Val Leu Asp Leu Ile Ser Arg Gly Lys His Trp Val Leu
            180                 185                 190

Val Thr Leu Leu Leu Ser Asn Val Ile Thr Asn Glu Thr Leu Pro Ile
        195                 200                 205

Val Leu Asp Arg Cys Leu Gly Gly Gly Trp Gln Ala Val Val Ser Ser
    210                 215                 220

Thr Ile Leu Ile Val Ile Phe Gly Glu Ile Ile Pro Gln Ser Val Cys
225                 230                 235                 240

Val Lys Tyr Gly Leu Gln Val Gly Ala Phe Phe Cys Pro Phe Val Leu
                245                 250                 255

Val Leu Met Tyr Leu Met Tyr Pro Val Ala Tyr Pro Ile Ala Thr Leu
            260                 265                 270

Leu Asp Tyr Met Leu Gly Glu Asp His Gly Thr Met Tyr Lys Lys Ser
        275                 280                 285

Gly Leu Lys Thr Leu Val Thr Leu His Arg Thr Met Gly Val Glu Arg
    290                 295                 300

Leu Thr Lys Asp Glu Val Thr Ile Ile Ser Ala Val Leu Asp Leu Lys
305                 310                 315                 320

Ala Lys Arg Val Glu Glu Ile Met Thr Pro Ile Glu Asn Val Phe Thr

```
                        325                 330                 335
Met Ser Ala Asp Thr Ile Leu Asp Asp Lys Thr Val Glu Lys Ile Phe
                340                 345                 350
Asn Ser Gly Phe Ser Arg Ile Pro Ile Phe Leu Pro Asn Glu Pro Asn
                355                 360                 365
Asn Phe Ile Gly Met Leu Leu Val Arg Val Leu Ile Ser Tyr Asp Pro
            370                 375                 380
Asp Asp Cys Leu Pro Ile Ser His Phe Pro Leu Ala Thr Leu Pro Glu
385                 390                 395                 400
Thr Ser Pro Asn Thr Ser Cys Leu Asn Ile Leu Asn Tyr Phe Gln Glu
                405                 410                 415
Gly Lys Ala His Met Cys Val Val Ser Lys Glu Pro Gly Ser Ser His
                420                 425                 430
Gly Ala Ile Gly Val Leu Thr Leu Glu Asp Val Ile Glu Glu Leu Ile
                435                 440                 445
Gly Glu Glu Ile Val Asp Glu Ser Asp Val Phe Val Asp Met His Gln
            450                 455                 460
His Ile Met Arg Gln Gln Pro Gly Pro Leu Ser Lys Arg His Ile Thr
465                 470                 475                 480
Ser Tyr Leu His His Leu Tyr Thr Ser Ser His Lys Glu His Lys Ala
                485                 490                 495
Ala Asp Gln Ala Asp Glu Ser Ser Pro Leu Leu Ser Pro Ser Asn Ser
                500                 505                 510
Asn His Pro Ser Glu His Pro Gln Gln Asp Leu Asn Asn Lys Ser Trp
                515                 520                 525
Lys Gln Lys Ser Asn Asp Gly Tyr Asp Arg Ser Asn Ala Val Leu Ser
                530                 535                 540
Pro Thr Pro Gln Val Thr Glu His Gly Thr Ile Ile Pro Ser Asn Leu
545                 550                 555                 560
Ala Ser Asn Pro Leu Asn Val Asn Lys Ser Phe Val Thr Ile Lys Lys
                565                 570                 575
Pro Ala Asn Val Pro Lys Ile Ile Thr Thr His Thr Pro His Ser Ser
                580                 585                 590
Lys Glu Pro Ser Pro Ala Pro His Ser Asn Asp Lys Ser Leu Ser Ala
                595                 600                 605
Glu Glu Gln Gln Leu Leu Ser Asp His Ala Glu Leu Ser Arg Gln Ala
                610                 615                 620
Val Leu His Thr Gln Arg Ser Gly Gln Pro Thr Gln Val Thr Thr Ser
625                 630                 635                 640
Thr Lys Thr Thr Arg Asn Ser Pro Asp Ser Ile Ser Ile Pro Asn Ser
                645                 650                 655
Gly Ala Asn His Gly Asn Glu Asn Gln Asn Val Thr Ile Ser Thr Ser
                660                 665                 670
Tyr Gln Asn Thr Lys Asn Gly Ile Val Glu Ser Val Ile Thr Val Lys
                675                 680                 685
Gly Val Pro Lys Thr Ile Ile Gly Pro Ala Lys Asp Trp Asp Glu Ser
                690                 695                 700
Lys Ser Glu Tyr Gly Asn Glu Asn Ile Asn Gln Glu Asn Ser Asn Arg
705                 710                 715                 720
Ser Asp Asp Arg Glu Ser Ser Ser Asn Ala Ser Leu Phe Ser Ser
                725                 730                 735
Ile Lys Asn Lys Phe Lys Asn Glu Asn Ala Asn Asn Asp Arg Ser
                740                 745                 750
```

```
Asn Phe Thr Asp Ser Leu Ser Arg Thr Ser Asn Tyr Asp Ala Asn Gly
        755                 760                 765

Ser Ser Ser Thr Ile Lys Arg
    770                 775

<210> SEQ ID NO 91
<211> LENGTH: 767
<212> TYPE: PRT
<213> ORGANISM: Saccharomyces cerevisiae

<400> SEQUENCE: 91

Met Asp Asp Ile Ile Thr Gln Val Ser Pro Asp Asn Ala Glu Ser Ala
1               5                   10                  15

Pro Ile Leu Gln Glu Gln Gln Gln Gln Asn Ser Gln Tyr Glu Gly
            20                  25                  30

Asn Glu Glu Asp Tyr Gly Asp Ser Leu Ile His Leu Asn Ile Gln Glu
            35                  40                  45

Asn His Tyr Phe Ile Thr Arg Asp Gln Leu Met Ser Leu Pro Glu Ser
        50                  55                  60

Leu Leu Leu Cys Leu Phe Pro Ser Gly Val Phe Leu Asp Arg Cys Gly
65                  70                  75                  80

Gln Val Ile Thr Asn Leu Thr Arg Asp Asp Glu Val Tyr Ile Val Asn
                85                  90                  95

Phe Pro Pro Asp Cys Phe Glu Tyr Ile Met Glu Ile Tyr Thr Lys Ala
            100                 105                 110

His Asp Asp Leu Tyr Asn His Pro Val Glu Lys Phe Phe Asp Arg Pro
        115                 120                 125

Ser Ser Ser Phe Val Ser Asn Ala Lys Gly Phe Phe Gly Leu Ser Ser
    130                 135                 140

Asn Asn Ser Ile Ser Ser Asn Asn Glu Gln Asp Ile Leu His Gln Lys
145                 150                 155                 160

Pro Ala Ile Ile Val Leu Arg Glu Asp Leu Asp Tyr Tyr Cys Val Pro
                165                 170                 175

Gln Glu Glu Phe Gln Phe Asp Ser Thr Asn Glu Glu Asn Asn Glu Asp
            180                 185                 190

Leu Leu Arg His Phe Met Ala Gln Val Lys Met Ala Ala Gly Ser Tyr
        195                 200                 205

Leu Thr Ser Lys Thr Ser Ile Phe Gln Gly Leu Tyr Ser Ser Asn Arg
    210                 215                 220

Leu Lys Gln Gln Gln Gln Gln Lys Ile Glu Lys Gly Ser Asn Ser
225                 230                 235                 240

Ser Ser Asn Thr Lys Ser Thr Ser Lys Lys Leu Gly Pro Ala Glu Gln
                245                 250                 255

His Leu Met Asp Met Leu Cys Ser Ser Gly Phe Thr Lys Glu Thr Cys
            260                 265                 270

Trp Gly Asn Arg Thr Gln Glu Thr Gly Lys Thr Val Ile Ser Ser Leu
        275                 280                 285

Ser Leu Cys Arg Leu Ala Asn Glu Thr Thr Glu Gly Phe Arg Gln Lys
    290                 295                 300

Phe Asn Glu Ala Lys Ala Lys Trp Glu Ala His Lys Pro Ser Gln
305                 310                 315                 320

Asp Asn Phe Ile Thr Pro Met Gln Ser Asn Ile Ser Ile Asn Ser Leu
                325                 330                 335

Ser Ala Ser Lys Ser Asn Ser Thr Ile Ser Thr Ala Arg Asn Leu Thr
```

```
                340             345             350
        Ser Gly Ser Thr Ala Pro Ala Thr Ala Arg Asp Lys Arg Lys Ser Arg
                355             360             365

Leu Ser Lys Leu Ala Asp Asn Val Arg Ser His Ser Ser Arg His
                370             375             380

Ser Ser Gln Thr Arg Ser Lys Pro Pro Glu Leu Pro Lys Leu Tyr Asp
        385             390             395             400

Leu Val Pro Lys Pro Asn Ile Asn Ala Lys Leu Leu Leu Phe Trp Arg
                        405             410             415

Lys Pro Ala Arg Lys Cys Trp Trp Gly Glu Asp Ile Glu Leu Glu
                        420             425             430

Val Glu Val Phe Gly Ser Trp Lys Asp Glu Ser Lys Lys Ile Ile Glu
                        435             440             445

Leu Ile Leu Pro Thr Asn Val Asp Pro Glu Ala Glu Leu His Lys Ile
                        450             455             460

Ile Val Pro Val Arg Leu His Ile Arg Arg Val Trp Thr Leu Glu Leu
        465             470             475             480

Ser Val Ile Gly Val Gln Gly Ser Ala Ala Pro Gly Ala Ser Ala Ala
                        485             490             495

Pro Gly Ala Gly Ser Gly Ser Gly Ser Gly Met Ala Arg Gly Pro Lys
                        500             505             510

Lys His Leu Lys Arg Leu Ala Ala Pro His His Trp Leu Leu Asp Lys
                        515             520             525

Leu Ser Gly Cys Tyr Ala Pro Arg Pro Ser Ala Gly Pro His Lys Leu
                        530             535             540

Arg Glu Ser Leu Pro Leu Ile Val Phe Leu Arg Asn Arg Leu Lys Tyr
        545             550             555             560

Ala Leu Asn Gly Arg Glu Val Lys Ala Ile Leu Met Gln Arg His Val
                        565             570             575

Lys Val Asp Gly Lys Val Arg Thr Asp Thr Thr Tyr Pro Ala Gly Phe
                        580             585             590

Met Asp Val Ile Thr Leu Asp Ala Thr Asn Glu Asn Phe Arg Leu Val
                        595             600             605

Tyr Asp Val Lys Gly Arg Phe Ala Val His Arg Ile Thr Asp Glu Glu
                        610             615             620

Ala Ser Tyr Lys Leu Gly Lys Val Lys Lys Val Gln Leu Gly Lys Lys
        625             630             635             640

Gly Val Pro Tyr Val Val Thr His Asp Gly Arg Thr Ile Arg Tyr Pro
                        645             650             655

Asp Pro Asn Ile Lys Val Asn Asp Thr Val Lys Ile Asp Leu Ala Ser
                        660             665             670

Gly Lys Ile Thr Asp Phe Ile Lys Phe Asp Ala Gly Lys Leu Val Tyr
                        675             680             685

Val Thr Gly Gly Arg Asn Leu Gly Arg Ile Gly Thr Ile Val His Lys
                        690             695             700

Glu Arg His Asp Gly Gly Phe Asp Leu Val His Ile Lys Asp Ser Leu
        705             710             715             720

Asp Asn Thr Phe Val Thr Arg Leu Asn Asn Val Phe Val Ile Gly Glu
                        725             730             735

Gln Gly Lys Pro Tyr Ile Ser Leu Pro Lys Gly Lys Gly Ile Lys Leu
                        740             745             750

Ser Ile Ala Glu Glu Arg Asp Arg Arg Ala Gln Gln Gly Leu
                        755             760             765
```

-continued

<210> SEQ ID NO 92
<211> LENGTH: 1008
<212> TYPE: PRT
<213> ORGANISM: Saccharomyces cerevisiae

<400> SEQUENCE: 92

Met Asp Asp Ile Ile Thr Gln Val Ser Pro Asp Asn Ala Glu Ser Ala
1               5                   10                  15

Pro Ile Leu Gln Glu Gln Gln Gln Gln Asn Ser Gln Tyr Glu Gly
            20                  25                  30

Asn Glu Glu Asp Tyr Gly Asp Ser Leu Ile His Leu Asn Ile Gln Glu
            35                  40                  45

Asn His Tyr Phe Ile Thr Arg Asp Gln Leu Met Ser Leu Pro Glu Ser
        50                  55                  60

Leu Leu Leu Cys Leu Phe Pro Ser Gly Val Phe Leu Asp Arg Cys Gly
65              70                  75                  80

Gln Val Ile Thr Asn Leu Thr Arg Asp Asp Glu Val Tyr Ile Val Asn
                85                  90                  95

Phe Pro Pro Asp Cys Phe Glu Tyr Ile Met Glu Ile Tyr Thr Lys Ala
            100                 105                 110

His Asp Asp Leu Tyr Asn His Pro Val Glu Lys Phe Asp Arg Pro
            115                 120                 125

Ser Ser Ser Phe Val Ser Asn Ala Lys Gly Phe Phe Gly Leu Ser Ser
    130                 135                 140

Asn Asn Ser Ile Ser Ser Asn Glu Gln Asp Ile Leu His Gln Lys
145                 150                 155                 160

Pro Ala Ile Ile Val Leu Arg Glu Asp Leu Asp Tyr Tyr Cys Val Pro
                165                 170                 175

Gln Glu Glu Phe Gln Phe Asp Ser Thr Asn Glu Glu Asn Asn Glu Asp
            180                 185                 190

Leu Leu Arg His Phe Met Ala Gln Val Lys Met Ala Ala Gly Ser Tyr
            195                 200                 205

Leu Thr Ser Lys Thr Ser Ile Phe Gln Gly Leu Tyr Ser Ser Asn Arg
    210                 215                 220

Leu Lys Gln Gln Gln Gln Gln Lys Ile Glu Lys Gly Ser Asn Ser
225                 230                 235                 240

Ser Ser Asn Thr Lys Ser Thr Ser Lys Lys Leu Gly Pro Ala Glu Gln
                245                 250                 255

His Leu Met Asp Met Leu Cys Ser Ser Gly Phe Thr Lys Glu Thr Cys
            260                 265                 270

Trp Gly Asn Arg Thr Gln Glu Thr Gly Lys Thr Val Ile Ser Ser Leu
        275                 280                 285

Ser Leu Cys Arg Leu Ala Asn Glu Thr Thr Glu Gly Phe Arg Gln Lys
    290                 295                 300

Phe Asn Glu Ala Lys Ala Lys Trp Glu Ala Glu His Lys Pro Ser Gln
305                 310                 315                 320

Asp Asn Phe Ile Thr Pro Met Gln Ser Asn Ile Ser Ile Asn Ser Leu
                325                 330                 335

Ser Ala Ser Lys Ser Asn Ser Thr Ile Ser Thr Ala Arg Asn Leu Thr
            340                 345                 350

Ser Gly Ser Thr Ala Pro Ala Thr Ala Arg Asp Lys Arg Lys Ser Arg
        355                 360                 365

Leu Ser Lys Leu Ala Asp Asn Val Arg Ser His Ser Ser Ser Arg His

```
            370                 375                 380
Ser Ser Gln Thr Arg Ser Lys Pro Pro Glu Leu Pro Lys Leu Tyr Asp
385                 390                 395                 400

Leu Val Pro Lys Pro Asn Ile Asn Ala Lys Leu Leu Leu Phe Trp Arg
                405                 410                 415

Lys Pro Ala Arg Lys Cys Trp Trp Gly Glu Asp Ile Glu Leu Glu
            420                 425                 430

Val Glu Val Phe Gly Ser Trp Lys Asp Glu Ser Lys Lys Ile Ile Glu
            435                 440                 445

Leu Ile Leu Pro Thr Asn Val Asp Pro Glu Ala Glu Leu His Lys Ile
450                 455                 460

Ile Val Pro Val Arg Leu His Ile Arg Arg Val Trp Thr Leu Glu Leu
465                 470                 475                 480

Ser Val Ile Gly Val Gln Gly Ser Ala Ala Pro Gly Ala Ser Ala Ala
                485                 490                 495

Pro Gly Ala Gly Ser Gly Ser Gly Met Leu Leu Asp Val Asn
            500                 505                 510

Thr Asn His Thr Leu Met His Asp Ala His Val His Glu His Cys Leu
            515                 520                 525

Ile Lys Ser Ile Arg Asp Asp Gly Ala Leu His Ser Trp Ser Asp Ser
530                 535                 540

Ser Lys Val Phe Tyr Pro Lys Ser Phe Tyr Ala Thr Ala Thr Asn Lys
545                 550                 555                 560

Lys Asn Asn Lys Leu Ala Ser Ala Ser Met Asn Lys Thr Ala Thr Ser
                565                 570                 575

Asn Arg Thr Val Ser Asp Glu Ile Tyr Phe His Ser Thr Lys Pro Gln
            580                 585                 590

Phe Asp Gly Gln Gly Ser Ala Glu Arg Thr Arg Thr Leu Thr Lys Arg
            595                 600                 605

Asn Ser Phe Lys Arg Thr Arg Ile Leu Lys Ala Arg Asp Asp Ser Glu
            610                 615                 620

Leu Leu Asn Glu Asn Arg Ser Ser Leu Met Thr Pro Ser Leu Ser Ser
625                 630                 635                 640

Val Met Ser Gln Val Arg Lys Thr Asn Ser Ala Lys Thr Leu Ser Gly
                645                 650                 655

Glu Cys Pro Ile His Glu Gly His Leu Thr Gln Ser Ile Lys Arg Lys
                660                 665                 670

Phe Ser Glu Glu Ala Gln Ser Asp Cys Ser Ser Leu Ser Ser Ser Lys
            675                 680                 685

Leu His Pro Leu Thr Asp Asp Ile Ala Asp Ala Val Asp Leu Gln Thr
690                 695                 700

Pro Ala Ile Gly Asp Glu Val Leu Ala Glu Pro Val Val Pro Lys Met
705                 710                 715                 720

Lys Ile Ile Asn Ile Asn Asp Leu Asp Leu Phe Asp Asp Trp Glu Val
                725                 730                 735

Lys Asp Leu Val Asp Ile Phe Pro Pro Val Tyr Glu Arg Arg Pro Arg
            740                 745                 750

Ser Ser Ser Ala Leu Ser Leu Val Ser Ala Ser Ser Asp Ala Lys Leu
            755                 760                 765

Arg Pro Thr Ser Val Asp Phe Gln Ile Ile Asp Lys Lys Gly Gly Lys
            770                 775                 780

Thr Ser Arg Arg Lys Ser Arg Ser Lys Ser Thr Thr Glu Asn Met Ile
785                 790                 795                 800
```

```
Tyr Glu Asn Asp Leu Val Glu Leu Glu Gln Trp Pro Ser Ala Ser Pro
                805                 810                 815

Ser Pro Glu Thr Asp Gly Ser Ile Ala Ser Ser Glu Leu Leu Pro Asn
            820                 825                 830

Lys Arg Ile Arg Gln Lys Ser Leu Asn Thr Asn Phe Leu Lys Leu Tyr
        835                 840                 845

Ser Ile Glu Thr Ser Cys Lys Arg Lys Ser Ile Leu Pro Glu Val Glu
    850                 855                 860

Val Asp Asp His Leu Leu Lys Gln Leu Thr Tyr Ser Glu Ile Arg Ser
865                 870                 875                 880

Leu Glu Ile Lys Lys Glu Pro Asn Val Ser Thr Asn Asp Ile Lys Leu
                885                 890                 895

Ala Leu Ile Thr Arg Lys Lys Leu Trp Ser Asp Met Val His Glu Thr
            900                 905                 910

Arg Asn Asp Leu Phe Gly Asp Ser Thr Pro Trp Asn Leu His Phe Val
        915                 920                 925

Ala Thr Thr Ser Asn Thr Glu Pro Ser Gln Gly Arg Glu Ser Ala Ser
    930                 935                 940

Glu His Ala Thr Ala Asp Leu Lys Ser Ser Leu Val Arg Val His Ser
945                 950                 955                 960

Asp Val Lys Pro Trp Phe Asn Asn Gly Gly Thr Met Leu Lys Pro Cys
                965                 970                 975

Gly Lys Leu Asn Leu Gly Lys Val Thr Asn Lys Thr Ser Ala Pro Thr
            980                 985                 990

Arg Glu Ile Gln Tyr Val Val Lys  Gly Trp Cys Asp Ser  Arg Phe Leu
        995                 1000                1005

<210> SEQ ID NO 93
<211> LENGTH: 610
<212> TYPE: PRT
<213> ORGANISM: Saccharomyces cerevisiae

<400> SEQUENCE: 93

Met Val Thr Gln Leu Lys Ser Ala Ser Glu Tyr Asp Ser Ala Leu Ala
1               5                   10                  15

Ser Gly Asp Lys Leu Val Val Asp Phe Phe Ala Thr Trp Cys Gly
            20                  25                  30

Pro Cys Lys Met Ile Ala Pro Met Ile Glu Lys Phe Ala Glu Gln Tyr
        35                  40                  45

Ser Asp Ala Ala Phe Tyr Lys Leu Asp Val Asp Glu Val Ser Asp Val
    50                  55                  60

Ala Gln Lys Ala Glu Val Ser Ser Met Pro Thr Leu Ile Phe Tyr Lys
65                  70                  75                  80

Gly Gly Lys Glu Val Thr Arg Val Val Gly Ala Asn Pro Ala Ala Ile
                85                  90                  95

Lys Gln Ala Ile Ala Ser Asn Val Gly Ser Ala Ala Pro Gly Ala Ser
            100                 105                 110

Ala Ala Pro Gly Ala Gly Ser Gly Ser Gly Ser Gly Met Asp Asp Ile
        115                 120                 125

Ile Thr Gln Val Ser Pro Asp Asn Ala Glu Ser Ala Pro Ile Leu Gln
    130                 135                 140

Glu Gln Gln Gln Gln Gln Asn Ser Gln Tyr Glu Gly Asn Glu Glu Asp
145                 150                 155                 160

Tyr Gly Asp Ser Leu Ile His Leu Asn Ile Gln Glu Asn His Tyr Phe
```

```
                165                 170                 175
Ile Thr Arg Asp Gln Leu Met Ser Leu Pro Glu Ser Leu Leu Leu Cys
                180                 185                 190

Leu Phe Pro Ser Gly Val Phe Leu Asp Arg Cys Gly Gln Val Ile Thr
                195                 200                 205

Asn Leu Thr Arg Asp Asp Glu Val Tyr Ile Val Asn Phe Pro Pro Asp
                210                 215                 220

Cys Phe Glu Tyr Ile Met Glu Ile Tyr Thr Lys Ala His Asp Asp Leu
225                 230                 235                 240

Tyr Asn His Pro Val Glu Lys Phe Phe Asp Arg Pro Ser Ser Ser Phe
                245                 250                 255

Val Ser Asn Ala Lys Gly Phe Phe Gly Leu Ser Ser Asn Asn Ser Ile
                260                 265                 270

Ser Ser Asn Asn Glu Gln Asp Ile Leu His Gln Lys Pro Ala Ile Ile
                275                 280                 285

Val Leu Arg Glu Asp Leu Asp Tyr Tyr Cys Val Pro Gln Glu Glu Phe
                290                 295                 300

Gln Phe Asp Ser Thr Asn Glu Glu Asn Asn Glu Asp Leu Leu Arg His
305                 310                 315                 320

Phe Met Ala Gln Val Lys Met Ala Ala Gly Ser Tyr Leu Thr Ser Lys
                325                 330                 335

Thr Ser Ile Phe Gln Gly Leu Tyr Ser Ser Asn Arg Leu Lys Gln Gln
                340                 345                 350

Gln Gln Gln Gln Lys Ile Glu Lys Gly Ser Asn Ser Ser Asn Thr
                355                 360                 365

Lys Ser Thr Ser Lys Lys Leu Gly Pro Ala Glu Gln His Leu Met Asp
370                 375                 380

Met Leu Cys Ser Ser Gly Phe Thr Lys Glu Thr Cys Trp Gly Asn Arg
385                 390                 395                 400

Thr Gln Glu Thr Gly Lys Thr Val Ile Ser Ser Leu Ser Leu Cys Arg
                405                 410                 415

Leu Ala Asn Glu Thr Thr Glu Gly Phe Arg Gln Lys Phe Asn Glu Ala
                420                 425                 430

Lys Ala Lys Trp Glu Ala Glu His Lys Pro Ser Gln Asp Asn Phe Ile
                435                 440                 445

Thr Pro Met Gln Ser Asn Ile Ser Ile Asn Ser Leu Ser Ala Ser Lys
                450                 455                 460

Ser Asn Ser Thr Ile Ser Thr Ala Arg Asn Leu Thr Ser Gly Ser Thr
465                 470                 475                 480

Ala Pro Ala Thr Ala Arg Asp Lys Arg Lys Ser Arg Leu Ser Lys Leu
                485                 490                 495

Ala Asp Asn Val Arg Ser His Ser Ser Ser Arg His Ser Ser Gln Thr
                500                 505                 510

Arg Ser Lys Pro Pro Glu Leu Pro Lys Leu Tyr Asp Leu Val Pro Lys
                515                 520                 525

Pro Asn Ile Asn Ala Lys Leu Leu Leu Phe Trp Arg Lys Pro Ala Arg
                530                 535                 540

Lys Cys Trp Trp Gly Glu Glu Asp Ile Glu Leu Glu Val Glu Val Phe
545                 550                 555                 560

Gly Ser Trp Lys Asp Glu Ser Lys Lys Ile Ile Glu Leu Ile Leu Pro
                565                 570                 575

Thr Asn Val Asp Pro Glu Ala Glu Leu His Lys Ile Ile Val Pro Val
                580                 585                 590
```

```
Arg Leu His Ile Arg Arg Val Trp Thr Leu Glu Leu Ser Val Ile Gly
            595                 600                 605
Val Gln
    610

<210> SEQ ID NO 94
<211> LENGTH: 654
<212> TYPE: PRT
<213> ORGANISM: Saccharomyces cerevisiae

<400> SEQUENCE: 94

Met Asp Ser Tyr Ser Ile Thr Asn Val Lys Tyr Leu Asp Pro Thr Glu
1               5                   10                  15

Leu His Arg Trp Met Gln Glu Gly His Thr Thr Leu Arg Glu Pro
            20                  25                  30

Phe Gln Val Val Asp Val Arg Gly Ser Asp Tyr Met Gly Gly His Ile
            35                  40                  45

Lys Asp Gly Trp His Tyr Ala Tyr Ser Arg Leu Lys Gln Asp Pro Glu
    50                  55                  60

Tyr Leu Arg Glu Leu Lys His Arg Leu Leu Glu Lys Gln Ala Asp Gly
65                  70                  75                  80

Arg Gly Ala Leu Asn Val Ile Phe His Cys Met Leu Ser Gln Gln Arg
                85                  90                  95

Gly Pro Ser Ala Ala Met Leu Leu Leu Arg Ser Leu Asp Thr Ala Glu
            100                 105                 110

Leu Ser Arg Cys Arg Leu Trp Val Leu Arg Gly Phe Ser Arg Trp
            115                 120                 125

Gln Ser Val Tyr Gly Asp Asp Glu Ser Val Thr Ala Gly Tyr Leu Pro
            130                 135                 140

Asp Leu Trp Arg Gly Ser Ala Ala Pro Gly Ala Ser Ala Ala Pro Gly
145                 150                 155                 160

Ala Gly Ser Gly Ser Gly Ser Gly Met Asp Asp Ile Ile Thr Gln Val
                165                 170                 175

Ser Pro Asp Asn Ala Glu Ser Ala Pro Ile Leu Gln Glu Gln Gln Gln
            180                 185                 190

Gln Gln Asn Ser Gln Tyr Glu Gly Asn Glu Glu Asp Tyr Gly Asp Ser
            195                 200                 205

Leu Ile His Leu Asn Ile Gln Glu Asn His Tyr Phe Ile Thr Arg Asp
    210                 215                 220

Gln Leu Met Ser Leu Pro Glu Ser Leu Leu Cys Leu Phe Pro Ser
225                 230                 235                 240

Gly Val Phe Leu Asp Arg Cys Gly Gln Val Ile Thr Asn Leu Thr Arg
                245                 250                 255

Asp Asp Glu Val Tyr Ile Val Asn Phe Pro Pro Asp Cys Phe Glu Tyr
            260                 265                 270

Ile Met Glu Ile Tyr Thr Lys Ala His Asp Leu Tyr Asn His Pro
    275                 280                 285

Val Glu Lys Phe Phe Asp Arg Pro Ser Ser Phe Val Ser Asn Ala
    290                 295                 300

Lys Gly Phe Phe Gly Leu Ser Ser Asn Asn Ile Ser Ser Asn Asn
305                 310                 315                 320

Glu Gln Asp Ile Leu His Gln Lys Pro Ala Ile Ile Val Leu Arg Glu
                325                 330                 335

Asp Leu Asp Tyr Tyr Cys Val Pro Gln Glu Glu Phe Gln Phe Asp Ser
```

```
            340                 345                 350
Thr Asn Glu Glu Asn Glu Asp Leu Leu Arg His Phe Met Ala Gln
            355                 360                 365
Val Lys Met Ala Ala Gly Ser Tyr Leu Thr Ser Lys Thr Ser Ile Phe
370                 375                 380
Gln Gly Leu Tyr Ser Ser Asn Arg Leu Lys Gln Gln Gln Gln Gln
385                 390                 395                 400
Lys Ile Glu Lys Gly Ser Asn Ser Ser Asn Thr Lys Ser Thr Ser
                    405                 410                 415
Lys Lys Leu Gly Pro Ala Glu Gln His Leu Met Asp Met Leu Cys Ser
                420                 425                 430
Ser Gly Phe Thr Lys Glu Thr Cys Trp Gly Asn Arg Thr Gln Glu Thr
            435                 440                 445
Gly Lys Thr Val Ile Ser Leu Ser Leu Cys Arg Leu Ala Asn Glu
            450                 455                 460
Thr Thr Glu Gly Phe Arg Gln Lys Phe Asn Glu Ala Lys Ala Lys Trp
465                 470                 475                 480
Glu Ala Glu His Lys Pro Ser Gln Asp Asn Phe Ile Thr Pro Met Gln
                    485                 490                 495
Ser Asn Ile Ser Ile Asn Ser Leu Ser Ala Ser Lys Ser Asn Ser Thr
                500                 505                 510
Ile Ser Thr Ala Arg Asn Leu Thr Ser Gly Ser Thr Ala Pro Ala Thr
            515                 520                 525
Ala Arg Asp Lys Arg Lys Ser Arg Leu Ser Lys Leu Ala Asp Asn Val
            530                 535                 540
Arg Ser His Ser Ser Arg His Ser Ser Gln Thr Arg Ser Lys Pro
545                 550                 555                 560
Pro Glu Leu Pro Lys Leu Tyr Asp Leu Val Pro Lys Pro Asn Ile Asn
                    565                 570                 575
Ala Lys Leu Leu Leu Phe Trp Arg Lys Pro Ala Arg Lys Cys Trp Trp
                580                 585                 590
Gly Glu Glu Asp Ile Glu Leu Glu Val Glu Val Phe Gly Ser Trp Lys
            595                 600                 605
Asp Glu Ser Lys Lys Ile Ile Glu Leu Ile Leu Pro Thr Asn Val Asp
            610                 615                 620
Pro Glu Ala Glu Leu His Lys Ile Ile Val Pro Val Arg Leu His Ile
625                 630                 635                 640
Arg Arg Val Trp Thr Leu Glu Leu Ser Val Ile Gly Val Gln
                    645                 650

<210> SEQ ID NO 95
<211> LENGTH: 668
<212> TYPE: PRT
<213> ORGANISM: Saccharomyces cerevisiae

<400> SEQUENCE: 95

Met Val Met Leu His Ser Lys Asn Val Lys Gly Phe Leu Glu Asn Thr
1               5                   10                  15

Leu Lys Pro Tyr Asp Leu His Ser Val Asp Phe Lys Thr Ser Ser Leu
            20                  25                  30

Gln Ser Ser Met Ile Ile Thr Ala Thr Asn Gly Gly Ile Leu Ser Tyr
        35                  40                  45

Ala Thr Ser Asn Asn Asp Val Pro Lys Asn Ser Ile Asn Glu Ile Asn
    50                  55                  60
```

```
Ser Val Asn Asn Leu Lys Met Met Ser Leu Leu Ile Lys Asp Lys Trp
 65                  70                  75                  80

Ser Glu Asp Glu Asn Asp Thr Glu Glu Gln His Ser Asn Ser Cys Tyr
                 85                  90                  95

Pro Val Glu Ile Asp Ser Phe Lys Thr Lys Ile Tyr Thr Tyr Glu Met
            100                 105                 110

Glu Asp Leu His Thr Cys Val Ala Gln Ile Pro Asn Ser Asp Leu Leu
        115                 120                 125

Leu Leu Phe Ile Ala Glu Gly Ser Phe Pro Tyr Gly Leu Leu Val Ile
130                 135                 140

Lys Ile Glu Arg Ala Met Arg Glu Leu Thr Asp Leu Phe Gly Tyr Lys
145                 150                 155                 160

Leu Gly Gly Ser Ala Ala Pro Gly Ala Ser Ala Ala Pro Gly Ala Gly
                165                 170                 175

Ser Gly Ser Gly Ser Gly Met Asp Asp Ile Ile Thr Gln Val Ser Pro
            180                 185                 190

Asp Asn Ala Glu Ser Ala Pro Ile Leu Gln Glu Gln Gln Gln Gln Gln
        195                 200                 205

Asn Ser Gln Tyr Glu Gly Asn Glu Glu Asp Tyr Gly Asp Ser Leu Ile
210                 215                 220

His Leu Asn Ile Gln Glu Asn His Tyr Phe Ile Thr Arg Asp Gln Leu
225                 230                 235                 240

Met Ser Leu Pro Glu Ser Leu Leu Leu Cys Leu Phe Pro Ser Gly Val
                245                 250                 255

Phe Leu Asp Arg Cys Gly Gln Val Ile Thr Asn Leu Thr Arg Asp Asp
            260                 265                 270

Glu Val Tyr Ile Val Asn Phe Pro Pro Asp Cys Phe Glu Tyr Ile Met
        275                 280                 285

Glu Ile Tyr Thr Lys Ala His Asp Asp Leu Tyr Asn His Pro Val Glu
290                 295                 300

Lys Phe Phe Asp Arg Pro Ser Ser Phe Val Ser Asn Ala Lys Gly
305                 310                 315                 320

Phe Phe Gly Leu Ser Ser Asn Asn Ser Ile Ser Ser Asn Asn Glu Gln
                325                 330                 335

Asp Ile Leu His Gln Lys Pro Ala Ile Ile Val Leu Arg Glu Asp Leu
            340                 345                 350

Asp Tyr Tyr Cys Val Pro Gln Glu Glu Phe Gln Phe Asp Ser Thr Asn
        355                 360                 365

Glu Glu Asn Asn Glu Asp Leu Leu Arg His Phe Met Ala Gln Val Lys
370                 375                 380

Met Ala Ala Gly Ser Tyr Leu Thr Ser Lys Thr Ser Ile Phe Gln Gly
385                 390                 395                 400

Leu Tyr Ser Ser Asn Arg Leu Lys Gln Gln Gln Gln Gln Lys Ile
                405                 410                 415

Glu Lys Gly Ser Asn Ser Ser Asn Thr Lys Ser Thr Ser Lys Lys
            420                 425                 430

Leu Gly Pro Ala Glu Gln His Leu Met Asp Met Leu Cys Ser Ser Gly
        435                 440                 445

Phe Thr Lys Glu Thr Cys Trp Gly Asn Arg Thr Gln Glu Thr Gly Lys
                450                 455                 460

Thr Val Ile Ser Ser Leu Ser Leu Cys Arg Leu Ala Asn Glu Thr Thr
465                 470                 475                 480

Glu Gly Phe Arg Gln Lys Phe Asn Glu Ala Lys Ala Lys Trp Glu Ala
```

```
            485                 490                 495
Glu His Lys Pro Ser Gln Asp Asn Phe Ile Thr Pro Met Gln Ser Asn
                500                 505                 510

Ile Ser Ile Asn Ser Leu Ser Ala Ser Lys Ser Asn Ser Thr Ile Ser
            515                 520                 525

Thr Ala Arg Asn Leu Thr Ser Gly Ser Thr Ala Pro Ala Thr Ala Arg
    530                 535                 540

Asp Lys Arg Lys Ser Arg Leu Ser Lys Leu Ala Asp Asn Val Arg Ser
545                 550                 555                 560

His Ser Ser Ser Arg His Ser Ser Gln Thr Arg Ser Lys Pro Pro Glu
                565                 570                 575

Leu Pro Lys Leu Tyr Asp Leu Val Pro Lys Pro Asn Ile Asn Ala Lys
            580                 585                 590

Leu Leu Leu Phe Trp Arg Lys Pro Ala Arg Lys Cys Trp Trp Gly Glu
            595                 600                 605

Glu Asp Ile Glu Leu Glu Val Glu Val Phe Gly Ser Trp Lys Asp Glu
            610                 615                 620

Ser Lys Lys Ile Ile Glu Leu Ile Leu Pro Thr Asn Val Asp Pro Glu
625                 630                 635                 640

Ala Glu Leu His Lys Ile Ile Val Pro Val Arg Leu His Ile Arg Arg
                645                 650                 655

Val Trp Thr Leu Glu Leu Ser Val Ile Gly Val Gln
                660                 665

<210> SEQ ID NO 96
<211> LENGTH: 608
<212> TYPE: PRT
<213> ORGANISM: Saccharomyces cerevisiae

<400> SEQUENCE: 96

Met Ala Gly Asp Ser Ile Ser Ala Asp Gly Thr Gly Val His Pro Val
1               5                   10                  15

Glu Leu Ser Val Tyr Ser Val Leu Ser Thr Asp Leu Asp Gly Leu Tyr
                20                  25                  30

Gln Ser Ile Asn Glu Leu Arg Glu Ser Gln Ala Leu Leu Ile Leu Met
            35                  40                  45

Leu Arg Lys Val Arg Asp Lys Leu Arg Arg Glu Gly Gln Val Leu Tyr
    50                  55                  60

Asp Pro Glu Pro Phe Lys Pro Thr Met Asp Lys Leu Ala Asp Leu Ser
65                  70                  75                  80

Ala Arg Val Arg Ile Leu Ser Gln Arg Tyr Glu Glu Leu Gln Gly Asn
                85                  90                  95

Ala Arg Ala Leu Asn Asn Gly Ser Ala Ala Pro Gly Ala Ser Ala Ala
            100                 105                 110

Pro Gly Ala Gly Ser Gly Ser Gly Ser Met Asp Asp Ile Ile Thr
    115                 120                 125

Gln Val Ser Pro Asp Asn Ala Glu Ser Ala Pro Ile Leu Gln Glu Gln
    130                 135                 140

Gln Gln Gln Gln Asn Ser Gln Tyr Glu Gly Asn Glu Glu Asp Tyr Gly
145                 150                 155                 160

Asp Ser Leu Ile His Leu Asn Ile Gln Glu Asn His Tyr Phe Ile Thr
                165                 170                 175

Arg Asp Gln Leu Met Ser Leu Pro Glu Ser Leu Leu Leu Cys Leu Phe
            180                 185                 190
```

```
Pro Ser Gly Val Phe Leu Asp Arg Cys Gly Gln Val Ile Thr Asn Leu
    195                 200                 205

Thr Arg Asp Asp Glu Val Tyr Ile Val Asn Phe Pro Asp Cys Phe
210                 215                 220

Glu Tyr Ile Met Glu Ile Tyr Thr Lys Ala His Asp Asp Leu Tyr Asn
225                 230                 235                 240

His Pro Val Glu Lys Phe Phe Asp Arg Pro Ser Ser Phe Val Ser
                245                 250                 255

Asn Ala Lys Gly Phe Phe Gly Leu Ser Ser Asn Ser Ile Ser Ser
            260                 265                 270

Asn Asn Glu Gln Asp Ile Leu His Gln Lys Pro Ala Ile Ile Val Leu
        275                 280                 285

Arg Glu Asp Leu Asp Tyr Tyr Cys Val Pro Gln Glu Glu Phe Gln Phe
290                 295                 300

Asp Ser Thr Asn Glu Glu Asn Asn Glu Asp Leu Leu Arg His Phe Met
305                 310                 315                 320

Ala Gln Val Lys Met Ala Ala Gly Ser Tyr Leu Thr Ser Lys Thr Ser
                325                 330                 335

Ile Phe Gln Gly Leu Tyr Ser Ser Asn Arg Leu Lys Gln Gln Gln Gln
            340                 345                 350

Gln Gln Lys Ile Glu Lys Gly Ser Asn Ser Ser Asn Thr Lys Ser
        355                 360                 365

Thr Ser Lys Lys Leu Gly Pro Ala Glu Gln His Leu Met Asp Met Leu
    370                 375                 380

Cys Ser Ser Gly Phe Thr Lys Glu Thr Cys Trp Gly Asn Arg Thr Gln
385                 390                 395                 400

Glu Thr Gly Lys Thr Val Ile Ser Ser Leu Ser Leu Cys Arg Leu Ala
                405                 410                 415

Asn Glu Thr Thr Glu Gly Phe Arg Gln Lys Phe Asn Glu Ala Lys Ala
            420                 425                 430

Lys Trp Glu Ala Glu His Lys Pro Ser Gln Asp Asn Phe Ile Thr Pro
    435                 440                 445

Met Gln Ser Asn Ile Ser Ile Asn Ser Leu Ser Ala Ser Lys Ser Asn
450                 455                 460

Ser Thr Ile Ser Thr Ala Arg Asn Leu Thr Ser Gly Ser Thr Ala Pro
465                 470                 475                 480

Ala Thr Ala Arg Asp Lys Arg Lys Ser Arg Leu Ser Lys Leu Ala Asp
                485                 490                 495

Asn Val Arg Ser His Ser Ser Arg His Ser Ser Gln Thr Arg Ser
            500                 505                 510

Lys Pro Pro Glu Leu Pro Lys Leu Tyr Asp Leu Val Pro Lys Pro Asn
    515                 520                 525

Ile Asn Ala Lys Leu Leu Leu Phe Trp Arg Lys Pro Ala Arg Lys Cys
530                 535                 540

Trp Trp Gly Glu Glu Asp Ile Glu Leu Glu Val Glu Val Phe Gly Ser
545                 550                 555                 560

Trp Lys Asp Glu Ser Lys Lys Ile Ile Glu Leu Ile Leu Pro Thr Asn
                565                 570                 575

Val Asp Pro Glu Ala Glu Leu His Lys Ile Ile Val Pro Val Arg Leu
            580                 585                 590

His Ile Arg Arg Val Trp Thr Leu Glu Leu Ser Val Ile Gly Val Gln
    595                 600                 605
```

<210> SEQ ID NO 97
<211> LENGTH: 964
<212> TYPE: PRT
<213> ORGANISM: Saccharomyces cerevisiae

<400> SEQUENCE: 97

Met Gly Lys Glu Lys Ser His Ile Asn Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
            35                  40                  45

Leu Gly Lys Gly Ser Phe Lys Tyr Ala Trp Val Leu Asp Lys Leu Lys
        50                  55                  60

Ala Glu Arg Glu Arg Gly Ile Thr Ile Asp Ile Ala Leu Trp Lys Phe
65                  70                  75                  80

Glu Thr Pro Lys Tyr Gln Val Thr Val Ile Asp Ala Pro Gly His Arg
                85                  90                  95

Asp Phe Ile Lys Asn Met Ile Thr Gly Thr Ser Gln Ala Asp Cys Ala
            100                 105                 110

Ile Leu Ile Ile Ala Gly Gly Val Gly Glu Phe Glu Ala Gly Ile Ser
        115                 120                 125

Lys Asp Gly Gln Thr Arg Glu His Ala Leu Leu Ala Phe Thr Leu Gly
130                 135                 140

Val Arg Gln Leu Ile Val Ala Val Asn Lys Met Asp Ser Val Lys Trp
145                 150                 155                 160

Asp Glu Ser Arg Phe Gln Glu Ile Val Lys Glu Thr Ser Asn Phe Ile
                165                 170                 175

Lys Lys Val Gly Tyr Asn Pro Lys Thr Val Pro Phe Val Pro Ile Ser
            180                 185                 190

Gly Trp Asn Gly Asp Asn Met Ile Glu Ala Thr Thr Asn Ala Pro Trp
        195                 200                 205

Tyr Lys Gly Trp Glu Lys Glu Thr Lys Ala Gly Val Val Lys Gly Lys
210                 215                 220

Thr Leu Leu Glu Ala Ile Asp Ala Ile Glu Gln Pro Ser Arg Pro Thr
225                 230                 235                 240

Asp Lys Pro Leu Arg Leu Pro Leu Gln Asp Val Tyr Lys Ile Gly Gly
                245                 250                 255

Ile Gly Thr Val Pro Val Gly Arg Val Glu Thr Gly Val Ile Lys Pro
            260                 265                 270

Gly Met Val Val Thr Phe Ala Pro Ala Gly Val Thr Thr Glu Val Lys
        275                 280                 285

Ser Val Glu Met His His Glu Gln Leu Glu Gln Gly Val Pro Gly Asp
290                 295                 300

Asn Val Gly Phe Asn Val Lys Asn Val Ser Val Lys Glu Ile Arg Arg
305                 310                 315                 320

Gly Asn Val Cys Gly Asp Ala Lys Asn Asp Pro Pro Lys Gly Cys Ala
                325                 330                 335

Ser Phe Asn Ala Thr Val Ile Val Leu Asn His Pro Gly Gln Ile Ser
            340                 345                 350

Ala Gly Tyr Ser Pro Val Leu Asp Cys His Thr Ala His Ile Ala Cys
        355                 360                 365

Arg Phe Asp Glu Leu Leu Glu Lys Asn Asp Arg Arg Ser Gly Lys Lys
370                 375                 380

```
Leu Glu Asp His Pro Lys Phe Leu Lys Ser Gly Asp Ala Ala Leu Val
385                 390                 395                 400

Lys Phe Val Pro Ser Lys Pro Met Cys Val Glu Ala Phe Ser Glu Tyr
                405                 410                 415

Pro Pro Leu Gly Arg Phe Ala Val Arg Asp Met Arg Gln Thr Val Ala
            420                 425                 430

Val Gly Val Ile Lys Ser Val Asp Lys Thr Glu Lys Ala Ala Lys Val
        435                 440                 445

Thr Lys Ala Ala Gln Lys Ala Lys Lys Gly Ser Ala Ala Pro Gly
450                 455                 460

Ala Ser Ala Ala Pro Gly Ala Gly Ser Gly Ser Gly Ser Gly Met Asp
465                 470                 475                 480

Asp Ile Ile Thr Gln Val Ser Pro Asp Asn Ala Glu Ser Ala Pro Ile
                485                 490                 495

Leu Gln Glu Gln Gln Gln Gln Asn Ser Gln Tyr Glu Gly Asn Glu
            500                 505                 510

Glu Asp Tyr Gly Asp Ser Leu Ile His Leu Asn Ile Gln Glu Asn His
            515                 520                 525

Tyr Phe Ile Thr Arg Asp Gln Leu Met Ser Leu Pro Glu Ser Leu Leu
            530                 535                 540

Leu Cys Leu Phe Pro Ser Gly Val Phe Leu Asp Arg Cys Gly Gln Val
545                 550                 555                 560

Ile Thr Asn Leu Thr Arg Asp Asp Glu Val Tyr Ile Val Asn Phe Pro
                565                 570                 575

Pro Asp Cys Phe Glu Tyr Ile Met Glu Ile Tyr Thr Lys Ala His Asp
            580                 585                 590

Asp Leu Tyr Asn His Pro Val Glu Lys Phe Phe Asp Arg Pro Ser Ser
            595                 600                 605

Ser Phe Val Ser Asn Ala Lys Gly Phe Phe Gly Leu Ser Ser Asn Asn
            610                 615                 620

Ser Ile Ser Ser Asn Asn Glu Gln Asp Ile Leu His Gln Lys Pro Ala
625                 630                 635                 640

Ile Ile Val Leu Arg Glu Asp Leu Asp Tyr Tyr Cys Val Pro Gln Glu
                645                 650                 655

Glu Phe Gln Phe Asp Ser Thr Asn Glu Glu Asn Asn Glu Asp Leu Leu
            660                 665                 670

Arg His Phe Met Ala Gln Val Lys Met Ala Ala Gly Ser Tyr Leu Thr
            675                 680                 685

Ser Lys Thr Ser Ile Phe Gln Gly Leu Tyr Ser Ser Asn Arg Leu Lys
            690                 695                 700

Gln Gln Gln Gln Gln Lys Ile Glu Lys Gly Ser Asn Ser Ser Ser
705                 710                 715                 720

Asn Thr Lys Ser Thr Ser Lys Lys Leu Gly Pro Ala Glu Gln His Leu
                725                 730                 735

Met Asp Met Leu Cys Ser Ser Gly Phe Thr Lys Glu Thr Cys Trp Gly
            740                 745                 750

Asn Arg Thr Gln Glu Thr Gly Lys Thr Val Ile Ser Ser Leu Ser Leu
            755                 760                 765

Cys Arg Leu Ala Asn Glu Thr Thr Glu Gly Phe Arg Gln Lys Phe Asn
            770                 775                 780

Glu Ala Lys Ala Lys Trp Glu Ala Glu His Lys Pro Ser Gln Asp Asn
785                 790                 795                 800

Phe Ile Thr Pro Met Gln Ser Asn Ile Ser Ile Asn Ser Leu Ser Ala
```

```
                805                 810                 815
Ser Lys Ser Asn Ser Thr Ile Ser Thr Ala Arg Asn Leu Thr Ser Gly
                820                 825                 830

Ser Thr Ala Pro Ala Thr Ala Arg Asp Lys Arg Lys Ser Arg Leu Ser
                835                 840                 845

Lys Leu Ala Asp Asn Val Arg Ser His Ser Ser Arg His Ser Ser
    850                 855                 860

Gln Thr Arg Ser Lys Pro Pro Glu Leu Pro Lys Leu Tyr Asp Leu Val
865                 870                 875                 880

Pro Lys Pro Asn Ile Asn Ala Lys Leu Leu Phe Trp Arg Lys Pro
                885                 890                 895

Ala Arg Lys Cys Trp Trp Gly Glu Glu Asp Ile Glu Leu Glu Val Glu
                900                 905                 910

Val Phe Gly Ser Trp Lys Asp Glu Ser Lys Lys Ile Ile Glu Leu Ile
                915                 920                 925

Leu Pro Thr Asn Val Asp Pro Glu Ala Glu Leu His Lys Ile Ile Val
                930                 935                 940

Pro Val Arg Leu His Ile Arg Arg Val Trp Thr Leu Glu Leu Ser Val
945                 950                 955                 960

Ile Gly Val Gln

<210> SEQ ID NO 98
<211> LENGTH: 594
<212> TYPE: PRT
<213> ORGANISM: Saccharomyces cerevisiae

<400> SEQUENCE: 98

Met Thr Ser Lys Arg Glu Lys Ser Leu Asp His Thr Leu Glu Leu Lys
1               5                   10                  15

Ile Pro Phe Glu Thr Glu Arg Gln Ala Thr Ile Ala Thr Lys Val Leu
                20                  25                  30

Ser Pro Asp Pro Ile Leu Lys Pro Gln Asp Phe Gln Val Asp Tyr Ser
                35                  40                  45

Ser Glu Lys Asn Val Met Leu Val Gln Phe Arg Ser Ile Asp Asp Arg
    50                  55                  60

Val Leu Arg Val Gly Val Ser Ser Ile Ile Asp Ser Ile Lys Thr Ile
65                  70                  75                  80

Val Glu Ala Met Asp Val Leu Ser Gly Ser Ala Ala Pro Gly Ala Ser
                85                  90                  95

Ala Ala Pro Gly Ala Gly Ser Gly Ser Gly Ser Gly Met Asp Asp Ile
                100                 105                 110

Ile Thr Gln Val Ser Pro Asp Asn Ala Glu Ser Ala Pro Ile Leu Gln
                115                 120                 125

Glu Gln Gln Gln Gln Asn Ser Gln Tyr Glu Gly Asn Glu Glu Asp
                130                 135                 140

Tyr Gly Asp Ser Leu Ile His Leu Asn Ile Gln Glu Asn His Tyr Phe
145                 150                 155                 160

Ile Thr Arg Asp Gln Leu Met Ser Leu Pro Glu Ser Leu Leu Leu Cys
                165                 170                 175

Leu Phe Pro Ser Gly Val Phe Leu Asp Arg Cys Gly Gln Val Ile Thr
                180                 185                 190

Asn Leu Thr Arg Asp Asp Glu Val Tyr Ile Val Asn Phe Pro Pro Asp
                195                 200                 205

Cys Phe Glu Tyr Ile Met Glu Ile Tyr Thr Lys Ala His Asp Asp Leu
```

```
            210                 215                 220
Tyr Asn His Pro Val Glu Lys Phe Phe Asp Arg Pro Ser Ser Ser Phe
225                 230                 235                 240

Val Ser Asn Ala Lys Gly Phe Phe Gly Leu Ser Ser Asn Asn Ser Ile
                245                 250                 255

Ser Ser Asn Asn Glu Gln Asp Ile Leu His Gln Lys Pro Ala Ile Ile
            260                 265                 270

Val Leu Arg Glu Asp Leu Asp Tyr Tyr Cys Val Pro Gln Glu Glu Phe
        275                 280                 285

Gln Phe Asp Ser Thr Asn Glu Glu Asn Asn Glu Asp Leu Leu Arg His
    290                 295                 300

Phe Met Ala Gln Val Lys Met Ala Ala Gly Ser Tyr Leu Thr Ser Lys
305                 310                 315                 320

Thr Ser Ile Phe Gln Gly Leu Tyr Ser Ser Asn Arg Leu Lys Gln Gln
                325                 330                 335

Gln Gln Gln Gln Lys Ile Glu Lys Gly Ser Asn Ser Ser Ser Asn Thr
            340                 345                 350

Lys Ser Thr Ser Lys Lys Leu Gly Pro Ala Glu Gln His Leu Met Asp
        355                 360                 365

Met Leu Cys Ser Ser Gly Phe Thr Lys Glu Thr Cys Trp Gly Asn Arg
370                 375                 380

Thr Gln Glu Thr Gly Lys Thr Val Ile Ser Ser Leu Ser Leu Cys Arg
385                 390                 395                 400

Leu Ala Asn Glu Thr Thr Glu Gly Phe Arg Gln Lys Phe Asn Glu Ala
                405                 410                 415

Lys Ala Lys Trp Glu Ala Glu His Lys Pro Ser Gln Asp Asn Phe Ile
            420                 425                 430

Thr Pro Met Gln Ser Asn Ile Ser Ile Asn Ser Leu Ser Ala Ser Lys
        435                 440                 445

Ser Asn Ser Thr Ile Ser Thr Ala Arg Asn Leu Thr Ser Gly Ser Thr
    450                 455                 460

Ala Pro Ala Thr Ala Arg Asp Lys Arg Lys Ser Arg Leu Ser Lys Leu
465                 470                 475                 480

Ala Asp Asn Val Arg Ser His Ser Ser Arg His Ser Ser Gln Thr
                485                 490                 495

Arg Ser Lys Pro Pro Glu Leu Pro Lys Leu Tyr Asp Leu Val Pro Lys
            500                 505                 510

Pro Asn Ile Asn Ala Lys Leu Leu Leu Phe Trp Arg Lys Pro Ala Arg
        515                 520                 525

Lys Cys Trp Trp Gly Glu Glu Asp Ile Glu Leu Glu Val Glu Val Phe
    530                 535                 540

Gly Ser Trp Lys Asp Glu Ser Lys Lys Ile Ile Glu Leu Ile Leu Pro
545                 550                 555                 560

Thr Asn Val Asp Pro Glu Ala Glu Leu His Lys Ile Ile Val Pro Val
                565                 570                 575

Arg Leu His Ile Arg Arg Val Trp Thr Leu Glu Leu Ser Val Ile Gly
            580                 585                 590

Val Gln

<210> SEQ ID NO 99
<211> LENGTH: 650
<212> TYPE: PRT
<213> ORGANISM: Saccharomyces cerevisiae
```

<400> SEQUENCE: 99

```
Met Gly Lys Lys Ala His Gly Gly Lys Met Lys Pro Glu Ile Asp Glu
1               5                   10                  15

Asn Gly Thr Leu Leu Val Pro Pro Arg Thr Ile Ala Asn Gln Asp
            20                  25                  30

His Phe His Arg Leu Asn Tyr Leu Tyr Gln Ile Ser Ala Tyr Gln Thr
            35                  40                  45

Arg Ala Arg Gln Lys Ala Arg Thr Asp Ala His Thr Pro Leu Ala Arg
    50                  55                  60

Asn Tyr Ile Lys Ser Met Asp Leu Ile Ser Lys Lys Thr Lys Thr Ser
65                  70                  75                  80

Leu Leu Pro Thr Ile Lys Arg Thr Ile Cys Lys Lys Cys His Arg Leu
            85                  90                  95

Leu Trp Thr Pro Lys Lys Leu Glu Ile Thr Ser Asp Gly Ala Leu Ser
            100                 105                 110

Val Met Cys Gly Cys Gly Thr Val Lys Arg Phe Asn Ile Gly Ala Asp
            115                 120                 125

Pro Asn Tyr Arg Thr Tyr Ser Glu Arg Glu Gly Asn Leu Leu Asn Ser
    130                 135                 140

Gly Ser Ala Ala Pro Gly Ala Ser Ala Ala Pro Gly Ala Gly Ser Gly
145                 150                 155                 160

Ser Gly Ser Gly Met Asp Asp Ile Ile Thr Gln Val Ser Pro Asp Asn
            165                 170                 175

Ala Glu Ser Ala Pro Ile Leu Gln Glu Gln Gln Gln Gln Asn Ser
    180                 185                 190

Gln Tyr Glu Gly Asn Glu Glu Asp Tyr Gly Asp Ser Leu Ile His Leu
    195                 200                 205

Asn Ile Gln Glu Asn His Tyr Phe Ile Thr Arg Asp Gln Leu Met Ser
210                 215                 220

Leu Pro Glu Ser Leu Leu Leu Cys Leu Phe Pro Ser Gly Val Phe Leu
225                 230                 235                 240

Asp Arg Cys Gly Gln Val Ile Thr Asn Leu Thr Arg Asp Asp Glu Val
            245                 250                 255

Tyr Ile Val Asn Phe Pro Pro Asp Cys Phe Glu Tyr Ile Met Glu Ile
            260                 265                 270

Tyr Thr Lys Ala His Asp Asp Leu Tyr Asn His Pro Val Glu Lys Phe
            275                 280                 285

Phe Asp Arg Pro Ser Ser Ser Phe Val Ser Asn Ala Lys Gly Phe Phe
    290                 295                 300

Gly Leu Ser Ser Asn Asn Ser Ile Ser Ser Asn Asn Glu Gln Asp Ile
305                 310                 315                 320

Leu His Gln Lys Pro Ala Ile Ile Val Leu Arg Glu Asp Leu Asp Tyr
            325                 330                 335

Tyr Cys Val Pro Gln Glu Glu Phe Gln Phe Asp Ser Thr Asn Glu Glu
            340                 345                 350

Asn Asn Glu Asp Leu Leu Arg His Phe Met Ala Gln Val Lys Met Ala
            355                 360                 365

Ala Gly Ser Tyr Leu Thr Ser Lys Thr Ser Ile Phe Gln Gly Leu Tyr
    370                 375                 380

Ser Ser Asn Arg Leu Lys Gln Gln Gln Gln Gln Lys Ile Glu Lys
385                 390                 395                 400

Gly Ser Asn Ser Ser Ser Asn Thr Lys Ser Thr Ser Lys Lys Leu Gly
            405                 410                 415
```

Pro Ala Glu Gln His Leu Met Asp Met Leu Cys Ser Ser Gly Phe Thr
                420                 425                 430

Lys Glu Thr Cys Trp Gly Asn Arg Thr Gln Glu Thr Gly Lys Thr Val
            435                 440                 445

Ile Ser Ser Leu Ser Leu Cys Arg Leu Ala Asn Glu Thr Thr Glu Gly
        450                 455                 460

Phe Arg Gln Lys Phe Asn Glu Ala Lys Ala Lys Trp Glu Ala Glu His
465                 470                 475                 480

Lys Pro Ser Gln Asp Asn Phe Ile Thr Pro Met Gln Ser Asn Ile Ser
                485                 490                 495

Ile Asn Ser Leu Ser Ala Ser Lys Ser Asn Ser Thr Ile Ser Thr Ala
            500                 505                 510

Arg Asn Leu Thr Ser Gly Ser Thr Ala Pro Thr Ala Arg Asp Lys
        515                 520                 525

Arg Lys Ser Arg Leu Ser Lys Leu Ala Asp Asn Val Arg Ser His Ser
530                 535                 540

Ser Ser Arg His Ser Ser Gln Thr Arg Ser Lys Pro Pro Glu Leu Pro
545                 550                 555                 560

Lys Leu Tyr Asp Leu Val Pro Lys Pro Asn Ile Asn Ala Lys Leu Leu
                565                 570                 575

Leu Phe Trp Arg Lys Pro Ala Arg Lys Cys Trp Trp Gly Glu Glu Asp
            580                 585                 590

Ile Glu Leu Glu Val Glu Val Phe Gly Ser Trp Lys Asp Glu Ser Lys
        595                 600                 605

Lys Ile Ile Glu Leu Ile Leu Pro Thr Asn Val Asp Pro Glu Ala Glu
            610                 615                 620

Leu His Lys Ile Ile Val Pro Val Arg Leu His Ile Arg Arg Val Trp
625                 630                 635                 640

Thr Leu Glu Leu Ser Val Ile Gly Val Gln
                645                 650

<210> SEQ ID NO 100
<211> LENGTH: 629
<212> TYPE: PRT
<213> ORGANISM: Saccharomyces cerevisiae

<400> SEQUENCE: 100

Met Lys Leu Pro Val Ala Gln Tyr Ser Ala Pro Asp Gly Val Glu Lys
1               5                   10                  15

Ser Phe Ala Pro Ile Arg Asp Asp Pro Arg Tyr Met Thr Thr Glu Gly
                20                  25                  30

Arg Thr Thr Gly Pro Ser Asp His Val Leu Asn Ala Gly Gln Ile Asp
            35                  40                  45

Arg Asp Lys Pro Ser Glu Pro Glu Arg Thr Lys Asp Gly Ser Gln Leu
        50                  55                  60

Thr Tyr Leu Gly Gln Leu Arg Thr Gln Leu Thr Gly Leu Gln Asp Asp
65                  70                  75                  80

Ile Asn Glu Phe Leu Thr Gly Arg Met Glu Leu Ala Lys Asn Lys Lys
                85                  90                  95

Lys Ala Gly Ala Asp Glu Lys Arg Ile Gln Glu Glu Ile Asn Gln Leu
            100                 105                 110

Leu Asp Gly Gly Asp Gly Asp Glu Asp Ala Val Gly Ser Ala Ala Pro
        115                 120                 125

Gly Ala Ser Ala Ala Pro Gly Ala Gly Ser Gly Ser Gly Ser Gly Met

-continued

```
                130                 135                 140
Asp Asp Ile Ile Thr Gln Val Ser Pro Asp Asn Ala Glu Ser Ala Pro
145                 150                 155                 160

Ile Leu Gln Glu Gln Gln Gln Gln Asn Ser Gln Tyr Glu Gly Asn
                165                 170                 175

Glu Glu Asp Tyr Gly Asp Ser Leu Ile His Leu Asn Ile Gln Glu Asn
                180                 185                 190

His Tyr Phe Ile Thr Arg Asp Gln Leu Met Ser Leu Pro Glu Ser Leu
                195                 200                 205

Leu Leu Cys Leu Phe Pro Ser Gly Val Phe Leu Asp Arg Cys Gly Gln
                210                 215                 220

Val Ile Thr Asn Leu Thr Arg Asp Asp Glu Val Tyr Ile Val Asn Phe
225                 230                 235                 240

Pro Pro Asp Cys Phe Glu Tyr Ile Met Glu Ile Tyr Thr Lys Ala His
                245                 250                 255

Asp Asp Leu Tyr Asn His Pro Val Glu Lys Phe Phe Asp Arg Pro Ser
                260                 265                 270

Ser Ser Phe Val Ser Asn Ala Lys Gly Phe Phe Gly Leu Ser Ser Asn
                275                 280                 285

Asn Ser Ile Ser Ser Asn Asn Glu Gln Asp Ile Leu His Gln Lys Pro
                290                 295                 300

Ala Ile Ile Val Leu Arg Glu Asp Leu Asp Tyr Tyr Cys Val Pro Gln
305                 310                 315                 320

Glu Glu Phe Gln Phe Asp Ser Thr Asn Glu Glu Asn Asn Glu Asp Leu
                325                 330                 335

Leu Arg His Phe Met Ala Gln Val Lys Met Ala Ala Gly Ser Tyr Leu
                340                 345                 350

Thr Ser Lys Thr Ser Ile Phe Gln Gly Leu Tyr Ser Ser Asn Arg Leu
                355                 360                 365

Lys Gln Gln Gln Gln Gln Lys Ile Glu Lys Gly Ser Asn Ser Ser
                370                 375                 380

Ser Asn Thr Lys Ser Thr Ser Lys Lys Leu Gly Pro Ala Glu Gln His
385                 390                 395                 400

Leu Met Asp Met Leu Cys Ser Ser Gly Phe Thr Lys Glu Thr Cys Trp
                405                 410                 415

Gly Asn Arg Thr Gln Glu Thr Gly Lys Thr Val Ile Ser Ser Leu Ser
                420                 425                 430

Leu Cys Arg Leu Ala Asn Glu Thr Thr Glu Gly Phe Arg Gln Lys Phe
                435                 440                 445

Asn Glu Ala Lys Ala Lys Trp Glu Ala Glu His Lys Pro Ser Gln Asp
450                 455                 460

Asn Phe Ile Thr Pro Met Gln Ser Asn Ile Ser Ile Asn Ser Leu Ser
465                 470                 475                 480

Ala Ser Lys Ser Asn Ser Thr Ile Ser Thr Ala Arg Asn Leu Thr Ser
                485                 490                 495

Gly Ser Thr Ala Pro Ala Thr Ala Arg Asp Lys Arg Lys Ser Arg Leu
                500                 505                 510

Ser Lys Leu Ala Asp Asn Val Arg Ser His Ser Ser Ser Arg His Ser
                515                 520                 525

Ser Gln Thr Arg Ser Lys Pro Pro Glu Leu Pro Lys Leu Tyr Asp Leu
                530                 535                 540

Val Pro Lys Pro Asn Ile Asn Ala Lys Leu Leu Leu Phe Trp Arg Lys
545                 550                 555                 560
```

```
Pro Ala Arg Lys Cys Trp Trp Gly Glu Glu Asp Ile Glu Leu Glu Val
                565                 570                 575

Glu Val Phe Gly Ser Trp Lys Asp Glu Ser Lys Lys Ile Ile Glu Leu
            580                 585                 590

Ile Leu Pro Thr Asn Val Asp Pro Glu Ala Glu Leu His Lys Ile Ile
        595                 600                 605

Val Pro Val Arg Leu His Ile Arg Arg Val Trp Thr Leu Glu Leu Ser
    610                 615                 620

Val Ile Gly Val Gln
625

<210> SEQ ID NO 101
<211> LENGTH: 209
<212> TYPE: PRT
<213> ORGANISM: Saccharomyces cerevisiae

<400> SEQUENCE: 101

Met Ser Ser Val Glu Ser Ser Pro Ile Ser Arg Tyr Glu Asp Glu Val
1               5                   10                  15

Phe Pro Leu Ser Phe Ser Asn Val Ala Phe Glu Pro Pro Met Leu Ser
            20                  25                  30

His Ser Pro Asp Arg Ser Thr Tyr Ala Asp Asp Phe Ser Gln Ser Tyr
        35                  40                  45

Gln Gln Glu Leu Leu Thr Phe Pro Leu Ser Tyr Pro Ile Val Asp Glu
    50                  55                  60

Ser Glu Cys Thr His Thr Lys Asp Lys Thr Asp Ser Asn Ile Ile Thr
65                  70                  75                  80

Ser Thr Glu Asp Asp Cys Met Phe Asp Met Glu Phe Asn Gly Asn Ala
                85                  90                  95

Ala Ser Ala Val Ala Ala Ala Ser Lys Glu Ser Asn Ser Ala Ser Gly
            100                 105                 110

Phe Ala Phe Ala Ser Asn Asp Ala Phe Ala Asn Val Ala Gln Gln Asn
        115                 120                 125

Tyr Arg Leu Trp Leu Ser Ser Val Gly Ser Ala Ala Pro Gly Ala Ser
    130                 135                 140

Ala Ala Pro Gly Ala Gly Ser Gly Ser Gly Ser Gly Met Val Gln Tyr
145                 150                 155                 160

Ala Pro Phe Leu Leu Gly Lys Phe Ser Asp Pro Leu Leu Ala Ile Met
                165                 170                 175

Val Gly Cys Leu Ser Tyr Tyr Val Tyr Glu Arg Lys Met Gly Arg Pro
            180                 185                 190

Gln Gly His His Leu His Glu Leu Ile Lys Lys Arg Trp Asp Asp Arg
        195                 200                 205

Lys

<210> SEQ ID NO 102
<211> LENGTH: 709
<212> TYPE: PRT
<213> ORGANISM: Saccharomyces cerevisiae

<400> SEQUENCE: 102

Met Ser Gln Gly Arg Lys Ala Ala Glu Arg Leu Ala Lys Lys Thr Val
1               5                   10                  15

Leu Ile Thr Gly Ala Ser Ala Gly Ile Gly Lys Ala Thr Ala Leu Glu
            20                  25                  30
```

-continued

Tyr Leu Glu Ala Ser Asn Gly Asp Met Lys Leu Ile Leu Ala Ala Arg
             35                  40                  45

Arg Leu Glu Lys Leu Glu Leu Lys Lys Thr Ile Asp Gln Glu Phe
 50                  55                  60

Pro Asn Ala Lys Val His Val Ala Gln Leu Asp Ile Thr Gln Ala Glu
 65                  70                  75                  80

Lys Ile Lys Pro Phe Ile Glu Asn Leu Pro Gln Glu Phe Lys Asp Ile
                 85                  90                  95

Asp Ile Leu Val Asn Asn Ala Gly Lys Ala Leu Gly Ser Asp Arg Val
                100                 105                 110

Gly Gln Ile Ala Thr Glu Asp Ile Gln Asp Val Phe Asp Thr Asn Val
            115                 120                 125

Thr Ala Leu Ile Asn Ile Thr Gln Ala Val Leu Pro Ile Phe Gln Ala
        130                 135                 140

Lys Asn Ser Gly Asp Ile Val Asn Leu Gly Ser Ile Ala Gly Arg Asp
145                 150                 155                 160

Ala Tyr Pro Thr Gly Ser Ile Tyr Cys Ala Ser Lys Phe Ala Val Gly
                165                 170                 175

Ala Phe Thr Asp Ser Leu Arg Lys Glu Leu Ile Asn Thr Lys Ile Arg
            180                 185                 190

Val Ile Leu Ile Ala Pro Gly Leu Val Glu Thr Glu Phe Ser Leu Val
        195                 200                 205

Arg Tyr Arg Gly Asn Glu Glu Gln Ala Lys Asn Val Tyr Lys Asp Thr
210                 215                 220

Thr Pro Leu Met Ala Asp Asp Val Ala Asp Leu Ile Val Tyr Ala Thr
225                 230                 235                 240

Ser Arg Lys Gln Asn Thr Val Ile Ala Asp Thr Leu Ile Phe Pro Thr
                245                 250                 255

Asn Gln Ala Ser Pro His His Ile Phe Arg Gly Gly Ser Ala Ala Pro
            260                 265                 270

Gly Ala Ser Ala Ala Pro Gly Ala Gly Ser Gly Ser Gly Ser Gly Met
        275                 280                 285

Asn Gln Cys Ala Lys Asp Ile Thr His Glu Ala Ser Ser Ile Pro Ile
290                 295                 300

Asp Leu Gln Glu Arg Tyr Ser His Trp Lys Lys Asn Thr Lys Leu Leu
305                 310                 315                 320

Tyr Asp Tyr Leu Asn Thr Asn Ser Thr Lys Trp Pro Ser Leu Thr Cys
                325                 330                 335

Gln Phe Phe Pro Asp Leu Asp Thr Thr Ser Asp Glu His Arg Ile Leu
            340                 345                 350

Leu Ser Ser Phe Thr Ser Ser Gln Lys Pro Glu Asp Glu Thr Ile Tyr
        355                 360                 365

Ile Ser Lys Ile Ser Thr Leu Gly His Ile Lys Trp Ser Ser Leu Asn
370                 375                 380

Asn Phe Asp Met Asp Glu Met Glu Phe Lys Pro Glu Asn Ser Thr Arg
385                 390                 395                 400

Phe Pro Ser Lys His Leu Val Asn Asp Ile Ser Ile Phe Pro Asn
                405                 410                 415

Gly Glu Cys Asn Arg Ala Arg Tyr Leu Pro Gln Asn Pro Asp Ile Ile
            420                 425                 430

Ala Gly Ala Ser Ser Asp Gly Ala Ile Tyr Ile Phe Asp Arg Thr Lys
        435                 440                 445

His Gly Ser Thr Arg Ile Arg Gln Ser Lys Ile Ser His Pro Phe Glu

```
                    450                 455                 460
        Thr Lys Leu Phe Gly Ser His Gly Val Ile Gln Asp Val Glu Ala Met
        465                 470                 475                 480

Asp Thr Ser Ser Ala Asp Ile Asn Glu Ala Thr Ser Leu Ala Trp Asn
                            485                 490                 495

Leu Gln Gln Glu Ala Leu Leu Leu Ser Ser His Ser Asn Gly Gln Val
                        500                 505                 510

Gln Val Trp Asp Ile Lys Gln Tyr Ser His Glu Asn Pro Ile Ile Asp
                        515                 520                 525

Leu Pro Leu Val Ser Ile Asn Ser Asp Gly Thr Ala Val Asn Asp Val
        530                 535                 540

Thr Trp Met Pro Thr His Asp Ser Leu Phe Ala Ala Cys Thr Glu Gly
        545                 550                 555                 560

Asn Ala Val Ser Leu Leu Asp Leu Arg Thr Lys Lys Glu Lys Leu Gln
                            565                 570                 575

Ser Asn Arg Glu Lys His Asp Gly Gly Val Asn Ser Cys Arg Phe Asn
                        580                 585                 590

Tyr Lys Asn Ser Leu Ile Leu Ala Ser Ala Asp Ser Asn Gly Arg Leu
                        595                 600                 605

Asn Leu Trp Asp Ile Arg Asn Met Asn Lys Ser Pro Ile Ala Thr Met
        610                 615                 620

Glu His Gly Thr Ser Val Ser Thr Leu Glu Trp Ser Pro Asn Phe Asp
        625                 630                 635                 640

Thr Val Leu Ala Thr Ala Gly Gln Glu Asp Gly Leu Val Lys Leu Trp
                            645                 650                 655

Asp Thr Ser Cys Glu Glu Thr Ile Phe Thr His Gly Gly His Met Leu
                        660                 665                 670

Gly Val Asn Asp Ile Ser Trp Asp Ala His Asp Pro Trp Leu Met Cys
                        675                 680                 685

Ser Val Ala Asn Asp Asn Ser Val His Ile Trp Lys Pro Ala Gly Asn
                        690                 695                 700

Leu Val Gly His Ser
        705

<210> SEQ ID NO 103
        <211> LENGTH: 663
        <212> TYPE: PRT
        <213> ORGANISM: Saccharomyces cerevisiae

<400> SEQUENCE: 103

Met Ser Asp Glu Glu His Thr Phe Glu Thr Ala Asp Ala Gly Ser Ser
        1               5                   10                  15

Ala Thr Tyr Pro Met Gln Cys Ser Ala Leu Arg Lys Asn Gly Phe Val
                        20                  25                  30

Val Ile Lys Ser Arg Pro Cys Lys Ile Val Asp Met Ser Thr Ser Lys
                    35                  40                  45

Thr Gly Lys His Gly His Ala Lys Val His Leu Val Ala Ile Asp Ile
                50                  55                  60

Phe Thr Gly Lys Lys Leu Glu Asp Leu Ser Pro Ser Thr His Asn Met
        65                  70                  75                  80

Glu Val Pro Val Val Lys Arg Asn Glu Tyr Gln Leu Leu Asp Ile Asp
                        85                  90                  95

Asp Gly Phe Leu Ser Leu Met Asn Met Asp Gly Asp Thr Lys Asp Asp
                        100                 105                 110
```

-continued

Val Lys Ala Pro Glu Gly Glu Leu Gly Asp Ser Leu Gln Thr Ala Phe
            115                 120                 125

Asp Glu Gly Lys Asp Leu Met Val Thr Ile Ile Ser Ala Met Gly Glu
130                 135                 140

Glu Ala Ala Ile Ser Phe Lys Glu Ala Ala Arg Thr Asp Gly Ser Ala
145                 150                 155                 160

Ala Pro Gly Ala Ser Ala Pro Gly Ala Gly Ser Gly Ser Gly Ser
                165                 170                 175

Gly Met Asp Asp Ile Ile Thr Gln Val Ser Pro Asp Asn Ala Glu Ser
            180                 185                 190

Ala Pro Ile Leu Gln Glu Gln Gln Gln Gln Asn Ser Gln Tyr Glu
            195                 200                 205

Gly Asn Glu Glu Asp Tyr Gly Asp Ser Leu Ile His Leu Asn Ile Gln
            210                 215                 220

Glu Asn His Tyr Phe Ile Thr Arg Asp Gln Leu Met Ser Leu Pro Glu
225                 230                 235                 240

Ser Leu Leu Leu Cys Leu Phe Pro Ser Gly Val Phe Leu Asp Arg Cys
                245                 250                 255

Gly Gln Val Ile Thr Asn Leu Thr Arg Asp Asp Glu Val Tyr Ile Val
            260                 265                 270

Asn Phe Pro Pro Asp Cys Phe Glu Tyr Ile Met Glu Ile Tyr Thr Lys
            275                 280                 285

Ala His Asp Asp Leu Tyr Asn His Pro Val Glu Lys Phe Phe Asp Arg
            290                 295                 300

Pro Ser Ser Ser Phe Val Ser Asn Ala Lys Gly Phe Phe Gly Leu Ser
305                 310                 315                 320

Ser Asn Asn Ser Ile Ser Ser Asn Asn Glu Gln Asp Ile Leu His Gln
                325                 330                 335

Lys Pro Ala Ile Ile Val Leu Arg Glu Asp Leu Asp Tyr Tyr Cys Val
            340                 345                 350

Pro Gln Glu Glu Phe Gln Phe Asp Ser Thr Asn Glu Glu Asn Asn Glu
            355                 360                 365

Asp Leu Leu Arg His Phe Met Ala Gln Val Lys Met Ala Ala Gly Ser
370                 375                 380

Tyr Leu Thr Ser Lys Thr Ser Ile Phe Gln Gly Leu Tyr Ser Ser Asn
385                 390                 395                 400

Arg Leu Lys Gln Gln Gln Gln Gln Lys Ile Glu Lys Gly Ser Asn
                405                 410                 415

Ser Ser Ser Asn Thr Lys Ser Thr Ser Lys Lys Leu Gly Pro Ala Glu
            420                 425                 430

Gln His Leu Met Asp Met Leu Cys Ser Ser Gly Phe Thr Lys Glu Thr
            435                 440                 445

Cys Trp Gly Asn Arg Thr Gln Glu Thr Gly Lys Thr Val Ile Ser Ser
450                 455                 460

Leu Ser Leu Cys Arg Leu Ala Asn Glu Thr Thr Glu Gly Phe Arg Gln
465                 470                 475                 480

Lys Phe Asn Glu Ala Lys Ala Lys Trp Glu Ala Glu His Lys Pro Ser
                485                 490                 495

Gln Asp Asn Phe Ile Thr Pro Met Gln Ser Asn Ile Ser Ile Asn Ser
            500                 505                 510

Leu Ser Ala Ser Lys Ser Asn Ser Thr Ile Ser Thr Ala Arg Asn Leu
            515                 520                 525

Thr Ser Gly Ser Thr Ala Pro Ala Thr Ala Arg Asp Lys Arg Lys Ser

```
                530                 535                 540
Arg Leu Ser Lys Leu Ala Asp Asn Val Arg Ser His Ser Ser Arg
545                 550                 555                 560

His Ser Ser Gln Thr Arg Ser Lys Pro Pro Glu Leu Pro Lys Leu Tyr
                565                 570                 575

Asp Leu Val Pro Lys Pro Asn Ile Asn Ala Lys Leu Leu Leu Phe Trp
                580                 585                 590

Arg Lys Pro Ala Arg Lys Cys Trp Trp Gly Glu Glu Asp Ile Glu Leu
                595                 600                 605

Glu Val Glu Val Phe Gly Ser Trp Lys Asp Glu Ser Lys Lys Ile Ile
                610                 615                 620

Glu Leu Ile Leu Pro Thr Asn Val Asp Pro Glu Ala Glu Leu His Lys
625                 630                 635                 640

Ile Ile Val Pro Val Arg Leu His Ile Arg Arg Val Trp Thr Leu Glu
                645                 650                 655

Leu Ser Val Ile Gly Val Gln
                660

<210> SEQ ID NO 104
<211> LENGTH: 642
<212> TYPE: PRT
<213> ORGANISM: Saccharomyces cerevisiae

<400> SEQUENCE: 104

Met Ser Ser Val Glu Ser Ser Pro Ile Ser Arg Tyr Glu Asp Glu Val
1               5                   10                  15

Phe Pro Leu Ser Phe Ser Asn Val Ala Phe Glu Pro Pro Met Leu Ser
                20                  25                  30

His Ser Pro Asp Arg Ser Thr Tyr Ala Asp Asp Phe Ser Gln Ser Tyr
                35                  40                  45

Gln Gln Glu Leu Leu Thr Phe Pro Leu Ser Tyr Pro Ile Val Asp Glu
50                  55                  60

Ser Glu Cys Thr His Thr Lys Asp Lys Thr Asp Ser Asn Ile Ile Thr
65                  70                  75                  80

Ser Thr Glu Asp Asp Cys Met Phe Asp Met Glu Phe Asn Gly Asn Ala
                85                  90                  95

Ala Ser Ala Val Ala Ala Ser Lys Glu Ser Asn Ser Ala Ser Gly
                100                 105                 110

Phe Ala Phe Ala Ser Asn Asp Ala Phe Ala Asn Val Ala Gln Gln Asn
                115                 120                 125

Tyr Arg Leu Trp Leu Ser Ser Val Gly Ser Ala Ala Pro Gly Ala Ser
                130                 135                 140

Ala Ala Pro Gly Ala Gly Ser Gly Ser Gly Ser Gly Met Asp Asp Ile
145                 150                 155                 160

Ile Thr Gln Val Ser Pro Asp Asn Ala Glu Ser Ala Pro Ile Leu Gln
                165                 170                 175

Glu Gln Gln Gln Gln Asn Ser Gln Tyr Glu Gly Asn Glu Glu Asp
                180                 185                 190

Tyr Gly Asp Ser Leu Ile His Leu Asn Ile Gln Glu Asn His Tyr Phe
                195                 200                 205

Ile Thr Arg Asp Gln Leu Met Ser Leu Pro Glu Ser Leu Leu Leu Cys
                210                 215                 220

Leu Phe Pro Ser Gly Val Phe Leu Asp Arg Cys Gly Gln Val Ile Thr
225                 230                 235                 240
```

-continued

```
Asn Leu Thr Arg Asp Asp Glu Val Tyr Ile Val Asn Phe Pro Pro Asp
                245                 250                 255

Cys Phe Glu Tyr Ile Met Glu Ile Tyr Thr Lys Ala His Asp Asp Leu
            260                 265                 270

Tyr Asn His Pro Val Glu Lys Phe Phe Asp Arg Pro Ser Ser Ser Phe
        275                 280                 285

Val Ser Asn Ala Lys Gly Phe Phe Gly Leu Ser Ser Asn Asn Ser Ile
    290                 295                 300

Ser Ser Asn Asn Glu Gln Asp Ile Leu His Gln Lys Pro Ala Ile Ile
305                 310                 315                 320

Val Leu Arg Glu Asp Leu Asp Tyr Tyr Cys Val Pro Gln Glu Glu Phe
                325                 330                 335

Gln Phe Asp Ser Thr Asn Glu Glu Asn Asn Glu Asp Leu Leu Arg His
            340                 345                 350

Phe Met Ala Gln Val Lys Met Ala Ala Gly Ser Tyr Leu Thr Ser Lys
        355                 360                 365

Thr Ser Ile Phe Gln Gly Leu Tyr Ser Ser Asn Arg Leu Lys Gln Gln
    370                 375                 380

Gln Gln Gln Gln Lys Ile Glu Lys Gly Ser Asn Ser Ser Ser Asn Thr
385                 390                 395                 400

Lys Ser Thr Ser Lys Lys Leu Gly Pro Ala Glu Gln His Leu Met Asp
                405                 410                 415

Met Leu Cys Ser Ser Gly Phe Thr Lys Glu Thr Cys Trp Gly Asn Arg
            420                 425                 430

Thr Gln Glu Thr Gly Lys Thr Val Ile Ser Ser Leu Ser Leu Cys Arg
        435                 440                 445

Leu Ala Asn Glu Thr Thr Glu Gly Phe Arg Gln Lys Phe Asn Glu Ala
    450                 455                 460

Lys Ala Lys Trp Glu Ala Glu His Lys Pro Ser Gln Asp Asn Phe Ile
465                 470                 475                 480

Thr Pro Met Gln Ser Asn Ile Ser Ile Asn Ser Leu Ser Ala Ser Lys
                485                 490                 495

Ser Asn Ser Thr Ile Ser Thr Ala Arg Asn Leu Thr Ser Gly Ser Thr
            500                 505                 510

Ala Pro Ala Thr Ala Arg Asp Lys Arg Lys Ser Arg Leu Ser Lys Leu
        515                 520                 525

Ala Asp Asn Val Arg Ser His Ser Ser Ser Arg His Ser Ser Gln Thr
    530                 535                 540

Arg Ser Lys Pro Pro Glu Leu Pro Lys Leu Tyr Asp Leu Val Pro Lys
545                 550                 555                 560

Pro Asn Ile Asn Ala Lys Leu Leu Leu Phe Trp Arg Lys Pro Ala Arg
                565                 570                 575

Lys Cys Trp Trp Gly Glu Glu Asp Ile Glu Leu Glu Val Glu Val Phe
            580                 585                 590

Gly Ser Trp Lys Asp Glu Ser Lys Lys Ile Ile Glu Leu Ile Leu Pro
        595                 600                 605

Thr Asn Val Asp Pro Glu Ala Glu Leu His Lys Ile Ile Val Pro Val
    610                 615                 620

Arg Leu His Ile Arg Arg Val Trp Thr Leu Glu Leu Ser Val Ile Gly
625                 630                 635                 640

Val Gln

<210> SEQ ID NO 105
```

```
<211> LENGTH: 171
<212> TYPE: PRT
<213> ORGANISM: Saccharomyces cerevisiae

<400> SEQUENCE: 105

Met Trp Arg Arg Arg Glu Pro Trp Glu Glu Leu Ser Phe Leu Leu
1               5                   10                  15

Asn Ser Leu Ser Pro Arg Asn Trp Phe Ile Arg Arg Trp Gly Leu Met
                20                  25                  30

Ala Gly Arg Gly Gln His Leu Cys Trp Leu Arg Cys Ala Cys Asp Gly
            35                  40                  45

Pro Gly Ser Ala Ala Pro Gly Ala Ser Ala Ala Pro Gly Ala Gly Ser
50                  55                  60

Gly Ser Gly Ser Gly Met Ser Ser Glu Arg Ala Cys Met Leu Cys Gly
65                  70                  75                  80

Ile Val Gln Thr Thr Asn Glu Phe Asn Arg Asp Gly Cys Pro Asn Cys
                85                  90                  95

Gln Gly Ile Phe Glu Glu Ala Gly Val Ser Thr Met Glu Cys Thr Ser
            100                 105                 110

Pro Ser Phe Glu Gly Leu Val Gly Met Cys Lys Pro Thr Lys Ser Trp
        115                 120                 125

Val Ala Lys Trp Leu Ser Val Asp His Ser Ile Ala Gly Met Tyr Ala
130                 135                 140

Ile Lys Val Asp Gly Arg Leu Pro Ala Glu Val Val Glu Leu Leu Pro
145                 150                 155                 160

His Tyr Lys Pro Arg Asp Gly Ser Gln Val Glu
                165                 170

<210> SEQ ID NO 106
<211> LENGTH: 716
<212> TYPE: PRT
<213> ORGANISM: Saccharomyces cerevisiae

<400> SEQUENCE: 106

Met Met Ser Gln Val Ser His Ser Gln Glu Gly Ser Gly Arg Phe Trp
1               5                   10                  15

Asn Lys Phe Lys Ser Ser Thr Lys Ser Leu Ser Thr Ser Leu Ala His
                20                  25                  30

Leu Ser Ile Lys Ala Glu Lys Asp Gly Asp Thr Val Asn Thr Thr Leu
            35                  40                  45

Val His Lys Gly Leu Val Lys Phe Tyr Glu Asn Gln His Pro Phe Gln
50                  55                  60

Gly Phe Pro Gly Trp Leu Gly Glu Lys Glu Asp Leu Pro Asn Glu Arg
65                  70                  75                  80

Lys Ile Leu Asp Thr Gln Val Lys His Asp Met Lys Lys Gln Asn Ser
                85                  90                  95

Arg His Phe Ser Pro Ser Phe Ser Asn Arg Arg Lys Ala Ser Ser Glu
            100                 105                 110

Asp Pro Met Gly Thr Pro Ser Ser Asn Gly Asn Thr Pro Glu Tyr Thr
        115                 120                 125

Pro Ala Ser Lys Ser Phe Gln Asp Ile Tyr Asn Asn His Thr Ser Ser
130                 135                 140

Ser Ser Ala Thr Pro Arg Arg Ala Ser Ser Arg Pro Thr Arg Pro Ser
145                 150                 155                 160

Ala Gly Gln Glu Phe Arg Ala Ser Leu Gly Arg Ser Lys Thr Ser Asn
                165                 170                 175
```

```
Ser Phe Asn Thr Ser Ser Thr Pro Thr Pro Pro Asp Ala Ser Ser
            180                 185                 190

Gly Val Met Ala Met Lys Asp Arg Leu Lys Arg Arg Asn Asn Asp Tyr
        195                 200                 205

Gly Phe Gly Ser Ala Ala Pro Gly Ala Ser Ala Ala Pro Gly Ala Gly
        210                 215                 220

Ser Gly Ser Gly Ser Gly Met Asp Asp Ile Ile Thr Gln Val Ser Pro
225                 230                 235                 240

Asp Asn Ala Glu Ser Ala Pro Ile Leu Gln Glu Gln Gln Gln Gln Gln
                245                 250                 255

Asn Ser Gln Tyr Glu Gly Asn Glu Glu Asp Tyr Gly Asp Ser Leu Ile
            260                 265                 270

His Leu Asn Ile Gln Glu Asn His Tyr Phe Ile Thr Arg Asp Gln Leu
        275                 280                 285

Met Ser Leu Pro Glu Ser Leu Leu Leu Cys Leu Phe Pro Ser Gly Val
    290                 295                 300

Phe Leu Asp Arg Cys Gly Gln Val Ile Thr Asn Leu Thr Arg Asp Asp
305                 310                 315                 320

Glu Val Tyr Ile Val Asn Phe Pro Pro Asp Cys Phe Glu Tyr Ile Met
                325                 330                 335

Glu Ile Tyr Thr Lys Ala His Asp Asp Leu Tyr Asn His Pro Val Glu
            340                 345                 350

Lys Phe Phe Asp Arg Pro Ser Ser Ser Phe Val Ser Asn Ala Lys Gly
        355                 360                 365

Phe Phe Gly Leu Ser Ser Asn Asn Ser Ile Ser Ser Asn Asn Glu Gln
    370                 375                 380

Asp Ile Leu His Gln Lys Pro Ala Ile Ile Val Leu Arg Glu Asp Leu
385                 390                 395                 400

Asp Tyr Tyr Cys Val Pro Gln Glu Glu Phe Gln Phe Asp Ser Thr Asn
                405                 410                 415

Glu Glu Asn Asn Glu Asp Leu Leu Arg His Phe Met Ala Gln Val Lys
            420                 425                 430

Met Ala Ala Gly Ser Tyr Leu Thr Ser Lys Thr Ser Ile Phe Gln Gly
        435                 440                 445

Leu Tyr Ser Ser Asn Arg Leu Lys Gln Gln Gln Gln Gln Gln Lys Ile
    450                 455                 460

Glu Lys Gly Ser Asn Ser Ser Asn Thr Lys Ser Thr Ser Lys Lys
465                 470                 475                 480

Leu Gly Pro Ala Glu Gln His Leu Met Asp Met Leu Cys Ser Ser Gly
                485                 490                 495

Phe Thr Lys Glu Thr Cys Trp Gly Asn Arg Thr Gln Glu Thr Gly Lys
            500                 505                 510

Thr Val Ile Ser Ser Leu Ser Leu Cys Arg Leu Ala Asn Glu Thr Thr
        515                 520                 525

Glu Gly Phe Arg Gln Lys Phe Asn Glu Ala Lys Ala Lys Trp Glu Ala
    530                 535                 540

Glu His Lys Pro Ser Gln Asp Asn Phe Ile Thr Pro Met Gln Ser Asn
545                 550                 555                 560

Ile Ser Ile Asn Ser Leu Ser Ala Ser Lys Ser Asn Ser Thr Ile Ser
                565                 570                 575

Thr Ala Arg Asn Leu Thr Ser Gly Ser Thr Ala Pro Thr Ala Arg
            580                 585                 590
```

```
Asp Lys Arg Lys Ser Arg Leu Ser Lys Leu Ala Asp Asn Val Arg Ser
            595                 600                 605

His Ser Ser Ser Arg His Ser Ser Gln Thr Arg Ser Lys Pro Pro Glu
    610                 615                 620

Leu Pro Lys Leu Tyr Asp Leu Val Pro Lys Pro Asn Ile Asn Ala Lys
625                 630                 635                 640

Leu Leu Leu Phe Trp Arg Lys Pro Ala Arg Lys Cys Trp Trp Gly Glu
                645                 650                 655

Glu Asp Ile Glu Leu Glu Val Glu Val Phe Gly Ser Trp Lys Asp Glu
            660                 665                 670

Ser Lys Lys Ile Ile Glu Leu Ile Leu Pro Thr Asn Val Asp Pro Glu
    675                 680                 685

Ala Glu Leu His Lys Ile Ile Val Pro Val Arg Leu His Ile Arg Arg
690                 695                 700

Val Trp Thr Leu Glu Leu Ser Val Ile Gly Val Gln
705                 710                 715

<210> SEQ ID NO 107
<211> LENGTH: 744
<212> TYPE: PRT
<213> ORGANISM: Saccharomyces cerevisiae

<400> SEQUENCE: 107

Met Ser His Lys Leu Thr Ile Leu Pro Phe Leu Ile Lys Phe Thr Pro
1               5                   10                  15

Lys Phe Pro Gln Ser Ile Asp His Asp Glu His Gly Leu Asn Val Tyr
                20                  25                  30

Ala Phe Asp Leu Asp His Thr Ile Ile Lys Pro Lys Ser Pro Asn Ile
            35                  40                  45

Ser Phe Ser Arg Ser Ala Ser Asp Trp Gln Phe Ile Asn Phe Asn Ser
        50                  55                  60

Lys Lys Ser Thr Leu Asp Tyr Leu Cys Asn Ile Ile Asp Asn Asp Pro
65                  70                  75                  80

Thr Ala Val Ile Val Ile Phe Ser Asn Gln Gly Gly Val Ile Thr Val
                85                  90                  95

Pro Arg Thr Ser Lys Ser Cys Thr Lys Tyr Thr Asn Lys Ile Leu Leu
            100                 105                 110

Phe Leu Lys Ala Ile Lys Asn Asp Glu Arg Gly Glu Thr Leu Ser His
        115                 120                 125

Arg Leu Trp Leu Tyr Ala Ala Pro Lys Arg Pro Lys Thr Phe Ala Ala
    130                 135                 140

Asn His Ser Lys Ile Thr Phe Ala Ser Leu Gly Glu Ser Tyr Asn Asn
145                 150                 155                 160

Asp Pro Asn Ile Phe Glu Lys Val Arg Lys Pro Met Thr Gly Met Val
                165                 170                 175

Glu Phe Phe Lys Arg Asp Leu Glu Ser Ala Tyr Arg Val Ser Glu Gln
            180                 185                 190

Ile Ser Pro Ile Lys Leu Asn Trp Ile Tyr Tyr Cys Gly Asp Ala Ala
        195                 200                 205

Gly Arg Lys Lys Asp Phe Ser Asp Ser Asp Ile Lys Phe Ala Glu Asn
    210                 215                 220

Leu His Val Glu Phe Lys Tyr Pro Glu Glu Ile Phe His Gly Gly Ser
225                 230                 235                 240

Ala Ala Pro Gly Ala Ser Ala Ala Pro Gly Ala Gly Ser Gly Ser Gly
                245                 250                 255
```

-continued

Ser Gly Met Asp Asp Ile Ile Thr Gln Val Ser Pro Asp Asn Ala Glu
            260                 265                 270

Ser Ala Pro Ile Leu Gln Glu Gln Gln Gln Gln Asn Ser Gln Tyr
        275                 280                 285

Glu Gly Asn Glu Glu Asp Tyr Gly Asp Ser Leu Ile His Leu Asn Ile
    290                 295                 300

Gln Glu Asn His Tyr Phe Ile Thr Arg Asp Gln Leu Met Ser Leu Pro
305                 310                 315                 320

Glu Ser Leu Leu Leu Cys Leu Phe Pro Ser Gly Val Phe Leu Asp Arg
                325                 330                 335

Cys Gly Gln Val Ile Thr Asn Leu Thr Arg Asp Asp Glu Val Tyr Ile
            340                 345                 350

Val Asn Phe Pro Pro Asp Cys Phe Glu Tyr Ile Met Glu Ile Tyr Thr
        355                 360                 365

Lys Ala His Asp Asp Leu Tyr Asn His Pro Val Glu Lys Phe Phe Asp
370                 375                 380

Arg Pro Ser Ser Ser Phe Val Ser Asn Ala Lys Gly Phe Phe Gly Leu
385                 390                 395                 400

Ser Ser Asn Asn Ser Ile Ser Ser Asn Asn Glu Gln Asp Ile Leu His
                405                 410                 415

Gln Lys Pro Ala Ile Ile Val Leu Arg Glu Asp Leu Asp Tyr Tyr Cys
            420                 425                 430

Val Pro Gln Glu Glu Phe Gln Phe Asp Ser Thr Asn Glu Glu Asn Asn
        435                 440                 445

Glu Asp Leu Leu Arg His Phe Met Ala Gln Val Lys Met Ala Ala Gly
    450                 455                 460

Ser Tyr Leu Thr Ser Lys Thr Ser Ile Phe Gln Gly Leu Tyr Ser Ser
465                 470                 475                 480

Asn Arg Leu Lys Gln Gln Gln Gln Gln Lys Ile Glu Lys Gly Ser
                485                 490                 495

Asn Ser Ser Ser Asn Thr Lys Ser Thr Ser Lys Lys Leu Gly Pro Ala
            500                 505                 510

Glu Gln His Leu Met Asp Met Leu Cys Ser Ser Gly Phe Thr Lys Glu
        515                 520                 525

Thr Cys Trp Gly Asn Arg Thr Gln Glu Thr Gly Lys Thr Val Ile Ser
530                 535                 540

Ser Leu Ser Leu Cys Arg Leu Ala Asn Glu Thr Thr Glu Gly Phe Arg
545                 550                 555                 560

Gln Lys Phe Asn Glu Ala Lys Ala Lys Trp Glu Ala Glu His Lys Pro
                565                 570                 575

Ser Gln Asp Asn Phe Ile Thr Pro Met Gln Ser Asn Ile Ser Ile Asn
            580                 585                 590

Ser Leu Ser Ala Ser Lys Ser Asn Ser Thr Ile Ser Thr Ala Arg Asn
        595                 600                 605

Leu Thr Ser Gly Ser Thr Ala Pro Ala Thr Ala Arg Asp Lys Arg Lys
    610                 615                 620

Ser Arg Leu Ser Lys Leu Ala Asp Asn Val Arg Ser His Ser Ser Ser
625                 630                 635                 640

Arg His Ser Ser Gln Thr Arg Ser Lys Pro Pro Glu Leu Pro Lys Leu
                645                 650                 655

Tyr Asp Leu Val Pro Lys Pro Asn Ile Asn Ala Lys Leu Leu Leu Phe
            660                 665                 670

Trp Arg Lys Pro Ala Arg Lys Cys Trp Trp Gly Glu Glu Asp Ile Glu
            675                 680                 685

Leu Glu Val Glu Val Phe Gly Ser Trp Lys Asp Glu Ser Lys Lys Ile
    690                 695                 700

Ile Glu Leu Ile Leu Pro Thr Asn Val Asp Pro Glu Ala Glu Leu His
705                 710                 715                 720

Lys Ile Ile Val Pro Val Arg Leu His Ile Arg Arg Val Trp Thr Leu
                725                 730                 735

Glu Leu Ser Val Ile Gly Val Gln
            740

<210> SEQ ID NO 108
<211> LENGTH: 751
<212> TYPE: PRT
<213> ORGANISM: Saccharomyces cerevisiae

<400> SEQUENCE: 108

Met Asn Gln Cys Ala Lys Asp Ile Thr His Glu Ala Ser Ser Ile Pro
1               5                   10                  15

Ile Asp Leu Gln Glu Arg Tyr Ser His Trp Lys Lys Asn Thr Lys Leu
            20                  25                  30

Leu Tyr Asp Tyr Leu Asn Thr Asn Ser Thr Lys Trp Pro Ser Leu Thr
        35                  40                  45

Cys Gln Phe Phe Pro Asp Leu Asp Thr Thr Ser Asp Glu His Arg Ile
    50                  55                  60

Leu Leu Ser Ser Phe Thr Ser Ser Gln Lys Pro Glu Asp Glu Thr Ile
65                  70                  75                  80

Tyr Ile Ser Lys Ile Ser Thr Leu Gly His Ile Lys Trp Ser Ser Leu
                85                  90                  95

Asn Asn Phe Asp Met Asp Glu Met Glu Phe Lys Pro Glu Asn Ser Thr
            100                 105                 110

Arg Phe Pro Ser Lys His Leu Val Asn Asp Ile Ser Ile Phe Phe Pro
        115                 120                 125

Asn Gly Glu Cys Asn Arg Ala Arg Tyr Leu Pro Gln Asn Pro Asp Ile
    130                 135                 140

Ile Ala Gly Ala Ser Ser Asp Gly Ala Ile Tyr Ile Phe Asp Arg Thr
145                 150                 155                 160

Lys His Gly Ser Thr Arg Ile Arg Gln Ser Lys Ile Ser His Pro Phe
                165                 170                 175

Glu Thr Lys Leu Phe Gly Ser His Gly Val Ile Gln Asp Val Glu Ala
            180                 185                 190

Met Asp Thr Ser Ser Ala Asp Ile Asn Glu Ala Thr Ser Leu Ala Trp
        195                 200                 205

Asn Leu Gln Gln Glu Ala Leu Leu Ser Ser His Ser Asn Gly Gln
    210                 215                 220

Val Gln Val Trp Asp Ile Lys Gln Tyr Ser His Glu Asn Pro Ile Ile
225                 230                 235                 240

Asp Leu Pro Leu Val Ser Ile Asn Ser Asp Gly Thr Ala Val Asn Asp
                245                 250                 255

Val Thr Trp Met Pro Thr His Asp Ser Leu Phe Ala Ala Cys Thr Glu
            260                 265                 270

Gly Asn Ala Val Ser Leu Leu Asp Leu Arg Thr Lys Lys Glu Lys Leu
        275                 280                 285

Gln Ser Asn Arg Glu Lys His Asp Gly Gly Val Asn Ser Cys Arg Phe
    290                 295                 300

```
Asn Tyr Lys Asn Ser Leu Ile Leu Ala Ser Ala Asp Ser Asn Gly Arg
305                 310                 315                 320

Leu Asn Leu Trp Asp Ile Arg Asn Met Asn Lys Ser Pro Ile Ala Thr
            325                 330                 335

Met Glu His Gly Thr Ser Val Ser Thr Leu Glu Trp Ser Pro Asn Phe
            340                 345                 350

Asp Thr Val Leu Ala Thr Ala Gly Gln Glu Asp Gly Leu Val Lys Leu
            355                 360                 365

Trp Asp Thr Ser Cys Glu Glu Thr Ile Phe Thr His Gly Gly His Met
    370                 375                 380

Leu Gly Val Asn Asp Ile Ser Trp Asp Ala His Asp Pro Trp Leu Met
385                 390                 395                 400

Cys Ser Val Ala Asn Asp Asn Ser Val His Ile Trp Lys Pro Ala Gly
                405                 410                 415

Asn Leu Val Gly His Ser Gly Ser Ala Ala Pro Gly Ala Ser Ala Ala
                420                 425                 430

Pro Gly Ala Gly Ser Gly Ser Gly Met Gln Gly Asn Lys Ser
            435                 440                 445

Thr Ile Arg Glu Tyr Lys Ile Val Val Gly Gly Gly Val Gly
450                 455                 460

Lys Ser Ala Leu Thr Ile Gln Phe Ile Gln Ser Tyr Phe Val Asp Glu
465                 470                 475                 480

Tyr Asp Pro Thr Ile Glu Asp Ser Tyr Arg Lys Gln Val Val Ile Asp
            485                 490                 495

Asp Lys Val Ser Ile Leu Asp Ile Leu Asp Thr Ala Gly Gln Glu Glu
                500                 505                 510

Tyr Ser Ala Met Arg Glu Gln Tyr Met Arg Thr Gly Glu Gly Phe Leu
                515                 520                 525

Leu Val Tyr Ser Val Thr Ser Arg Asn Ser Phe Asp Glu Leu Leu Ser
    530                 535                 540

Tyr Tyr Gln Gln Ile Gln Arg Val Lys Asp Ser Asp Tyr Ile Pro Val
545                 550                 555                 560

Val Val Val Gly Asn Lys Leu Asp Leu Glu Asn Glu Arg Gln Val Ser
                565                 570                 575

Tyr Glu Asp Gly Leu Arg Leu Ala Lys Gln Leu Asn Ala Pro Phe Leu
            580                 585                 590

Glu Thr Ser Ala Lys Gln Ala Ile Asn Val Asp Glu Ala Phe Tyr Ser
            595                 600                 605

Leu Ile Arg Leu Val Arg Asp Asp Gly Gly Lys Tyr Asn Ser Met Asn
    610                 615                 620

Arg Gln Leu Asp Asn Thr Asn Glu Ile Arg Asp Ser Glu Leu Thr Ser
625                 630                 635                 640

Ser Ala Thr Ala Asp Arg Glu Lys Lys Asn Asn Gly Ser Tyr Val Leu
                645                 650                 655

Asp Asn Ser Leu Thr Asn Ala Gly Thr Gly Ser Ser Ser Lys Ser Ala
                660                 665                 670

Val Asn His Asn Gly Glu Thr Thr Lys Arg Thr Asp Glu Lys Asn Tyr
                675                 680                 685

Val Asn Gln Asn Asn Asn Asn Glu Gly Asn Thr Lys Tyr Ser Ser Asn
                690                 695                 700

Gly Asn Gly Asn Arg Ser Asp Ile Ser Arg Gly Asn Gln Asn Asn Ala
705                 710                 715                 720
```

```
Leu Asn Ser Arg Ser Lys Gln Ser Ala Glu Pro Gln Lys Asn Ser Ser
            725                 730                 735

Ala Asn Ala Arg Lys Glu Ser Ser Gly Gly Cys Cys Ile Ile Cys
        740                 745                 750

<210> SEQ ID NO 109
<211> LENGTH: 670
<212> TYPE: PRT
<213> ORGANISM: Saccharomyces cerevisiae

<400> SEQUENCE: 109

Met Asp Ser Tyr Ser Ile Thr Asn Val Lys Tyr Leu Asp Pro Thr Glu
1               5                   10                  15

Leu His Arg Trp Met Gln Glu Gly His Thr Thr Leu Arg Glu Pro
            20                  25                  30

Phe Gln Val Val Asp Val Arg Gly Ser Asp Tyr Met Gly Gly His Ile
        35                  40                  45

Lys Asp Gly Trp His Tyr Ala Tyr Ser Arg Leu Lys Gln Asp Pro Glu
    50                  55                  60

Tyr Leu Arg Glu Leu Lys His Arg Leu Leu Glu Lys Gln Ala Asp Gly
65                  70                  75                  80

Arg Gly Ala Leu Asn Val Ile Phe His Cys Met Leu Ser Gln Gln Arg
                85                  90                  95

Gly Pro Ser Ala Ala Met Leu Leu Leu Arg Ser Leu Asp Thr Ala Glu
            100                 105                 110

Leu Ser Arg Cys Arg Leu Trp Val Leu Arg Gly Gly Phe Ser Arg Trp
        115                 120                 125

Gln Ser Val Tyr Gly Asp Asp Glu Ser Val Thr Ala Gly Tyr Leu Pro
    130                 135                 140

Asp Leu Trp Arg Gly Ser Ala Pro Gly Ala Ser Ala Ala Pro Gly
145                 150                 155                 160

Ala Gly Ser Gly Ser Gly Ser Gly Met Leu Leu Asp Val Asn Thr Asn
                165                 170                 175

His Thr Leu Met His Asp Ala His Val His Glu His Cys Leu Ile Lys
            180                 185                 190

Ser Ile Arg Asp Asp Gly Ala Leu His Ser Trp Ser Asp Ser Ser Lys
        195                 200                 205

Val Phe Tyr Pro Lys Ser Phe Tyr Ala Thr Ala Thr Asn Lys Lys Asn
    210                 215                 220

Asn Lys Leu Ala Ser Ala Ser Met Asn Lys Thr Ala Thr Ser Asn Arg
225                 230                 235                 240

Thr Val Ser Asp Glu Ile Tyr Phe His Ser Thr Lys Pro Gln Phe Asp
                245                 250                 255

Gly Gln Gly Ser Ala Glu Arg Thr Thr Leu Thr Lys Arg Asn Ser
            260                 265                 270

Phe Lys Arg Thr Arg Ile Leu Lys Ala Arg Asp Asp Ser Glu Leu Leu
        275                 280                 285

Asn Glu Asn Arg Ser Ser Leu Met Thr Pro Ser Leu Ser Ser Val Met
    290                 295                 300

Ser Gln Val Arg Lys Thr Asn Ser Ala Lys Thr Leu Ser Gly Glu Cys
305                 310                 315                 320

Pro Ile His Glu Gly His Leu Thr Gln Ser Ile Lys Arg Lys Phe Ser
                325                 330                 335

Glu Glu Ala Gln Ser Asp Cys Ser Ser Leu Ser Ser Ser Lys Leu His
            340                 345                 350
```

Pro Leu Thr Asp Asp Ile Ala Asp Ala Val Asp Leu Gln Thr Pro Ala
            355                 360                 365

Ile Gly Asp Glu Val Leu Ala Glu Pro Val Val Pro Lys Met Lys Ile
    370                 375                 380

Ile Asn Ile Asn Asp Leu Asp Leu Phe Asp Asp Trp Glu Val Lys Asp
385                 390                 395                 400

Leu Val Asp Ile Phe Pro Pro Val Tyr Glu Arg Arg Pro Arg Ser Ser
                405                 410                 415

Ser Ala Leu Ser Leu Val Ser Ala Ser Ser Asp Ala Lys Leu Arg Pro
            420                 425                 430

Thr Ser Val Asp Phe Gln Ile Ile Asp Lys Lys Gly Gly Lys Thr Ser
        435                 440                 445

Arg Arg Lys Ser Arg Ser Lys Ser Thr Thr Glu Asn Met Ile Tyr Glu
    450                 455                 460

Asn Asp Leu Val Glu Leu Glu Gln Trp Pro Ser Ala Ser Pro Ser Pro
465                 470                 475                 480

Glu Thr Asp Gly Ser Ile Ala Ser Ser Glu Leu Leu Pro Asn Lys Arg
                485                 490                 495

Ile Arg Gln Lys Ser Leu Asn Thr Asn Phe Leu Lys Leu Tyr Ser Ile
            500                 505                 510

Glu Thr Ser Cys Lys Arg Lys Ser Ile Leu Pro Glu Val Glu Val Asp
        515                 520                 525

Asp His Leu Leu Lys Gln Leu Thr Tyr Ser Glu Ile Arg Ser Leu Glu
    530                 535                 540

Ile Lys Lys Glu Pro Asn Val Ser Thr Asn Asp Ile Lys Leu Ala Leu
545                 550                 555                 560

Ile Thr Arg Lys Lys Leu Trp Ser Asp Met Val His Glu Thr Arg Asn
                565                 570                 575

Asp Leu Phe Gly Asp Ser Thr Pro Trp Asn Leu His Phe Val Ala Thr
            580                 585                 590

Thr Ser Asn Thr Glu Pro Ser Gln Gly Arg Glu Ser Ala Ser Glu His
        595                 600                 605

Ala Thr Ala Asp Leu Lys Ser Ser Leu Val Arg Val His Ser Asp Val
    610                 615                 620

Lys Pro Trp Phe Asn Asn Gly Gly Thr Met Leu Lys Pro Cys Gly Lys
625                 630                 635                 640

Leu Asn Leu Gly Lys Val Thr Asn Lys Thr Ser Ala Pro Thr Arg Glu
                645                 650                 655

Ile Gln Tyr Val Val Lys Gly Trp Cys Asp Ser Arg Phe Leu
            660                 665                 670

<210> SEQ ID NO 110
<211> LENGTH: 567
<212> TYPE: PRT
<213> ORGANISM: Saccharomyces cerevisiae

<400> SEQUENCE: 110

Met Phe Ser Glu Leu Ile Asn Phe Gln Asn Glu Gly His Glu Cys Gln
1               5                   10                  15

Cys Gln Cys Gly Ser Cys Lys Asn Asn Glu Gln Cys Gln Lys Ser Cys
            20                  25                  30

Ser Cys Pro Thr Gly Cys Asn Ser Asp Asp Lys Cys Pro Cys Gly Asn
        35                  40                  45

Lys Ser Glu Glu Thr Lys Lys Ser Cys Cys Ser Gly Lys Gly Ser Ala

```
            50                  55                  60
Ala Pro Gly Ala Ser Ala Pro Gly Ala Gly Ser Gly Ser
 65                  70                  75                  80
Gly Met Asp Asp Ile Ile Thr Gln Val Ser Pro Asp Asn Ala Glu Ser
                     85                  90                  95
Ala Pro Ile Leu Gln Glu Gln Gln Gln Gln Asn Ser Gln Tyr Glu
                100                 105                 110
Gly Asn Glu Glu Asp Tyr Gly Asp Ser Leu Ile His Leu Asn Ile Gln
                115                 120                 125
Glu Asn His Tyr Phe Ile Thr Arg Asp Gln Leu Met Ser Leu Pro Glu
                130                 135                 140
Ser Leu Leu Leu Cys Leu Phe Pro Ser Gly Val Phe Leu Asp Arg Cys
145                 150                 155                 160
Gly Gln Val Ile Thr Asn Leu Thr Arg Asp Asp Glu Val Tyr Ile Val
                165                 170                 175
Asn Phe Pro Pro Asp Cys Phe Glu Tyr Ile Met Glu Ile Tyr Thr Lys
                180                 185                 190
Ala His Asp Asp Leu Tyr Asn His Pro Val Glu Lys Phe Phe Asp Arg
                195                 200                 205
Pro Ser Ser Ser Phe Val Ser Asn Ala Lys Gly Phe Phe Gly Leu Ser
210                 215                 220
Ser Asn Asn Ser Ile Ser Ser Asn Asn Glu Gln Asp Ile Leu His Gln
225                 230                 235                 240
Lys Pro Ala Ile Ile Val Leu Arg Glu Asp Leu Asp Tyr Tyr Cys Val
                245                 250                 255
Pro Gln Glu Glu Phe Gln Phe Asp Ser Thr Asn Glu Glu Asn Asn Glu
                260                 265                 270
Asp Leu Leu Arg His Phe Met Ala Gln Val Lys Met Ala Ala Gly Ser
                275                 280                 285
Tyr Leu Thr Ser Lys Thr Ser Ile Phe Gln Gly Leu Tyr Ser Ser Asn
                290                 295                 300
Arg Leu Lys Gln Gln Gln Gln Gln Lys Ile Glu Lys Gly Ser Asn
305                 310                 315                 320
Ser Ser Ser Asn Thr Lys Ser Thr Ser Lys Lys Leu Gly Pro Ala Glu
                325                 330                 335
Gln His Leu Met Asp Met Leu Cys Ser Ser Gly Phe Thr Lys Glu Thr
                340                 345                 350
Cys Trp Gly Asn Arg Thr Gln Glu Thr Gly Lys Thr Val Ile Ser Ser
                355                 360                 365
Leu Ser Leu Cys Arg Leu Ala Asn Glu Thr Thr Glu Gly Phe Arg Gln
                370                 375                 380
Lys Phe Asn Glu Ala Lys Ala Lys Trp Glu Ala Glu His Lys Pro Ser
385                 390                 395                 400
Gln Asp Asn Phe Ile Thr Pro Met Gln Ser Asn Ile Ser Ile Asn Ser
                405                 410                 415
Leu Ser Ala Ser Lys Ser Asn Ser Thr Ile Ser Thr Ala Arg Asn Leu
                420                 425                 430
Thr Ser Gly Ser Thr Ala Pro Ala Thr Ala Arg Asp Lys Arg Lys Ser
                435                 440                 445
Arg Leu Ser Lys Leu Ala Asp Asn Val Arg Ser His Ser Ser Ser Arg
                450                 455                 460
His Ser Ser Gln Thr Arg Ser Lys Pro Pro Glu Leu Pro Lys Leu Tyr
465                 470                 475                 480
```

```
Asp Leu Val Pro Lys Pro Asn Ile Asn Ala Lys Leu Leu Phe Trp
                485                 490                 495

Arg Lys Pro Ala Arg Lys Cys Trp Trp Gly Glu Glu Asp Ile Glu Leu
            500                 505                 510

Glu Val Glu Val Phe Gly Ser Trp Lys Asp Glu Ser Lys Lys Ile Ile
        515                 520                 525

Glu Leu Ile Leu Pro Thr Asn Val Asp Pro Glu Ala Glu Leu His Lys
    530                 535                 540

Ile Ile Val Pro Val Arg Leu His Ile Arg Arg Val Trp Thr Leu Glu
545                 550                 555                 560

Leu Ser Val Ile Gly Val Gln
                565

<210> SEQ ID NO 111
<211> LENGTH: 617
<212> TYPE: PRT
<213> ORGANISM: Saccharomyces cerevisiae

<400> SEQUENCE: 111

Met Arg Trp Asp Val Ile Ile Leu Tyr Ala Ile Ser Arg Pro Tyr Ala
1               5                   10                  15

Thr Arg Arg Thr Gly Ser His Thr His Pro Arg Asp Ser Arg Tyr Ile
            20                  25                  30

Ala Ala Asn Gln Arg Arg Pro Pro Ser Ala Cys Arg Val Gly Pro Ser
        35                  40                  45

Pro Ala Lys Gln Arg Lys Asp Ile Pro Ile Phe Glu Leu Leu Asp Thr
    50                  55                  60

Thr Leu Ile Lys Asn Ala Leu Phe Ala Leu Thr Ser Phe Leu Tyr Tyr
65                  70                  75                  80

Arg Thr Asn Ile Leu Thr Cys Pro Phe Leu Asn Phe Leu Tyr Leu Ser
                85                  90                  95

Arg Thr Gly Gln Leu Asp Lys Phe Cys Lys Asp Gln Thr Val Thr Gln
            100                 105                 110

Ile Leu Ala Thr Gly Ser Ala Ala Pro Gly Ala Ser Gly Ser Gly Ser
        115                 120                 125

Gly Ser Gly Met Asp Asp Ile Ile Thr Gln Val Ser Pro Asp Asn Ala
    130                 135                 140

Glu Ser Ala Pro Ile Leu Gln Glu Gln Gln Gln Gln Asn Ser Gln
145                 150                 155                 160

Tyr Glu Gly Asn Glu Glu Asp Tyr Gly Asp Ser Leu Ile His Leu Asn
                165                 170                 175

Ile Gln Glu Asn His Tyr Phe Ile Thr Arg Asp Gln Leu Met Ser Leu
            180                 185                 190

Pro Glu Ser Leu Leu Leu Cys Leu Phe Pro Ser Gly Val Phe Leu Asp
        195                 200                 205

Arg Cys Gly Gln Val Ile Thr Asn Leu Thr Arg Asp Asp Glu Val Tyr
    210                 215                 220

Ile Val Asn Phe Pro Pro Asp Cys Phe Glu Tyr Ile Met Glu Ile Tyr
225                 230                 235                 240

Thr Lys Ala His Asp Asp Leu Tyr Asn His Pro Val Glu Lys Phe Phe
                245                 250                 255

Asp Arg Pro Ser Ser Ser Phe Val Ser Asn Ala Lys Gly Phe Phe Gly
            260                 265                 270

Leu Ser Ser Asn Asn Ser Ile Ser Ser Asn Asn Glu Gln Asp Ile Leu
```

His Gln Lys Pro Ala Ile Ile Val Leu Arg Glu Asp Leu Asp Tyr Tyr
            275                 280                 285
Cys Val Pro Gln Glu Glu Phe Gln Phe Asp Ser Thr Asn Glu Glu Asn
    290                 295                 300
Asn Glu Asp Leu Leu Arg His Phe Met Ala Gln Val Lys Met Ala Ala
305                 310                 315                 320
Gly Ser Tyr Leu Thr Ser Lys Thr Ser Ile Phe Gln Gly Leu Tyr Ser
            325                 330                 335
Ser Asn Arg Leu Lys Gln Gln Gln Gln Gln Lys Ile Glu Lys Gly
    340                 345                 350
Ser Asn Ser Ser Ser Asn Thr Lys Ser Thr Ser Lys Lys Leu Gly Pro
        355                 360                 365
Ala Glu Gln His Leu Met Asp Met Leu Cys Ser Ser Gly Phe Thr Lys
370                 375                 380
Glu Thr Cys Trp Gly Asn Arg Thr Gln Glu Thr Gly Lys Thr Val Ile
385                 390                 395                 400
Ser Ser Leu Ser Leu Cys Arg Leu Ala Asn Glu Thr Thr Glu Gly Phe
            405                 410                 415
Arg Gln Lys Phe Asn Glu Ala Lys Ala Lys Trp Glu Ala Glu His Lys
    420                 425                 430
Pro Ser Gln Asp Asn Phe Ile Thr Pro Met Gln Ser Asn Ile Ser Ile
435                 440                 445
Asn Ser Leu Ser Ala Ser Lys Ser Asn Ser Thr Ile Ser Thr Ala Arg
450                 455                 460
Asn Leu Thr Ser Gly Ser Thr Ala Pro Ala Thr Ala Arg Asp Lys Arg
465                 470                 475                 480
Lys Ser Arg Leu Ser Lys Leu Ala Asp Asn Val Arg Ser His Ser Ser
            485                 490                 495
Ser Arg His Ser Ser Gln Thr Arg Ser Lys Pro Pro Glu Leu Pro Lys
    500                 505                 510
Leu Tyr Asp Leu Val Pro Lys Pro Asn Ile Asn Ala Lys Leu Leu Leu
515                 520                 525
Phe Trp Arg Lys Pro Ala Arg Lys Cys Trp Trp Gly Glu Glu Asp Ile
530                 535                 540
Glu Leu Glu Val Glu Val Phe Gly Ser Trp Lys Asp Glu Ser Lys Lys
545                 550                 555                 560
Ile Ile Glu Leu Ile Leu Pro Thr Asn Val Asp Pro Glu Ala Glu Leu
            565                 570                 575
His Lys Ile Ile Val Pro Val Arg Leu His Ile Arg Arg Val Trp Thr
    580                 585                 590
Leu Glu Leu Ser Val Ile Gly Val Gln
595                 600

<210> SEQ ID NO 112
<211> LENGTH: 562
<212> TYPE: PRT
<213> ORGANISM: Saccharomyces cerevisiae

<400> SEQUENCE: 112

Met Phe Ser Glu Leu Ile Asn Phe Gln Asn Glu Gly His Glu Cys Gln
1               5                   10                  15
Cys Gln Cys Gly Ser Cys Lys Asn Asn Glu Gln Cys Gln Lys Ser Cys
            20                  25                  30

```
Ser Cys Pro Thr Gly Cys Asn Ser Asp Asp Lys Cys Pro Cys Gly Asn
         35                  40                  45

Lys Ser Glu Glu Thr Lys Lys Ser Cys Cys Ser Gly Lys Gly Ser Ala
 50                  55                  60

Ala Pro Gly Ala Ser Gly Ser Gly Ser Gly Met Asp Asp Ile
 65              70                  75                  80

Ile Thr Gln Val Ser Pro Asp Asn Ala Glu Ser Ala Pro Ile Leu Gln
                 85                  90                  95

Glu Gln Gln Gln Gln Asn Ser Gln Tyr Glu Gly Asn Glu Glu Asp
                 100                 105                 110

Tyr Gly Asp Ser Leu Ile His Leu Asn Ile Gln Glu Asn His Tyr Phe
         115                 120                 125

Ile Thr Arg Asp Gln Leu Met Ser Leu Pro Glu Ser Leu Leu Leu Cys
         130                 135                 140

Leu Phe Pro Ser Gly Val Phe Leu Asp Arg Cys Gly Gln Val Ile Thr
145                 150                 155                 160

Asn Leu Thr Arg Asp Asp Glu Val Tyr Ile Val Asn Phe Pro Pro Asp
                 165                 170                 175

Cys Phe Glu Tyr Ile Met Glu Ile Tyr Thr Lys Ala His Asp Asp Leu
                 180                 185                 190

Tyr Asn His Pro Val Glu Lys Phe Phe Asp Arg Pro Ser Ser Ser Phe
         195                 200                 205

Val Ser Asn Ala Lys Gly Phe Phe Gly Leu Ser Ser Asn Asn Ser Ile
         210                 215                 220

Ser Ser Asn Asn Glu Gln Asp Ile Leu His Gln Lys Pro Ala Ile Ile
225                 230                 235                 240

Val Leu Arg Glu Asp Leu Asp Tyr Tyr Cys Val Pro Gln Glu Glu Phe
                 245                 250                 255

Gln Phe Asp Ser Thr Asn Glu Glu Asn Asn Glu Asp Leu Leu Arg His
                 260                 265                 270

Phe Met Ala Gln Val Lys Met Ala Ala Gly Ser Tyr Leu Thr Ser Lys
         275                 280                 285

Thr Ser Ile Phe Gln Gly Leu Tyr Ser Ser Asn Arg Leu Lys Gln Gln
         290                 295                 300

Gln Gln Gln Gln Lys Ile Glu Lys Gly Ser Asn Ser Ser Asn Thr
305                 310                 315                 320

Lys Ser Thr Ser Lys Lys Leu Gly Pro Ala Glu Gln His Leu Met Asp
                 325                 330                 335

Met Leu Cys Ser Ser Gly Phe Thr Lys Glu Thr Cys Trp Gly Asn Arg
         340                 345                 350

Thr Gln Glu Thr Gly Lys Thr Val Ile Ser Ser Leu Ser Leu Cys Arg
         355                 360                 365

Leu Ala Asn Glu Thr Thr Glu Gly Phe Arg Gln Lys Phe Asn Glu Ala
         370                 375                 380

Lys Ala Lys Trp Glu Ala Glu His Lys Pro Ser Gln Asp Asn Phe Ile
385                 390                 395                 400

Thr Pro Met Gln Ser Asn Ile Ser Ile Asn Ser Leu Ser Ala Ser Lys
                 405                 410                 415

Ser Asn Ser Thr Ile Ser Thr Ala Arg Asn Leu Thr Ser Gly Ser Thr
                 420                 425                 430

Ala Pro Ala Thr Ala Arg Asp Lys Arg Lys Ser Arg Leu Ser Lys Leu
         435                 440                 445

Ala Asp Asn Val Arg Ser His Ser Ser Ser Arg His Ser Ser Gln Thr
```

```
            450                 455                 460
Arg Ser Lys Pro Pro Glu Leu Pro Lys Leu Tyr Asp Leu Val Pro Lys
465                 470                 475                 480

Pro Asn Ile Asn Ala Lys Leu Leu Phe Trp Arg Lys Pro Ala Arg
                485                 490                 495

Lys Cys Trp Trp Gly Glu Glu Asp Ile Glu Leu Glu Val Glu Val Phe
                500                 505                 510

Gly Ser Trp Lys Asp Glu Ser Lys Lys Ile Ile Glu Leu Ile Leu Pro
            515                 520                 525

Thr Asn Val Asp Pro Glu Ala Glu Leu His Lys Ile Ile Val Pro Val
        530                 535                 540

Arg Leu His Ile Arg Arg Val Trp Thr Leu Glu Leu Ser Val Ile Gly
545                 550                 555                 560

Val Gln

<210> SEQ ID NO 113
<211> LENGTH: 659
<212> TYPE: PRT
<213> ORGANISM: Saccharomyces cerevisiae

<400> SEQUENCE: 113

Met Val Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Val Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Ile Met Lys Gln Phe
    130                 135                 140

Ile Asp Glu Arg Pro Gln Asp Trp Phe Glu Asp Ile Gly Glu Gly Ser
145                 150                 155                 160

Ala Ala Pro Gly Ala Ser Gly Ser Gly Ser Gly Met Asp Asp
                165                 170                 175

Ile Ile Thr Gln Val Ser Pro Asp Asn Ala Glu Ser Ala Pro Ile Leu
            180                 185                 190

Gln Glu Gln Gln Gln Gln Asn Ser Gln Tyr Glu Gly Asn Glu Glu
        195                 200                 205

Asp Tyr Gly Asp Ser Leu Ile His Leu Asn Ile Gln Glu Asn His Tyr
    210                 215                 220

Phe Ile Thr Arg Asp Gln Leu Met Ser Leu Pro Glu Ser Leu Leu Leu
225                 230                 235                 240

Cys Leu Phe Pro Ser Gly Val Phe Leu Asp Arg Cys Gly Gln Val Ile
                245                 250                 255

Thr Asn Leu Thr Arg Asp Asp Glu Val Tyr Ile Val Asn Phe Pro Pro
```

```
                260                 265                 270
Asp Cys Phe Glu Tyr Ile Met Glu Ile Tyr Thr Lys Ala His Asp Asp
            275                 280                 285
Leu Tyr Asn His Pro Val Glu Lys Phe Phe Asp Arg Pro Ser Ser Ser
            290                 295                 300
Phe Val Ser Asn Ala Lys Gly Phe Phe Gly Leu Ser Ser Asn Asn Ser
305                 310                 315                 320
Ile Ser Ser Asn Asn Glu Gln Asp Ile Leu His Gln Lys Pro Ala Ile
                325                 330                 335
Ile Val Leu Arg Glu Asp Leu Asp Tyr Tyr Cys Val Pro Gln Glu Glu
                340                 345                 350
Phe Gln Phe Asp Ser Thr Asn Glu Glu Asn Asn Glu Asp Leu Leu Arg
                355                 360                 365
His Phe Met Ala Gln Val Lys Met Ala Ala Gly Ser Tyr Leu Thr Ser
            370                 375                 380
Lys Thr Ser Ile Phe Gln Gly Leu Tyr Ser Ser Asn Arg Leu Lys Gln
385                 390                 395                 400
Gln Gln Gln Gln Gln Lys Ile Glu Lys Gly Ser Asn Ser Ser Ser Asn
                405                 410                 415
Thr Lys Ser Thr Ser Lys Lys Leu Gly Pro Ala Glu Gln His Leu Met
            420                 425                 430
Asp Met Leu Cys Ser Ser Gly Phe Thr Lys Glu Thr Cys Trp Gly Asn
            435                 440                 445
Arg Thr Gln Glu Thr Gly Lys Thr Val Ile Ser Ser Leu Ser Leu Cys
450                 455                 460
Arg Leu Ala Asn Glu Thr Thr Glu Gly Phe Arg Gln Lys Phe Asn Glu
465                 470                 475                 480
Ala Lys Ala Lys Trp Glu Ala Glu His Lys Pro Ser Gln Asp Asn Phe
            485                 490                 495
Ile Thr Pro Met Gln Ser Asn Ile Ser Ile Asn Ser Leu Ser Ala Ser
            500                 505                 510
Lys Ser Asn Ser Thr Ile Ser Thr Ala Arg Asn Leu Thr Ser Gly Ser
            515                 520                 525
Thr Ala Pro Ala Thr Ala Arg Asp Lys Arg Lys Ser Arg Leu Ser Lys
            530                 535                 540
Leu Ala Asp Asn Val Arg Ser His Ser Ser Arg His Ser Ser Ser Gln
545                 550                 555                 560
Thr Arg Ser Lys Pro Pro Glu Leu Pro Lys Leu Tyr Asp Leu Val Pro
                565                 570                 575
Lys Pro Asn Ile Asn Ala Lys Leu Leu Leu Phe Trp Arg Lys Pro Ala
                580                 585                 590
Arg Lys Cys Trp Trp Gly Glu Glu Asp Ile Glu Leu Gly Val Glu Val
            595                 600                 605
Phe Gly Ser Trp Lys Asp Glu Ser Lys Lys Ile Ile Glu Leu Ile Leu
            610                 615                 620
Pro Thr Asn Val Asp Pro Glu Ala Glu Leu His Lys Ile Ile Val Pro
625                 630                 635                 640
Val Arg Leu His Ile Arg Arg Val Trp Thr Leu Glu Leu Ser Val Ile
                645                 650                 655
Gly Val Gln

<210> SEQ ID NO 114
<211> LENGTH: 564
```

```
<212> TYPE: PRT
<213> ORGANISM: Saccharomyces cerevisiae

<400> SEQUENCE: 114

Met Ser Ser Asn Tyr Ala Thr Pro Leu Asp Asp Glu Val Phe Pro Leu
1               5                   10                  15

Ser Phe Ala Asn Tyr Gln Phe Thr Glu His Val Ser Leu Gly Glu His
            20                  25                  30

Tyr Ser Leu Asn Thr Ser Glu Asp Ala Lys Tyr Asn Asn Leu Asn Gly
        35                  40                  45

Pro Phe Val Val Pro Arg Asp Thr Gly Lys Phe Asp Leu Asn Thr Ser
    50                  55                  60

Ser Ala Ser Asp Glu Thr Val Phe Ser Leu Asp Asn Pro Gln Glu Asn
65                  70                  75                  80

Asn Tyr Lys His Gln Ala Met Asn Asn Val Gln Asp Cys Arg Met Ala
                85                  90                  95

Val Ala Ala Lys Thr Thr Gln Ser Cys Asp Lys Leu Thr Asp Leu Tyr
            100                 105                 110

Ala Asn Ala Ala Gln Gln Asn Tyr Arg Leu Trp Leu Ser Ser Phe Gly
        115                 120                 125

Ser Ala Pro Gly Ala Ser Gly Ser Gly Ser Gly Met Asn
    130                 135                 140

Gln Cys Ala Lys Asp Ile Thr His Glu Ala Ser Ser Ile Pro Ile Asp
145                 150                 155                 160

Leu Gln Glu Arg Tyr Ser His Trp Lys Lys Asn Thr Lys Leu Leu Tyr
                165                 170                 175

Asp Tyr Leu Asn Thr Asn Ser Thr Lys Trp Pro Ser Leu Thr Cys Gln
            180                 185                 190

Phe Phe Pro Asp Leu Asp Thr Thr Ser Asp Glu His Arg Ile Leu Leu
        195                 200                 205

Ser Ser Phe Thr Ser Ser Gln Lys Pro Glu Asp Glu Thr Ile Tyr Ile
    210                 215                 220

Ser Lys Ile Ser Thr Leu Gly His Ile Lys Trp Ser Ser Leu Asn Asn
225                 230                 235                 240

Phe Asp Met Asp Glu Met Glu Phe Lys Pro Glu Asn Ser Thr Arg Phe
                245                 250                 255

Pro Ser Lys His Leu Val Asn Asp Ile Ser Ile Phe Phe Pro Asn Gly
            260                 265                 270

Glu Cys Asn Arg Ala Arg Tyr Leu Pro Gln Asn Pro Asp Ile Ile Ala
        275                 280                 285

Gly Ala Ser Ser Asp Gly Ala Ile Tyr Ile Phe Asp Arg Thr Lys His
    290                 295                 300

Gly Ser Thr Arg Ile Arg Gln Ser Lys Ile Ser His Pro Phe Glu Thr
305                 310                 315                 320

Lys Leu Phe Gly Ser His Gly Val Ile Gln Asp Val Glu Ala Met Asp
                325                 330                 335

Thr Ser Ser Ala Asp Ile Asn Glu Ala Thr Ser Leu Ala Trp Asn Leu
            340                 345                 350

Gln Gln Glu Ala Leu Leu Leu Ser Ser His Ser Asn Gly Gln Val Gln
        355                 360                 365

Val Trp Asp Ile Lys Gln Tyr Ser His Glu Asn Pro Ile Ile Asp Leu
    370                 375                 380

Pro Leu Val Ser Ile Asn Ser Asp Gly Thr Ala Val Asn Asp Val Thr
385                 390                 395                 400
```

```
Trp Met Pro Thr His Asp Ser Leu Phe Ala Ala Cys Thr Glu Gly Asn
            405                 410                 415

Ala Val Ser Leu Leu Asp Leu Arg Thr Lys Lys Glu Lys Leu Gln Ser
            420                 425                 430

Asn Arg Glu Lys His Asp Gly Gly Val Asn Ser Cys Arg Phe Asn Tyr
            435                 440                 445

Lys Asn Ser Leu Ile Leu Ala Ser Ala Asp Ser Asn Gly Arg Leu Asn
            450                 455                 460

Leu Trp Asp Ile Arg Asn Met Asn Lys Ser Pro Ile Ala Thr Met Glu
465                 470                 475                 480

His Gly Thr Ser Val Ser Thr Leu Glu Trp Ser Pro Asn Phe Asp Thr
            485                 490                 495

Val Leu Ala Thr Ala Gly Gln Glu Asp Gly Leu Val Lys Leu Trp Asp
            500                 505                 510

Thr Ser Cys Glu Glu Thr Ile Phe Thr His Gly Gly His Met Leu Gly
            515                 520                 525

Val Asn Asp Ile Ser Trp Asp Ala His Asp Pro Trp Leu Met Cys Ser
            530                 535                 540

Val Ala Asn Asp Asn Ser Val His Ile Trp Lys Pro Ala Gly Asn Leu
545                 550                 555                 560

Val Gly His Ser

<210> SEQ ID NO 115
<211> LENGTH: 619
<212> TYPE: PRT
<213> ORGANISM: Saccharomyces cerevisiae

<400> SEQUENCE: 115

Met Gln His Thr Leu Thr Arg Thr Ala Ser Leu Pro Glu Arg Ser Ser
1               5                   10                  15

Ser Ala His Ser Ala Ala Thr Ala Leu Pro Ala Leu Arg Arg Pro Pro
            20                  25                  30

Asp Ser Cys Glu Thr Leu Val Pro Leu Leu Cys Ile Phe Trp Phe Val
            35                  40                  45

Phe Val Ser Met Ser Pro Leu Pro Pro Ala Arg Ala Asn Lys Ser Asp
    50                  55                  60

Asn Lys Gly Leu Ile Ser Ala Asp Arg Asn Asn Lys Ala Thr Leu Leu
65                  70                  75                  80

Leu Thr Ile Pro Arg Cys Thr Ser Lys Ser Tyr Thr Asn Asp Leu Ser
            85                  90                  95

Pro Leu Lys Met Thr Leu Leu Ser Ala Gly Lys His Pro Arg Pro Phe
            100                 105                 110

Arg Gln Glu His Arg Cys Gly Ser Ala Ala Pro Gly Ala Ser Gly Ser
            115                 120                 125

Gly Ser Gly Ser Gly Met Asp Asp Ile Ile Thr Gln Val Ser Pro Asp
            130                 135                 140

Asn Ala Glu Ser Ala Pro Ile Leu Gln Glu Gln Gln Gln Gln Gln Asn
145                 150                 155                 160

Ser Gln Tyr Glu Gly Asn Glu Glu Asp Tyr Gly Asp Ser Leu Ile His
            165                 170                 175

Leu Asn Ile Gln Glu Asn His Tyr Phe Ile Thr Arg Asp Gln Leu Met
            180                 185                 190

Ser Leu Pro Glu Ser Leu Leu Leu Cys Leu Phe Pro Ser Gly Val Phe
            195                 200                 205
```

```
Leu Asp Arg Cys Gly Gln Val Ile Thr Asn Leu Thr Arg Asp Asp Glu
    210                 215                 220

Val Tyr Ile Val Asn Phe Pro Pro Asp Cys Phe Glu Tyr Ile Met Glu
225                 230                 235                 240

Ile Tyr Thr Lys Ala His Asp Asp Leu Tyr Asn His Pro Val Glu Lys
                245                 250                 255

Phe Phe Asp Arg Pro Ser Ser Ser Phe Val Ser Asn Ala Lys Gly Phe
            260                 265                 270

Phe Gly Leu Ser Ser Asn Asn Ser Ile Ser Ser Asn Asn Glu Gln Asp
        275                 280                 285

Ile Leu His Gln Lys Pro Ala Ile Ile Val Leu Arg Glu Asp Leu Asp
    290                 295                 300

Tyr Tyr Cys Val Pro Gln Glu Glu Phe Gln Phe Asp Ser Thr Asn Glu
305                 310                 315                 320

Glu Asn Asn Glu Asp Leu Leu Arg His Phe Met Ala Gln Val Lys Met
                325                 330                 335

Ala Ala Gly Ser Tyr Leu Thr Ser Lys Thr Ser Ile Phe Gln Gly Leu
            340                 345                 350

Tyr Ser Ser Asn Arg Leu Lys Gln Gln Gln Gln Gln Lys Ile Glu
        355                 360                 365

Lys Gly Ser Asn Ser Ser Ser Asn Thr Lys Ser Thr Ser Lys Lys Leu
    370                 375                 380

Gly Pro Ala Glu Gln His Leu Met Asp Met Leu Cys Ser Ser Gly Phe
385                 390                 395                 400

Thr Lys Glu Thr Cys Trp Gly Asn Arg Thr Gln Glu Thr Gly Lys Thr
                405                 410                 415

Val Ile Ser Ser Leu Ser Leu Cys Arg Leu Ala Asn Glu Thr Thr Glu
            420                 425                 430

Gly Phe Arg Gln Lys Phe Asn Glu Ala Lys Ala Lys Trp Glu Ala Glu
        435                 440                 445

His Lys Pro Ser Gln Asp Asn Phe Ile Thr Pro Met Gln Ser Asn Ile
    450                 455                 460

Ser Ile Asn Ser Leu Ser Ala Ser Lys Ser Asn Ser Thr Ile Ser Thr
465                 470                 475                 480

Ala Arg Asn Leu Thr Ser Gly Ser Thr Ala Pro Ala Thr Ala Arg Asp
                485                 490                 495

Lys Arg Lys Ser Arg Leu Ser Lys Leu Ala Asp Asn Val Arg Ser His
            500                 505                 510

Ser Ser Ser Arg His Ser Ser Gln Thr Arg Ser Lys Pro Pro Glu Leu
        515                 520                 525

Pro Lys Leu Tyr Asp Leu Val Pro Lys Pro Asn Ile Asn Ala Lys Leu
    530                 535                 540

Leu Leu Phe Trp Arg Lys Pro Ala Arg Lys Cys Trp Trp Gly Glu Glu
545                 550                 555                 560

Asp Ile Glu Leu Glu Val Glu Val Phe Gly Ser Trp Lys Asp Glu Ser
                565                 570                 575

Lys Lys Ile Ile Glu Leu Ile Leu Pro Thr Asn Val Asp Pro Glu Ala
            580                 585                 590

Glu Leu His Lys Ile Ile Val Pro Val Arg Leu His Ile Arg Arg Val
        595                 600                 605

Trp Thr Leu Glu Leu Ser Val Ile Gly Val Gln
    610                 615
```

```
<210> SEQ ID NO 116
<211> LENGTH: 628
<212> TYPE: PRT
<213> ORGANISM: Saccharomyces cerevisiae

<400> SEQUENCE: 116

Met Ser Ser Asn Tyr Ala Thr Pro Leu Asp Asp Glu Val Phe Pro Leu
1               5                   10                  15

Ser Phe Ala Asn Tyr Gln Phe Thr Glu His Val Ser Leu Gly Glu His
            20                  25                  30

Tyr Ser Leu Asn Thr Ser Glu Asp Ala Lys Tyr Asn Asn Leu Asn Gly
        35                  40                  45

Pro Phe Val Val Pro Arg Asp Thr Gly Lys Phe Asp Leu Asn Thr Ser
    50                  55                  60

Ser Ala Ser Asp Glu Thr Val Phe Ser Leu Asp Asn Pro Gln Glu Asn
65                  70                  75                  80

Asn Tyr Lys His Gln Ala Met Asn Asn Val Gln Asp Cys Arg Met Ala
                85                  90                  95

Val Ala Ala Lys Thr Thr Gln Ser Cys Asp Lys Leu Thr Asp Leu Tyr
            100                 105                 110

Ala Asn Ala Ala Gln Gln Asn Tyr Arg Leu Trp Leu Ser Ser Phe Gly
        115                 120                 125

Ser Ala Ala Pro Gly Ala Ser Gly Ser Gly Ser Gly Met Asp
    130                 135                 140

Asp Ile Ile Thr Gln Val Ser Pro Asp Asn Ala Glu Ser Ala Pro Ile
145                 150                 155                 160

Leu Gln Glu Gln Gln Gln Gln Asn Ser Gln Tyr Glu Gly Asn Glu
                165                 170                 175

Glu Asp Tyr Gly Asp Ser Leu Ile His Leu Asn Ile Gln Glu Asn His
            180                 185                 190

Tyr Phe Ile Thr Arg Asp Gln Leu Met Ser Leu Pro Glu Ser Leu Leu
        195                 200                 205

Leu Cys Leu Phe Pro Ser Gly Val Phe Leu Asp Arg Cys Gly Gln Val
    210                 215                 220

Ile Thr Asn Leu Thr Arg Asp Asp Glu Val Tyr Ile Val Asn Phe Pro
225                 230                 235                 240

Pro Asp Cys Phe Glu Tyr Ile Met Glu Ile Tyr Thr Lys Ala His Asp
                245                 250                 255

Asp Leu Tyr Asn His Pro Val Glu Lys Phe Phe Asp Arg Pro Ser Ser
            260                 265                 270

Ser Phe Val Ser Asn Ala Lys Gly Phe Phe Gly Leu Ser Ser Asn Asn
        275                 280                 285

Ser Ile Ser Ser Asn Asn Glu Gln Asp Ile Leu His Gln Lys Pro Ala
    290                 295                 300

Ile Ile Val Leu Arg Glu Asp Leu Asp Tyr Tyr Cys Val Pro Gln Glu
305                 310                 315                 320

Glu Phe Gln Phe Asp Ser Thr Asn Glu Glu Asn Asn Glu Asp Leu Leu
                325                 330                 335

Arg His Phe Met Ala Gln Val Lys Met Ala Ala Gly Ser Tyr Leu Thr
            340                 345                 350

Ser Lys Thr Ser Ile Phe Gln Gly Leu Tyr Ser Ser Asn Arg Leu Lys
        355                 360                 365

Gln Gln Gln Gln Gln Gln Lys Ile Glu Lys Gly Ser Asn Ser Ser Ser
    370                 375                 380
```

```
Asn Thr Lys Ser Thr Ser Lys Lys Leu Gly Pro Ala Glu Gln His Leu
385                 390                 395                 400

Met Asp Met Leu Cys Ser Ser Gly Phe Thr Lys Glu Thr Cys Trp Gly
            405                 410                 415

Asn Arg Thr Gln Glu Thr Gly Lys Thr Val Ile Ser Ser Leu Ser Leu
        420                 425                 430

Cys Arg Leu Ala Asn Glu Thr Thr Glu Gly Phe Arg Gln Lys Phe Asn
    435                 440                 445

Glu Ala Lys Ala Lys Trp Glu Ala Glu His Lys Pro Ser Gln Asp Asn
450                 455                 460

Phe Ile Thr Pro Met Gln Ser Asn Ile Ser Ile Asn Ser Leu Ser Ala
465                 470                 475                 480

Ser Lys Ser Asn Ser Thr Ile Ser Thr Ala Arg Asn Leu Thr Ser Gly
                485                 490                 495

Ser Thr Ala Pro Ala Thr Ala Arg Asp Lys Arg Lys Ser Arg Leu Ser
            500                 505                 510

Lys Leu Ala Asp Asn Val Arg Ser His Ser Ser Ser Arg His Ser Ser
        515                 520                 525

Gln Thr Arg Ser Lys Pro Pro Glu Leu Pro Lys Leu Tyr Asp Leu Val
    530                 535                 540

Pro Lys Pro Asn Ile Asn Ala Lys Leu Leu Phe Trp Arg Lys Pro
545                 550                 555                 560

Ala Arg Lys Cys Trp Trp Gly Glu Glu Asp Ile Glu Leu Glu Val Glu
                565                 570                 575

Val Phe Gly Ser Trp Lys Asp Glu Ser Lys Lys Ile Ile Glu Leu Ile
            580                 585                 590

Leu Pro Thr Asn Val Asp Pro Glu Ala Glu Leu His Lys Ile Ile Val
        595                 600                 605

Pro Val Arg Leu His Ile Arg Arg Val Trp Thr Leu Glu Leu Ser Val
610                 615                 620

Ile Gly Val Gln
625

<210> SEQ ID NO 117
<211> LENGTH: 574
<212> TYPE: PRT
<213> ORGANISM: Saccharomyces cerevisiae

<400> SEQUENCE: 117

Met Ala Glu Ile Lys His Tyr Gln Phe Asn Val Val Met Thr Cys Ser
1               5                   10                  15

Gly Cys Ser Gly Ala Val Asn Lys Val Leu Thr Lys Leu Glu Pro Asp
            20                  25                  30

Val Ser Lys Ile Asp Ile Ser Leu Glu Lys Gln Leu Val Asp Val Tyr
        35                  40                  45

Thr Thr Leu Pro Tyr Asp Phe Ile Leu Glu Lys Ile Lys Lys Thr Gly
    50                  55                  60

Lys Glu Val Arg Ser Gly Lys Gln Leu Gly Ser Ala Ala Pro Gly Ala
65                  70                  75                  80

Ser Gly Ser Gly Ser Gly Ser Gly Met Asp Asp Ile Ile Thr Gln Val
                85                  90                  95

Ser Pro Asp Asn Ala Glu Ser Ala Pro Ile Leu Gln Glu Gln Gln Gln
            100                 105                 110

Gln Gln Asn Ser Gln Tyr Glu Gly Asn Glu Glu Asp Tyr Gly Asp Ser
```

```
            115                 120                 125
Leu Ile His Leu Asn Ile Gln Glu Asn His Tyr Phe Ile Thr Arg Asp
            130                 135                 140
Gln Leu Met Ser Leu Pro Glu Ser Leu Leu Cys Leu Phe Pro Ser
145                 150                 155                 160
Gly Val Phe Leu Asp Arg Cys Gly Gln Val Ile Thr Asn Leu Thr Arg
                165                 170                 175
Asp Asp Glu Val Tyr Ile Val Asn Phe Pro Pro Asp Cys Phe Glu Tyr
                180                 185                 190
Ile Met Glu Ile Tyr Thr Lys Ala His Asp Asp Leu Tyr Asn His Pro
            195                 200                 205
Val Glu Lys Phe Phe Asp Arg Pro Ser Ser Ser Phe Val Ser Asn Ala
            210                 215                 220
Lys Gly Phe Phe Gly Leu Ser Ser Asn Ser Ile Ser Ser Asn Asn
225                 230                 235                 240
Glu Gln Asp Ile Leu His Gln Lys Pro Ala Ile Ile Val Leu Arg Glu
                245                 250                 255
Asp Leu Asp Tyr Tyr Cys Val Pro Gln Glu Glu Phe Gln Phe Asp Ser
                260                 265                 270
Thr Asn Glu Glu Asn Asn Glu Asp Leu Leu Arg His Phe Met Ala Gln
            275                 280                 285
Val Lys Met Ala Ala Gly Ser Tyr Leu Thr Ser Lys Thr Ser Ile Phe
            290                 295                 300
Gln Gly Leu Tyr Ser Ser Asn Arg Leu Lys Gln Gln Gln Gln Gln
305                 310                 315                 320
Lys Ile Glu Lys Gly Ser Asn Ser Ser Ser Asn Thr Lys Ser Thr Ser
                325                 330                 335
Lys Lys Leu Gly Pro Ala Glu Gln His Leu Met Asp Met Leu Cys Ser
                340                 345                 350
Ser Gly Phe Thr Lys Glu Thr Cys Trp Gly Asn Arg Thr Gln Glu Thr
            355                 360                 365
Gly Lys Thr Val Ile Ser Ser Leu Ser Leu Cys Arg Leu Ala Asn Glu
            370                 375                 380
Thr Thr Glu Gly Phe Arg Gln Lys Phe Asn Glu Ala Lys Ala Lys Trp
385                 390                 395                 400
Glu Ala Glu His Lys Pro Ser Gln Asp Asn Phe Ile Thr Pro Met Gln
                405                 410                 415
Ser Asn Ile Ser Ile Asn Ser Leu Ser Ala Ser Lys Ser Asn Ser Thr
                420                 425                 430
Ile Ser Thr Ala Arg Asn Leu Thr Ser Gly Ser Thr Ala Pro Ala Thr
            435                 440                 445
Ala Arg Asp Lys Arg Lys Ser Arg Leu Ser Lys Leu Ala Asp Asn Val
            450                 455                 460
Arg Ser His Ser Ser Arg His Ser Ser Gln Thr Arg Ser Lys Pro
465                 470                 475                 480
Pro Glu Leu Pro Lys Leu Tyr Asp Leu Val Pro Lys Pro Asn Ile Asn
                485                 490                 495
Ala Lys Leu Leu Leu Phe Trp Arg Lys Pro Ala Arg Lys Cys Trp Trp
            500                 505                 510
Gly Glu Glu Asp Ile Glu Leu Glu Val Glu Val Phe Gly Ser Trp Lys
            515                 520                 525
Asp Glu Ser Lys Lys Ile Ile Glu Leu Ile Leu Pro Thr Asn Val Asp
            530                 535                 540
```

```
Pro Glu Ala Glu Leu His Lys Ile Ile Val Pro Val Arg Leu His Ile
545                 550                 555                 560

Arg Arg Val Trp Thr Leu Glu Leu Ser Val Ile Gly Val Gln
                565                 570
```

<210> SEQ ID NO 118
<211> LENGTH: 920
<212> TYPE: PRT
<213> ORGANISM: Saccharomyces cerevisiae

<400> SEQUENCE: 118

```
Met Ser Glu Ala Gln Glu Thr His Val Glu Gln Leu Pro Glu Ser Val
1               5                   10                  15

Val Asp Ala Pro Val Glu Glu Gln His Gln Glu Pro Pro Gln Ala Pro
                20                  25                  30

Asp Ala Pro Gln Glu Pro Gln Val Pro Gln Glu Ser Ala Pro Gln Glu
            35                  40                  45

Ser Ala Pro Gln Glu Pro Pro Ala Pro Gln Glu Gln Asn Asp Val Pro
    50                  55                  60

Pro Pro Ser Asn Ala Pro Ile Tyr Glu Gly Glu Glu Ser His Ser Val
65                  70                  75                  80

Gln Asp Tyr Gln Glu Ala His Gln His His Gln Pro Pro Glu Pro Gln
                85                  90                  95

Pro Tyr Tyr Pro Pro Pro Pro Gly Glu His Met His Gly Arg Pro
                100                 105                 110

Pro Met His His Arg Gln Glu Gly Glu Leu Ser Asn Thr Arg Leu Phe
            115                 120                 125

Val Arg Pro Phe Pro Leu Asp Val Gln Glu Ser Glu Leu Asn Glu Ile
    130                 135                 140

Phe Gly Pro Phe Gly Pro Met Lys Glu Val Lys Ile Leu Asn Gly Phe
145                 150                 155                 160

Ala Phe Val Glu Phe Glu Glu Ala Glu Ser Ala Ala Lys Ala Ile Glu
                165                 170                 175

Glu Val His Gly Lys Ser Phe Ala Asn Gln Pro Leu Glu Val Val Tyr
                180                 185                 190

Ser Lys Leu Pro Ala Lys Arg Tyr Arg Ile Thr Met Lys Asn Leu Pro
            195                 200                 205

Glu Gly Cys Ser Trp Gln Asp Leu Lys Asp Leu Ala Arg Glu Asn Ser
    210                 215                 220

Leu Glu Thr Thr Phe Ser Ser Val Asn Thr Arg Asp Phe Asp Gly Thr
225                 230                 235                 240

Gly Ala Leu Glu Phe Pro Ser Glu Glu Ile Leu Val Glu Ala Leu Glu
                245                 250                 255

Arg Leu Asn Asn Ile Glu Phe Arg Gly Ser Val Ile Thr Val Glu Arg
                260                 265                 270

Asp Asp Asn Pro Pro Ile Arg Arg Ser Asn Arg Gly Gly Phe Arg
            275                 280                 285

Gly Arg Gly Gly Phe Arg Gly Gly Phe Arg Gly Gly Phe Arg Gly Gly
    290                 295                 300

Phe Ser Arg Gly Gly Phe Gly Gly Pro Arg Gly Gly Phe Gly Gly Pro
305                 310                 315                 320

Arg Gly Gly Tyr Gly Gly Tyr Ser Arg Gly Gly Tyr Gly Gly Tyr Ser
                325                 330                 335

Arg Gly Gly Tyr Gly Gly Ser Arg Gly Gly Tyr Asp Ser Pro Arg Gly
```

```
                340                 345                  350
    Gly Tyr Asp Ser Pro Arg Gly Tyr Ser Arg Gly Tyr Gly Gly
                355                  360                365

Pro Arg Asn Asp Tyr Gly Pro Pro Arg Gly Ser Tyr Gly Gly Ser Arg
                370                 375                 380

Gly Gly Tyr Asp Gly Pro Arg Gly Asp Tyr Gly Pro Pro Arg Asp Ala
    385                 390                 395                 400

Tyr Arg Thr Arg Asp Ala Pro Arg Glu Arg Ser Pro Thr Arg Gly Ser
                    405                 410                 415

Ala Ala Pro Gly Ala Ser Ala Ala Pro Gly Ala Gly Ser Gly Ser Gly
                420                 425                 430

Ser Gly Met Asp Asp Ile Ile Thr Gln Val Ser Pro Asp Asn Ala Glu
                435                 440                 445

Ser Ala Pro Ile Leu Gln Glu Gln Gln Gln Gln Asn Ser Gln Tyr
                450                 455                 460

Glu Gly Asn Glu Glu Asp Tyr Gly Asp Ser Leu Ile His Leu Asn Ile
    465                 470                 475                 480

Gln Glu Asn His Tyr Phe Ile Thr Arg Asp Gln Leu Met Ser Leu Pro
                    485                 490                 495

Glu Ser Leu Leu Leu Cys Leu Phe Pro Ser Gly Val Phe Leu Asp Arg
                500                 505                 510

Cys Gly Gln Val Ile Thr Asn Leu Thr Arg Asp Asp Glu Val Tyr Ile
                515                 520                 525

Val Asn Phe Pro Pro Asp Cys Phe Glu Tyr Ile Met Glu Ile Tyr Thr
    530                 535                 540

Lys Ala His Asp Asp Leu Tyr Asn His Pro Val Glu Lys Phe Phe Asp
    545                 550                 555                 560

Arg Pro Ser Ser Ser Phe Val Ser Asn Ala Lys Gly Phe Phe Gly Leu
                    565                 570                 575

Ser Ser Asn Asn Ser Ile Ser Ser Asn Asn Glu Gln Asp Ile Leu His
                580                 585                 590

Gln Lys Pro Ala Ile Ile Val Leu Arg Glu Asp Leu Asp Tyr Tyr Cys
                595                 600                 605

Val Pro Gln Glu Glu Phe Gln Phe Asp Ser Thr Asn Glu Glu Asn Asn
    610                 615                 620

Glu Asp Leu Leu Arg His Phe Met Ala Gln Val Lys Met Ala Ala Gly
    625                 630                 635                 640

Ser Tyr Leu Thr Ser Lys Thr Ser Ile Phe Gln Gly Leu Tyr Ser Ser
                    645                 650                 655

Asn Arg Leu Lys Gln Gln Gln Gln Gln Lys Ile Glu Lys Gly Ser
                660                 665                 670

Asn Ser Ser Ser Asn Thr Lys Ser Thr Ser Lys Lys Leu Gly Pro Ala
                675                 680                 685

Glu Gln His Leu Met Asp Met Leu Cys Ser Ser Gly Phe Thr Lys Glu
    690                 695                 700

Thr Cys Trp Gly Asn Arg Thr Gln Glu Thr Gly Lys Thr Val Ile Ser
    705                 710                 715                 720

Ser Leu Ser Leu Cys Arg Leu Ala Asn Glu Thr Thr Glu Gly Phe Arg
                    725                 730                 735

Gln Lys Phe Asn Glu Ala Lys Ala Lys Trp Glu Ala Glu His Lys Pro
                740                 745                 750

Ser Gln Asp Asn Phe Ile Thr Pro Met Gln Ser Asn Ile Ser Ile Asn
                755                 760                 765
```

```
Ser Leu Ser Ala Ser Lys Ser Asn Ser Thr Ile Ser Thr Ala Arg Asn
    770                 775                 780

Leu Thr Ser Gly Ser Thr Ala Pro Ala Thr Ala Arg Asp Lys Arg Lys
785                 790                 795                 800

Ser Arg Leu Ser Lys Leu Ala Asp Asn Val Arg Ser His Ser Ser Ser
                805                 810                 815

Arg His Ser Ser Gln Thr Arg Ser Lys Pro Pro Glu Leu Pro Lys Leu
            820                 825                 830

Tyr Asp Leu Val Pro Lys Pro Asn Ile Asn Ala Lys Leu Leu Leu Phe
        835                 840                 845

Trp Arg Lys Pro Ala Arg Lys Cys Trp Trp Gly Glu Glu Asp Ile Glu
    850                 855                 860

Leu Glu Val Glu Val Phe Gly Ser Trp Lys Asp Glu Ser Lys Lys Ile
865                 870                 875                 880

Ile Glu Leu Ile Leu Pro Thr Asn Val Asp Pro Glu Ala Glu Leu His
                885                 890                 895

Lys Ile Ile Val Pro Val Arg Leu His Ile Arg Arg Val Trp Thr Leu
            900                 905                 910

Glu Leu Ser Val Ile Gly Val Gln
        915                 920

<210> SEQ ID NO 119
<211> LENGTH: 687
<212> TYPE: PRT
<213> ORGANISM: Saccharomyces cerevisiae

<400> SEQUENCE: 119

Met Asp Asp Ile Ile Thr Gln Val Ser Pro Asp Asn Ala Glu Ser Ala
1               5                   10                  15

Pro Ile Leu Gln Glu Gln Gln Gln Gln Asn Ser Gln Tyr Glu Gly
            20                  25                  30

Asn Glu Glu Asp Tyr Gly Asp Ser Leu Ile His Leu Asn Ile Gln Glu
        35                  40                  45

Asn His Tyr Phe Ile Thr Arg Asp Gln Leu Met Ser Leu Pro Glu Ser
    50                  55                  60

Leu Leu Leu Cys Leu Phe Pro Ser Gly Val Phe Leu Asp Arg Cys Gly
65                  70                  75                  80

Gln Val Ile Thr Asn Leu Thr Arg Asp Asp Glu Val Tyr Ile Val Asn
                85                  90                  95

Phe Pro Pro Asp Cys Phe Glu Tyr Ile Met Glu Ile Tyr Thr Lys Ala
            100                 105                 110

His Asp Asp Leu Tyr Asn His Pro Val Glu Lys Phe Phe Asp Arg Pro
        115                 120                 125

Ser Ser Ser Phe Val Ser Asn Ala Lys Gly Phe Phe Gly Leu Ser Ser
    130                 135                 140

Asn Asn Ser Ile Ser Ser Asn Glu Gln Asp Ile Leu His Gln Lys
145                 150                 155                 160

Pro Ala Ile Ile Val Leu Arg Glu Asp Leu Asp Tyr Tyr Cys Val Pro
                165                 170                 175

Gln Glu Glu Phe Gln Phe Asp Ser Thr Asn Glu Glu Asn Asn Glu Asp
            180                 185                 190

Leu Leu Arg His Phe Met Ala Gln Val Lys Met Ala Ala Gly Ser Tyr
        195                 200                 205

Leu Thr Ser Lys Thr Ser Ile Phe Gln Gly Leu Tyr Ser Ser Asn Arg
```

```
                    210                 215                 220
Leu Lys Gln Gln Gln Gln Gln Lys Ile Glu Lys Gly Ser Asn Ser
225                 230                 235                 240

Ser Ser Asn Thr Lys Ser Thr Ser Lys Lys Leu Gly Pro Ala Glu Gln
                245                 250                 255

His Leu Met Asp Met Leu Cys Ser Ser Gly Phe Thr Lys Glu Thr Cys
                260                 265                 270

Trp Gly Asn Arg Thr Gln Glu Thr Gly Lys Thr Val Ile Ser Ser Leu
                275                 280                 285

Ser Leu Cys Arg Leu Ala Asn Glu Thr Thr Glu Gly Phe Arg Gln Lys
        290                 295                 300

Phe Asn Glu Ala Lys Ala Lys Trp Glu Ala His Lys Pro Ser Gln
305                 310                 315                 320

Asp Asn Phe Ile Thr Pro Met Gln Ser Asn Ile Ser Ile Asn Ser Leu
                        325                 330                 335

Ser Ala Ser Lys Ser Asn Ser Thr Ile Ser Thr Ala Arg Asn Leu Thr
                340                 345                 350

Ser Gly Ser Thr Ala Pro Ala Thr Ala Arg Asp Lys Arg Lys Ser Arg
            355                 360                 365

Leu Ser Lys Leu Ala Asp Asn Val Arg Ser His Ser Ser Arg His
        370                 375                 380

Ser Ser Gln Thr Arg Ser Lys Pro Pro Glu Leu Pro Lys Leu Tyr Asp
385                 390                 395                 400

Leu Val Pro Lys Pro Asn Ile Asn Ala Lys Leu Leu Leu Phe Trp Arg
                    405                 410                 415

Lys Pro Ala Arg Lys Cys Trp Trp Gly Glu Glu Asp Ile Glu Leu Glu
                420                 425                 430

Val Glu Val Phe Gly Ser Trp Lys Asp Glu Ser Lys Lys Ile Ile Glu
                435                 440                 445

Leu Ile Leu Pro Thr Asn Val Asp Pro Glu Ala Glu Leu His Lys Ile
        450                 455                 460

Ile Val Pro Val Arg Leu His Ile Arg Arg Val Trp Thr Leu Glu Leu
465                 470                 475                 480

Ser Val Ile Gly Val Gln Gly Ser Ala Ala Pro Gly Ala Ser Ala Ala
                485                 490                 495

Pro Gly Ala Gly Ser Gly Ser Gly Ser Gly Met Val Val Ser Ile Ile
                500                 505                 510

Pro Gln Phe Pro Asp Ile Lys Val Ser Leu Ala Leu Phe Glu Gln Val
        515                 520                 525

Lys Asn Ala Lys Glu Ile Arg Ser Lys Met Ser Glu Leu Ser Thr Ser
        530                 535                 540

Phe Ala Phe Ile Asp Pro Arg Leu Val Cys Ser Gly Glu Gln Met Tyr
545                 550                 555                 560

Ser Ala Ile Tyr Lys Thr Leu Ile Glu Val Lys Tyr Asn Lys Met Arg
                565                 570                 575

Thr Arg Asn Leu Asn Ser Glu Cys Val Leu Cys Leu Ser Pro Thr Ser
                580                 585                 590

Asn Ile Ser Asp Ala Phe Leu Lys Phe Gly Ile Lys Asp Ser Ser
            595                 600                 605

Gln Leu Ile Cys Leu Lys Phe His Thr Asn Thr Asp Asp Val Asp Lys
        610                 615                 620

Glu Gln Leu Arg Thr Ile Met Thr Ser Ile Val Lys Gly Gln Glu Ile
625                 630                 635                 640
```

Glu Phe Asn Asp Asp Asn Leu Ser Arg Phe Tyr Asp Glu Ala Leu Ile
            645                 650                 655

Arg Lys Ile Tyr Lys Leu Ser Asp Asp Phe Lys Pro Gln Asp Val Asn
        660                 665                 670

Gly Leu Ser Arg Ala Leu Val Asp Ala Ile Gln Leu Arg Gly Val
            675                 680                 685

<210> SEQ ID NO 120
<211> LENGTH: 319
<212> TYPE: PRT
<213> ORGANISM: Saccharomyces cerevisiae

<400> SEQUENCE: 120

Met Arg Arg Leu Tyr Arg His Leu Ala Ser Phe Phe Leu Leu Pro Ser
1               5                   10                  15

Cys Pro Gly Asn Thr Ile Gln Ser Ile Thr Ser Tyr Pro Ala Asn Ala
            20                  25                  30

Leu Leu Arg Ser Phe Arg His Val Ser Thr Glu Thr Pro Val Arg Asn
        35                  40                  45

Arg Val His Asn Arg Asp Ser Gln Ser Cys Pro Phe Phe Pro Leu Met
50                  55                  60

Asp Asp Gly Ser Ala Ala Pro Gly Ala Ser Ala Ala Pro Gly Ala Gly
65                  70                  75                  80

Ser Gly Ser Gly Ser Gly Met Phe Ala Lys Thr Ala Ala Ala Asn Leu
            85                  90                  95

Thr Lys Lys Gly Gly Leu Ser Leu Leu Ser Thr Thr Ala Arg Arg Thr
            100                 105                 110

Lys Val Thr Leu Pro Asp Leu Lys Trp Asp Phe Gly Ala Leu Glu Pro
        115                 120                 125

Tyr Ile Ser Gly Gln Ile Asn Glu Leu His Tyr Thr Lys His His Gln
    130                 135                 140

Thr Tyr Val Asn Gly Phe Asn Thr Ala Val Asp Gln Phe Gln Glu Leu
145                 150                 155                 160

Ser Asp Leu Leu Ala Lys Glu Pro Ser Pro Ala Asn Ala Arg Lys Met
            165                 170                 175

Ile Ala Ile Gln Gln Asn Ile Lys Phe His Gly Gly Gly Phe Thr Asn
            180                 185                 190

His Cys Leu Phe Trp Glu Asn Leu Ala Pro Glu Ser Gln Gly Gly Gly
        195                 200                 205

Glu Pro Pro Thr Gly Ala Leu Ala Lys Ala Ile Asp Glu Gln Phe Gly
    210                 215                 220

Ser Leu Asp Glu Leu Ile Lys Leu Thr Asn Thr Lys Leu Ala Gly Val
225                 230                 235                 240

Gln Gly Ser Gly Trp Ala Phe Ile Val Lys Asn Leu Ser Asn Gly Gly
            245                 250                 255

Lys Leu Asp Val Val Gln Thr Tyr Asn Gln Asp Thr Val Thr Gly Pro
            260                 265                 270

Leu Val Pro Leu Val Ala Ile Asp Ala Trp Glu His Ala Tyr Tyr Leu
        275                 280                 285

Gln Tyr Gln Asn Lys Lys Ala Asp Tyr Phe Lys Ala Ile Trp Asn Val
    290                 295                 300

Val Asn Trp Lys Glu Ala Ser Arg Arg Phe Asp Ala Gly Lys Ile
305                 310                 315

<210> SEQ ID NO 121
<211> LENGTH: 326
<212> TYPE: PRT
<213> ORGANISM: Saccharomyces cerevisiae

<400> SEQUENCE: 121

```
Met Ala Ser Ile Asp Ala Phe Ser Asp Leu Glu Arg Arg Met Asp Gly
1               5                   10                  15

Phe Gln Lys Asp Val Ala Gln Val Leu Ala Arg Gln Gln Asn His Ala
            20                  25                  30

Arg Gln Gln Leu Gln Gln Phe Gln Ala Glu Met Arg Gln Leu His Asn
        35                  40                  45

Gln His Gln His Leu Ile Asp Glu Leu Gln Arg Leu Ala Thr Gln Arg
    50                  55                  60

Thr Ala Leu Gln Gln Ile His Ala Ala Gln Gln Ala Thr Asn Thr
65                  70                  75                  80

Thr Arg Glu Gln Trp Arg Ser Tyr His Glu Arg Glu Ser Glu Leu Ser
                85                  90                  95

Arg Arg Gln Ser Thr Leu Ala Ala Gln Ser Arg Glu Leu Asp Ser Leu
            100                 105                 110

Leu Gln Gln Arg Gly Lys Glu Cys Val Gln Leu Arg Ala Arg Trp Ala
        115                 120                 125

Ala Gln Ser Gly Asn Asp Ala Ala Glu Val Ala Leu Tyr Glu Arg Leu
    130                 135                 140

Leu Gln Leu Arg Val Leu Pro Gly Ala Ser Asp Val His Asp Val Arg
145                 150                 155                 160

Phe Val Phe Gly Asp Asp Ser Arg Cys Trp Ile Glu Val Ala Met His
                165                 170                 175

Gly Asp His Val Ile Gly Asn Ser His Pro Ala Leu Asp Pro Lys Ser
            180                 185                 190

Arg Ala Thr Leu Glu His Val Leu Thr Val Gln Gly Asp Leu Ala Ala
        195                 200                 205

Phe Leu Val Val Ala Arg Asp Met Leu Leu Ala Ser Leu Gly Ser Ala
    210                 215                 220

Ala Pro Gly Ala Ser Ala Ala Pro Gly Ala Gly Ser Gly Ser Gly Ser
225                 230                 235                 240

Gly Met Ile Leu Ala Leu Gly Asp Phe Leu Pro Lys Gln Glu Asp Lys
                245                 250                 255

Ala Cys Glu Arg Pro Trp Val Gln Phe Pro Ala Arg Pro Val Ile Phe
            260                 265                 270

Phe His His Gln Gly Gly Ile Phe Leu Phe Ser Ile Asn Gln Pro Asn
        275                 280                 285

Leu Ser Cys Phe Ser Lys Leu Lys Glu Val Asn Ser Leu Tyr Val Arg
    290                 295                 300

Val Ala Thr Tyr Ile Cys Gln Lys Asn Glu Ser Arg Phe Arg Thr Asn
305                 310                 315                 320

Arg Leu Lys Gly Asp Gln
                325
```

<210> SEQ ID NO 122
<211> LENGTH: 401
<212> TYPE: PRT
<213> ORGANISM: Saccharomyces cerevisiae

<400> SEQUENCE: 122

Met Arg Arg Leu Tyr Arg His Leu Ala Ser Phe Phe Leu Leu Pro Ser

```
1               5                   10                  15
Cys Pro Gly Asn Thr Ile Gln Ser Ile Thr Ser Tyr Pro Ala Asn Ala
                20                  25                  30

Leu Leu Arg Ser Phe Arg His Val Ser Thr Glu Thr Pro Val Arg Asn
            35                  40                  45

Arg Val His Asn Arg Asp Ser Gln Ser Cys Pro Phe Pro Leu Met
        50                  55                  60

Asp Asp Gly Ser Ala Ala Pro Gly Ala Ser Ala Ala Pro Gly Ala Gly
65                  70                  75                  80

Ser Gly Ser Gly Ser Gly Met Gly Arg Thr Phe Ile His Ala Ser Lys
                85                  90                  95

Ile Lys His Ala Ala Arg Lys Arg Lys His His Ser Asn Phe Arg Thr
                100                 105                 110

Leu Ile Lys Leu Leu Asn Asn Asp Ala Tyr Lys Ile Glu Ser Ser Lys
            115                 120                 125

Pro Leu Lys Asn Gly Lys Leu Phe Lys Tyr Trp Lys Asn Arg Arg Arg
        130                 135                 140

Leu Phe Ser Lys Ile Asp Ser Ala Ser Ile Tyr Met Thr Asp Glu Leu
145                 150                 155                 160

Trp Phe Ser Val Thr Pro Glu Arg Ile Ala Cys Phe Leu Ala Asn Phe
                165                 170                 175

Val Lys Ala Cys Met Pro Asn Ala Glu Arg Ile Leu Asp Val Phe Cys
                180                 185                 190

Gly Gly Gly Gly Asn Thr Ile Gln Phe Ala Met Gln Phe Pro Tyr Val
                195                 200                 205

Tyr Gly Val Asp Tyr Ser Ile Glu His Ile Tyr Cys Thr Ala Lys Asn
        210                 215                 220

Ala Gln Ser Tyr Gly Val Asp Asp Arg Ile Trp Leu Lys Arg Gly Ser
225                 230                 235                 240

Trp Lys Lys Leu Val Ser Lys Gln Lys Leu Ser Lys Ile Lys Tyr Asp
                245                 250                 255

Cys Val Phe Gly Ser Pro Pro Trp Gly Gly Pro Glu Tyr Leu Arg Asn
            260                 265                 270

Asp Val Tyr Asp Leu Glu Gln His Leu Lys Pro Met Gly Ile Thr Lys
        275                 280                 285

Met Leu Lys Ser Phe Leu Lys Leu Ser Pro Asn Val Ile Met Phe Leu
        290                 295                 300

Pro Arg Asn Ser Asp Leu Asn Gln Leu Ser Arg Ala Thr Arg Lys Val
305                 310                 315                 320

Leu Gly Pro Phe Ala Lys Cys Lys Val Leu Tyr Val Lys Glu Asn Gly
                325                 330                 335

Tyr Met Lys Gly Ile Phe Cys Met Trp Gly Cys Phe Phe Asn Tyr
            340                 345                 350

Glu Pro Ala Ser Thr Glu Asn Ser Arg Arg Glu Ser Ser Lys Glu
        355                 360                 365

Glu Leu Ser Ser Glu Asn Glu Leu Ser Lys Arg Lys His Glu
        370                 375             380

Ser Thr Thr Thr Lys Asp Asn Thr Val Asp Ile Tyr Asp Val Asn
385                 390                 395                 400

Gly

<210> SEQ ID NO 123
<211> LENGTH: 739
```

```
<212> TYPE: PRT
<213> ORGANISM: Saccharomyces cerevisiae

<400> SEQUENCE: 123

Met Gly Val Lys Gln Thr Pro Pro Val Gln Val Lys Val Ser Asp Ala
1               5                   10                  15

Asp Ser Thr Asn Arg Arg Lys Ser Ser Ser Gln Glu Gly Asn Pro Gln
            20                  25                  30

Leu Val Gln Leu Lys Ala Lys Ser Asp Lys Asp Lys Arg Lys Gly Ser
        35                  40                  45

Ser Asp Ser Thr Ala Ser Ile Met Gly Ser Ser Asn Ala Leu Pro Thr
50                  55                  60

Lys Asn Leu Thr Thr Pro Pro Ala Leu Asn Pro Leu Thr Thr Ser Ile
65                  70                  75                  80

Ser Arg Gly Asn Thr Ala Tyr Glu Arg Ser Val Asn Gly Ser Arg Ile
                85                  90                  95

Thr Met His Ser Asn Leu Ala Pro Thr Glu Thr Gln Asp Val Ser Trp
            100                 105                 110

Ser Glu Ile Asp Thr Leu Asp Asp Val Lys Lys Met Ala Lys Glu Pro
        115                 120                 125

Ile Val Asn Asp Gly Phe Pro Arg Asp Phe Glu Ser Asn Leu Thr Gln
130                 135                 140

Met Arg Lys Ser His Ala Gln Leu Leu Arg Leu Met Arg Glu Arg Asn
145                 150                 155                 160

Gln Arg Leu Lys Tyr Ala Lys Leu Arg Ser Pro Pro His Lys Asp Gln
                165                 170                 175

His Asn Ser Ala Thr Asn Lys Asp Gln Glu Pro Asp Glu Val Leu His
            180                 185                 190

Asp Pro Glu Ile Ala Leu Asp Gly Glu Lys Tyr Val Ser Gln Val Val
        195                 200                 205

Asp Thr Ile Lys Asp Val His Arg Cys Gly Ser Ala Ala Pro Gly Ala
210                 215                 220

Ser Ala Pro Gly Ala Gly Ser Gly Ser Gly Ser Gly Met Leu Leu
225                 230                 235                 240

Asp Val Asn Thr Asn His Thr Leu Met His Asp Ala His Val His Glu
                245                 250                 255

His Cys Leu Ile Lys Ser Ile Arg Asp Asp Gly Ala Leu His Ser Trp
            260                 265                 270

Ser Asp Ser Ser Lys Val Phe Tyr Pro Lys Ser Phe Tyr Ala Thr Ala
        275                 280                 285

Thr Asn Lys Lys Asn Asn Lys Leu Ala Ser Ala Ser Met Asn Lys Thr
290                 295                 300

Ala Thr Ser Asn Arg Thr Val Ser Asp Glu Ile Tyr Phe His Ser Thr
305                 310                 315                 320

Lys Pro Gln Phe Asp Gly Gln Gly Ser Ala Glu Arg Thr Arg Thr Leu
                325                 330                 335

Thr Lys Arg Asn Ser Phe Lys Arg Thr Arg Ile Leu Lys Ala Arg Asp
            340                 345                 350

Asp Ser Glu Leu Leu Asn Glu Asn Arg Ser Ser Leu Met Thr Pro Ser
        355                 360                 365

Leu Ser Ser Val Met Ser Gln Val Arg Lys Thr Asn Ser Ala Lys Thr
370                 375                 380

Leu Ser Gly Glu Cys Pro Ile His Glu Gly His Leu Thr Gln Ser Ile
385                 390                 395                 400
```

```
Lys Arg Lys Phe Ser Glu Glu Ala Gln Ser Asp Cys Ser Ser Leu Ser
                405                 410                 415

Ser Ser Lys Leu His Pro Leu Thr Asp Asp Ile Ala Asp Ala Val Asp
            420                 425                 430

Leu Gln Thr Pro Ala Ile Gly Asp Glu Val Leu Ala Glu Pro Val Val
        435                 440                 445

Pro Lys Met Lys Ile Ile Asn Ile Asn Asp Leu Asp Leu Phe Asp Asp
    450                 455                 460

Trp Glu Val Lys Asp Leu Val Asp Ile Phe Pro Pro Val Tyr Glu Arg
465                 470                 475                 480

Arg Pro Arg Ser Ser Ala Leu Ser Leu Val Ser Ala Ser Ser Asp
                485                 490                 495

Ala Lys Leu Arg Pro Thr Ser Val Asp Phe Gln Ile Ile Asp Lys Lys
            500                 505                 510

Gly Gly Lys Thr Ser Arg Arg Lys Ser Arg Ser Lys Ser Thr Thr Glu
        515                 520                 525

Asn Met Ile Tyr Glu Asn Asp Leu Val Glu Leu Gln Trp Pro Ser
    530                 535                 540

Ala Ser Pro Ser Pro Glu Thr Asp Gly Ser Ile Ala Ser Ser Glu Leu
545                 550                 555                 560

Leu Pro Asn Lys Arg Ile Arg Gln Lys Ser Leu Asn Thr Asn Phe Leu
                565                 570                 575

Lys Leu Tyr Ser Ile Glu Thr Ser Cys Lys Arg Lys Ser Ile Leu Pro
            580                 585                 590

Glu Val Glu Val Asp Asp His Leu Leu Lys Gln Leu Thr Tyr Ser Glu
        595                 600                 605

Ile Arg Ser Leu Glu Ile Lys Lys Glu Pro Asn Val Ser Thr Asn Asp
    610                 615                 620

Ile Lys Leu Ala Leu Ile Thr Arg Lys Lys Leu Trp Ser Asp Met Val
625                 630                 635                 640

His Glu Thr Arg Asn Asp Leu Phe Gly Asp Ser Thr Pro Trp Asn Leu
                645                 650                 655

His Phe Val Ala Thr Thr Ser Asn Thr Glu Pro Ser Gln Gly Arg Glu
            660                 665                 670

Ser Ala Ser Glu His Ala Thr Ala Asp Leu Lys Ser Ser Leu Val Arg
        675                 680                 685

Val His Ser Asp Val Lys Pro Trp Phe Asn Asn Gly Gly Thr Met Leu
    690                 695                 700

Lys Pro Cys Gly Lys Leu Asn Leu Gly Lys Val Thr Asn Lys Thr Ser
705                 710                 715                 720

Ala Pro Thr Arg Glu Ile Gln Tyr Val Val Lys Gly Trp Cys Asp Ser
                725                 730                 735

Arg Phe Leu

<210> SEQ ID NO 124
<211> LENGTH: 608
<212> TYPE: PRT
<213> ORGANISM: Saccharomyces cerevisiae

<400> SEQUENCE: 124

Met Ser Gly Lys Ala Ser Thr Glu Gly Ser Val Thr Thr Glu Phe Leu
1               5                   10                  15

Ser Asp Ile Ile Gly Lys Thr Val Asn Val Lys Leu Ala Ser Gly Leu
            20                  25                  30
```

```
Leu Tyr Ser Gly Arg Leu Glu Ser Ile Asp Gly Phe Met Asn Val Ala
            35                  40                  45

Leu Ser Ser Ala Thr Glu His Tyr Glu Ser Asn Asn Asn Lys Leu Leu
 50                  55                  60

Asn Lys Phe Asn Ser Asp Val Phe Leu Arg Gly Thr Gln Val Met Tyr
 65                  70                  75                  80

Ile Ser Glu Gln Lys Ile Gly Ser Ala Ala Pro Gly Ala Ser Ala Ala
                 85                  90                  95

Pro Gly Ala Gly Ser Gly Ser Gly Met Leu Leu Asp Val Asn
                100                 105                 110

Thr Asn His Thr Leu Met His Asp Ala His Val His Glu His Cys Leu
            115                 120                 125

Ile Lys Ser Ile Arg Asp Asp Gly Ala Leu His Ser Trp Ser Asp Ser
            130                 135                 140

Ser Lys Val Phe Tyr Pro Lys Ser Phe Tyr Ala Thr Ala Thr Asn Lys
145                 150                 155                 160

Lys Asn Asn Lys Leu Ala Ser Ala Ser Met Asn Lys Thr Ala Thr Ser
                165                 170                 175

Asn Arg Thr Val Ser Asp Glu Ile Tyr Phe His Ser Lys Pro Gln
            180                 185                 190

Phe Asp Gly Gln Gly Ser Ala Glu Arg Thr Arg Thr Leu Thr Lys Arg
            195                 200                 205

Asn Ser Phe Lys Arg Thr Arg Ile Leu Lys Ala Arg Asp Asp Ser Glu
210                 215                 220

Leu Leu Asn Glu Asn Arg Ser Ser Leu Met Thr Pro Ser Leu Ser Ser
225                 230                 235                 240

Val Met Ser Gln Val Arg Lys Thr Asn Ser Ala Lys Thr Leu Ser Gly
            245                 250                 255

Glu Cys Pro Ile His Glu Gly His Leu Thr Gln Ser Ile Lys Arg Lys
            260                 265                 270

Phe Ser Glu Glu Ala Gln Ser Asp Cys Ser Ser Leu Ser Ser Ser Lys
            275                 280                 285

Leu His Pro Leu Thr Asp Asp Ile Ala Asp Ala Val Asp Leu Gln Thr
            290                 295                 300

Pro Ala Ile Gly Asp Glu Val Leu Ala Glu Pro Val Val Pro Lys Met
305                 310                 315                 320

Lys Ile Ile Asn Ile Asn Asp Leu Asp Leu Phe Asp Asp Trp Glu Val
                325                 330                 335

Lys Asp Leu Val Asp Ile Phe Pro Pro Val Tyr Glu Arg Arg Pro Arg
            340                 345                 350

Ser Ser Ser Ala Leu Ser Leu Val Ser Ala Ser Ser Asp Ala Lys Leu
            355                 360                 365

Arg Pro Thr Ser Val Asp Phe Gln Ile Ile Asp Lys Lys Gly Gly Lys
            370                 375                 380

Thr Ser Arg Arg Lys Ser Arg Ser Lys Ser Thr Glu Asn Met Ile
385                 390                 395                 400

Tyr Glu Asn Asp Leu Val Glu Leu Glu Gln Trp Pro Ser Ala Ser Pro
                405                 410                 415

Ser Pro Glu Thr Asp Gly Ser Ile Ala Ser Ser Glu Leu Leu Pro Asn
            420                 425                 430

Lys Arg Ile Arg Gln Lys Ser Leu Asn Thr Asn Phe Leu Lys Leu Tyr
            435                 440                 445
```

```
Ser Ile Glu Thr Ser Cys Lys Arg Lys Ser Ile Leu Pro Glu Val Glu
    450                 455                 460
Val Asp Asp His Leu Leu Lys Gln Leu Thr Tyr Ser Glu Ile Arg Ser
465                 470                 475                 480
Leu Glu Ile Lys Lys Glu Pro Asn Val Ser Thr Asn Asp Ile Lys Leu
                485                 490                 495
Ala Leu Ile Thr Arg Lys Lys Leu Trp Ser Asp Met Val His Glu Thr
            500                 505                 510
Arg Asn Asp Leu Phe Gly Asp Ser Thr Pro Trp Asn Leu His Phe Val
        515                 520                 525
Ala Thr Thr Ser Asn Thr Glu Pro Ser Gln Gly Arg Glu Ser Ala Ser
    530                 535                 540
Glu His Ala Thr Ala Asp Leu Lys Ser Ser Leu Val Arg Val His Ser
545                 550                 555                 560
Asp Val Lys Pro Trp Phe Asn Gly Gly Thr Met Leu Lys Pro Cys
                565                 570                 575
Gly Lys Leu Asn Leu Gly Lys Val Thr Asn Lys Thr Ser Ala Pro Thr
            580                 585                 590
Arg Glu Ile Gln Tyr Val Val Lys Gly Trp Cys Asp Ser Arg Phe Leu
        595                 600                 605

<210> SEQ ID NO 125
<211> LENGTH: 608
<212> TYPE: PRT
<213> ORGANISM: Saccharomyces cerevisiae

<400> SEQUENCE: 125

Met Ser Ser Glu Arg Ala Cys Met Leu Cys Gly Ile Val Gln Thr Thr
1               5                   10                  15
Asn Glu Phe Asn Arg Asp Gly Cys Pro Asn Cys Gln Gly Ile Phe Glu
            20                  25                  30
Glu Ala Gly Val Ser Thr Met Glu Cys Thr Ser Pro Ser Phe Glu Gly
        35                  40                  45
Leu Val Gly Met Cys Lys Pro Thr Lys Ser Trp Val Ala Lys Trp Leu
    50                  55                  60
Ser Val Asp His Ser Ile Ala Gly Met Tyr Ala Ile Lys Val Asp Gly
65                  70                  75                  80
Arg Leu Pro Ala Glu Val Val Glu Leu Leu Pro His Tyr Lys Pro Arg
                85                  90                  95
Asp Gly Ser Gln Val Glu Gly Ser Ala Ala Pro Gly Ala Ser Ala Ala
            100                 105                 110
Pro Gly Ala Gly Ser Gly Ser Gly Ser Gly Met Asp Asp Ile Ile Thr
        115                 120                 125
Gln Val Ser Pro Asp Asn Ala Glu Ser Ala Pro Ile Leu Gln Glu Gln
    130                 135                 140
Gln Gln Gln Gln Asn Ser Gln Tyr Glu Gly Asn Glu Glu Asp Tyr Gly
145                 150                 155                 160
Asp Ser Leu Ile His Leu Asn Ile Gln Glu Asn His Tyr Phe Ile Thr
                165                 170                 175
Arg Asp Gln Leu Met Ser Leu Pro Glu Ser Leu Leu Cys Leu Phe
            180                 185                 190
Pro Ser Gly Val Phe Leu Asp Arg Cys Gly Gln Val Ile Thr Asn Leu
        195                 200                 205
Thr Arg Asp Asp Glu Val Tyr Ile Val Asn Phe Pro Pro Asp Cys Phe
    210                 215                 220
```

Glu Tyr Ile Met Glu Ile Tyr Thr Lys Ala His Asp Asp Leu Tyr Asn
225                 230                 235                 240

His Pro Val Glu Lys Phe Phe Asp Arg Pro Ser Ser Phe Val Ser
            245                 250                 255

Asn Ala Lys Gly Phe Phe Gly Leu Ser Ser Asn Asn Ser Ile Ser Ser
            260                 265                 270

Asn Asn Glu Gln Asp Ile Leu His Gln Lys Pro Ala Ile Ile Val Leu
            275                 280                 285

Arg Glu Asp Leu Asp Tyr Tyr Cys Val Pro Gln Glu Glu Phe Gln Phe
            290                 295                 300

Asp Ser Thr Asn Glu Glu Asn Asn Glu Asp Leu Leu Arg His Phe Met
305                 310                 315                 320

Ala Gln Val Lys Met Ala Ala Gly Ser Tyr Leu Thr Ser Lys Thr Ser
            325                 330                 335

Ile Phe Gln Gly Leu Tyr Ser Ser Asn Arg Leu Lys Gln Gln Gln Gln
            340                 345                 350

Gln Gln Lys Ile Glu Lys Gly Ser Asn Ser Ser Asn Thr Lys Ser
            355                 360                 365

Thr Ser Lys Lys Leu Gly Pro Ala Glu Gln His Leu Met Asp Met Leu
370                 375                 380

Cys Ser Ser Gly Phe Thr Lys Glu Thr Cys Trp Gly Asn Arg Thr Gln
385                 390                 395                 400

Glu Thr Gly Lys Thr Val Ile Ser Ser Leu Ser Leu Cys Arg Leu Ala
            405                 410                 415

Asn Glu Thr Thr Glu Gly Phe Arg Gln Lys Phe Asn Glu Ala Lys Ala
            420                 425                 430

Lys Trp Glu Ala Glu His Lys Pro Ser Gln Asp Asn Phe Ile Thr Pro
            435                 440                 445

Met Gln Ser Asn Ile Ser Ile Asn Ser Leu Ser Ala Ser Lys Ser Asn
450                 455                 460

Ser Thr Ile Ser Thr Ala Arg Asn Leu Thr Ser Gly Ser Thr Ala Pro
465                 470                 475                 480

Ala Thr Ala Arg Asp Lys Arg Lys Ser Arg Leu Ser Lys Leu Ala Asp
            485                 490                 495

Asn Val Arg Ser His Ser Ser Ser Arg His Ser Ser Gln Thr Arg Ser
            500                 505                 510

Lys Pro Pro Glu Leu Pro Lys Leu Tyr Asp Leu Val Pro Lys Pro Asn
            515                 520                 525

Ile Asn Ala Lys Leu Leu Leu Phe Trp Arg Lys Pro Ala Arg Lys Cys
            530                 535                 540

Trp Trp Gly Glu Glu Asp Ile Glu Leu Glu Val Glu Val Phe Gly Ser
545                 550                 555                 560

Trp Lys Asp Glu Ser Lys Lys Ile Ile Glu Leu Ile Leu Pro Thr Asn
            565                 570                 575

Val Asp Pro Glu Ala Glu Leu His Lys Ile Ile Val Pro Val Arg Leu
            580                 585                 590

His Ile Arg Arg Val Trp Thr Leu Glu Leu Ser Val Ile Gly Val Gln
            595                 600                 605

<210> SEQ ID NO 126
<211> LENGTH: 999
<212> TYPE: PRT
<213> ORGANISM: Saccharomyces cerevisiae

<400> SEQUENCE: 126

```
Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
    370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415
```

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
            485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
            515                 520                 525

Asp Asn Ser Lys Ile Arg Met Ile Glu Ile Met Leu Pro Val Phe Asp
            530                 535                 540

Ala Pro Gln Asn Leu Val Glu Gln Ala Lys Leu Thr Ala Ala Thr Asn
545                 550                 555                 560

Ala Lys Gln Gly Ser Ala Ala Pro Gly Ala Ser Ala Ala Pro Gly Ala
            565                 570                 575

Gly Ser Gly Ser Gly Ser Gly Met Val Ser Ser Leu Pro Lys Glu Ser
            580                 585                 590

Gln Ala Glu Leu Gln Leu Phe Gln Asn Glu Ile Asn Ala Ala Asn Pro
            595                 600                 605

Ser Asp Phe Leu Gln Phe Ser Ala Asn Tyr Phe Asn Lys Arg Leu Glu
            610                 615                 620

Gln Gln Arg Ala Phe Leu Lys Ala Arg Glu Pro Glu Phe Lys Ala Lys
625                 630                 635                 640

Asn Ile Val Leu Phe Pro Glu Pro Glu Ser Phe Ser Arg Pro Gln
            645                 650                 655

Ser Ala Gln Ser Gln Ser Arg Ser Arg Ser Ser Val Met Phe Lys Ser
            660                 665                 670

Pro Phe Val Asn Glu Asp Pro His Ser Asn Val Phe Lys Ser Gly Phe
            675                 680                 685

Asn Leu Asp Pro His Glu Gln Asp Thr His Gln Gln Ala Gln Glu Glu
            690                 695                 700

Gln Gln His Thr Arg Glu Lys Thr Ser Thr Pro Pro Leu Pro Met His
705                 710                 715                 720

Phe Asn Ala Gln Arg Arg Thr Ser Val Ser Gly Glu Thr Leu Gln Pro
            725                 730                 735

Asn Asn Phe Asp Asp Trp Thr Pro Asp His Tyr Lys Glu Lys Ser Glu
            740                 745                 750

Gln Gln Leu Gln Arg Leu Glu Lys Ser Ile Arg Asn Asn Phe Leu Phe
            755                 760                 765

Asn Lys Leu Asp Ser Asp Ser Lys Arg Leu Val Ile Asn Cys Leu Glu
            770                 775                 780

Glu Lys Ser Val Pro Lys Gly Ala Thr Ile Ile Lys Gln Gly Asp Gln
785                 790                 795                 800

Gly Asp Tyr Phe Tyr Val Val Glu Lys Gly Thr Val Asp Phe Tyr Val
            805                 810                 815

Asn Asp Asn Lys Val Asn Ser Ser Gly Pro Gly Ser Ser Phe Gly Glu
            820                 825                 830

| | | | | | | | | | | | | |
|---|---|---|---|---|---|---|---|---|---|---|---|---|
|Leu|Ala|Leu|Met|Tyr|Asn|Ser|Pro|Arg|Ala|Ala|Thr|Val|Ala|Thr|
| | |835| | | | |840| | | | |845| | |
|Ser|Asp|Cys|Leu|Leu|Trp|Ala|Leu|Asp|Arg|Leu|Thr|Phe|Arg|Lys|Ile|
| |850| | | | |855| | | | |860| | | | |
|Leu|Leu|Gly|Ser|Ser|Phe|Lys|Lys|Arg|Leu|Met|Tyr|Asp|Asp|Leu|Leu|
|865| | | | |870| | | | |875| | | | |880|
|Lys|Ser|Met|Pro|Val|Leu|Lys|Ser|Leu|Thr|Thr|Tyr|Asp|Arg|Ala|Lys|
| | | | |885| | | | |890| | | | |895| |
|Leu|Ala|Asp|Ala|Leu|Asp|Thr|Lys|Ile|Tyr|Gln|Pro|Gly|Glu|Thr|Ile|
| | | |900| | | | |905| | | | |910| | |
|Ile|Arg|Glu|Gly|Asp|Gln|Gly|Glu|Asn|Phe|Tyr|Leu|Ile|Glu|Tyr|Gly|
| | |915| | | | |920| | | | |925| | | |
|Ala|Val|Asp|Val|Ser|Lys|Lys|Gly|Gln|Gly|Val|Ile|Asn|Lys|Leu|Lys|
| |930| | | | |935| | | | |940| | | | |
|Asp|His|Asp|Tyr|Phe|Gly|Glu|Val|Ala|Leu|Leu|Asn|Asp|Leu|Pro|Arg|
|945| | | | |950| | | | |955| | | | |960|
|Gln|Ala|Thr|Val|Thr|Ala|Thr|Lys|Arg|Thr|Lys|Val|Ala|Thr|Leu|Gly|
| | | | |965| | | | |970| | | | |975| |
|Lys|Ser|Gly|Phe|Gln|Arg|Leu|Leu|Gly|Pro|Ala|Val|Asp|Val|Leu|Lys|
| | | |980| | | | |985| | | | |990| | |
|Leu|Asn|Asp|Pro|Thr|Arg|His| | | | | | | | | |
| | | | |995| | | | | | | | | | | |

<210> SEQ ID NO 127
<211> LENGTH: 5535
<212> TYPE: DNA
<213> ORGANISM: Saccharomyces cerevisiae

<400> SEQUENCE: 127

```
taggacggat cgcttgcctg taacttacac gcgcctcgta tcttttaatg atggaataat      60
ttgggaattt actctgtgtt tatttatttt tatgttttgt atttggattt tagaaagtaa     120
ataaagaagg tagaagagtt acggaatgaa gaaaaaaaaa taaacaaagg tttaaaaaat     180
ttcaacaaaa agcgtacttt acatatatat ttattagaca agaaaagcag attaaataga     240
tatacattcg attaacgata agtaaaatgt aaaatcacag gattttcgtg tgtggtcttc     300
tacacagaca agatgaaaca attcggcatt aatacctgag agcaggaaga gcaagataaa     360
aggtagtatt tgttggcgat ccccctagag tcttttacat cttcgaaaaa caaaaactat     420
ttttctttta atttcttttt ttactttcta tttttaattt atatatttat attaaaaaat     480
ttaaattata attattttta tagcacgtga tgaaaaggac ccaggtggca cttttcgggg     540
aaatgtgcgc ggaacccta tttgtttatt tttctaaata cattcaaata tgtatccgct      600
catgagacaa taaccctgat aaatgcttca ataatattga aaaggaaga gtatgagtat      660
tcaacatttc cgtgtcgccc ttattccctt ttttgcggca ttttgccttc ctgttttttgc    720
tcacccagaa acgctggtga agtaaaaga tgctgaagat cagttgggtg cacgagtggg     780
ttacatcgaa ctggatctca acagcggtaa gatccttgag agttttcgcc ccgaagaacg     840
ttttccaatg atgagcactt ttaaagttct gctatgtggc gcggtattat cccgtattga     900
cgccgggcaa gagcaactcg gtcgccgcat acactattct cagaatgact tggttgagta     960
ctcaccagtc acagaaaagc atcttacgga tggcatgaca gtaagagaat tatgcagtgc    1020
tgccataacc atgagtgata acactgcggc caacttactt ctgacaacga tcggaggacc    1080
gaaggagcta accgcttttt tgcacaacat ggggatcat gtaactcgcc ttgatcgttg    1140
```

```
ggaaccggag ctgaatgaag ccataccaaa cgacgagcgt gacaccacga tgcctgtagc    1200
aatggcaaca acgttgcgca aactattaac tggcgaacta cttactctag cttcccggca    1260
acaattaata gactggatgg aggcggataa agttgcagga ccacttctgc gctcggccct    1320
tccggctggc tggtttattg ctgataaatc tggagccggt gagcgtgggt ctcgcggtat    1380
cattgcagca ctggggccag atggtaagcc ctcccgtatc gtagttatct acacgacggg    1440
gagtcaggca actatggatg aacgaaatag acagatcgct gagataggtg cctcactgat    1500
taagcattgg taactgtcag accaagttta ctcatatata ctttagattg atttaaaact    1560
tcatttttaa tttaaaagga tctaggtgaa gatcctttt gataatctca tgaccaaaat    1620
cccttaacgt gagttttcgt tccactgagc gtcagacccc gtagaaaaga tcaaaggatc    1680
ttcttgagat cctttttttc tgcgcgtaat ctgctgcttg caaacaaaaa aaccaccgct    1740
accagcggtg gtttgtttgc cggatcaaga gctaccaact ctttttccga aggtaactgg    1800
cttcagcaga gcgcagatac caaatactgt ccttctagtg tagccgtagt taggccacca    1860
cttcaagaac tctgtagcac cgcctacata cctcgctctg ctaatcctgt taccagtggc    1920
tgctgccagt ggcgataagt cgtgtcttac cgggttggac tcaagacgat agttaccgga    1980
taaggcgcag cggtcgggct gaacggggg ttcgtgcaca cagcccagct tggagcgaac    2040
gacctacacc gaactgagat acctacagcg tgagctatga gaaagcgcca cgcttcccga    2100
agggagaaag gcggacaggt atccggtaag cggcagggtc ggaacaggag agcgcacgag    2160
ggagcttcca gggggaaacg cctggtatct ttatagtcct gtcgggtttc gccacctctg    2220
acttgagcgt cgatttttgt gatgctcgtc aggggggcgg agcctatgga aaaacgccag    2280
caacgcggcc ttttacggt tcctggcctt ttgctggcct tttgctcaca tgttctttcc    2340
tgcgttatcc cctgattctg tggataaccg tattaccgcc tttgagtgag ctgataccgc    2400
tcgccgcagc cgaacgaccg agcgcagcga gtcagtgagc gaggaagcgg aagagcgccc    2460
aatacgcaaa ccgcctctcc ccgcgcgttg gccgattcat taatgcagct ggcacgacag    2520
gtttcccgac tggaaagcgg gcagtgagcg caacgcaatt aatgtgagtt acctcactca    2580
ttaggcaccc caggctttac actttatgct tccggctcct atgttgtgtg gaattgtgag    2640
cggataacaa tttcacacag gaaacagcta tgaccatgat tacgccaagc gcgcaattaa    2700
ccctcactaa agggaacaaa agctggagct ctagtacgga ttagaagccg ccgagcgggt    2760
gacagccctc cgaaggaaga ctctcctccg tgcgtcctcg tcttcaccgg tcgcgttcct    2820
gaaacgcaga tgtgcctcgc gccgcactgc tccgaacaat aaagattcta caatactagc    2880
ttttatggtt atgaagagga aaaattggca gtaacctggc cccacaaacc ttcaaatgaa    2940
cgaatcaaat taacaaccat aggatgataa tgcgattagt ttttagcct tatttctggg    3000 gtaattaatc agcgaagcga tgatttttga tctattaaca gatatataaa tgcaaaaact    3060
gcataaccac tttaactaat actttcaaca ttttcggttt gtattacttc ttattcaaat    3120
gtaataaaag tatcaacaaa aaattgttaa tatacctcta ctttaacg tcaaggagaa    3180 aaaactataa ggatccagct agcaaactcg agtcatgtaa ttagttatgt cacgcttaca    3240
ttcacgccct ccccccacat ccgctctaac cgaaaaggaa ggagttagac aacctgaagt    3300
ctaggtccct atttattttt ttatagttat gttagtatta agaacgttat ttatatttca    3360
aatttttctt ttttttctgt acagacgcgt gtacgcatgt aacattatac tgaaaacctt    3420
gcttgagaag ttttgggac gctcgaaggc tttaatttgc ggccggtacc caattcgccc    3480
tatagtgagt cgtattacgc gcgctcactg gccgtcgttt tacaacgtcg tgactgggaa    3540
```

```
aaccctggcg ttacccaact taatcgcctt gcagcacatc cccctttcgc cagctggcgt    3600
aatagcgaag aggcccgcac cgatcgccct tcccaacagt tgcgcagcct gaatggcgaa    3660
tggcgcgacg cgccctgtag cggcgcatta agcgcggcgg gtgtggtggt tacgcgcagc    3720
gtgaccgcta cacttgccag cgccctagcg cccgctcctt tcgctttctt cccttccttt    3780
ctcgccacgt tcgccggctt tccccgtcaa gctctaaatc gggggctccc tttagggttc    3840
cgatttagtg ctttacggca cctcgacccc aaaaaacttg attagggtga tggttcacgt    3900
agtgggccat cgcccctgata gacggttttt cgcccttga cgttggagtc cacgttcttt    3960
aatagtggac tcttgttcca aactggaaca acactcaacc ctatctcggt ctattctttt    4020
gatttataag ggattttgcc gatttcggcc tattggttaa aaaatgagct gatttaacaa    4080
aaatttaacg cgaattttaa caaaatatta acgtttacaa tttcctgatg cggtattttc    4140
tccttacgca tctgtgcggt atttcacacc gcatagggta ataactgata taattaaatt    4200
gaagctctaa tttgtgagtt tagtatacat gcatttactt ataatacagt tttttagttt    4260
tgctggccgc atcttctcaa atatgcttcc cagcctgctt ttctgtaacg ttcaccctct    4320
accttagcat ccccttccctt tgcaaatagt cctcttccaa caataataat gtcagatcct    4380
gtagagacca catcatccac ggttctatac tgttgaccca atgcgtctcc cttgtcatct    4440
aaacccacac cgggtgtcat aatcaaccaa tcgtaacctt catctcttcc acccatgtct    4500
ctttgagcaa taaagccgat aacaaaatct ttgtcgctct tcgcaatgtc aacagtaccc    4560
ttagtatatt ctccagtaga tagggagccc ttgcatgaca attctgctaa catcaaaagg    4620
cctctaggtt cctttgttac ttcttctgcc gcctgcttca aaccgctaac aatacctggg    4680
cccaccacac cgtgtgcatt cgtaatgtct gcccattctg ctattctgta tacacccgca    4740
gagtactgca atttgactgt attaccaatg tcagcaaatt ttctgtcttc gaagagtaaa    4800
aaattgtact tggcggataa tgcctttagc ggcttaactg tgccctccat ggaaaaatca    4860
gtcaagatat ccacatgtgt ttttagtaaa caaattttgg gacctaatgc ttcaactaac    4920
tccagtaatt ccttggtggt acgaacatcc aatgaagcac acaagtttgt ttgcttttcg    4980
tgcatgatat taaatagctt ggcagcaaca ggactaggat gagtagcagc acgttcctta    5040
tatgtagctt tcgacatgat ttatcttcgt ttcctgcagg tttttgttct gtgcagttgg    5100
gttaagaata ctgggcaatt tcatgtttct tcaacactac atatgcgtat atataccaat    5160
ctaagtctgt gctccttcct tcgttcttcc ttctgttcgg agattaccga atcaaaaaaa    5220
tttcaaagaa accgaaatca aaaaaagaa taaaaaaaaa atgatgaatt gaattgaaaa    5280
gctgtggtat ggtgcactct cagtacaatc tgctctgatg ccgcatagtt aagccagccc    5340
cgacacccgc caacacccgc tgacgcgccc tgacgggctt gtctgctccc ggcatccgct    5400
tacagacaag ctgtgaccgt ctccgggagc tgcatgtgtc agaggttttc accgtcatca    5460
ccgaaacgcg cgagacgaaa gggcctcgtg atacgcctat ttttataggt taatgtcatg    5520
ataataatgg tttct                                                    5535
```

<210> SEQ ID NO 128
<211> LENGTH: 2510
<212> TYPE: DNA
<213> ORGANISM: Escherichia coli

<400> SEQUENCE: 128

```
gagcgcccaa tacgcaaacc gcctctcccc gcgcgttggc cgattcatta atgcagctgg      60
```

-continued

| | |
|---|---|
| cacgacaggt ttcccgactg gaaagcgggc agtgagcgca acgcaattaa tgtgagttag | 120 |
| ctcactcatt aggcacccca ggctttacac tttatgcttc cggctcgtat gttgtgtgga | 180 |
| attgtgagcg gataacaatt taagcttagg atccacacac aggaaacagc ttgacctgca | 240 |
| ggactcgagc cggcttatcg gtcagtttca cctgatttac gtaaaaaccc gcttcggcgg | 300 |
| gttttttgctt ttggaggggc agaaagatga atgactgtcc acgacgctat acccaaaaga | 360 |
| aatagttaag ccagcccccga cacccgccaa cacccgctga cgcgccctga cgggcttgtc | 420 |
| tgctcccggc atccgcttac agacaagctg tgaccgtctc cgggagctgc atgtgtcaga | 480 |
| ggttttcacc gtcatcaccg aaacgcgcga cgcgaaaggg cctcgtgata cgcctatttt | 540 |
| tataggttaa tgtcatgata ataatggttt cttagacgtc aggtggcact tttcggggaa | 600 |
| atgtgcgcgg aaccccctatt tgttttatttt tctaaataca ttcaaatatg tatccgctca | 660 |
| tgagacaata accctgataa atgcttcaat aatattgaaa aggaagagt atgagtattc | 720 |
| aacatttccg tgtcgccctt attccctttt ttgcggcatt ttgccttcct gtttttgctc | 780 |
| acccagaaac gctggtgaaa gtaaaagatg ctgaagatca gttgggtgca cgagtgggtt | 840 |
| acatcgaact ggatctcaac agcggtaaga tccttgagag ttttcgcccc gaagaacgtt | 900 |
| ttccaatgat gagcactttt aaagttctgc tatgtggcgc ggtattatcc cgtattgacg | 960 |
| ccgggcaaga gcaactcggt cgccgcatac actattctca gaatgacttg gttgagtact | 1020 |
| caccagtcac agaaaagcat cttacggatg gcatgacagt aagagaatta tgcagtgctg | 1080 |
| ccataaccat gagtgataac actgcggcca acttacttct gacaacgatc ggaggaccga | 1140 |
| aggagctaac cgcttttttg cacaacatgg ggatcatgt aactcgcctt gatcgttggg | 1200 |
| aaccggagct gaatgaagcc ataccaaacg acgagcgtga ccacgatg cctgtagcaa | 1260 |
| tggcaacaac gttgcgcaaa ctattaactg gcgaactact tactctagct tcccggcaac | 1320 |
| aattaataga ctggatggag gcggataaag ttgcaggacc acttctgcgc tcggcccttc | 1380 |
| cggctggctg gtttattgct gataaatctg gagccggtga gcgtgggtct cgcggtatca | 1440 |
| ttgcagcact ggggccagat ggtaagccct cccgtatcgt agttatctac acgacgggga | 1500 |
| gtcaggcaac tatggatgaa cgaaatagac agatcgctga gataggtgcc tcactgatta | 1560 |
| agcattggta actgtcagac caagtttact catatatact ttagattgat ttaaaacttc | 1620 |
| attttttaatt taaaaggatc taggtgaaga tccttttgga taatctcatg accaaaatcc | 1680 |
| cttaacgtga gttttcgttc cactgagcgt cagaccccgt agaaaagatc aaaggatctt | 1740 |
| cttgagatcc tttttttctg cgcgtaatct gctgcttgca acaaaaaaa ccaccgctac | 1800 |
| cagcggtggt ttgtttgccg gatcaagagc taccaactct ttttccgaag gtaactggct | 1860 |
| tcagcagagc gcagatacca aatactgtcc ttctagtgta gccgtagtta ggccaccact | 1920 |
| tcaagaactc tgtagcaccg cctacatacc tcgctctgct aatcctgtta ccagtggctg | 1980 |
| ctgccagtgg cgataagtcg tgtcttaccg ggttggactc aagacgatag ttaccggata | 2040 |
| aggcgcagcg gtcgggctga acgggggtt cgtgcacaca gcccagcttg gagcgaacga | 2100 |
| cctacaccga actgagatac ctacagcgtg agctatgaga aagcgccacg cttcccgaag | 2160 |
| ggagaaaggc ggacaggtat ccggtaagcg gcagggtcgg aacaggagag cgcacgaggg | 2220 |
| agcttccagg gggaaacgcc tggtatcttt atagtcctgt cgggtttcgc cacctctgac | 2280 |
| ttgagcgtcg attttgtga tgctcgtcag ggggcggag cctatggaaa aacgccagca | 2340 |
| acgcggcctt tttacggttc ctggcctttt gctggccttt tgctcacatg ttctttcctg | 2400 |
| cgttatcccc tgattctgtg gataaccgta ttaccgcctt tgagtgagct gataccgctc | 2460 | gccgcagccg aacgaccgag cgcagcgagt cagtgagcga ggaagcggaa        2510

<210> SEQ ID NO 129
<211> LENGTH: 24
<212> TYPE: DNA
<213> ORGANISM: Escherichia coli

<400> SEQUENCE: 129
agctgtttcc tgtgtgtgga tcct        24

<210> SEQ ID NO 130
<211> LENGTH: 24
<212> TYPE: DNA
<213> ORGANISM: Escherichia coli

<400> SEQUENCE: 130
cctgcaggac tcgagccggc ttat        24

<210> SEQ ID NO 131
<211> LENGTH: 24
<212> TYPE: DNA
<213> ORGANISM: Escherichia coli

<400> SEQUENCE: 131
aggatccaca cacaggaaac agct        24

<210> SEQ ID NO 132
<211> LENGTH: 24
<212> TYPE: DNA
<213> ORGANISM: Escherichia coli

<400> SEQUENCE: 132
ggtagcccag ctggtgcaag tggc        24

<210> SEQ ID NO 133
<211> LENGTH: 24
<212> TYPE: DNA
<213> ORGANISM: Escherichia coli

<400> SEQUENCE: 133
ggtagcccag ctggtgcaag tggc        24

<210> SEQ ID NO 134
<211> LENGTH: 24
<212> TYPE: DNA
<213> ORGANISM: Escherichia coli

<400> SEQUENCE: 134
cctgcaggac tcgagccggc ttat        24

<210> SEQ ID NO 135
<211> LENGTH: 24
<212> TYPE: DNA
<213> ORGANISM: Escherichia coli

<400> SEQUENCE: 135
aggatccaca cacaggaaac agct        24

<210> SEQ ID NO 136
<211> LENGTH: 24
<212> TYPE: DNA
<213> ORGANISM: Escherichia coli

```
<400> SEQUENCE: 136
gccacttgca ccagctgggc tacc                                          24

<210> SEQ ID NO 137
<211> LENGTH: 24
<212> TYPE: DNA
<213> ORGANISM: Escherichia coli

<400> SEQUENCE: 137
ggtagcccag ctggtgcaag tggc                                          24

<210> SEQ ID NO 138
<211> LENGTH: 24
<212> TYPE: DNA
<213> ORGANISM: Escherichia coli

<400> SEQUENCE: 138
ataagccggc tcgagtcctg cagg                                          24

<210> SEQ ID NO 139
<211> LENGTH: 23
<212> TYPE: DNA
<213> ORGANISM: Saccharomyces cerevisiae

<400> SEQUENCE: 139
actataagga tccagctagc aaa                                           23

<210> SEQ ID NO 140
<211> LENGTH: 32
<212> TYPE: DNA
<213> ORGANISM: Saccharomyces cerevisiae

<400> SEQUENCE: 140
ggaagtgcag ctcctggtgc atcaggttct gg                                 32

<210> SEQ ID NO 141
<211> LENGTH: 29
<212> TYPE: DNA
<213> ORGANISM: Saccharomyces cerevisiae

<400> SEQUENCE: 141
gtgcatcagg ttctggaagt ggttcagga                                     29

<210> SEQ ID NO 142
<211> LENGTH: 27
<212> TYPE: DNA
<213> ORGANISM: Saccharomyces cerevisiae

<400> SEQUENCE: 142
ctcgagtcat gtaattagtt atgtcac                                       27

<210> SEQ ID NO 143
<211> LENGTH: 26
<212> TYPE: DNA
<213> ORGANISM: Saccharomyces cerevisiae

<400> SEQUENCE: 143
actataagga tccagctagc aaaatg                                        26

<210> SEQ ID NO 144
<211> LENGTH: 32
<212> TYPE: DNA
<213> ORGANISM: Saccharomyces cerevisiae
```

```
<400> SEQUENCE: 144
ccagaacctg atgcaccagg agctgcactt cc                                    32

<210> SEQ ID NO 145
<211> LENGTH: 32
<212> TYPE: DNA
<213> ORGANISM: Saccharomyces cerevisiae

<400> SEQUENCE: 145
gtgcatcagg ttctggaagt ggttcaggaa tg                                    32

<210> SEQ ID NO 146
<211> LENGTH: 27
<212> TYPE: DNA
<213> ORGANISM: Saccharomyces cerevisiae

<400> SEQUENCE: 146
gtgacataac taattacatg actcgag                                          27

<210> SEQ ID NO 147
<211> LENGTH: 26
<212> TYPE: DNA
<213> ORGANISM: Saccharomyces cerevisiae

<400> SEQUENCE: 147
cattttgcta gctggatcct tatagt                                           26

<210> SEQ ID NO 148
<211> LENGTH: 27
<212> TYPE: DNA
<213> ORGANISM: Saccharomyces cerevisiae

<400> SEQUENCE: 148
ctcgagtcat gtaattagtt atgtcac                                          27
```

METHODS AND COMPOSITIONS FOR CREATING ALTERED AND IMPROVED CELLS AND ORGANISMS

This application is the National Phase Under 35 U.S.C. § 371 of PCT International Application No. PCT/US2015/010812 filed on Jan. 9, 2015, which claims priority under 35 U.S.C. § 119 on Patent Application No. 61/925,230 filed on Jan. 9, 2014, the entire contents of each of which are hereby incorporated by reference.

BACKGROUND

Numerous agricultural and industrial production systems and processes depend on specific organisms, such as plants, algae, bacteria, fungi, yeasts, protozoa and cultured animal cells, for production of useful materials and compounds, such as food, fiber, structural materials, fuel, chemicals, pharmaceuticals, or feedstocks. In the process of the current shift to biological production systems for a variety of chemicals and fuels, a wide assortment of organisms will be used for production, most of them microbes, with an increasing tendency towards photosynthetic organisms (Dismukes 2008). The ability to grow robustly, and the ability to efficiently produce the materials and compounds of interest, are desirable properties of these organisms.

Optimization of the growth of these organisms and augmentation of their yield of useful materials and compounds is an ongoing activity of many companies and individuals, with the goal of achieving a higher productivity or yield, or lower production cost of commercially important materials and compounds. Such improvements can occur through the modification of production systems, or through the modification of the organisms themselves.

Polynucleotide fusions, involving joining of intact or partial open reading frames encoded by separate polynucleotides, is a known way of altering a polynucleotide sequence to change the properties of the encoded RNA or protein and to alter the phenotype of an organism. There are two general mechanisms by which polynucleotide fusions can alter an organism's phenotype. These two mechanisms can be illustrated with the case of polynucleotide A (encoding protein A') fused to polynucleotide B (encoding protein B'), in which proteins A' and B' have different functions or activities and/or are localized to different parts of the cell. The first mechanism applies to sub-cellular localization of the two proteins. The fusion protein encoded by the polynucleotide fusion of the two polynucleotides may be localized to the part of the cell where protein A' normally resides, or to the part of the cell where protein B' normally resides, or to both. This alteration of cellular distribution of the activities encoded by proteins A' and B' may cause a phenotypic change in the organism.

The second general mechanism by which fusion proteins alter the phenotypic property of a cell or organism relates to the direct association of two different, normally separate functions or activities in the same protein. In the case of proteins A' and B', their fusion may lead to an altered activity of protein A' or of protein B' or of the multiprotein complex in which these proteins normally reside, or of combinations thereof. The altered activity includes but is not limited to: qualitative alterations in activity; altered levels of activity; altered specificities of activity; altered regulation of the activity by the cell; altered association of the protein with other proteins, DNA or RNA molecules in the cell, leading to changes in the cell's biochemical or genetic pathways. As a result, a system for creating artificial polynucleotide fusions has the potential to create many phenotypes that are rarely or never found in nature.

To date, no attempt has been made to take advantage of the function-generating capability of fusion polypeptides in a large-scale and systematic manner. There are no published examples of large-scale collections of randomized, in-frame polynucleotide fusions. Previous examples of fusion proteins have been generated in a limited and directed fashion with specific outcomes in mind. The present invention describes the creation and use of systematic, randomized, large-scale and in-frame polynucleotide fusions for the purpose of altering protein function, generating new protein functions, and/or generating novel phenotypes of interest in biological organisms.

The present invention also describes methods by which large-scale collections of randomized, in-frame fusion polynucleotides can be selected in an iterative fashion to arrive at smaller collections of in-frame fusion polynucleotides enriched for a particular function or ability to confer a phenotype of interest to an organism.

BRIEF SUMMARY OF THE INVENTION

The present invention relates to methods and compositions that bring about changes in phenotypes in an organism through the introduction of randomized in-frame fusion polynucleotides into the genome of the organism. The random association of multiple sequences results in randomized in-frame fusion polynucleotides that disrupt or alter existing genetic or biochemical mechanisms or pathways in the cell or organism, thus creating novel characteristics of the transformed cell or organism. This method is useful for increasing diversity within populations of organisms, and creating new and useful phenotypes or characteristics in such organisms.

The present invention uses randomized in-frame fusion polynucleotides to create previously unknown phenotypes, or enhance existing phenotypes, in a target cell or organism. The present invention is directed to a composition comprising at least 2 discrete random polynucleotides randomly fused in-frame to form at least one randomized in-frame fusion polynucleotide. The randomized in-frame fusion polynucleotide can be operably linked to at least one regulatory sequence that controls expression of the randomized in-frame fusion polynucleotide where the regulatory sequence is a promoter, a terminator, or an untranslated sequence. In one embodiment, the randomized in-frame fusion polynucleotide is operably linked to a vector. The randomized in-frame fusion polynucleotide can be introduced into a host cell. In some cases the host cell can be regenerated into the organism from which the host cell was derived. The randomized fusion polypeptide causes a phenotype that is not present in a control cell or a control organism.

The invention is also directed to large scale methods of producing randomized in-frame fused polynucleotides by isolating polynucleotides from an organism and randomly joining the fragments in-frame. Another embodiment presents a method of altering the phenotype of a cell comprising introducing into a host cell the randomized in-frame fusion polynucleotide. Yet another embodiment presents a method for altering the phenotype of an organism by introducing a randomized in-frame fusion polypeptide into a host cell and then regenerating the organism from that cell. Yet another embodiment presents a method for identifying a randomized in-frame fusion polypeptide responsible for an altered phenotype by comparing the life cycle of the cell or organism containing the randomized in-frame fusion polypeptide to a control cell or organism, selecting the cell or organism containing the randomized in-frame fusion polypeptide that displays a phenotype absent in the control organism, isolating the randomized in-frame fusion polynucleotide encoding the randomized in-frame fusion polypeptide from the selected organism, introducing the isolated randomized in-frame fusion polynucleotide into another host cell and, if appropriate regenerating the organism from that host cell, and then comparing the randomized in-frame fusion polynucleotide containing cell or regenerated organism to a control organism to confirm that the observed altered phenotype remains.

In some embodiments, a collection of coding sequences (open reading frames or ORFs) is generated, and random pairs of ORFs are cloned into an expression vector as randomized translational fusions. This is done in a manner that each ORF present in the starting collection can be positioned in a 5' orientation with respect to the ORF it is fused to, or in a 3' orientation. The resulting library of randomized in-frame fusion polynucleotides is introduced into a target organism, and transformed cells or organisms are selected for the presence of the randomized in-frame fusion polynucleotide. In another embodiment, populations of transformed organisms are selected or screened for a novel phenotype. Transformed organisms with the desirable phenotype are of direct utility in a process that the target organism is typically used for.

The large-scale collections of randomized, in-frame fusion polynucleotides described can also be selected in an iterative fashion to arrive at smaller collections of in-frame fusion polynucleotides enriched for a particular function or ability to confer a phenotype of interest to an organism. Such enrichments can be performed in a manner that the in-frame fusion polynucleotides isolated at the end of each round of selection are kept intact. Alternatively, the enrichment is performed in a manner where the component sequences represented within the in-frame fusion polynucleotides isolated at the end of each round of selection are recombined with each other to arrive at potentially new combinations of sequences. This method may enrich for sequence combinations that may not have been represented at high levels in the starting collection. Such iterative procedures of introducing collections of randomized, in-frame fusion polynucleotides into an organism, performing a functional selection on the organism, re-isolating the in-frame fusion polynucleotides from the population of organisms present at the end of the selection, optionally recombining the polynucleotides present in this re-isolated population of fusion polynucleotides, and then repeating the procedure, is a very powerful way of obtaining polynucleotides capable of conferring specific phenotypes of interest.

BRIEF DESCRIPTION OF THE DRAWINGS

FIG. 6: *Escherichia coli* culture plates showing the results of cell survival assays performed on individual, cloned in-frame fusion polynucleotides to test for salt and heat tolerance of cells transformed with each clone. *E. coli* strain EC100 (Epicentre Technologies), transformed with 47 different in-frame fusion polynucleotides and the modified pUC19 control plasmid was cultured in the presence of 2.5M NaCl (A) or grown at 48° C. (B). After growth under selective conditions, each culture was diluted 1:10 in fresh medium, and 3 µl of the diluted and undiluted culture were spotted onto fresh medium and allowed to grow for 16 hours. A map of the plate identifying all clones tested and their relative position in the plate is shown (C). The data shown in this figure is a subset of the data represented in Table 3.

DETAILED DESCRIPTION OF THE INVENTION

Definitions

Figure 1:
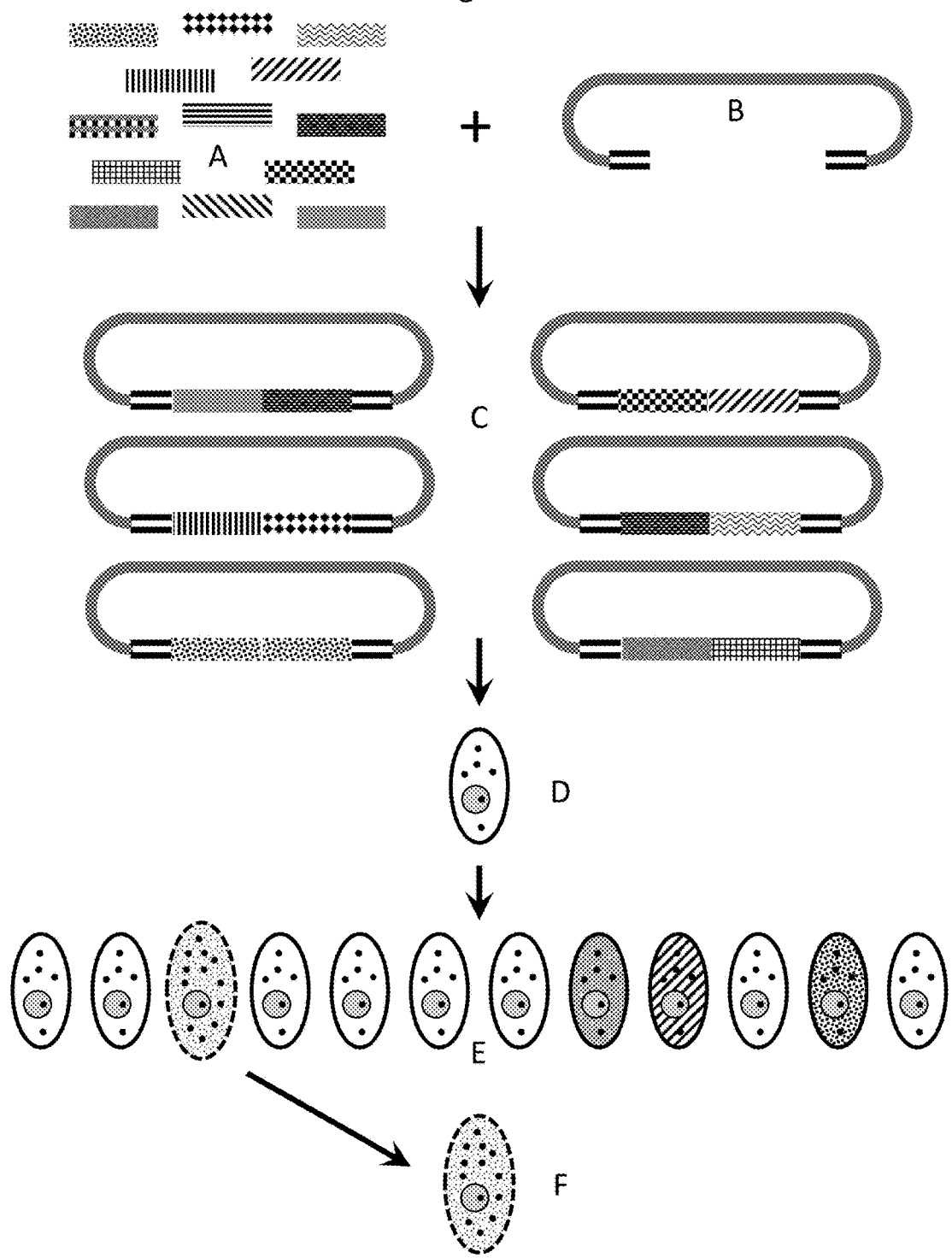
FIG. 1: Example of randomizing a collection of ORFs into randomized in-frame fusion polynucleotides and using these to alter an organism phenotypically. A collection of ORFs (A) is combined with a vector DNA molecule (B) in a manner where ORFs are combined in a randomized pairwise fashion, resulting in a large collection of randomized fused ORFs (C). The vector molecule in this example contains sequences mediating expression of the ORFs (double lines). The collection of randomized in-frame fusion polynucleotides is introduced into an organism (D), and transformants are isolated (E), some of which have altered phenotypes. Modified organisms with phenotypes of interest (F) are isolated from this population.

Composite open reading frame: As used herein, a composite open reading frame results from the in-frame fusion of at least two different starting open reading frames, resulting in a new open reading frame comprising all starting open reading frames and encoding a fusion protein comprising the sequences encoded by all starting open reading frames.

Degenerate Sequence: In this application degenerate sequences are defined as populations of sequences where specific sequence positions differ between different molecules or clones in the population. The sequence differences may be a single nucleotide or multiple nucleotides of any number, examples being 2, 3, 4, 5, 6, 7, 8, 9, 10, 20, 30, 40, 50, 60, 70, 80, 90, 100, 200, 300, 400, 500, 600, 700, 800, 900 or 1000 nucleotides, or any number in between. Sequence differences in a degenerate sequence may involve the presence of 2, 3 or 4 different nucleotides in that position within the population of sequences, molecules or clones. Examples of degenerate nucleotides in a specific position of a sequence are: A or C; A or G; A or T; C or G; C or T; G or T; C or G; A, C or T; A, G or T; C, or T; A, C, G or T.

Discrete Random Polynucleotide: A discrete random polynucleotide refers to a specific polynucleotide within a mixed collection of polynucleotides, chosen randomly from the collection.

Full-length Open Reading Frame: As used herein, a full-length open reading frame refers to an open reading frame encoding a full-length protein which extends from its natural initiation codon to its natural final amino-acid coding codon, as expressed in a cell or organism. In cases where a particular open reading frame sequence gives rise to multiple distinct full-length proteins expressed within a cell or an organism, each open reading frame within this sequence, encoding one of the multiple distinct proteins, can be considered full-length. A full-length open reading frame can be continuous or may be interrupted by introns.

Fusion polynucleotide: A fusion polynucleotide as used in this application refers to a polynucleotide that results from the operable joining of two separate and distinct polynucleotides into a single polynucleotide. In the context of this application, the term "in-frame fusion polynucleotide" is defined as a fusion polynucleotide encoding a fusion polypeptide.

Fusion polypeptide: A fusion polypeptide is an expression product resulting from the fusion of two or more open reading frames that originally coded for separate proteins.

In-Frame: The term "in-frame" in this application, and particularly in the phrase "in-frame fusion polynucleotide," refers to the reading frame of codons in an upstream or 5' polynucleotide or ORF as being the same as the reading frame of codons in a polynucleotide or ORF placed downstream or 3' of the upstream polynucleotide or ORF that is fused with the upstream or 5' polynucleotide or ORF. Such in-frame fusion polynucleotides typically encode a fusion protein or fusion peptide encoded by both the 5' polynucleotide and the 3' polynucleotide. Collections of such in-frame fusion polynucleotides can vary in the percentage of fusion polynucleotides that contain upstream and downstream polynucleotides that are in-frame with respect to one another. The percentage in the total collection is at least 10% and can number 10%, 11%, 12%, 13%, 14%, 15%, 20%, 25%, 30%, 35%, 40%, 45%, 50%, 55%, 60%, 65%, 70%, 75%, 80%, 85%, 90%, 95%, 96%, 97%, 98%, 99% or 100% or any number in between.

Iterate/Iterative: In this application, to iterate means to apply a method or procedure repeatedly to a material or sample. Typically, the processed, altered or modified material or sample produced from each round of processing, alteration or modification is then used as the starting material for the next round of processing, alteration or modification. Iterative selection refers to a selection process that iterates or repeats the selection two or more times, using the survivors of one round of selection as starting material for the subsequent rounds.

Non-homologous: The term "non-homologous" in this application is defined as having sequence identity at the nucleotide level of less than 50%.

Open Reading Frame (ORF): An ORF is defined as any sequence of nucleotides in a nucleic acid that encodes a protein or peptide as a string of codons in a specific reading frame. Within this specific reading frame, an ORF can contain any codon specifying an amino acid, but does not contain a stop codon. The ORFs in the starting collection need not start or end with any particular amino acid. The ORF may be continuous or may be interrupted by introns.

Percentage of sequence identity: The term "percent sequence identity" refers to the degree of identity between any given query sequence, e.g. SEQ ID NO:102, and a subject sequence. A subject sequence typically has a length that is from about 80 percent to 200 percent of the length of the query sequence, e.g., 80, 82, 85, 87, 89, 90, 93, 95, 97, 99, 100, 105, 110, 115, or 120, 130, 140, 150, 160, 170, 180, 190 or 200 percent of the length of the query sequence. A percent identity for any subject nucleic acid or polypeptide relative to a query nucleic acid or polypeptide can be determined as follows. A query sequence (e.g. a nucleic acid or amino acid sequence) is aligned to one or more subject nucleic acid or amino acid sequences using the computer program ClustalW (version 1.83, default parameters), which allows alignments of nucleic acid or protein sequences to be carried out across their entire length (global alignment, Chenna 2003).

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher website and at the European Bioinformatics Institute website on the World Wide Web (ebi.ac.uk/clustalw).

To determine a percent identity of a subject or nucleic acid or amino acid sequence to a query sequence, the sequences are aligned using Clustal W, the number of identical matches in the alignment is divided by the query length, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Phenotypic Value: Phenotypic value refers to a quantitative measure of a phenotype or a trait exhibited by an organism. For example, height measured in feet is a phenotypic value corresponding to body height in humans.

Random/Randomized: made or chosen without method or conscious decision.

Randomized In-frame Fusion Polynucleotides: As used herein, this phrase refers to polynucleotides in one or more starting populations fused to each other in a random manner to form randomized fusion polynucleotides, each randomized fusion polynucleotide comprising two or more members of the starting population(s). The random nature of the fusion is such that the association between different polynucleotides capable of fusing is not deliberately biased or directed, so that each starting polynucleotide has an equal or similar probability to be represented in the final population of fusion polynucleotides, and that it has an equal or similar probability to be fused with any other member of the starting population(s).

Randomized Translational Fusion: A randomized translational fusion is a process by which polynucleotides are randomly fused in a manner that the ORFs specified by the individual polynucleotide sequences are fused in-frame, to result in a fusion polynucleotide that encodes a fusion protein.

Randomly Fused: The term "randomly fused" refers to a process by which a collection of fused polynucleotides is generated from one or more collections of starting polynucleotides, where each member of the starting polynucleotide collection(s) has an equal or similar probability of joining to each other member. The objective of generating randomly fused polynucleotides is typically to generate possible combinations, or as many combinations as possible, of fused members or sequences.

Stringency of selection: The term "stringency of selection" refers to selection intensity, or the degree to which selective conditions affect the probability of an organism surviving the selection. A higher stringency of selection implies a higher selection intensity, with lower survival rates expected; a lower stringency of selection implies a lower selection intensity, with higher survival rates expected. Survival of a particular organism or population of organisms under selection ultimately depends on the fitness or viability of that organism or population of organisms under the selective conditions.

Transformed: The term "transformed" means genetic modification by introduction of a polynucleotide sequence.

Transformed Organism: A transformed organism is an organism that has been genetically altered by introduction of a polynucleotide sequence into the organism's genome.

One embodiment of the present invention is directed to a method for screening and sampling a large number of biochemical, genetic and interactive functions for a desired phenotype. Another embodiment of the present invention discloses a novel method of producing altered or improved cells or organisms by creating randomized in-frame fusions of open reading frames (ORFs), or fragments thereof, to create large libraries of polynucleotide combinations, which generate novel phenotypes and characteristics in organisms. Yet another embodiment of the present invention is directed to methods to generate collections of randomized in-frame fusion polynucleotides.

A collection of ORFs is generated as separate DNA fragments, or separate sequences of larger DNA fragments. A library of randomized in-frame fusion polynucleotides is then generated from one or more collections or pools of polynucleotides containing ORFs by combining two or more random polynucleotides, or fragments thereof, in a manner such that the combined polynucleotides can be expressed in the target cell as a randomized in-frame fusion peptide or polypeptide. The library of randomized in-frame fusion polynucleotides is generated in a fashion that allows many or all of the possible sequence combinations to be formed. The library is then introduced into an organism and allowed to express. The resulting collection of organisms expressing the randomized in-frame fusion polynucleotides is screened and/or selected for desirable phenotypes or characteristics. The polynucleotides responsible for the changes in the properties of a specific transformant can be recovered and used repeatedly.

The general concept of this approach is illustrated in FIG. 1. As an example, all polynucleotides encoded by an organism can be used in the construction of the randomized in-frame fusion polynucleotide library. In the case of the laboratory bacterium E. coli, for example, every one of the 5,286 proteins encoded by E. coli can be present in the initial collection of ORFs used to make the randomized in-frame fusion polynucleotide library. The randomized in-frame fusion polynucleotide library thus contains a very high number of polynucleotide combinations (5,286×5,286=2.8× $10^7$ total combinations), and the presence of novel functions within this combinatorial set of polynucleotides is consequently high.

The polynucleotides used to make up the initial set of ORFs, or fragments thereof, can be from any source (genome, metagenome, cDNA, etc) and can be any subset of polynucleotides from such a source, selected by sequence composition, function or other criteria. The method can thus be tailored to capture specific biochemical functions, or functions from specific source organisms or source environments.

The polynucleotides used to make up the initial set of ORFs will contain sequences that are primarily non-homologous and distinct from one another, as opposed to ORFs that share extensive sequence homology.

The ORFs in the starting collection can number at least 5 or higher, including at least 5, 6, 7, 8, 9, 10, 15, 20, 30, 40, 50, 100, 200, 300, 400, 500, 1000, 2000, 3000, 4000, 5000, 10000, 20000, 30000, 40000, 50000, 100000, 200000, 300000, 400000, 500000, 1000000 or higher. The number of randomized in-frame fusion polynucleotides in the library typically equals at least the number of ORFs in the starting collection and can be as many as the square of the number of ORFs in the starting collection, which would be the expected number of all possible polynucleotide combinations assuming that each ORF is present in both possible positions (5' and 3') and in combination with each other ORF. The number of randomized in-frame fusion polynucleotides in a library generated from fragments of ORFs would be expected to have an even greater number of combinations.

The ORFs in the starting collection can be derived from a single organism or from multiple organisms. Potential sources of the ORFs include, but are not limited to, random pieces of genomic DNA or amplified genomic DNA from any virus, bacterium, archaeon, prokaryote, eukaryote, protozoan, yeast, fungus, animal, alga or plant or mixed population thereof; bacterial ORFs present as complete or partial collections or pools of protein-coding sequences derived from the genomes of one or more bacteria, archaea or other prokaryote; collections of cDNAs present as individual clones or pools of protein-coding sequences from bacteria, archaea, any prokaryote or any eukaryotic organism randomized or partially randomized oligonucleotides; partially or fully random DNA sequences derived from randomized oligonucleotides by amplification.

The ORFs in the starting collection can comprise the entire collection of ORFs from an organism's genome, or a fraction thereof. The ORFs in a collection or pool can be pre-selected based on known function, sequence composition, sequence content, sequence homology, amino acid composition of the encoded proteins, sequence homology of the encoded proteins, length, presence of specific motifs, charge, hydrophobicity, isoelectric point, 3-dimensional structure or fold, ability to associate with other proteins, or any other property.

The ORFs in the starting collection can contain natural sequences or mutagenized sequences, including known variants of certain polynucleotides known to have a gain or loss of function, or an altered function. They can also contain degenerate sequences or sequences altered by mutagenesis. Multiple, degenerate nucleotides may be adjacent or separated by constant or fixed sequences that are not degenerate. The ORFs in the starting collection can be free of introns, such as the ORFs typically found in prokaryotes, or they may contain introns as are typically found in the ORFs of eukaryotes.

The ORFs in the starting collection can be derived from PCR fragments, PCR fragment pools, cDNAs, random pieces of genomic DNA, synthetic DNA, cloned DNA, DNA isolated directly from source organisms or from the environment, or from any other source, or any combination of sources.

The ORFs in a starting collection can be added in molar amounts corresponding to the concentrations of other ORFs, or in lower or higher amounts that change their representation within the final randomized in-frame fusion polynucleotide library. For example, if a polynucleotide coding for a specific protein conferring a desirable phenotype is suspected to have a particularly high chance of conferring that phenotype in a target organism, it is possible to over-represent this sequence in the ORF collection to ensure that most or all in-frame fusion polynucleotide combinations are tested in combination with the prioritized sequence.

The randomized in-frame fusion polypeptides can be designed in a manner that the ORFs are fused directly to each other, without any sequence inserted between the final codon of the upstream 5'ORF and the first codon of the downstream 3'ORF (or the other way around). Alternatively, the randomized in-frame fusion polypeptides are designed to have sequence insertions that encode additional amino acids between the two ORFs. These sequence insertions can range between 1 and 1000 codons in length, and encode "linker" peptide or polypeptide sequences that are suitable for separating the two parts of the randomized in-frame fusion polynucleotide. Small amino acids, such as glycine, alanine, serine, proline, threonine, aspartic acid or asparagine are suitable for linker peptides because they tend to form flexible and unstructured domains, or alpha-helical domains lacking bulky side groups. This allows separation between the two parts of the encoded randomized fusion polypeptide and allows each part of the encoded randomized fusion polypeptide to move independently relative to the other. Accordingly, sequence insertions separating the two fused ORFs may contain codons specifying these amino acids. Alternatively, the linker peptide sequence may be designed to contain a specific secondary structure, such as an alpha helix, beta sheet, coiled coil or turn, or combinations thereof, which permit the two domains of the encoded randomized fusion polypeptide to be separated by a specific structure or combinations of specific structures.

Each ORF can be generated to contain conserved 5' and 3' flanking sequences that match those at the 5' and 3' ends of other ORFs in the starting collection. These sequences are not part of the natural ORF and allow the ORFs to be amplified, cloned, isolated, and/or joined to other ORFs or to pieces of vector DNA. The conserved 5' and 3' flanking sequences can contain restriction sites, recombination sites, or any other sequence that permits specific joining to other ORFs, to vector sequences, or other sequences aiding in the transfer of the randomized in-frame fusion polynucleotide into an organism, replication within that organism, stability in that organism, or expression within that organism.

The ORFs in the starting collection can be full-length ORFs or partial ORFs and can range in size from 15 nucleotides to 100,000 nucleotides.

The ORFs in the starting collection can be configured to allow them to be placed at the 5' end of the resulting randomized in-frame fusion polynucleotide, or in the middle, or at the 3' end, or randomly at either position. The conserved sequences at the ends of the ORFs can be designed to allow such specific or non-specific placement. The library of randomized in-frame fusion polynucleotides may contain the same collection of ORFs at the 5' end, in the middle, and at the 3' end, or distinct collections of ORFs at each position.

The randomized in-frame fusion polynucleotides can be generated by a variety of methods for joining or cloning DNA molecules known to those skilled in the art including, but not limited to, traditional cloning using restriction enzymes and DNA ligase (ligation-dependent cloning), agarose gel-free cloning, ligation-independent (or ligation-free) cloning, site-specific recombination, homology-dependent cloning, recombinational cloning, homology-dependent end joining, annealing of single-stranded ends, linker tailing, topoisomerase-catalyzed cloning, enzyme-free cloning, and others. "Joining nucleic acid molecules" as used herein refers to any method that results in the molecules being operably linked at room temperature. Such methods include, but are not limited to, covalent linkage (ligation), annealing of complementary strands of nucleic acid molecules and other ways of associating two or more nucleic acid molecules.

Figure 2:
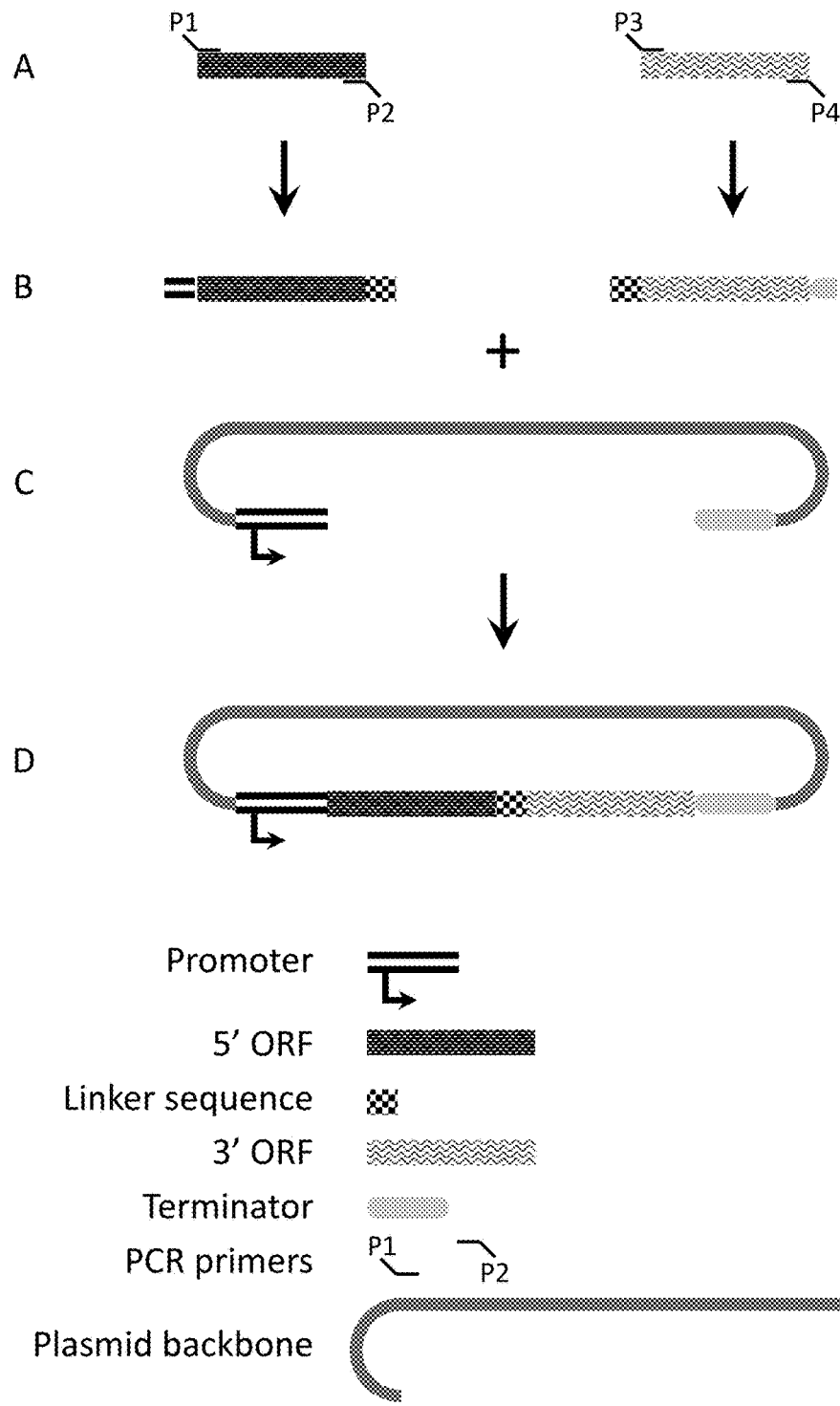
FIG. 2: Example of assembling two ORFs into an expression vector in a single step by homology-dependent cloning. (A) A 5' ORF and a 3' ORF are PCR amplified using sequence-specific primers (P1, P2, P3, P4). Each primer contains extra sequences at its 5' end that specifies homology to sequences in the other ORF or in the vector, corresponding to the order in which the fragments are to be assembled (see B). (B) The PCR-amplified ORFs containing the sequences homologous to each other and to the cloning vector. (C) The cloning vector is prepared to receive the PCR-amplified ORFs. (D) The PCR-amplified ORFs are combined with the cloning vector and assembled into a final construct by allowing the regions of homology between the three fragments to direct each fragment into the correct position and orientation. For simplicity, the Figure shows a single 5' ORF and a single 3' ORF, but the same method will work with mixtures containing any number of ORFs.

In a specific embodiment of the invention, homologous sequences at the ends of the 5' and 3' ORFs to be joined can be used to direct or mediate the joining event. A large number of methods exist that can be used to accomplish such homology-dependent assembly (Lobban 1973), including linker tailing (Lathe 1984) or derivatives thereof (da Costa 1998, Liu 2010), In-Fusion cloning (Zhu 2007, Irwin 2012), Sequence and Ligation-Independent Cloning (SLIC, Li 2007, Li 2012), FastCloning (Li 2011), Circular Polymerase Extension Cloning (Quan 2009, Quan 2011), the Gibson assembly method (Gibson 2009, Gibson 2010), Quick and Clean Cloning (Thieme 2011), and others (Vroom 2008). FIG. 2 shows an example of how homologous end sequence can direct construction of a precisely assembled circular molecule from three linear starting fragments.

Randomized in-frame fusion polynucleotides of this sort can impart new functions to an organism and change the organism's phenotype(s) in many different manners. To achieve such a change of phenotype, the library of randomized in-frame fusion polynucleotides is transformed into a target organism. The target organisms can be the source organism of some or all of the ORFs or ORF fragments used to make the randomized in-frame fusion polynucleotide library, or it can be a different organism. Target organisms include but are not limited to: E. coli, yeast, any species of bacteria, archaea, yeast, fungi, algae, cultured algal cells, insects, nematodes, vertebrates, animals, cultured animal cells, plants, or cultured plant cells. The target organism is generally an organism which is used for specific purposes, including, but not limited to, use in industry or agriculture, or in the production of chemicals, foods, fibers, structural materials, fuels, pharmaceuticals, agrochemicals, dyes, cosmetics or other useful substances.

Transformants of the target organism are generated which express members of the randomized in-frame fusion polynucleotide library. The transformants are be selected or screened for presence of the randomized in-frame fusion polynucleotides encoding the randomized fusion polypeptides, and allowed to express the polypeptides. The population of transformants is then selected or screened for any observable, selectable or measurable phenotype. Such phenotypes include, but are not limited to, changes or alterations in the following properties: growth rate; rate of cell division; generation time; size; color; texture; morphology; population density; productivity; yield; shape; growth habit; composition; metabolism; uptake or utilization of nutrients, minerals, salts, ions, toxins or water; photosynthetic efficiency; sensitivity to or resistance to abiotic stresses such as temperature, osmotic strength, salinity, pH, electromagnetic radiation, organic solvents, oxidation, oxidizing agents, detergents, drought, wind, desiccation, flood, nutrient limitation, starvation, oxygen limitation, light, pressure, compaction, shear or ionizing radiation; tolerance or resistance to biotic stresses such as diseases, pests, phages, viruses, infective agents, parasites or pathogens; appearance; reflective properties; fluorescent properties; refractivity; light-transmitting properties; electrical resistance, impedance or conductance; growth in the presence of specific nutrients; binding or adhesive properties; permeability; association or symbiosis with other organisms; pathogenicity; physical properties such as density, strength, hardness, brittleness, flexibility, rigidity, turgor pressure, electrical impedance, electrical resistance, electrical conductivity, magnetism, permeability, viscosity, color, texture or grain; behavior; response to environmental stimuli; expression of a polynucleotide; activity of an enzyme; rates of genetic or epigenetic change or mutation; ability to take up and/or integrate homologous or heterologous nucleic acid sequences; phenotypic diversity of a population; ability to be stained by dyes or compounds eliciting a change in color; resistance to antibiotics or toxins; resistance to penetration; quality of or production of products such as food, feed, fuel, fiber, structural materials, pharmaceutical compounds, cosmetics, dyes, chemicals, proteins, lipids, nucleic acids, fertilizers, feedstocks for the production thereof, or combinations or precursors thereof.

Organisms expressing one or more specific randomized in-frame fusion polynucleotide can be re-transformed with the same library of randomized in-frame fusion polynucleotides, a similar library, or a different library, and the process of selecting or screening for altered properties of the organism repeated. In this manner, an iterative approach of transformation, selection, re-transformation, re-selection, etc. can be used to continue altering properties or phenotypes of the organism.

A randomized in-frame fusion polynucleotide can also be re-isolated from an organism transformed with the randomized in-frame fusion polynucleotide. The re-isolation can be done using any of a number of methods including, but not limited to, PCR amplification and plasmid rescue (Ward 1990, Dolganov 1993) followed by plasmid transformation into a laboratory organism such as E. coli. After re-isolation, it is possible to re-transform the randomized in-frame fusion polynucleotide into the same organism and/or a different organism to confirm that the randomized in-frame fusion polynucleotide reproducibly confers the same phenotype in repeated experiments.

Figure 3:
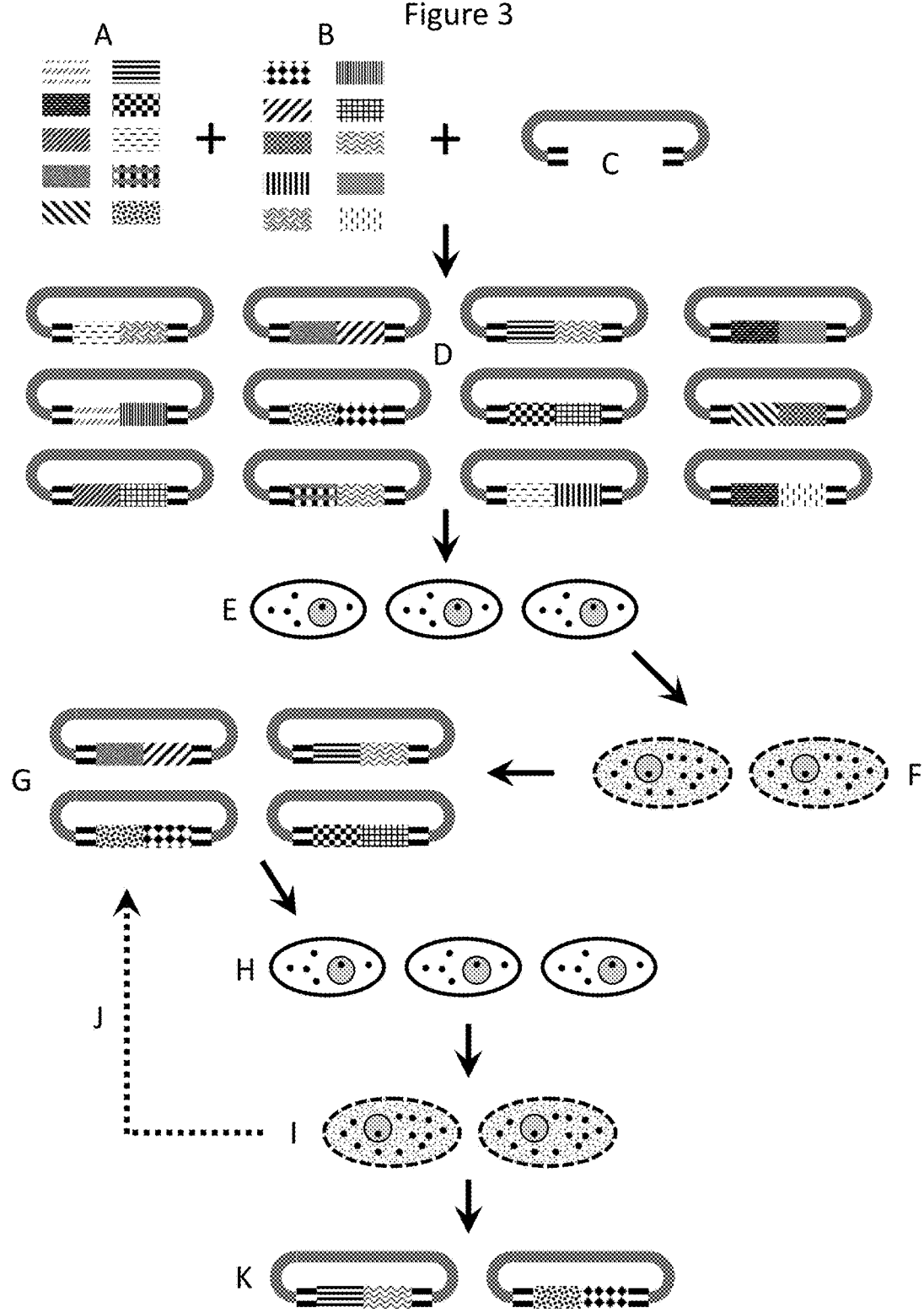
FIG. 3: Schematic representation of iterative selection of fusion genes to arrive at genes with high activity. A collection of 5' ORFs (A) and 3' ORFs (B) are combined with an expression vector molecule (C) in a manner that ORFs are combined in a randomized pairwise fashion, resulting in a large randomized collection of paired ORFs fused in-frame (D). The vector molecule in this example contains sequences mediating expression of the ORFs (double lines). The collection of randomized in-frame fusion polynucleotides is introduced into an organism (E), and transformants are isolated, some of which have altered phenotypes. Modified organisms with phenotypes of interest are isolated from this population (F). The randomized fusion polynucleotides expressed in transformants with altered phenotypes are re-isolated (G), re-transformed into the original cell population (H) and selected for a desirable phenotype (I), resulting in a smaller collection of in-frame fusion polynucleotides conferring the desirable phenotype (K). The steps of re-isolation (G), re-transformation (H) and re-selection (I) can be repeated one or more additional times if necessary (J). Multiple phenotypes can be selected for in the course of this iterative procedure. At the end of this iterative selection procedure, individual active fusion polynucleotides are obtained (K) that reproducibly confer the phenotype of interest.

In another embodiment of the invention, an iterative selection can be performed with the library of randomized in-frame fusion polynucleotides to arrive at sequentially smaller collections of in-frame fusion polynucleotides capable of conferring a phenotype of interest. FIG. 3 shows an example of such an iterative selection, in which a library of randomized in-frame fusion polynucleotides is introduced into an organism, selected for a phenotype of interest, and the plasmids encoding putative active in-frame fusion polynucleotides re-isolated from the population of selected organisms. This selected population of plasmids encoding putative active in-frame fusion polynucleotides conferring a phenotype of interest can now be re-introduced into the organism, or introduced into another organism, for a second round of phenotypic selections. After two or more rounds of selection, active in-frame fusion polynucleotides may be obtained that are different, or that have different activity, than those obtained in a single round of selection.

Figure 4:
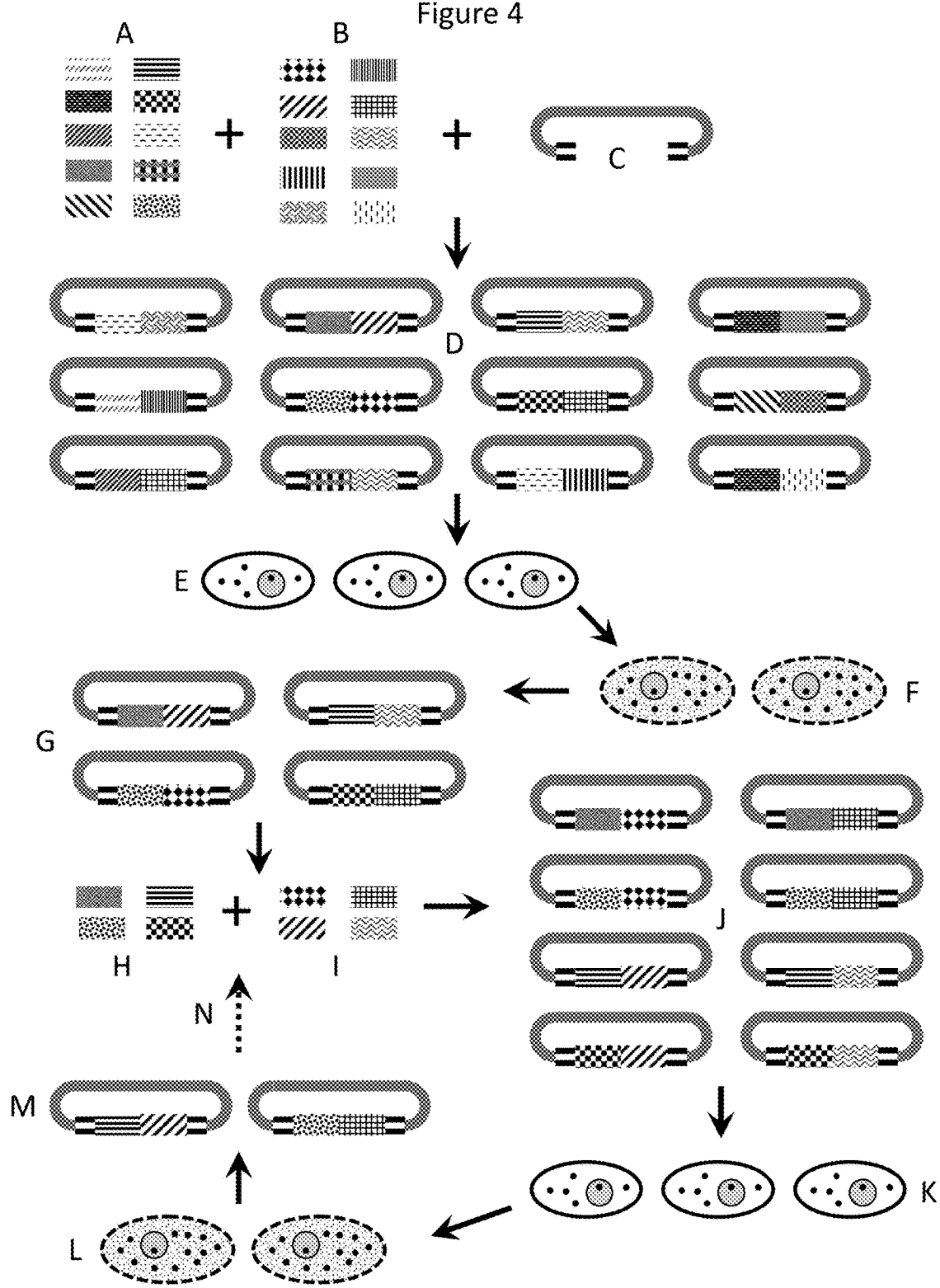
FIG. 4: Schematic representation of iterative selection of in-frame fusion polynucleotides accompanied by recombination of selected in-frame fusion polynucleotides to arrive at proteins conferring a phenotype of interest. A collection of 5' ORFs (A) and 3' ORFs (B) are combined with an expression vector molecule (C) in a manner where the ORFs are combined in a randomized pairwise fashion, resulting in a large randomized collection of paired ORFs fused in-frame (D). The vector molecule in this example contains sequences mediating expression of the ORFs (double lines). The collection of randomized in-frame fusion polynucleotides (D) is introduced into an organism (E), and transformants are isolated, some of which have altered phenotypes. Modified organisms with phenotypes of interest (F) are isolated from this population and the randomized in-frame fusion polynucleotides are purified (G) from the selected transformants. The 5' ORFs (H) and 3' ORFs (I) contained therein are re-isolated. These selected ORF sets are assembled together with an expression vector molecule to result in a new and smaller collection of randomized in-frame fusion polynucleotides (J). The new collection is re-transformed into the organism (K), transformants are selected for a desirable phenotype (L), and the randomized in-frame fusion polynucleotides (M) are isolated from the selected transformants, resulting in a smaller collection of randomized in-frame fusion polynucleotides conferring the desirable phenotype. The steps of re-isolation (G, H, I), re-assembly of a randomized fusion polynucleotide library (J), re-transformation (K), re-selection (L) and subsequent isolation of the resulting randomized in-frame fusion polynucleotide (M) can be repeated one or more additional times if desired (N). Multiple phenotypes can be selected for during the course of this iterative procedure. At the end of the iterative selection procedure, individual randomized in-frame fusion polynucleotides are obtained (M) that reproducibly confer the phenotype of interest.

In another embodiment of the invention, an iterative selection can be performed with the library of randomized in-frame fusion polynucleotides in a manner that the 5' and 3' ORFs are recombined with each other to arrive at sequentially smaller collections of randomized in-frame fused polypeptides conferring a higher frequency of desirable phenotypes of interest and/or more desirable phenotypic values. FIG. 4 shows an example of such an iterative selection, in which a library of randomized in-frame fusion polynucleotides is introduced into an organism, selected for a phenotype of interest, and the plasmids encoding the in-frame fusion polynucleotides re-isolated from the population of selected organisms. The 5' ORFs and 3' ORFs are then isolated from the population of plasmids, for example by PCR amplification, and are used as starting sequence collections for construction of a new library of iterated in-frame fusion polynucleotides.

The resulting recombined or re-assembled library of in-frame fusion polynucleotides contains the sequences isolated from cells obtained by selection, and allows the sequences enriched during selection to be recombined with each other randomly. In the process it is possible that new combinations of in-frame fusion polynucleotides are formed that were not present in the starting library used for the first or previous round of selection. It is also possible that specific sequences are represented at different levels in the re-assembled library of in-frame fusion polynucleotides than in the original library. The re-assembled library can now be re-introduced into the organism, or introduced into another organism, for a second or subsequent round of phenotypic selections. After two or more rounds of selection, in-frame fusion polynucleotides may be obtained that are different, confer different phenotypes and/or phenotypic values, or that have different activity than those obtained in a single round of selection.

In the context of iterative selection of randomized in-frame fusion polynucleotides capable of conferring a phenotype of interest, specific sequences may be added to a collection of 5' ORFs and 3' ORFs, to be included in the re-assembled library or collection of iterated randomized in-frame fusion polynucleotides.

In another embodiment of the invention, error-prone PCR can be used during such iterative selection methods, specifically for re-amplification of 5' ORFs and/or 3' ORFs from plasmids isolated from a population of selected organisms, to introduce additional sequence diversity into polynucleotide sequences associated with a specific phenotype of interest. For example, use of lower-fidelity thermostable polymerases (Cline 1996, Biles 2004), or PCR-based incorporation of mutagenic nucleotide analogs such as 8-oxo-dGTP, dPTP, 5-bromo-dUTP, 2-hydroxy-dATP and dITP (Spec 1993, Kuipers 1996, Zaccolo 1996, Zaccolo 1999, Kamiya 2004, Kamiya 2007, Ma 2008, Petrie 2010, Wang 2012a) can be used to introduce random mutations into target sequences during PCR amplification, and to increase the sequence diversity of a starting sequence or population of sequences.

The iterative rounds of phenotypic selection as described above can be for the same phenotype, or the same phenotype at a different stringency of selection, or for a different phenotype. For example, when selecting for tolerance to a toxic compound, an initial selection can be performed at a concentration of the compound of 2%, which may be growth inhibitory but not lethal. One round of selection under such conditions may result in a selected population of organisms that exhibit a growth advantage at 2% of the selective agent. The in-frame fusion polynucleotides represented within this selected population of organisms can be re-introduced into the same organism or another organism, and subjected to either the same selection, or to a more stringent selection, for example at 3% of the compound. At this concentration, the toxic compound may be lethal to the wild-type organism. Introduction of the selected in-frame fusion polynucleotides, or of a new library of iterated and/or re-assembled in-frame fusion polynucleotides produced from the selected in-frame fusion polynucleotides, into the organism may result in a higher proportion of the organisms that are tolerant of or capable of growth in 3% of the toxic compound than would be the case if the initial selection had been performed at 3%. Alternatively, the selected in-frame fusion polynucleotides can be iterated and re-assembled to form a new library for introduction into the organism. Moreover, due to the enrichment for specific sequences that may have occurred during the first round of selection of in-frame fusion polynucleotides capable of conferring tolerance or resistance to the toxic compound, a different set of in-frame fusion polynucleotides may be represented after the second round of selection than would have been found if the selection had been performed in a single round at 3% of the toxic compound. In addition, this final set of in-frame fusion polynucleotides may contain polynucleotides that confer a higher level of tolerance or resistance to the toxic product than would have been found if the selection had been performed in a single round at 3% of the toxic product.

Iterative selections performed after introduction of libraries of randomized in-frame fusion polynucleotides into an organism, as described above and represented in FIG. 3, can be performed using 2 or more rounds of selection, such as 2, 3, 4, 5, 6, 7, 8, 9, 10, 20, 30, 40, 50, 60, 70, 80, 90 or 100 rounds, or more, or any number in between.

Iterative selections performed after introduction of libraries of random in-frame fusion polynucleotides into an organism, accompanied by isolation of the component polynucleotides and their re-assembly into a new collection of random in-frame fusion polynucleotides as described above and represented in FIG. 4, can be performed using 2 or more rounds of selection, such as 2, 3, 4, 5, 6, 7, 8, 9, 10, 20, 30, 40, 50, 60, 70, 80, 90 or 100 rounds, or more, or any number in between, with re-assembly of new collections of random in-frame fusion polynucleotides between 1 or more of these rounds of selection.

An organism expressing a randomized in-frame fusion polynucleotide and having an altered phenotype as a result of the randomized in-frame fusion polynucleotide can be used as a starting point for further phenotypic changes by transforming this organism again with a library of randomized in-frame fusion polynucleotides. The library of random in-frame fusion polynucleotides in the second round of improvement can be the same library that was used to generate the organism with an altered phenotype, or it can be a different library. Such iterative rounds of transformation of an organism with randomized in-frame fusion polynucleotide libraries and selection for phenotypes can result in multiple phenotypic changes, or phenotypic changes that are more profound than can be achieved with a single round of transformation and selection.

In another embodiment of this invention, a collection of organisms transformed with a library of randomized in-frame fusion polynucleotides is selected or screened for alterations in the expression of polynucleotide sequences, either homologous or heterologous to the organism, compared to control organisms transformed with empty vector sequences.

In another embodiment of this invention, a collection of organisms transformed with a library of randomized in-frame fusion polynucleotides is selected or screened for altered rates of genomic or genetic changes. These genomic and genetic changes include but are not limited to: point mutations; sequence insertions, deletions, or inversions; repeat copy number variation; chromosomal translocations; chromosome crossovers; gene conversion; alterations in the distribution, prevalence, position or expression of transposons; uptake of foreign nucleic acid sequences; integration of foreign nucleic acid sequences; or combinations thereof resulting in complex sequence changes and genome rearrangements.

In yet another embodiment of this invention, a collection of organisms transformed with a library of randomized in-frame fusion polynucleotides is selected or screened for higher yield of a material or compound produced by the organism.

In a further embodiment of the invention, a collection of organisms transformed with a library of randomized in-frame fusion polynucleotides is selected or screened for the absence of genetic checkpoints that limit the growth rate, productivity or other properties of the cell or organism. In particular, this allows isolation of organisms with constitutive production of a material or compound that is naturally produced only in certain physiological or growth states, or is produced at maximal levels only in certain physiological or growth states.

In another embodiment of the invention, a collection of organisms transformed with a library of randomized in-frame fusion polynucleotides is selected or screened for altered activity or specificity of enzymes or biochemical pathways expressed by the cell.

In a still further embodiment of the invention, the collection of randomized in-frame fusion polynucleotides is made by randomly fusing one or a small number of polynucleotides of interest with a larger collection of polynucleotides. In this manner it is possible to create a collection of variants or mutants of the polynucleotides of interest, which can be screened for specific properties. In particular, in this manner it is possible to screen for enzymes with higher activity, altered activity, altered temperature optimum, altered pH optimum, resistance to high temperatures or extreme pHs, resistance to acids or bases, resistance to desiccation, resistance to organic solvents, resistance to high salt concentrations, resistance to proteases, or other desirable properties of an enzyme.

EXAMPLES

Example 1: Isolation of Randomized In-Frame Fusion Polynucleotides Capable of Conferring Heat, Salt, Ethanol and Butanol Tolerance to *Saccharomyces cerevisiae*

Product tolerance traits of production microbes are important factors that contribute to maximal yields and titers of fermentation products (Ding 2009, Jia 2009, Dunlop 2011). Ethanol and butanol are industrial products that are toxic and therefore the subject of various efforts aimed at increasing the tolerance of yeast cells to these alcohols. Butanol is featured as a target of this example because it is representative of medium-chain fuels and chemicals, many of which have high toxicity and whose production is being attempted and optimized in microbes (Dunlop 2011, Jang 2012, Lee 2012). Butanol is a chemical feedstock used for the production of many other chemicals (Mascal 2012). Tolerance to heat, salt and low pH are also industrially relevant properties of production organisms as many production systems generate heat, are conducted in an environment containing salts (i.e. NaCl) or an otherwise high-osmotic environment, or are conducted at or generate low pH.

Producing a *Saccharomyces cereviseae* Collection of Randomized In-Frame Fusion Polynucleotides A collection or library of *Saccharomyces cerevisiae* in-frame fusion polynucleotides is prepared as described in U.S. patent application Ser. No. 14/134,619 and International Patent Application Serial Number PCT/US13/76526. The randomized in-frame fusion polynucleotides are cloned into a vector molecule, such as a p416-GAL1 derivative. This p416-GAL1 derivative vector is derived from the yeast centromeric plasmid p416-GAL (Funk 2002), which contains the following sequences for plasmid propagation in yeast and *E. coli* and expression of an inserted polynucleotide: the bacterial replicon of plasmid pMB1, the bacterial ampicillin/carbenicillin-resistance gene, the yeast CEN6/ARSH4 cassette (Sikorski 1989) containing the chromosome 6 centromere and the yeast histone H4-associated autonomously replicating sequence (ARS), the yeast URA3 prototrophic marker gene, and the yeast GAL1 promoter and CYC1 terminator placed adjacent to each other in a manner that allows insertion of coding regions in between to allow their expression. The sequence of this p416-GAL1 derivative is given in SEQ ID NO:127. All randomized in-frame fusion polynucleotides are cloned between nucleotide numbers 3206 and 3207 of SEQ ID NO:127. The vector is PCR amplified using oligonucleotides PG0085A (SEQ ID NO:147) and PG0088A (SEQ ID NO:148) for use in assembly of the randomized in-frame fusion polynucleotide collection.

Each of the 5' ORFs prepared for the randomized in-frame fusion polynucleotide collection is flanked by the conserved sequence SEQ ID NO:139 at its 5' end and by the conserved sequence SEQ ID NO:140 at its 3' end. For re-assembly of 5' ORFs into new randomized in-frame fusion polynucleotide collections (described below), pools of 5' ORFs are PCR amplified using oligonucleotides PG0085 (SEQ ID NO:143) and PG0100 (SEQ ID NO:144).

Each of the 3' ORFs prepared for the randomized in-frame fusion polynucleotide collection is flanked by the conserved sequence SEQ ID NO:141 at its 5' end and by the conserved sequence SEQ ID NO:142 at its 3' end. For re-assembly of 3' ORFs into new randomized in-frame fusion polynucleotide collections (described below), pools of 3' ORFs are PCR amplified using oligonucleotides PG0101 (SEQ ID NO:145) and PG0088 (SEQ ID NO:146).

Sequence Amplification General Method

All PCR amplifications are performed using the following method.

The two amplification primers, each at a final concentration of 1.2 µM, are combined with 10 ng of template DNA, PCR buffer and thermostable polymerase in a total reaction volume of 50 µl. A high-fidelity thermostable polymerase such as Phusion™ Hot Start II thermostable high-fidelity polymerase (Thermo Scientific) can be used. For Phusion™ polymerase, the 5× HF amplification buffer supplied with the enzyme is used for all amplifications. All amplifications are performed on T100 thermal cyclers (Bio-Rad Laboratories) containing 96-well blocks. The deoxynucleotide triphosphates (dNTPs) used in all amplifications are a stock containing 10 mM of each dNTP, also obtained from Thermo Scientific. Deionized water is used in all reactions and to make all solutions not supplied with the polymerase. PCR amplicons are generated by denaturing at 95° C. for 2 minutes followed by 10-35 cycles of: 20 seconds at 95° C., 20 seconds at 60° C., and 1 min/kb at 72° C. (but a minimum of 30 seconds at 72° C.). The efficiency of formation of the PCR product is measured by agarose electrophoresis or by fluorescent spectroscopy using a fluorometer, such as a Qubit® fluorometer (Life Technologies). Successful PCR reactions can be purified using silica resins suitable for DNA purification. Unsuccessful reactions are repeated by varying the $Mg^{+2}$ concentrations in the PCR reaction and/or other reaction conditions. Following successful amplification of each ORF, the concentration of each PCR product is normalized, and products corresponding to specific size ranges are pooled.

All PCR amplifications follow the same general procedure:

1. A PCR mix as described below is prepared for each stage of the PCR reaction, and is kept cold until inserted into the thermal cycler.

2. The samples are mixed thoroughly and then centrifuged at 4000 rpm for 1 minute to bring the reaction contents to the bottom of the tube or well in a plate.

3. The plates or tubes are inserted into a thermal cycler.

Yeast Transformation

Yeast transformations are performed by the lithium acetate—heat shock method (Gietz 2002, Gietz 2006, Gietz 2007). The yeast strain BY4741 (Brachmann 1998) from a plate or an overnight culture is inoculated into 50 ml of YPD medium (20 g Bacto Peptone, 10 g Bacto Yeast Extract and 20 g Glucose per liter) at 30° C. on a shaker at 225 rpm from a starting density of $5×10^6$ cells/ml, and grown over several hours to a final cell density of $2×10^7$ cells/ml. The cells are harvested by centrifuging at 3000 g for 5 mM, are then resuspended in 25 ml of sterile deionized water, centrifuged again. Cells are resuspended in 1 ml of sterile water, transferred to a 1.5 ml microcentrifuge tube, centrifuged for 30 sec at 3000 rpm and the supernatant aspirated. The cell pellet is then resuspended in 0.4 ml of sterile deionized water. The cell suspension is combined with 3.26 ml of transformation mix (2.4 ml of 50% w/v PEG 3350, 360 µl 1M Lithium acetate and 500 µl 10 mg/ml sheared, boiled salmon sperm DNA) and mixed well. Aliquots of DNA (100 ng-1 µg) are pipetted into separate 1.5 ml microcentrifuge tubes and combined with 380 µl of the cell suspension in transformation mix. The cell/DNA mixture is mixed thoroughly and is incubated at 42° C. on a shaker at 250 rpm for 40 minutes. The transformations are then centrifuged for 1 minute at 3000 rpm in a microcentrifuge, the supernatant aspirated and each cell aliquot resuspended in 0.5-1 ml sterile deionized water. Depending on the desired density of colonies, 10 µl to 1 ml of the cell suspension are plated with sterile 4 mm glass beads onto one 10 cm or 15 cm plate containing synthetic complete uracil dropout medium having glucose as a carbon source (for 1 L, 6.7 g yeast nitrogen base, 0.77 g uracil dropout mix, 15 g Bacto agar, 120 µl 10N NaOH to bring the pH to 5.6-5.8, and 20 g glucose). After drying, the plates are covered and incubated at 30° C. or at a selective temperature for several days until colonies of transformants have formed.

Screening for In-Frame Polynucleotides Conferring Heat, Salt, Low pH, Ethanol and Butanol Tolerance After formation of colonies or lawns of cells transformed with randomized in-frame fusion polynucleotides, the transformed cells are removed from the selective plates by scraping with glass beads. This is done by adding to each 10 cm plate 5 ml synthetic complete uracil dropout medium with galactose as a carbon source (for 1 L, 6.7 g yeast nitrogen base, 0.77 g uracil dropout mix, 120 µl 10N NaOH to bring the pH to 5.6-5.8 and, added after autoclaving, 100 ml sterile-filtered 20% galactose) together with 10×4 mm glass beads. Proportionally higher volumes of medium are added to larger plates. Using swirling and horizontal shaking motions to allow the glass beads to dislodge the yeast cells from the surface of the agar, the resuspended cells are collected with a pipet, using additional medium if desired to wash any remaining cells off the plate. Cells collected in this fashion are pelleted by centrifugation at 4000 rpm for 5 minutes. Cells are resuspended in synthetic complete uracil dropout medium with galactose as a carbon source at a cell density of $5×10^6$ cells/ml and cultured at 30° C. shaking at 250 rpm for 4-12 hours. This pre-culturing step allows induction of the GAL1 promoter used to express the randomized in-frame fusion polynucleotides.

For heat tolerance selection, cells are plated on synthetic complete uracil dropout medium with galactose as a carbon source. The cells are spread on the plate using 10-15 4 mm sterile glass beads. After drying, the plates are incubated at 30° C. for 24 hours followed by incubation at 40° C. for four days. Individual colonies able to resist the high temperature are visible 5 days after plating.

Alternatively, heat tolerant cells are selected in liquid culture. Population of yeast transformants containing in-frame fusion polynucleotides are suspended in synthetic complete uracil dropout medium with galactose as a carbon source at a cell density of $5×10^6$ cells/ml in 50 ml of medium in a 500 ml flask and cultured at 40-42° C. shaking at 250 rpm for 7 days.

For selection of randomized in-frame fusion polynucleotides conferring salt tolerance, cells are pre-cultured in synthetic complete uracil dropout medium with galactose as a carbon source, and are then plated on synthetic complete uracil dropout medium with galactose as a carbon source and containing 1M NaCl (for 1 L, 6.7 g yeast nitrogen base, 0.77 g uracil dropout mix, 120 µl 10N NaOH to bring the pH to 5.6-5.8, 15 g Bacto Agar, 58.44 g NaCl and, added after autoclaving, 100 ml sterile-filtered 20% galactose). The cells are spread on the plate using 10-15 4 mm sterile glass beads. After drying, the plates are incubated at 30° C. for five days. Individual colonies able to resist the high salt are visible 5 days after plating.

Alternatively, salt tolerant cells are selected in liquid culture. Populations of yeast transformants containing randomized in-frame fusion polynucleotides are suspended in synthetic complete uracil dropout medium with galactose as a carbon source and containing 1.5-2M NaCl, at a cell density of $5×10^6$ cells/ml in 50 ml of medium in a 500 ml flask, and cultured at 30° C. with shaking at 250 rpm for 7 days.

For selection of randomized in-frame fusion polynucleotides conferring low pH tolerance, populations of yeast transformants containing randomized in-frame fusion polynucleotides are suspended in synthetic complete uracil dropout medium with galactose as a carbon source and containing 0.1M sodium acetate pH 3.0 (prepared by mixing 2.74 ml glacial acetic acid with 0.11 g anhydrous sodium acetate in 50 ml final volume in a 50 ml tube and filter sterilized by filtering through a 0.2 micron filter), at a cell density of $5 \times 10^6$ cells/ml in 50 ml of medium in a 500 ml flask and cultured at 30° C. with shaking at 250 rpm for 7 days.

For selection of randomized in-frame fusion polynucleotides conferring ethanol tolerance, populations of yeast transformants containing randomized in-frame fusion polynucleotides are suspended in synthetic complete uracil dropout medium with galactose as a carbon source and containing 15% ethanol, at a cell density of $5 \times 10^6$ cells/ml in 50 ml of medium in a 500 ml flask and cultured at 30° C. with shaking at 250 rpm for 7 days.

For selection of randomized in-frame fusion polynucleotides conferring butanol tolerance, populations of yeast transformants containing randomized in-frame fusion polynucleotides are suspended in synthetic complete uracil dropout medium with galactose as a carbon source and containing 3% butanol, at a cell density of $5 \times 10^6$ cells/ml in 50 ml of medium in a 500 ml flask and cultured at 30° C. with shaking at 250 rpm for 7 days.

Alternative conditions can also be used for selection of randomized in-frame fusion polynucleotides conferring tolerance to heat, salt, low pH, ethanol and butanol. For most yeast strains the following conditions are growth inhibitory and can be used for selections: temperatures at or above 39° C.; salt concentrations above 1.25 M; pH values at or below pH 4.0; ethanol concentrations above 9%; and butanol concentrations above 1.5%.

After completing selections in liquid medium for heat, salt, low pH, ethanol and/or butanol tolerance, the selected cultures are transferred to 50 ml centrifuge tubes, pelleted by centrifugation for 5 minutes at 4000 rpm, and the supernatant decanted. The cell pellet is resuspended in 0.2-1.0 ml of synthetic complete uracil dropout medium containing glucose as a carbon source (volume dependent on the size of the cell pellet), and aliquots of the cell suspension plated on synthetic complete uracil dropout medium containing glucose as a carbon source (for 1 L, 6.7 g yeast nitrogen base, 0.77 g uracil dropout mix, 15 g Bacto agar, 120 µl 10N NaOH to bring the pH to 5.6-5.8, and 20 g glucose). After drying, the plates are incubated at 30° C. for 2-3 days. Colonies arising on the plates are then processed in the same manner as colonies arising on solid selective media (described for heat and salt tolerance selections above) before further manipulation.

Iterative Selection of Randomized In-Frame Fusion Polynucleotides Conferring Heat, Salt, Low pH, Ethanol and Butanol Tolerance To enrich for randomized in-frame fusion polynucleotides that confer the most desirable possible phenotypic values of a desirable trait, it is often useful to perform iterative selections. This procedure allows for gradual enrichment of randomized in-frame polynucleotides conferring tolerance to various abiotic stresses, and for isolation of in-frame fusion polynucleotides containing the best combinations of sequences for conferring tolerance phenotypes or other phenotypes of interest. Successive cycles of yeast transformation, selection, plasmid extraction, cloning into *E. coli* and plasmid purification will result in populations of randomized in-frame fusion polynucleotides that effectively confer a trait of interest. This cycle of manipulations can be performed efficiently with populations of polynucleotides as opposed to individual isolates that are all maintained separately.

Starting with yeast cells recovered from colonies grown from transformants containing randomized in-frame fusion polynucleotides that survived selections with heat, salt, low pH, ethanol or butanol, iterative selections are performed as follows.

The cells are collected by centrifugation and plasmid DNA is purified using a commercial kit (for example the Zymoprep™ yeast plasmid miniprep kit from Zymo Research), following the manufacturer's instructions. The resuspended DNA is introduced into the DH10B (Life Technologies) or EC100 (Epicentre Technologies) strain of *E. coli* by electroporation. 1 µl DNA is combined with 25 µl electrocompetent cells on ice, transferred into a 1 mm gap size electroporation cuvette, and electroporated at 1.5 kV using a Bio-Rad MicroPulser™ electroporator. Cells are suspended in 0.5 ml LB broth, allowed to recover for 1 hour at 37° C. on a shaker and transformed cells plated in 0.2 ml aliquots onto plates containing LB agar medium with 50 µg/ml carbenicillin.

Bacterial colonies or lawns arising on the plate are removed from the plate by scraping with glass beads as described above, the cells are pelleted by centrifugation, and plasmid DNA is purified from them using standard methods (Sambrook 1989).

The recovered, purified plasmid DNA is then re-introduced into yeast by lithium acetate heat shock transformation as described above (Gietz 2006). Colonies or lawns of cells arising from the re-introduction transformation are scraped from the cells with glass beads as described above, and the cells are suspended in minimal synthetic complete uracil dropout medium containing galactose as a carbon source. The cells are then used for another round of selections for heat, salt, ethanol, butanol of low pH tolerance, or selections for other desirable phenotypes.

Iterative Selection of Randomized In-Frame Fusion Polynucleotides Conferring Heat, Salt, Low pH, Ethanol and Butanol Tolerance by Re-Amplifying and Re-Assembling Polynucleotides Represented in the Selected Population As noted above, iterative selections for heat and salt tolerance can be performed by serial rounds of transforming yeast with collections of randomized in-frame fusion polynucleotides contained within plasmids, selecting for heat or salt tolerance, extracting the plasmid DNA from surviving cells and reintroducing the extracted plasmid DNA into *E. coli* and purifying plasmid from the resulting *E. coli* transformants. However, improved results can be obtained with additional steps of re-amplifying the 5' ORFs and 3' ORFs represented in the survivors of the previous round of selection and re-assembling these re-amplified ORFs into a new collection of randomized in-frame fusion polynucleotides, which is then introduced into yeast and the resulting transformants used for one or more additional rounds of selection.

The randomized in-frame fusion polynucleotide plasmid DNA isolated from cells/colonies surviving a selection for heat, salt, low pH, ethanol or butanol tolerance, or complete genomic DNA isolated from the same cells, is used to re-amplify the 5' ORFs and 3' ORFs present in the randomized in-frame fusion polynucleotides. The amplification is performed as described above, using oligonucleotides PG0085 (SEQ ID NO:143) and PG0100 (SEQ ID NO:144) for amplifying the 5' ORFs, and using oligonucleotides PG0101 (SEQ ID NO:145) and PG0088 (SEQ ID NO:146) for amplifying the 3' ORFs. Optionally, mutations can be introduced into the 5' ORFs and 3' ORFs in the course of PCR amplification, using either lower-fidelity thermostable polymerases (Cline 1996, Biles 2004), or PCR-based incorporation of mutagenic nucleotide analogs such as 8-oxo-dGTP, dPTP, 5-bromo-dUTP, 2-hydroxy-dATP and dITP (Spee 1993, Kuipers 1996, Zaccolo 1996, Zaccolo 1999, Kamiya 2004, Kamiya 2007, Ma 2008, Petrie 2010, Wang 2012a). The re-amplified 5' ORFs and 3' ORFs are electrophoresed on a 1.5% agarose gel to remove amplification products below 200 bp in size and are purified from the gel using a commercial kit. The p416-GAL1 vector DNA is also re-amplified and purified after electrophoresis.

Re-Assembly of Re-Amplified ORFs into a Random In-Frame Fusion Polynucleotide Collection The purified, re-amplified 5' ORFs and 3' ORFs are re-assembled with the p416-GAL1 vector DNA as described below and are introduced into E. coli as a new collection of randomized in-frame fusion polynucleotides, and the resulting plasmid DNA is purified using a commercially available plasmid purification kit, following the manufacturer's recommendations. This is done using a ligation-independent cloning method. The following single-tube procedure uses a single-stranded exonuclease to create single-stranded tails at the ends of the DNA molecules to be assembled, followed by annealing of the homologous ends and fill-in of the remaining single-stranded regions. The purified DNA fragments resulting from PCR amplification of the expression vector backbone and 5' and 3' ORFs (see above) are combined in roughly equimolar amounts for a total of approximately 100 ng DNA in a 10 μl reaction. A 10× assembly buffer (500 mM Tris-HCl pH 8.0, 100 mM MgCl$_2$, 100 mM β-mercaptoethanol, 1 mM each of the 4 dNTPs) is added to produce a 1× concentration. Also added to the reaction are 0.01 unit of a single-stranded exonuclease and 1 unit of a thermostable, high-fidelity hot-start polymerase such as Phusion™ polymerase. Hot start implies that at physiological temperatures the polymerase is in an inactive form, for example being bound by an antibody or other compound, preventing it from competing with the exonuclease for binding to DNA ends in the early stages of the reaction. The reaction volume is adjusted to 10 μl, the reaction is mixed gently and incubated at 37° C. for 5 minutes allowing the exonuclease to act on the DNA ends. The temperature is then raised to 50-60° C. to inactivate the exonuclease and activate the polymerase while promoting annealing of single-stranded ends of the DNA molecules. The mixture is incubated at 50-60° C. for 30 minutes and the temperature is then reduced to 4° C. to stop the reaction. The reaction can be performed in a PCR machine for efficient temperature changes. After completion, the reaction mixture can be stored at −20° C. and is ready to be transformed into competent Saccharomyces cerevisiae as described above.

Exonucleases that are suitable for this procedure are T4 DNA polymerase, Exonuclease III, lambda exonuclease, T5 exonuclease or T7 exonuclease. Exonucleases with 5' to 3' activity directionality (i.e. T4 polymerase, lambda exonuclease, T5 exonuclease or T7 exonuclease) are preferred as they result in higher numbers of base pairs of annealed sequence between the two nicks at each cloning junction, thus stabilizing the desired product. The reaction may also be supplemented with polyethylene glycol (molecular weight 4000-10000) at a final concentration of 5-10% to promote annealing of single-stranded DNA ends if desired.

After production of new re-assembled randomized in-frame polynucleotide collections, populations of yeast cells transformed with these collections are exposed to the same selective conditions to select cells containing plasmids and polynucleotides conferring heat, salt, low pH, ethanol, and butanol tolerance. Selections performed on cell populations containing collections of re-assembled randomized in-frame fusion polynucleotides may contain randomized in-frame fusion polynucleotides with different sequence combinations, or randomized in-frame fusion polynucleotides with sequence combinations at different frequencies or concentrations, compared to the initial randomized in-frame fusion polynucleotide collection, or compared to smaller populations of randomized in-frame fusion polynucleotides selected directly from the initial collection as described above. The sequence combinations formed by the reassembly process may confer better protection against abiotic stresses and selective agents, resulting in more desirable phenotypic values of transformants containing such sequence combinations.

The phenotypic values conferred by individual in-frame fusion polynucleotides isolated from randomized in-frame fusion polynucleotide collections using any of the selection methods described above, can be measured and compared between different transformants to find randomized in-frame fusion polynucleotides conferring the highest level of protection.

Testing of Individual Randomized In-Frame Fusion Polynucleotides for Conferral Heat, Salt, Ethanol, Butanol and Low pH Tolerance in Cell Survival Assays Cell survival assays are performed to allow comparative testing of individual, randomized in-frame fusion polynucleotides isolated from colonies of cells grown from survivors of heat, salt, low pH, ethanol or butanol selections as described above. The procedure replies extensively on nucleic acid and cell transfers that occur from 96-well plate to 96-well plate, retaining the original order of the plasmids of the first plate used for cultivation of E. coli transformants and plasmid DNA prepping.

Plasmid DNA isolated from individual yeast colonies is transformed into competent E. coli cells and plated at low cell densities onto LB agar plates containing 50 μg/ml carbenicillin, allowing individual E. coli colonies to grow. Individual E. coli colonies are transferred to 96-well deep-well plates, each well containing 1 ml LB containing 50 μg/ml carbenicillin and grown over night at 37° C. Certain wells in the plate are reserved for cells transformed with control plasmids that either lack an insert or contain inserts known not to confer abiotic stress tolerance. After incubation, the randomized in-frame fusion polynucleotide plasmid DNA is isolated from all clones in the plate.

The isolated, purified randomized in-frame fusion polynucleotide plasmid DNA is then re-introduced into yeast by lithium acetate—heat shock transformation as described above but using a 96-well plating format so that each transformation is plated separately into a well of a 2 ml deep-well plate containing synthetic complete uracil dropout medium with glucose as a carbon source. The transformants are allowed to grow under selection for three days at 30° C.

Cells are removed from the 96-well transformation plate by adding 500 μl synthetic complete uracil dropout medium with glucose as a carbon source and shaking the plate on a microshaker at 1000 rpm for 30 minutes. Aliquots of 250 μl of each cell suspension are then added to a fresh 2 ml deep-well 96-well plate containing in each well 500 μl of synthetic complete uracil dropout medium with galactose as a carbon source, and grown over night at 30° C. and shaking at 1000 rpm. This culturing step generates sufficient cell numbers for all subsequent assays while simultaneously exhausting the glucose in the growth medium and allowing induction of the GAL1 promoter from which the fusion genes are expressed.

Cell densities are determined by hemocytometer counting for 6 overnight cultures (6 different wells) per plate and averaged. This average is used to calculate a transfer volume of the cell suspensions for addition to 1.3 ml fresh medium, to result in a final cell density of $10^7$ cells/ml. The calculated volume of suspended cells is added from each culture (each well in the plate) to a fresh 96-well plate having 1.3 ml per well of YPGal rich medium with galactose as a carbon source (20 g Bacto Peptone, 10 g Bacto Yeast Extract and 20 g galactose per liter). This YPGal starter plate is grown for four hours at 30° C., with shaking at 1000 rpm.

Five 96-well 2 ml deep-well plates serve as selective culture plates and are inoculated from the YPGal starter plate, by adding 025 ml YPGAL starter culture from each well of the starter plate to 0.25 ml of 2× selective medium in each well of the selective culture plate. The 2× selective media used in the five selective culture plates are: 1) YPGal to select for heat tolerance by incubation at 42° C., 2) YPGal+4M NaCl to select for salt tolerance; 3) YPGal+ 0.2M sodium acetate pH 3.0 to select for low pH tolerance; 4) YPGal+30% ethanol to select for ethanol tolerance and 5) YPGal+6% butanol to select for butanol tolerance. The final concentrations of the selective agents are as follows: NaCl: 2M; low pH: 0.1M sodium acetate pH 3.0; ethanol: 15%; butanol: 3%.

The selective plates are incubated at 30° C. (42° C. for the heat selection), with shaking at 1000 rpm for 72 hours. The plates are then removed from the shaker and each culture spotted, without dilution and at a 1:10 dilution, in 3 µl spots onto 15 cm plates containing YPD agar (for 1 L, 20 g Bacto Peptone, 10 g Bacto Yeast Extract, 20 g glucose and 15 g Bacto Agar) using a Bel-Art Products Bel-Art 96-well replicating tool. The plates are incubated at 30° C. for 48 hours.

Figure 5:
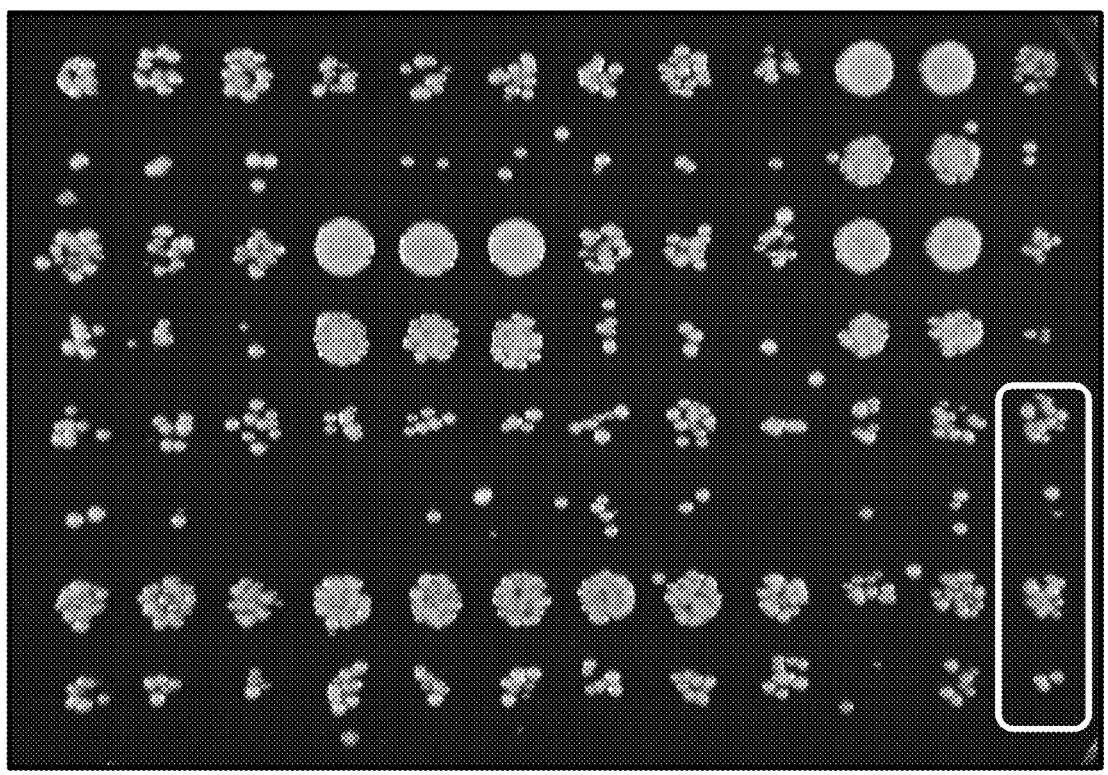
FIG. 5: *Saccharomyces cerevisiae* culture plates showing the results of cell survival assays performed on individual, cloned in-frame fusion polynucleotides to test for heat, salt, ethanol, butanol and low pH tolerance of yeast cells transformed with randomized in-frame fusion polynucleotides. Yeast strain BY4741 transformed with 16 different in-frame fusion polynucleotides and the p416-GAL1 control plasmid were cultured in triplicate cultures at high temperature or in the presence of selective agents. After growth under selective conditions, a portion of each culture was diluted 1:10 in fresh medium, and 3 µl of the diluted and undiluted culture were spotted onto fresh medium, and allowed to grow for 2 days. The selective agents were (A), ethanol; (B), butanol; (C), heat; (D), sail; (E), low pH. A map of the plate identifying all clones tested and their relative position in the plate is shown (F). The data shown in this figure is a subset of the data represented in Table 1.

The density of the cells growing on each pair of undiluted-diluted spots, indicates the number of surviving cells in each culture. Spots are scored on a scale from 0 to 3, 0 being no growth, 1 slight growth, 2 significant growth and 3 confluent growth; both spots, resulting from the two dilutions, are taken into account to generate the score. A panel of plate images, with results of the cell survival assay for 16 randomized in-frame fusion polynucleotides, is shown in FIG. 5. Each randomized in-frame polynucleotide fusion is scored in triplicate in this manner, scores added, and the average background subtracted to generate the final score. All scores are tabulated and are shown in Table 1.

Resistance and tolerance to ethanol and butanol of the 63 yeast transformants are also measured in minimal media containing raffinose and galactose as carbon sources. The 63 strains are compared to a negative control strain transformed with the empty p416-GAL1 plasmid. To perform these experiments, the 63 strains plus control strain are first grown in 96 well plates containing minimal uracil dropout medium containing 2% raffinose as a carbon source for 6 hours at 30° C. with constant shaking at 200 rpm, following which the fusion-genes are induced for expression with galactose at a final concentration of 2% and incubation continued overnight. Subsequently, 0.1 OD cultures from each well are inoculated into fresh minimal uracil dropout medium containing 1% raffinose and 2% galactose, but containing different concentrations of ethanol and butanol. Four concentrations of ethanol (8, 11, 14 and 17% v/v) and n-butanol (2, 2.5, 3 and 3.5% v/v are used. The 96 well culture plates are covered with air-permeable sealing films, and all plates are together further sealed in a large airtight plastic bag. This creates a semi-aerobic condition, and the cultures are incubated in a shaking incubator at 30° C. for 3 days. Two dilutions of each culture (1:10 and 1:100) are spotted on minimal media containing glucose as a carbon source using a Bel-Art Products Bel-Art 96-well replicating tool. The plates are incubated at 30° C. for 2 days. An image is taken of each plate and is scored for each dilutions for each fusion gene. A score of 0 to 5 is given to each spot based on growth of each spot compared to the negative control strain containing the empty vector. For each randomized in-frame fusion polynucleotide construct and for each dilution, the score is multiplied by its corresponding concentration of butanol/ethanol, and averaged. The same scoring method is followed for the strain with the negative control plasmid on the same plate, providing the background score. The final score is obtained by subtracting the background score strain from the average score of the strain with the individual randomized in-frame fusion polynucleotides.

The scores in Table 1 can be considered phenotypic values of each randomized in-frame fusion polynucleotide for each selection imposed on the transformants. High scores represent high phenotypic values for the corresponding randomized in-frame fusion polynucleotide.

Two types of randomized in-frame fusion polynucleotides are represented in Table 1. Seven unique in-frame fusion polynucleotides (M25-E1, M25-F4, M25-G8, M25-G10, M25-H11, M26-A12 and M26-D6) were selected by 1 round of direct selection, followed by 1 round of PCR amplification of the 5' and 3' ORFs and their re-assembly, followed by another round of direct selection. These 7 randomized in-frame fusion polynucleotides are referred to as "Re-assembled." The remaining 56 unique in-frame fusion polynucleotides were selected by two iterative rounds of selection. These 56 in-frame fusion polynucleotides are referred to as "Directly selected."

Average activities for the 7 selection categories shown in Table 1 are computed separately for the two classes of randomized in-frame fusion polynucleotides. The average scores are shown at the bottom of the table. In 6 out of 7 cases the average scores for the reassembled randomized in-frame fusion polynucleotides are higher than those of the directly selected randomized in-frame fusion polynucleotides. This data indicates that a reassembly step can be advantageous for isolating in-frame fusion polynucleotides conferring high phenotypic values.

Characterization of Positive Randomized In-Frame Fusion Polynucleotides and Additional Screens Randomized in-frame fusion polynucleotide expression constructs conferring the most dramatic or broad phenotypes are sequenced to identify the randomized in-frame fusion polynucleotides. The results are tabulated and the best randomized in-frame fusion polynucleotides chosen for future work. Table 2 shows the identities of the open reading frames found in all 63 yeast in-frame fusion polynucleotides. Their sequences nucleic acid and protein are contained in SEQ IDs NO.: 1-126.

All resistance and tolerance scores are listed in Table 1 below.

TABLE 1

Resistance and tolerance activities of 63 randomized in-frame fusion polynucleotides in *S. cerevisiae*

| Fusion polynucleotide name | Fusion polynucleotide nucleic acid sequence SEQ ID | Fusion polynucleotide encoded protein sequence SEQ ID | Activity scores (rich medium) | | | | | Activity scores (minimal medium) | |
|---|---|---|---|---|---|---|---|---|---|
| | | | Heat (42° C.) | Ethanol (15%) | Butanol (3%) | pH 3 (0.1M sodium acetate) | Salt (2M NaCl) | Butanol (3%) | Ethanol (15%) |
| Y1-5A | 1 | 64 | 3.75 | 0.00 | 4.75 | 2.75 | 4.75 | 0.0 | 35.0 |
| Y1-7A | 2 | 65 | 3.75 | 1.75 | 7.75 | 7.75 | 7.75 | 0.0 | 3.5 |
| Y1-9A | 3 | 66 | 0.00 | 1.75 | 4.75 | 4.75 | 4.75 | 0.0 | 0.8 |
| Y1-13A | 4 | 67 | 5.75 | 2.75 | 10.75 | 6.75 | 6.75 | 0.0 | 10.5 |
| Y1-17A | 5 | 68 | 6.75 | 2.75 | 7.75 | 8.75 | 7.75 | 0.0 | 7.0 |
| Y1-18A | 6 | 69 | 0.00 | 0.00 | 1.75 | 2.75 | 3.75 | 0.0 | 0.0 |
| Y1-19A | 7 | 70 | 0.75 | 5.75 | 7.75 | 8.75 | 7.75 | 0.0 | 9.8 |
| Y1-20A | 8 | 71 | 6.75 | 0.00 | 3.75 | 2.75 | 2.75 | 0.0 | 23.8 |
| Y1-21A | 9 | 72 | 5.75 | 0.00 | 4.75 | 5.75 | 7.75 | 0.0 | 0.0 |
| Y1-23A | 10 | 73 | 6.75 | 0.00 | 4.75 | 5.75 | 4.75 | 0.0 | 0.8 |
| Y1-25A | 11 | 74 | 0.75 | 0.00 | 1.75 | 2.75 | 1.75 | 0.0 | 7.0 |
| Y1-28A | 12 | 75 | 3.75 | 2.75 | 5.75 | 7.75 | 6.75 | 0.0 | 17.5 |
| Y1-33A | 13 | 76 | 6.75 | 0.00 | 0.00 | 1.75 | 4.75 | 0.0 | 0.0 |
| Y1-34B | 14 | 77 | 6.75 | 5.75 | 7.75 | 8.75 | 7.75 | 0.0 | 14.0 |
| Y1-38A | 15 | 78 | 6.75 | 2.75 | 7.75 | 8.75 | 4.75 | 0.0 | 7.0 |
| Y1-39B | 16 | 79 | 6.75 | 3.75 | 7.75 | 6.75 | 5.75 | 0.0 | 14.0 |
| Y1-40A | 17 | 80 | 5.75 | 0.00 | 1.75 | 5.75 | 4.75 | 0.0 | 7.0 |
| Y1-43A | 18 | 81 | 6.75 | 5.75 | 6.75 | 8.75 | 7.75 | 0.0 | 14.0 |
| Y1-45A | 19 | 82 | 6.75 | 0.00 | 0.00 | 0.00 | 1.75 | 0.0 | 0.0 |
| Y1-47A | 20 | 83 | 8.75 | 5.75 | 4.75 | 4.75 | 4.75 | 0.0 | 14.8 |
| Y1-48A | 21 | 84 | 6.75 | 5.75 | 4.75 | 8.75 | 7.75 | 0.0 | 10.5 |
| Y1-49A | 22 | 85 | 1.75 | 0.00 | 0.00 | 0.00 | 1.75 | 0.0 | 0.0 |
| Y1-58B | 23 | 86 | 0.00 | 0.00 | 0.00 | 0.00 | 0.00 | 0.0 | 0.0 |
| Y1-58C | 24 | 87 | 0.00 | 0.00 | 0.00 | 0.00 | 0.00 | 0.0 | 0.0 |
| Y1-66C | 25 | 88 | 0.00 | 0.00 | 0.00 | 0.00 | 0.00 | 0.0 | 0.0 |
| Y1-67B | 26 | 89 | 0.75 | 0.00 | 0.00 | 0.00 | 2.75 | 3.0 | 0.0 |
| Y2-28A | 27 | 90 | 0.75 | 0.00 | 0.00 | 0.00 | 0.00 | 0.0 | 0.0 |
| M21-A02 | 28 | 91 | 3.75 | 2.75 | 4.75 | 7.25 | 7.75 | 4.5 | 0.0 |
| M21-A03 | 29 | 92 | 6.75 | 5.75 | 10.75 | 11.75 | 7.75 | 16.0 | 0.0 |
| M21-A04 | 30 | 93 | 6.75 | 0.00 | 4.75 | 5.75 | 4.75 | 4.5 | 0.0 |
| M21-A09 | 31 | 94 | 5.75 | 2.75 | 4.75 | 4.75 | 3.75 | 4.5 | 2.8 |
| M21-C08 | 32 | 95 | 6.75 | 2.75 | 6.25 | 5.75 | 4.75 | 4.5 | 2.8 |
| M21-D06 | 33 | 96 | 7.75 | 0.00 | 4.00 | 3.25 | 9.75 | 1.0 | 0.0 |
| M22-C01 | 34 | 97 | 6.75 | 3.00 | 7.00 | 9.25 | 9.75 | 16.4 | 0.0 |
| M22-C05 | 35 | 98 | 6.75 | 3.00 | 8.00 | 6.25 | 6.75 | 2.5 | 0.0 |
| M22-D01 | 36 | 99 | 4.75 | 3.00 | 7.00 | 6.25 | 9.75 | 3.0 | 0.0 |
| M23-C03 | 37 | 100 | 9.75 | 9.00 | 10.00 | 9.25 | 9.75 | 11.8 | 0.0 |
| M23-D02 | 38 | 101 | 0.00 | 0.00 | 0.00 | 3.25 | 6.75 | 0.0 | 0.0 |
| M23-D09 | 39 | 102 | 0.00 | 9.00 | 10.00 | 12.25 | 12.75 | 6.5 | 0.0 |
| M23-E02 | 40 | 103 | 9.75 | 1.00 | 5.00 | 6.25 | 6.75 | 3.5 | 0.0 |
| M23-F02 | 41 | 104 | 9.75 | 9.00 | 10.00 | 12.25 | 12.75 | 1.6 | 0.8 |
| M23-H01 | 42 | 105 | 2.75 | 0.00 | 3.00 | 6.25 | 6.75 | 0.0 | 0.0 |
| M24-A05 | 43 | 106 | 0.75 | 3.00 | 7.00 | 6.25 | 9.75 | 3.5 | 13.0 |
| M24-B12 | 44 | 107 | 3.75 | 0.00 | 3.00 | 6.25 | 9.75 | 4.5 | 4.3 |
| M24-D11 | 45 | 108 | 0.00 | 0.00 | 10.00 | 6.25 | 12.75 | 18.3 | 0.0 |
| M24-E05 | 46 | 109 | 0.00 | 6.00 | 7.00 | 12.25 | 12.75 | 14.9 | 0.0 |
| M24-F06 | 47 | 110 | 6.75 | 6.00 | 7.00 | 9.25 | 9.75 | 7.8 | 0.0 |
| M25-E1 | 48 | 111 | 9.75 | 3.00 | 4.00 | 6.25 | 9.75 | 4.0 | 0.0 |
| M25-F4 | 49 | 112 | 9.75 | 0.00 | 0.00 | 6.25 | 6.75 | 2.5 | 0.0 |
| M25-G8 | 50 | 113 | 9.75 | 0.00 | 1.00 | 6.25 | 6.75 | 2.5 | 0.0 |
| M25-G10 | 51 | 114 | 1.75 | 6.00 | 1.00 | 8.25 | 8.75 | 0.0 | 0.0 |
| M25-H11 | 52 | 115 | 6.75 | 0.00 | 0.00 | 1.25 | 4.75 | 2.5 | 0.0 |
| M26-A12 | 53 | 116 | 9.75 | 9.00 | 10.00 | 12.25 | 12.75 | 19.1 | 14.3 |
| M26-D6 | 54 | 117 | 9.75 | 0.00 | 0.00 | 6.25 | 5.75 | 20.0 | 17.8 |
| M27-A1 | 55 | 118 | 6.75 | 9.00 | 4.00 | 12.25 | 12.75 | 20.0 | 21.3 |
| M27-B7 | 56 | 119 | 9.75 | 0.00 | 1.00 | 6.25 | 6.75 | 5.6 | 0.0 |
| M27-F8 | 57 | 120 | 0.00 | 0.00 | 0.00 | 0.00 | 0.75 | 0.8 | 0.0 |
| M28-A4 | 58 | 121 | 0.00 | 0.00 | 0.00 | 0.00 | 3.75 | 0.0 | 0.0 |
| M28-C9 | 59 | 122 | 0.00 | 0.00 | 0.00 | 0.00 | 6.75 | 0.0 | 0.0 |
| M28-D6 | 60 | 123 | 3.75 | 0.00 | 4.00 | 6.25 | 9.75 | 2.5 | 0.0 |
| M28-E4 | 61 | 124 | 3.75 | 3.00 | 4.00 | 9.25 | 12.75 | 0.0 | 0.0 |
| M29-E7 | 62 | 125 | 6.75 | 3.00 | 7.00 | 9.25 | 7.75 | 4.4 | 7.0 |
| M30-E11 | 63 | 126 | 0.75 | 0.00 | 0.00 | 0.25 | 8.25 | 13.0 | 0.0 |
| Directly selected average | | | 4.29 | 2.34 | 4.58 | 5.62 | 6.37 | 3.19 | 4.44 |
| Re-assembled average | | | 8.18 | 2.57 | 2.29 | 6.68 | 7.89 | 7.23 | 4.57 |

TABLE 2

Table 2: Yeast randomized in-frame fusion polynucleotides + component open reading frames (ORFs)

| Fusion poly- nucleotide name | NA se- quence SEQ ID | Protein se- quence SEQ ID | 5' ORF ID | 5' poly nucleotide name | 5' ORF description | 5' ORF length (bp) | 3' ORF ID | 3' poly nucleotide name | 3' ORF description | 3' ORF length + stop codon (bp) |
|---|---|---|---|---|---|---|---|---|---|---|
| Y1-5A | 1 | 64 | YDR246W-A | | Putative protein of unknown function | 198 | YOR043W | WHI2 | Activator of the general stress response | 1461 |
| Y1-7A | 2 | 65 | YHR126C | ANS1 | Putative protein of unknown function | 477 | YOR043W | WHI2 | Activator of the general stress response | 1461 |
| Y1-9A | 3 | 66 | YOL026C | MIM1 | Mitochondrial outer membrane protein | 339 | YLR094C | GIS3 | Protein of unknown function | 1509 |
| Y1-13A | 4 | 67 | YDR488C | PAC11 | Dynein intermediate chain | 1599 | YOR043W | WHI2 | Activator of the general stress response | 1461 |
| Y1-17A | 5 | 68 | YOR043W | WHI2 | Activator of the general Stress response | 1458 | YJL185C | | Putative protein of unknown function | 882 |
| Y1-18A | 6 | 69 | YLR375W | STP3 | Zinc-finger protein of unknown function | 1029 | YOR085W | OST3 | Oligosaccharyltransferase gamma subunit | 1053 |
| Y1-19A | 7 | 70 | YOR043W | WHI2 | Activator of the general stress response | 1458 | YFL066C | | Y' element helicase-like protein | 1179 |
| Y1-20A | 8 | 71 | YHL028W | WSC4 | ER membrane protein involved in translocation | 1815 | YOR043W | WHI2 | Activator of the general stress response | 1461 |
| Y1-21A | 9 | 72 | YOL054W | PSH1 | E3 ubiquitin ligase | 789 | YLR094C | GIS3 | Protein of unknown function | 1509 |
| Y1-23A | 10 | 73 | YFL066C | | Y' element helicase-like protein | 1176 | YOR043W | WHI2 | Activator of the general stress response | 1461 |
| Y1-25A | 11 | 74 | YGR060W | ERG25 | C-4 methyl sterol oxidase | 927 | YOR043W | WHI2 | Activator of the general stress response | 1461 |
| Y1-28A | 12 | 75 | YJL065C | DLS1 | ISW2 chromatin accessibility complex subunit | 501 | YOR043W | WHI2 | Activator of the general stress response | 1461 |
| Y1-33A | 13 | 76 | YLR094C | GIS3 | Protein of unknown function | 1506 | YKL117W | SBA1 | Hsp90 family co-chaperone | 651 |
| Y1-34B | 14 | 77 | YML064C | TEM1 | GTP-binding protein of the ras superfamily | 726 | YOR043W | WHI2 | Activator of the general stress response | 1461 |
| Y1-38A | 15 | 78 | YML036W | CGI121 | EKC/KEOPS protein complex component | 649 | YOR043W | WHI2 | Activator of the general stress response | 1461 |
| Y1-39B | 16 | 79 | YLR466C-B | | Dubious open reading frame | 114 | YOR043W | WHI2 | Activator of the general stress response | 1461 |
| Y1-40A | 17 | 80 | YDL109C | | Putative lipase; involved in lipid metabolism | 1941 | YOR043W | WHI2 | Activator of the general stress response | 1461 |
| Y1-43A | 18 | 81 | YLR154C-G | | Putative protein of unknown function | 147 | YOR043W | WHI2 | Activator of the general stress response | 1461 |
| Y1-45A | 19 | 82 | YIR016W | | Putative protein of | 795 | YOR043W | WHI2 | Activator of the general stress | 1461 |

TABLE 2-continued

Table 2: Yeast randomized in-frame fusion polynucleotides + component open reading frames (ORFs)

| Fusion poly-nucleotide name | NA sequence SEQ ID | Protein sequence SEQ ID | 5' ORF ID | 5' polynucleotide name | 5' ORF description | 5' ORF length (bp) | 3' ORF ID | 3' polynucleotide name | 3' ORF description | 3' ORF length + stop codon (bp) |
|---|---|---|---|---|---|---|---|---|---|---|
| Y1-47A | 20 | 83 | YER018C | SPC25 | Kinetochore-assoc. Ndc80 complex component | 663 | YOR043W | WHI2 | Activator of the general stress response | 1461 |
| Y1-48A | 21 | 84 | YML116W | ATR1 | Multidrug efflux pump | 1626 | YOR043W | WHI2 | Activator of the general stress response | 1461 |
| Y1-49A | 22 | 85 | YLR094C | GIS3 | Protein of unknown function | 1506 | YHR219W | | Putative helicase | 1946 |
| Y1-58B | 23 | 86 | YDR378C | LSM6 | Lsm (Like Sm) protein | 258 | YBL075C | SSA3 | ATPase involved in protein folding, stress response | 1950 |
| Y1-58C | 24 | 87 | YDR462W | MRPL28 | Mitochondrial large subunit ribosomal protein | 441 | YGL236C | MTO1 | Mitochondrial protein | 2010 |
| Y1-66C | 25 | 88 | YGL235W | | Putative protein of unknown function | 534 | YLR369W | SSQ1 | Mitochondrial hsp70-type molecular chaperone | 1974 |
| Y1-67B | 26 | 89 | YLL039C | UBI4 | Ubiquitin essential for the cellular stress response | 231 | YBL081W | | Non-essential protein of unknown function | 1107 |
| Y2-28A | 27 | 90 | YLR154C-G | | Putative protein of unknown function | 147 | YOL060C | MAM3 | Protein required for mitochondrial morphology | 2121 |
| M21-A02 | 28 | 91 | YOR043W | WHI2 | Activator of the general stress response | 1458 | YHR203C | RPS4B | 40S ribosomal subunit protein | 1055 |
| M21-A03 | 29 | 92 | YOR043W | WHI2 | Activator of the general stress response | 1458 | YLR094C | GIS3 | Protein of unknown function | 1509 |
| M21-A04 | 30 | 93 | YGR209C | TRX2 | Cytoplasmic thioredoxin isoenzyme | 312 | YOR043W | WHI2 | Activator of the general stress response | 1461 |
| M21-A09 | 31 | 94 | YGR203W | YCH1 | Phosphatase similar to Cdc25p | 444 | YOR043W | WHI2 | Activator of the general stress response | 1461 |
| M21-C08 | 32 | 95 | YBR077C | SLM4 | Component of the EGO complex | 486 | YOR043W | WHI2 | Activator of the general stress response | 1461 |
| M21-D06 | 33 | 96 | YNL086W | SNN1 | Putative protein of unknown function | 306 | YOR043W | WHI2 | Activator of the general stress response | 1461 |
| M22-C01 | 34 | 97 | YPR080W | TEF1 | Translational elongation factor EF-1 alpha | 1374 | YOR043W | WHI2 | Activator of the general stress response | 1461 |
| M22-C05 | 35 | 98 | YKR095W-A | PCC1 | EKC/KEOPS protein complex component | 339 | YOR043W | WHI2 | Activator of the general stress response | 1461 |
| M22-D01 | 36 | 99 | YIR015W | RPR2 | Subunit of nuclear RNase P | 432 | YOR043W | WHI2 | Activator of the general stress response | 1461 |
| M23-C03 | 37 | 100 | YJL184W | GON7 | EKC/KEOPS protein complex component | 369 | YOR043W | WHI2 | Activator of the general stress response | 1461 |

TABLE 2-continued

Table 2: Yeast randomized in-frame fusion polynucleotides + component open reading frames (ORFs)

| Fusion poly-nucleotide name | NA sequence SEQ ID | Protein sequence SEQ ID | 5' ORF ID | 5' poly nucleotide name | 5' ORF description | 5' ORF length (bp) | 3' ORF ID | 3' poly nucleotide name | 3' ORF description | 3' ORF length + stop codon (bp) |
|---|---|---|---|---|---|---|---|---|---|---|
| M23-D02 | 38 | 101 | YPL250C | ICY2 | Protein of unknown function | 408 | YJL205C | NCE101 | Protein of unknown function | 305 |
| M23-D09 | 39 | 102 | YMR226C | | NADP(+)-dependent dehydrogenase | 801 | YBR195C | MSI1 | Subunit of chromatin assembly factor I | 1269 |
| M23-E02 | 40 | 103 | YEL034W | HYP2 | Translation elongation factor eIF-5A | 471 | YOR043W | WHI2 | Activator of the general stress response | 1461 |
| M23-F02 | 41 | 104 | YPL250C | ICY2 | Protein of unknown function | 408 | YOR043W | WHI2 | Activator of the general stress response | 1461 |
| M23-H01 | 42 | 105 | YLR154C-G | | Putative protein of unknown function | 147 | YGR063C | SPT4 | Pol I and Pol II transcriptional regulator | 309 |
| M24-A05 | 43 | 106 | YNR049C | MSO1 | Secretory vesicle docking complex component | 630 | YOR043W | WHI2 | Activator of the general stress response | 1461 |
| M24-B12 | 44 | 107 | YMR156C | TPP1 | DNA 3'-phosphatase | 714 | YOR043W | WHI2 | Activator of the general stress response | 1461 |
| M24-D11 | 45 | 108 | YBR195C | MSI1 | Subunit of chromatin assembly factor I | 1266 | YOR101W | RAS1 | G-protein signaling GTPase | 930 |
| M24-E05 | 46 | 109 | YGR203W | YCH1 | Phosphatase similar to Cdc25p | 444 | YLR094C | GIS3 | Protein of unknown function | 1509 |
| M24-F06 | 47 | 110 | YHR055C | CUP1-2 | Metallothionein binding copper and cadmium | 183 | YOR043W | WHI2 | Activator of the general stress response | 1461 |
| M25-E1 | 48 | 111 | YJR120W | | Protein of unknown function | 348 | YOR043W | WHI2 | Activator of the general stress response | 1461 |
| M25-F4 | 49 | 112 | YHR055C | CUP1-2 | Metallothionein | 183 | YOR043W | WHI2 | Activator of the general stress response | 1461 |
| M25-G8 | 50 | 113 | YPR062W | FCY1 | Cytosine deaminase | 474 | YOR043W | WHI2 | Activator of the general stress response | 1461 |
| M25-G10 | 51 | 114 | YMR195W | ICY1 | Protein of unknown function | 381 | YBR195C | MSI1 | Subunit of chromatin assembly factor I | 1269 |
| M25-H11 | 52 | 115 | YLR162W | | Putative protein of unknown function | 354 | YOR043W | WHI2 | Activator of the general stress response | 1461 |
| M26-A12 | 53 | 116 | YMR195W | ICY1 | Protein of unknown function | 381 | YOR043W | WHI2 | Activator of the general stress response | 1461 |
| M26-D6 | 54 | 117 | YNL259C | ATX1 | Cytosolic copper metallochaperone | 219 | YOR043W | WHI2 | Activator of the general stress response | 1461 |
| M27-A1 | 55 | 118 | YDR432W | NPL3 | RNA-binding protein | 1242 | YOR043W | WHI2 | Activator of the general stress response | 1461 |
| M27-B7 | 56 | 119 | YOR043W | WHI2 | Activator of the general stress response | 1458 | YML036W | CGI121 | EKC/KEOPS protein complex component | 652 |
| M27-F8 | 57 | 120 | YDR246W-A | | Putative protein of unknown function | 198 | YHR008C | SOD2 | Mitochondrial manganese superoxide dismutase | 702 |
| M28-A4 | 58 | 121 | YER018C | SPC25 | Kinetochore-assoc. | 663 | YNL042W-B | | Putative protein of unknown function | 258 |

TABLE 2-continued

Table 2: Yeast randomized in-frame fusion polynucleotides + component open reading frames (ORFs)

| Fusion poly-nucleotide name | NA sequence SEQ ID | Protein sequence SEQ ID | 5' ORF ID | 5' poly nucleotide name | 5' ORF description | 5' ORF length (bp) | 3' ORF ID | 3' poly nucleotide name | 3' ORF description | 3' ORF length + stop codon (bp) |
|---|---|---|---|---|---|---|---|---|---|---|
| M28-C9 | 59 | 122 | YDR246W-A | | Ndc80 complex component Putative protein of unknown function | 198 | YPL157W | TGS1 | Trimethyl guanosine synthase | 948 |
| M28-D6 | 60 | 123 | YBR197C | | Putative protein of unknown function | 651 | YLR094C | GIS3 | Protein of unknown function | 1509 |
| M28-E4 | 61 | 124 | YDR378C | LSM6 | Lsm (Like Sm) protein | 258 | YLR094C | GIS3 | Protein of unknown function | 1509 |
| M29-E7 | 62 | 125 | YGR063C | SPT4 | Pol I and Pol II transcriptional regulator | 306 | YOR043W | WHI2 | Activator of the general stress response | 1461 |
| M30-E11 | 63 | 126 | YLR044C | PDC1 | Pyruvate decarboxylase | 1689 | YIL033C | BCY1 | cAMP-dependent protein kinase (PKA) regulatory subunit | 1251 |

(NA = nucleic acid)

Example 2: Isolation of Randomized In-Frame Fusion Polynucleotides Capable of Conferring Stress Tolerance to *Escherichia Coli*

Producing an *E. coli* Collection of Randomized In-Frame Fusion Polynucleotides

A collection or library of *E. coli* randomized in-frame fusion polynucleotides is prepared as described in U.S. patent application Ser. No. 14/134,619 and International Patent Application Serial Number PCT/US13/76526. The randomized in-frame fusion polypeptides are cloned into a vector molecule (SEQ ID NO:128). This vector is derived from the pUC19 high-copy plasmid and contains sequences for the ampicillin/carbenicillin resistance gene, pMB1 plasmid origin of replication, and the *E. coli* lac promoter and terminator. The vector is PCR amplified using oligonucleotides PG0185A (SEQ ID NO:129) and PG0188A (SEQ ID NO:130) for use in assembly of the randomized in-frame fusion polynucleotide collection.

Each 5' ORF prepared for the randomized in-frame fusion polynucleotide collection is flanked by a conserved sequence (SEQ ID NO:131) at its 5' end and by a conserved sequence (SEQ ID NO:132) at its 3' end. For re-assembly of 5' ORFs into new randomized in-frame fusion polynucleotide collections (described below), 5' ORFs are PCR amplified using oligonucleotides PG0185 (SEQ ID NO:135) and PG0186 (SEQ ID NO:136).

Each 3' ORF prepared for the randomized in-frame fusion polynucleotide collection is flanked by a conserved sequence (SEQ ID NO:133) at its 5' end and by a conserved sequence (SEQ ID NO:134) at its 3' end. For re-assembly of 3' ORFs into new randomized in-frame fusion polynucleotide collections (described below), 3' ORFs are PCR amplified using oligonucleotides PG0187 (SEQ ID NO:137) and PG0188 (SEQ ID NO:138).

Sequence Amplification General Method

PCR amplifications are performed using the following method.

The two amplification primers, each at a final concentration of 1.2 µM, are combined with 10 ng of template DNA, PCR buffer and thermostable polymerase in a total reaction volume of 50 µl. A high-fidelity thermostable polymerase such as Phusion™ Hot Start II thermostable high-fidelity polymerase (Thermo Scientific) can be used. For Phusion™ polymerase, the 5× HF amplification buffer supplied with the enzyme is used for all amplifications. All amplifications are performed on T100 thermal cyclers (Bio-Rad Laboratories) containing 96-well blocks. The deoxynucleotide triphosphates (dNTPs) used in amplifications are a stock containing 10 mM of each dNTP, also obtained from Thermo Scientific. Deionized water is used in all reactions and to make all solutions not supplied with the polymerase. PCR amplicons are generated by denaturing at 95° C. for 2 minutes followed by 10-35 cycles of 20 seconds at 95° C., 20 seconds at 60° C. and 1 min/kb at 72° C. (but a minimum of 30 seconds at 72° C.). The efficiency of formation of the PCR product is measured by agarose electrophoresis or by fluorescent spectroscopy using a fluorometer such as a Qubit® fluorometer (Life Technologies). Successful PCR reactions can be purified using silica resins suitable for DNA purification. Unsuccessful reactions are repeated by varying the $Mg^{+2}$ concentrations in the PCR reaction and/or other reaction conditions. Following successful amplification of each ORF, the concentration of each PCR product is normalized, and products corresponding to specific size ranges are pooled.

All PCR Amplifications Follow the Same General Procedure:

1. A PCR mix as described below is prepared for each stage of the PCR reaction, and is kept cold until inserted into the thermal cycler.

2. The samples are mixed thoroughly and then centrifuged at 4000 rpm for 1 minute to bring the reaction contents to the bottom of the tube or well in a plate.

3. The plates or tubes are inserted into a thermal cycler.

Selective Conditions Used for Selection of Heat and Salt Tolerance

Populations of E. coli cells transformed with the randomized in-frame fusion polynucleotide collection are selected for randomized in-frame fusion polynucleotide constructs conferring enhanced cell viability at high temperature (47-50° C. for 48-72 hours), or in the presence of high concentrations of salt (1.5-2.5M NaCl for 72 h to 7 days). All selections are performed in LB liquid medium (per liter, 10 g tryptone 5 g yeast extract, 10 g NaCl) containing 50 µg/ml carbenicillin and IPTG or lactose to induce expression of the randomized in-frame fusion polynucleotides from the lac promoter; all chemicals are purchased from Thermo Scientific. The cells are allowed to grow for 30 minutes at 37° C. on a shaker before inoculating the selections at a cell density of approximately $10^7$ cells/ml. Initial selections, performed with high-complexity collections of randomized in-frame fusion polynucleotides, are performed in 50-100 ml of liquid medium in 500 ml Erlenmeyer shake flasks tightly closed with a screw top to prevent medium evaporation during selection. Subsequent selections performed with smaller collections of randomized in-frame fusion polynucleotides can be performed in lower volumes at the same overall cell density. The volume of a selective culture can be chosen such that the total number of cells is a multiple of 20 or higher of the total expected number of randomized in-frame fusion polynucleotides being tested.

After selection, the cells are collected by centrifugation, are plated on LB solid medium (per liter, 10 g tryptone, 5 g yeast extract, 10 g NaCl, 15 g Bacto agar) containing 50 µg/ml carbenicillin and are allowed to grow overnight at 37° C. Colonies or lawns of cells arising after overnight growth are removed from the plates by scraping with glass beads. This is done by adding 5 ml LB broth+50 µg/ml carbenicillin to each 10 cm plate together with 10×4 mm glass beads. Proportionally higher volumes of medium are added to larger plates. Using swirling and shaking motions to allow the glass beads to dislodge the bacterial cells from the surface of the agar, the resuspended cells are collected with a pipet, using additional medium to wash any remaining cells off the plate, if desired. Cells collected in this fashion are pelleted by centrifugation at 4000 rpm for 15 minutes and plasmid DNA isolated using a silica resin column such as the Macherey Nagel NucleoSpin® Plasmid kit following the manufacturer's instructions.

The recovered plasmid DNA containing randomized in-frame fusion polynucleotides is transformed into competent E. coli cells such as DH10B (Life Technologies) or EC100 (Epicentre Technologies) strain of E. coli by electroporation. Alternative strains can be used if so desired for the subsequent round of phenotypic selections. 1 µl DNA is combined with 25 µl electrocompetent cells on ice, transferred into a 1 mm gap size electroporation cuvette, and electroporated at 1.5 kV using a Bio-Rad MicroPulser™ electroporator. Cells are suspended in 0.5 ml LB broth, allowed to recover for 1 hour at 37° C. on a shaker and plated in 0.25 ml aliquotes onto 10 cm plates containing LB agar medium with 50 µg/ml carbenicillin. Colonies are grown overnight at 37° C. Colonies or lawns of cells arising after overnight growth are removed from the plates by scraping with glass beads, resuspended in LB medium containing 50 µg/ml carbenicillin and IPTG or lactose to induce expression of the fusion polynucleotides from the lac promoter, and are subjected to another round of selection as described above, if desired.

Iterative Selection of Randomized In-Frame Fusion Polynucleotides Conferring Heat and Salt Tolerance and Resistance For iterative selection of randomized in-frame fusion polynucleotides conferring tolerance and resistance to heat and salt, populations of E. coli cells transformed with randomized in-frame fusion polynucleotide collection DNA are subjected to repetitive selections such as the ones described above. This procedure allows for gradual enrichment of randomized in-frame polynucleotides conferring tolerance and/or resistance to heat and salt, and for isolation of in-frame fusion polynucleotides containing the best combinations of ORFs for conferring tolerance to lethal temperatures and salt concentrations.

Alternatively, after a round of selection, the 5' ORFs and 3' ORFs contained in the randomized in-frame fusion polynucleotides recovered from survivors of the selection are re-isolated by PCR amplification and then recombined with each other to form anew re-assembled randomized in-frame fusion polynucleotide collection. This process may allow new sequence combinations to arise that encode in-frame fusion polynucleotides capable of conferring traits of interest. Selections performed on cell populations containing collections of re-assembled in-frame fusion polynucleotides may contain random in-frame fusion polynucleotides with different sequence combinations, or random in-frame fusion polynucleotides with sequence combinations at different frequencies or concentrations, compared to the initial randomized in-frame fusion polynucleotide collection, or compared to smaller populations of randomized in-frame fusion polynucleotides selected directly from the initial collection as described above. The sequence combinations formed by the reassembly process may confer better protection against heat and salt, resulting in more desirable phenotypic values of transformants containing such sequence combinations.

The randomized in-frame fusion polynucleotide plasmid DNA isolated from cells/colonies surviving heat or salt selections is used to re-amplify the 5' ORFs and 3' ORFs present in the randomized in-frame fusion polynucleotides. The amplification is performed as described above, using oligonucleotides PG0185 (SEQ ID NO:135) and PG0186 (SEQ ID NO:136) for amplifying the 5' ORFs, and using oligonucleotides PG0187 (SEQ ID NO:137) and PG0188 (SEQ ID NO:138) for amplifying the 3' ORFs. Optionally, mutations can be introduced into the 5' ORFs and 3' ORFs in the course of PCR amplification, using either lower-fidelity thermostable polymerases (Cline 1996, Biles 2004), or PCR-based incorporation of mutagenic nucleotide analogs such as 8-oxo-dGTP, dPTP, 5-bromo-dUTP, 2-hydroxy-dATP and dITP (Spec 1993, Kuipers 1996, Zaccolo 1996, Zaccolo 1999, Kamiya 2004, Kamiya 2007, Ma 2008, Petrie 2010, Wang 2012a). The re-amplified 5' ORFs and 3' ORFs are electrophoresed on a 1.5% agarose gel to remove amplification products below 200 bp in size and are purified from the gel using a commercial kit. The pUC19 vector DNA is also re-amplified and purified after electrophoresis.

Re-Assembly of Re-Amplified ORFs into a Randomized In-Frame Fusion Polynucleotide Collection The purified, re-amplified 5' ORFs and 3' ORFs are re-assembled with the pUC19 vector DNA as described below and are introduced into E. coli as a new collection of randomized in-frame fusion polynucleotides using the assembly methods described below. The resulting plasmid DNA is purified using a commercially available plasmid purification kit, following the manufacturer's recommendations.

The re-assembly is done using a ligation-independent cloning method. The following single-tube procedure uses a single-stranded exonuclease to create single-stranded tails at the ends of the DNA molecules to be assembled, followed by annealing of the homologous ends and fill-in of the remaining single-stranded regions. The purified DNA fragments resulting from PCR amplification of the expression vector backbone and the 5' and 3' ORFs (see above are combined in roughly equimolar amounts for a total of approximately 100 ng DNA in a 10 µl reaction. A 10× assembly buffer (500 mM Tris-HCl pH 8.0, 100 mM MaCl$_2$, 100 mM β-mercaptoethanol, 1 mM each of the 4 dNTPs) is added to produce a 1× concentration. Also added to the reaction are 0.01 unit of a single-stranded exonuclease and 1 unit of a thermostable, high-fidelity hot-start polymerase such as Phusion™ polymerase. Hot start implies that at physiological temperatures the polymerase is in an inactive for, for example being bound by an antibody or other compound, preventing it from competing with the exonuclease for binding to DNA ends in the early stages of the reaction. The reaction volume is adjusted to 10 µl, the reaction is mixed gently and incubated at 37° C. for 5 minutes allowing the exonuclease to act on the DNA ends The temperature is then raised to 50-60° C. to inactivate the exonuclease and activate the polymerase while promoting annealing of single-stranded ends of the DNA molecules. The mixture is incubated at 50-60° C. for 30 minutes and the temperature is then reduced to 4° C. to stop the reaction. The reaction can be performed in a PCR machine for efficient temperature changes. After completion, the reaction mixture can be stored at −20° C. and is ready to be transformed into competent coli as described above.

Exonucleases that are suitable for this procedure are T4 DNA polymerase, Exonuclease III, lambda exonuclease, T5 exonuclease or T7 exonuclease. Exonucleases with 5' to 3' activity directionality (i.e. T4 polymerase, lambda exonuclease, T5 exonuclease or T7 exonuclease) are preferred as they result in higher numbers of base pairs of annealed sequence between the two nicks at each cloning junction, thus stabilizing the desired product. The reaction may also be supplemented with polyethylene glycol (molecular weight 4000-10000) at a final concentration of 5-10% to promote annealing of single-stranded DNA ends, if desired.

After production of new re-assembled randomized in-frame polynucleotide collections, populations of cells are transformed with these collections using methods similar to those described above. The populations of transformed cells are then again exposed to selective conditions to select cells containing plasmids and polynucleotides conferring heat and salt tolerance.

The phenotypic values conferred by individual in-frame fusion polynucleotides isolated from randomized in-frame fusion polynucleotide collections using any of the selection methods described above, can be measured and compared between different transformants to find randomized in-frame fusion polynucleotides conferring the highest level of protection.

Testing of Individual, Randomized In-Frame Fusion Polynucleotides for Conferral of Heat and Salt Tolerance in Cell Survival Assays Plasmid DNA isolated from colonies or lawns of cells grown from survivors of killing heat or salt selections, is transformed into competent *E. coli* cells and plated at low cell densities onto LB agar plates containing 50 µg/ml carbenicillin. Individual colonies are placed into 96-well deep-well plates and grown over night at 37° C., each well containing 1 ml LB containing 50 µg/ml carbenicillin. Certain wells in the plate are reserved for cells transformed with control plasmids that either lack an insert or contain inserts known not to confer heat or salt tolerance.

For heat tolerance cell survival assays, after overnight growth the cell densities of 10-15 cultures in different wells are measured by optical density measurements on a spectrophotometer at 600 nm, such as the NanoDrop™ Spectrophotometer (Thermo Scientific). The optical densities are averaged and a dilution factor is calculated for preparing test cultures at an OD600 of 0.01, which corresponds roughly to a cell density of $10^7$ cells/ml. The 96-well culture is then diluted by the calculated factor into a fresh plate with each well containing the appropriate amount of LB medium with 50 µg/ml carbenicillin and either IPTG or galactose to induce expression of the in-frame fusion polynucleotides. This selection plate is incubated at 48° C. for 48-72 hours while shaking at 250 rpm. After selection, the cells in each well are thoroughly resuspended by pipetting, diluted 1:10 in LB medium in a separate plate, and 3 µl aliquots of the undiluted and diluted selections spotted in arrays of 96 spots, representing 48 randomized in-frame fusion polynucleotides, onto LB agar containing 50 µg/ml carbenicillin using a Bel-Art Products Bel-Art 96-well replicating tool. The spots are allowed to dry and the plates are incubated at 37° C. overnight.

For salt tolerance cell survival assays, after overnight growth the cell densities of 10-15 cultures in different wells are measured by optical density measurements on a spectrophotometer at 600 nm, such as the NanoDrop™ Spectrophotometer (Thermo Scientific). The optical densities are averaged and a dilution factor is calculated for preparing test cultures at an OD600 of 0.01, which corresponds roughly to a cell density of $10^7$ cells/ml. The 96-well culture is then diluted by the calculated factor into a fresh plate with each well containing the appropriate amount of LB medium with 50 µg/ml carbenicillin, 2.5M NaCl and either IPTG or galactose to induce expression of the in-frame fusion polynucleotides. The plate is incubated at 37° C. for 48-72 hours while shaking at 250 rpm. After selection, the cells in each well are thoroughly resuspended by pipetting, diluted 1:10 in LB medium in a separate plate, and 3 µl aliquots of the undiluted and diluted selections spotted in arrays of 96 spots, representing 48 randomized in-frame fusion polynucleotides, onto LB agar with 50 carbenicillin using a Bel-Art Products Bel-Art 96-well replicating tool. The spots are allowed to dry and the plates are incubated at 37° C. overnight.

The intensity of the cell spots on the test plates resulting from the heat and salt tolerance cell survival assays after overnight growth are indicative of the extent of cell survival under selection. Spot intensities are scored based on a scale of 0-3, 0 being no growth, 1 slight growth, 2 significant growth and 3 confluent growth. Both spats, resulting from the two dilutions, are taken into account to generate the score. This method allows identification of the best randomized in-frame fusion polynucleotides conferring heat and salt tolerance.

A panel of two plate images, with results of the heat and salt tolerance cell survival assay for 48 in-frame fusion polynucleotides, are shown in FIG. 6. The heat tolerance assays represented in FIG. 6 were performed with a stringent heat selection of 72 hours at 48° C., which resulted in survival of only the bacterial cultures harboring in-frame fusion polynucleotide clones capable of conferring maximal heat tolerance.

Table 3 shows averaged scores from a set of 24 randomized in-frame fusion polynucleotides selected from a randomized in-frame fusion polynucleotide collection by 2 rounds of iterative selection, compared to 160 randomized in-frame fusion polynucleotides selected from a randomized in-frame fusion polynucleotide collection that was re-assembled from plasmids isolated from survivors of a single round of heat or salt selections, and subjected to one more round of heat or salt selection after re-assembly. The 24 randomized in-frame fusion polynucleotides represented in the plate that were isolated by direct selection, were selected from a larger earlier set of 192 clones that were tested earlier for heat and salt tolerance by cell survival assays as described above. The 24 polynucleotides selected from this set of 192 clones represented the ones with the best heat and salt tolerance phenotypes, and were chosen for comparison to the 160 polynucleotides resulting from the reassembly process. The data of this comparison is shown in FIG. 6 and Table 3.

The scores in Table 3 can be considered phenotypic values conferred by each randomized in-frame fusion polynucleotide for each selection imposed on the transformants. High scores represent high phenotypic values conferred by the corresponding randomized in-frame fusion polynucleotide.

Two types of in-frame fusion polynucleotides are represented in Table 3, Twenty-four randomly selected randomized in-frame fusion polynucleotides (M43-A04, M43-C04, M43-D09, M44-D01, M44-D09, M44-F05, M44-F07, M44-F08, M44-F10, M44-F11, M44-F12, M44-G01, M44-G02, M44-G04, M44-G05, M44-G06, M44-G07, M44-G08, M44-G09, M44-G10, M44-G11, M44-H01, M44-H03 and M44-H04) were selected by two iterative rounds of selection. These 24 randomized in-frame fusion polynucleotides are referred to as type "Direct selection" in Table 3. The remaining 160 randomized in-frame fusion polynucleotides were selected by 1 round of direct selection, followed by 1 round of PCR amplification and re-assembly, followed by another round of direct selection and picking of random colonies formed from cells surviving the last round of selection. These 160 randomized in-frame fusion polynucleotides are referred to as type "Re-assembly" in Table 3.

Average activities are computed separately for the two classes of randomized in-frame fusion polynucleotides, for both heat and salt selections shown in Table 3. The average scores are shown at the bottom of the Table. For both heat and salt selection, the average scores for the re-assembled randomized in-frame fusion polynucleotides are higher than those of the directly selected randomized in-frame fusion polynucleotides. This data indicates that a re-assembly step can be advantageous for isolating in-frame fusion polynucleotides conferring high phenotypic values.

Characterization of Positive Randomized In-Frame Fusion Polynucleotides and Additional Screens Randomized in-frame fusion polynucleotide expression constructs conferring the most dramatic or broad phenotypes are sequenced to identify the randomized in-frame fusion polynucleotides.

TABLE 3

Table 3: Resistance and tolerance activities of 184 fusion polynucleotides in E. coli

| Fusion gene name | Type | Salt tolerance score | Heat tolerance score | Fusion gene name | Type | Salt tolerance score | Heat tolerance score |
|---|---|---|---|---|---|---|---|
| M43-A04 | Direct selection | 0.00 | 0.00 | M47-G12 | Re-assembly | 0.00 | 0.00 |
| M43-C04 | Direct selection | 0.00 | 2.00 | M47-H01 | Re-assembly | 1.90 | 0.00 |
| M43-D09 | Direct selection | 0.00 | 0.00 | M47-H02 | Re-assembly | 1.90 | 0.00 |
| M44-D01 | Direct selection | 0.00 | 0.00 | M47-H03 | Re-assembly | 1.90 | 0.00 |
| M44-D09 | Direct selection | 0.90 | 0.00 | M47-H04 | Re-assembly | 0.00 | 0.00 |
| M44-F05 | Direct selection | 0.00 | 0.00 | M47-H05 | Re-assembly | 1.90 | 0.00 |
| M44-F07 | Direct selection | 0.00 | 0.00 | M47-H06 | Re-assembly | 0.00 | 0.00 |
| M44-F08 | Direct selection | 0.00 | 1.00 | M47-H07 | Re-assembly | 0.00 | 0.00 |
| M44-F10 | Direct selection | 0.00 | 0.00 | M47-H09 | Re-assembly | 0.00 | 0.00 |
| M44-F11 | Direct selection | 0.00 | 0.00 | M47-H10 | Re-assembly | 1.90 | 0.00 |
| M44-F12 | Direct selection | 0.00 | 0.00 | M47-H11 | Re-assembly | 1.90 | 0.00 |
| M44-G01 | Direct selection | 0.00 | 0.00 | M47-H12 | Re-assembly | 0.90 | 0.00 |
| M44-G02 | Direct selection | 0.00 | 0.00 | M48-A02 | Re-assembly | 0.00 | 0.00 |
| M44-G04 | Direct selection | 0.00 | 1.00 | M48-A03 | Re-assembly | 1.90 | 0.00 |
| M44-G05 | Direct selection | 0.00 | 0.00 | M48-A05 | Re-assembly | 0.00 | 0.00 |
| M44-G06 | Direct selection | 0.00 | 0.00 | M48-A06 | Re-assembly | 0.00 | 0.00 |
| M44-G07 | Direct selection | 0.00 | 0.00 | M48-A07 | Re-assembly | 0.00 | 0.00 |
| M44-G08 | Direct selection | 0.00 | 0.00 | M48-A08 | Re-assembly | 0.00 | 0.00 |
| M44-G09 | Direct selection | 0.00 | 0.00 | M48-A09 | Re-assembly | 1.90 | 0.00 |
| M44-G10 | Direct selection | 0.00 | 0.00 | M48-A10 | Re-assembly | 1.90 | 0.00 |
| M44-G11 | Direct selection | 0.00 | 0.00 | M48-A11 | Re-assembly | 1.90 | 0.00 |
| M44-H01 | Direct selection | 0.00 | 0.00 | M48-B01 | Re-assembly | 1.90 | 0.00 |
| M44-H03 | Direct selection | 0.00 | 0.00 | M48-B03 | Re-assembly | 0.90 | 0.00 |
| M44-H04 | Direct selection | 0.00 | 0.00 | M48-B04 | Re-assembly | 0.00 | 0.00 |
| M47-A02 | Re-assembly | 1.90 | 0.00 | M48-B05 | Re-assembly | 0.00 | 0.00 |
| M47-A03 | Re-assembly | 1.90 | 0.00 | M48-B06 | Re-assembly | 1.90 | 0.00 |
| M47-A05 | Re-assembly | 1.90 | 0.00 | M48-B07 | Re-assembly | 0.00 | 0.00 |
| M47-A06 | Re-assembly | 1.90 | 0.00 | M48-B08 | Re-assembly | 1.90 | 0.00 |
| M47-A07 | Re-assembly | 0.00 | 0.00 | M48-B09 | Re-assembly | 1.90 | 0.00 |
| M47-A08 | Re-assembly | 1.90 | 0.00 | M48-B10 | Re-assembly | 0.00 | 0.00 |
| M47-A09 | Re-assembly | 0.00 | 0.00 | M48-B11 | Re-assembly | 0.00 | 0.00 |
| M47-A10 | Re-assembly | 1.90 | 0.00 | M48-B12 | Re-assembly | 0.00 | 0.00 |
| M47-A11 | Re-assembly | 0.90 | 0.00 | M48-C01 | Re-assembly | 0.90 | 0.00 |
| M47-B01 | Re-assembly | 1.90 | 0.00 | M48-C02 | Re-assembly | 1.90 | 0.00 |
| M47-B03 | Re-assembly | 0.90 | 0.00 | M48-C04 | Re-assembly | 0.00 | 0.00 |
| M47-B04 | Re-assembly | 0.90 | 0.00 | M48-C05 | Re-assembly | 1.90 | 0.00 |
| M47-B05 | Re-assembly | 0.00 | 0.00 | M48-C06 | Re-assembly | 0.90 | 0.00 |
| M47-B06 | Re-assembly | 0.90 | 0.00 | M48-C07 | Re-assembly | 0.00 | 0.00 |
| M47-B07 | Re-assembly | 0.00 | 0.00 | M48-C08 | Re-assembly | 0.00 | 0.00 |
| M47-B08 | Re-assembly | 0.90 | 0.00 | M48-C09 | Re-assembly | 0.00 | 0.00 |
| M47-B09 | Re-assembly | 1.90 | 0.00 | M48-C10 | Re-assembly | 0.00 | 2.00 |

TABLE 3-continued

Table 3: Resistance and tolerance activities of 184 fusion polynucleotides in E. coli

| Fusion gene name | Type | Salt tolerance score | Heat tolerance score | Fusion gene name | Type | Salt tolerance score | Heat tolerance score |
|---|---|---|---|---|---|---|---|
| M47-B10 | Re-assembly | 1.90 | 0.00 | M48-C12 | Re-assembly | 0.00 | 0.00 |
| M47-B11 | Re-assembly | 0.00 | 0.00 | M48-D01 | Re-assembly | 0.00 | 3.00 |
| M47-B12 | Re-assembly | 1.90 | 0.00 | M48-D02 | Re-assembly | 1.90 | 0.00 |
| M47-C01 | Re-assembly | 1.90 | 0.00 | M48-D03 | Re-assembly | 0.00 | 0.00 |
| M47-C02 | Re-assembly | 0.90 | 0.00 | M48-D05 | Re-assembly | 0.00 | 3.00 |
| M47-C04 | Re-assembly | 0.00 | 0.00 | M48-D06 | Re-assembly | 0.00 | 0.00 |
| M47-C05 | Re-assembly | 0.90 | 0.00 | M48-D07 | Re-assembly | 0.90 | 1.00 |
| M47-C06 | Re-assembly | 1.90 | 0.00 | M48-D08 | Re-assembly | 0.00 | 3.00 |
| M17-C07 | Re-assembly | 1.90 | 0.00 | M48-D10 | Re-assembly | 0.00 | 2.00 |
| M47-C08 | Re-assembly | 0.00 | 0.00 | M48-D11 | Re-assembly | 0.00 | 2.00 |
| M47-C09 | Re-assembly | 1.90 | 0.00 | M48-D12 | Re-assembly | 0.00 | 3.00 |
| M47-C10 | Re-assembly | 1.90 | 0.00 | M48-E01 | Re-assembly | 0.00 | 0.00 |
| M47-C12 | Re-assembly | 0.90 | 0.00 | M48-E02 | Re-assembly | 0.00 | 3.00 |
| M47-D01 | Re-assembly | 0.90 | 0.00 | M48-E03 | Re-assembly | 0.00 | 0.00 |
| M47-D02 | Re-assembly | 0.00 | 0.00 | M48-E04 | Re-assembly | 0.00 | 0.00 |
| M47-D03 | Re-assembly | 0.00 | 0.00 | M48-E06 | Re-assembly | 1.90 | 0.00 |
| M47-D05 | Re-assembly | 0.00 | 0.00 | M48-E07 | Re-assembly | 0.00 | 0.00 |
| M47-D06 | Re-assembly | 0.00 | 0.00 | M48-E08 | Re-assembly | 0.00 | 0.00 |
| M47-D07 | Re-assembly | 0.00 | 0.00 | M48-E09 | Re-assembly | 0.00 | 0.00 |
| M47-D08 | Re-assembly | 0.00 | 0.00 | M48-E11 | Re-assembly | 1.90 | 0.00 |
| M47-D11 | Re-assembly | 1.90 | 0.00 | M48-E12 | Re-assembly | 0.00 | 0.00 |
| M47-D12 | Re-assembly | 0.00 | 0.00 | M48-F01 | Re-assembly | 0.00 | 0.00 |
| M47-E01 | Re-assembly | 0.00 | 0.00 | M48-F03 | Re-assembly | 0.90 | 2.00 |
| M47-E02 | Re-assembly | 1.90 | 0.00 | M48-F04 | Re-assembly | 0.00 | 0.00 |
| M47-E03 | Re-assembly | 0.00 | 0.00 | M48-F05 | Re-assembly | 0.00 | 2.00 |
| M47-E04 | Re-assembly | 0.00 | 0.00 | M48-F07 | Re-assembly | 0.00 | 3.00 |
| M47-E06 | Re-assembly | 1.90 | 0.00 | M48-F08 | Re-assembly | 0.00 | 1.00 |
| M47-E07 | Re-assembly | 1.90 | 0.00 | M48-F09 | Re-assembly | 0.00 | 3.00 |
| M47-E08 | Re-assembly | 1.90 | 0.00 | M48-F10 | Re-assembly | 0.90 | 0.00 |
| M47-E09 | Re-assembly | 0.00 | 0.00 | M48-F11 | Re-assembly | 0.90 | 0.00 |
| M47-E10 | Re-assembly | 0.90 | 0.00 | M48-F12 | Re-assembly | 0.00 | 0.00 |
| M47-E11 | Re-assembly | 1.90 | 0.00 | M48-G01 | Re-assembly | 0.90 | 0.00 |
| M47-E12 | Re-assembly | 0.90 | 0.00 | M48-G02 | Re-assembly | 0.00 | 0.00 |
| M47-F01 | Re-assembly | 0.00 | 0.00 | M48-G03 | Re-assembly | 0.00 | 0.00 |
| M47-F03 | Re-assembly | 1.90 | 0.00 | M48-G05 | Re-assembly | 0.00 | 0.00 |
| M47-F04 | Re-assembly | 1.90 | 0.00 | M48-G06 | Re-assembly | 0.00 | 0.00 |
| M47-F05 | Re-assembly | 1.90 | 0.00 | M48-G08 | Re-assembly | 0.00 | 0.00 |
| M47-F07 | Re-assembly | 0.00 | 0.00 | M48-G10 | Re-assembly | 0.00 | 0.00 |
| M47-F08 | Re-assembly | 0.00 | 0.00 | M48-G11 | Re-assembly | 1.90 | 0.00 |
| M47-F09 | Re-assembly | 1.90 | 0.00 | M48-G12 | Re-assembly | 0.00 | 0.00 |
| M47-F10 | Re-assembly | 0.90 | 0.00 | M48-H01 | Re-assembly | 0.00 | 0.00 |
| M47-F11 | Re-assembly | 0.90 | 0.00 | M48-H02 | Re-assembly | 0.00 | 0.00 |
| M47-F12 | Re-assembly | 0.00 | 1.00 | M48-H03 | Re-assembly | 0.00 | 0.00 |
| M47-G01 | Re-assembly | 1.90 | 0.00 | M48-H04 | Re-assembly | 1.90 | 0.00 |
| M47-G02 | Re-assembly | 1.90 | 0.00 | M48-H05 | Re-assembly | 0.00 | 0.00 |
| M47-G03 | Re-assembly | 0.90 | 0.00 | M48-H06 | Re-assembly | 0.00 | 0.00 |
| M47-G05 | Re-assembly | 0.90 | 0.00 | M48-H07 | Re-assembly | 0.00 | 0.00 |
| M47-G06 | Re-assembly | 0.00 | 0.00 | M48-H09 | Re-assembly | 0.90 | 0.00 |
| M47-G08 | Re-assembly | 1.90 | 1.00 | M48-H10 | Re-assembly | 0.00 | 0.00 |
| M47-G10 | Re-assembly | 1.90 | 0.00 | M48-H11 | Re-assembly | 1.90 | 0.00 |
| M47-G11 | Re-assembly | 1.90 | 0.00 | M48-H12 | Re-assembly | 0.00 | 0.00 |
| Average | Direct selection | 0.013 | 0.167 | | | | |
| Average | Re-assembly | 0.728 | 0.219 | | | | |

REFERENCES

Biles B D, Connolly B A (2004). Low-fidelity *Pyrococcus furiosus* DNA polymerase mutants useful in error-prone PCR. Nucleic Acids Res. 32(22):e176.

Brachmann C B, Davies A, Cost G J, Caputo E, Li J, Hieter P, Boeke J D (1998). Designer deletion strains derived from *Saccharomyces cerevisiae* S288C: a useful set of strains and plasmids for PCR-mediated gene disruption and other applications. Yeast 14(2):115-132.

Chenna R, Sugawara H, Koike T, Lopez R, Gibson T J, Higgins D G, Thompson J D (2003). Multiple sequence alignment with the Clustal series of programs. Nucleic Acids Res. 31(13):3497-3500.

Cline J, Braman J C, Hogrefe H H (1996). PCR fidelity of pfu DNA polymerase and other thermostable DNA polymerases. Nucleic Acids Res. 24(18):3546-3551.

da Costa L J, Tanuri A (1998). Use of T7 gene 6 exonuclease and phosphorothioated primers for the manipulation of HIV-1 infectious clones. J Virol Methods 72(1):117-121.

Ding J, Huang X, Zhang L, Zhao N, Yang D, Zhang K (2009). Tolerance and stress response to ethanol in the yeast *Saccharomyces cerevisiae*. Appl Microbiol Biotechnol. 85(2):253-263.

Dismukes G C, Carrieri D, Bennette N, Ananyev G M, Posewitz M C (2008). Aquatic phototrophs: efficient alternatives to land-based crops for biofuels. Curr Opin Biotechnol. 19(3):235-240.

Dolganov N, Grossman A R (1993). Insertional inactivation of genes to isolate mutants of *Synechococcus* sp. strain PCC 7942: isolation of filamentous strains. J Bacteriol. 175(23):7644-7651.

Dunlop M J (2011). Engineering microbes for tolerance to next-generation biofuels. Biotechnol Biofuels 4:32.

Funk M, Niedenthal R, Mumberg D, Brinkmann K, Rönicke V, Henkel T (2002). Vector systems for heterologous expression of proteins in *Saccharomyces cerevisiae*. Methods Enzymol. 350:248-57.

Gibson D G, Young L, Chuang R Y, Venter J C, Hutchison C A 3rd, Smith H O (2009). Enzymatic assembly of DNA molecules up to several hundred kilobases. Nat Methods. 6(5):343-345.

Gibson D G, Smith H O, Hutchison C A 3rd, Venter J C, Merryman C. (2010). Chemical synthesis of the mouse mitochondrial genome. Nat Methods. 7(11):901-903.

Gietz R D, Woods R A (2002). Transformation of yeast by lithium acetate/single-stranded carrier DNA/polyethylene glycol method. Methods Enzymol. 350:87-96.

Gietz R D, Woods R A (2006). Yeast transformation by the LiAc/SS Carrier DNA/PEG method. Methods Mol Biol. 313:107-120.

Gietz R D, Schiestl R H (2007) High-efficiency yeast transformation using the LiAc/SS carrier DNA/PEG method. Nat Protocols 2(1):31-34.

Irwin C R, Farmer A, Willer D O, Evans D H (2012). In-Fusion® cloning with vaccinia virus DNA polymerase. Methods Mol Biol. 890:23-35.

Jang Y S, Kim B, Shin J H, Choi Y J, Choi S, Song C W, Lee Park H G, Lee S Y (2012). Bio-based production of C2-C6 platform chemicals. Biotechnol Bioeng. 109(10): 2437-2459.

Jia, Kaizhi; Zhang, Yanping; Li, Yin (2009). Systematic engineering of microorganisms to improve alcohol tolerance. Engineering in Life Sciences 10(5): 422-429.

Kamiya H, Ito M, Harashima H (2004). Induction of transition and transversion mutations during random mutagenesis PCR by the addition of 2-hydroxy-dATP. Biol Pharm Bull. 27(5):621-623.

Kamiya. H, Ito M, Harashima H (2007). Induction of various mutations during PCRs with manganese and 8-hydroxy-dGTP. Biol Pharm Bull. 30(4):842-844.

Kuipers O P (1996). Random mutagenesis by using mixtures of dNTP and dITP in PCR. Methods Mol Biol. 57:351-356.

Lathe R, Kieny M P, Skory S, Lecocq J P (1984). Linker tailing: unphospholylated linker oligonucleotides for joining DNA termini. DNA 3(2): 173-182.

Lee J W, Na D, Park J M, Lee J. Choi S. Lee S Y (2012). Systems metabolic engineering of microorganisms for natural and non-natural chemicals. Nat Chem Biol. 8(6): 536-546.

Li M Z, Elledge S J. (2007). Harnessing homologous recombination in vitro to generate recombinant DNA via SLIC. Nat Methods. 4(3): 251-256.

Li C, Wen A, Shen B, Lu J, Huang Y, Chang Y. (2011). FastCloning: a highly simplified, purification-free, sequence- and ligation-independent PCR cloning method. BMC Biotechnol. 11:92.

Li M Z, Elledge S J. (2012). SLIC: a method for sequence- and ligation-independent cloning. Methods Mol Biol. 852:51-59.

Liu X P, Liu J H (2010). The terminal 5' phosphate and proximate phosphorothioate promote ligation-independent cloning. Protein Sci. 19(5):967-973.

Lobban P E, Kaiser A D (1973). Enzymatic end-to end joining of DNA molecules. J Mol Biol. 78(3): 453-471.

Ma X, Ke T, Mao P, Jin X, Ma L, He G (2008). The mutagenic properties of BrdUTP in a random mutagenesis process. Mol Biol Rep. 35(4):663-667.

Mascal M (2012). Chemicals from biobutanol: technologies and markets. Biofuels, Bioprod. Bioref. 6(4):483-493.

Petrie K L, Joyce G F (2010). Deep sequencing analysis of mutations resulting from the incorporation of dNTP analogs. Nucleic Acids Res. 38(22):8095-8104.

Quan J, Tian J (2009). Circular polymerase extension cloning of complex gene libraries and pathways. PLoS One. 4(7): e6441.

Quan J, Tian J (2011). Circular polymerase extension cloning for high-throughput cloning of complex and combinatorial DNA libraries. Nat Protoc. 6(2):242-251.

Sambrook, J., Fritsch, E. F., and Maniatis, T. (1989) Molecular Cloning: A Laboratory Manual, Second Ed., Cold Spring Harbor Laboratory Press, Plainview, N.Y.

Sikorski R S, Hieter P (1989). A system of shuttle vectors and yeast host strains designed for efficient manipulation of DNA in *Saccharomyces cerevisiae*. Genetics 122(1): 19-27.

Spee J H, de Vos W M, Kuipers O P (1993). Efficient random mutagenesis method with adjustable mutation frequency by use of PCR and dITP. Nucleic Acids Res. 21(3):777-778.

Thieme F, Engler C, Kandzia R, Marillonnet S (2011). Quick and clean cloning: a ligation-independent cloning strategy for selective cloning of specific PCR products from non-specific mixes. PLoS One 6(6): e20556.

Vroom J A, Wang C L (2008). Modular construction of plasmids through ligation-free assembly of vector components with oligonucleotide linkers. Biotechniques 44(7): 924-926.

Wang Z, Wang H Y, Feng H (2012a). A simple and reproducible method for directed evolution: combination of random mutation with dITP and DNA fragmentation with endonuclease V. Mol Biotechnol. 53(1):49-54.

Ward A C (1990). Single-step purification of shuttle vectors from yeast for high frequency back-transformation into *E. coli*. Nucleic Acids Res. 8(17):5319.

Zaccolo M, Williams D M, Brown D M, Gherardi E (1996). An approach to random mutagenesis of DNA using mixtures of triphosphate derivatives of nucleoside analogues. J Mol Biol. 255(4):589-603.

Zaccolo M, Gherardi E (1999). The effect of high-frequency random mutagenesis on in vitro protein evolution: a study on TEM-1 beta-lactamase. J Mol Biol. 285(2):775-783.

Zhu B, Cai G, Hall E O, Freeman G J (2007). In-fusion assembly: seamless engineering of multidomain fusion proteins, modular vectors, and mutations. BioTechniques 43:354-359.

All publications, databases, GenBank sequences, patents and patent applications cited in this Specification are herein incorporated by reference as if each was specifically and individually indicated to be incorporated by reference.

I claim:

1. A method of producing an organism with a new or altered phenotype, comprising:
   (a) introducing a composition comprising a plurality of random in-frame fusion polynucleotides having sequences different from each other into an organism to produce one or more transformed organisms, each random in-frame fusion polynucleotide comprising at least two open reading frames isolated from the genome of the same species of organism, one designated as a 5' open reading frame and one designated as a 3' open reading frame, the 5' open reading frame being joined either directly, or indirectly via at least one intervening open reading frame, to the 3' open reading frame to form a composite open reading frame encoding a fusion polypeptide;
   (b) isolating at least two transformed organisms exhibiting a different phenotype as compared to a control organism cultivated under the same conditions;
   (c) isolating at least the 5' open reading frame and the 3' frame from each of the at least two fusion polynucleotides present in the organisms of step (b);
   (d) randomly combining the isolated open reading frames of step (c) to form at least two random in-frame polynucleotides, each comprising a composite open reading frame encoding a fusion polypeptide;
   (e) introducing the polynucleotide(s) of step (d) into an organism to produce one or more transformed organisms; and
   (f) isolating at least one transformed organism from the organism(s) in step (e) exhibiting a different phenotype as compared to a control organism cultivated under the same conditions,
   wherein steps (c) through (f) are optionally repeated one or more times, wherein the organism is a yeast, a bacterium, a cyanobacterium, an archaeon, or a protozoan.

2. The method of claim 1, wherein each 5' open reading frame is selected from a collection comprising a plurality of open reading frames having sequences different from each other and each 3' open reading frame is selected from a second collection comprising a plurality of open reading frames having sequences different from each other.

3. The method according to claim 1, wherein the at least two open reading frames are nonhomologous.

4. The method according to claim 1, wherein the at least two open reading frames are joined via a linker sequence.

5. The method according to claim 4, wherein the linker sequence is 1 to 1,000 codons in length.

6. The method according to claim 1, wherein the random in-frame fusion polynucleotide further comprises an expression vector sequence.

7. The method according to claim 1, wherein the random in-frame fusion polynucleotide further comprises at least one regulatory sequence.

8. The method according to claim 7, wherein the regulatory sequence is a promoter or a terminator.

9. The method according to claim 1, wherein the composite open reading frame encoding the fusion polypeptide of step (d) is different from the fusion polypeptide present in the organisms of step (b).

10. The method according to claim 1, wherein the at least two open reading frames isolated from the genome of the same organism are full-length.

11. The method according to claim 1, wherein the organism is a bacterium or a yeast.

12. A method of producing an organism with a new or altered phenotype, comprising:
  (a) introducing a composition comprising a plurality of random in-frame fusion polynucleotides having sequences different from each other into an organism to produce one or more transformed organisms, each random in-frame fusion polynucleotide comprising at least two open reading frames isolated from the genome of at least two different species of organism, one designated as a 5' open reading frame and one designated as a 3' open reading frame, the 5' open reading frame being joined either directly, or indirectly via at least one intervening open reading frame, to the 3' open reading frame to form a composite open reading frame encoding a fusion polypeptide, wherein the species are, bacteria, archaea, protozoa, yeast, yeast, cyanobacteria, fungus, alga, or plant;
  (b) isolating at least two transformed organisms exhibiting a different phenotype as compared to a control organism cultivated under the same conditions;
  (c) isolating at least the 5' open reading frame and the 3' frame from each of at least two fusion polynucleotides present in the organisms of step (b);
  (d) randomly combining the isolated open reading frames of step (c) to form at least two random in-frame polynucleotides, each comprising a composite open reading frame encoding a fusion polypeptide;
  (e) introducing the polynucleotide(s) of step (d) into an organism to produce one or more transformed organisms; and
  (f) isolating at least one transformed organism from the organism(s) in step (e) exhibiting a different phenotype as compared to a control organism cultivated under the same conditions,
wherein steps (c) through (f) are optionally repeated one or more times, wherein the organism is a yeast, a bacterium, a cyanobacterium, an archaeon, or a protozoan.

13. The method of claim 12, wherein the at least two different species of step (a) are species of bacteria, yeast, or cyanobacteria.

14. The method of claim 12, wherein the at least two different species of step (a) are both bacteria.

15. The method of claim 12, wherein the at least two different species of step (a) are both yeast.

16. The method of claim 12, wherein the at least two different species of step (a) are both cyanobacteria.

* * * * *